United States Patent
Lee et al.

(10) Patent No.: US 11,981,658 B2
(45) Date of Patent: May 14, 2024

(54) SUBSTITUTED AMINOPYRIDINE COMPOUNDS AS EGFR INHIBITORS

(71) Applicants: YUHAN CORPORATION, Seoul (KR); JANSSEN BIOTECH, INC., Horsham, PA (US)

(72) Inventors: Byoungmoon Lee, Hwaseong-si (KR); Hyunjoo Lee, Suwon-si (KR); Gyu Jin Lee, Yongin-si (KR); Su Bin Choi, Hwaseong-si (KR); Sol Park, Yongin-si (KR); Heejun Kim, Hwaseong-si (KR); Misong Kim, Suwon-si (KR); Young Ae Yoon, Seongnam-si (KR); Kwan Hoon Hyun, Icheon (KR); Tae Kyun Kim, Hwaseong-si (KR); Jae Young Sim, Yongin-si (KR); Marian C. Bryan, Spring House, PA (US); Scott Kuduk, Spring House, PA (US); James Campbell Robertson, Spring House, PA (US)

(73) Assignees: Yuhan Corporation, Seoul (KR); Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/822,450

(22) Filed: Aug. 26, 2022

(65) Prior Publication Data
US 2023/0086884 A1 Mar. 23, 2023

Related U.S. Application Data

(60) Provisional application No. 63/237,647, filed on Aug. 27, 2021.

(51) Int. Cl.
*C07D 401/14* (2006.01)

(52) U.S. Cl.
CPC .................. *C07D 401/14* (2013.01)

(58) Field of Classification Search
CPC .. C07D 401/14; C07D 405/14; C07D 409/14; C07D 417/14; C07D 451/02; C07D 471/04; C07D 471/10; C07D 487/04; C07D 491/107; C07D 493/08; A61P 35/00; A61P 37/00
See application file for complete search history.

(56) References Cited

U.S. PATENT DOCUMENTS

| | | |
|---|---|---|
| 6,884,804 B2 | 4/2005 | Choon-Moon |
| 7,560,464 B2 | 7/2009 | Wang et al. |
| 7,642,354 B2 | 1/2010 | Wang et al. |
| 8,058,045 B2 | 11/2011 | Collins et al. |
| 8,367,658 B2 | 2/2013 | Collins et al. |
| 9,242,984 B2 | 1/2016 | Machacek et al. |
| 9,868,720 B2 | 1/2018 | Cohen et al. |
| 10,822,327 B2 | 11/2020 | Liu et al. |
| 2003/0144309 A1 | 7/2003 | Choon-Moon |
| 2004/0236084 A1 | 11/2004 | Biwersi et al. |
| 2005/0239800 A1 | 10/2005 | Wang et al. |
| 2005/0267089 A1 | 12/2005 | Wang et al. |
| 2008/0108600 A1 | 5/2008 | Wang et al. |
| 2010/0311730 A1 | 12/2010 | Collins et al. |
| 2012/0040967 A1 | 2/2012 | Collins et al. |
| 2015/0191461 A1 | 7/2015 | Machacek et al. |
| 2016/0046608 A1 | 2/2016 | Cohen et al. |
| 2019/0375727 A1 | 12/2019 | Liu et al. |
| 2020/0392156 A1 | 12/2020 | Kesicki |
| 2021/0317136 A1 | 10/2021 | Lindstrom et al. |
| 2022/0177459 A1 | 6/2022 | Du et al. |
| 2022/0298140 A1 * | 9/2022 | Chen ............. A61P 35/02 |
| 2022/0411407 A1 | 12/2022 | Wang et al. |

FOREIGN PATENT DOCUMENTS

| | | | |
|---|---|---|---|
| CN | 104761585 A | 7/2015 | |
| KR | 10-2020-0016567 A | 2/2020 | |
| WO | WO-2010123870 A1 * | 10/2010 | ........... A61K 31/505 |
| WO | 2019/222538 A1 | 11/2019 | |

OTHER PUBLICATIONS

Cancer Vaccines: The Types, How They Work, and Which Cancers They Treat, obtained from https://www.mskcc.org/cancer-care/diagnosis-treatment/cancer-treatments/immunotherapy/cancer-vaccines on Sep. 6, 2023. (Year: 2023).*
Can Lung Cancer Be Prevented?, obtained from https://www.cancer.org/cancer/types/lung-cancer/causes-risks-prevention/prevention.html on Sep. 6, 2023. (Year: 2023).*
Can I Lower My Risk of Breast Cancer?, obtained from https://www.cancer.org/cancer/types/breast-cancer/risk-and-prevention/can-i-lower-my-risk.html on Sep. 6, 2023. (Year: 2023).*
Can Stomach Cancer Be Prevented?, obtained from https://www.cancer.org/cancer/types/stomach-cancer/causes-risks-prevention/prevention.html on Sep. 6, 2023. (Year: 2023).*
Hanan et al., "Discovery of Selective and Noncovalent Diaminopyrimidine-Based Inhibitors of Epidermal Growth Factor Receptor Containing the T790M Resistance Mutation", J. Med. Chem., 2014, vol. 57, pp. 10176-10191.

* cited by examiner

*Primary Examiner* — Matthew P Coughlin
*Assistant Examiner* — Ashli Ariana Chicks
(74) *Attorney, Agent, or Firm* — Vorys, Sater, Seymour and Pease LLP; Mih Suhn Koh

(57) ABSTRACT

Provided are aminopyridine compounds and pharmaceutically acceptable compositions thereof which exhibit inhibition activity against certain mutated forms of EGFR.

39 Claims, No Drawings

SUBSTITUTED AMINOPYRIDINE COMPOUNDS AS EGFR INHIBITORS

FIELD OF THE INVENTION

The present invention relates to novel aminopyridine compounds and pharmaceutically acceptable compositions thereof which exhibit inhibition activity against certain mutated forms of EGFR.

BACKGROUND

A distinct subtype of lung cancer is epidermal growth factor receptor (EGFR) mutation positive non-small cell lung cancer (NSCLC). The human EGFR is a membrane-bound receptor tyrosine kinase of the ErbB family. The activation causes downstream effects via several signaling pathways including the RAS/RAF/MEK/ERK/MAPK and PI3K/PTEN/Akt/mTOR (Chen et al., 2020). The EGFR signaling pathway regulate a series of important events including proliferation, migration, differentiation, apoptosis, as well as those that regulate intercellular communication during development (Wee et al., 2017; Huang et al., 2015; Yewale et al., 2013).

Approximately 10% to 50% of NSCLC patients have EGFR activating mutations, such as in-frame deletions in exon 19 deletion (Del19) or a missense mutation in exon 21 (L858R). (Yang et al., 2018; Shigematsu et al., 2005; Shu et al., 2017; Zhang et al., 2010). These patients respond well to first and second-generation EGFR tyrosine kinase inhibitors (TKI), including gefitinib (IRESSA™), erlotinib (TARCEVA™), and afatinib (GIOTRIF™) allowing them as the initial therapy for in patients with advanced NSCLC harboring common EGFR mutations (Kashima et al., 2020; Mok et al., 2009; Zhou et al., 2011; Sequist et al., 2013). But ultimately acquired resistance to therapy with gefitinib or erlotinib arises predominantly by mutation of the gatekeeper residue T790M, which is detected in approximately half of clinically resistant patients, resulting in double mutants, L858R/T790M and Del19/T790M.

Several third-generation EGFR TKIs were being explored to overcome this resistance. Currently, osimertinib is the third-generation EGFR-TKI approved by major regulatory agencies for treatment of T790M-positive patients who have progressed on first- or second generation EGFR-TKIs (Leonetti et al., 2019; Soria et al., 2018).

Osimertinib is a powerful inhibitor that inhibits EGFR mutations and T790M resistant mutations, but it causes ineffective binding and C797S subsequent resistance in NSCLC patients (Arulananda et al., 2017). Unfortunately, it has been reported that acquired resistance mutations occur in lung cancer patients after the treatment with third-generation EGFR-TKIs. The C797S mutation is the frequently arise after the use of third generation EGFR TKIs in 10% to 30% of these patients. (Ramalingam et al., 2018; Thress et al., 2015; Oxnard et al., 2018; Starrett et al., 2020; Mehlman et al., 2019; Rangachari et al., 2019; Zhou et al., 2019). Osimertinib resistance resulting from EGFR triple mutations (Del19/T790M/C797S and L858R/T790M/C797S) has been reported, requiring the next generation EGFR-TKI to overcome the osimertinib resistant EGFR triple mutations (Kashima et al., 2020).

In front-line therapy with third generation TKI, C797S develops in the absence of T790M (Chen et al., 2020). Osimertinib was also approved in 2018 as first-line therapy for locally advanced or metastatic EGFR-mutated NSCLC, regardless of T790M mutation status (Leonetti et al., 2019). When osimertinib was administered as a front-line therapy, the frequency of the C797S mutation was 7%, making it the second most frequent mechanism, behind MET amplification, of drug resistance in this setting (Leonetti et al., 2019; Ramalingam et al., 2018).

When osimertinib was administered as a front-line therapy, the most common resistance mechanisms resulted to be the C797S mutation (7%) and MET amplification (15%). Other mechanisms included HER2 amplification, PIK3CA and RAS mutations (Ramalingam et al., 2018). Also, selectivity to wild-type (WT) EGFR is important for EGFR-TKIs, because WT EGFR inhibition causes adverse effects such as rashes and/or diarrhea, and these WT EGFR-derived toxicities cause dose-limiting effects (Kashima et al., 2020; Fakih et al., 2010; Takeda et al., 2015).

The next generation EGFR compounds would need to inhibit Del19/T790M/C797S, L858R/T790M/C797S, Del19/C797S and L858R/C797S and be highly selective versus WT EGFR to avoid adverse effects. Recently, mutant selective inhibitors, BI-4020 and BLU-945 were reported as potertial therapeutic strategies to overcome the EGFR Del19/T790M/C797S mutations (Engelhardt et al., 2019; Schalm et al., 2020).

However, there have been no reports of these compounds inhibiting Del19/C797S and L858R/C797S. Therefore, novel EGFR-TKIs potertly effective against EGFR triple/double mutations are urgently needed.

To address this unmet need, we are developing a next generation TKI targeting both C797S triple and double mutants. It is necessary to develop a novel selective (next generation) inhibitor for NSCLC patients with advanced or metastatic diseases carrying Del19/T790M/C797S, L858R/T790M/C797S, Del19/C797S and L858R/C797S mutation following second-line or upfront use of third-generation EGFR TKIs.

REFERENCES

Arulananda S, John T, Dobrovic A. et al. Combination Osimertinib and Gefitinib in C797S and T790M EGFR-Mutated Non-Small Cell Lung Cancer. Journal of Thoracic Oncology Vol. 12 No. 11: 1728-1732, 2017.

Chen J S, Riess J W. Advances in targeting acquired resistance mechanisms to epidermal growth factor receptor tyrosine kinase inhibitors. Justin A. Chen, Jonathan W. Riess. J Thorac Dis 2020; 12(5):2859-2876.

Engelhardt H, et al. Start Selective and Rigidify: The Discovery Path toward a Next Generation of EGFR Tyrosine Kinase Inhibitors. Cite This: J. Med. Chem. 2019, 62, 10272-10293.

Fakih M, Vincent M. Adverse events associated with anti-EGFR therapies for the treatment of metastatic colorectal cancer. Curr. Oncol. 2010; 17: S 18-30.

Huang L, Fu L. Mechanisms of resistance to EGFR tyrosine kinase inhibitors. Acta Pharm Sin B 2015; 5:390-401.

Kashima K, et al. CH7233163 Overcomes Osimertinib-Resistant EGFR-Del19/T790M/C797S Mutation. Mol Cancer Ther; 19(11) November 2020.

Leonetti A, et al. Resistance mechanisms to osimertinib in EGFR-mutated non-small cell lung cancer. British Journal of Cancer (2019) 121:725-737.

Mok T S, Wu Y L, Thongprasert S, Yang C H, Chu D T, Saijo N, et al. Gefitinib or carboplatin-paclitaxel in pulmonary adenocarcinoma. N Engl J Med 2009; 361: 947-57.

Mehlman C, Cadranel J, Rousseau-Bussac G, Lacave R, Pujals A, Girard N, et al. Resistance mechanisms to osimertinib in EGFR-mutated advanced non-smallcell lung cancer: A multicentric retrospective French study. Lung Cancer 2019; 137:149-56.

Oxnard G R, Hu Y, Mileham K F, Husain H, Costa D B, Tracy P, et al. Assessment of resistance mechanisms and clinical implications in patients with EGFR T790M-positive lung cancer and acquired resistance to osimertinib. JAMA Oncol. 2018; 4:1527-34.

Ramalingam S S, Yang J C, Lee C K, Kurata T, Kim D W, John T, et al. Osimertinib as first-line treatment of EGFR mutation-positive advanced non-small-cell lung cancer. J. Clin. Oncol. 2018; 36:841-9.

Rangachari D, To C, Shpilsky J E, VanderLaan P A, Kobayashi S S, Mushajiang M, et al. EGFR-mutated lung cancers resistant to osimertinib through EGFR C797S respond to first-generation reversible EGFR inhibitors but eventually acquire EGFR T790M/C797S in preclinical models and clinical samples. J. Thorac. Oncol. 2019; 14:1995-2002.

Schalm S, et al. BLU-945, a highly potent and selective 4th-generation EGFR TKI for the treatment of EGFR+/T790M/C797S resistant NSCLC. 2020, ESMO.

Sequist L V, Yang J C, Yamamoto N, O'Byrne K, Hirsh V, Mok T, et al. Phase III study of afatinib or cisplatin plus pemetrexed in patients with metastatic lung adenocarcinoma with EGFR mutations. J. Clin. Oncol. 2013; 31:3327-34.

Shigematsu H, Lin L, Takahashi T, Nomura M, Suzuki M, Wistuba I I, et al. Clinical and biological features associated with epidermal growth factor receptor gene mutations in lung cancers. J Natl Cancer Inst 2005; 97:339-46.

Shu Y, WuX, Tong X, WangX, Chang Z, MaoY, et al. Circulating tumor DNA mutation profiling by targeted next generation sequencing provides guidance for personalized treatments in multiple cancer types. Sci Rep 2017; 7:583.

Soria, J.-C., Ohe, Y., Vansteenkiste, J., Reungwetwattana, T., Chewaskulyong, B., Lee, K. H. et al. Osimertinib in untreated EGFR-mutated advanced non-small cell lung cancer. N. Engl. J. Med 378, 113-125 (2018).

Starrett J H, Guernet A A, Cuomo M E, Poels K E, van Alderwerelt van Rosenburgh I K, Nagelberg A, et al. Drug sensitivity and allele-specificity of first-line osimertinib resistance EGFR mutations. Cancer Res 2020; 80:2017-30.

Takeda M, Okamoto I, Nakagawa K. Pooled safety analysis of EGFR-TKI treatment for EGFR mutation-positive non-small cell lung cancer. Lung Cancer 2015; 88:74-9.

Thress K S, Paweletz C P, Felip E, Cho B C, Stetson D, Dougherty B, et al. Acquired EGFR C797S mutation mediates resistance to AZD9291 in non-small cell lung cancer harboring EGFR T790M. Nat Med 2015; 21:560-2.

Wee, P.; Wang, Z. Epidermal Growth Factor Receptor Cell Proliferation Signaling Pathways. Cancers 2017, 9, 52.

Yewale C, Baradia D, Vhora I, et al. Epidermal growth factor receptor targeting in cancer: a review of trends and strategies. Biomaterials 2013; 34:8690-707.

Yang Z, Yang N, et al. Investigating Novel Resistance Mechanisms to Third-Generation EGFR Tyrosine Clin Cancer Res; 2018

Zhang Z, Stiegler A L, Boggon T J, Kobayashi S, Halmos B. EGFR-mutated lung cancer: a paradigm of molecular oncology. Oncotarget 2010; 1:497-514.

Zhou C, Wu Y L, Chen G, Feng J, Liu X Q, Wang C, et al. Erlotinib versus chemotherapy as first-line treatment for patients with advanced EGFR mutation-positive non-small-cell lung cancer (OPTIMAL, CTONG-0802): a multicentre, open-label, randomised, phase 3 study. Lancet Oncol. 2011; 12:735-42.

Zhou Z, Zhao Y, Shen S, Gu L, Niu X, Xu Y, et al. Durable clinical response of lung adenocarcinoma harboring EGFR 19Del/T790M/in trans-C797S to combination therapy of first- and third-generation EGFR tyrosine kinase inhibitors. J. Thorac. Oncol. 2019; 14:e157-e9.

SUMMARY OF INVENTION

The present invention relates to novel aminopyridine compounds of Formula (I) shown below, or a pharmaceutically acceptable salt thereof:

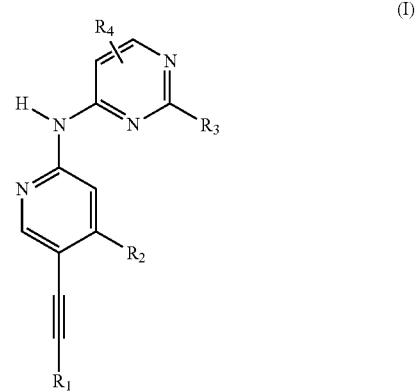

(I)

wherein $R_1$ is selected from the group consisting of

—H;

—Si($C_{1-6}$ alkyl)$_3$;

$C_{1-6}$ alkyl optionally or independently substituted by one or more substituents selected from the group consisting of OH, halogen, $C_{1-3}$alkoxy, $C_{3-6}$ cycloalkyl, —NH$C_{1-6}$alkyl, —NH$C_{1-6}$haloalkyl, —N($C_{1-6}$alkyl)$_2$, —N($C_{1-6}$haloalkyl)$_2$, —NHC(O)$C_{1-6}$alkyl, —NHC(O)$C_{1-6}$haloalkyl, —NHC(O)$C_{3-6}$ cycloalkyl, —NHC(O)-4-7 membered heterocyclyl, —C(O)-4-7 membered heterocyclyl, and 4-7 membered heterocyclyl optionally or independently substituted by one or more substituents selected from the group consisting of $C_{1-6}$alkyl, halogen, OH, and oxo;

$C_{2-5}$alkenyl;

—C(O)NH$C_{1-6}$alkyl;

—C(O)N($C_{1-6}$alkyl)$_2$;

—C(O)-4-7 membered heterocyclyl;

—NH$C_{1-6}$alkyl optionally or independently substituted by one or more substituents selected from the group consisting of OH; and halogen;

—N($C_{1-6}$alkyl)$_2$ optionally or independently substituted by one or more substituents selected from the group consisting of OH; and halogen; and -A-(R$_{1A}$)$_m$, A is selected from the group consisting of $C_{3-6}$ cycloalkyl; $C_{6-10}$ aryl; 4-8 membered heterocyclyl; and 5-10 membered heteroaryl, $R_{1A}$ is independently selected from the group consisting of H;
OH;
$NH_2$;
halogen;
$C_{1-6}$alkyl optionally substituted by one or more substituents selected from the group consisting of OH, halogen, $C_{3-6}$ cycloalkyl, —$NHC_{1-6}$alkyl, —$NHC_{3-6}$cycloalkyl, —$N(C_{1-6}alkyl)_2$,
—$C(O)N(C_{1-6}alkyl)_2$, —C(O)N-4-7 membered heterocyclyl, —$NHC(O)C_{1-6}$alkyl, 4-7 membered heterocyclyl optionally substituted by one or more substituents selected from the group consisting of halogen, $C_{1-6}$alkyl, $C_{1-6}$haloalkyl, $C_{1-6}$hydroxyalkyl, and —$C(O)C_{1-6}$ alkyl;
$C_{3-6}$cycloalkyl optionally substituted by one or more substituents selected from the group consisting of OH, halogen and —$N(C_{1-6}alkyl)_2$;
—$C(O)C_{1-6}$alkyl optionally substituted by one or more substituents selected from the group consisting of OH and halogen;
—$C(O)N(C_{1-6}alkyl)_2$;
—C(O)-4-7 membered heterocyclyl optionally substituted by one or more substituents selected from the group consisting of OH and halogen;
—$NHC_{1-6}$alkyl optionally substituted by 4-7 membered heterocyclyl;
—$N(C_{1-6}alkyl)_2$;
—$S(O)_2C_{1-6}$alkyl;
—$S(O)_2C_{3-6}$cycloalkyl;
oxo; and
4-11 membered heterocyclyl optionally or independently substituted by one or more substituents selected from the group consisting of halogen, $C_{1-6}$alkyl optionally substituted by —$N(C_{1-6}alkyl)_2$, $C_{3-6}$cycloalkyl, $C_{1-6}$haloalkyl, —$C(O)C_{1-6}$alkyl, and 4-7 membered heterocyclyl,
m is an integer of 0-2,
$R_2$ is selected from the group consisting of —$N(C_{1-6}$ alkyl)$_2$ optionally substituted by one or more OHs; —$XC_{1-6}$alkyl optionally substituted by OH, halogen, $C_{3-6}$cycloalkyl, $C_{1-3}$alkoxy, —$NHC_{1-6}$alkyl, or —$N(C_{1-6}alkyl)_2$; and —$X(CH2)_n$—B—$(R_{2A})_o$,
X is bond, —NH— or —O—,
n is an integer of 0-1,
o is an integer of 0-3,
B is selected from the group consisting of $C_{3-7}$cycloalkyl; $C_{6-10}$ aryl; 4-12 membered heterocyclyl; and 5-6 membered heteroaryl,
$R_{2A}$ is each independently selected from the group consisting of
H;
OH;
halogen;
$C_{1-6}$alkyl optionally or independently substituted by one or more substituents selected from the group consisting of OH, halogen, —$NHC_{1-6}$alkyl, —$NHC_{1-6}$haloalkyl, —$N(C_{1-6}alkyl)_2$, 4-7 membered heterocyclyl, and $C_{1-3}$alkoxy;
$C_{3-6}$cycloalkyl optionally or independently substituted by one or more substituents selected from the group consisting of OH, and halogen;
$C_{1-3}$alkoxy optionally or independently substituted by one or more halogens;
—$C(O)NHC_{1-6}$alkyl;
—$C(O)N(C_{1-6}alkyl)_2$; —$C(O)NHC_{3-6}$cycloalkyl;
—$NHC_{1-6}$alkyl optionally or independently substituted by one or more substituents
selected from the group consisting of OH, halogen, $C_{3-6}$cycloalkyl, $C_{1-3}$alkoxy, —$NHC_{1-6}$alkyl, —$N(C_{1-6}alkyl)_2$, and 4-7 membered heterocyclyl;
—$NHC_{3-6}$cycloalkyl optionally or independently substituted by one or more substituents selected from the group consisting of OH and halogen;
—$N(C_{1-6}alkyl)_2$ optionally or independently substituted by one or more substituents selected from the group consisting of OH and halogen; —$NHC(O)C_{1-6}$alkyl;
—$NHC(O)C_{3-6}$cycloalkyl;
—$NHS(O)_2C_{1-6}$alkyl;
—$S(O)_2C_{1-6}$alkyl;
4-7 membered heterocyclyl optionally or independently substituted by one or more substituents selected from the group consisting of halogen and $C_{1-6}$alkyl;
=O; and
$C(O)C_{1-6}$alkyl,
$R_3$ is Y-Q-$(R_{3A})_p$,
Y is —NH— or bond,
p is an integer of 0 to 2,
Q is selected from the group consisting of 4-7 membered heterocyclyl; $C_{6-10}$ aryl; and 5-6 membered heteroaryl,
$R_{3A}$ is independently selected from the group consisting of H; halogen; $C_{1-6}$alkyl optionally substituted by one or more substituents selected from the group consisting of halogen and $C_{3-6}$cycloalkyl; $C_{3-6}$cycloalkyl; 4-7 membered heterocyclyl; —$S(O)_2C_{1-6}$alkyl optionally substituted by one to three halogens; —$S(O)_2C_{3-6}$cycloalkyl optionally substituted by one or more halogens; and —$S(O)_2N(C_{1-6}alkyl)$, and
$R_4$ is selected from the group consisting of H, halogen and $C_{1-6}$alkyl.

The present invention also relates to methods of treating protein kinase-mediated disease, particularly mutant EGFR-mediated disease in a subject in need thereof comprising administering to said subject a therapeutically effective amount of said compounds of Formula (I) or a pharmaceutically acceptable salt thereof.

The present invention also relates to pharmaceutically acceptable compositions comprising said compounds of Formula (I) or a pharmaceutically acceptable salt thereof, which exhibit inhibition activity against at least one mutant EGFR selectively as compared to wild type EGFR.

DETAILED DESCRIPTION OF THE INVENTION

Hereinafter, the present invention will be described in more detail.

Unless otherwise defined, all technical terms used herein have the same meaning as commonly understood by one of ordinary skill in the art to which this invention belongs. Also, although the invention has been described in conjunction with specific methods and samples, their analogs or equivalents should be within the scope of the present invention. Furthermore, the numerical values set forth herein are considered to include the meaning of "about" unless explicitly stated. All publications and other references mentioned herein are hereby incorporated by reference in their entirety.

The definition of residues used herein is described in detail. Unless otherwise indicated, each residue has the following definition and is used in the sense as commonly understood by one of ordinary skill in the art.

As used herein, the term "halo" "halogen", "halide (s)" includes fluoro, chloro, bromo and iodo.

As used herein, the "alkyl" refers to an aliphatic hydrocarbon radical, and includes both linear and branched hydrocarbon radicals. For example, $C_{1-6}$ alkyl is an aliphatic hydrocarbon having 1 to 6 carbon atoms and includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. Unless otherwise defined, the alkyl refers to $C_{1-6}$ alkyl, preferably $C_{1-4}$ alkyl, more preferably $C_{1-3}$ alkyl.

As used herein, the "alkenyl" refers to an aliphatic hydrocarbon radical comprising at least one carbon-carbon double bond, and includes both linear and branched hydrocarbon radicals. The unlimited example of the "alkenyl" is vinyl, allyl, but-1-enyl or but-2-enyl.

As used herein, the "alkynyl" refers to an aliphatic hydrocarbon radical comprising at least one carbon-carbon triple bond, and includes both linear and branched hydrocarbon radicals. The unlimited example of the "alkynyl" is ethynyl, propargyl, but-1-ynyl or but-2-ynyl.

As used herein, the "haloalkyl" refers to an alkyl group substituted with one or more halogen atom, and the alkyl group is defined as above. The "halo" refers to F, Cl, Br, or I, and the term is compatibly used with the term "halogen". Unless otherwise defined, the haloalkyl refers to fluoromethyl, difluoromethyl, chloromethyl, trifluoromethyl or 2,2,2-trifluoroethyl.

As used herein, the term "alkoxy" refers to -O-alkyl or alkyl-O-group, and the alkyl group is defined as shown above. For example, it includes methoxy, ethoxy, n-propoxy, n-butoxy and t-butoxy.

As used herein, the term "hydroxy" or "hydroxyl" alone or in combination with other terms means —OH.

As used herein, the term "hydroxyalkyl" refers to any hydroxyl derivative of alkyl radical.

The term "hydroxyalkyl" includes any alkyl radical having one or more hydrogen atoms replaced by a hydroxy group.

As used herein, "amino" refers to —NH$_2$.

As used herein, the term "cycloalkyl" refers to a cyclic alkyl which may be substituted or unsubstituted, and for example, the $C_{3-20}$ cycloalkyl represents a monovalent saturated hydrocarbon ring system having 3 to 20 carbon atoms. Examples of the cycloalkyl include, but are not limited to, cyclopropyl, cyclobutyl, cyclopentyl, cyclohexyl, cycloheptyl, cyclooctyl and the like. Preferably, unless otherwise defined, the cycloalkyl may be $C_{3-8}$cycloalkyl, or $C_{3-6}$ cycloalkyl.

As used herein, the term "aryl" refers to a monovalent aromatic hydrocarbon having, for example, 6 to 20 carbon atoms ($C_{6-20}$) that is derived by the removal of one hydrogen atom from a single carbon atom of a parent aromatic ring system. The aryl may include a bicyclic radical containing an aromatic ring fused to a saturated or partially unsaturated ring. Exemplary aryl groups may include radicals derived from benzene (phenyl), substituted phenyl, biphenyl, naphthyl, toluyl, naphthalenyl, anthracenyl, indenyl, indanyl, and the like. Unless otherwise defined, the aryl refers to $C_{6-12}$ aryl, preferably $C_{6-10}$ aryl.

As used herein, the "heterocycle" refers to an aromatic, saturated or partially unsaturated mono-, bi- or poly-ring system containing the specified number of ring atoms, and include one or more heteroatoms selected from N, O, and S as a ring member, wherein the heterocyclic ring is connected to the base molecule via a ring atom, which may be C or N. Bicyclic systems may be connected via a 1,1-fusion (spiro), a 1,2-fusion (fused) or a 1,>2-fusion (bridgehead).

As used herein, the "heteroaryl" refers to a monovalent or divalent substituent derived from a monoheterocyclic or polyheterocyclic aromatic hydrocarbon having 1 to 10 carbon ring members containing one or more, preferably one to three, heteroatoms selected among N, O, and S. Examples of the heteroaryl include, but are not limited to, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazoly, 1,1,3,4-oxadiazolyl, 1,2,4-thiadiazolyl, 1,3,4-thiadiazolyl, triazolyl, tetrazolyl, triazinyl, indolyl, and the like. Examples of the bicyclic heteroaryl include indolyl, benzothiophenyl, benzofuranyl, benzimidazolyl, benzoxazolyl, benzisoxazolyl, benzthiazolyl, benzthiadiazolyl, quinolinyl, isoquinolinyl, furopyridinyl and similar groups thereof, but are not limited thereto. Unless otherwise defined, the heteroaryl is 4-12 membered heteroaryl 1, preferably 4-10 membered heteroaryl, more preferably 4-7 heteroaryl.

As used herein, the "heterocycloalkyl" refers to monocyclic, bicyclic, tricyclic or higher cyclic alkyl having 3 to 10 carbon ring members containing one or more, for example, one to four, heteroatoms selected among N, O, and S. In addition, the heterocycle according to the present invention may also be a fused or bridged heterocycloalkyl. Examples of non-aromatic rings include azetidinyl, oxetanyl, tetrahydrothienyl, tetrahydrofuranyl, pyrrolinyl, pyrrolidinyl, imidazolinyl, imidazolidinyl, oxazolinyl, oxazolidinyl, oxapiperazinyl, oxapiperidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyranyl, dihydropyranyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, teterahydropyrazolopyridinyl, morpholinyl, indolinyl, thiomorpholinyl, azepanyl, diazepanyl, azaadamantanyl, diazamantanyl, and the like, but are not limited thereto. Attachment of a heterocycloalkyl substituent can occur via a carbon atom or a heteroatom. A heterocycloalkyl group may be optionally substituted with one or more suitable groups via one or more aforementioned groups. Unless otherwise defined, heterocycloalkyl refers to 4-12 membered heterocycloalkyl, preferably 4-10 membered heterocycloalkyl, more preferably 4-7 heterocycloalkyl.

The present invention provides novel compounds, a pharmaceutically acceptable salt, diastereomers, enantiomers, racemates, tautomers, prodrugs, hydrates, and solvates thereof that are useful for inhibiting epidermal growth factor receptor (EGFR) and for treating diseases and disorders that are mediated by the protein kinase, for example, cell proliferative diseases and disorders such as cancer, immune diseases such as arthritis, rheumatoid arthritis or autoimmune diseases, infections, cardiovascular diseases, and neurodegenerative diseases and disorders.

The present invention also provides pharmaceutical compositions comprising at least one of the compounds of Formula (I) together with a pharmaceutically acceptable carrier, diluent or excipient therefor.

The present invention provides compositions and methods for modulating the activity of the epidermal growth factor receptor (EGFR) mutants. In one aspect, the present invention provides compounds which act as inhibitors of EGFR mutants.

In one embodiment, provided herein is a compound of Formula (I) shown below, a pharmaceutically acceptable salt, diastereomers, enantiomers, racemates, tautomers, prodrugs, hydrates, or solvates thereof:

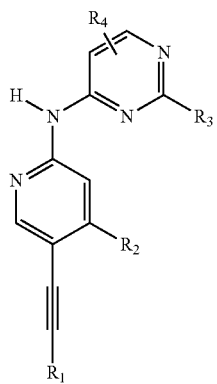

(I)

wherein
R₁ is selected from the group consisting of
—H;
—Si(C₁₋₆ alkyl)₃;
C₁₋₆ alkyl optionally or independently substituted by one or more substituents selected from the group consisting of OH, halogen, C₁₋₃alkoxy, C₃₋₆ cycloalkyl, —NHC₁₋₆alkyl, —NHC₁₋₆haloalkyl, —N(C₁₋₆alkyl)₂, —N(C₁₋₆haloalkyl)₂, —NHC(O)C₁₋₆alkyl, —NHC(O)C₁₋₆haloalkyl, —NHC(O)C₃₋₆ cycloalkyl, —NHC(O)-4-7 membered heterocyclyl, —C(O)-4-7 membered heterocyclyl, and 4-7 membered heterocyclyl optionally or independently substituted by one or more substituents selected from the group consisting of C₁₋₆alkyl, halogen, OH, and oxo;
C₂₋₅alkenyl;
—C(O)NHC₁₋₆alkyl;
—C(O)N(C₁₋₆alkyl)₂;
—C(O)-4-7 membered heterocyclyl;
—NHC₁₋₆alkyl optionally or independently substituted by one or more substituents selected from the group consisting of OH; and halogen;
—N(C₁₋₆alkyl)₂ optionally or independently substituted by one or more substituents selected from the group consisting of OH; and halogen; and
-A-(R₁ₐ)ₘ,
A is selected from the group consisting of C₃₋₆ cycloalkyl; C₆₋₁₀ aryl; 4-8 membered heterocyclyl; and 5-10 membered heteroaryl,
R₁ₐ is independently selected from the group consisting of
H;
OH;
NH₂;
halogen;
C₁₋₆alkyl optionally substituted by one or more substituents selected from the group consisting of OH, halogen, C₃₋₆ cycloalkyl, —NHC₁₋₆alkyl, —NHC₃₋₆cycloalkyl, —N(C₁₋₆alkyl)₂, —C(O)N(C₁₋₆alkyl)₂, —C(O)N-4-7 membered heterocyclyl, —NHC(O)C₁₋₆alkyl, 4-7 membered heterocyclyl optionally substituted by one or more substituents selected from the group consisting of halogen, C₁₋₆alkyl, C₁₋₆haloalkyl, C₁₋₆hydroxyalkyl, and —C(O)C₁₋₆alkyl;
C₃₋₆cycloalkyl optionally substituted by one or more substituents selected from the group consisting of OH, halogen and —N(C₁₋₆alkyl)₂;
—C(O)C₁₋₆alkyl optionally substituted by one or more substituents selected from the group consisting of OH and halogen;
—C(O)N(C₁₋₆alkyl)₂;
—C(O)-4-7 membered heterocyclyl optionally substituted by one or more substituents selected from the group consisting of OH and halogen;
—NHC₁₋₆alkyl optionally substituted by 4-7 membered heterocyclyl;
—N(C₁₋₆alkyl)₂;
—S(O)₂C₁₋₆alkyl;
—S(O)₂C₃₋₆cycloalkyl;
oxo; and
4-11 membered heterocyclyl optionally or independently substituted by one or more substituents selected from the group consisting of halogen, C₁₋₆alkyl optionally substituted by —N(C₁₋₆alkyl)₂, C₃₋₆cycloalkyl, C₁₋₆haloalkyl, —C(O)C₁₋₆alkyl, and 4-7 membered heterocyclyl,
m is an integer of 0-2,
R₂ is selected from the group consisting of —N(C₁₋₆ alkyl)₂ optionally substituted by one or more OHs; —XC₁₋₆alkyl optionally substituted by OH, halogen, C₃₋₆cycloalkyl, C₁₋₃alkoxy, —NHC₁₋₆alkyl, or —N(C₁₋₆alkyl)₂; and —X(CH₂)ₙ—B—(R₂ₐ)ₒ,
X is bond, —NH— or —O—,
n is an integer of 0-1,
o is an integer of 0-3,
B is selected from the group consisting of C₃₋₇cycloalkyl; C₆₋₁₀ aryl; 4-12 membered heterocyclyl; and 5-6 membered heteroaryl,
R₂ₐ is each independently selected from the group consisting of
H;
OH;
halogen;
C₁₋₆alkyl optionally or independently substituted by one or more substituents selected from the group consisting of OH, halogen, —NHC₁₋₆alkyl, —NHC₁₋₆haloalkyl, —N(C₁₋₆alkyl)₂, 4-7 membered heterocyclyl, and C₁₋₃alkoxy;
C₃₋₆cycloalkyl optionally or independently substituted by one or more substituents selected from the group consisting of OH, and halogen;
C₁₋₃alkoxy optionally or independently substituted by one or more halogens;
—C(O)NHC₁₋₆alkyl;
—C(O)N(C₁₋₆alkyl)₂; —C(O)NHC₃₋₆cycloalkyl;
—NHC₁₋₆alkyl optionally or independently substituted by one or more substituents selected from the group consisting of OH, halogen, C₃₋₆cycloalkyl, C₁₋₃alkoxy, —NHC₁₋₆alkyl, —N(C₁₋₆alkyl)₂, and 4-7 membered heterocyclyl;
—NHC₃₋₆cycloalkyl optionally or independently substituted by one or more substituents selected from the group consisting of OH and halogen;
—N(C₁₋₆alkyl)₂ optionally or independently substituted by one or more substituents selected from the group consisting of OH and halogen;
—NHC(O)C₁₋₆alkyl;
—NHC(O)C₃₋₆cycloalkyl;
—NHS(O)₂C₁₋₆alkyl;
—S(O)₂C₁₋₆alkyl;
4-7 membered heterocyclyl optionally or independently substituted by one or more substituents selected from the group consisting of halogen and C₁₋₆alkyl;
=O; and
C(O)C₁₋₆alkyl,
R₃ is Y-Q-(R₃ₐ)ₚ,
Y is —NH— or bond,
p is an integer of 0 to 2, Q is selected from the group consisting of 4-7 membered heterocyclyl; $C_{6-10}$ aryl; and 5-6 membered heteroaryl, $R_{3A}$ is independently selected from the group consisting of H; halogen; $C_{1-6}$alkyl optionally substituted by one or more substituents selected from the group consisting of halogen and $C_{3-6}$cycloalkyl; $C_{3-6}$cycloalkyl; 4-7 membered heterocyclyl; —S(O)$_2$C$_{1-6}$alkyl optionally substituted by one to three halogens; —S(O)$_2$C$_{3-6}$cycloalkyl optionally substituted by one or more halogens; and —S(O)$_2$N(C$_{1-6}$alkyl), and $R_4$ is selected from the group consisting of H, halogen and $C_{1-6}$alkyl.

In certain embodiment, $R_1$ is selected from the group consisting of H; Si(C$_{1-3}$alkyl)$_3$; $C_{1-4}$alkyl optionally or independently substituted by one to three substituents selected from the group consisting of OH, F, Cl, $C_{1-3}$alkoxy, —NHC$_{1-4}$alkyl, —NHC$_{1-4}$haloalkyl, —N(C$_{1-4}$alkyl)$_2$, —N(C$_{1-4}$haloalkyl)$_2$, —NHC(O)C$_{1-4}$alkyl, —NHC(O)C$_{3-6}$cycloalkyl, —NHC(O)-4-6 membered heterocyclyl, —C(O)-4-6 membered heterocyclyl having one to three heteroatoms selected from a group consisting of N, O and S, 4-6 membered heterocyclyl having one to three heteroatoms selected from a group consisting of N, O and S, optionally or independently substituted by one to three substituents selected from the group consisting of $C_{1-4}$alkyl, F, Cl, OH, and oxo; $C_{2-5}$alkenyl; —C(O)NHC$_{1-6}$alkyl; —C(O)N(C$_{1-4}$alkyl)$_2$; —C(O)-4-6 membered heterocyclyl having one to three heteroatoms selected from a group consisting of N, O and S; —NHC$_{1-4}$alkyl optionally or independently substituted by one to three substituents selected from the group consisting of OH; F; Cl; —N(C$_{1-4}$alkyl)$_2$ optionally or independently substituted by one to three substituents selected from the group consisting of OH, F and Cl; and A-(R$_{1A}$)$_m$.

In further certain embodiment, $R_1$ is selected from the group consisting of —H; —Si(C$_{1-6}$alkyl)$_3$; $C_{1-6}$alkyl optionally or independently substituted by one or more substituents selected from the group consisting of OH, halogen, $C_{1-3}$alkoxy, —NHC(O)C$_{1-6}$haloalkyl, —NHC(O)-4-7 membered heterocyclyl, —C(O)-4-7 membered heterocyclyl, and 4-7 membered heterocyclyl optionally or independently substituted by oxo; $C_{2-5}$alkenyl; and -A-(R$_{1A}$)$_n$.

In the above embodiments of $R_1$, the 4-7 membered heterocyclyl may be selected from the group consisting of morpholinyl, pyrrolidinyl, 1,1-dioxo-1,4-thiazinanyl, and oxetanyl.

In certain embodiment, A is selected from the group consisting of $C_{3-6}$cycloalkyl; phenyl; 4-7 membered heterocycloalkyl; 5-6 membered heteroaryl; and 9-10 membered heteroaryl.

In further certain embodiment, A is selected from the group consisting of $C_{3-6}$cycloalkyl; phenyl; pyrazolyl; pyridinyl; 4,5,6,7-tetrahydropyrazolo[1,5-a]pyrazinyl; triazolyl; thiazolyl; pyrazinyl; tetrahydropyranyl, pyrrolidinyl, piperidinyl, thienyl, pyrimidinyl, tetrahydrofuranyl, imidazolyl, pyrrolyl, pyrrolo[3,2-c]pyridinyl, oxetanyl, 7-oxabicyclo[2.2.1]heptanyl, and 1,1-dioxo-thiolanyl.

In certain embodiment, $R_{1A}$ is selected from the group consisting of H; OH; NH$_2$; F; Cl; $C_{1-4}$alkyl optionally substituted by one to three substituents selected from the group consisting of OH, F, Cl, $C_{3-6}$cycloalkyl, —NHC$_{1-4}$alkyl, —NHC$_{3-4}$cycloalkyl, —N(C$_{1-4}$alkyl)$_2$, —C(O)N(C$_{1-4}$alkyl)$_2$, —C(O)N-4-7 membered heterocyclyl having one to three heteroatoms selected from a group consisting of N, O and S, —NHC(O)C$_{1-4}$alkyl, 4-7 membered heterocyclyl having one to three heteroatoms selected from a group consisting of N, O and S, optionally substituted by one to three substituents selected from the group consisting of F, Cl, $C_{1-4}$alkyl, $C_{1-4}$haloalkyl, $C_{1-4}$hydroxyalkyl, and —C(O) $C_{1-4}$alkyl; $C_{3-6}$cycloalkyl optionally substituted by one to three substituents selected from the group consisting of OH, F, Cl and —N(C$_{1-4}$alkyl)$_2$; —C(O)C$_{1-6}$alkyl optionally substituted by one to three substituents selected from the group consisting of OH, F and Cl; —C(O)N(C$_{1-4}$alkyl)$_2$; —C(O)-4-7 membered heterocyclyl having one to three heteroatoms selected from a group consisting of N, O and S, optionally substituted by one to three OHs; —NHC$_{1-6}$alkyl optionally substituted by 4-7 membered heterocyclyl having one to three heteroatoms selected from a group consisting of N, O and S; —N(C$_{1-6}$alkyl)$_2$; —S(O)$_2$Calkyl; —S(O)$_2$C$_{3-6}$cycloalkyl; and 4-11 membered heterocyclyl optionally or independently substituted by one to three substituents selected from the group consisting of F, Cl, $C_{1-4}$alkyl optionally substituted by —N(C$_{1-4}$alkyl)$_2$, $C_{3-6}$cycloalkyl, $C_{1-4}$haloalkyl, —C(O)C$_{1-4}$alkyl, and 4-7 membered heterocyclyl having one to three heteroatoms selected from a group consisting of N, O and S.

In further certain embodiment, $R_{1A}$ is selected from the group consisting of $C_{1-6}$alkyl optionally substituted by one or more substituents selected from the group consisting of OH, halogen, $C_{3-6}$cycloalkyl, —NHC$_{1-6}$alkyl, —NHC$_{3-6}$cycloalkyl, —N(C$_{1-6}$alkyl)$_2$, —C(O)N(C$_{1-6}$alkyl)$_2$,
—C(O)N-4-7 membered heterocyclyl, —NHC(O)C$_{1-6}$alkyl, 4-7 membered heterocyclyl optionally substituted by one or more substituents selected from the group consisting of halogen, $C_{1-6}$alkyl, $C_{1-6}$haloalkyl, $C_{1-6}$hydroxyalkyl, and —C(O)C$_{1-6}$alkyl; $C_{3-6}$cycloalkyl optionally substituted by one or more substituents selected from the group consisting of OH, halogen and —N(C$_{1-6}$alkyl)$_2$; and 4-7 membered heterocyclyl optionally or independently substituted by one or more substituents selected from the group consisting of halogen, $C_{1-6}$alkyl optionally substituted by —N(C$_{1-6}$alkyl)$_2$, $C_{3-6}$cycloalkyl, $C_{1-4}$haloalkyl, —C(O)C$_{1-6}$alkyl, and 4-7 membered heterocyclyl.

In another further certain embodiment, Rip is selected from the group consisting of

H;

OH;

NH$_2$;

halogen;

$C_{1-6}$alkyl optionally substituted by one or more substituents selected from the group consisting of OH, halogen, $C_{3-6}$cycloalkyl, —N(C$_{1-6}$alkyl)$_2$, —C(O)N(C$_{1-6}$alkyl)$_2$, 4-7 membered heterocyclyl optionally substituted by one or more substituents selected from the group consisting of halogen, and $C_{1-6}$alkyl;

$C_{3-6}$cycloalkyl optionally substituted by one or more halogens;

—C(O)C$_{1-6}$alkyl optionally substituted by one or more halogens;

—C(O)N(C$_{1-6}$alkyl)$_2$;

—C(O)-4-7 membered heterocyclyl optionally substituted by one or more Otis; —NHC$_{1-6}$alkyl optionally substituted by 4-7 membered heterocyclyl;

—S(O)$_2$C$_{1-6}$alkyl;

—S(O)$_2$C$_{3-6}$cycloalkyl; and 4-11 membered heterocyclyl optionally or independently substituted by one or more substituents selected from the group consisting of $C_{1-6}$alkyl and —C(O)C$_{1-6}$alkyl.

In the above embodiments of $R_{1A}$, the 4-7 membered heterocyclyl or 4-11 membered_heterocyclyl may be selected from the group consisting of tetrahydropyranyl, piperidinyl, azetidinyl, morpholinyl, piperazinyl, dioxanyl, tetrahydropuranyl, and oxetanyl.

In certain embodiment, $R_2$ is selected from the group consisting of —N($C_{1-6}$alkyl)$_2$ optionally or independently substituted by one to three OHs; —X$C_{1-4}$alkyl optionally substituted by OH, F, Cl, $C_{3-6}$cycloalkyl, $C_{1-3}$alkoxy, —NH$C_{1-4}$alkyl, or —N($C_{1-4}$alkyl)$_2$; and X(CH$_2$)$_n$—B—(R$_{2A}$)$_o$ wherein X is bond, —NH— or —O—; n is an integer of 0-1; o is an integer of 0-3.

In further certain embodiment, $R_2$ is selected from the group consisting of —N(C1-6alkyl)$_2$ optionally substituted by one or more OHs; —X$C_{1-6}$alkyl optionally substituted by OH; and —X(CH$_2$)$_n$—B—(R$_{2A}$)$_o$.

In certain embodiment, B is selected from the group consisting of $C_{3-6}$cycloalkyl; phenyl; 4-11 membered heterocycloalkyl having one to three heteroatoms selected from a group consisting of N, O and S; and 5-6 membered heteroaryl having one to three heteroatoms selected from a group consisting of N, O and S.

In further certain embodiment, B is selected from the group consisting of $C_{3-6}$cycloalkyl; phenyl; piperazinyl, piperidinyl, 4-oxopiperidinyl, azaspiro[3.5]nonanyl, pyrrolidinyl, azetidinyl, azepanyl, 2,8-diazaspiro[4.5]decan-onyl, 2,8-diazaspiro[4.5]decanyl, 2,7-diazaspiro[3.5]nonanyl, pyrzaolyl, 1-oxa-8-azaspiro[4.5]decanyl, 1-oxa-7-azaspiro[3.5]nonanyl, 3,9-diazaspiro[5.5]undecanyl, 3-azabicyclo[3.1.0]hexanyl, 8-azabicyclo[3.2.1]octanyl, and 1-azaspiro[4.5]decanonyl.

In certain embodiment, $R_{2A}$ is each independently selected from the group consisting of H; OH; F; Cl; $C_{1-6}$alkyl optionally or independently substituted by one to three substituents selected from the group consisting of OH, F, Cl, —NH$C_{1-4}$alkyl, —NH$C_{1-4}$haloalkyl, —N($C_{1-4}$alkyl)$_2$, and $C_{1-3}$alkoxy; $C_{3-6}$cycloalkyl optionally substituted by one to three OHs; $C_{1-3}$alkoxy optionally or independently substituted by one to three substituents selected from the group consisting of F and Cl; —C(O)NH$C_{1-4}$alkyl; —C(O)NH$C_{3-6}$cycloalkyl; —NH$C_{1-4}$alkyl optionally or independently substituted by one or more substituents selected from the group consisting of OH, F, Cl, $C_{3-6}$cycloalkyl, $C_{1-3}$alkoxy, —NH$C_{1-4}$alkyl, —N($C_{1-4}$alkyl)$_2$, and 4-7 membered heterocyclyl having one to three heteroatoms selected from a group consisting of N, O and S; —NH$C_{3-6}$cycloalkyl optionally or independently substituted by one to three substituents selected from the group consisting of OH, F and Cl; —N($C_{1-4}$ alkyl)$_2$ optionally or independently substituted by one to three substituents selected from the group consisting of OH, F and Cl; —NHC(O)$C_{1-4}$alkyl; —NHC(O)$C_{3-6}$cycloalkyl; —NHS(O)$_2$C$_{1-4}$alkyl; —S(O)$_2$C$_{1-4}$alkyl; 4-7 membered heterocyclyl having one to three heteroatoms selected from a group consisting of N, O and S, optionally or independently substituted by one to three substituents selected from the group consisting of F, Cl and $C_{1-6}$alkyl; —C(O)$C_{1-6}$alkyl; and =O.

In further certain embodiment, $R_{2A}$ is each independently selected from the group consisting of OH; halogen; $C_{1-6}$alkyl optionally or independently substituted by one or more substituents selected from the group consisting of OH, halogen, —NH$C_{1-6}$alkyl, —NH$C_{1-6}$haloalkyl, —N($C_{1-6}$alkyl)$_2$, and $C_{1-3}$alkoxy; $C_{3-6}$cycloalkyl; —NH$C_{1-6}$alkyl optionally or independently substituted by one or more substituents selected from the group consisting of OH, halogen, $C_{3-6}$cycloalkyl, $C_{1-3}$alkoxy, —NH$C_{1-6}$alkyl, —N($C_{1-6}$alkyl)$_2$, and 4-7 membered heterocyclyl; —NH$C_{3-6}$ cycloalkyl optionally or independently substituted by one or more substituents selected from the group consisting of OH and halogen; and —N($C_{1-6}$alkyl)$_2$ optionally or independently substituted by one or more substituents selected from the group consisting of OH and halogen.

In another further certain embodiment, $R_{2A}$ is each independently selected from the group consisting of

H;

OH;

halogen;

$C_{1-6}$alkyl optionally or independently substituted by one or more substituents selected from the group consisting of OH, halogen, —NH$C_{1-6}$alkyl, —NH$C_{1-6}$haloalkyl, and —N($C_{1-6}$alkyl)$_2$;

$C_{3-6}$cycloalkyl optionally or independently substituted by one or more OHs;

$C_{1-3}$alkoxy optionally or independently substituted by one or more halogens;

—NH$C_{1-6}$alkyl optionally or independently substituted by one or more substituents selected from the group consisting of OH, halogen, $C_{3-6}$cycloalkyl, $C_{1-3}$alkoxy, and —N($C_{1-6}$alkyl)$_2$;

—NHS(O)$_2$C$_{1-6}$alkyl;

—S(O)$_2$C$_{1-6}$alkyl;

4-7 membered heterocyclyl optionally or independently substituted by one or more substituents selected from the group consisting of halogen and $C_{1-6}$alkyl;

=O; and

C(O)$C_{1-6}$alkyl.

In the above embodiments of $R_{2A}$, the 4-7 membered heterocyclyl may be piperazinyl or azetidinyl.

In certain embodiment, Q is selected from the group consisting of pyrazolyl, pyridinyl, phenyl, and piperzinyl.

In certain embodiment, $R_{3A}$ is selected from the group consisting of H; halogen; $C_{1-4}$alkyl optionally substituted by one to three substituents selected from the group consisting of F, $C_1$ and $C_{3-6}$cycloalkyl; $C_{3-6}$cycloalkyl; 4-7 membered heterocyclyl having one to three heteroatoms selected from a group consisting of N, O and S; —S(O)$_2$C$_{1-4}$alkyl; —S(O)$_2$ $C_{3-6}$cycloalkyl optionally substituted by one to three F and Cl; and —S(O)$_2$N($C_{1-4}$alkyl).

In further certain embodiment, $R_3$ is selected from the group consisting of halogen; $C_{1-6}$alkyl optionally substituted by one or more halogens; —S(O)$_2$C$_{1-6}$alkyl; —S(O)$_2$C$_{3-6}$cycloalkyl; and —S(O)$_2$N($C_{1-6}$alkyl).

In certain embodiment, $R_4$ is H.

Representative compounds of Formula (I) are listed below:

(1) 2-(1-(Cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine;

(2) N$^4$-Cyclohexyl-N$^2$-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine;

(3) 2-(1-(Cyclopropylsulfonyl)-1H-pyrazol-4-yl)-N-(4-(4-(ethylsulfonyl)piperazin-1-yl)-5-((1-methyl-1H-pyrazol-4-yl)ethynyl)pyridin-2-yl)pyrimidin-4-amine;

(4) (R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)butan-1-ol;

(5) (S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-2-methylbutan-2-ol;

(6) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol;

(7) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one;

(8) 2-(1-(Cyclopropylsulfonyl)-1H-pyrazol-4-yl)-N-(4-(4-fluoropiperidin-1-yl)-5-((1-methyl-1H-pyrazol-4-yl)ethynyl)pyridin-2-yl)pyrimidin-4-amine;

(9) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-yl)methanol;

(10) 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol;

(11) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)propan-2-ol;

(12) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol;

(13) 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol;

(14) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-2-methylpropan-1-ol;

(15) 2-(1-(Cyclopropylsulfonyl)-1H-pyrazol-4-yl)-N-(4-(4-methoxypiperidin-1-yl)-5-((1-methyl-1H-pyrazol-4-yl)ethynyl)pyridin-2-yl)pyrimidin-4-amine;

(16) 2-(4-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperazin-1-yl)ethan-1-ol;

(17) 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)ethan-1-ol;

(18) $N^2$-(2-(1-(Cyclopropylsulfonyl)-1H-pyrazol-4-yl)pyrimidin-4-yl)-$N^4$-isopropyl-5-((1-methyl-1H-pyrazol-4-yl)ethynyl)pyridine-2,4-diamine;

(19) $N^2$-(2-(1-(Cyclopropylsulfonyl)-1H-pyrazol-4-yl)pyrimidin-4-yl)-$N^4$-isopropyl-5-((l-isopropyl-1H-pyrazol-4-yl)ethynyl)pyridine-2,4-diamine;

(20) $N^2$-(2-(1-(Cyclopropylsulfonyl)-1H-pyrazol-4-yl)pyrimidin-4-yl)-5-((1-(2-fluoroethyl)-1H-pyrazol-4-yl)ethynyl)-$N^4$-isopropylpyridine-2,4-diamine;

(21) $N^2$-(2-(1-(Cyclopropylsulfonyl)-1H-pyrazol-4-yl)pyrimidin-4-yl)-$N^4$-isopropyl-5-(pyridin-3-ylethynyl)pyridine-2,4-diamine;

(22) $N^2$-(2-(1-(Cyclopropylsulfonyl)-1H-pyrazol-4-yl)pyrimidin-4-yl)-$N^4$-isopropyl-5-(4-methoxybut-1-yn-1-yl)pyridine-2,4-diamine;

(23) $N^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-$N^4$-isopropylpyridine-2,4-diamine;

(24) $N^4$-(sec-Butyl)-$N^2$-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine;

(25) $N^4$-(sec-Butyl)-$N^2$-(2-(1-(cyclopropylsulfonyl)-1H-pyrazol-4-yl)pyrimidin-4-yl)-5-((1-isopropyl-1H-pyrazol-4-yl)ethynyl)pyridine-2,4-diamine;

(26) $N^4$-(sec-Butyl)-$N^2$-(2-(1-(cyclopropylsulfonyl)-1H-pyrazol-4-yl)pyrimidin-4-yl)-5-((1-(2-fluoroethyl)-1H-pyrazol-4-yl)ethynyl)pyridine-2,4-diamine;

(27) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol;

(28) 1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-ol;

(29) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanol;

(30) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol;

(31) (R)-1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-ol;

(32) (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-ol;

(33) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-yl)methanol;

(34) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-yl)methanol;

(35) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol;

(36) 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)azetidin-3-yl)propan-2-ol;

(37) 2-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)(methyl)amino)ethan-1-ol;

(38) 2-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)(methyl)amino)ethan-1-ol;

(39) 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)-2,2-dimethyl-propan-1-ol;

(40) 3-((2-((2-(1-Cyclopropylsulfonylpyrazol-4-yl)pyrimidin-4-yl)amino)-5-(2-(1-(2-fluoroethyl)pyrazol-4-yl)ethynyl)-4-pyridyl)amino)-2,2-dimethyl-propan-1-ol;

(41) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(42) (1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(43) (1 S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(44) (1 S,3S)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(45) (1 S,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(46) (1S,3R)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(47) (1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(48) (1-(5-((1-(Cyclopropylmethyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(49) (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol;

(50) N²-(2-(1-(Cyclopropylsulfonyl)-1H-pyrazol-4-yl)pyrimidin-4-yl)-N⁴-(4-((dimethylamino)methyl)benzyl)-5-((1-methyl-1H-pyrazol-4-yl)ethynyl)pyridine-2,4-diamine;

(51) N²-(2-(1-(Cyclopropylsulfonyl)-1H-pyrazol-4-yl)pyrimidin-4-yl)-N⁴-(4-((dimethylamino)methyl)benzyl)-5-((1-(2-fluoroethyl)-1H-pyrazol-4-yl)ethynyl)pyridine-2,4-diamine;

(52) N²-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N⁴-(4-((dimethylamino)methyl)benzyl)pyridine-2,4-diamine;

(53) N²-(2-(1-(Cyclopropylsulfonyl)-1H-pyrazol-4-yl)pyrimidin-4-yl)-N⁴-(((1r,4r)-4-((dimethylamino)methyl)cyclohexyl)methyl)-5-((1-methyl-1H-pyrazol-4-yl)ethynyl)pyridine-2,4-diamine;

(54) 2-(1-(Cyclopropylsulfonyl)-1H-pyrazol-4-yl)-N-(4-isopropoxy-5-((1-methyl-1H-pyrazol-4-yl)ethynyl)pyridin-2-yl)pyrimidin-4-amine;

(55) 2-(1-(Cyclopropylsulfonyl)-1H-pyrazol-4-yl)-N-(5-((1-(2-fluoroethyl)-1H-pyrazol-4-yl)ethynyl)-4-isopropoxypyridin-2-yl)pyrimidin-4-amine;

(56) N-(4-(sec-Butoxy)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(57) N-(4-(sec-Butoxy)-5-((1-isopropyl-1H-pyrazol-4-yl)ethynyl)pyridin-2-yl)-2-(1-(cyclopropylsulfonyl)-1H-pyrazol-4-yl)pyrimidin-4-amine;

(58) 2-(1-(Cyclopropylsulfonyl)-1H-pyrazol-4-yl)-N-(4-(((1r,4r)-4-((dimethylamino)methyl)cyclohexyl)methoxy)-5-((1-methyl-1H-pyrazol-4-yl)ethynyl)pyridin-2-yl)pyrimidin-4-amine;

(59) 2-(1-(Cyclopropylsulfonyl)-1H-pyrazol-4-yl)-N-(4-(((1r,4r)-4-((dimethylamino)methyl)cyclohexyl)methoxy)-5-((1-isopropyl-1H-pyrazol-4-yl)ethynyl)pyridin-2-yl)pyrimidin-4-amine;

(60) N-(5-((1-Cyclopropyl-1H-pyrazol-4-yl)ethynyl)-4-(((1r,4r)-4-((dimethylamino)methyl)cyclohexyl)methoxy)pyridin-2-yl)-2-(1-(cyclopropylsulfonyl)-1H-pyrazol-4-yl)pyrimidin-4-amine;

(61) 2-(1-(Cyclopropylsulfonyl)-1H-pyrazol-4-yl)-N-(4-(((1r,4r)-4-((dimethylamino)methyl)cyclohexyl)methoxy)-5-((1-(2-fluoroethyl)-1H-pyrazol-4-yl)ethynyl)pyridin-2-yl)pyrimidin-4-amine;

(62) 2-(1-(Cyclopropylsulfonyl)-1H-pyrazol-4-yl)-N-(4-(((1r,4r)-4-((dimethylamino)methyl)cyclohexyl)methoxy)-5-(pyridin-3-ylethynyl)pyridin-2-yl)pyrimidin-4-amine;

(63) N-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanesulfonamide;

(64) 2-(1-(Cyclopropylsulfonyl)-1H-pyrazol-4-yl)-N-(4-(4-(isopropylamino)piperidin-1-yl)-5-((1-methyl-1H-pyrazol-4-yl)ethynyl)pyridin-2-yl)pyrimidin-4-amine;

(65) 2-(1-(Cyclopropylsulfonyl)-1H-pyrazol-4-yl)-N-(5-((1-methyl-1H-pyrazol-4-yl)ethynyl)-4-(4-(trifluoromethyl)piperidin-1-yl)pyridin-2-yl)pyrimidin-4-amine;

(66) 2-(1-(Cyclopropylsulfonyl)-1H-pyrazol-4-yl)-N-(4-(4-fluoro-4-(trifluoromethyl)piperidin-1-yl)-5-((1-methyl-1H-pyrazol-4-yl)ethynyl)pyridin-2-yl)pyrimidin-4-amine;

(67) 2-(1-(Cyclopropylsulfonyl)-1H-pyrazol-4-yl)-N-(5-((1-methyl-1H-pyrazol-4-yl)ethynyl)-4-(4-(trifluoromethoxy)piperidin-1-yl)pyridin-2-yl)pyrimidin-4-amine;

(68) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-difluoropiperidin-4-ol;

(69) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-dimethylpiperidin-4-ol;

(70) 2-(1-(Cyclopropylsulfonyl)-1H-pyrazol-4-yl)-N-(4-(3-fluoropiperidin-1-yl)-5-((1-methyl-1H-pyrazol-4-yl)ethynyl)pyridin-2-yl)pyrimidin-4-amine;

(71) 2-(1-(Cyclopropylsulfonyl)-1H-pyrazol-4-yl)-N-(5-((1-methyl-1H-pyrazol-4-yl)ethynyl)-4-(3-(trifluoromethyl)piperidin-1-yl)pyridin-2-yl)pyrimidin-4-amine;

(72) 2-(1-(Cyclopropylsulfonyl)-1H-pyrazol-4-yl)-N-(4-(3-(fluoromethyl)piperidin-1-yl)-5-((1-methyl-1H-pyrazol-4-yl)ethynyl)pyridin-2-yl)pyrimidin-4-amine;

(73) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol;

(74) N²-(2-(1-(Cyclopropylsulfonyl)-1H-pyrazol-4-yl)pyrimidin-4-yl)-N⁴-(3-fluorocyclohexyl)-5-((1-methyl-1H-pyrazol-4-yl)ethynyl)pyridine-2,4-diamine;

(75) (1R,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(76) (1R,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(77) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-ol;

(78) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-yl)methanol;

(79) 8-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2,8-diazaspiro[4.5]decan-1-one;

(80) N²-(2-(1-(Cyclopropylsulfonyl)-1H-pyrazol-4-yl)pyrimidin-4-yl)-N⁴-(1s,4s)-4-((2-fluoroethyl)amino)cyclohexyl)-5-((1-methyl-1H-pyrazol-4-yl)ethynyl)pyridine-2,4-diamine;

(81) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-1-methylcyclohexan-1-ol;

(82) 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol;

(83) (1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)methanol;

(84) 2-(1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)ethan-1-ol;

(85) (1s, 4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol;

(86) 1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-ol;

(87) 2-(1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-yl)ethan-1-ol;

(88) (1s,4s)-4-((5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(89) 1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-ol;

(90) (1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)methanol;

(91) 2-(1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)ethan-1-ol;

(92) (1s,4s)-4-((2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)amino)cyclohexan-1-ol;

(93) 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one;

(94) (1s, 4s)-4-((2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)amino)cyclohexan-1-ol;

(95) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-methylpiperidin-4-yl)methanol;

(96) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-fluoropiperidin-4-yl)methanol;

(97) 2-(1-(Cyclopropylsulfonyl)-1H-pyrazol-4-yl)-N-(4-(4-fluoropiperidin-1-yl)-5-((1-(tetrahydro-2H-pyran-4-yl)-1H-pyrazol-4-yl)ethynyl)pyridin-2-yl)pyrimidin-4-amine;

(98) 2-(1-(Cyclopropylsulfonyl)-1H-pyrazol-4-yl)-N-(4-(4-methoxypiperidin-1-yl)-5-((1-(tetrahydro-2H-pyran-4-yl)-1H-pyrazol-4-yl)ethynyl)pyridin-2-yl)pyrimidin-4-amine;

(99) 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-ol;

(100) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-3-yl)methanol;

(101) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(102) (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol;

(103) (1 S,3S)-3-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol;

(104) 7-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-2-methyl-7-azaspiro[3.5]nonan-2-ol;

(105) (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)-1-methylcyclohexan-1-ol;

(106) (1s,4s)-4-((2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)amino)cyclohexan-1-ol;

(107) (1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)-4-methylpiperidin-4-yl)methanol;

(108) 1-(5-((1-(1-Acetylpiperidin-4-yl)-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-one;

(109) 1-(4-(4-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)-1H-pyrazol-1-yl)piperidin-1-yl)ethan-1-one;

(110) 1-(4-(4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-1H-pyrazol-1-yl)piperidin-1-yl)ethan-1-one;

(1H) 1-(4-(4-((6-((2-(1-(Cyclopropylsulfonyl)-1H-pyrazol-4-yl)pyrimidin-4-yl)amino)-4-(4-fluoro-4-(hydroxymethyl)piperidin-1-yl)pyridin-3-yl)ethynyl)-1H-pyrazol-1-yl)piperidin-1-yl)ethan-1-one;

(112) 1-(4-(4-((6-((2-(1-(Cyclopropylsulfonyl)-1H-pyrazol-4-yl)pyrimidin-4-yl)amino)-4-(4-fluoropiperidin-1-yl)pyridin-3-yl)ethynyl)-1H-pyrazol-1-yl)piperidin-1-yl)ethan-1-one;

(113) 1-(4-(4-((6-((2-(1-(Cyclopropylsulfonyl)-1H-pyrazol-4-yl)pyrimidin-4-yl)amino)-4-(4-methoxypiperidin-1-yl)pyridin-3-yl)ethynyl)-1H-pyrazol-1-yl)piperidin-1-yl)ethan-1-one;

(114) 1-(4-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)-1H-pyrazol-1-yl)piperidin-1-yl)ethan-1-one;

(115) 1-(4-(4-((6-((2-(1-(Cyclopropylsulfonyl)-1H-pyrazol-4-yl)pyrimidin-4-yl)amino)-4-(3-(hydroxymethyl)piperidin-1-yl)pyridin-3-yl)ethynyl)-1H-pyrazol-1-yl)piperidin-1-yl)ethan-1-one;

(116) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-methylpiperidin-4-yl)methanol;

(117) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-fluoropiperidin-4-yl)methanol;

(118) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)piperidin-3-yl)methanol;

(119) (1s,4s)-4-((2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)amino)cyclohexan-1-ol;

(120) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-methylpiperidin-4-yl)methanol;

(121) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-fluoropiperidin-4-yl)methanol;

(122) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)piperidin-3-yl)methanol;

(123) (1s,4s)-4-((2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)amino)cyclohexan-1-ol;

(124) N-(4-(4-((Cyclopropylmethyl)amino)piperidin-1-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(125) 2-(1-(Cyclopropylsulfonyl)-1H-pyrazol-4-yl)-N-(4-(4-(isopentylamino)piperidin-1-yl)-5-((1-methyl-1H-pyrazol-4-yl)ethynyl)pyridin-2-yl)pyrimidin-4-amine;

(126) 2-(1-(Cyclopropylsulfonyl)-1H-pyrazol-4-yl)-N-(4-(4-((2,2-difluoroethyl)amino)piperidin-1-yl)-5-((1-methyl-1H-pyrazol-4-yl)ethynyl)pyridin-2-yl)pyrimidin-4-amine;

(127) 2-(1-(Cyclopropylsulfonyl)-1H-pyrazol-4-yl)-N-(5-((1-methyl-1H-pyrazol-4-yl)ethynyl)-4-(4-((3,3,3-trifluoropropyl)amino)piperidin-1-yl)pyridin-2-yl)pyrimidin-4-amine;

(128) 2-(1-(Cyclopropylsulfonyl)-1H-pyrazol-4-yl)-N-(4-(4-(3,3-difluoroazetidin-1-yl)piperidin-1-yl)-5-((1-methyl-1H-pyrazol-4-yl)ethynyl)pyridin-2-yl)pyrimidin-4-amine;

(129) 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine;

(130) 2-(1-(Cyclopropylsulfonyl)-1H-pyrazol-4-yl)-N-(5-((1-methyl-1H-pyrazol-4-yl)ethynyl)-4-(4-(methylamino)piperidin-1-yl)pyridin-2-yl)pyrimidin-4-amine;

(131) 2-((1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)amino)ethan-1-ol;

(132) 2-(1-(Cyclopropylsulfonyl)-1H-pyrazol-4-yl)-N-(4-(4-((2-methoxyethyl)amino)piperidin-1-yl)-5-((1-methyl-1H-pyrazol-4-yl)ethynyl)pyridin-2-yl)pyrimidin-4-amine;

(133) $N^4$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-$N^2$,$N^2$-dimethylethane-1,2-diamine;

(134) $N^4$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-$N^2$,$N^2$,2-trimethylpropane-1,2-diamine;

(135) 2-(1-(Cyclopropylsulfonyl)-1H-pyrazol-4-yl)-N-(5-((1-methyl-1H-pyrazol-4-yl)ethynyl)-4-(4-((2,2,2-trifluoroethyl)amino)piperidin-1-yl)pyridin-2-yl)pyrimidin-4-amine;

(136) 2-(1-(Cyclopropylsulfonyl)-1H-pyrazol-4-yl)-N-(4-(4-((2-fluoroethyl)amino)piperidin-1-yl)-5-((1-(tetrahydro-2H-pyran-4-yl)-1H-pyrazol-4-yl)ethynyl)pyridin-2-yl)pyrimidin-4-amine;

(137) 2-((1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)amino)ethan-1-ol;

(138) $N^1$-(1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)-$N^2$,$N^2$-dimethylethane-1,2-diamine;

(139) 1-(4-(4-((6-((2-(1-(Cyclopropylsulfonyl)-1H-pyrazol-4-yl)pyrimidin-4-yl)amino)-4-(4-((2-(dimethylamino)ethyl)amino)piperidin-1-yl)pyridin-3-yl)ethynyl)-1H-pyrazol-1-yl)piperidin-1-yl)ethan-1-one;

(140) 2-(1-(Cyclopropylsulfonyl)-1H-pyrazol-4-yl)-N-(5-((1-methyl-1H-pyrazol-3-yl)ethynyl)-4-(4-(methylamino)piperidin-1-yl)pyridin-2-yl)pyrimidin-4-amine;

(141) 2-(1-(Cyclopropylsulfonyl)-1H-pyrazol-4-yl)-N-(4-(4-((2-fluoroethyl)amino)piperidin-1-yl)-5-((1-methyl-1H-pyrazol-3-yl)ethynyl)pyridin-2-yl)pyrimidin-4-amine;

(142) $N^1$-(1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-yl)-$N^2$,$N^2$-dimethylethane-1,2-diamine;

(143) $N^1$-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)-$N^2$,$N^2$-dimethylethane-1,2-diamine;

(144) 2-(1-(Cyclopropylsulfonyl)-1H-pyrazol-4-yl)-N-(5-((1-(2-(dimethylamino)ethyl)-1H-pyrazol-4-yl)ethynyl)-4-(4-((2-fluoroethyl)amino)piperidin-1-yl)pyridin-2-yl)pyrimidin-4-amine;

(145) 2-(1-(Cyclopropylsulfonyl)-1H-pyrazol-4-yl)-N-(5-((1-(3-(dimethylamino)propyl)-1H-pyrazol-4-yl)ethynyl)-4-(4-((2-fluoroethyl)amino)piperidin-1-yl)pyridin-2-yl)pyrimidin-4-amine;

(146) 2-(1-(Cyclopropylsulfonyl)-1H-pyrazol-4-yl)-N-(5-((1-methyl-1H-pyrazol-4-yl)ethynyl)-4-(4-methyl-4-((methylamino)methyl)piperidin-1-yl)pyridin-2-yl)pyrimidin-4-amine;

(147) (1-(2-((2-(1-(Cyclopropylsulfonyl)-1H-pyrazol-4-yl)pyrimidin-4-yl)amino)-5-((1-(1-methylpiperidin-4-yl)-1H-pyrazol-4-yl)ethynyl)pyridin-4-yl)-4-methylpiperidin-4-yl)methanol;

(148) (1-(2-((2-(1-(Cyclopropylsulfonyl)-1H-pyrazol-4-yl)pyrimidin-4-yl)amino)-5-((1-(1-methylazetidin-3-yl)-1H-pyrazol-4-yl)ethynyl)pyridin-4-yl)-4-methylpiperidin-4-yl)methanol;

(149) (1-(2-((2-(1-(Cyclopropylsulfonyl)-1H-pyrazol-4-yl)pyrimidin-4-yl)amino)-5-((4,5,6,7-tetrahydropyrazolo[1,5-a]pyrazin-3-yl)ethynyl)pyridin-4-yl)-4-methylpiperidin-4-yl)methanol;

(150) (1-(2-((2-(1-(Cyclopropylsulfonyl)-1H-pyrazol-4-yl)pyrimidin-4-yl)amino)-5-((5-methyl-4,5,6,7-tetrahydropyrazolo[1,5-a]pyrazin-3-yl)ethynyl)pyridin-4-yl)-4-methylpiperidin-4-yl)methanol;

(151) (1-(2-((2-(1-(Cyclopropylsulfonyl)-1H-pyrazol-4-yl)pyrimidin-4-yl)amino)-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol;

(152) 7-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-2-methyl-7-azaspiro[3.5]nonan-2-ol;

(153) 2-(1-(Cyclopropylsulfonyl)-1H-pyrazol-4-yl)-N-(5-((1-methyl-1H-pyrazol-4-yl)ethynyl)-4-(4-(2-(methylamino)ethyl)piperidin-1-yl)pyridin-2-yl)pyrimidin-4-amine;

(154) 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-2-yl)pyridin-2-yl)pyrimidin-4-amine;

(155) 2-(1-(Cyclopropylsulfonyl)-1H-pyrazol-4-yl)-N-(5-((1-methyl-1H-pyrazol-4-yl)ethynyl)-4-(2,7-diazaspiro[3.5]nonan-2-yl)pyridin-2-yl)pyrimidin-4-amine;

(156) 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-8-yl)pyridin-2-yl)pyrimidin-4-amine;

(157) (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(158) (1 s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)-1-methylcyclohexan-1-ol;

(159) (1R,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(160) (1S,3R)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(161) (1 S,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(162) 2-((1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexyl)propan-2-ol;

(163) (1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexan-1-ol;

(164) (1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-yl)methanol;

(165) (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)cyclohexan-1-ol;

(166) (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)-1-methylcyclohexan-1-ol;

(167) (1s,4s)-4-((2-((2-(1-(Cyclopropylsulfonyl)-1H-pyrazol-4-yl)pyrimidin-4-yl)amino)-5-((1-methyl-1,2,4-triazol-3-yl)ethynyl)pyridin-4-yl)amino)cyclohexan-1-ol;

(168) (1S,3R)-3-((2-((2-(1-(Cyclopropylsulfonyl)-1H-pyrazol-4-yl)pyrimidin-4-yl)amino)-5-((5-ethylthiazol-2-yl)ethynyl)pyridin-4-yl)amino)cyclohexan-1-ol;

(169) (1S,3R)-3-((5-((3-Aminophenyl)ethynyl)-2-((2-(1-(cyclopropylsulfonyl)-1H-pyrazol-4-yl)pyrimidin-4-yl)amino)pyridin-4-yl)amino)cyclohexan-1-ol;

(170) (1 S,3R)-3-((2-((2-(1-(Cyclopropylsulfonyl)-1H-pyrazol-4-yl)pyrimidin-4-yl)amino)-5-((5-methylpyrazin-2-yl)ethynyl)pyridin-4-yl)amino)cyclohexan-1-ol;

(171) (1 s,4s)-4-((2-((2-(1-(Cyclopropylsulfonyl)-1H-pyrazol-4-yl)pyrimidin-4-yl)amino)-5-(3-(pyrrolidin-1-yl)prop-1-yn-1-yl)pyridin-4-yl)amino)cyclohexan-1-ol;

(172) (1 s,4s)-4-((2-((2-(1-(Cyclopropylsulfonyl)-1H-pyrazol-4-yl)pyrimidin-4-yl)amino)-5-((4-((2-morpholinoethyl)amino)phenyl)ethynyl)pyridin-4-yl)amino)cyclohexan-1-ol;

(173) (1 s,4s)-4-((2-((2-(1-(Cyclopropylsulfonyl)-1H-pyrazol-4-yl)pyrimidin-4-yl)amino)-5-((3-((2-morpholinoethyl)amino)phenyl)ethynyl)pyridin-4-yl)amino)cyclohexan-1-ol;

(174) 1-((6-((2-(1-(Cyclopropylsulfonyl)-1H-pyrazol-4-yl)pyrimidin-4-yl)amino)-4-(((1s, 4s)-4-hydroxycyclohexyl)amino)pyridin-3-yl)ethynyl)cyclohexan-1-ol;

(175) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclohexan-1-ol;

(176) (1s,4s)-4-((2-((2-(1-(Cyclopropylsulfonyl)-1H-pyrazol-4-yl)pyrimidin-4-yl)amino)-5-((1-hydroxycyclopentyl)ethynyl)pyridin-4-yl)amino)cyclohexan-1-ol;

(177) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclopentan-1-ol;

(178) (1s,4s)-4-((2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)amino)cyclohexan-1-ol;

(179) (1-(2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)-4-methylpiperidin-4-yl)methanol;

(180) (1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methylpiperidin-4-yl)methanol;

(181) (1s,4s)-4-((2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)amino)cyclohexan-1-ol;

(182) (1-(2-((2-(1-(Cyclopropylsulfonyl)-1H-pyrazol-4-yl)pyrimidin-4-yl)amino)-5-((1-methylpiperidin-4-yl)ethynyl)pyridin-4-yl)-4-methylpiperidin-4-yl)methanol;

(183) (1-(2-((2-(1-(Cyclopropylsulfonyl)-1H-pyrazol-4-yl)pyrimidin-4-yl)amino)-5-((4-methyltetrahydro-2H-pyran-4-yl)ethynyl)pyridin-4-yl)-4-methylpiperidin-4-yl)methanol;

(184) (1s,4s)-4-((2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)amino)cyclohexan-1-ol;

(185) (1-(2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)-4-methylpiperidin-4-yl)methanol;

(186) (1s,4s)-4-((2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)amino)cyclohexan-1-ol;

(187) (1-(2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)-4-methylpiperidin-4-yl)methanol;

(188) (1s,4s)-4-((2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)amino)cyclohexan-1-ol;

(189) (1-(2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)-4-methylpiperidin-4-yl)methanol;

(190) (1s,4s)-4-((2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)amino)cyclohexan-1-ol;

(191) (1-(2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)-4-methylpiperidin-4-yl)methanol;

(192) (1-(2-((2-(1-(Cyclopropylsulfonyl)-1H-pyrazol-4-yl)pyrimidin-4-yl)amino)-5-((2-(morpholinomethyl)thiazol-5-yl)ethynyl)pyridin-4-yl)-4-methylpiperidin-4-yl)methanol;

(193) (1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-yl)methanol;

(194) (1s,4s)-4-((2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)amino)cyclohexan-1-ol;

(195) 4-((6-((2-(1-(cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-4-ol;

(196) 4-((6-((2-(1-(Cyclopropylsulfonyl)-1H-pyrazol-4-yl)pyrimidin-4-yl)amino)-4-(((1s, 4s)-4-hydroxycyclohexyl)amino)pyridin-3-yl)ethynyl)tetrahydro-2H-pyran-4-ol;

(197) (1-(2-((2-(1-(Cyclopropylsulfonyl)-1H-pyrazol-4-yl)pyrimidin-4-yl)amino)-5-((tetrahydrofuran-3-yl)ethynyl)pyridin-4-yl)-4-methylpiperidin-4-yl)methanol;

(198) (1s,4s)-4-((2-((2-(1-(Cyclopropylsulfonyl)-1H-pyrazol-4-yl)pyrimidin-4-yl)amino)-5-((tetrahydrofuran-3-yl)ethynyl)pyridin-4-yl)amino)cyclohexan-1-ol;

(199) $N^2$-(2-(1-(Cyclopropylsulfonyl)-1H-pyrazol-4-yl)pyrimidin-4-yl)-$N^4$-isopropyl-5-((2-methylthiazol-4-yl)ethynyl)pyridine-2,4-diamine;

(200) $N^2$-(2-(1-(cyclopropylsulfonyl)-1H-pyrazol-4-yl)pyrimidin-4-yl)-5-((2-(fluoromethyl)thiazol-4-yl)ethynyl)-$N^4$-isopropylpyridine-2,4-diamine;

(201) 4-(3-(6-((2-(1-(Cyclopropylsulfonyl)-1H-pyrazol-4-yl)pyrimidin-4-yl)amino)-4-(isopropylamino)pyridin-3-yl)prop-2-yn-1-yl)thiomorpholine 1,1-dioxide;

(202) $N^2$-(2-(1-(Cyclopropylsulfonyl)-1H-pyrazol-4-yl)pyrimidin-4-yl)-$N^1$-isopropyl-5-(3-morpholinoprop-1-yn-1-yl)pyridine-2,4-diamine;

(203) $N^2$-(2-(1-(Cyclopropylsulfonyl)-1H-pyrazol-4-yl)pyrimidin-4-yl)-$N^4$-isopropyl-5-(3-(pyrrolidin-1-yl)prop-1-yn-1-yl)pyridine-2,4-diamine;

(204) 4-(6-((2-(1-(Cyclopropylsulfonyl)-1H-pyrazol-4-yl)pyrimidin-4-yl)amino)-4-(isopropylamino)pyridin-3-yl)-2-methylbut-3-yn-2-ol;

(205) $N^2$-(2-(1-(Cyclopropylsulfonyl)-1H-pyrazol-4-yl)pyrimidin-4-yl)-5-((2-cyclopropylthiazol-4-yl)ethynyl)-$N^4$-isopropylpyridine-2,4-diamine;

(206) $N^2$-(2-(1-(Cyclopropylsulfonyl)-1H-pyrazol-4-yl)pyrimidin-4-yl)-$N^4$-isopropyl-5-((tetrahydro-2H-pyran-4-yl)ethynyl)pyridine-2,4-diamine;

(207) N-(5-(6-((2-(1-(Cyclopropylsulfonyl)-1H-pyrazol-4-yl)pyrimidin-4-yl)amino)-4-(isopropylamino)pyridin-3-yl)pent-4-yn-1-yl)morpholine-4-carboxamide;

(208) 6-(6-((2-(1-(Cyclopropylsulfonyl)-1H-pyrazol-4-yl)pyrimidin-4-yl)amino)-4-(isopropylamino)pyridin-3-yl)-1-morpholinohex-5-yn-1-one;

(209) N-(6-(6-((2-(1-(Cyclopropylsulfonyl)-1H-pyrazol-4-yl)pyrimidin-4-yl)amino)-4-(isopropylamino)pyridin-3-yl)hex-5-yn-1-yl)morpholine-4-carboxamide;

(210) 7-(6-((2-(1-(Cyclopropylsulfonyl)-1H-pyrazol-4-yl)pyrimidin-4-yl)amino)-4-(isopropyl amino)pyridin-3-yl)-1-morpholinohept-6-yn-1-one;

(2H) 1-(2-((2-(1-(Cyclopropylsulfonyl)-1H-pyrazol-4-yl)pyrimidin-4-yl)amino)-5-((2-methylthiazol-4-yl)ethynyl)pyridin-4-yl)piperidin-4-ol;

(212) 1-(2-((2-(1-(Cyclopropylsulfonyl)-1H-pyrazol-4-yl)pyrimidin-4-yl)amino)-5-((2-(fluoromethyl)thiazol-4-yl)ethynyl)pyridin-4-yl)piperidin-4-ol;

(213) 1-(2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)piperidin-4-ol;

(214) 1-(2-((2-(1-(Cyclopropylsulfonyl)-1H-pyrazol-4-yl)pyrimidin-4-yl)amino)-5-((1-methyl-1H-1,2,4-triazol-3-yl)ethynyl)pyridin-4-yl)piperidin-4-ol;

(215) 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-4-ol;

(216) (1 s,4s)-4-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclohexan-1-ol;

(217) (1s,4s)-4-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol;

(218) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)cyclohexan-1-ol;

(219) (1s,4s)-4-((2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)amino)cyclohexan-1-ol;

(220) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl.)-1H-pyrazol-4-yl)ethynyl)pyridin-4-yl)amino)-1-methylcyclohexan-1-ol;

(221) 2-(4-((6-((2-(1-(Cyclopropylsulfonyl)-1H-pyrazol-4-yl)pyrimidin-4-yl)amino)-4-(((1s, 4s)-4-hydroxy-4-methylcyclohexyl)amino)pyridin-3-yl)ethynyl)-1H-pyrazol-1-yl)-N,N-dimethylacetamide;

(222) (1S,3S)-3-((2-((2-(1-(Cyclopropylsulfonyl)-1H-pyrazol-4-yl)pyrimidin-4-yl)amino)-5-((2-methylthiazol-4-yl)ethynyl)pyridin-4-yl)amino)cyclopentan-1-ol;

(223) (1 S,3R)-3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclopentan-1-ol;

(224) 3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)-2,2-dimethylpropan-1-ol;

(225) (1S,3S)-3-((2-((2-(1-(Cyclopropylsulfonyl)-1H-pyrazol.-4-yl)pyrimidin-4-yl)amino)-5-(thiophen-3-ylethynyl)pyridin-4-yl)amino)cyclohexan-1-ol;

(226) 2-(1-(Cyclopropylsulfonyl)-1H-pyrazol-4-yl)-N-(4-(4-(4-methylpiperazin-1-yl)piperidin-1-yl)-5-(thiophen-3-ylethynyl)pyridin-2-yl)pyrimidin-4-amine;

(227) 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-3-ol;

(228) (5)-1-(2-((2-(1-(Cyclopropylsulfonyl)-1H-pyrazol-4-yl)pyrimidin-4-yl)amino)-5-(thiophen-3-ylethynyl)pyridin-4-yl)piperidin-3-ol;

(229) 1-(2-((2-(1-(Cyclopropylsulfonyl)-1H-pyrazol-4-yl)pyrimidin-4-yl)amino)-5-(thiophen-3-ylethynyl)pyridin-4-yl)-3,3-dimethylpiperidin-4-ol;

(230) (1s,4s)-4-((2-((2-(1-(Cyclopropylsulfonyl)-1H-pyrazol-4-yl)pyrimidin-4-yl)amino)-5-(3-methyl-3-morpholinobut-1-yn-1-yl)pyridin-4-yl)amino)cyclohexan-1-ol;

(231) (1-(2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)-4-methylpiperidin-4-yl)methanol;

(232) (1-(2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)-4-methylpiperidin-4-yl)methanol;

(233) 2-(1-(Cyclopropylsulfonyl)-1H-pyrazol-4-yl)-N-(4-(1-methyl-1H-pyrazol-4-yl)-5-((1-methyl-1H-pyrazol-4-yl)ethynyl)pyridin-2-yl)pyrimidin-4-amine;

(234) 2-(1-(Cyclopropylsulfonyl)-1H-pyrazol-4-yl)-N-(5-((1-(2-fluoroethyl)-1H-pyrazol-4-yl)ethynyl)-4-(1-methyl-1H-pyrazol-4-yl)pyridin-2-yl)pyrimidin-4-amine;

(235) N-(4-(1-Cyclopropyl-1H-pyrazol-4-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(236) N-(4-(1-cyclopropyl-1H-pyrazol-4-yl)-5-((1-isopropyl-1H-pyrazol-4-yl)ethynyl)pyridin-2-yl)-2-(1-(cyclopropylsulfonyl)-1H-pyrazol-4-yl)pyrimidin-4-amine;

(237) N-(4-(1-Cyclopropyl-1H-pyrazol-4-yl)-5-((1-(2-fluoroethyl)-1H-pyrazol-4-yl)ethynyl)pyridin-2-yl)-2-(1-(cyclopropylsulfonyl)-1H-pyrazol-4-yl)pyrimidin-4-amine;

(238) 2-(1-(Cyclopropylsulfonyl)-1H-pyrazol-4-yl)-N-(4-(((1r,4r)-4-((dimethylamino)methyl)cyclohexyl)methoxy)-5-((2-methylthiazol-4-yl)ethynyl)pyridin-2-yl)pyrimidin-4-amine;

(239) 4-(3-(6-((2-(1-(Cyclopropylsulfonyl)-1H-pyrazol-4-yl)pyrimidin-4-yl)amino)-4-(((1 r,4r)-4-((dimethylamino)methyl)cyclohexyl)methoxy)pyridin-3-yl)prop-2-yn-1-yl)thiomorpholine 1,1-dioxide;

(240) 2-(1-(Cyclopropylsulfonyl)-1H-pyrazol-4-yl)-N-(4-(((1r,4r)-4-((dimethylamino)methyl)cyclohexyl)methoxy)-5-(3-(pyrrolidin-1-yl)prop-1-yn-1-yl)pyridin-2-yl)pyrimidin-4-amine;

(241) (1-(2-((2-(1-(Cyclopropylsulfonyl)-1H-pyrazol-4-yl)pyrimidin-4-yl)amino)-5-((1-((tetrahydro-2H-pyran-3-yl)methyl)-1H-pyrazol-4-yl)ethynyl)pyridin-4-yl)-4-methylpiperidin-4-yl)methanol;

(242) (1-(5-((1-((1,4-Dioxan-2-yl)methyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(243) (1-(2-((2-(1-(Cyclopropylsulfonyl)-1H-pyrazol-4-yl)pyrimidin-4-yl)amino)-5-((1-((tetrahydrofuran-3-yl)methyl)-1H-pyrazol-4-yl)ethynyl)pyridin-4-yl)-4-methylpiperidin-4-yl)methanol;

(244) (1-(2-((2-(1-(Cyclopropylsulfonyl)-1H-pyrazol-4-yl)pyrimidin-4-yl)amino)-5-((1-(tetrahydrofuran-3-yl)-1H-pyrazol-4-yl)ethynyl)pyridin-4-yl)-4-methylpiperidin-4-yl)methanol;

(245) (1-(2-((2-(1-(Cyclopropylsulfonyl)-1H-pyrazol-4-yl)pyrimidin-4-yl)amino)-5-((1-(oxetan-3-yl)-1H-pyrazol-4-yl)ethynyl)pyridin-4-yl)-4-methylpiperidin-4-yl)methanol;

(246) (1-(2-((2-(1-(Cyclopropylsulfonyl)-1H-pyrazol-4-yl)pyrimidin-4-yl)amino)-5-((trimethylsilyl)ethynyl)pyridin-4-yl)-4-methylpiperidin-4-yl)methanol;

(247) (1-(2-((2-(1-(Cyclopropylsulfonyl)-1H-pyrazol-4-yl)pyrimidin-4-yl)amino)-5-ethynylpyridin-4-yl)-4-methylpiperidin-4-yl)methanol;

(248) (1-(2-((2-(1-(Cyclopropylsulfonyl)-1H-pyrazol-4-yl)pyrimidin-4-yl)amino)-5-((5-((3,3-difluoroazetidin-1-yl)methyl)-1-(2,2-difluoroethyl)-1H-pyrrol-3-yl)ethynyl)pyridin-4-yl)-4-methylpiperidin-4-yl)methanol;

(249) (1-(2-((2-(1-(Cyclopropylsulfonyl)-1H-pyrazol-4-yl)pyrimidin-4-yl)amino)-5-((1-(2,2-difluoroethyl)-1H-pyrrolo[3,2-c]pyridin-3-yl)ethynyl)pyridin-4-yl)-4-methylpiperidin-4-yl)methanol;

(250) (1-(5-(Cyclopropylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(251) (1-(5-(Cyclopentylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(252) (1-(5-(Cyclohexylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(253) (1-(2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol;

(254) (1-(2-((2-(1-(Cyclopropylsulfonyl)-1H-pyrazol-4-yl)pyrimidin-4-yl)amino)-5-((4-((dimethylamino)methyl)phenyl)ethynyl)pyridin-4-yl)-4-methylpiperidin-4-yl)methanol;

(255) (1-(2-((2-(1-(Cyclopropylsulfonyl)-1H-pyrazol-4-yl)pyrimidin-4-yl)amino)-5-((3-((dimethylamino)methyl)phenyl)ethynyl)pyridin-4-yl)-4-methylpiperidin-4-yl)methanol;

(256) (1-(2-((2-(1-(Cyclopropylsulfonyl)-1H-pyrazol-4-yl)pyrimidin-4-yl)amino)-5-(phenyl ethynyl)pyridin-4-yl)-4-methylpiperidin-4-yl)methanol;

(257) (1-(2-((2-(1-(Cyclopropylsulfonyl)-1H-pyrazol-4-yl)pyrimidin-4-yl)amino)-5-((2-fluorophenyl)ethynyl)pyridin-4-yl)-4-methylpiperidin-4-yl)methanol;

(258) (1-(2-((2-(1-(Cyclopropylsulfonyl)-1H-pyrazol-4-yl)pyrimidin-4-yl)amino)-5-(pyridin-4-ylethynyl)pyridin-4-yl)-4-methylpiperidin-4-yl)methanol;

(259) (1-(2-((2-(1-(Cyclopropylsulfonyl)-1H-pyrazol-4-yl)pyrimidin-4-yl)amino)-5-(pyridin-2-ylethynyl)pyridin-4-yl)-4-methylpiperidin-4-yl)methanol;

(260) (1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-yl)methanol;

(261) (3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(262) 4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylbenzamide;

(263) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(264) 6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylpicolinamide;

(265) (6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyridin-2-yl)(morpholino)methanone;

(266) 2-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutyl)propan-2-ol;

(267) (1-(2-((2-(1-(2,2-Difluoroethyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(268) (4-Methyl-1-(2-((2-(1-(methylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)methanol;

(269) (1-(2-((2-(6-Fluoropyridin-3-yl)pyrimidin-4-yl)amino)-5-((1-(trifluoromethyl)-1H-pyrazol-4-yl)ethynyl)pyridin-4-yl)-4-methylpiperidin-4-yl)methanol;

(270) (4-Methyl-1-(5-((1-methyl-1H-pyrazol-4-yl)ethynyl)-2-((2-((2-(methylsulfonyl)phenyl)amino)pyrimidin-4-yl)amino)pyridin-4-yl)piperidin-4-yl)methanol;

(271) (1-(5-((1-(Difluoromethyl)-1H-pyrazol-4-yl)ethynyl)-2-((2-((2-(methylsulfonyl)phenyl)amino)pyrimidin-4-yl)amino)pyridin-4-yl)-4-methylpiperidin-4-yl)methanol;

(272) 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N,3-trimethyl-1H-pyrazole-1-sulfonamide;

(273) 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N-dimethyl-1H-pyrazole-1-sulfonamide;

(274) 4-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol;

(275) (1-(2-((2-(1-(Cyclopropylsulfonyl)-1H-pyrazol-4-yl)pyrimidin-4-yl)amino)-5-(4,4,4-trifluorobut-1-yn-1-yl)pyridin-4-yl)-4-methylpiperidin-4-yl)methanol;

(276) (1-(2-((2-(1-(Cyclopropylsulfonyl)-1H-pyrazol-4-yl)pyrimidin-4-yl)amino)-5-(4-fluorobut-1-yn-1-yl)pyridin-4-yl)-4-methylpiperidin-4-yl)methanol;

(277) (1-(5-(But-3-en-1-yn-1-yl)-2-((2-(1-(cyclopropylsulfonyl)-1H-pyrazol-4-yl)pyrimidin-4-yl)amino)pyridin-4-yl)-4-methylpiperidin-4-yl)methanol;

(278) (1-(2-((2-(1-(Cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol;

(279) (1-(2-((2-(1-(Cyclopropylsulfonyl)-1H-pyrazol-4-yl)pyrimidin-4-yl)amino)-5-((6-((4-methylpiperazin-1-yl)methyl)pyridin-3-yl)ethynyl)pyridin-4-yl)-4-methylpiperidin-4-yl)methanol;

(280) 1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-ol;

(281) 2-(1-(Cyclopropylsulfonyl)-1H-pyrazol-4-yl)-N-(4-(4-methoxy-4-methylpiperidin-1-yl)-5-(pyridin-3-ylethynyl)pyridin-2-yl)pyrimidin-4-amine;

(282) 2-(1-(Cyclopropylsulfonyl)-1H-pyrazol-4-yl)-N-(5-(pyridin-3-ylethynyl)-4-(1-oxa-8-azaspiro[4.5]decan-8-yl)pyridin-2-yl)pyrimidin-4-amine;

(283) 2-(1-(Cyclopropylsulfonyl)-1H-pyrazol-4-yl)-N-(5-(pyridin-3-ylethynyl)-4-(1-oxa-7-azaspiro[3.5]nonan-7-yl)pyridin-2-yl)pyrimidin-4-amine;

(284) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)-2-methylpent-4-yn-2-ol;

(285) (1-(2-((2-(1-(Cyclopropylsulfonyl)-1H-pyrazol-4-yl)pyrimidin-4-yl)amino)-5-(4-morpholinobut-1-yn-1-yl)pyridin-4-yl)-4-methylpiperidin-4-yl)methanol;

(286) 3-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)oxetan-3-ol;

(287) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)pent-4-yn-2-ol;

(288) N-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)-2,2,2-trifluoroacetamide;

(289) 4-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)thiomorpholine 1,1-dioxide;

(290) (1-(2-((2-(1-(Cyclopropylsulfonyl)-1H-pyrazol-4-yl)pyrimidin-4-yl)amino)-5-((3-(trifluoromethyl)-1H-pyrazol-5-yl)ethynyl)pyridin-4-yl)-4-methylpiperidin-4-yl)methanol;

(291) (1-(2-((2-(1-(Cyclopropylsulfonyl)-1H-pyrazol-4-yl)pyrimidin-4-yl)amino)-5-((4-(trifluoromethyl)thiazol-2-yl)ethynyl)pyridin-4-yl)-4-methylpiperidin-4-yl)methanol;

(292) (1-(2-((2-(1-(Cyclopropylsulfonyl)-1H-pyrazol-4-yl)pyrimidin-4-yl)amino)-5-((2-(trifluoromethyl)thiazol-5-yl)ethynyl)pyridin-4-yl)-4-methylpiperidin-4-yl)methanol;

(293) 2-(1-(Cyclopropylsulfonyl)-1H-pyrazol-4-yl)-N-(4-(4-((dimethylamino)methyl)-4-fluoropiperidin-1-yl)-5-((1-methyl-1H-pyrazol-4-yl)ethynyl)pyridin-2-yl)pyrimidin-4-amine formate;

(294) 2-(1-(Cyclopropylsulfonyl)-1H-pyrazol-4-yl)-N-(4-(4-(2-(dimethylamino)ethyl)piperidin-1-yl)-5-((1-methyl-1H-pyrazol-4-yl)ethynyl)pyridin-2-yl)pyrimidin-4-amine formate;

(295) 2-(1-(Cyclopropylsulfonyl)-1H-pyrazol-4-yl)-N-(4-(4-((dimethylamino)methyl)piperidin-1-yl)-5-((l-methyl-1H-pyrazol-4-yl)ethynyl)pyridin-2-yl)pyrimidin-4-amine;

(296) 2-(1-(Cyclopropylsulfonyl)-1H-pyrazol-4-yl)-N-(4-(4-((dimethylamino)methyl)-4-methylpiperidin-1-yl)-5-((1-methyl-1H-pyrazol-4-yl)ethynyl)pyridin-2-yl)pyrimidin-4-amine;

(297) 2-(1-(Cyclopropylsulfonyl)-1H-pyrazol-4-yl)-N-(5-((1-methyl-1H-pyrazol-4-yl)ethynyl)-4-(2-methyl-2,8-diazaspiro[4.5]decan-8-yl)pyridin-2-yl)pyrimidin-4-amine formate;

(298) N-(5-((1-Cyclopropyl-1H-pyrazol-4-yl)ethynyl)-4-(4-((dimethylamino)methyl)piperidin-1-yl)pyridin-2-yl)-2-(1-(cyclopropylsulfonyl)-1H-pyrazol-4-yl)pyrimidin-4-amine;

(299) N-(5-((1-Cyclopropyl-1H-pyrazol-4-yl)ethynyl)-4-(4-((dimethylamino)methyl)-4-methylpiperidin-1-yl)pyridin-2-yl)-2-(1-(cyclopropylsulfonyl)-1H-pyrazol-4-yl)pyrimidin-4-amine;

(300) N-(5-((1-Cyclopropyl-1H-pyrazol-4-yl)ethynyl)-4-(4-((dimethylamino)methyl)-4-fluoropiperidin-1-yl)pyridin-2-yl)-2-(1-(cyclopropylsulfonyl)-1H-pyrazol-4-yl)pyrimidin-4-amine;

(301) 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)piperidin-1-yl)pyridin-2-yl)pyrimidin-4-amine;

(302) 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)-4-methylpiperidin-1-yl)pyridin-2-yl)pyrimidin-4-amine;

(303) 2-(1-(Cyclopropylsulfonyl)-1H-pyrazol-4-yl)-N-(5-((1-(2,2-difluoroethyl)-1H-pyrazol-4-yl)ethynyl)-4-(4-(2-(dimethylamino)ethyl)piperidin-1-yl)pyridin-2-yl)pyrimidin-4-amine;

(304) (1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)-1-(hydroxymethyl)cyclohexan-1-ol;

(305) (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol;

(306) (1R,3S)-3-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclopentan-1-ol;

(307) (1 r,4r)-4-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclohexan-1-ol;

(308) ((1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)cyclohexyl)methanol;

(309) 5-((1-(Cyclopropylmethyl)-1H-pyrazol-4-yl)ethynyl)-N²-(2-(1-cyclopropylsulfonyl)-1H-pyrazol-4-yl)pyrimidin-4-yl)-N⁴-((1 s, 4s)-4-((dimethylamino)methyl)cyclohexyl)pyridine-2,4-diamine;

(310) N²-(2-(1-(Cyclopropylsulfonyl)-1H-pyrazol-4-yl)pyrimidin-4-yl)-5-((1-(difluoromethyl)-1H-pyrazol-4-yl)ethynyl)-N⁴-((1 s,4s)-4-((dimethylamino)methyl)cyclohexyl)pyridine-2,4-diamine;

(3H) N²-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N⁴-((1 s, 4s)-4-((dimethylamino)methyl)cyclohexyl)pyridine-2,4-diamine;

(312) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-((1-methyl-1H-pyrazol-4-yl)ethynyl)pyridine-2,4-diamine;

(313) 5-((1-Cyclopropyl-1H-pyrazol-4-yl)ethynyl)-N²-(2-(1-(cyclopropylsulfonyl)-1H-pyrazol-4-yl)pyrimidin-4-yl)-N⁴-((1s,4s)-4-((dimethylamino)methyl)cyclohexyl)pyridine-2,4-diamine;

(314) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-((1-(trifluoromethyl)-1H-pyrazol-4-yl)ethynyl)pyridine-2,4-diamine;

(315) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-((dimethylamino)methyl)piperidin-4-ol;

(316) 1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-((dimethylamino)methyl)piperidin-4-ol;

(317) 1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-((dimethylamino)methyl)piperidin-4-ol;

(318) 2-(1-(Cyclopropylsulfonyl)-1H-pyrazol-4-yl)-N-(5-((1-methyl-1H-pyrazol-4-yl)ethynyl)-4-(9-methyl-3,9-diazaspiro[5.5]undecan-3-yl)pyridin-2-yl)pyrimidin-4-amine;

(319) N-(5-((1-Cyclopropyl-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine;

(320) N-(5-((1-(Cyclopropylmethyl)-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine;

(321) 2-(1-(Cyclopropylsulfonyl)-1H-pyrazol-4-yl)-N-(5-((1-(difluoromethyl)-1H-pyrazol-4-yl)ethynyl)-4-(9-methyl-3,9-diazaspiro[5.5]undecan-3-yl)pyridin-2-yl)pyrimidin-4-amine;

(322) 2-(1-(Cyclopropylsulfonyl)-1H-pyrazol-4-yl)-N-(5-((1-(2,2-difluoroethyl)-1H-pyrazol-4-yl)ethynyl)-4-(9-methyl-3,9-diazaspiro[5.5]undecan-3-yl)pyridin-2-yl)pyrimidin-4-amine;

(323) (1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)-1-methylcyclohexan-1-ol;

(324) ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol;

(325) 2-((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)propan-2-ol;

(326) (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)-1-methylcyclohexan-1-ol;

(327) ((1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol;

(328) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-ol;

(329) 2-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)propan-2-ol;

(330) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)cyclopropan-1-ol;

(331) ((1R,5S,6r)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-6-yl)methanol;

(332) ((1R,3s,5S)-8-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-8-azabicyclo[3.2.1]octan-3-yl)methanol;

(333) ((1 S,5S)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-1-yl)methanol;

(334) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-one;

(335) 2-(1-(Cyclopropylsulfonyl)-1H-pyrazol-4-yl)-N-(4-(4-(2-(dimethylamino)ethyl)piperidin-1-yl)-5-((1-(trifluoromethyl)-1H-pyrazol-4-yl)ethynyl)pyridin-2-yl)pyrimidin-4-amine;

(336) ((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)methanol;

(337) 2-((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)propan-2-ol;

(338) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-fluoropiperidin-4-yl)methanol;

(339) (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol;

(340) ((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)methanol;

(341) (1S,3S)-3-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol;

(342) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-fluoropiperidin-4-yl)methanol;

(343) 1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)piperidin-3-ol;

(344) (1s, 4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)-1-methylcyclohexan-1-ol;

(345) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-((1-(2,2,2-trifluoroethyl)-1H-pyrazol-4-yl)ethynyl)pyridine-2,4-diamine;

(346) 2-((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)propan-2-ol;

(347) 7-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-2-methyl-7-azaspiro[3.5]nonan-2-ol;

(348) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-methylpiperidin-4-yl)methanol;

(349) 2-(1-(Cyclopropylsulfonyl)-1H-pyrazol-4-yl)-N-(4-(4-(2-(dimethylamino)ethyl)piperidin-1-yl)-5-((1-(2,2,2-trifluoroethyl)-1H-pyrazol-4-yl)ethynyl)pyridin-2-yl)pyrimidin-4-amine;

(350) (1s,4s)-4-((2-((2-(1-(Cyclopropylsulfonyl)-1H-pyrazol-4-yl)pyrimidin-4-yl)amino)-5-((3-methyloxetan-3-yl)ethynyl)pyridin-4-yl)amino)cyclohexan-1-ol;

(351) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutan-1-ol;

(352) (1-(2-((2-(1-(Cyclopropylsulfonyl)-1H-pyrazol-4-yl)pyrimidin-4-yl)amino)-5-(oxetan-3-ylethynyl)pyridin-4-yl)-4-methylpiperidin-4-yl)methanol;

(353) (1s,4s)-4-((2-((2-(1-(Cyclopropylsulfonyl)-1H-pyrazol-4-yl)pyrimidin-4-yl)amino)-5-(oxetan-3-ylethynyl)pyridin-4-yl)amino)cyclohexan-1-ol;

(354) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)oxetan-3-ol;

(355) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrofuran-3-ol;

(356) 3-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)tetrahydrofuran-3-ol;

(357) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-3-ol;

(358) (1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-yl)methanol;

(359) (1s,4s)-4-((2-((2-(1-(Cyclopropylsulfonyl)-1H-pyrazol.-4-yl)pyrimidin-4-yl)amino)-5-((1-methylcyclopropyl)ethynyl)pyridin-4-yl)amino)cyclohexan-1-ol;

(360) ((1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol;

(361) (1 r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)cyclohexan-1-ol;

(362) (5s,8s)-8-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)-1-azaspiro[4.5]decan-2-one;

(363) (1r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)-1-methylcyclohexan-1-ol;

(364) 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-ol;

(365) 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methoxypiperidin-4-ol;

(366) 2-(1-(Cyclopropylsulfonyl)-1H-pyrazol-4-yl)-N-(5-((5-(morpholinomethyl)pyrimidin-2-yl)ethynyl)-4-(1-oxa-8-azaspiro[4.5]decan-8-yl)pyridin-2-yl)pyrimidin-4-amine;

(367) 2-(1-(Cyclopropylsulfonyl)-1H-pyrazol-4-yl)-N-(5-((5-(morpholinomethyl)pyrimidin-2-yl)ethynyl)-4-(1-oxa-7-azaspiro[3.5]nonan-7-yl)pyridin-2-yl)pyrimidin-4-amine;

(368) 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-ol;

(369) 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methoxypiperidin-4-ol;

(370) 2-(1-(Cyclopropylsulfonyl)-1H-pyrazol-4-yl)-N-(5-((4-((4-methylpiperazin-1-yl)methyl)phenyl)ethynyl)-4-(1-oxa-7-azaspiro[3.5]nonan-7-yl)pyridin-2-yl)pyrimidin-4-amine;

(371) 1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methoxypiperidin-4-ol;

(372) 2-(1-(Cyclopropylsulfonyl)-1H-pyrazol-4-yl)-N-(5-((1-methylpyrrolidin-3-yl)ethynyl)-4-(1-oxa-8-azaspiro[4.5]decan-8-yl)pyridin-2-yl)pyrimidin-4-amine;

(373) 2-(1-(Cyclopropylsulfonyl)-1H-pyrazol-4-yl)-N-(5-((1-methylpyrrolidin-3-yl)ethynyl)-4-(1-oxa-7-azaspiro[3.5]nonan-7-yl)pyridin-2-yl)pyrimidin-4-amine;

(374) ((1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexyl)methanol;

(375) (1 r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)cyclohexan-1-ol;

(376) (1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexan-1-ol;

(377) (1 r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)-1-methylcyclohexan-1-ol;

(378) (1-(2-((2-(1-(Cyclopropylsulfonyl)-1H-pyrazol-4-yl)pyrimidin-4-yl)amino)-5-((tetrahydrofuran-2-yl)ethynyl)pyridin-4-yl)-4-methylpiperidin-4-yl)methanol;

(379) ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol;

(380) (1 r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)-1-methylcyclohexan-1-ol;

(381) ((1 r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)cyclohexyl)methanol;

(382) 2-(1-(Cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine;

(383) 2-(1-(Cyclopropylsulfonyl)-1H-pyrazol-4-yl)-N-(4-(4-fluoro-4-(((2-fluoroethyl)amino)methyl)piperidin-1-yl)-5-((1-methyl-1H-pyrazol-4-yl)ethynyl)pyridin-2-yl)pyrimidin-4-amine;

(384) (S)-2-(1-(Cyclopropylsulfonyl)-1H-pyrazol-4-yl)-N-(4-(3-((dimethylamino)methyl)piperidin-1-yl)-5-((1-methyl-1H-pyrazol-4-yl)ethynyl)pyridin-2-yl)pyrimidin-4-amine;

(385) (S)-2-(1-(Cyclopropylsulfonyl)-1H-pyrazol-4-yl)-N-(4-(3-((dimethylamino)methyl)piperidin-1-yl)-5-((1-(2-fluoroethyl)-1H-pyrazol-4-yl)ethynyl)pyridin-2-yl)pyrimidin-4-amine;

(386) 2-(1-(Cyclopropylsulfonyl)-1H-pyrazol-4-yl)-N-(4-(3-(2-(dimethylamino)ethyl)piperidin-1-yl)-5-((1-(2-fluoroethyl)-1H-pyrazol-4-yl)ethynyl)pyridin-2-yl)pyrimidin-4-amine;

(387) ((1s,4s)-4-((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)cyclohexyl)methanol;

(388) ((1r,4r)-4-(((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)methyl)cyclohexyl)methanol;

(389) (1-(2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)-4-methylpiperidin-4-yl)methanol;

(390) ((1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexyl)methanol;

(391) (1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexan-1-ol;

(392) ((1r,4r)-4-(((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)methyl)cyclohexyl)methanol;

(393) ((1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexyl)methanol;

(394) (1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexan-1-ol;

(395) (1-(2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)-4-methylpiperidin-4-yl)methanol;

(396) 2-(1-(Cyclopropylsulfonyl)-1H-pyrazol-4-yl)-N-(4-(3-(2-(dimethylamino)ethyl)piperidin-1-yl)-5-((1-methyl-1H-pyrazol-4-yl)ethynyl)pyridin-2-yl)pyrimidin-4-amine;

(397) ((1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexyl)methanol;

(398) (1 r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexan-1-ol;

(399) (1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexan-1-ol;

(400) ((1r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexyl)methanol;

(401) (1-(2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)-4-methylpiperidin-4-yl)methanol;

(402) ((1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexyl)methanol;

(403) (1r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexan-1-ol;

(404) 1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-ol;

(405) ((1r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexyl)methanol;

(406) 2-(1-(Cyclopropylsulfonyl)-1H-pyrazol-4-yl)-N-(4-(4-(((dimethylamino)methyl)-4-methylpiperidin-1-yl)-5-((1-methylcyclopropyl)ethynyl)pyridin-2-yl)pyrimidin-4-amine;

(407) 2-(1-(Cyclopropylsulfonyl)-1H-pyrazol-4-yl)-N-(4-(4-(2-(dimethylamino)ethyl)piperidin-1-yl)-5-((1-methylcyclopropyl)ethynyl)pyridin-2-yl)pyrimidin-4-amine;

(408) 1-(3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)pyrrolidin-1-yl)-2,2,2-trifluoroethan-1-one;

(409) 1-(3-((6-((2-(1-(Cyclopropylsulfonyl)-1H-pyrazol-4-yl)pyrimidin-4-yl)amino)-4-((((1 r,4r)-4-hydroxycyclohexyl)methyl)amino)pyridin-3-yl)ethynyl)pyrrolidin-1-yl)-2,2,2-trifluoroethan-1-one;

(410) 1-(3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)pyrrolidin-1-yl)-2,2,2-trifluoroethan-1-one;

(4H) 1-(3-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)pyrrolidin-1-yl)-2,2,2-trifluoroethan-1-one;

(412) 1-(3-((6-((2-(1-(Cyclopropylsulfonyl)-1H-pyrazol-4-yl)pyrimidin-4-yl)amino)-4-(4-((dimethylamino)methyl)-4-methylpiperidin-1-yl)pyridin-3-yl)ethynyl)pyrrolidin-1-yl)-2,2,2-trifluoroethan-1-one;

(413) 1-(3-((6-((2-(1-(Cyclopropylsulfonyl)-1H-pyrazol-4-yl)pyrimidin-4-yl)amino)-4-(4-(2-(dimethylamino)ethyl)piperidin-1-yl)pyridin-3-yl)ethynyl)pyrrolidin-1-yl)-2,2,2-trifluoroethan-1-one;

(414) 1-(3-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)pyrrolidin-1-yl)-2,2,2-trifluoroethan-1-one;

(415) 1-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyrrolidin-1-yl)-2,2,2-trifluoroethan-1-one;

(416) ((1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexyl)methanol;

(417) 1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-ol;

(418) 2-(1-(Cyclopropylsulfonyl)-1H-pyrazol-4-yl)-N-(4-(4-((dimethylamino)methyl)-4-methylpiperidin-1-yl)-5-(((2R)-2-(trifluoromethyl)tetrahydrofuran-3-yl)ethynyl)pyridin-2-yl)pyrimidin-4-amine;

(419) 2-(1-(Cyclopropylsulfonyl)-1H-pyrazol-4-yl)-N-(4-(4-(2-(dimethylamino)ethyl)piperidin-1-yl)-5-(((2R)-2-(trifluoromethyl)tetrahydrofuran-3-yl)ethynyl)pyridin-2-yl)pyrimidin-4-amine;

(420) (1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexan-1-ol;

(421) (1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-yl)methanol;

(422) ((1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexyl)methanol;

(423) (1r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexan-1-ol;

(424) 1-(5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)-4-methylpiperidin-4-o 1;

(425) ((1r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexyl)methanol;

(426) N-(5-((7-Oxabicyclo[2.2.1]heptan-2-yl)ethynyl)-4-(4-(2-(dimethylamino)ethyl)piperidin-1-yl)pyridin-2-yl)-2-(1-(cyclopropylsulfonyl)-1H-pyrazol-4-yl)pyrimidin-4-amine;

(427) (1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(428) 3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)tetrahydrothiophene 1,1-dioxide;

(429) 3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)tetrahydrothiophene 1,1-dioxide;

(430) ((1s,4s)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexyl)methanol;

(431) (1 r,4r)-4-(((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)methyl)cyclohexan-1-ol;

(432) 1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-ol;

(433) (1 s,4s)-4-((2-((2-(1-(cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexan-1-ol;

(434) ((1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexyl)methanol;

(435) 1-(2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)-4-methylpiperidin-4-ol;

(436) (1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexan-1-ol;

(437) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrothiophene 1,1-dioxide;

(438) (1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-yl)methanol;

(439) (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-3-ol;

(440) (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-3-ol;

(441) (4-((6-((2-(1-(Cyclopropylsulfonyl)-1H-pyrazol-4-yl)pyrimidin-4-yl)amino)-4-(((l s, 4s)-4-(hydroxymethyl)cyclohexyl)amino)pyridin-3-yl)ethynyl)phenyl)(4-hydroxypiperidin-1-yl)methanone;

(442) (4-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)phenyl)(4-hydroxypiperidin-1-yl)methanone;

(443) (4-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)phenyl)(4-hydroxypiperidin-1-yl)methanone;

(444) (R)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone;

(445) (S)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone;

(446) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(4-hydroxypiperidin-1-yl)methanone;

(447) (5)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)-3-methylpiperidin-3-ol;

(448) (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-methylpiperidin-3-ol; and (449) (1-(2-((2-(4-(Cyclopropylsulfonyl)piperazin-1-yl)pyrimidin-4-yl)amino)-5-((1-(trifluoromethyl)-1H-pyrazol-4-yl)ethynyl)pyridin-4-yl)-4-methylpiperidin-4-yl)methanol.

Further representative compounds of Formula (I) are listed below:

(1) 2-(1-(Cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine;

(4) (R)-3-((2-(2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)butan-1-ol;

(5) 0)-3-((2-((2-(1-(Cyclopropylsulfonyl)-1H-pyrazol-4-yl)pyrimidin-4-yl)amino)-5-((1 methyl-1H-pyrazol-4-yl)ethynyl)pyridin-4-yl)amino)-2-methylbutan-2-ol;

(6) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol;

(7) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one;

(8) 2-(1-(Cyclopropylsulfonyl)-1H-pyrazol-4-yl)-N-(4-(4-fluoropiperidin-1-yl)-5-((1-methyl-1H-pyrazol-4-yl)ethynyl)pyridin-2-yl)pyrimidin-4-amine;

(9) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-yl)methanol;

(10) 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol;

(11) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)propan-2-ol;

(12) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol;

(13) 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol;

(14) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-2-methylpropan-1-ol;

(15) 2-(1-(Cyclopropylsulfonyl)-1H-pyrazol-4-yl)-N-(4-(4-methoxypiperidin-1-yl)-5-((1-methyl-1H-pyrazol-4-yl)ethynyl)pyridin-2-yl)pyrimidin-4-amine;

(17) 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)ethan-1-ol;

(18) $N^2$-(2-(1-(Cyclopropylsulfonyl)-1H-pyrazol-4-yl)pyrimidin-4-yl)-$N^4$-isopropyl-5-((1-methyl-1H-pyrazol-4-yl)ethynyl)pyridine-2,4-diamine;

(19) $N^2$-(2-(1-(Cyclopropylsulfonyl)-1H-pyrazol-4-yl)pyrimidin-4-yl)-$N^4$-isopropyl-5-((1-isopropyl-1H-pyrazol-4-yl)ethynyl)pyridine-2,4-diamine;

(20) $N^2$-(2-(1-(Cyclopropylsulfonyl)-1H-pyrazol-4-yl)pyrimidin-4-yl)-5-((1-(2-fluoroethyl)-1H-pyrazol-4-yl)ethynyl)-$N^4$-isopropylpyridine-2,4-diamine;

(21) $N^2$-(2-(1-(Cyclopropylsulfonyl)-1H-pyrazol-4-yl)pyrimidin-4-yl)-$N^4$-isopropyl-5-(pyridin-3-ylethynyl)pyridine-2,4-diamine;

(23) $N^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-$N^4$-isopropylpyridine-2,4-diamine;

(26) $N^4$-(sec-Butyl)-$N^2$-(2-(1-(cyclopropylsulfonyl)-1H-pyrazol-4-yl)pyrimidin-4-yl)-5-((1-(2-fluoroethyl)-1H-pyrazol-4-yl)ethynyl)pyridine-2,4-diamine;

(27) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol;

(28) 1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-ol;

(29) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanol;

(30) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol;

(31) (R)-1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-ol;

(32) (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-ol;

(33) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-yl)methanol;

(34) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-yl)methanol;

(35) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol;

(39) 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)-2,2-dimethyl-propan-1-ol;

(40) 3-((2-((2-(1-Cyclopropylsulfonylpyrazol-4-yl)pyrimidin-4-yl)amino)-5-(2-(1-(2-fluoroethyl)pyrazol-4-yl)ethynyl)-4-pyridyl)amino)-2,2-dimethyl-propan-1-ol;

(41) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(42) (1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(43) (1 S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(44) (1S,3S)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(45) (1S,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(47) (1-(5-(((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(48) (1-(5-((1-(Cyclopropylmethyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(49) (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol;

(53) N²-(2-(1-(Cyclopropylsulfonyl)-1H-pyrazol-4-yl)pyrimidin-4-yl)-N⁴-(((1r,4r)-4-((dimethylamino)methyl)cyclohexyl)methyl)-5-((1-methyl-1H-pyrazol-4-yl)ethynyl)pyridine-2,4-diamine;

(58) 2-(1-(Cyclopropylsulfonyl)-1H-pyrazol-4-yl)-N-(4-(((1r,4r)-4-((dimethylamino)methyl)cyclohexyl)methoxy)-5-((1-methyl-1H-pyrazol-4-yl)ethynyl)pyridin-2-yl)pyrimidin-4-amine;

(59) 2-(1-(Cyclopropylsulfonyl)-1H-pyrazol-4-yl)-N-(4-(((1r,4r)-4-((dimethylamino)methyl)cyclohexyl)methoxy)-5-((1-isopropyl-1H-pyrazol-4-yl)ethynyl)pyridin-2-yl)pyrimidin-4-amine;

(60) N-(5-(((1-Cyclopropyl-1H-pyrazol-4-yl)ethynyl)-4-(((1r,4r)-4-((dimethylamino)methyl)cyclohexyl)methoxy)pyridin-2-yl)-2-(1-(cyclopropylsulfonyl)-1H-pyrazol-4-yl)pyrimidin-4-amine;

(68) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-difluoropiperidin-4-ol;

(73) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol;

(75) (1R,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(81) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-1-methylcyclohexan-1-ol;

(82) 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol;

(83) (1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)methanol;

(84) 2-(1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)ethan-1-ol;

(85) (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol;

(86) 1-(5-(((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-ol;

(87) 2-(1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-yl)ethan-1-ol;

(88) (1s,4s)-4-((5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(90) (1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)methanol;

(91) 2-(1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)ethan-1-ol;

(94) (1s,4s)-4-((2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)amino)cyclohexan-1-ol;

(95) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-methylpiperidin-4-yl)methanol;

(96) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-fluoropiperidin-4-yl)methanol;

(99) 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-ol;

(100) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-yl)methanol;

(101) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(106) (1s,4s)-4-((2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)amino)cyclohexan-1-ol;

(107) (1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)-4-methylpiperidin-4-yl)methanol;

(110) 1-(4-(4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-1H-pyrazol-1-yl)piperidin-1-yl)ethan-1-one;

(112) 1-(4-(4-((6-((2-(1-(Cyclopropylsulfonyl)-1H-pyrazol-4-yl)pyrimidin-4-yl)amino)-4-(4-fluoropiperidin-1-yl)pyridin-3-yl)ethynyl)-1H-pyrazol-1-yl)piperidin-1-yl)ethan-1-one;

(113) 1-(4-(4-((6-((2-(1-(Cyclopropylsulfonyl)-1H-pyrazol-4-yl)pyrimidin-4-yl)amino)-4-(4-methoxypiperidin-1-yl)pyridin-3-yl)ethynyl)-1H-pyrazol-1-yl)piperidin-1-yl)ethan-1-one;

(114) 1-(4-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)-1H-pyrazol-1-yl)piperidin-1-yl)ethan-1-one;

(116) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-methylpiperidin-4-yl)methanol;

(117) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-fluoropiperidin-4-yl)methanol;

(118) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)piperidin-3-yl)methanol;

(119) (1s,4s)-4-((2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)amino)cyclohexan-1-ol;

(120) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-methylpiperidin-4-yl)methanol;

(121) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-fluoropiperidin-4-yl)methanol;

(122) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)piperidin-3-yl)methanol;

(123) (1s,4s)-4-((2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)amino)cyclohexan-1-ol;

(126) 2-(1-(Cyclopropylsulfonyl)-1H-pyrazol-4-yl)-N-(4-(4-((2,2-difluoroethyl)amino)piperidin-1-yl)-5-((l-methyl-1H-pyrazol-4-yl)ethynyl)pyridin-2-yl)pyrimidin-4-amine;

(129) 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine;

(136) 2-(1-(Cyclopropylsulfonyl)-1H-pyrazol-4-yl)-N-(4-(4-((2-fluoroethyl)amino)piperidin-1-yl)-5-((1-(tetrahydro-2H-pyran-4-yl)-1H-pyrazol-4-yl)ethynyl)pyridin-2-yl)pyrimidin-4-amine;

(147) (1-(2-((2-(1-(Cyclopropylsulfonyl)-1H-pyrazol-4-yl)pyrimidin-4-yl)amino)-5-((1-(1-methylpiperidin-4-yl)-1H-pyrazol-4-yl)ethynyl)pyridin-4-yl)-4-methylpiperidin-4-yl)methanol;

(148) (1-(2-((2-(1-(Cyclopropylsulfonyl)-1H-pyrazol-4-yl)pyrimidin-4-yl)amino)-5-((1-(1-methylazetidin-3-yl)-1H-pyrazol-4-yl)ethynyl)pyridin-4-yl)-4-methylpiperidin-4-yl)methanol;

(149) (1-(2-((2-(1-(Cyclopropylsulfonyl)-1H-pyrazol-4-yl)pyrimidin-4-yl)amino)-5-((4,5,6,7-tetrahydropyrazolo[1,5-a]pyrazin-3-yl)ethynyl)pyridin-4-yl)-4-methylpiperidin-4-yl)methanol;

(150) (1-(2-((2-(1-(Cyclopropylsulfonyl)-1H-pyrazol.-4-yl)pyrimidin-4-yl)amino)-5-((5-methyl-4,5,6,7-tetrahydropyrazolo[1,5-a]pyrazin-3-yl)ethynyl)pyridin-4-yl)-4-methylpiperidin-4-yl)methanol;

(152) 7-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-2-methyl-7-azaspiro[3.5]nonan-2-ol;

(157) (1 s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(164) (1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-yl)methanol;

(169) (1S,3R)-3-((5-((3-Aminophenyl)ethynyl)-2-((2-(1-(cyclopropylsulfonyl)-1H-pyrazol-4-yl)pyrimidin-4-yl)amino)pyridin-4-yl)amino)cyclohexan-1-ol;

(177) 1-((6-((2-(1-(Cyclopropylsulfonyl)-1H-pyrazol-4-yl)pyrimidin-4-yl)amino)-4-(hydroxymethyl)-4-methylpiperidin-1-yl)pyridin-3-yl)ethynyl)cyclopentan-1-ol;

(178) (1s,4s)-4-((2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)amino)cyclohexan-1-ol;

(179) (1-(2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)-4-methylpiperidin-4-yl)methanol;

(180) (1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methylpiperidin-4-yl)methanol;

(182) (1-(2-((2-(1-(Cyclopropylsulfonyl)-1H-pyrazol-4-yl)pyrimidin-4-yl)amino)-5-((1-methylpiperidin-4-yl)ethynyl)pyridin-4-yl)-4-methylpiperidin-4-yl)methanol;

(185) (1-(2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)-4-methylpiperidin-4-yl)methanol;

(186) (1s,4s)-4-((2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)amino)cyclohexan-1-ol;

(187) (1-(2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)-4-methylpiperidin-4-yl)methanol;

(189) (1-(2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)-4-methylpiperidin-4-yl)methanol;

(191) (1-(2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)-4-methylpiperidin-4-yl)methanol;

(192) (1-(2-((2-(1-(Cyclopropylsulfonyl)-1H-pyrazol-4-yl)pyrimidin-4-yl)amino)-5-((2-(morpholinomethyl)thiazol-5-yl)ethynyl)pyridin-4-yl)-4-methylpiperidin-4-yl)methanol;

(193) (1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-yl)methanol;

(197) (1-(2-((2-(1-(Cyclopropylsulfonyl)-1H-pyrazol-4-yl)pyrimidin-4-yl)amino)-5-((tetrahydrofuran-3-yl)ethynyl)pyridin-4-yl)-4-methylpiperidin-4-yl)methanol;

(207) N-(5-(6-((2-(1-(Cyclopropylsulfonyl)-1H-pyrazol-4-yl)pyrimidin-4-yl)amino)-4-(isopropylamino)pyridin-3-yl)pent-4-yn-1-yl)morpholine-4-carboxamide;

(210) 7-(6-((2-(1-(Cyclopropylsulfonyl)-1H-pyrazol-4-yl)pyrimidin-4-yl)amino)-4-(isopropylamino)pyridin-3-yl)-1-morpholinohept-6-yn-1-one;

(2H) 1-2-((2-(1-(Cyclopropylsulfonyl)-1H-pyrazol-4-yl)pyrimidin-4-yl)amino)-5-((2-methylthiazol-4-yl)ethynyl)pyridin-4-yl)piperidin-4-ol;

(216) (1s,4s)-4-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclohexan-1-ol;

(217) (1s,4S)-4-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol;

(218) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)cyclohexan-1-ol;

(219) (1s,4s)-4-((2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)amino)cyclohexan-1-ol;

(220) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)-1-methylcyclohexan-1-ol;

(231) (1-(2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)-4-methylpiperidin-4-yl)methanol;

(232) (1-(2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)-4-methylpiperidin-4-yl)methanol;

(238) 2-(1-(Cyclopropylsulfonyl)-1H-pyrazol-4-yl)-N-(4-(((1r,4r)-4-((dimethylamino)methyl)cyclohexyl)methoxy)-5-((2-methylthiazol-4-yl)ethynyl)pyridin-2-yl)pyrimidin-4-amine;

(241) (1-(2-((2-(1-(Cyclopropylsulfonyl)-1H-pyrazol-4-yl)pyrimidin-4-yl)amino)-5-((1-((tetrahydro-2H-pyran-3-yl)methyl)-1H-pyrazol-4-yl)ethynyl)pyridin-4-yl)-4-methylpiperidin-4-yl)methanol;

(242) (1-(5-((1-((1,4-Dioxan-2-yl)methyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(243) (1-(2-((2-(1-(Cyclopropylsulfonyl)-1H-pyrazol-4-yl)pyrimidin-4-yl)amino)-5-((1-((tetrahydrofuran-3-yl)methyl)-1H-pyrazol-4-yl)ethynyl)pyridin-4-yl)-4-methylpiperidin-4-yl)methanol;

(244) (1-(2-((2-(1-(Cyclopropylsulfonyl)-1H-pyrazol-4-yl)pyrimidin-4-yl)amino)-5-((1-(tetrahydrofuran-3-yl)-1H-pyrazol-4-yl)ethynyl)pyridin-4-yl)-4-methylpiperidin-4-yl)methanol;

(245) (1-(2-((2-(1-(Cyclopropylsulfonyl)-1H-pyrazol-4-yl)pyrimidin-4-yl)amino)-5-((1-(oxetan-3-yl)-1H-pyrazol-4-yl)ethynyl)pyridin-4-yl)-4-methylpiperidin-4-yl)methanol;

(248) (1-(2-((2-(1-(Cyclopropylsulfonyl)-1H-pyrazol-4-yl)pyrimidin-4-yl)amino)-5-((5-((3,3-difluoroazetidin-1-yl)methyl)-1-(2,2-difluoroethyl)-1H-pyrrol-3-yl)ethynyl)pyridin-4-yl)-4-methylpiperidin-4-yl)methanol;

(253) (1-(2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol;

(254) (1-(2-((2-(1-(Cyclopropylsulfonyl)-1H-pyrazol-4-yl)pyrimidin-4-yl)amino)-5-((4-((dimethylamino)methyl)phenyl)ethynyl)pyridin-4-yl)-4-methylpiperidin-4-yl)methanol;

(255) (1-(2-((2-(1-(Cyclopropylsulfonyl)-1H-pyrazol-4-yl)pyrimidin-4-yl)amino)-5-((3-((dimethylamino)methyl)phenyl)ethynyl)pyridin-4-yl)-4-methylpiperidin-4-yl)methanol;

(258) (1-(2-((2-(1-(Cyclopropylsulfonyl)-1H-pyrazol-4-yl)pyrimidin-4-yl)amino)-5-(pyridin-4-ylethynyl)pyridin-4-yl)-4-methylpiperidin-4-yl)methanol;

(260) (1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-yl)methanol;

(261) (3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(262) 4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylbenzamide;

(263) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(264) 6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylpicol inamide;

(266) 2-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutyl)propan-2-ol;

(274) 4-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol;

(276) (1-(2-((2-(1-(Cyclopropylsulfonyl)-1H-pyrazol-4-yl)pyrimidin-4-yl)amino)-5-(4-fluorobut-1-yn-1-yl)pyridin-4-yl)-4-methylpiperidin-4-yl)methanol;

(277) (1-(5-(But-3-en-1-yn-1-yl)-2-((2-(1-cyclopropylsulfonyl)-1H-pyrazol-4-yl)pyrimidin-4-yl)amino)pyridin-4-yl)-4-methylpiperidin-4-yl)methanol;

(278) (1-(2-((2-(1-(Cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol;

(279) (1-(2-((2-(1-(Cyclopropylsulfonyl)-1H-pyrazol-4-yl)pyrimidin-4-yl)amino)-5-((6-((4-methylpiperazin-1-yl)methyl)pyridin-3-yl)ethynyl)pyridin-4-yl)-4-methylpiperidin-4-yl)methanol;

(280) 1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-ol;

(283) 2-(1-(Cyclopropylsulfonyl)-1H-pyrazol-4-yl)-N-(5-(pyridin-3-ylethynyl)-4-(1-oxa-7-azaspiro[3.5]nonan-7-yl)pyridin-2-yl)pyrimidin-4-amine;

(284) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)-2-methylpent-4-yn-2-ol;

(287) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)pent-4-yn-2-ol;

(288) N-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)-2,2,2-trifluoroacetamide;

(294) 2-(1-(Cyclopropylsulfonyl)-1H-pyrazol-4-yl)-N-(4-(4-(2-(dimethylamino)ethyl)piperidin-1-yl)-5-((1-methyl-1H-pyrazol-4-yl)ethynyl)pyridin-2-yl)pyrimidin-4-amine formate;

(305) (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol;

(306) (1R,3S)-3-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclopentan-1-ol;

(308) ((1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)cyclohexyl)methanol;

(309) 5-((1-(Cyclopropylmethyl)-1H-pyrazol-4-yl)ethynyl)-$N^2$-(2-(1-(cyclopropylsulfonyl)-1H-pyrazol-4-yl)pyrimidin-4-yl)-$N^4$-((1s, 4s)-4-((dimethylamino)methyl)cyclohexyl)pyridine-2,4-diamine;

(310) N²-(2-(1-(Cyclopropylsulfonyl)-1H-pyrazol-4-yl)pyrimidin-4-yl)-5-((1-(difluoromethyl)-1H-pyrazol-4-yl)ethynyl)-N⁴-((1s, 4s)-4-((dimethylamino)methyl)cyclohexyl)pyridine-2,4-diamine;

(3H) N²-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N⁴-((1s,4s)-4-((dimethylamino)methyl)cyclohexyl)pyridine-2,4-diamine;

(312) N²-(2-(1-(Cyclopropylsulfonyl)-1H-pyrazol-4-yl)pyrimidin-4-yl)-N²-((1s,4s)-4-((dimethylamino)methyl)cyclohexyl)-5-((1-methyl-1H-pyrazol-4-yl)ethynyl)pyridine-2,4-diamine;

(313) 5-((1-Cyclopropyl-1H-pyrazol-4-yl)ethynyl)-N²-(2-(1-(cyclopropylsulfonyl)-1H-pyrazol-4-yl)pyrimidin-4-yl)-N⁴-((1 s, 4s)-4-((dimethylamino)methyl)cyclohexyl)pyridine-2,4-diamine;

(314) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-((1-(trifluoromethyl)-1H-pyrazol-4-yl)ethynyl)pyridine-2,4-diamine;

(324) ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol;

(327) ((1s,4S)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol;

(339) (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol;

(340) ((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)methanol;

(342) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-fluoropiperidin-4-yl)methanol;

(347) 7-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-2-methyl-7-azaspiro[3.5]nonan-2-ol;

(348) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-methylpiperidin-4-yl)methanol;

(352) (1-(2-((2-(1-(Cyclopropylsulfonyl)-1H-pyrazol-4-yl)pyrimidin-4-yl)amino)-5-(oxetan-3-ylethynyl)pyridin-4-yl)-4-methylpiperidin-4-yl)methanol;

(353) (1s,4s)-4-((2-((2-(1-(Cyclopropylsulfonyl)-1H-pyrazol-4-yl)pyrimidin-4-yl)amino)-5-(oxetan-3-ylethynyl)pyridin-4-yl)amino)cyclohexan-1-ol;

(358) (1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-yl)methanol;

(360) ((1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol;

(368) 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-ol;

(374) ((1 s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexyl)methanol;

(376) (1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexan-1-ol;

(378) (1-(2-((2-(1-(Cyclopropylsulfonyl)-1H-pyrazol-4-yl)pyrimidin-4-yl)amino)-5-((tetrahydrofuran-2-yl)ethynyl)pyridin-4-yl)-4-methylpiperidin-4-yl)methanol;

(379) ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol;

(396) 2-(1-(Cyclopropylsulfonyl)-1H-pyrazol-4-yl)-N-(4-(3-(2-(dimethylamino)ethyl)piperidin-1-yl)-5-((1-methyl-1H-pyrazol-4-yl)ethynyl)pyridin-2-yl)pyrimidin-4-amine;

(397) ((1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexyl)methanol;

(399) (1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexan-1-ol;

(401) (1-(2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)-4-methylpiperidin-4-yl)methanol;

(402) ((l s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexyl)methanol;

(404) 1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-ol;

(407) 2-(1-(Cyclopropylsulfonyl)-1H-pyrazol-4-yl)-N-(4-(4-(2-(dimethylamino)ethyl)piperidin-1-yl)-5-((1-methylcyclopropyl)ethynyl)pyridin-2-yl)pyrimidin-4-amine;

(408) 1-(3-((6-((2-(1-(Cyclopropylsulfonyl)-1H-pyrazol-4-yl)pyrimidin-4-yl)amino)-4-(((1 s,4s)-4-(hydroxymethyl)cyclohexyl)amino)pyridin-3-yl)ethynyl)pyrrolidin-1-yl)-2,2,2-trifluoroethan-1-one;

(422) ((1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexyl)methanol;

(427) (1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(430) ((1s,4s)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexyl)methanol;

(433) (1s,4s)-4-((2-((2-(1-(cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexan-1-ol;

(442) (4-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)phenyl)(4-hydroxypiperidin-1-yl)methanone;

(446) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(4-hydroxypiperidin-1-yl)methanone; and (447) (S)-1-2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)-3-methylpiperidin-3-ol.

Further preferable representative compounds of Formula (I) are listed below:

(6) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol;

(10) 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol;

(12) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol;

(13) 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol;

(18) $N^2$-(2-(1-(Cyclopropylsulfonyl)-1H-pyrazol-4-yl)pyrimidin-4-yl)-$N^4$-isopropyl-5-((1-methyl-1H-pyrazol-4-yl)ethynyl)pyridine-2,4-diamine;

(19) $N^2$-(2-(1-(Cyclopropylsulfonyl)-1H-pyrazol-4-yl)pyrimidin-4-yl)-$N^4$-isopropyl-5-((1-isopropyl-1H-pyrazol-4-yl)ethynyl)pyridine-2,4-diamine;

(20) $N^2$-(2-(1-(Cyclopropylsulfonyl)-1H-pyrazol-4-yl)pyrimidin-4-yl)-5-((1-(2-fluoroethyl)-1H-pyrazol-4-yl)ethynyl)-$N^4$-isopropylpyridine-2,4-diamine;

(27) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol;

(30) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol;

(35) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol;

(39) 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)-2,2-dimethyl-propan-1-ol;

(41) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(43) (1S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(47) (1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(49) (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol;

(73) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol;

(82) 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol;

(85) (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol;

(101) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(126) 2-(1-(Cyclopropylsulfonyl)-1H-pyrazol-4-yl)-N-(4-(4-((2,2-difluoroethyl)amino)piperidin-1-yl)-5-((1-methyl-1H-pyrazol-4-yl)ethynyl)pyridin-2-yl)pyrimidin-4-amine;

(129) 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine;

(157) (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(260) (1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-yl)methanol;

(305) (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol;

(324) ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol;

(327) ((1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol;

(360) ((1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol; and (379) ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol.

Further more preferable representative compounds of Formula (I) are listed below:

(6) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol;

(10) 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol;

(12) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol;

(13) 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol;

(35) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol;

(47) (1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(49) (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol;

(101) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(126) 2-(1-(Cyclopropylsulfonyl)-1H-pyrazol-4-yl)-N-(4-(4-((2,2-difluoroethyl)amino)piperidin-1-yl)-5-((1-methyl-1H-pyrazol-4-yl)ethynyl)pyridin-2-yl)pyrimidin-4-amine; and (129) 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine.

Single stereochemical isomers, enantiomers, diastereomers, and pharmaceutically acceptable salts of the above exemplified compounds are also within the scope of the present invention. Pharmaceutically acceptable salts may be, for example, derived from suitable inorganic and organic acids and bases.

Acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+(C_{1-4}alkyl)_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

The compounds of the present invention may be synthesized by methods known in the art or by methods illustrated in Examples 1-449 below.

Pharmaceutical Compositions, Methods and Use

In one embodiment, the present invention relates to a method for treating protein kinase-mediated disease in a subject in need thereof, comprising administering to said subject a therapeutically effective amount of a compound of Formula (I) or a pharmaceutically acceptable salt, diastereomers, enantiomers, racemates, tautomers, prodrugs, hydrates, or solvates thereof In specific embodiment, the protein kinase-mediated disease is a cancer or immune disease.

As used herein, the term "cancer" refers to an abnormal growth of cells which tend to proliferate in an uncontrolled way and, in some cases, to metastasize. The types of cancer include, but is not limited to, solid tumors, such as those of the bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, or other endocrine organ (thyroid cancer), prostate cancer, skin (melanoma) or hematological tumors (such as the leukemias). In another embodiment, the cancer is non-small cell lung cancer (NSCLC).

In one embodiment, the method disclosed herein relates to treatment of cancer, wherein the cancer results from at least one mutation of EGFR.

In one embodiment, the method of treatment of cancer is particularly useful for patient who is resistant to a kinase inhibitor other that a compound of the invention, or a pharmaceutically acceptable salt, solvate, ester, or prodrug thereof. In another embodiment, the kinase inhibitor is a mutated EGFR inhibitor.

The invention also relates to a method for inhibiting at least one mutant of EGFR selectively as compared to wild type EGFR, in biological sample or in a patient, comprising contacting the biological sample with or administering to the patient a compound to the patient a therapeutically effective amount of a compound of the invention, or a pharmaceutically acceptable salt thereof.

In one embodiment, the at least one mutant is at least one single mutant selected from Table 1 shown below.

In one embodiment, the at least one mutant is at least one double mutant selected from Table 1 shown below.

In one embodiment, the at least one mutant is at least one triple mutant selected from Table 1 shown below.

TABLE 1

| Number (#) | Mutation type |
| --- | --- |
| 1 | EGFR Del19 (Del E746-A750) |
| 2 | EGFR L858R |
| 3 | EGFR Del19/T790M |
| 4 | EGFR Del19/C797S |
| 5 | EGFR Del19/C797X (X = G, N) |
| 6 | EGFR Del19/L792X (X = F, H, P, R, V, Y) |
| 7 | EGFR Del19/L718X (X = Q, V) |
| 8 | EGFR L858R/T790M |
| 9 | EGFR L858R/C797S |
| 10 | EGFR L858R/C797X (X = G, N) |
| 11 | EGFR L858R/L792X (X = F, H, P, R, V, Y) |
| 12 | EGFR L858R/L718X (X = Q, V) |
| 13 | EGFR Del19/T790M/C797S |
| 14 | EGFR Del19/T790M/C797X (X = G, N) |
| 15 | EGFR Del19/T790M/L792X (X = F, H, P, R, V, Y) |
| 16 | EGFR Del19/T790M/L718X (X = Q, V) |
| 17 | EGFR L858R/T790M/C797S |
| 18 | EGFR L858R/T790M/C797X (X = G, N) |
| 19 | EGFR L858R/T790M/L792X (X = F, H, P, R, V, Y) |
| 20 | EGFR L858R/T790M/L718X (X = Q, V) |

The invention further relates to therapeutic methods and uses comprising administering the compounds of the invention, or a pharmaceutically acceptable salt, diastereomers, enantiomers, racemates, tautomers, prodrugs, hydrates, or solvates thereof alone or in combination with other therapeutic or palliative agents.

A further embodiment of the invention relates to a compound of the invention for use as a medicament, and in particular for use in the treatment of diseases where the inhibition of mutated EGFR protein (e.g., those described in Table 1) activity may induce benefit, such as cancer. A still further embodiment of the present invention relates to the use of the compounds of the invention, or a pharmaceutically acceptable salt, diastereomers, enantiomers, racemates, tautomers, prodrugs, hydrates, or solvates thereof, for the manufacture of a drug having an EGFR inhibitory activity for the treatment of EGFR mediated diseases and/or conditions, in particular the diseases and/or conditions listed above.

The term "therapeutically effective amount" refers to that amount of a compound being administered which will relieve to some extert one or more of the symptoms of the disorder being treated. Regarding the treatment of cancer, a therapeutically effective amount refers to that amount which has the effect of reducing the size of the tumor, inhibiting (i.e., slowing or stopping) tumor metastases, inhibiting (i.e.

slowing or stopping) tumor growth or tumor invasiveness, and/or relieving to some extert one or more signs or symptoms related to the cancer.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

The term "treating", as used herein, unless otherwise indicated, means reversing, alleviating, inhibiting the progress of, or preventing the disorder or condition to which such term applies, or one or more symptoms of such disorder or condition. The term "treatment" also refers to the act of treating as "treating" is defined immediately above. The term "treating" also includes adjuvant treatment of a mammal.

As used herein, the term "subject" or "patient" encompasses mammals and nonmammals. Examples of mammals include, but are not limited to, humans, chimpanzees, apes monkeys, cattle, horses, sheep, goats, swine; rabbits, dogs, cats, rats, mice, guineapigs, and the like. Examples of non-mammals include, but are not limited to, birds, fish and the like.

As used herein, the term "biological sample" encompasses cells, tissues, and body fluids obtained (isolated) from mammals, such as humans (e.g., patients having cancers) or nonmammals exemplified hereinabove, and cultures thereof.

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Also provided herein, in other aspects, is a pharmaceutical composition comprising a compound oft Formula (I), a pharmaceutically acceptable salt, diastereomers, enantiomers, racemates, tautomers, prodrugs, hydrates, or solvates thereof as an active ingredient, and pharmaceutically acceptable excipients. In one embodiment, the pharmaceutical composition is for treating a protein kinase-mediated disease. In another embodiment, the pharmaceutical composition is for selectively inhibiting at least one mutant of EGFR as compared to wild type EGFR.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid.

Examples of carriers, excipients and diluents that can be included in the composition, may include lactose, dextrose, sucrose, sorbitol, mannitol, xylitol, erythritol, maltitol, starch, arabic gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil, but are not limited thereto. When formulated into a preparation, a diluting agent or an excipient, such as commonly-used fillers, stabilizing agents, binding agents, disintegrating agents, and surfactants can be used. Solid preparations for oral administration include tablets, pills, powders, granules, capsules, and the like, and these solid preparations may be prepared by mixing the compound of the present invention with at least one excipient, for example, starch, microcrystalline cellulose, sucrose, lactose, low-substituted hydroxypropyl cellulose, hypromellose or the like. In addition to the simple excipient, a lubricant such as magnesium stearate and talc are also used. Liquid preparations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used. In order to formulate the formulation for parenteral administration, the compound of Formula I or a pharmaceutically acceptable salt thereof may be mixed in water together with sterilized and/or contain adjuvants such as preservatives, stabilizers, auxiliary agents such as wettable powder or emulsifying accelerators, salt for controlling osmotic pressure and/or buffers and the like, and other therapeutically useful substances, to prepare a solution or suspension, which is then manufactured in the form of an ampoule or vial unit administration.

General Reaction Scheme and Summary of the Synthesis Route

The present invention includes, within its scope, a process for preparing a compound of formula (I) or a pharmaceutically acceptable salt thereof, in accordance with the following Scheme 1:

Scheme 1.

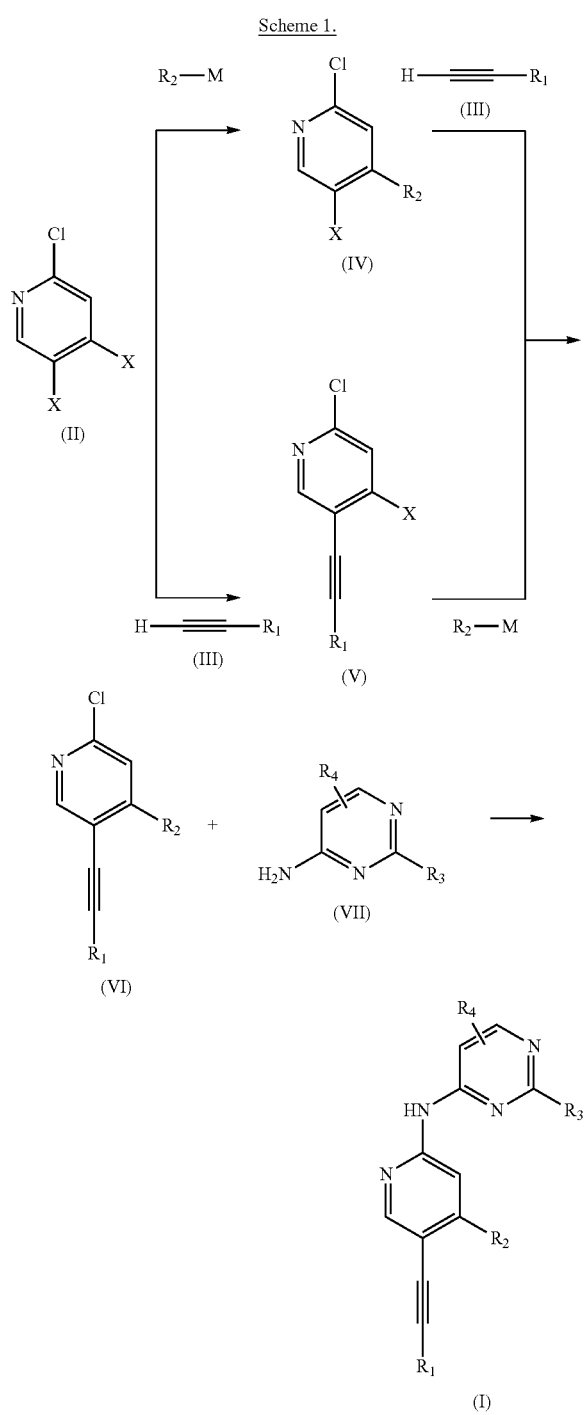

wherein, $R_1$, $R_2$, $R_3$, and $R_4$ are the same as defined in the above; X is halogen; and M is hydrogen, $B(OH)_2$ or BPin.

Specifically, the compound of formula (I) or its pharmaceutically acceptable salt may be prepared using a process which comprises: reacting a compound of formula (II) with $R_2$-M to obtain a compound of formula (IV), reacting the compound of formula (IV) with a compound of formula (III) to obtain a compound of formula (VI), and reacting the compound of formula (VI) with a compound of formula (VII) to obtain a compound of formula (I).

In the processes of Scheme 1, the compounds of formula (II), (III), (VII) and $R_2$-M are commercially available. The reaction of the compound of formula (II) and $R_2$-M may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that M is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that M is $B(OH)_2$ or BPin, the reaction may be carried out in an anhydrous organic solvent, e.g., THF, 1,4-dioxane, etc. under heating, e.g. at a temperature of 40-120° C.

The compound of formula (IV) is coupled with a compound of formula (III) to obtain a compound of formula (VI) by Sonogashira reaction. The reaction of the compound of formula (IV) and (III) may be performed in the presence of a base such as TEA, diethylamine, etc. and a palladium complex and a copper(I) halide such as $PdCl_2(PPh_3)_2$, $Pd(PPh_3)_4$, copper(I) iodide, etc. as catalysts. Further, the reaction may be carried out in an organic solvent, e.g., TEA or DMF, etc. at room temperature or under heating, e.g. at a temperature of 40-100° C.

Alternately, the compound of formula (VI) may be obtained by reacting a compound of formula (II) with a compound of formula (III) to obtain a compound of formula (V) and reacting a compound of formula (V) with $R_2$-M.

The compound of formula (II) is coupled with a compound of formula (III) to obtain a compound of formula (V) by Sonogashira reaction. The reaction of the compound of formula (II) and (III) may be performed in the presence of a base such as TEA, diethylamine, etc. and a palladium complex and a copper(I) halide such as $PdCl_2(PPh_3)_2$, $Pd(PPh_3)_4$, copper(I) iodide, etc. as catalysts. Further, the reaction may be carried out in an organic solvent, e.g., TEA or DMF, etc. at room temperature or under heating, e.g. at a temperature of 40-100° C.

The reaction of the compound of formula (V) and $R_2$-M may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that M is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that M is $B(OH)_2$ or BPin, the reaction may be carried out in an anhydrous organic solvent, e.g., THF, 1,4-dioxane, etc. under heating, e.g. at a temperature of 40-120° C.

The compound of formula (VI) is coupled with a compound of formula (VII) to obtain a compound of formula (I) by Buchwald-Hartwig reaction. The reaction of the compound of formula (VI) and (VII) may be performed in the presence of a base such as sodium carbonate potassium carbonate, cesium carbonate, etc. Further, the reaction may be performed in the presence of a palladium catalyst such as $Pd(OAc)_2$, $Pd_2(dba)_3$, $Pd(PPh_3)_4$, $Pd(dppf)Cl_2$, BrettPhos Pd G1 methyl t-butyl ether adduct etc. and a ligand such as BINAP, SPhos, XPhos, Xantphos, BrettPhos, etc. Further, the reaction may be carried out in an anhydrous organic solvent, e.g., 1,4-dioxane or toluene under heating, e.g. at a temperature of 80-120° C.

In accordance with another aspect of the present invention, the compound of formula (I) or its pharmaceutically acceptable salt may be prepared in accordance with the following Scheme 2:

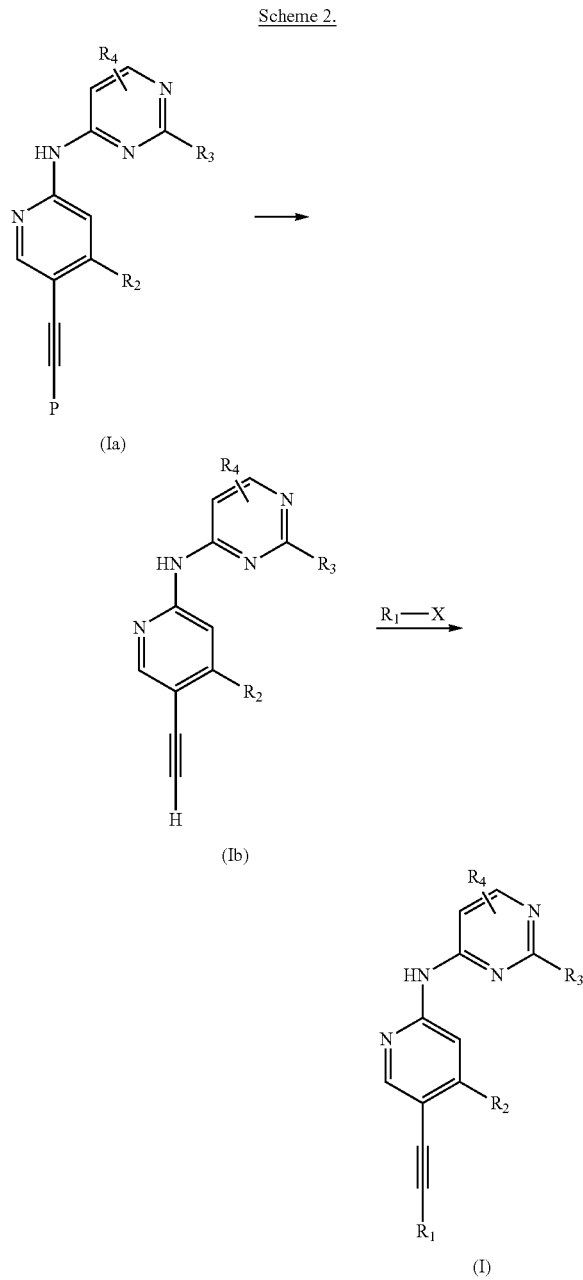

wherein, $R_1$ is A-$(R_{1A})_n$, and P is a trialkylsilyl protecting group such as TMS, TES, TBS, TIPS, TBDMS, etc. A, $R_{1A}$, $R_2$, $R_3$, $R_4$, and m are the same as defined in the above; X is halogen.

Specifically, the compound of formula (I) or its pharmaceutically acceptable salt may be prepared using a process which comprises: removing a protecting group from a compound of formula (Ia) to obtain a compound of formula (Ib) and reacting a compound of formula (Ib) and $R_1$—X to obtain a compound of formula (I).

The trialkylsilyl protecting group of the compound of formula (Ia) may be removed in the presence of a base, such as potassium carbonate or a fluorinated reagent, such as TBAF. Further, the reaction may be carried out in an anhydrous organic solvent, e.g., THF, DCM, or MeOH at room temperature or under heating.

The compound of formula (Ib) is coupled with $R_1$—X to obtain a compound of formula (I) by Sonogashira reaction. The reaction of the compound of formula (Ib) and $R_1$—X may be performed in the presence of a base such as TEA, diethylamine, etc. and a palladium complex and a copper(I) halide such as $PdCl_2(PPh_3)_2$, $Pd(PPh_3)_4$, copper(I) iodide, etc. as catalysts. Further, the reaction may be carried out in an organic solvent, e.g., TEA or DMF, etc. at room temperature or under heating, e.g. at a temperature of 40-100° C.

Alternately, the compound of formula (VII) may be obtained by reacting a compound of formula (VIII) with a compound of formula $R_3$-M. in accordance with the following Scheme 3:

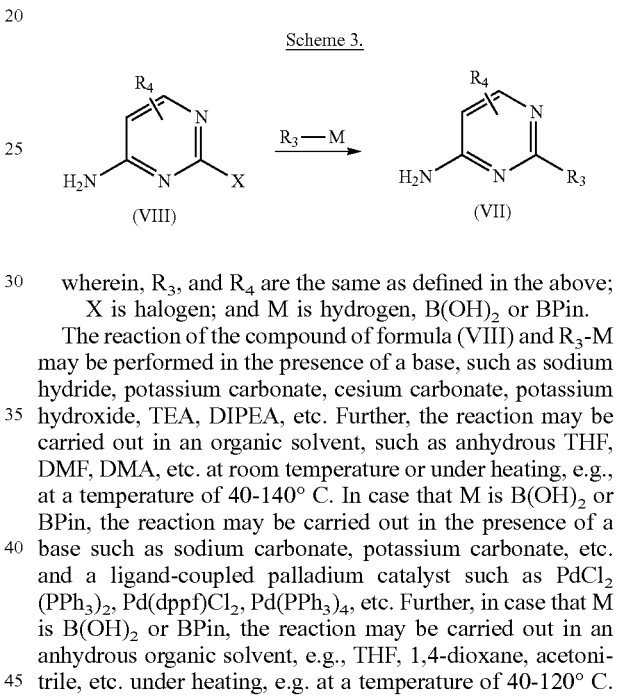

wherein, $R_3$, and $R_4$ are the same as defined in the above; X is halogen; and M is hydrogen, $B(OH)_2$ or BPin.

The reaction of the compound of formula (VIII) and $R_3$-M may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. at room temperature or under heating, e.g., at a temperature of 40-140° C. In case that M is $B(OH)_2$ or BPin, the reaction may be carried out in the presence of a base such as sodium carbonate, potassium carbonate, etc. and a ligand-coupled palladium catalyst such as $PdCl_2(PPh_3)_2$, $Pd(dppf)Cl_2$, $Pd(PPh_3)_4$, etc. Further, in case that M is $B(OH)_2$ or BPin, the reaction may be carried out in an anhydrous organic solvent, e.g., THF, 1,4-dioxane, acetonitrile, etc. under heating, e.g. at a temperature of 40-120° C.

EXAMPLES

The present invention is further exemplified by the following Examples that illustrate the preparation of compounds of Formula (I) according to the invention. The Examples are for illustrative purpose only and are not intended, nor should they be construed as limiting the invention in any manner. Those skilled in the art will appreciate that variations and modifications can be made without changing the scope of the invention.

The analyses of the compounds prepared in the following Examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+(ESI-MS (cation), which is represented by the [M+H]+peak). Column chromatography was carried out on silica gel (Merck, 70-230 mesH) (W. C. Still, J. Org. Chem., 43, 2923, 1978). Further, the starting materials in each Example are known compounds, which were synthesized according to literatures or obtained from the market such as Sigma-Aldrich. Further, the abbreviations used in the following Examples are as follows:

TABLE 2

List of abbreviations are hereinbelow:

| | |
|---|---|
| 2-BuOH | sec-butyl alcohol |
| AcOH | Acetic acid |
| $Cs_2CO_3$ | Cesium carbonate |
| CuI | Copper(I) iodide |
| DCE | 1,2-Dichloroethane |
| DCM | Methylene chloride |
| DIPEA | N,N-Diisopropylethylamine |
| DMA | N,N-Dimethylacetamide |
| DMEN | N,N-Dimethylethylenediamine |
| DMF | N,N-Dimethylformamide |
| DMSO | Dimethyl sulfoxide |
| EA | Ethyl acetate |
| $K_2CO_3$ | Potassium carbonate |
| MeCN | Acetonitrile |
| MeOH | Methanol |
| $MgSO_4$ | Magnesium sulfate |
| $NaBH(OAc)_3$ | Sodium triacetoxyborohydride |
| NaH | Sodium hydride |
| n-Hex | n-Hexane |
| NMP | N-Methyl-2-pyrrolidone |
| $Pd(dppf)Cl_2$ | [1,1'-Bis(diphenylphosphino)ferrocene]dichloropalladium(II) |
| $Pd(PPh_3)_4$ | Tetrakis(triphenylphosphine)palladium(0) |
| $Pd_2(dba)_3$ | Tris(dibenzylideneacetone)dipalladium(0) |
| $PdCl_2(PPh_3)_2$ | Bis(triphenylphosphine)palladium(II) dichloride |
| $PPh_3$ | Triphenylphosphine |
| sat. $NH_4Cl$ soln. | saturated ammonium chloride solution |
| sat. $NaHCO_3$ soln. | saturated sodium bicarbonate solution |
| TEA | Triethylamine |
| TFA | Trifluoroacetic acid |
| THF | Tetrahydrofuran |
| TMA | Trimethylamine |
| XPhos | [2-Dicyclohexylphosphino-2',4',6'-triisopropylbiphenyl] |

Reference Example 1.
N-(sec-Butyl)-2-chloro-5-iodopyridin-4-amine

The suspension of 2-chloro-5-iodo-pyridin-4-amine (1.00 g, 3.930 mmol), 2-iodobutane (0.54 mL, 4.716 mmol), and $Cs_2CO_3$ (2.56 g, 7.680 mmol) in 1,4-dioxane (10 mL) was stirred at 80° C. overnight. The reaction mixture was cooled, diluted in EA, washed by water, dried over $MgSO_4$, and then concentrated. The crude product was purified by column chromatography (EA/n-Hex=0-10%) to yield N-(sec-butyl)-2-chloro-5-iodopyridin-4-amine (134 mg) as a light yellow oil. MS (ESI) m/z=311.0 (M+H)+

Reference Example 2.1-(2-Chloro-5-iodopyridin-4-yl)piperidin-4-ol

The suspension of 2,4-dichloro-5-iodopyridine (400 mg, 1.46 mmol), 4-hydroxypiperidine (221 mg, 2.191 mmol), and DIPEA (0.51 mL, 2.921 mmol) in DMA (7 mL) was stirred at 100° C. overnight. After the reaction mixture was cooled, diluted in EA, washed by water, dried over $MgSO_4$, and then concentrated. The crude product was purified by column chromatography MeOH/DCM=0-15%) to yield 1-(2-chloro-5-iodopyridin-4-yl)piperidin-4-ol (468 mg) as a yellow solid. MS (ESI) m/z=339.0 (M+H)+

Reference Example 3. (1-(2-Chloro-5-iodopyridin-4-yl)piperidin-4-yl)methanol The title compound as a solid (458 mg) was prepared in the same fashion as Reference Example 2 except that 4-piperidinemethanol (252 mg, 2.191 mmol) was used instead of 4-hydroxypiperidine. MS (ESI) m/z=353.0 (M+H)+

Reference Example 4. (R)-1-(2-Chloro-5-iodopyridin-4-yl)pyrrolidin-3-ol

The title compound as a solid (245.1 mg) was prepared in the same fashion as Reference Example 2 except that (R)-pyrrolidin-3-ol HCl (270 mg, 2.191 mmol) was used instead of 4-hydroxypiperidine. MS (ESI) m/z=325.0 (M+H)+

Reference Example 5. (1-(2-Chloro-5-iodopyridin-4-yl)pyrrolidin-3-yl)methanol The title compound as a solid (413 mg) was prepared in the same fashion as Reference Example 2 except that pyrrolidin-3-ylmethanol (221 mg, 2.191 mmol) was used instead of 4-hydroxypiperidine. MS (ESI) m/z=339.0 (M+H)+

Reference Example 6. 2-(1-(2-Chloro-5-iodopyridin-4-yl)azetidin-3-yl)propan-2-ol The title compound as a solid (261 mg) was prepared in the same fashion as Reference Example 2 except that 2-(azetidin-3-yl)propan-2-ol HCl(215 mg, 1.424 mmol) was used instead of 4-hydroxypiperidine. MS (ESI) m/z=353.0 (M+H)+

Reference Example 7. 2-((2-Chloro-5-iodopyridin-4-yl)(methyl)amino)ethan-1-ol The title compound as a solid (569 mg) was prepared in the same fashion as Reference Example 2 except that 2-(methylamino)ethanol (205 mg, 2.738 mmol) was used instead of 4-hydroxypiperidine. MS (ESI) m/z=313.0 (M+H)+

Reference Example 8. 3-((2-Chloro-5-iodopyridin-4-yl)amino)-2,2-dimethylpropan-1-ol The title compound as a solid (319 mg) was prepared in the same fashion as Reference Example 2 except that 3-amino-2,2-dimethyl-1-propanol (225 mg, 2.191 mmol) was used instead of 4-hydroxypiperidine. MS (ESI) m/z=341.0 (M+H)+

Reference Example 9. (1s,4s)-4-((2-chloro-5-iodopyridin-4-yl)amino)cyclohexan-1-ol The title compound as a solid (836 mg) was prepared in the same fashion as Reference Example 2 except that (1s,4s)-4-aminocyclohexan-1-ol HCl (1.06 g, 6.992 mmol) was used instead of 4-hydroxypiperidine. MS (ESI) m/z=353.0 (M+H)+

Reference Example 10. (1S,3S)-3-((2-Chloro-5-iodopyridin-4-yl)amino)cyclohexan-1-ol The title compound as a solid (790 mg) was prepared in the same fashion as Reference Example 2 except that (1S,3S)-3-aminocyclohexan-1-ol HCl(1S,3S)(1.06 g, 6.992 mmol) was used instead of 4-hydroxypiperidine. MS (ESI) m/z=353.0 (M+H)+

Reference Example 11. (1S,3R)-3-((2-Chloro-5-iodopyridin-4-yl)amino)cyclohexan-1-ol The title compound as a solid (953 mg) was prepared in the same fashion as Reference Example 2 except that (1S,3R)-3-aminocyclohexan-1-ol (805 mg, 6.992 mmol) was used instead of 4-hydroxypiperidine. MS (ESI) m/z=353.0 (M+H)+

Reference Example 12. (1-(2-Chloro-5-iodopyridin-4-yl)-4-methylpiperidin-4-yl)methanol The title compound as a solid (2.3 g) was prepared in the same fashion as Reference Example 2 except that (4-methylpiperidin-4-yl)methanol (1.30 g, 10.100 mmol) was used instead of 4-hydroxypiperidine. MS (ESI) m/z=366.9 (M+H)+

Reference Example 13. 2-Chloro-N-(4-((dimethylamino)methyl)benzyl)-5-iodopyridin-4-amine The title compound as a solid (756 mg) was prepared in the same fashion as Reference Example 2 except that 1-(4-(aminomethyl)phenyl)-N,N-dimethylmethanamine (539 mg, 3.286 mmol) was used instead of 4-hydroxypiperidine. MS (ESI) m/z=402.0 (M+H)+

Reference Example 14. 2-Chloro-5-iodo-4-isopropoxypyridine

To the suspension of 2,4-dichloro-5-iodo-pyridine (500 mg, 1.826 mmol) and NaH (109 mg, 2.738 mmol) in THE (10 mL), 2-propanol (131 mg, 2.191 mmol) was added. After the reaction mixture was stirred at room temperature for 2 hours, quenched with water, extracted with EA, dried over MgSO4, and then concentrated. The crude product was purified by column chromatography (EA/n-Hex=0-20%) to yield 2-chloro-5-iodo-4-isopropoxypyridine (270 mg) as an off-white solid. MS (ESI) m/z=298.0 (M+H)+

Reference Example 15. 4-(sec-Butoxy)-2-chloro-5-iodopyridine

The title compound as a solid (250 mg) was prepared in the same fashion as Reference Example 14 except that 2-butanol (162 mg, 2.191 mmol) was used instead of 2-propanol. MS (ESI) m/z=312.0 (M+H)+

Reference Example 16. 1-((1 r,4r)-4-(((2-Chloro-5-iodopyridin-4-yl)oxy)methyl)cyclohexyl)-N,N-dimethylmethanamine Step 1. tert-Butyl (((1r,4r)-4-(((2-chloro-5-iodopyridin-4-yl)oxy)methyl)cyclohexyl)methyl)carbamate The title compound as a solid (1.46 g) was prepared in the same fashion as Reference Example 14 except that tert-butyl (trans-4-hydroxymethylcyclohexylmethyl)-carbamate (3.20 g, 13.144 mmol) was used instead of 2-propanol. MS (ESI) m/z=481.0 (M+H)+

Step 2. 1-((1 r,4r)-4-(((2-Chloro-5-iodopyridin-4-yl) oxy)methyl)cyclohexyl)-N,N-dimethylmethanamine The 20% TFA in DCM (10 mL) solution of tert-butyl (((1r,4r)-4-(((2-chloro-5-iodopyridin-4-yl)oxy)methyl)cyclohexyl)methyl)carbamate (1.00 g, 2.080 mmol) prepared in Step 1 was stirred at room temperature overnight. The reaction mixture was quenched with sat. NaHCO3 soln., extracted with DCM, dried over MgSO4, and then concentrated. After the residue was dissolved with MeOH (10 mL), formaldehyde (4.65 mL, 62.400 mmol) and NaBH(OAc)3 (1.32 g, 6.240 mmol) were added. After the reaction mixture was stirred at 60° C. overnight, quenched with sat. NaHCO3soln., extracted with DCM, dried over MgSO4, and then concentrated. The crude product was purified by column chromatography (MeOH/DCM=0-10%) to yield 1-((1r, 4r)-4-(((2-chloro-5-iodopyridin-4-yl)oxy)methyl)cyclohexyl)-N,N-dimethylmethanamine (549 mg) as an off-white solid. MS (ESI) m/z=409.0 (M+H)+

Reference Example 17. tert-Butyl (1-(2-((2-(1-(cyclopropylsulfonyl)-1H-pyrazol-4-yl)pyrimidin-4-yl) amino)-5-((1-methyl-1H-pyrazol-4-yl)ethynyl)pyridin-4-yl)piperidin-4-yl)carbamate Step 1. tert-Butyl (1-(2-chloro-5-iodopyridin-4-yl) piperidin-4-yl)carbamate The title compound as a solid (1.65 g) was prepared in the same fashion as Reference Example 2 except that 4-(tert-butoxycarbonylamino)piperidine (1.42 g, 7.120 mmol) was used instead of 4-hydroxypiperidine. MS (ESI) m/z=438.0 (M+H)+

Step 2. tert-Butyl (1-(2-chloro-5-((1-methyl-1H-pyrazol-4-yl)ethynyl)pyridin-4-yl)piperidin-4-yl) carbamate The mixture of tert-butyl (1-(2-chloro-5-iodopyridin-4-yl)piperidin-4-yl)carbamate (1.5 g, 3.427 mmol) prepared in Step 1, 4-ethynyl-1-methylpyrazole (436 mg, 4.112 mmol), PdCl2(PPh3)2 (120 mg, 0.171 mmol), and CuI (130.6 mg, 0.685 mmol) was charged nitrogen gas for 10 minutes. After DMF (30 mL) and TEA (0.96 mL, 6.854 mmol) were added, the reaction mixture was stirred at 50° C. for 1 hour. The reaction mixture was cooled, diluted in EA, washed by water, dried over MgSO4, and then concentrated. The crude product was purified by column chromatography (MeOH/DCM=0-10%) to yield (11)))tert-butyl (1-(2-chloro-5-((1-methyl-1H-pyrazol-4-yl)ethynyl)pyridin-4-yl)piperidin-4-yl)carbamate (1.05 g) as a yellow solid. MS (ESI) m/z=416.2 (M+H)+

Step 3. tert-Butyl (1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)carbamate The suspension of 2-(1-cyclopropylsulfonylpyrazol-4-yl) pyrimidin-4-amine (428 mg, 1.615 mmol), tert-butyl (1-(2-chloro-5-((1-methyl-1H-pyrazol-4-yl)ethynyl)pyridin-4-yl) piperidin-4-yl)carbamate (590 mg, 1.468 mmol) prepared in Step 2, Cs2CO3 (956 mg, 2.936 mmol), XPhos (139 mg, 0.294 mmol), and Tris(dibenzylideneacetone)dipalladium (0) (134 mg, 0.147 mmol) in 1,4-dioxane (9 mL) was stirred at 90° C. for 4 hours. The reaction mixture was cooled, filtered through Celite, and then concentrated. The crude product was purified by column chromatography (EA/n-Hex=0-100%) to yield tert-butyl (1-(2-((2-(1-(cyclopropylsulfonyl)-1H-pyrazol-4-yl)pyrimidin-4-yl)amino)-5-((1- methyl-1H-pyrazol-4-yl)ethynyl)pyridin-4-yl)piperidin-4-yl)carbamate (372 mg) as an yellow solid. MS (ESI) m/z=645.3 (M+H)+

Reference Example 18. 2-Chloro-4-fluoro-5-((1-methyl-1H-pyrazol-4-yl)ethynyl)pyridine The mixture of 2-chloro-4-fluoro-5-iodopyridine (3.50 g, 13.600 mmol), 4-ethynyl-1-methylpyrazole (1.59 g, 14.956 mmol), $PdCl_2(PPh_3)_2$ (477 mg, 0.680 mmol), and CuI (518 mg, 2.719 mmol) was charged nitrogen gas for 10 minutes. After DMF (40 mL) and TEA (3.79 mL, 27.192 mmol) were added, the reaction mixture was stirred at 50° C. for 1 hour. The reaction mixture was cooled, diluted in EA, washed by water, dried over $MgSO_4$, and then concentrated. The crude product was purified by column chromatography (EA/n-Hex=0-40%) to yield 2-chloro-4-fluoro-5-((1-methyl-1H-pyrazol-4-yl)ethynyl)pyridine (2.00 g) as an off-white solid. $^1$H-NMR (CDCl$_3$, 600 MHz) δ 8.49 (d, 1H), 7.68 (s, 1H), 7.62 (s, 1H), 7.13 (d, 1H), 3.93 (s, 3H); MS (ESI) m/z=236.0 (M+H)+

Reference Example 19. 2-Chloro-5-((1-(2,2-difluorocyclopropyl)-1H-pyrazol-4-yl)ethynyl)-4-fluoropyridine The title compound as a solid (669.6 mg) was prepared in the same fashion as Reference Example 18 except that 1-(2,2-difluorocyclopropyl)-4-ethynylpyrazole (517 mg, 3.077 mmol) was used instead of 4-ethynyl-1-methylpyrazole. MS (ESI) m/z=298.0 (M+H)+

Reference Example 20. 2-Chloro-5-((5-cyclopropyl-1-methyl-1H-pyrazol-4-yl)ethynyl)-4-fluoropyridine The title compound as a solid (545 mg) was prepared in the same fashion as Reference Example 18 except that 5-cyclopropyl-4-ethynyl-1-methylpyrazole (449 mg, 3.077 mmol) was used instead of 4-ethynyl-1-methylpyrazole. MS (ESI) m/z=276.0 (M+H)+

Reference Example 21. 2-Chloro-4-fluoro-5-(2-(1-methyl-3-(trifluoromethyl)pyrazol-4-yl)ethynyl)pyridine The title compound as a solid (651 mg) was prepared in the same fashion as Reference Example 18 except that 4-ethynyl-1-methyl-3-(trifluoromethyl)pyrazole (535 mg, 3.077 mmol) was used instead of 4-ethynyl-1-methylpyrazole. MS (ESI) m/z=304.0 (M+FI)+

Reference Example 22. 2-Chloro-4-fluoro-5-((1-(tetrahydro-2H-pyran-4-yl)-1H-pyrazol-4-yl)ethynyl)pyridine The title compound as a solid (838 mg) was prepared in the same fashion as Reference Example 18 except that 4-ethynyl-1-tetrahydropyran-4-ylpyrazole (1.13 g, 6.410 mmol) was used instead of 4-ethynyl-1-methylpyrazole. MS (ESI) m/z=306.1 (M+H)+

Reference Example 23. 2-Chloro-4-fluoro-5-((1-(trifluoromethyl)-1H-pyrazol-4-yl)ethynyl)pyridine The title compound as a solid (460 mg) was prepared in the same fashion as Reference Example 18 except that 4-ethynyl-1-(trifluoromethyl)pyrazole (1.03 g, 6.410 mmol) was used instead of 4-ethynyl-1-methylpyrazole. MS (ESI) m/z=290.0 (M+H)+

Reference Example 24. 2-Chloro-4-fluoro-5-((1-methyl-1H-pyrazol-3-yl)ethynyl)pyridine The title compound as a solid (950 mg) was prepared in the same fashion as Reference Example 18 except that 3-ethynyl-1-methylpyrazole (680 mg, 6.410 mmol) was used instead of 4-ethynyl-1-methylpyrazole. MS (ESI) m/z=236.0 (M+H)+

Reference Example 25. 1-(4-(4-((6-Chloro-4-fluoropyridin-3-yl)ethynyl)-1H-pyrazol-1-yl)piperidin-1-yl)ethan-1-one Step 1. tert-Butyl 4-(4-((6-chloro-4-fluoropyridin-3-yl)ethynyl)-1H-pyrazol-1-yl)piperidine-1-carboxylate The title compound as a solid (3.20 g) was prepared in the same fashion as Reference Example 18 except that tert-butyl 4-(4-ethynylpyrazol-1-yl)piperidine-1-carboxylate (3.53 g, 12.819 mmol) was used instead of 4-ethynyl-1-methylpyrazole. MS (ESI) m/z=349.0 (M+H)+

Step 2. 1-(4-(4-((6-Chloro-4-fluoropyridin-3-yl)ethynyl)-1H-pyrazol-1-yl)piperidin-1-yl)ethan-1-one tert-Butyl 4-(4-((6-chloro-4-fluoropyridin-3-yl)ethynyl)-1H-pyrazol-1-yl)piperidine-1-carboxylate (1.00 g, 2.470 mmol) prepared in Step 1 was dissolved with 4.0 M HCl in 1,4-dioxane (10 mL) and stirred at 60° C. overnight. After the reaction mixture was concentrated, the residue was dissolved with DCM (10 mL). Acetyl chloride (1.1 mL, 7.410 mmol) and TEA (2.07 mL, 14.820 mmol) was added and the reaction mixture was stirred at room temperature for 3 hours. The mixture was washed with water, dried over $MgSO_4$, and then concentrated. The crude product was purified by column chromatography (EA/n-Hex=0-100%) to yield 1-(4-(4-((6-chloro-4-fluoropyridin-3-yl)ethynyl)-1H-pyrazol-1-yl)piperidin-1-yl)ethan-1-one (820 mg) as an yellow solid. MS (ESI) m/z=347.0 (M+H)+

Reference Example 26. 2-(4-((6-Chloro-4-fluoropyridin-3-yl)ethynyl)-1H-pyrazol-1-yl)-N,N-dimethylethan-1-amine Step 1. 2-(4-Ethynyl-1H-pyrazol-1-yl)-N,N-dimethylethan-1-amine The suspension of 4-ethynyl-1H-pyrazole (400 mg, 4.343 mmol), 2-iodo-N,N-dimethylethan-1-amine HCl (1.33 g, 5.646 mmol) and $Cs_2CO_3$ (4.25 g, 13.030 mmol) in DMA (40 mL) was stirred at 80° C. overnight. The reaction mixture was cooled, diluted with EA, washed with water, dried over $MgSO_4$, and then concentrated. The crude product was purified by column chromatography (MeOH/DCM=0-15%) to yield 2-(4-ethynyl-1H-pyrazol-1-yl)-N,N-dimethylethan-1-amine (545 mg) as a yellow oil. MS (ESI) m/z=164.1 (M+H)+

Step 2. 2-(4-((6-Chloro-4-fluoropyridin-3-yl)ethynyl)-1H-pyrazol-1-yl)-N,N-dimethylethan-1-amine The title compound as an oil (544 mg) was prepared in the same fashion as Reference Example 18 except that 2-(4- ethynyl-1H-pyrazol-1-yl)-N,N-dimethylethan-1-amine (532 mg, 3.263 mmol) prepared in Step 1 was used instead of 4-ethynyl-1-methylpyrazole. MS (ESI) m/z=293.0 (M+H)+

Reference Example 27. 3-(4-((6-Chloro-4-fluoropyridin-3-yl)ethynyl)-1H-pyrazol-1-yl)-N,N-dimethylpropan-1-amine

Step 1. 3-(4-Ethynyl-1H-pyrazol-1-yl)-N,N-dimethylpropan-1-amine

The title compound as an oil (583 mg) was prepared in the same fashion as Step 1 in Reference Example 26 except that 3-chloro-N,N-dimethylpropan-1-amine HCl (892 mg, 5.646 mmol) was used instead of 2-iodo-N,N-dimethylethan-1-amine HCl. MS (ESI) m/z=178.2 (M+H)+

Step 2. 3-(4-((6-Chloro-4-fluoropyridin-3-yl)ethynyl)-1H-pyrazol-1-yl)-N,N-dimethylpropan-1-amine The title compound as a solid (577 mg) was prepared in the same fashion as Reference Example 18 except that 3-(4-ethynyl-1H-pyrazol-1-yl)-N,N-dimethylpropan-1-amine (578 mg, 3.263 mmol) prepared in Step 1 was used instead of 4-ethynyl-1-methylpyrazole. MS (ESI) m/z=307.0 (M+H)+

Reference Example 28. 1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-one

Step 1. 1-(2-Chloro-5-((1-methyl-1H-pyrazol-3-yl)ethynyl)pyridin-4-yl)piperidin-4-one The suspension of 2-chloro-4-fluoro-5-((1-methyl-1H-pyrazol-3-yl)ethynyl)pyridine (300 mg, 1.273 mmol) prepared in Reference Example 24, piperidin-4-one HCl hydrate (293 mg, 1.91 mmol), and DIPEA (0.67 mL, 3.819 mmol) in DMA (7 mL) was stirred at 50° C. for 3 hours. The reaction mixture was cooled, diluted in EA, washed by water, dried over MgSO4, and then concentrated. The crude product was purified by column chromatography (MeOH/DCM=0-5%) to yield 1-(2-chloro-5-((1-methyl-1H-pyrazol-3-yl)ethynyl)pyridin-4-yl)piperidin-4-one (340 mg) as a yellow solid. MS (ESI) m/z=315.0 (M+H)+

Step 2. 1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-one The title compound as a solid (129 mg) was prepared in the same fashion as Step 3 in Reference Example 17 except that 1-(2-chloro-5-((1-methyl-1H-pyrazol-3-yl)ethynyl)pyridin-4-yl)piperidin-4-one (330 mg, 1.048 mmol) prepared in Step 1 was used instead of tert-butyl (1-(2-chloro-5-((1-methyl-1H-pyrazol-4-yl)ethynyl)pyridin-4-yl)piperidin-4-yl)carbamate. MS (ESI) m/z=544.0 (M+H)+

Reference Example 29. (1-(2-Chloro-5-((4,5,6,7-tetrahydropyrazolo[1,5-a]pyrazin-3-yl)ethynyl)pyridin-4-yl)-4-methylpiperidin-4-yl)methanol

Step 1. tert-Butyl 3-((6-chloro-4-(4-(hydroxymethyl)-4-methylpiperidin-1-yl)pyridin-3-yl)ethynyl)-6,7-dihydropyrazolo[1,5-a]pyrazine-5(4H)-carboxylate The title compound as a solid (550 mg) was prepared in the same fashion as Reference Example 18 except that tert-butyl 3-ethynyl-6,7-dihydropyrazolo[1,5-a]pyrazine-5(4H)-carboxylate (323 mg, 1.309 mmol) and (1-(2-chloro-5-iodopyridin-4-yl)-4-methylpiperidin-4-yl)methanol (400 mg, 1.091 mmol) prepared in Reference Example 12 were used instead of 4-ethynyl-1-methylpyrazole and 2-chloro-4-fluoro-5-iodopyridine. MS (ESI) m/z=486.0 (M+H)+

Step 2. (1-(2-Chloro-5-((4,5,6,7-tetrahydropyrazolo[1,5-a]pyrazin-3-yl)ethynyl)pyridin-4-yl)-4-methylpiperidin-4-yl)methanol The 20% TFA in DCM (5 mL) solution of tert-butyl 3-((6-chloro-4-(4-(hydroxymethyl)-4-methylpiperidin-1-yl)pyridin-3-yl)ethynyl)-6,7-dihydropyrazolo[1,5-a]pyrazine-5(4H)-carboxylate (800 mg, 1.646 mmol) prepared in Step 1 was stirred at room temperature. After the reaction mixture was concentrated, the residue was quenched by sat. NaHCO3 soln., extracted with DCM, dried over MgSO4, and then concentrated. The crude product was purified by column chromatography (MeOH/DCM=0-20%) to yield (1-(2-chloro-5-((4,5,6,7-tetrahydropyrazolo[1,5-a]pyrazin-3-yl)ethynyl)pyridin-4-yl)-4-methylpiperidin-4-yl)methanol (480 mg) as an off-white solid. MS (ESI) m/z=400.2 (M+H)+

Reference Example 30. 4-(4-((6-Chloro-4-fluoropyridin-3-yl)ethynyl)benzyl)morpholine The title compound as an off-white solid (2.16 g) was prepared in the same fashion as Reference Example 18 except that 4-(4-ethynylbenzyl)morpholine (1.50 g, 7.453 mmol) was used instead of 4-ethynyl-1-methylpyrazole. 1H-NMR (CDCl3, 400 MHz) δ 8.54-8.51 (d, 1H), 7.53-7.51 (d, 2H), 7.37-7.35 (d, 2H), 7.16-7.14 (d, 1H), 3.73-3.71 (t, 4H), 3.52 (s, 2H), 2.46-2.44 (t, 4H); MS (ESI) m/z=331.1 (M+H)+

Reference Example 31. 1-(4-((6-Chloro-4-fluoropyridin-3-yl)ethynyl)benzyl)-4-methylpiperazine The title compound as a solid (1.49 g) was prepared in the same fashion as Reference Example 18 except that 1-(4-ethynylbenzyl)-4-methylpiperazine (1.14 g, 5.34 mmol) was used instead of 4-ethynyl-1-methylpyrazole. MS (ESI) m/z=344.1 (M+H)+

Reference Example 32. 4-(3-(6-Chloro-4-fluoropyridin-3-yl)prop-2-yn-1-yl)morpholine The title compound as a solid (1169 mg) was prepared in the same fashion as Reference Example 18 except that 4-(2-propyn-1-yl)morpholine (668 mg, 5.341 mmol) was used instead of 4-ethynyl-1-methylpyrazole. MS (ESI) m/z=255.0 (M+H)+

Reference Example 33. 1-((6-Chloro-4-fluoropyridin-3-yl)ethynyl)cyclohexan-1-ol The title compound as an off-white solid (505 mg) was prepared in the same fashion as Reference Example 18 except that 1-ethynylcyclohexan-1-ol (300 mg, 2.416 mmol) was used instead of 4-ethynyl-1-methylpyrazole. 1H-NMR (CDCl3, 400 MHz) δ 8.42-8.40 (d, 1H), 7.10-7.08 (d, 1H), 3.24 (s, 1H), 2.01 (s, 1H), 1.74-1.62 (m, 5H), 1.59-1.47 (m, 4H); MS (ESI) m/z=254.1 (M+H)+

Reference Example 34. 1-((6-Chloro-4-fluoropyridin-3-yl)ethynyl)cyclopentan-1-ol The title compound as an off-white solid (447 mg) was prepared in the same fashion as Reference Example 18 except that 1-ethynylcyclopentan-1-ol (266 mg, 2.416 mmol) was used instead of 4-ethynyl-1-methylpyrazole. $^1$H-NMR (CDCl$_3$, 400 MHz) δ 8.40-8.37 (d, 1H), 7.07-7.05 (d, 1H), 3.56 (s, 1H), 2.04-1.95 (m, 2H), 1.89-1.88 (d, 2H), 1.86-1.72 (m, 4H); MS (ESI) m/z=240.1 (M+H)$^+$

Reference Example 35. 2-Chloro-4-fluoro-5-((tetrahydro-2H-pyran-4-yl)ethynyl)pyridine The title compound as an off-white solid (296 mg) was prepared in the same fashion as Reference Example 18 except that 4-ethynyltetrahydro-2H-pyran (200 mg, 1.816 mmol) was used instead of 4-ethynyl-1-methylpyrazole. $^1$H-NMR (CDCl$_3$, 400 MHz) δ 8.42-8.40 (d, 1H), 7.12-7.09 (d, 1H), 3.97-3.93 (m, 2H), 3.60-3.57 (m, 2H), 2.92-2.90 (t, 1H), 1.96-1.90 (m, 2H), 1.82-1.76 (m, 2H); MS (ESI) m/z=240.1 (M+H)$^+$

Reference Example 36. 2-Chloro-4-fluoro-5-((1-methylpyrrolidin-3-yl)ethynyl)pyridine The title compound as an off-white solid (131 mg) was prepared in the same fashion as Reference Example 18 except that 3-ethynyl-1-methylpyrrolidine HCl (228 mg, 1.566 mmol) was used instead of 4-ethynyl-1-methylpyrazole. $^1$H-NMR (CDCl$_3$, 400 MHz) δ 8.41-8.38 (q, 1H), 7.10-7.07 (q, 1H), 3.24 (d, 1H), 3.00-2.96 (q, 1H), 2.73-2.68 (q, 1H), 2.60-2.50 (m, 2H), 2.41-2.40 (d, 3H), 2.36-2.29 (q, 1H), 2.04-2.00 (q, 1H); MS (ESI) m/z=239.1 (M+H)$^+$

Reference Example 37. 4-((5-((6-Chloro-4-fluoropyridin-3-yl)ethynyl)thiophen-2-yl)methyl)morpholine The title compound as an off-white solid (261 mg) was prepared in the same fashion as Reference Example 18 except that 4-((5-ethynylthiophen-2-yl)methyl)morpholine (300 mg, 1.447 mmol) was used instead of 4-ethynyl-1-methylpyrazole. $^1$H-NMR (CDCl$_3$, 400 MHz) δ 8.49-8.46 (d, 1H), 7.19-7.18 (d, 1H), 7.14-7.12 (d, 1H), 6.83-6.82 (d, 1H), 3.71-3.70 (d, 4H), 3.69-3.67 (d, 2H), 2.49-2.48 (d, 4H); MS (ESI) m/z=337.0 (M+H)$^+$

Reference Example 38. 4-((6-((6-Chloro-4-fluoropyridin-3-yl)ethynyl)pyridin-3-yl)methyl)morpholine

Step 1. 4-((6-Ethynylpyridin-3-yl)methyl)morpholine

The reaction mixture of 6-ethynylpyridine-3-carbaldehyde (1.0 g, 7.626 mmol) and morpholine (664 mg, 7.626 mmol) in DCE (30 mL)/AcOH (0.1 mL) was stirred at room temperature for 30 mins. The reaction mixture was added NaBH(OAc)$_3$ (2.42 g, 11.439 mmol) and stirred at room temperature overnight. The reaction mixture was added sat. NaHCO$_3$ soln. extracted with DCM, washed by water, dried over MgSO$_4$, and then concentrated. The crude product was purified by column chromatography (EA/n-Hex=0-80%) to yield 4-((6-ethynyl-3-pyridyl)methyl)morpholine (1085 mg) as an off-white solid. $^1$H-NMR (CDCl$_3$, 400 MHz) δ 8.50 (d, 1H), 7.65-7.63 (q, 1H), 7.43-7.41 (d, 1H), 3.69-3.66 (t, 4H), 3.48 (s, 2H), 2.42-2.40 (t, 4H); MS (ESI) m/z=203.1 (M+H)$^+$

Step 2. 4-((6-((6-Chloro-4-fluoropyridin-3-yl)ethynyl)pyridin-3-yl)methyl)morpholine The title compound as an off-white solid (466 mg) was prepared in the same fashion as Reference Example 18 except that 4-((6-ethynylpyridin-3-yl)methyl)morpholine (485 mg, 2.398 mmol) prepared in Step 1 was used instead of 4-ethynyl-1-methylpyrazole. $^1$H-NMR (CDCl$_3$, 400 MHz) δ 8.57 (d, 1H), 7.73-7.70 (q, 1H), 7.67-7.62 (m, 1H), 7.54-7.51 (m, 1H), 7.47-7.44 (q, 1H), 7.17-7.15 (d, 1H), 3.71-3.68 (t, 4H), 3.53 (s, 2H), 2.45-2.43 (t, 4H); MS (ESI) m/z=332.0 (M+H)$^+$

Reference Example 39. 4-((5-((6-Chloro-4-fluoropyridin-3-yl)ethynyl)pyridin-2-yl)methyl)morpholine

Step 1. 4-((5-Ethynylpyridin-2-yl)methyl)morpholine

The title compound as an off-white solid (1.22 g) was prepared in the same fashion as Step 1 in Reference Example 38 except that 5-ethynylpicolinaldehyde (1.00 g, 7.626 mmol) was used instead of 6-ethynylpyridine-3-carbaldehyde. $^1$H-NMR (CDCl$_3$, 400 MHz) δ 8.68-8.67 (d, 1H), 7.76-7.73 (q, 1H), 7.41-7.39 (d, 1H), 3.75-3.73 (t, 4H), 3.66 (s, 2H), 3.20 (s, 1H), 2.52-2.49 (t, 4H); MS (ESI) m/z=203.1 (M+H)$^+$

Step 2. 4-((5-((6-Chloro-4-fluoropyridin-3-yl)ethynyl)pyridin-2-yl)methyl)morpholine The title compound as an off-white solid (658 mg) was prepared in the same fashion as Reference Example 18 except that 4-((5-ethynylpyridin-2-yl)methyl)morpholine (572 mg, 2.828 mmol) prepared in Step 1 was used instead of 4-ethynyl-1-methylpyrazole. MS (ESI) m/z=332.0 (M+H)$^+$

Reference Example 40. 4-((4-((6-Chloro-4-fluoropyridin-3-yl)ethynyl)thiazol-2-yl)methyl)morpholine

Step 1. 4-((4-Ethynylthiazol-2-yl)methyl)morpholine

The title compound as an off-white solid (1.42 g) was prepared in the same fashion as Step 1 in Reference Example 38 except that 4-ethynylthiazole-2-carbaldehyde (1.00 g, 7.291 mmol) was used instead of 6-ethynylpyridine-3-carbaldehyde. $^1$H-NMR (CDCl$_3$, 400 MHz) δ 7.49 (s, 1H), 3.83 (s, 2H), 3.75-3.73 (t, 4H), 3.11 (s, 1H), 2.61-2.59 (t, 4H); MS (ESI) m/z=209.0 (M+H)$^+$

Step 2. 4-((4-((6-Chloro-4-fluoropyridin-3-yl)ethynyl)thiazol-2-yl)methyl)morpholine The title compound as an off-white solid (491 mg) was prepared in the same fashion as Reference Example 18 except that 4-((4-ethynylthiazol-2-yl)methyl)morpholine (417 mg, 2.002 mmol) prepared in Step 1 was used instead of 4-ethynyl-1-methylpyrazole. $^1$H-NMR (CDCl$_3$, 400

MHz) δ 8.54-8.52 (d, 1H), 7.59 (s, 1H), 7.14-7.12 (d, 1H), 3.85 (s, 2H), 3.74-3.71 (t, 4H), 2.60-2.58 (t, 4H); MS (ESI) m/z=338.0 (M+H)⁺

Reference Example 41. 4-((2-((6-Chloro-4-fluoropyridin-3-yl)ethynyl)pyrimidin-5-yl)methyl)morpholine Step 1. 4-((2-Ethynylpyrimidin-5-yl)methyl)morpholine The title compound as an off-white solid (896 mg) was prepared in the same fashion as Step 1 in Reference Example 38 except that 2-ethynylpyrimidine-5-carbaldehyde (1.00 g, 7.569 mmol) was used instead of 6-ethynylpyridine-3-carbaldehyde. ¹H-NMR (CDCl₃, 400 MHz) δ 8.69 (s, 1H), 3.78-3.77 (d, 4H), 3.73-3.71 (t, 2H), 3.13 (s, 1H), 2.47-2.45 (t, 4H)

Step 2. 4-((2-((6-Chloro-4-fluoropyridin-3-yl)ethynyl)pyrimidin-5-yl)methyl)morpholine The title compound as an off-white solid (558 mg) was prepared in the same fashion as Reference Example 18 except that 4-((2-ethynylpyrimidin-5-yl)methyl)morpholine (365 mg, 1.752 mmol) prepared in Step 1 was used instead of 4-ethynyl-1-methylpyrazole. ¹H-NMR (CDCl₃, 400 MHz) δ 8.74-8.73 (d, 2H), 8.65-8.62 (q, 1H), 7.20-7.17 (q, 1H), 3.71-3.70 (d, 4H), 3.54 (s, 2H), 2.46 (s, 4H)

Reference Example 42. 4-((6-Chloro-4-fluoropyridin-3-yl)ethynyl)tetrahydro-2H-pyran-4-ol The title compound as an off-white solid (687 mg) was prepared in the same fashion as Reference Example 18 except that 4-ethynyltetrahydro-2H-pyran-4-ol (508 mg, 4.029 mmol) was used instead of 4-ethynyl-1-methylpyrazole. ¹H-NMR (CDCl₃, 400 MHz) δ 8.46-8.44 (d, 1H), 7.15-7.13 (d, 1H), 3.99-3.94 (m, 2H), 3.73-3.67 (m, 2H), 2.09-2.05 (q, 2H), 1.95-1.88 (m, 2H)

Reference Example 43. 2-Chloro-4-fluoro-5-((tetrahydrofuran-3-yl)ethynyl)pyridine The title compound as an off-white solid (723 mg) was prepared in the same fashion as Reference Example 18 except that 3-ethynyltetrahydrofuran (503 mg, 5.238 mmol) was used instead of 4-ethynyl-1-methylpyrazole. ¹H-NMR (CDCl₃, 400 MHz) δ 8.37-8.34 (d, 1H), 7.08-7.06 (d, 1H), 4.10-4.03 (m, 1H), 3.96-3.82 (m, 2H), 3.74-3.71 (q, 1H), 3.25-3.18 (m, 1H), 2.32-2.29 (q, 1H), 2.10-2.05 (m, 1H)

Reference Example 44. 5-Bromo-2-chloro-N-isopropylpyridin-4-amine

The reaction mixture of 5-bromo-2-chloro-4-iodopyridine (1.00 g, 3.141 mmol), isopropylamine HCl (330 mg, 3.455 mmol) and Cs₂CO₃ (2.05 g, 6.283 mmol) in DMF (5 mL) was stirred at 100° C. for 5 hours. The reaction mixture was cooled to room temperature room temperature, diluted in DCM, washed by water, dried over MgSO₄, and then concentrated. The crude product was purified by column chromatography (EA/n-Hex=0-50%) to yield 5-bromo-2-chloro-N-isopropylpyridin-4-amine (305 mg) as pale yellow liquid. MS (ESI) m/z=250.9 (M+H)⁺

Reference Example 45. (1s,4s)-4-((2-Chloro-5-iodopyridin-4-yl)amino)-1-methylcyclohexan-1-ol The title compound as a pale yellow liquid (1.33 g) was prepared in the same fashion as Reference Example 2 except that cis-4-amino-1-methylcyclohexanol (1.13 g, 8.74 mmol) was used instead of 4-hydroxypiperidine. MS (ESI) m/z=367.0 (M+H)⁺

Reference Example 46. 2-Chloro-4-fluoro-5-(thiophen-3-ylethynyl)pyridine

The title compound as a pale yellow solid (715 mg) was prepared in the same fashion as Reference Example 18 except that 3-ethynylthiophene (462 mg, 4.273 mmol) was used instead of 4-ethynyl-1-methylpyrazole. MS (ESI) m/z=237.9 (M+H)⁺

Reference Example 47. 5-Bromo-2-chloro-4-(1-cyclopropylpyrazol-4-yl)pyridine The reaction mixture of 5-bromo-2-chloro-4-iodo-pyridine (2.00 g, 6.283 mmol), 1-cyclopropyl-4-(4,4,5,5-tetramethyl-1,3,2-dioxaborolan-2-yl)pyrazole (1.76 g, 7.539 mmol), Pd(dppf)Cl₂ (256 mg, 0.314 mmol) and 2M K₂CO₃ soln. (9.42 mL) in 1,4-dioxane (20 mL) was stirred at 90° C. for 3 hours. The reaction mixture was cooled, diluted in DCM, washed by water, dried over MgSO₄, and then concentrated. The crude product was purified by column chromatography (EA/n-Hex=0-20%) to yield 5-bromo-2-chloro-4-(1-methylpyrazol-4-yl)pyridine (1.30 g) as a white solid. ¹H-NMR (CDCl₃, 400 MHz) δ 8.52 (s, 1H), 8.10 (s, 1H), 7.90 (s, 1H), 7.38 (s, 1H), 3.69 (s, 1H), 1.21-1.11 (m, 4H); MS (ESI) m/z=299.0 (M+H)⁺

Reference Example 48. 5-Bromo-2-chloro-4-(1-methylpyrazol-4-yl)pyridine

The title compound as an off-white solid (1.3 g) was prepared in the same fashion as Reference Example 47 except that 1-methyl-4-(4,4,5,5-tetramethyl-1,3,2-dioxaborolan-2-yl)-1H-pyrazole (1.57 g, 7.539 mmol) was used instead of 1-cyclopropyl-4-(4,4,5,5-tetramethyl-1,3,2-dioxaborolan-2-yl)pyrazole. ¹H-NMR (CDCl₃, 400 MHz) δ 8.53 (s, 1H), 8.03 (s, 1H), 7.92 (s, 1H), 7.39 (s, 1H), 4.00 (s, 3H); MS (ESI) m/z=272.9 (M+H)⁺

Reference Example 49. 4-(4-Aminopyrimidin-2-yl)-N,N-dimethyl-1H-pyrazole-1-sulfonamide To a solution of 4-amino-2-chloropyrimidine (250 mg, 1.93 mmol) in 1,4-dioxane (7 mL) were added [1,1'-bis(diphenylphosphino)ferrocene]dichloropalladium(II), complex with dichloromethane (158 mg, 0.1900 mmol), 3M K₂CO₃ (1.93 mL, 5.79 mmol) and N,N-dimethyl-4-(4,4,5,5-tetramethyl-1,3,2-dioxaborolan-2-yl)pyrazole-1-sulfonamide (697 mg, 2.32 mmol). The reaction mixture was stirred at 90° C. for 3 hours. The reaction mixture was cooled to room temperature, quenched with water, and then extracted with DCM. The organic layer was dried over MgSO₄, filtered, and concentrated. The crude residue was purified by silica gel column chromatography (EA/n-Hex=0-60%) to give 4-(4-aminopyrimidin-2-yl)-N,N-dimethyl-1H-pyrazole-1-sulfonamide (344 mg) as a yellowish solid. 1H-NMR (CDCl₃, 400 MHz) δ 8.59 (s, 1H), 8.33 (s, 1H), 8.25 (d, 1H), 6.31 (d, 1H), 4.95 (s, 2H), 2.98 (s, 6H)

Reference Example 50. 4-(4-Aminopyrimidin-2-yl)-N,N,3-trimethyl-1H-pyrazole-1-sulfonamide The title compound as a white solid (325 mg) was prepared in the same fashion as Reference Example 49, except that (1-(N,N-dimethylsulfamoyl)-3-methyl-1H-pyrazol-4-yl)boronic acid (647.61 mg, 2.779 mmol) was used instead of N,N-dimethyl-4-(4,4,5,5-tetramethyl-1,3,2-dioxaborolan-2-yl)pyrazole-1-sulfonamide. MS (ESI) m/z=283.2 (M+)$^+$

Reference Example 51. 2-chloro-5-((1-cyclopropyl-1H-pyrazol-4-yl)ethynyl)-4-fluoropyridine The title compound as a liquid (400 mg) was prepared in the same fashion as Reference Example 18 except that 1-cyclopropyl-4-ethynyl-1H-pyrazole (257 mg, 1.942 mmol) was used instead of 4-ethynyl-1-methylpyrazole. $^1$H-NMR (CDCl$_3$, 400 MHz) δ 8.47 (d, 1H), 7.71 (s, 1H), 7.66 (s, 1H), 7.13 (d, 1H), 3.65-3.60 (m, 1H), 1.18-1.04 (m, 4H); MS (ESI) m/z=272.9 (M+H)$^+$

Reference Example 52. 2-Chloro-5-((1-(2,2-difluoroethyl)-1H-pyrazol-4-yl)ethynyl)-4-fluoropyridine The title compound as a liquid (400 mg) was prepared in the same fashion as Reference Example 18 except that 1-(2,2-difluoroethyl)-4-ethynyl-1H-pyrazole (303 mg, 1.942 mmol) was used instead of 4-ethynyl-1-methylpyrazole. MS (ESI) m/z=285.9 (M+H)$^+$

Reference Example 53. (1-(2-Chloro-5-((1-(trifluoromethyl)-1H-pyrazol-4-yl)ethynyl)pyridin-4-yl)-4-methylpiperidin-4-yl)methanol The title compound as a solid (154.2 mg) was prepared in the same fashion as Step 2 in Example 1 except that (1-(2-chloro-5-iodopyridin-4-yl)-4-methylpiperidin-4-yl)methanol (150 mg, 0.409 mmol) prepared in Reference Example 12 and 4-ethynyl-1-(trifluoromethyl)-1H-pyrazole (72.05 mg, 0.45 mmol) were used instead of 1-(2-chloro-5-iodopyridin-4-yl)-4-methylpiperazine and 4-ethynyl-1-methyl-1H-pyrazole. MS (ESI) m/z=399.0 (M+H)$^+$

Reference Example 54. 2-Chloro-4-fluoro-5-((3-methyloxetan-3-yl)ethynyl)pyridine The mixture of 2-chloro-4-fluoro-5-iodopyridine (1.41 g, 5.461 mmol), 3-ethynyl-3-methyloxetane (0.50 g, 5.201 mmol), PdCl$_2$(PPh$_3$)$_2$ (182 mg, 0.260 mmol), and CuI (198 mg, 1.040 mmol) was charged nitrogen gas for 10 minutes. After DMF (30 mL) and TEA (1.45 mL, 10.403 mmol) were added, the reaction mixture was stirred at 50° C. overnight. The reaction mixture was cooled, diluted in EA, washed by water, dried over MgSO$_4$, and then concentrated. The crude product was purified by column chromatography (EA/n-Hex=0-40%) to yield 2-chloro-4-fluoro-5-((3-methyloxetan-3-yl)ethynyl)pyridine (0.52 g) as an off-white solid. $^1$H-NMR (CDCl$_3$, 400 MHz) δ 8.43-8.41 (d, 1H), 7.13-7.11 (d, 1H), 4.93-4.92 (d, 2H), 4.50-4.49 (d, 2H), 1.73 (s, 3H)

Reference Example 55. 1-((6-Chloro-4-fluoropyridin-3-yl)ethynyl)cyclobutan-1-ol The title compound as a solid (476 mg) was prepared in the same fashion as Reference Example 54 except that 1-ethynylcyclobutan-1-ol (500 mg, 5.201 mmol) was used instead of 3-ethynyl-3-methyloxetane. $^1$H-NMR (CDCl$_3$, 400 MHz) δ 8.43-8.41 (d, 1H), 7.11-7.09 (d, 1H), 2.55-2.52 (m, 2H), 2.39-2.31 (m, 2H), 1.90-1.82 (m, 2H)

Reference Example 56. 2-Chloro-4-fluoro-5-(oxetan-3-ylethynyl)pyridine

The title compound as a solid (712 mg) was prepared in the same fashion as Reference Example 54 except that 3-ethynyloxetane (555 mg, 6.762 mmol) was used instead of 3-ethynyl-3-methyloxetane. $^1$H-NMR (CDCl$_3$, 400 MHz) δ 8.40-8.37 (d, 1H), 7.10-7.07 (d, 1H), 4.87-4.84 (q, 2H), 4.79-4.76 (q, 2H), 4.12-4.04 (m, 1H)

Reference Example 57. 3-((6-Chloro-4-fluoropyridin-3-yl)ethynyl)oxetan-3-ol

The title compound as a solid (674 mg) was prepared in the same fashion as Reference Example 54 except that 3-ethynyl-3-oxetanol (490 mg, 4.996 mmol) was used instead of 3-ethynyl-3-methyloxetane. $^1$H-NMR (CDCl$_3$, 400 MHz) δ 8.49-8.47 (d, 1H), 7.17-7.15 (d, 1H), 4.95-4.94 (d, 2H), 4.82-4.81 (d, 2H), 3.48 (s, 1H)

Reference Example 58. 3-((6-Chloro-4-fluoropyridin-3-yl)ethynyl)tetrahydrofuran-3-ol The title compound as a solid (712 mg) was prepared in the same fashion as Reference Example 54 except that 3-ethynyltetrahydrofuran-3-ol (560 mg, 4.996 mmol) was used instead of 3-ethynyl-3-methyloxetane. $^1$H-NMR (CDCl$_3$, 400 MHz) δ 8.47-8.44 (d, 1H), 7.15-7.13 (d, 1H), 4.15-4.07 (m, 2H), 4.05-3.96 (m, 2H), 2.80-2.72 (t, 1H), 2.47-2.32 (m, 2H)

Reference Example 59. 3-((6-Chloro-4-fluoropyridin-3-yl)ethynyl)tetrahydro-2H-pyran-3-ol The title compound as a solid (310 mg) was prepared in the same fashion as Reference Example 54 except that 3-ethynyltetrahydro-2H-pyran-3-ol (500 mg, 3.964 mmol) was used instead of 3-ethynyl-3-methyloxetane. $^1$H-NMR (CDCl$_3$, 400 MHz) δ 8.46-8.43 (d, 1H), 7.13-7.11 (d, 1H), 3.79-3.63 (m, 4H), 3.01 (s, 1H), 2.08-2.00 (m, 2H), 1.93-1.86 (m, 1H), 1.78-1.72 (q, 1H)

Reference Example 60. 2-Chloro-4-fluoro-5-((1-methylcyclopropyl)ethynyl)pyridine The title compound as a solid (1105 mg) was prepared in the same fashion as Reference Example 54 except that 1-ethynyl-1-methylcyclopropane (500 mg, 6.240 mmol) was used instead of 3-ethynyl-3-methyloxetane. $^1$H-NMR (CDCl$_3$, 400 MHz) δ 8.38-8.35 (d, 1H), 7.08-7.06 (d, 1H), 1.37 (s, 3H), 1.07-1.04 (q, 2H), 0.94-0.91 (q, 2H)

Reference Example 61. 2-Chloro-4-fluoro-5-((tetrahydrofuran-2-yl)ethynyl)pyridine The title compound as a solid (789 mg) was prepared in the same fashion as Reference Example 54 except that 2-ethynyloxolane (500 mg, 5.202 mmol) was used instead of 3-ethynyl-3-methyloxetane. $^1$H-NMR (CDCl$_3$, 400 MHz) δ 8.44-8.42 (d, 1H), 7.12-7.10 (d, 1H), 4.86-4.83 (m, 1H), 4.01-3.98 (t, 1H), 3.92-3.82 (m, 1H), 2.28-2.23 (m, 1H), 2.14-2.07 (m, 2H), 2.02-1.95 (m, 1H)

Reference Example 62. 2-Chloro-4-fluoro-5-((1-(2-fluoroethyl)-1H-pyrazol-4-yl)ethynyl)pyridine The title compound as a solid (437 mg) was prepared in the same fashion as Reference Example 54 except that 4-ethynyl-1-(2-fluoroethyl)pyrazole (282 mg, 2.039 mmol) was used instead of 3-ethynyl-3-methyloxetane. MS (ESI) m/z=268.1 (M+H)$^+$

Reference Example 63. (5)-1-(1-(2-Chloro-5-iodopyridin-4-yl)piperidin-3-yl)-N,N-dimethylmethanamine The title compound as a solid (1059 mg) was prepared in the same fashion as Reference Example 2 except that (R)-N,N-dimethyl-1-(piperidin-3-yl)methanamine 2HCI (580 mg, 4.079 mmol) was used instead of 4-hydroxypiperidine. MS (ESI) m/z=380.0 (M+H)$^+$

Reference Example 64. 2-(1-(2-Chloro-5-iodopyridin-4-yl)piperidin-3-yl)-N,N-dimethylethan-1-amine The title compound as a solid (1318 mg) was prepared in the same fashion as Reference Example 2 except that N,N-dimethyl-2-(piperidin-3-yl)ethan-1-amine 2HCI (934 mg, 4.079 mmol) was used instead of 4-hydroxypiperidine. MS (ESI) m/z=394.0 (M+H)$^+$

Reference Example 65. 2-Chloro-4-fluoro-5-((1-(methylsulfonyl)piperidin-4-yl)ethynyl)pyridine

Step 1. tert-Butyl 4-((6-chloro-4-fluoropyridin-3-yl)ethynyl)piperidine-1-carboxylate The title compound as a solid (9500 mg) was prepared in the same fashion as Reference Example 54 except that 1-boc-4-ethynylpiperidine (6429 mg, 30.720 mmol) was used instead of 3-ethynyl-3-methyloxetane. $^1$H-NMR (CDCl$_3$, 400 MHz) δ 8.28-8.25 (d, 1H), 7.00-6.98 (d, 1H), 3.63-3.59 (m, 2H), 3.18-3.12 (m, 2H), 2.76-2.74 (t, 1H), 1.78-1.73 (m, 2H), 1.59-1.55 (m, 2H), 1.34 (s, 9H)

Step 2. 2-Chloro-4-fluoro-5-(piperidin-4-ylethynyl)pyridine hydrochloride tert-Butyl 4-((6-chloro-4-fluoropyridin-3-yl)ethynyl)piperidine-1-carboxylate (9.50 g, 28.04 mmol) prepared in Step 1 was dissolved with 4.0 M HCl in 1,4-dioxane (26.8 mL) and stirred at room temperature for 2 hours. After the reaction mixture was concentrated, the residue was dissolved with EtOAc (20 mL). The reaction mixture was concentrated. The crude product was triturated by diethyl ether to yield 2-chloro-4-fluoro-5-(piperidin-4-ylethynyl)pyridine hydrochloride (6160 mg) as a white solid. $^1$H-NMR (CDCl$_3$, 400 MHz) δ 10.10-9.99 (d, 2H), 8.48-8.45 (d, 1H), 7.12-7.10 (d, 1H), 3.70 (s, 1H), 3.56 (s, 1H), 3.49-3.46 (t, 3H), 3.37 (s, 1H), 2.45-2.42 (t, 2H), 2.24-2.20 (q, 2H)

Step 3. 2-Chloro-4-fluoro-5-((1-(methylsulfonyl)piperidin-4-yl)ethynyl)pyridine To the solution of 2-chloro-4-fluoro-5-(piperidin-4-ylethynyl)pyridine hydrochloride (750 mg, 3.140 mmol) prepared in Step 2 in DCM (10 mL) were added methanesulfonyl chloride (0.27 mL, 3.46 mmol) and TEA (1.31 mL, 9.43 mmol). The reaction mixture was stirred at room temperature overnight. After water was added, the reaction mixture was extracted with DCM. The combined organic layers were washed with brine, dried over MgSO$_4$, and then concentrated. The crude product was purified by column chromatography (EA/n-Hex=0-100%) to yield 2-chloro-4-fluoro-5-((1-(methylsulfonyl)piperidin-4-yl)ethynyl)pyridine (606 mg) as an yellow solid. MS (ESI) m/z=317.0 (M+H)$^+$

Reference Example 66. 2-Chloro-5-((1-(cyclopropylsulfonyl)piperidin-4-yl)ethynyl)-4-fluoropyridine The title compound as a solid (853 mg) was prepared in the same fashion as Step 3 in Reference Example 65 step 3 except that cyclopropanesulfonyl chloride (0.35 mL, 3.46 mmol) was used instead of methanesulfonyl chloride. MS (ESI) m/z=343.0 (M+H)$^+$

Reference Example 67. 2-Chloro-5-((1-(cyclopropylsulfonyl)pyrrolidin-3-yl)ethynyl)-4-fluoropyridine

Step 1. Tert-Butyl 3-((6-chloro-4-fluoropyridin-3-yl)ethynyl)pyrrolidine-1-carboxylate The title compound as a solid (8730 mg) was prepared in the same fashion as Reference Example 54 except that tert-butyl-3-ethynylpyrrolidine-1-carboxylate (6000 mg, 30.72 mmol) was used instead of 3-ethynyl-3-methyloxetane. $^1$H-NMR (CDCl$_3$, 400 MHz) δ 8.38 8.35 (d, 1H), 7.09-7.07 (d, 1H), 3.70-3.65 (t, 1H), 3.56 (s, 1H), 3.40-3.36 (d, 2H), 3.23-3.20 (d, 1H), 2.24-2.18 (q, 1H), 2.04-1.95 (t, 1H), 1.44 (s, 9H)

Step 2. 2-Chloro-4-fluoro-5-(pyrrolidin-3-ylethynyl)pyridine hydrochloride

The title compound as a white solid (6450 mg) was prepared in the same fashion as Step 2 in Reference Example 65 except that tert-butyl 3-((6-chloro-4-fluoropyridin-3-yl)ethynyl)pyrrolidine-1-carboxylate (8.73 g, 26.88 mmol) prepared in Step 1 was used instead of tert-Butyl 4-((6-chloro-4-fluoropyridin-3-yl)ethynyl)piperidine-1-carboxylate. $^1$H-NMR (CDCl$_3$, 400 MHz) δ 9.66 (s, 2H), 8.42-8.39 (q, 1H), 7.14-7.11 (q, 1H), 3.39 (s, 2H), 3.27 (s, 2H), 3.11 (s, 1H), 2.34-2.29 (m, 2H), 2.11-2.07 (q, 2H)

Step 3. 2-Chloro-5-((1-(cyclopropylsulfonyl)pyrrolidin-3-yl)ethynyl)-4-fluoropyridine The title compound as a yellow solid (826 mg) was prepared in the same fashion as Step 3 in Reference Example 65 except that 2-chloro-4-fluoro-5-(pyrrolidin-3-ylethynyl)pyridine hydrochloride (760 mg, 3.38 mmol) prepared in Step 2 and cyclopropanesulfonyl chloride (0.38 mL, 3.72 mmol) were used instead of 2-chloro-4-fluoro-5-(piperidin-4-ylethynyl)pyridine hydrochloride and methanesulfonyl chloride. MS (ESI) m/z=329.0 (M+H)$^+$

Reference Example 68. 2-Chloro-4-fluoro-5-((1-(methylsulfonyl)pyrrolidin-3-yl)ethynyl)pyridine The title compound as a solid (1920 mg) was prepared in the same fashion as Reference Example 67 step 3 except that methanesulfonyl chloride (0.65 mL, 8.31 mmol) was used instead of cyclopropanesulfonyl chloride. $^1$H-NMR (CDCl$_3$, 400 MHz) δ 8.39-8.37 (d, 1H), 7.11-7.09 (d, 1H), 3.72-3.68 (q, 1H), 3.52-3.41 (m, 4H), 3.34-3.31 (t, 1H), 3.09-3.08 (d, 1H), 2.87 (d, 3H), 2.33-2.30 (t, 1H), 2.19-2.15 (t, 1H), 1.47-1.37 (q, 2H)

Reference Example 69. 1-(3-((6-Chloro-4-fluoro-pyridin-3-yl)ethynyl)pyrrolidin-1-yl)-2,2,2-trifluoro-ethan-1-one The title compound as a solid (1248 mg) was prepared in the same fashion as Reference Example 54 except that 1-(3-ethynylpyrrolidin-1-yl)-2,2,2-trifluoroethan-1-one (1000 mg, 5.23 mmol) was used instead of 3-ethynyl-3-methyloxetane. MS (ESI) m/z=321.0 (M+H)+

Reference Example 70. 2-Chloro-4-fluoro-5-(((2R)-2-(trifluoromethyl)tetrahydrofuran-3-yl)ethynyl) pyridine The title compound as a solid (1540 mg) was prepared in the same fashion as Reference Example 54 except that (2R)-3-ethynyl-2-(trifluoromethyl)tetrahydrofuran (1000 mg, 6.09 mmol) was used instead of 3-ethynyl-3-methyloxetane. MS (ESI) m/z=293.0 (M+H)+

Reference Example 71. 5-((7-Oxabicyclo[2.2.1]heptan-2-yl)ethynyl)-2-chloro-4-fluoropyridine The title compound as a solid (1490 mg) was prepared in the same fashion as Reference Example 54 except that 2-ethynyl-7-oxabicyclo[2.2.1]heptane (744 mg, 6.09 mmol) was used instead of 3-ethynyl-3-methyloxetane. MS (ESI) m/z=252.0 (M+H)+

Reference Example 72. 3-((6-Chloro-4-fluoropyridin-3-yl)ethynyl)tetrahydrothiophene 1,1-dioxide The title compound as a solid (1107 mg) was prepared in the same fashion as Reference Example 54 except that 3-ethynyl-1-lambda-6-thiolane-1,1-dione (1000 mg, 6.94 mmol) was used instead of 3-ethynyl-3-methyloxetane. MS (ESI) m/z=274.0 (M+H)+

Reference Example 73. 2-Chloro-4-fluoro-5-((2-methyltetrahydrofuran-3-yl)ethynyl)pyridine The title compound as a solid (983 mg) was prepared in the same fashion as Reference Example 54 except that 3-ethynyl-2-methyloxolane (763 mg, 6.94 mmol) was used instead of 3-ethynyl-3-methyloxetane. MS (ESI) m/z=240.0 (M+H)+

Reference Example 74. 2-Chloro-4-fluoro-5-((3-fluorotetrahydrofuran-3-yl)ethynyl)pyridine The title compound as a solid (1359 mg) was prepared in the same fashion as Reference Example 54 except that 3-ethynyl-3-fluorooxolane (792 mg, 6.94 mmol) was used instead of 3-ethynyl-3-methyloxetane. MS (ESI) m/z=244.0 (M+H)+

Reference Example 75. (4-((6-Chloro-4-fluoropyridin-3-yl)ethynyl)phenyl)(4-hydroxypiperidin-1-yl) methanone The title compound as a solid (1121 mg) was prepared in the same fashion as Reference Example 54 except that (4-ethynylphenyl)-(4-hydroxy-1-piperidinyl)methanone (1000 mg, 4.36 mmol) was used instead of 3-ethynyl-3-methyloxetane. MS (ESI) m/z=359.1 (M+H)+

Example 1. 2-(1-(Cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine

Step 1. 1-(2-Chloro-5-iodopyridin-4-yl)-4-methylpiperazine

The suspension of 2,4-dichloro-5-iodopyridine (400 mg, 1.460 mmol), 1-methylpiperazine (0.24 mL, 2.191 mmol), and DIPEA (0.51 mL, 2.921 mmol) in DMA (7 mL) was stirred at 100° C. overnight. After being cooled, the reaction mixture was diluted in EA, washed by water, dried over $MgSO_4$, and then concentrated. The crude product was purified by column chromatography (MeOH/DCM=0-15%) to yield 1-(2-chloro-5-iodopyridin-4-yl)-4-methylpiperazine (364 mg) as a yellow solid. MS (ESI) m/z=338.0 (M+H)+

Step 2. 1-(2-Chloro-5-((1-methyl-1H-pyrazol-4-yl) ethynyl)pyridin-4-yl)-4-methylpiperazine The mixture of 1-(2-chloro-5-iodopyridin-4-yl)-4-methylpiperazine (290 mg, 0.859 mmol) prepared in Step 1, 4-ethynyl-1-methylpyrazole (109.4 mg, 1.031 mmol), $PdCl_2(PPh_3)_2$ (30.15 mg, 0.043 mmol), and CuI (32 mg, 0.172 mmol) was charged nitrogen gas for 10 minutes. After DMF (6 mL) and TEA (0.24 mL, 1.718 mmol) were added, the reaction mixture was stirred at 50° C. for 1 hour. The reaction mixture was cooled, diluted in EA, washed by water, dried over $MgSO_4$, and then concentrated. The crude product was purified by column chromatography (MeOH/DCM=0-10%) to yield 1-(2-chloro-5-((1-methyl-1H-pyrazol-4-yl)ethynyl)pyridin-4-yl)-4-methylpiperazine (114 mg) as a yellow solid. MS (ESI) m/z=316.1 (M+H)+

Step 3. 2-(1-(Cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine The suspension of 2-(1-cyclopropylsulfonylpyrazol-4-yl)pyrimidin-4-amine (111 mg, 0.418 mmol), 1-(2-chloro-5-((1-methyl-1H-pyrazol-4-yl)ethynyl)pyridin-4-yl)-4-methylpiperazine (110 mg, 0.348 mmol) prepared in Step 2, $Cs_2CO_3$ (227 mg, 0.697 mmol), XPhos (33 mg, 0.070 mmol), and $Pd_2(dba)_3$ (32 mg, 0.035 mmol) in 1,4-dioxane (4 mL) was stirred at 80° C. overnight. The reaction mixture was cooled, filtered through Celite, and then concentrated. The crude product was purified by column chromatography (MeOH/DCM=0-20%) to yield 2-(1-(cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine (28.5 mg) as a yellow solid. $^1$H-NMR ($CDCl_3$, 600 MHz) δ 8.65 (s, 1H), 8.44 (s, 1H), 8.41 (d, 1H), 8.26 (s, 1H), 7.63 (s, 1H), 7.62 (s, 1H), 7.56 (s, 1H), 7.49 (s, 1H), 7.08 (s, 1H), 3.94 (s, 3H), 3.60-3.56 (m, 4H), 2.85-2.81 (m, 1H), 2.67-2.65 (m, 4H), 2.35 (s, 3H), 1.54-1.52 (m, 2H), 1.28-1.20 (m, 2H); MS (ESI) m/z=545.2 (M+H)+

Example 2. $N^4$-Cyclohexyl-$N^2$-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine

Step 1. 2-Chloro-N-cyclohexyl-5-iodopyridin-4-amine

The title compound as a solid (176 mg) was prepared in the same fashion as Step 1 in Example 1 except that cyclohexylamine (217 mg, 2.191 mmol) was used instead of 1-methylpiperazine. MS (ESI) m/z=337.0 (M+H)⁺

Step 2. 2-Chloro-N-cyclohexyl-5-((1-methyl-1H-pyrazol-4-yl)ethynyl)pyridin-4-amine The title compound as a solid (88.7 mg) was prepared in the same fashion as Step 2 in Example 1 except that 2-chloro-N-cyclohexyl-5-iodopyridin-4-amine (176 mg, 0.523 mmol) prepared in Step 1 was used instead of 1-(2-chloro-5-iodopyridin-4-yl)-4-methylpiperazine. MS (ESI) m/z=315.0 (M+H)⁺

Step 3. N⁴—Cyclohexyl-N²-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine-1H The title compound as a solid (17.5 mg) was prepared in the same fashion as Step 3 in Example 1 except that 2-chloro-N-cyclohexyl-5-((1-methyl-1H-pyrazol-4-yl)ethynyl)pyridin-4-amine (88 mg, 0.280 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.65 (s, 1H), 8.44 (s, 1H), 8.41 (d, 1H), 8.26 (s, 1H), 7.63 (s, 1H), 7.62 (s, 1H), 7.56 (s, 1H), 7.49 (s, 1H), 7.08 (s, 1H), 3.94 (s, 3H), 3.60-3.56 (m, 4H), 2.85-2.81 (m, 1H), 2.67-2.65 (m, 4H), 2.35 (s, 3H), 1.54-1.52 (m, 2H), 1.28-1.20 (m, 2H); MS (ESI) m/z=544.2 (M+H)⁺

Example 3. 2-(1-(Cyclopropylsulfonyl)-1H-pyrazol-4-yl)-N-(4-(4-(ethylsulfonyl)piperazin-1-yl)-5-((1-methyl-1H-pyrazol-4-yl)ethynyl)pyridin-2-yl)pyrimidin-4-amine

Step 1. 1-(2-Chloro-5-iodopyridin-4-yl)-4-(ethylsulfonyl)piperazine

The title compound as a solid (115 mg) was prepared in the same fashion as Step 1 in Example 1 except that 1-ethanesulfonyl piperazine (390 mg, 2.191 mmol) was used instead of 1-methylpiperazine. MS (ESI) m/z=416.1 (M+H)⁺

Step 2. 1-(2-Chloro-5-((1-methyl-1H-pyrazol-4-yl)ethynyl)pyridin-4-yl)-4-(ethylsulfonyl)piperazine The title compound as a solid (100 mg) was prepared in the same fashion as Step 2 in Example 1 except that 1-(2-chloro-5-iodopyridin-4-yl)-4-(ethylsulfonyl)piperazine (115 mg, 0.277 mmol) prepared in Step 1 was used instead of 1-(2-chloro-5-iodopyridin-4-yl)-4-methylpiperazine. MS (ESI) m/z=394.0 (M+H)⁺

Step 3. 2-(1-(Cyclopropylsulfonyl)-1H-pyrazol-4-yl)-N-(4-(4-(ethylsulfonyl)piperazin-1-yl)-5-((1-methyl-1H-pyrazol-4-yl)ethynyl)pyridin-2-yl)pyrimidin-4-amine The title compound as a solid (10.4 mg) was prepared in the same fashion as Step 3 in Example 1 except that 1-(2-chloro-5-((1-methyl-1H-pyrazol-4-yl)ethynyl)pyridin-4-yl)-4-(ethylsulfonyl)piperazine (100 mg, 0.254 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.43 (s, 1H), 8.42 (s, 1H), 8.28 (s, 1H), 8.03 (s, 1H), 7.62 (s, 1H), 7.60 (s, 1H), 7.56 (s, 1H), 7.04 (d, 1H), 3.95 (s, 3H), 3.56 (s, 8H), 3.08-3.04 (m, 2H), 2.87-2.84 (m, 1H), 1.56-1.54 (m, 2H), 1.43-1.29 (m, 3H), 1.27-1.14 (m, 2H); MS (ESI) m/z=623.2 (M+H)⁺

Example 4. (R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)butan-1-ol

Step 1. (R)-3-((2-Chloro-5-iodopyridin-4-yl)amino)butan-1-ol

The title compound as a solid (451 mg) was prepared in the same fashion as Step 1 in Example 1 except that (3R)-3-aminobutan-1-ol (866 mg, 9.711 mmol) was used instead of 1-methylpiperazine. MS (ESI) m/z=327.0 (M+H)⁺

Step 2. (R)-3-((2-Chloro-5-((1-methyl-1H-pyrazol-4-yl)ethynyl)pyridin-4-yl)amino)butan-1-ol The title compound as a solid (86.52 mg) was prepared in the same fashion as Step 2 in Example 1 except that (R)-3-((2-chloro-5-iodopyridin-4-yl)amino)butan-1-ol (228 mg, 0.698 mmol) prepared in Step 1 was used instead of 1-(2-chloro-5-iodopyridin-4-yl)-4-methylpiperazine. MS (ESI) m/z=305.1 (M+H)⁺

Step 3. (R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)butan-1-ol The title compound as a solid (81 mg) was prepared in the same fashion as Step 3 in Example 1 except that (R)-3-((2-chloro-5-((1-methyl-1H-pyrazol-4-yl)ethynyl)pyridin-4-yl)amino)butan-1-ol (184 mg, 0.604 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.69 (s, 1H), 8.47 (s, 1H), 8.39 (d, 1H), 8.09 (d, 1H), 7.58 (s, 1H), 7.54 (s, 1H), 7.44 (s, 1H), 7.35 (s, 1H), 7.01 (s, 1H), 5.40 (d, 1H), 4.02-4.00 (m, 1H), 3.93 (s, 3H), 3.90-3.83 (m, 2H), 2.96-2.82 (m, 1H), 2.05-1.99 (m, 1H), 1.98-1.84 (m, 1H), 1.55 (s, 3H), 1.38 (d, 4H), 1.27-1.20 (m, 2H); MS (ESI) m/z=534.2 (M+H)⁺

Example 5. (S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-2-methylbutan-2-ol

Step 1. (S)-3-((2-Chloro-5-iodopyridin-4-yl)amino)-2-methylbutan-2-ol

The title compound as a solid (429 mg) was prepared in the same fashion as Step 1 in Example 1 except that (S)-3-amino-2-methylbutan-2-ol HCl (1.36 g, 9.711 mmol) was used instead of 1-methylpiperazine. MS (ESI) m/z=341.0 (M+H)⁺

Step 2. (S)-3-((2-Chloro-5-((1-methyl-1H-pyrazol-4-yl)ethynyl)pyridin-4-yl)amino)-2-methylbutan-2-ol The title compound as a solid (291 mg) was prepared in the same fashion as Step 2 in Example 1 except that (S)-3-((2-chloro-5-iodopyridin-4-yl)amino)-2-methylbutan-2-ol (350 mg, 1.028 mmol) prepared in Step 1 was used instead of 1-(2-chloro-5-iodopyridin-4-yl)-4-methylpiperazine. MS (ESI) m/z=319.0 (M+H)$^+$ Step 3. (S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-2-methylbutan-2-ol The title compound as a solid (75 mg) was prepared in the same fashion as Step 3 in Example 1 except that (S)-3-((2-chloro-5-((1-methyl-1H-pyrazol-4-yl)ethynyl)pyridin-4-yl)amino)-2-methylbutan-2-ol (290 mg, 0.910 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.63 (s, 1H), 8.46 (s, 1H), 8.37 (s, 1H), 8.10 (s, 1H), 7.64 (s, 1H), 7.57 (s, 1H), 7.21 (s, 1H), 7.06 (s, 1H), 5.47 (d, 1H), 3.92 (s, 3H), 3.60-3.57 (m, 1H), 2.84-2.80 (m, 1H), 1.53-1.50 (m, 1H), 1.35-1.31 (m, 6H), 1.29-1.22 (m, 3H), 1.21-1.19 (m, 2H); MS (ESI) m/z=534.2 (M+H)$^+$ Example 6. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol Step 1. 1-(2-Chloro-5-iodopyridin-4-yl)piperidin-3-ol The title compound as a solid (320 mg) was prepared in the same fashion as Step 1 in Example 1 except that 3-hydroxypiperidine (255 mg, 2.525 mmol) was used instead of 1-methylpiperazine. MS (ESI) m/z=339.0 (M+H)$^+$ Step 2. 1-(2-Chloro-5-((1-methyl-1H-pyrazol-4-yl)ethynyl)pyridin-4-yl)piperidin-3-ol The title compound as a solid (170 mg) was prepared in the same fashion as Step 2 in Example 1 except that 1-(2-chloro-5-iodopyridin-4-yl)piperidin-3-ol (208 mg, 0.614 mmol) prepared in Step 1 was used instead of 1-(2-chloro-5-iodopyridin-4-yl)-4-methylpiperazine. MS (ESI) m/z=317.1 (M+H)$^+$ Step 3. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol The title compound as a solid (77 mg) was prepared in the same fashion as Step 3 in Example 1 except that 1-(2-chloro-5-((1-methyl-1H-pyrazol-4-yl)ethynyl)pyridin-4-yl)piperidin-3-ol (170 mg, 0.537 mmol) prepared in Step 2 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.23 (s, 1H), 8.67 (s, 1H), 8.45 (s, 1H), 8.44 (d, 1H), 8.15 (s, 1H), 8.00 (s, 1H), 7.66 (s, 1H), 7.54 (s, 1H), 7.41 (s, 1H), 4.97 (d, 1H), 4.00 (d, 1H), 3.85 (s, 3H), 3.67 (d, 2H), 3.27-3.24 (m, 1H), 2.96 (t, 1H), 2.69 (t, 1H), 1.97-1.95 (m, 1H), 1.86-1.84 (m, 1H), 1.60-1.58 (m, 1H), 1.37-1.33 (m, 2H), 1.26-1.24 (m, 2H); MS (ESI) m/z=546.2 (M+H)$^+$ Example 7. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one Step 1. 1-(2-Chloro-5-iodopyridin-4-yl)piperidin-4-one The title compound as a solid (1.54 g) was prepared in the same fashion as Step 1 in Example 1 except that piperidin-4-one HCl hydrate (1.43 g, 9.323 mmol) was used instead of 1-methylpiperazine. MS (ESI) m/z=337.0 (M+H)$^+$ Step 2. 1-(2-Chloro-5-((1-methyl-1H-pyrazol-4-yl)ethynyl)pyridin-4-yl)piperidin-4-one The title compound as a solid (720 mg) was prepared in the same fashion as Step 2 in Example 1 except that 1-(2-chloro-5-iodopyridin-4-yl)piperidin-4-one (1.00 g, 2.971 mmol) prepared in Step 1 was used instead of 1-(2-chloro-5-iodopyridin-4-yl)-4-methylpiperazine. MS (ESI) m/z=315.0 (M+H)$^+$ Step 3. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one The title compound as a solid (230 mg) was prepared in the same fashion as Step 3 in Example 1 except that 1-(2-chloro-5-((1-methyl-1H-pyrazol-4-yl)ethynyl)pyridin-4-yl)piperidin-4-one (700 mg, 2.224 mmol) prepared in Step 2 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.30 (s, 1H), 8.67 (s, 1H), 8.45 (s, 1H), 8.44 (s, 1H), 8.22 (s, 1H), 8.05 (s, 1H), 7.77 (s, 1H), 7.67 (s, 1H), 7.35 (s, 1H), 3.87 (s, 3H), 3.80 (t, 4H), 3.27-3.23 (m, 1H), 2.59 (t, 4H), 1.34-1.30 (m, 2H), 1.26-1.21 (m, 2H); MS (ESI) m/z=544.1 (M+H)$^+$ Example 8. 2-(1-(Cyclopropylsulfonyl)-1H-pyrazol-4-yl)-N-(4-(4-fluoropiperidin-1-yl)-5-((1-methyl-1H-pyrazol-4-yl)ethynyl)pyridin-2-yl)pyrimidin-4-amine Step 1. 2-Chloro-4-(4-fluoropiperidin-1-yl)-5-iodopyridine The title compound as a solid (686 mg) was prepared in the same fashion as Step 1 in Example 1 except that 4-fluoropiperidine HCl (423 mg, 3.030 mmol) was used instead of 1-methylpiperazine. MS (ESI) m/z=322.3 (M+H)$^+$ Step 2. 2-Chloro-4-(4-fluoropiperidin-1-yl)-5-((1-methyl-1H-pyrazol-4-yl)ethynyl)pyridine The title compound as a solid (163 mg) was prepared in the same fashion as Step 2 in Example 1 except that 2-chloro-4-(4-fluoropiperidin-1-yl)-5-iodopyridine (220 mg, 0.646 mmol) prepared in Step 1 was used instead of 1-(2-chloro-5-iodopyridin-4-yl)-4-methylpiperazine. MS (ESI) m/z=319.0 (M+H)$^+$ Step 3. 2-(1-(Cyclopropylsulfonyl)-1H-pyrazol-4-yl)-N-(4-(4-fluoropiperidin-1-yl)-5-((1-methyl-1H-pyrazol-4-yl)ethynyl)pyridin-2-yl)pyrimidin-4-amine The title compound as a solid (84.9 mg) was prepared in the same fashion as Step 3 in Example 1 except that 2-chloro-4-(4-fluoropiperidin-1-yl)-5-((1-methyl-1H-pyrazol-4-yl)ethynyl)pyridine (163 mg, 0.511 mmol) prepared in Step 2 was used instead of 1-(2-chloro-5-((1-methyl-1H-pyrazol-4-yl)ethynyl)pyridin-4-yl)-4-methylpiperazine.
$^1$H-NMR (CDCl$_3$, 600 MHz) δ 8.65 (s, 1H), 8.44 (s, 1H), 8.42 (d, 1H), 8.26 (s, 1H), 8.24 (s, 1H), 7.63 (s, 1H), 7.56 (s, 2H), 7.05 (s, 1H), 4.92 (d, 1H), 3.94 (s, 3H), 3.60-3.56 (m, 2H), 3.54-3.53 (m, 2H), 2.86-2.81 (m, 1H), 2.17-2.09 (m, 4H), 1.55-1.52 (m, 2H), 1.27-1.21 (m, 2H); MS (ESI) m/z=548.2 (M+H)$^+$ Example 9. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-yl)methanol Step 1. (1-(2-Chloro-5-iodopyridin-4-yl)piperidin-3-yl)methanol The title compound as a solid (732 mg) was prepared in the same fashion as Step 1 in Example 1 except that 3-piperidinemethanol (349 mg, 3.030 mmol) was used instead of 1-methylpiperazine. MS (ESI) m/z=353.0 (M+H)$^+$ Step 2. (1-(2-Chloro-5-((1-methyl-1H-pyrazol-4-yl)ethynyl)pyridin-4-yl)piperidin-3-yl)methanol The title compound as a solid (153 mg) was prepared in the same fashion as Step 2 in Example 1 except that (1-(2-chloro-5-iodopyridin-4-yl)piperidin-3-yl)methanol (240 mg, 0.681 mmol) prepared in Step 1 was used instead of 1-(2-chloro-5-iodopyridin-4-yl)-4-methylpiperazine. MS (ESI) m/z=331.1 (M+H)$^+$ Step 3. (1-(2-((2-(1-(Cyclopropylsulfonyl)-1H-pyrazol-4-yl)pyrimidin-4-yl)amino)-5-((l-methyl-1H-pyrazol-4-yl)ethynyl)pyridin-4-yl)piperidin-3-yl)methanol The title compound as a solid (34.4 mg) was prepared in the same fashion as Step 3 in Example 1 except that (1-(2-chloro-5-((1-methyl-1H-pyrazol-4-yl)ethynyl)pyridin-4-yl)piperidin-3-yl)methanol (153 mg, 0.463 mmol) prepared in Step 2 was used instead of 1-(2-chloro-5-((l-methyl-1H-pyrazol-4-yl)ethynyl)pyridin-4-yl)-4-methylpiperazine. $^1$H-NMR (CDCl$_3$, 600 MHz) δ 8.66 (s, 1H), 8.49 (s, 1H), 8.40 (d, 1H), 8.22 (s, 1H), 8.03 (s, 1H), 7.65 (s, 1H), 7.60 (s, 2H), 6.98 (s, 1H), 4.13 (d, 1H), 3.97 (d, 1H), 3.92 (s, 3H), 3.76-3.67 (m, 1H), 3.62-3.58 (m, 1H), 2.97-2.93 (m, 1H), 2.85-2.82 (m, 1H), 2.81-2.77 (m, 1H), 2.04 (s, 1H), 1.93-1.77 (m, 4H), 1.54 (s, 2H), 1.32-1.21 (m, 2H), 1.20 (s, 2H); MS (ESI) m/z=560.2 (M+H)$^+$ Example 10. 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol Step 1. 1-(1-(2-Chloro-5-iodopyridin-4-yl)piperidin-4-yl)ethan-1-ol The title compound as a solid (521 mg) was prepared in the same fashion as Step 1 in Example 1 except that 1-(4-piperidyl)ethanol (391 mg, 3.03 mmol) was used instead of 1-methylpiperazine. MS (ESI) m/z=367.0 (M+H)$^+$ Step 2. 1-(1-(2-Chloro-5-((1-methyl-1H-pyrazol-4-yl)ethynyl)pyridin-4-yl)piperidin-4-yl)ethan-1-ol The title compound as a solid (224 mg) was prepared in the same fashion as Step 2 in Example 1 except that 1-(1-(2-chloro-5-iodopyridin-4-yl)piperidin-4-yl)ethan-1-ol (300 mg, 0.818 mmol) prepared in Step 1 was used instead of 1-(2-chloro-5-iodopyridin-4-yl)-4-methylpiperazine. MS (ESI) m/z=345.1 (M+H)$^+$ Step 3. 1-(1-(2-((2-(1-(Cyclopropylsulfonyl)-1H-pyrazol.-4-yl)pyrimidin-4-yl)amino)-5-((1-methyl-1H-pyrazol-4-yl)ethynyl)pyridin-4-yl)piperidin-4-yl)ethan-1-ol The title compound as a solid (57.6 mg) was prepared in the same fashion as Step 3 in Example 1 except that 1-(1-(2-chloro-5-((1-methyl-1H-pyrazol-4-yl)ethynyl)pyridin-4-yl)piperidin-4-yl)ethan-1-ol (220 mg, 0.638 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.45 (s 1H), 8.41 (d, 1H), 8.23 (d, 1H), 7.99 (s, 1H), 7.63 (s, 1H), 7.55 (s, 2H), 7.03 (s, 1H), 4.22-4.16 (m, 2H), 3.93 (s, 3H), 3.68 (t, 1H), 2.91-2.82 (m, 3H), 2.07 (d, 1H), 1.85 (d, 1H), 1.73 (s, 3H), 1.55-1.51 (m, 5H), 1.26-1.25 (m, 3H), 1.23-1.21 (m, 2H); MS (ES) m/z=574.2 (M+H)$^+$ Example 11. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)propan-2-ol Step 1. 2-(1-(2-Chloro-5-iodopyridin-4-yl)piperidin-4-yl)propan-2-ol The title compound as a solid (748 mg) was prepared in the same fashion as Step 1 in Example 1 except that 2-(piperidin-4-yl)propan-2-ol (434 mg, 3.030 mmol) was used instead of 1-methylpiperazine. MS (ESI) m/z=381.0 (M+H)$^+$ Step 2. 2-(1-(2-Chloro-5-((1-methyl-1H-pyrazol-4-yl)ethynyl)pyridin-4-yl)piperidin-4-yl)propan-2-ol The title compound as a solid (236 mg) was prepared in the same fashion as Step 2 in Example 1 except that 2-(1-(2-chloro-5-iodopyridin-4-yl)piperidin-4-yl)propan-2-ol (300 mg, 0.788 mmol) prepared in Step 1 was used instead of 1-(2-chloro-5-iodopyridin-4-yl)-4-methylpiperazine. MS (ESI) m/z=359.1 (M+H)$^+$ Step 3. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)propan-2-ol The title compound as a solid (94.4 mg) was prepared in the same fashion as Step 3 in Example 1 except that 2-(1-(2-chloro-5-((1-methyl-1H-pyrazol-4-yl)ethynyl)pyridin-4-yl)piperidin-4-yl)propan-2-ol (236 mg, 0.657 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.45 (s, 1H), 8.40 (d, 1H), 8.24 (s, 1H), 8.17 (s, 1H), 7.63 (s, 1H), 7.58 (s, 1H), 7.55 (s, 1H), 7.01 (s, 1H), 4.23 (d, 2H), 3.94 (s, 3H), 2.87-2.83 (m, 3H), 1.98 (d, 2H), 1.81 (s, 2H), 1.59-1.53

(m, 3H), 1.52-1.51 (m, 2H), 1.25 (s, 6H), 1.23-1.20 (m, 2H); MS (ESI) m/z=588.3 (M+H)+

Example 12. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol Step 1. (1-(2-Chloro-5-iodopyridin-4-yl)-4-methylpiperidin-4-yl)methanol The title compound as a solid (667 mg) was prepared in the same fashion as Step 1 in Example 1 except that (4-methylpiperidin-4-yl)methanol (391 mg, 3.03 mmol) was used instead of 1-methylpiperazine. MS (ESI) m/z=367.0 (M+H)+

Step 2. (1-(2-Chloro-5-((1-methyl-1H-pyrazol-4-yl)ethynyl)pyridin-4-yl)-4-methylpiperidin-4-yl)methanol The title compound as a solid (221 mg) was prepared in the same fashion as Step 2 in Example 1 except that (1-(2-chloro-5-iodopyridin-4-yl)-4-methylpiperidin-4-yl)methanol (300 mg, 0.818 mmol) prepared in Step 1 was used instead of 1-(2-chloro-5-iodopyridin-4-yl)-4-methylpiperazine. MS (ESI) m/z=345.1 (M+H)+

Step 3. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol The title compound as a solid (46.7 mg) was prepared in the same fashion as Step 3 in Example 1 except that (1-(2-chloro-5-((1-methyl-1H-pyrazol-4-yl)ethynyl)pyridin-4-yl)-4-methylpiperidin-4-yl)methanol (220 mg, 0.638 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.66 (s, 1H), 8.45 (s, 1H), 8.41 (d, 1H), 8.23 (s, 1H), 7.92 (s, 1H), 7.63 (s, 2H), 7.55 (s, 1H), 6.97 (s, 1H), 3.93 (s, 3H), 3.70-3.67 (m, 2H), 3.51 (s, 2H), 3.40 (t, 2H), 2.85-2.82 (m, 1H), 1.80-1.76 (m, 2H), 1.59-1.57 (m, 2H), 1.54-1.52 (m, 2H), 1.27-1.22 (m, 2H), 1.09 (s, 3H); MS (ESI) m/z=574.2 (M+H)+

Example 13. 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol Step 1. 7-(2-Chloro-5-iodopyridin-4-yl)-2-methyl-7-azaspiro[3.5]nonan-2-ol The title compound as a solid (581 mg) was prepared in the same fashion as Step 1 in Example 1 except that 2-methyl-7-azaspiro[3.5]nonan-2-ol (470 mg, 3.030 mmol) was used instead of 1-methylpiperazine. MS (ESI) m/z=393.0 (M+H)+

Step 2. 7-(2-Chloro-5-((1-methyl-1H-pyrazol-4-yl)ethynyl)pyridin-4-yl)-2-methyl-7-azaspiro[3.5]nonan-2-ol The title compound as a solid (184 mg) was prepared in the same fashion as Step 2 in Example 1 except that 7-(2-chloro-5-iodopyridin-4-yl)-2-methyl-7-azaspiro[3.5]nonan-2-ol (300 mg, 0.764 mmol) prepared in Step 1 was used instead of 1-(2-chloro-5-iodopyridin-4-yl)-4-methylpiperazine. MS (ESI) m/z=371.2 (M+H)+

Step 3. 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol The title compound as a solid (82.6 mg) was prepared in the same fashion as Step 3 in Example 1 except that 7-(2-chloro-5-((1-methyl-1H-pyrazol-4-yl)ethynyl)pyridin-4-yl)-2-methyl-7-azaspiro[3.5]nonan-2-ol (183 mg, 0.493 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.65 (s, 1H), 8.45 (s, 1H), 8.40 (d, 1H), 8.23 (s, 1H), 8.18 (s, 1H), 7.63 (s, 1H), 7.59 (s, 1H), 7.55 (s, 1H), 6.98 (s, 1H), 3.94 (s, 3H), 3.46-3.41 (m, 4H), 2.86-2.83 (m, 1H), 2.07 (d, 2H), 2.03 (d, 2H), 1.91 (t, 2H), 1.81 (s, 1H), 1.80 (t, 3H), 1.54-1.51 (m, 2H), 1.44 (s, 3H), 1.27-1.21 (m, 2H); MS (ESI) m/z=600.3 (M+H)+

Example 14. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-2-methylpropan-1-ol Step 1. 2-(1-(2-Chloro-5-iodopyridin-4-yl)piperidin-4-yl)-2-methylpropan-1-ol The title compound as a solid (775 mg) was prepared in the same fashion as Step 1 in Example 1 except that 2-methyl-2-(4-piperidyl)propan-1-ol (476 mg, 3.030 mmol) was used instead of 1-methylpiperazine. MS (ESI) m/z=395.0 (M+H)+

Step 2. 2-(1-(2-Chloro-5-((1-methyl-1H-pyrazol-4-yl)ethynyl)pyridin-4-yl)piperidin-4-yl)-2-methylpropan-1-ol The title compound as a solid (204 mg) was prepared in the same fashion as Step 2 in Example 1 except that 2-(1-(2-chloro-5-iodopyridin-4-yl)piperidin-4-yl)-2-methylpropan-1-ol (300 mg, 0.760 mmol) prepared in Step 1 was used instead of 1-(2-chloro-5-iodopyridin-4-yl)-4-methylpiperazine. MS (ESI) m/z=373.1 (M+H)+

Step 3. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-2-methylpropan-1-ol The title compound as a solid (45 mg) was prepared in the same fashion as Step 3 in Example 1 except that 2-(1-(2-chloro-5-((1-methyl-1H-pyrazol-4-yl)ethynyl)pyridin-4-yl)piperidin-4-yl)-2-methylpropan-1-ol (203 mg, 0.544 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.68 (s, 1H), 8.46 (s, 1H), 8.41 (d, 1H), 8.23 (s, 1H), 8.02 (s, 1H), 7.64 (s, 2H), 7.55 (s, 1H), 6.98 (s, 1H), 4.21 (d, 2H), 3.94 (s, 3H), 2.96 (s, 2H), 2.85-8.82 (m, 3H), 1.87 (d, 2H), 1.75 (s, 2H), 1.58-1.52 (m, 3H), 1.25-1.22 (m, 3H), 0.90 (s, 6H); MS (ESI) m/z=602.2 (M+H)+

Example 15. 2-(1-(Cyclopropylsulfonyl)-1H-pyrazol-4-yl)-N-(4-(4-methoxypiperidin-1-yl)-5-((1-methyl-1H-pyrazol-4-yl)ethynyl)pyridin-2-yl)pyrimidin-4-amine

Step 1. 2-Chloro-5-iodo-4-(4-methoxypiperidin-1-yl)pyridine

The title compound as a solid (763 mg) was prepared in the same fashion as Step 1 in Example 1 except that 4-methoxypiperidine (349 mg, 3.030 mmol) was used instead of 1-methylpiperazine. MS (ESI) m/z=353.0 (M+H)$^+$

Step 2. 2-Chloro-4-(4-methoxypiperidin-1-yl)-5-((1-methyl-1H-pyrazol-4-yl)ethynyl)pyridine The title compound as a solid (331 mg) was prepared in the same fashion as Step 2 in Example 1 except that 2-chloro-5-iodo-4-(4-methoxypiperidin-1-yl)pyridine (500 mg, 1.418 mmol) was used instead of 1-(2-chloro-5-iodopyridin-4-yl)-4-methylpiperazine. MS (ESI) m/z=331.1 (M+H)$^+$

Step 3. 2-(1-(Cyclopropylsulfonyl)-1H-pyrazol-4-yl)-N-(4-(4-methoxypiperidin-1-yl)-5-((1-methyl-1H-pyrazol-4-yl)ethynyl)pyridin-2-yl)pyrimidin-4-amine The title compound as a solid (230 mg) was prepared in the same fashion as Step 3 in Example 1 except that 2-chloro-4-(4-methoxypiperidin-1-yl)-5-((1-methyl-1H-pyrazol-4-yl)ethynyl)pyridine (330 mg, 0.998 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.66 (s, 1H), 8.45 (s, 1H), 8.41 (d, 1H), 8.24 (s, 1H), 8.16 (s, 1H), 7.65 (s, 1H), 7.57 (s, 2H), 7.03 (s, 1H), 3.93 (s, 3H), 3.89-3.84 (m, 2H), 3.48-3.47 (m, 1H), 3.46-3.45 (m, 3H), 3.23-3.20 (m, 2H), 2.85-2.82 (m, 2H), 2.13-2.07 (m, 2H), 1.84-1.77 (m, 4H), 1.55-1.52 (m, 2H), 1.26-1.21 (m, 2H); MS (ESI) m/z=560.2 (M+H)$^+$

Example 16. 2-(4-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperazin-1-yl)ethan-1-ol

Step 1. 2-(4-(2-Chloro-5-iodopyridin-4-yl)piperazin-1-yl)ethan-1-ol

The title compound as a solid (443 mg) was prepared in the same fashion as Step 1 in Example 1 except that 2-(piperazin-1-yl)ethan-1-ol (285 mg, 2.191 mmol) was used instead of 1-methylpiperazine. MS (ESI) m/z=368.1 (M+H)$^+$

Step 2. 2-(4-(2-Chloro-5-((1-(2-fluoroethyl)-1H-pyrazol-4-yl)ethynyl)pyridin-4-yl)piperazin-1-yl)ethan-1-ol The title compound as a solid (201 mg) was prepared in the same fashion as Step 2 in Example 1 except that 2-(4-(2-chloro-5-iodopyridin-4-yl)piperazin-1-yl)ethan-1-ol (430 mg, 1.170 mmol) prepared in Step 1 and 4-ethynyl-1-(2-fluoroethyl)pyrazole (178 mg, 1.287 mmol) were used instead of 1-(2-chloro-5-iodopyridin-4-yl)-4-methylpiperazine and 4-ethynyl-1-methylpyrazole. MS (ESI) m/z=378.2 (M+H)$^+$

Step 3. 2-(4-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperazin-1-yl)ethan-1-ol The title compound as a solid (4.4 mg) was prepared in the same fashion as Step 3 in Example 1 except that 2-(4-(2-chloro-5-((1-(2-fluoroethyl)-1H-pyrazol-4-yl)ethynyl)pyridin-4-yl)piperazin-1-yl)ethan-1-ol (200 mg, 0.529 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.45 (s, 1H), 8.43 (d, 1H), 8.25 (s, 1H), 7.77 (s, 1H), 7.67 (s, 2H), 7.55 (s, 1H), 7.05 (d, 1H), 4.83 (t, 1H), 4.75 (t, 1H), 4.46 (t, 1H), 4.42 (t, 1H), 3.69 (t, 2H), 3.61 (s, 4H), 2.87-2.82 (m, 1H), 2.77 (t, 4H), 2.66-2.18 (m, 2H), 1.56-1.53 (m, 2H), 1.31-1.22 (m, 2H); MS (ESI) m/z=607.3 (M+H)$^+$

Example 17. 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)ethan-1-ol

Step 1. 2-(1-(2-Chloro-5-iodopyridin-4-yl)piperidin-4-yl)ethan-1-ol

The title compound as a solid (325 mg) was prepared in the same fashion as Step 1 in Example 1 except that 4-piperidineethanol (283 mg, 2.191 mmol) was used instead of 1-methylpiperazine. MS (ESI) m/z=367.0 (M+H)$^+$

Step 2. 2-(1-(2-Chloro-5-((1-(2-fluoroethyl)-1H-pyrazol-4-yl)ethynyl)pyridin-4-yl)piperidin-4-yl)ethan-1-ol The title compound as a solid (86 mg) was prepared in the same fashion as Step 2 in Example 1 except that 2-(1-(2-chloro-5-iodopyridin-4-yl)piperidin-4-yl)ethan-1-ol (140 mg, 0.382 mmol) prepared in Step 1 and 4-ethynyl-1-(2-fluoroethyl)pyrazole (53 mg, 0.382 mmol) were used instead of 1-(2-chloro-5-iodopyridin-4-yl)-4-methylpiperazine and 4-ethynyl-1-methylpyrazole. MS (ESI) m/z=345.2 (M+H)$^+$

Step 3. 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)ethan-1-ol The title compound as a solid (4.5 mg) was prepared in the same fashion as Step 3 in Example 1 except that 2-(1-(2-chloro-5-((1-(2-fluoroethyl)-1H-pyrazol-4-yl)ethynyl)pyridin-4-yl)piperidin-4-yl)ethan-1-ol (86 mg, 0.227 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.45 (s, 1H), 8.41 (s, 1H), 8.21 (s, 1H), 7.90 (s, 1H), 7.68 (d, 2H), 7.58 (s, 1H), 7.07 (d, 1H), 4.83 (t, 1H), 4.75 (t, 1H), 4.46 (t, 1H), 4.42 (t, 1H), 4.12 (d, 2H), 3.78-3.76 (m, 2H), 2.96-2.91 (m, 2H), 2.89-2.84 (m, 1H), 1.93-1.87 (m, 2H), 1.76-1.73 (m, 2H), 1.63-1.57 (m, 2H), 1.56-1.53 (m, 2H), 1.36-1.34 (m, 2H), 1.28-1.21 (m, 2H); MS (ESI) m/z=606.2 (M+H)$^+$

Example 18. N²-(2-(1-(Cyclopropylsulfonyl)-1H-pyrazol-4-yl)pyrimidin-4-yl)-N⁴-isopropyl-5-((1-methyl-1H-pyrazol-4-yl)ethynyl)pyridine-2,4-diamine

Step 1. 2-Chloro-N-isopropyl-5-((1-methyl-1H-pyrazol-4-yl)ethynyl)pyridin-4-amine The title compound as a solid (237 mg) was prepared in the same fashion as Step 2 in Example 1 except that 2-chloro-5-iodo-N-isopropylpyridin-4-amine (285 mg, 0.961 mmol) was used instead of 1-(2-chloro-5-iodopyridin-4-yl)-4-methylpiperazine. MS (ESI) m/z=275.1 (M+H)⁺

Step 2. N²-(2-(1-(Cyclopropylsulfonyl)-1H-pyrazol-4-yl)pyrimidin-4-yl)-N⁴-isopropyl-5-((1-methyl-1H-pyrazol-4-yl)ethynyl)pyridine-2,4-diamine The title compound as a solid (89 mg) was prepared in the same fashion as Step 3 in Example 1 except that 2-chloro-N-isopropyl-5-((1-methyl-1H-pyrazol-4-yl)ethynyl)pyridin-4-amine (107 mg, 0.39 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.45 (s, 1H), 8.39 (d, 1H), 8.34 (s, 1H), 8.13 (s, 1H), 7.66 (s, 1H), 7.60 (s, 1H), 7.32 (s, 1H) 7.01 (s, 1H), 4.95 (d, 1H), 3.94 (s, 3H), 3.88-3.83 (m, 1H), 2.85-2.81 (m, 1H), 1.54-1.51 (m, 2H), 1.38 (d, 6H), 1.23-1.20 (m, 2H); MS (ESI) m/z=504.0 (M+H)⁺

Example 19. N²-(2-(1-(Cyclopropylsulfonyl)-1H-pyrazol-4-yl)pyrimidin-4-yl)-N⁴-isopropyl-5-((1-isopropyl-1H-pyrazol-4-yl)ethynyl)pyridine-2,4-diamine

Step 1. 2-Chloro-N-isopropyl-5-((1-isopropyl-1H-pyrazol-4-yl)ethynyl)pyridin-4-amine The title compound as a solid (85 mg) was prepared in the same fashion as Step 2 in Example 1 except that 4-ethynyl-1-isopropylpyrazole (95 mg, 0.708 mmol) and 2-chloro-5-iodo-N-isopropylpyridin-4-amine (140 mg, 0.472 mmol) were used instead of 4-ethynyl-1-methylpyrazole and 1-(2-chloro-5-iodopyridin-4-yl)-4-methylpiperazine. MS (ESI) m/z=303.1 (M+H)⁺

Step 2. N²-(2-(1-(Cyclopropylsulfonyl)-1H-pyrazol-4-yl)pyrimidin-4-yl)-N⁴-isopropyl-5-((1 isopropyl-1H-pyrazol-4-yl)ethynyl)pyridine-2,4-diamine The title compound as a solid (17 mg) was prepared in the same fashion as Step 3 in Example 1 except that 2-chloro-N-isopropyl-5-((1-isopropyl-1H-pyrazol-4-yl)ethynyl)pyridin-4-amine (110 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.61 (s, 1H), 8.44-8.42 (s, 2H), 7.98 (s, 1H), 7.87 (s, 1H), 7.69 (s, 1H), 7.67 (s, 1H), 7.01 (S, 1H), 5.41 (d, 1H), 4.56-4.51 (m, 1H), 3.96-3.93 (m, 1H), 2.84 (t, 1H), 1.61-1.60 (m, 8H), 1.55 (d, 6H), 1.25-1.24 (m, 3H); MS (ESI) m/z=532.2 (M+H)⁺

Example 20. N²-(2-(1-(Cyclopropylsulfonyl)-1H-pyrazol-4-yl)pyrimidin-4-yl)-5-((1-(2-fluoroethyl)-1H-pyrazol-4-yl)ethynyl)-N⁴-isopropylpyridine-2,4-diamine

Step 1. 2-Chloro-5-((1-(2-fluoroethyl)-1H-pyrazol-4-yl)ethynyl)-N-isopropylpyridin-4-amine The title compound as a solid (115 mg) was prepared in the same fashion as Step 2 in Example 1 except that 4-ethynyl-1-(2-fluoroethyl)pyrazole (98 mg, 0.708 mmol) and 2-chloro-5-iodo-N-isopropylpyridin-4-amine (140 mg, 0.472 mmol) were used instead of 4-ethynyl-1-methylpyrazole and 1-(2-chloro-5-iodopyridin-4-yl)-4-methylpiperazine. MS (ESI) m/z=307.1 (M+H)⁺

Step 2. N²-(2-(1-(Cyclopropylsulfonyl)-1H-pyrazol-4-yl)pyrimidin-4-yl)-5-((1-(2-fluoroethyl)-1H-pyrazol-4-yl)ethynyl)-N⁴-isopropylpyridine-2,4-diamine The title compound as a solid (45 mg) was prepared in the same fashion as Step 3 in Example 1 except that 2-chloro-5-((1-(2-fluoroethyl)-1H-pyrazol-4-yl)ethynyl)-N-isopropylpyridin-4-amine (111 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.45 (s, 1H), 8.39 (d, 1H), 8.20 (s, 1H), 8.13 (s, 1H), 7.31 (d, 2H), 7.30 (s, 1H), 7.02 (d, 1H), 4.96 (d, 1H), 4.83 (t, 1H), 4.75 (t, 1H), 4.47 (t, 1H), 4.24 (t, 1H), 3.87-3.84 (m, 1H), 2.85-2.81 (m, 1H), 1.53-1.51 (m, 2H), 1.38 (d, 6H), 1.23-1.20 (m, 2H); MS (ESI) m/z=536.2 (M+H)⁺

Example 21. N²-(2-(1-(Cyclopropylsulfonyl)-1H-pyrazol-4-yl)pyrimidin-4-yl)-N⁴-isopropyl-5-(pyridin-3-ylethynyl)pyridine-2,4-diamine

Step 1. 2-Chloro-N-isopropyl-5-(pyridin-3-ylethynyl)pyridin-4-amine

The title compound as a solid (45 mg) was prepared in the same fashion as Step 2 in Example 1 except that 3-ethynylpyridine (73 mg, 0.708 mmol) and 2-chloro-5-iodo-N-isopropylpyridin-4-amine (140 mg, 0.472 mmol) were used instead of 4-ethynyl-1-methylpyrazole and 1-(2-chloro-5-iodopyridin-4-yl)-4-methylpiperazine. MS (ESI) m/z=272.1 (M+H)⁺

Step 2. N²-(2-(1-(Cyclopropylsulfonyl)-1H-pyrazol-4-yl)pyrimidin-4-yl)-N⁴-isopropyl-5-(pyridin-3-ylethynyl)pyridine-2,4-diamine The title compound as a solid (34 mg) was prepared in the same fashion as Step 3 in Example 1 except that 2-chloro-N-isopropyl-5-(pyridin-3-ylethynyl)pyridin-4-amine (98 mg, 0.362 mmol) was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.77 (s, 1H), 8.70 (s, 1H), 8.64 (s, 1H), 8.58 (d, 1H), 8.45 (s, 1H), 8.41 (d, 1H), 8.17 (s, 1H), 7.81 (d, 1H), 7.45 (s, 1H), 7.34-7.32 (m, 1H), 7.00 (d, 1H), 5.00 (d, 1H), 3.92-3.87 (m, 1H), 2.86-2.82 (m, 2H), 1.54-1.52 (m, 2H), 1.39 (d, 6H), 1.22-1.18 (d, 2H); MS (ESI) m/z=501.2 (M+H)⁺

Example 22. N²-(2-(1-(Cyclopropylsulfonyl)-1H-pyrazol-4-yl)pyrimidin-4-yl)-N⁴-isopropyl-5-(4-methoxybut-1-yn-1-yl)pyridine-2,4-diamine

Step 1. 2-Chloro-N-isopropyl-5-(4-methoxybut-1-yn-1-yl)pyridin-4-amine

The title compound as a solid (109 mg) was prepared in the same fashion as Step 2 in Example 1 except that 4-methoxybut-1-yne (102 mg, 1.214 mmol) and 2-chloro-5-iodo-N-isopropylpyridin-4-amine (240 mg, 0.809 mmol)

were used instead of 4-ethynyl-1-methylpyrazole and 1-(2-chloro-5-iodopyridin-4-yl)-4-methylpiperazine. MS (ESI) m/z=253.1 (M+H)+

Step 2. N²-(2-(1-(Cyclopropylsulfonyl)-1H-pyrazol-4-yl)pyrimidin-4-yl)-N⁴-isopropyl-5-(4-methoxybut-1-yn-1-yl)pyridine-2,4-diamine The title compound as a solid (3 mg) was prepared in the same fashion as Step 3 in Example 1 except that 2-chloro-N-isopropyl-5-(4-methoxybut-1-ynyl)pyridin-4-amine (91 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) S 8.63 (s, 1H), 8.44 (s, 1H), 8.40 (s, 1H), 8.01 (s, 1H), 7.43 (s, 1H), 7.08 (s, 1H), 3.62 (t, 2H), 3.44 (s, 3H), 2.77 (t, 2H), 1.36 (d, 6H), 1.22 (d, 2H), 0.87 (d, 2H); MS (ESI) m/z=482.2 (M+H)+

Example 23. N²-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N⁴-isopropylpyridine-2,4-diamine Step 1. 2-Chloro-5-((1-(2,2-difluoroethyl)-1H-pyrazol-4-yl)ethynyl)-N-isopropylpyridin-4-amine The title compound as a solid (165.4 mg) was prepared in the same fashion as Step 2 in Example 1 except that 1-(2,2-difluoroethyl)-4-ethynyl-pyrazole (139 mg, 0.890 mmol) and 2-chloro-5-iodo-N-isopropylpyridin-4-amine (220 mg, 0.742 mmol) were used instead of 4-ethynyl-1-methylpyrazole and 1-(2-chloro-5-iodopyridin-4-yl)-4-methylpiperazine. MS (ESI) m/z=325.1 (M+H)+

Step 2. N²-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N⁴-isopropylpyridine-2,4-diamine The title compound as a solid (39 mg) was prepared in the same fashion as Step 3 in Example 1 except that 2-chloro-5-((1-(2,2-difluoroethyl)-1H-pyrazol-4-yl)ethynyl)-N-isopropylpyridin-4-amine (160 mg, 0.493 mmol) prepared in Step 1 was used instead of 1-(2-chloro-5-((1-methyl-1H-pyrazol-4-yl)ethynyl)pyridin-4-yl)-4-methylpiperazine. ¹H-NMR (MeOD, 600 MHz) S 8.75 (s, 1H), 8.46 (s, 1H), 8.40 (d, 1H), 8.06 (s, 1H), 8.00 (s, 1H), 7.76 (s, 1H), 7.24 (s, 1H), 6.21 (t, 1H), 4.63-4.57 (m, 2H), 3.90-3.88 (m, 1H), 3.05-3.03 (m, 1H), 1.46-1.43 (m, 2H), 1.36 (d, 6H), 1.27-1.25 (m, 2H); MS (ESI) m/z=554.2 (M+H)+

Example 24. N⁴-(sec-Butyl)-N²-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine Step 1. N-(sec-Butyl)-2-chloro-5-((1-methyl-1H-pyrazol-4-yl)ethynyl)pyridin-4-amine The title compound as a solid (132 mg) was prepared in the same fashion as Step 2 in Example 1 except that N-(sec-butyl)-2-chloro-5-iodopyridin-4-amine (140 mg, 0.451 mmol) prepared in Reference Example 1 was used instead of 1-(2-chloro-5-iodopyridin-4-yl)-4-methylpiperazine. MS (ESI) m/z=289.0 (M+H)+

Step 2. N⁴-(sec-Butyl)-N²-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine The title compound as a solid (14 mg) was prepared in the same fashion as Step 3 in Example 1 except that N-(sec-butyl)-2-chloro-5-((1-methyl-1H-pyrazol-4-yl)ethynyl)pyridin-4-amine (104 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.45 (s, 1H), 8.40 (s, 1H), 8.39 (s, 1H), 8.10 (s, 1H), 7.65 (s, 1H), 7.59 (s, 1H), 7.22 (s, 1H), 7.09 (d, 1H), 4.97 (d, 1H), 3.94 (s, 3H), 3.67-3.62 (m, 1H), 2.85-2.80 (m, 1H), 1.74-1.64 (m, 2H), 1.54-1.51 (m, 2H), 1.33 (d, 2H), 1.29-1.23 (m, 2H), 1.22-1.18 (m, 2H), 1.13 (d, 2H), 1.00 (t, 3H); MS (ESI) m/z=518.2 (M+H)+

Example 25. N⁴-(sec-Butyl)-N²-(2-(1-(cyclopropylsulfonyl)-1H-pyrazol-4-yl)pyrimidin-4-yl)-5-((1-isopropyl-1H-pyrazol-4-yl)ethynyl)pyridine-2,4-diamine Step 1. N-(sec-Butyl)-2-chloro-5-((1-isopropyl-1H-pyrazol-4-yl)ethynyl)pyridin-4-amine The title compound as a solid (155 mg) was prepared in the same fashion as Step 2 in Example 1 except that N-(sec-butyl)-2-chloro-5-iodopyridin-4-amine (190 mg, 0.612 mmol) prepared in Reference Example 1 and 4-ethynyl-1-isopropylpyrazole (123 mg, 0.918 mmol) were used instead of 1-(2-chloro-5-iodopyridin-4-yl)-4-methylpiperazine and 4-ethynyl-1-methylpyrazole. MS (ESI) m/z=316.1 (M+H)+

Step 2. N⁴-(sec-Butyl)-N²-(2-(1-(cyclopropylsulfonyl)-1H-pyrazol-4-yl)pyrimidin-4-yl)-5-((1-isopropyl-1H-pyrazol-4-yl)ethynyl)pyridine-2,4-diamine The title compound as a solid (14 mg) was prepared in the same fashion as Step 3 in Example 1 except that N-(sec-butyl)-2-chloro-5-((1-isopropyl-1H-pyrazol-4-yl)ethynyl)pyridin-4-amine (115 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.45 (s, 1H), 8.40 (d, 1H), 8.08 (s, 1H), 7.67 (s, 1H), 7.65 (s, 1H), 7.48-7.45 (m, 1H), 7.24 (s, 1H), 7.11 (s, 1H), 5.00 (d, 1H), 4.55-4.50 (m, 1H), 3.67-3.63 (m, 1H), 2.85-2.80 (m, 1H), 1.75-1.64 (m, 2H), 1.54 (d, 6H), 1.52-1.51 (m, 1H), 1.34 (d, 3H), 1.22-1.18 (m, 2H), 1.01 (t, 3H); MS (ESI) m/z=546.2 (M+H)+

Example 26. N⁴-(sec-Butyl)-N²-(2-(1-(cyclopropylsulfonyl)-1H-pyrazol-4-yl)pyrimidin-4-yl)-5-((1-(2-fluoroethyl)-1H-pyrazol-4-yl)ethynyl)pyridine-2,4-diamine Step 1. N-(sec-Butyl)-2-chloro-5-((1-(2-fluoroethyl)-1H-pyrazol-4-yl)ethynyl)pyridin-4-amine The title compound as a solid (190 mg) was prepared in the same fashion as Step 2 in Example 1 except that N-(sec-butyl)-2-chloro-5-iodopyridin-4-amine (190 mg, 0.612 mmol) prepared in Reference Example 1 and 4-ethynyl-1-(2-fluoroethyl)pyrazole (127 mg, 0.918 mmol) were used instead of 1-(2-chloro-5-iodopyridin-4-yl)-4-methylpiperazine and 4-ethynyl-1-methylpyrazole. MS (ESI) m/z=320.1 (M+H)+

Step 2. N⁴-(sec-Butyl)-N²-(2-(1-(cyclopropylsulfonyl)-1H-pyrazol-4-yl)pyrimidin-4-yl)-5-((1-(2-fluoroethyl)-1H-pyrazol-4-yl)ethynyl)pyridine-2,4-diamine The title compound as a solid (16 mg) was prepared in the same fashion as Step 3 in Example 1 except that N-(sec-butyl)-2-chloro-5-((1-(2-fluoroethyl)-1H-pyrazol-4-yl)ethynyl)pyridin-4-amine (116 mg, 0.362 mmol) prepared in Step 1 was used instead of 1-(2-chloro-5-((1-methyl-H-pyrazol-4-yl)ethynyl)pyridin-4-yl)-4-methylpiperazine. ¹H-NMR (CDCl₃, 600 MHz) δ 8.64 (s, 1H), 8.55 (s, 1H), 8.45 (s, 1H), 8.40 (d, 1H), 8.10 (s, 1H), 7.71 (s, 2H), 7.08 (s, 1H), 4.98 (d, 1H), 4.83 (t, 1H), 4.75 (t, 1H), 4.47 (t, 1H), 4.42 (t, 1H), 3.68-3.63 (m, 1H), 2.85-2.81 (m, 1H), 1.75-1.65 (m, 2H), 1.54-1.51 (m, 2H), 1.34 (d, 3H), 1.24-1.20 (m, 2H), 1.01 (t, 3H); MS (ESI) m/z=550.2 (M+H)⁺

Example 27. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol

Step 1. 1-(2-Chloro-5-((1-methyl-1H-pyrazol-4-yl)ethynyl)pyridin-4-yl)piperidin-4-ol The title compound as a solid (385.4 mg) was prepared in the same fashion as Step 2 in Example 1 except that 1-(2-chloro-5-iodopyridin-4-yl)piperidin-4-ol (460 mg, 1.359 mmol) prepared in Reference Example 2 was used instead of 1-(2-chloro-5-iodopyridin-4-yl)-4-methylpiperazine. MS (ESI) m/z=317.0 (M+H)⁺

Step 2. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol The title compound as a solid (51 mg) was prepared in the same fashion as Step 3 in Example 1 except that 1-(2-chloro-5-((1-methyl-1H-pyrazol-4-yl)ethynyl)pyridin-4-yl)piperidin-4-ol (200 mg, 0.631 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) S 8.68 (s, 1H), 8.45 (s, 1H), 8.41 (d, 1H), 8.24 (s, 1H), 7.65 (s, 1H), 7.63 (s, 1H), 7.56 (s, 1H), 6.98 (d, 1H), 4.02-4.00 (m, 1H), 3.93 (s, 3H), 3.88-3.84 (m, 2H), 3.28-3.24 (m, 2H), 2.85-2.82 (m, 1H), 2.18-2.10 (m, 2H), 1.85-1.79 (m, 2H), 1.56-1.53 (m, 2H), 1.25-1.21 (m, 2H); MS (ESI) m/z=546.2 (M+H)⁺

Example 28. 1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-ol

Step 1. 1-(2-Chloro-5-((1-(2-fluoroethyl)-1H-pyrazol-4-yl)ethynyl)pyridin-4-yl)piperidin-4-ol The title compound as a solid (80 mg) was prepared in the same fashion as Step 2 in Example 1 except that 4-ethynyl-1-(2-fluoroethyl)pyrazole (67 mg, 0.487 mmol) and 1-(2-chloro-5-iodopyridin-4-yl)piperidin-4-ol (150 mg, 0.443 mmol) prepared in Reference Example 2 were used instead of 4-ethynyl-1-methylpyrazole and 1-(2-chloro-5-iodopyridin-4-yl)-4-methylpiperazine. MS (ESI) m/z=349.2 (M+H)⁺

Step 2. 1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-ol The title compound as a solid (7 mg) was prepared in the same fashion as Step 3 in Example 1 except that 1-(2-chloro-5-((1-(2-fluoroethyl)-1H-pyrazol-4-yl)ethynyl)pyridin-4-yl)piperidin-4-ol (80 mg, 0.229 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.68 (s, 1H), 8.45 (s, 1H), 8.41 (d, 1H), 8.24 (s, 1H), 7.83 (s, 1H), 7.69 (s, 2H), 7.64 (s, 1H), 6.99 (d, 1H), 4.82 (t, 1H), 4.75 (t, 1H), 4.46 (t, 1H), 4.41 (t, 1H), 4.02-4.00 (m, 1H), 3.88-3.84 (m, 2H), 3.28-3.25 (m, 2H), 2.85-2.82 (m, 1H), 2.12-2.10 (m, 2H), 1.85-1.79 (m, 2H), 1.55-1.53 (m, 2H), 1.26-1.21 (m, 2H); MS (ESI) m/z=560.2 (M+H)⁺

Example 29. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanol

Step 1. (1-(2-Chloro-5-((1-methyl-1H-pyrazol-4-yl)ethynyl)pyridin-4-yl)piperidin-4-yl)methanol The title compound as a solid (78 mg) was prepared in the same fashion as Step 2 in Example 1 except that (1-(2-chloro-5-iodopyridin-4-yl)piperidin-4-yl)methanol (150 mg, 0.425 mmol) prepared in Reference Example 3 was used instead of 1-(2-chloro-5-iodopyridin-4-yl)-4-methylpiperazine. MS (ESI) m/z=331.1 (M+H)⁺

Step 2. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanol The title compound as a solid (5 mg) was prepared in the same fashion as Step 3 in Example 1 except that (1-(2-chloro-5-((1-methyl-1H-pyrazol-4-yl)ethynyl)pyridin-4-yl)piperidin-4-yl)methanol (78 mg, 0.235 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.66 (s, 1H), 8.45 (s, 1H), 8.41 (d, 1H), 8.22 (s, 1H), 7.82 (s, 1H), 7.63 (s, 1H), 7.54 (s, 2H), 7.04 (s, 1H), 4.15 (d, 2H), 3.96 (s, 3H), 3.75 (d, 2H), 2.93 (t, 2H), 2.84-2.82 (m, 1H), 1.95 (d, 2H), 1.55-1.47 (m, 5H), 1.25-1.20 (m, 2H); MS (ESI) m/z=578.2 (M+H)⁺

Example 30. (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol

Step 1. (1-(2-Chloro-5-((1-(2-fluoroethyl)-1H-pyrazol-4-yl)ethynyl)pyridin-4-yl)piperidin-4-yl)methanol The title compound as a solid (225 mg) was prepared in the same fashion as Step 2 in Example 1 except that 4-ethynyl-1-(2-fluoroethyl)pyrazole (194 mg, 1.404 mmol) and (1-(2-chloro-5-iodopyridin-4-yl)piperidin-4-yl)methanol (450 mg, 1.276 mmol) prepared in Reference Example 3 were used instead of 4-ethynyl-1-methylpyrazole and 1-(2-chloro-5-iodopyridin-4-yl)-4-methylpiperazine. MS (ESI) m/z=363.1 (M+H)$^+$ Step 2. (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol The title compound as a solid (17 mg) was prepared in the same fashion as Step 3 in Example 1 except that (1-(2-chloro-5-((1-(2-fluoroethyl)-1H-pyrazol-4-yl)ethynyl)pyridin-4-yl)piperidin-4-yl)methanol (220 mg, 0.606 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.45 (s, 1H), 8.40 (d, 1H), 8.27 (s, 1H), 8.24 (s, 1H), 7.68 (s, 2H), 7.56 (s, 1H), 7.02 (s, 1H), 4.82 (t, 1H), 4.75 (t, 1H), 4.46 (t, 1H), 4.41 (t, 1H), 4.16-4.12 (m, 2H), 2.94 (t, 2H), 2.84-2.82 (m, 1H), 1.87-1.77 (m, 2H), 1.54-1.47 (m, 4H), 1.27-1.20 (m, 2H); MS (ESI) m/z=592.2 (M+H)$^+$ Example 31. (R)-1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-ol Step 1. (R)-1-(2-Chloro-5-((1-methyl-1H-pyrazol-4-yl)ethynyl)pyridin-4-yl)pyrrolidin-3-ol The title compound as a solid (56.6 mg) was prepared in the same fashion as Step 2 in Example 1 except that (R)-1-(2-chloro-5-iodopyridin-4-yl)pyrrolidin-3-ol (200 mg, 0.616 mmol) prepared in Reference Example 4 was used instead of 1-(2-chloro-5-iodopyridin-4-yl)-4-methylpiperazine. MS (ESI) m/z=317.1 (M+H)$^+$ Step 2. (R)-1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-ol The title compound as a solid (39 mg) was prepared in the same fashion as Step 3 in Example 1 except that (R)-1-(2-chloro-5-((1-methyl-1H-pyrazol-4-yl)ethynyl)pyridin-4-yl)pyrrolidin-3-ol (118 mg, 0.390 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.08 (s, 1H), 8.66 (s, 1H), 8.44 (s, 1H), 8.41 (d, 1H), 8.03 (s, 1H), 7.99 (s, 1H), 7.63 (s, 1H), 7.35 (s, 2H), 5.06 (s, 1H), 4.40 (s, 1H), 3.88-3.84 (m, 1H), 3.74-3.69 (m, 1H), 3.64-3.62 (m, 1H), 3.52-3.50 (m, 1H), 3.26-3.24 (m, 1H), 2.01 (s, 1H), 2.00 (s, 1H), 1.34-1.32 (m, 2H), 1.27-1.25 (m, 2H); MS (ESI) m/z=600.2 (M+H)$^+$ Example 32. (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-ol Step 1. (R)-1-(2-Chloro-5-((1-(2-fluoroethyl)-1H-pyrazol-4-yl)ethynyl)pyridin-4-yl)pyrrolidin-3-ol The title compound as a solid (52 mg) was prepared in the same fashion as Step 2 in Example 1 except that 4-ethynyl-1-(2-fluoroethyl)pyrazole (112 mg, 0.813 mmol) and (R)-1-(2-chloro-5-iodopyridin-4-yl)pyrrolidin-3-ol (240 mg, 0.739 mmol) prepared in Reference Example 4 were used instead of 4-ethynyl-1-methylpyrazole and 1-(2-chloro-5-iodopyridin-4-yl)-4-methylpiperazine. MS (ESI) m/z=335.1 (M+H)$^+$ Step 2. (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-ol The title compound as a solid (10 mg) was prepared in the same fashion as Step 3 in Example 1 except that (R)-1-(2-chloro-5-((1-(2-fluoroethyl)-1H-pyrazol-4-yl)ethynyl)pyridin-4-yl)pyrrolidin-3-ol (200 mg, 0.597 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 600 MHz) δ 8.75 (s, 1H), 8.46 (s, 1H), 8.35 (s, 1H), 8.05 (s, 1H), 7.89 (s, 1H), 7.67 (s, 1H), 7.28 (s, 2H), 4.79 (t, 1H), 4.71 (t, 1H), 4.55 (t, 1H), 4.43 (t, 1H), 4.01 (t, 1H), 3.91 (d, 1H), 3.85-3.82 (m, 2H), 3.05-3.03 (m, 1H), 2.19 (s, 1H), 1.59 (s, 2H), 1.45-1.22 (m, 2H), 0.91-0.89 (m, 1H); MS (ESI) m/z=564.3 (M+H)$^+$ Example 33. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-yl)methanol Step 1. (1-(2-Chloro-5-((1-methyl-1H-pyrazol-4-yl)ethynyl)pyridin-4-yl)pyrrolidin-3-yl)methanol The title compound as a solid (57 mg) was prepared in the same fashion as Step 2 in Example 1 except that (1-(2-chloro-5-iodopyridin-4-yl)pyrrolidin-3-yl)methanol (200 mg, 0.591 mmol) prepared in Reference Example 5 was used instead of 1-(2-chloro-5-iodopyridin-4-yl)-4-methylpiperazine. MS (ESI) m/z=303.1 (M+H)$^+$ Step 2. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-yl)methanol The title compound as a solid (23 mg) was prepared in the same fashion as Step 3 in Example 1 except that (1-(2-chloro-5-((1-methyl-1H-pyrazol-4-yl)ethynyl)pyridin-4-yl)pyrrolidin-3-yl)methanol (108 mg, 0.342 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.64 (s, 1H), 8.46 (s, 1H), 8.38 (s, 1H), 8.13 (s, 1H), 7.75 (s, 1H), 7.60 (s, 1H), 7.53 (s, 1H), 6.92 (s, 1H), 3.94 (s, 3H), 3.92-3.85 (m, 1H), 3.84-3.77 (m, 1H), 3.75-3.63 (m, 2H), 2.84-2.82 (m, 1H), 2.59-2.57 (m, 1H), 2.15-2.14 (m, 1H), 1.87-1.84 (m, 2H), 1.55-1.52 (m, 2H), 1.33-1.26 (m, 4H), 1.24-1.22 (m, 2H); MS (ESI) m/z=546.2 (M+H)$^+$ Example 34. (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-yl)methanol Step 1. (1-(2-Chloro-5-((1-(2-fluoroethyl)-1H-pyrazol-4-yl)ethynyl)pyridin-4-yl)pyrrolidin-3-yl)methanol The title compound as a solid (144 mg) was prepared in the same fashion as Step 2 in Example 1 except that 4-ethynyl-1-(2-fluoroethyl)pyrazole (90 mg, 0.650 mmol)

and (1-(2-chloro-5-iodopyridin-4-yl)pyrrolidin-3-yl)methanol (200 mg, 0.591 mmol) prepared in Reference Example 5 were used instead of 4-ethynyl-1-methylpyrazole and 1-(2-chloro-5-iodopyridin-4-yl)-4-methylpiperazine. MS (ESI) m/z=349.1 (M+H)$^+$ Step 2. (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-yl)methanol The title compound as a solid (15 mg) was prepared in the same fashion as Step 3 in Example 1 except that (1-(2-chloro-5-((1-(2-fluoroethyl)-1H-pyrazol-4-yl)ethynyl)pyridin-4-yl)pyrrolidin-3-yl)methanol (143 mg, 0.410 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.64 (s, 1H), 8.46 (s, 1H), 8.37 (d, 1H), 8.13 (s, 1H), 7.87 (s, 1H), 7.66 (s, 1H), 7.31 (s, 1H), 6.90 (s, 1H), 4.81 (t, 1H), 4.74 (t, 1H), 4.44 (t, 1H), 4.40 (t, 1H), 3.95-3.91 (m, 2H), 3.86-3.80 (m, 1H), 3.79-3.75 (m, 1H), 3.69-3.64 (m, 2H), 2.84-2.82 (m, 1H), 2.60-2.58 (m, 1H), 2.16-2.13 (m, 1H), 1.87-1.84 (m, 1H), 1.54-1.51 (m, 2H), 1.24-1.20 (m, 21-1); MS (ESI) m/z=578.2 (M+H)$^+$ Example 35. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol Step 1. 2-(1-(2-Chloro-5-((1-methyl-1H-pyrazol-4-yl)ethynyl)pyridin-4-yl)azetidin-3-yl)propan-2-ol The title compound as a solid (184 mg) was prepared in the same fashion as Step 2 in Example 1 except that 2-(1-(2-chloro-5-iodopyridin-4-yl)azetidin-3-yl)propan-2-ol (261 mg, 0.740 mmol) prepared in Reference Example 6 was used instead of 1-(2-chloro-5-iodopyridin-4-yl)-4-methylpiperazine. MS (ESI) m/z=331.1 (M+H)$^+$ Step 2. 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol The title compound as a solid (59 mg) was prepared in the same fashion as Step 3 in Example 1 except that 2-(1-(2-chloro-5-((1-methyl-1H-pyrazol-4-yl)ethynyl)pyridin-4-yl)azetidin-3-yl)propan-2-ol (184 mg, 0.555 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.59 (s, 1H), 8.40 (s, 1H), 8.26 (d, 1H), 7.95 (s, 1H), 7.58 (s, 1H), 7.50 (s, 1H), 7.10 (d, 1H), 6.69 (s, 1H), 4.28 (d, 4H), 3.92 (s, 3H), 2.84-2.80 (m, 2H), 1.54-1.50 (m, 2H), 1.27 (s, 6H), 1.23-1.20 (m, 2H); MS (ESI) m/z=560.2 (M+H)$^+$ Example 36. 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)azetidin-3-yl)propan-2-ol Step 1. 2-(1-(2-Chloro-5-((1-(2-fluoroethyl)-1H-pyrazol-4-yl)ethynyl)pyridin-4-yl)azetidin-3-yl)propan-2-ol The title compound as a solid (300 mg) was prepared in the same fashion as Step 2 in Example 1 except that 4-ethynyl-1-(2-fluoroethyl)pyrazole (129 mg, 0.936 mmol) and 2-(1-(2-chloro-5-iodopyridin-4-yl)azetidin-3-yl)propan-2-ol (261 mg, 0.740 mmol) prepared in Reference Example 6 were used instead of 4-ethynyl-1-methylpyrazole and 1-(2-chloro-5-iodopyridin-4-yl)-4-methylpiperazine. MS (ESI) m/z=363.1 (M+H)$^+$ Step 2. 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)azetidin-3-yl)propan-2-ol The title compound as a solid (13 mg) was prepared in the same fashion as Step 3 in Example 1 except that 2-(1-(2-chloro-5-((1-(2-fluoroethyl)-1H-pyrazol-4-yl)ethynyl)pyridin-4-yl)azetidin-3-yl)propan-2-ol (300 mg, 0.827 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.58 (s, 1H), 8.40 (s, 1H), 8.24 (d, 1H), 7.92 (s, 1H), 7.63 (d, 2H), 7.10 (d, 2H), 6.68 (s, 1H), 4.82 (t, 1H), 4.74 (t, 1H), 4.44 (t, 1H), 4.40 (t, 1H), 4.39-4.25 (m, 4H), 2.88-2.78 (m, 2H), 1.54-1.50 (m, 2H), 1.27-1.25 (m, 9H), 1.22-1.16 (m, 3H); MS (ESI) m/z=592.2 (M+H)$^+$ Example 37. 2-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)(methyl)amino)ethan-1-ol Step 1. 2-((2-Chloro-5-((1-methyl-1H-pyrazol-4-yl)ethynyl)pyridin-4-yl)(methyl)amino)ethan-1-ol The title compound as a solid (94 mg) was prepared in the same fashion as Step 2 in Example 1 except that 2-((2-chloro-5-iodopyridin-4-yl)(methyl)amino)ethan-1-ol (280 mg, 0.896 mmol) prepared in Reference Example 7 was used instead of 1-(2-chloro-5-iodopyridin-4-yl)-4-methylpiperazine. MS (ESI) m/z=291.1 (M+H)$^+$ Step 2. 2-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)(methyl)amino)ethan-1-ol The title compound as a solid (8 mg) was prepared in the same fashion as Step 3 in Example 1 except that 2-((2-chloro-5-((1-methyl-1H-pyrazol-4-yl)ethynyl)pyridin-4-yl)(methyl)amino)ethan-1-ol (94 mg, 0.322 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.66 (s, 1H), 8.43 (s, 1H), 8.38 (d, 1H), 8.18 (s, 1H), 8.03 (s, 1H), 7.63 (s, 1H), 7.58 (s, 1H), 7.53 (s, 1H), 7.02 (s, 1H), 4.12-3.97 (m, 2H), 3.94-3.85 (m, 5H), 3.18 (s, 3H), 2.86-2.81 (m, 1H), 1.54-1.48 (m, 2H), 1.27-1.20 (m, 2H); MS (ESI) m/z=520.1 (M+H)$^+$ Example 38. 2-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)(methyl)amino)ethan-1-ol Step 1. 2-((2-Chloro-5-((1-(2-fluoroethyl)-1H-pyrazol-4-yl)ethynyl)pyridin-4-yl)(methyl)amino)ethan-1-ol The title compound as a solid (322 mg) was prepared in the same fashion as Step 2 in Example 1 except that 4-ethynyl-1-(2-fluoroethyl)pyrazole (136 mg, 0.985 mmol) and 2-((2-chloro-5-iodopyridin-4-yl)(methyl)amino)ethan-1-ol (280 mg, 0.896 mmol) prepared in Reference Example 7 were used instead of 4-ethynyl-1-methylpyrazole and 1-(2-chloro-5-iodopyridin-4-yl)-4-methylpiperazine. MS (ESI) m/z=323.1 (M+H)$^+$ Step 2. 2-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)(methyl)amino)ethan-1-ol The title compound as a solid (20 mg) was prepared in the same fashion as Step 3 in Example 1 except that 2-((2-chloro-5-((1-(2-fluoroethyl)-1H-pyrazol-4-yl)ethynyl)pyridin-4-yl)(methyl)amino)ethan-1-ol (322 mg, 0.998 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.67 (s, 1H), 8.44 (s, 1H), 8.40 (d, 1H), 8.20 (s, 1H), 7.71-7.69 (m, 3H), 7.40 (s, 1H), 7.06 (d, 1H), 4.82 (t, 1H), 4.74 (t, 1H), 4.45 (t, 1H), 4.40 (t, 1H), 3.98 (t, 2H), 3.93 (t, 2H), 3.18 (s, 3H), 2.85-2.81 (m, 1H), 1.54-1.51 (m, 2H), 1.26-1.20 (m, 2H); MS (ESI) m/z=552.2 (M+H)$^+$ Example 39. 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)-2,2-dimethyl-propan-1-ol Step 1. 3-((2-Chloro-5-((1-methyl-1H-pyrazol-4-yl)ethynyl)pyridin-4-yl)amino)-2,2-dimethylpropan-1-ol The title compound as a solid (109 mg) was prepared in the same fashion as Step 2 in Example 1 except that 3-((2-chloro-5-iodopyridin-4-yl)amino)-2,2-dimethylpropan-1-ol (150 mg, 0.440 mmol) prepared in Reference Example 8 was used instead of 1-(2-chloro-5-iodopyridin-4-yl)-4-methylpiperazine. MS (ESI) m/z=319.1 (M+H)$^+$ Step 2. 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)$_{2,2}$-dimethylpropan-1-ol The title compound as a solid (24 mg) was prepared in the same fashion as Step 3 in Example 1 except that 3-((2-chloro-5-((1-methyl-1H-pyrazol-4-yl)ethynyl)pyridin-4-yl)amino)-2,2-dimethylpropan-1-ol (100 mg, 0.314 mmol) prepare in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44 (s, 1H), 8.33 (d, 1H), 7.59 (s, 1H), 7.54 (s, 1H), 7.18 (s, 1H), 7.03 (d, 1H), 3.87 (s, 3H), 3.53 (s, 2H), 3.21 (d, 2H), 2.82-2.78 (m, 1H), 1.51-1.47 (m, 2H), 1.22-1.15 (m, 2H), 1.04 (s, 6H); MS (ESI) m/z=548.2 (M+H)$^+$ Example 40. 3-((2-((2-(1-Cyclopropylsulfonylpyrazol-4-yl)pyrimidin-4-yl)amino)-5-(2-(1-(2-fluoroethyl)pyrazol-4-yl)ethynyl)-4-pyridyl)amino)-2,2-dimethyl-propan-1-ol Step 1. 3-((2-Chloro-5-((1-(2-fluoroethyl)-1H-pyrazol-4-yl)ethynyl)pyridin-4-yl)amino)-2,2-dimethyl-propan-1-ol The title compound as a solid (139 mg) was prepared in the same fashion as Step 2 in Example 1 except that 4-ethynyl-1-(2-fluoroethyl)pyrazole (67 mg, 0.484 mmol) and 3-((2-chloro-5-iodopyridin-4-yl)amino)-2,2-dimethyl-propan-1-ol (150 mg, 0.440 mmol) prepared in Reference Example 8 were used instead of 4-ethynyl-1-methylpyrazole and 1-(2-chloro-5-iodopyridin-4-yl)-4-methylpiperazine. MS (ESI) m/z=351.1 (M+H)$^+$ Step 2. 3-((2-((2-(1-Cyclopropylsulfonylpyrazol-4-yl)pyrimidin-4-yl)amino)-5-(2-(1-(2-fluoroethyl)pyrazol-4-yl)ethynyl)-4-pyridyl)amino)-2,2-dimethyl-propan-1-ol The title compound as a solid (6 mg) was prepared in the same fashion as Step 3 in Example 1 except that 3-((2-chloro-5-((1-(2-fluoroethyl)-1H-pyrazol-4-yl)ethynyl)pyridin-4-yl)amino)-2,2-dimethylpropan-1-ol (130 mg, 0.371 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.48 (s, 1H), 8.39 (d, 1H), 8.09 (s, 1H), 7.84 (s, 1H), 7.70 (s, 2H), 7.16-7.12 (m, 2H), 5.92-5.90 (m, 2H), 4.83 (t, 1H), 4.72 (t, 1H), 4.46 (t, 1H), 4.40 (t, 1H), 3.56 (s, 2H), 3.26 (d, 2H), 2.85-2.81 (m, 2H), 1.55-1.51 (m, 2H), 1.34-1.31 (m, 2H), 1.18 (s, 6H); MS (ESI) m/z=580.2 (M+H)$^+$ Example 41. (1s, 4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol Step 1. (1s, 4s)-4-((2-Chloro-5-((1-methyl-1H-pyrazol-4-yl)ethynyl)pyridin-4-yl)amino)cyclohexan-1-ol The title compound as a solid (206 mg) was prepared in the same fashion as Step 2 in Example 1 except that (1s,4s)-4-((2-chloro-5-iodopyridin-4-yl)amino)cyclohexan-1-ol (250 mg, 0.709 mmol) prepared in Reference Example 9 was used instead of 1-(2-chloro-5-iodopyridin-4-yl)-4-methylpiperazine. MS (ESI) m/z=331.1 (M+H)$^+$ Step 2. (1s,4S)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol The title compound as a solid (72 mg) was prepared in the same fashion as Step 3 in Example 1 except that (1s,4s)-4-((2-chloro-5-((1-methyl-1H-pyrazol-4-yl)ethynyl)pyridin-4-yl)amino)cyclohexan-1-ol (200 mg, 0.605 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.06 (s, 1H), 8.64 (s, 1H), 8.44 (s, 1H), 8.42 (d, 1H), 8.07 (s, 1H), 8.04 (s, 1H), 7.70 (s, 1H), 7.49 (s, 1H), 7.23 (s, 1H), 5.40 (d, 1H), 4.60 (d, 1H), 3.85 (s, 3H), 3.69 (s, 1H), 3.26-3.22 (m, 1H), 1.81-1.69 (m, 4H), 1.61-1.53 (m, 4H), 1.35-1.32 (m, 2H), 1.30-1.21 (m, 2H); MS (ESI) m/z=560.2 (M+H)$^+$ Example 42. (1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol Step 1. (1s,4s)-4-((2-Chloro-5-((1-(2-fluoroethyl)-1H-pyrazol-4-yl)ethynyl)pyridin-4-yl)amino)cyclohexan-1-ol The title compound as a solid (208 mg) was prepared in the same fashion as Step 2 in Example 1 except that 4-ethynyl-1-(2-fluoroethyl)pyrazole (108 mg, 0.780 mmol) and (1s,4s)-4-((2-chloro-5-iodopyridin-4-yl)amino)cyclohexan-1-ol (250 mg, 0.709 mmol) prepared in Reference Example 9 were used instead of 4-ethynyl-1-methylpyrazole and 1-(2-chloro-5-iodopyridin-4-yl)-4-methylpiperazine. MS (ESI) m/z=363.0 (M+H)$^+$ Step 2. (1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol The title compound as a solid (86 mg) was prepared in the same fashion as Step 3 in Example 1 except that (1s,4s)-4-((2-chloro-5-((1-(2-fluoroethyl)-1H-pyrazol-4-yl)ethynyl)pyridin-4-yl)amino)cyclohexan-1-ol (200 mg, 0.551 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.06 (s, 1H), 8.64 (s, 1H), 8.44 (s, 1H), 8.43 (d, 1H), 8.15 (s, 1H), 8.05 (s, 1H), 7.77 (s, 1H), 7.50 (s, 1H), 7.23 (s, 1H), 5.44 (d, 1H), 4.81 (t, 1H), 4.73 (t, 1H), 4.59 (d, 1H), 4.48 (t, 1H), 4.43 (t, 1H), 3.70 (s, 1H), 3.26-3.22 (m, 1H), 1.82-1.70 (m, 4H), 1.60-1.54 (m, 4H), 1.35-1.32 (m, 2H), 1.26-1.20 (m, 2H); MS (ESI) m/z=592.2 (M+H)$^+$ Example 43. (1S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol Step 1. (1S,3S)-3-((2-Chloro-5-((1-methyl-1H-pyrazol-4-yl)ethynyl)pyridin-4-yl)amino)cyclohexan-1-ol The title compound as a solid (155 mg) was prepared in the same fashion as Step 2 in Example 1 except that (1S,3S)-3-((2-chloro-5-iodopyridin-4-yl)amino)cyclohexan-1-ol (200 mg, 0.567 mmol) prepared in Reference Example 10 was used instead of 1-(2-chloro-5-iodopyridin-4-yl)-4-methylpiperazine. MS (ESI) m/z=331.1 (M+H)$^+$ Step 2. (1S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol The title compound as a solid (75 mg) was prepared in the same fashion as Step 3 in Example 1 except that (1S,3S)-3-((2-chloro-5-((1-methyl-1H-pyrazol-4-yl)ethynyl)pyridin-4-yl)amino)cyclohexan-1-ol (190 mg, 0.574 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.02 (s, 1H), 8.63 (s, 1H), 8.44 (s, 1H), 8.41 (d, 1H), 8.04 (s, 1H), 7.99 (s, 1H), 7.66 (s, 1H), 7.44 (s, 1H), 7.21 (s, 1H), 6.51 (s, 1H), 5.02 (d, 1H), 3.85 (s, 3H), 3.81 (s, 1H), 3.68 (s, 1H), 3.27-3.22 (m, 1H), 2.00 (d, 1H), 1.76-1.60 (m, 5H), 1.45 (s, 1H), 1.35-1.30 (m, 2H), 1.26-1.21 (m, 2H); MS (ESI) m/z=560.2 (M+H)$^+$ Example 44. (1S,3S)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol Step 1. (1S,3S)-3-((2-Chloro-5-((1-(2-fluoroethyl)-1H-pyrazol-4-yl)ethynyl)pyridin-4-yl)amino)cyclohexan-1-ol The title compound as a solid (173 mg) was prepared in the same fashion as Step 2 in Example 1 except that 4-ethynyl-1-(2-fluoroethyl)pyrazole (86 mg, 0.624 mmol) and (1S,3S)-3-((2-chloro-5-iodopyridin-4-yl)amino)cyclohexan-1-ol (200 mg, 0.567 mmol) prepared in Reference Example 10 were used instead of 4-ethynyl-1-methylpyrazole and 1-(2-chloro-5-iodopyridin-4-yl)-4-methylpiperazine. MS (ESI) m/z=363.2 (M+H)$^+$ Step 2. (1S,3S)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol The title compound as a solid (26 mg) was prepared in the same fashion as Step 3 in Example 1 except that (1S,3S)-3-((2-chloro-5-((1-(2-fluoroethyl)-1H-pyrazol-4-yl)ethynyl)pyridin-4-yl)amino)cyclohexan-1-ol (220 mg, 0.606 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.04 (s, 1H), 8.63 (s, 1H), 8.44 (s, 1H), 8.42 (d, 1H), 8.09 (s, 1H), 8.02 (s, 1H), 7.75 (s, 1H), 7.47 (s, 1H), 7.20 (s, 1H), 6.50 (s, 1H), 5.03 (s, 1H), 4.81 (t, 1H), 4.73 (t, 1H), 4.47 (s, 1H), 4.43 (s, 1H), 3.80 (s, 1H), 3.67 (s, 1H), 3.26-3.22 (m, 1H), 2.01 (d, 1H), 1.75-1.59 (d, 5H), 1.43 (s, 1H), 1.35-1.30 (m, 2H), 1.27-1.21 (m, 2H); MS (ESI) m/z=592.2 (M+H)$^+$ Example 45. (1S,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol Step 1. (1S,3R)-3-((2-Chloro-5-((1-methyl-1H-pyrazol-4-yl)ethynyl)pyridin-4-yl)amino)cyclohexan-1-ol The title compound as a solid (193 mg) was prepared in the same fashion as Step 2 in Example 1 except that (1S,3R)-3-((2-chloro-5-iodopyridin-4-yl)amino)cyclohexan-1-ol (270 mg, 0.766 mmol) prepared in Reference Example 11 was used instead of 1-(2-chloro-5-iodopyridin-4-yl)-4-methylpiperazine. MS (ESI) m/z=331.1 (M+H)$^+$ Step 2. (1S,3R)-3-((2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol The title compound as a solid (38 mg) was prepared in the same fashion as Step 3 in Example 1 except that (1S,3R)-3-((2-chloro-5-((1-methyl-1H-pyrazol-4-yl)ethynyl)pyridin-4-yl)amino)cyclohexan-1-ol (150 mg, 0.453 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.04 (s, 1H), 8.63 (s, 1H), 8.44 (s, 1H), 8.43 (d, 1H), 8.05 (s, 1H), 8.04 (s, 1H), 7.69 (s, 1H), 7.63 (s, 1H) 7.06 (s, 1H), 5.36 (d, 1H), 4.61 (d, 1H), 3.89 (s, 1H), 3.85 (s, 3H), 3.27-3.23 (m, 1H), 1.87-1.70 (m, 4H), 1.49-1.43 (m, 4H), 1.36-1.30 (m, 2H), 1.25-1.20 (m, 2H); MS (ESI) m/z=560.2 (M+H)$^+$ Example 46. (1S,3R)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol Step 1. (1S,3R)-3-((2-Chloro-5-((1-(2-fluoroethyl)-1H-pyrazol-4-yl)ethynyl)pyridin-4-yl)amino)cyclohexan-1-ol The title compound as a solid (221 mg) was prepared in the same fashion as Step 2 in Example 1 except that 4-ethynyl-1-(2-fluoroethyl)pyrazole (116 mg, 0.842 mmol) and (1S,3R)-3-((2-chloro-5-iodopyridin-4-yl)amino)cyclohexan-1-ol (270 mg, 0.766 mmol) prepared in Reference Example 11 were used instead of 4-ethynyl-1-methylpyrazole and 1-(2-chloro-5-iodopyridin-4-yl)-4-methylpiperazine. MS (ESI) m/z=363.1 (M+H)$^+$ Step 2. (1 S,3R)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol The title compound as a solid (20 mg) was prepared in the same fashion as Step 3 in Example 1 except that (1S,3R)-3-((2-chloro-5-((1-(2-fluoroethyl)-1H-pyrazol-4-yl)ethynyl)pyridin-4-yl)amino)cyclohexan-1-ol (170 mg, 0.469 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.06 (s, 1H), 8.64 (s, 1H), 8.44 (s, 1H), 5.42 (s, 1H), 3.85 (s, 1H), 8.43 (s, 1H), 8.15 (s, 1H), 8.05 (s, 1H), 7.77 (s, 1H), 7.63 (s, 1H), 7.04 (s, 1H), 4.81 (t, 1H), 4.73 (t, 1H), 4.60 (s, 1H), 4.48 (t, 1H), 4.43 (s, 1H), 3.91 (s, 1H), 3.27-3.23 (m, 2H), 1.88-1.70 (m, 5H), 1.49-1.43 (m, 3H), 1.35-1.33 (m, 2H), 1.26-1.21 (m, 2H); MS (ESI) m/z=592.2 (M+H)$^+$ Example 47. (1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol Step 1. (1-(2-Chloro-5-((1-cyclopropyl-1H-pyrazol-4-yl)ethynyl)pyridin-4-yl)-4-methylpiperidin-4-yl)methanol The title compound as a solid (103 mg) was prepared in the same fashion as Step 2 in Example 1 except that (1-(2-chloro-5-iodopyridin-4-yl)-4-methylpiperidin-4-yl)methanol (110 mg, 0.300 mmol) prepared in Reference Example 12 and 1-cyclopropyl-4-ethynylpyrazole (48 mg, 0.360 mmol) were used instead of 1-(2-chloro-5-iodopyridin-4-yl)-4-methylpiperazine and 4-ethynyl-1-methylpyrazole, respectively. MS (ESI) m/z=371.0 (M+H)$^+$ Step 2. (1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a solid (10 mg) was prepared in the same fashion as Step 3 in Example 1 except that (1-(2-chloro-5-((1-cyclopropyl-1H-pyrazol-4-yl)ethynyl)pyridin-4-yl)-4-methylpiperidin-4-yl)methanol (98 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.44 (s, 1H), 8.40 (s, 1H), 8.38 (s, 1H), 8.20 (s, 1H), 7.62-7.69 (m, 3H), 6.97 (d, 1H), 3.67-3.65 (m, 2H), 3.64-3.59 (m, 1H), 3.50 (s, 2H), 3.42-3.36 (m, 2H), 2.85-2.81 (m, 1H), 2.04-2.00 (m, 2H), 1.80-1.74 (m, 3H), 1.58-1.50 (m, 4H), 1.35-1.20 (m, 5H), 1.17-1.11 (m, 3H), 1.10-1.06 (m, 5H); MS (ESI) m/z=600.2 (M+H)$^+$ Example 48. (1-(5-((1-(Cyclopropylmethyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol Step 1. (1-(2-Chloro-5-((1-(cyclopropylmethyl)-1H-pyrazol-4-yl)ethynyl)pyridin-4-yl)-4-methylpiperidin-4-yl)methanol The title compound as a solid (89 mg) was prepared in the same fashion as Step 2 in Example 1 except that (1-(2-chloro-5-iodopyridin-4-yl)-4-methylpiperidin-4-yl)methanol (110 mg, 0.300 mmol) prepared in Reference Example 12 and 1-(cyclopropylmethyl)-4-ethynylpyrazole (53 mg, 0.360 mmol) were used instead of 1-(2-chloro-5-iodopyridin-4-yl)-4-methylpiperazine and 4-ethynyl-1-methylpyrazole, respectively. $^1$H-NMR (CDCl$_3$, 600 MHz) δ 8.22 (s, 1H), 8.01 (s, 1H), 7.72 (s, 1H), 7.63 (s, 1H), 6.72 (s, 1H), 4.00-3.96 (m, 2H), 3.72-3.68 (m, 2H), 3.45 (s, 2H), 3.28-3.24 (m, 2H), 1.95 (s, 1H), 1.86 (s, 1H), 1.75-1.71 (m, 2H), 1.51-1.47 (m, 2H), 1.32-1.27 (m, 1H), 1.06 (s, 3H), 0.70-0.67 (m, 2H), 0.41-0.38 (m, 2H)

Step 2. (1-(5-((1-(Cyclopropylmethyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a solid (12 mg) was prepared in the same fashion as Step 3 in Example 1 except that (1-(2-chloro-5-((1-(cyclopropylmethyl)-1H-pyrazol-4-yl)ethynyl)pyridin-4-yl)-4-methylpiperidin-4-yl)methanol (80 mg, 0.208 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.65 (s, 1H), 8.44 (s, 1H), 8.39 (d, 1H), 8.22 (s, 1H), 8.14 (s, 1H), 7.70 (s, 1H), 7.64 (s, 2H), 6.98 (s, 1H), 4.00 (d, 2H), 3.70-3.67 (m, 2H), 3.50 (s, 2H), 3.43-3.38 (m, 2H), 2.85-2.81 (m, 1H), 2.09-2.00 (m, 2H), 1.82-1.75 (m, 2H), 1.59-1.50 (m, 5H), 1.33-1.23 (m, 6H), 1.08 (s, 3H), 0.70 (d, 2H); MS (ESI) m/z=614.2 (M+H)$^+$ Example 49. (1-(2-((2-(1-(Cyclopropylsulfonyl)-1H-pyrazol-4-yl)pyrimidin-4-yl)amino)-5-((1-(2,2-di fluoroethyl)-1H-pyrazol-4-yl)ethynyl)pyridin-4-yl)-4-methylpiperidin-4-yl)methanol Step 1. (1-(2-Chloro-5-((1-(2,2-difluoroethyl)-1H-pyrazol-4-yl)ethynyl)pyridin-4-yl)-4-methylpiperidin-4-yl)methanol The title compound as a solid (110 mg) was prepared in the same fashion as Step 2 in Example 1 except that (1-(2-chloro-5-iodopyridin-4-yl)-4-methylpiperidin-4-yl)methanol (110 mg, 0.300 mmol) prepared in Reference Example 12 and 1-(2,2-difluoroethyl)-4-ethynylpyrazole (56 mg, 0.360 mmol) were used instead of 1-(2-chloro-5-iodopyridin-4-yl)-4-methylpiperazine and 4-ethynyl-1-methylpyrazole, respectively. MS (ESI) m/z=395.0 (M+H)$^+$ Step 2. (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol The title compound as a solid (9 mg) was prepared in the same fashion as Step 3 in Example 1 except that (1-(2- chloro-5-((1-(2,2-difluoroethyl)-1H-pyrazol-4-yl)ethynyl)pyridin-4-yl)-4-methylpiperidin-4-yl)methanol (104 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (s, 1H), 8.39 (d, 1H), 8.21 (s, 1H), 8.11 (s, 1H), 7.68-7.63 (m, 3H), 6.95 (d, 1H), 6.10-5.96 (m, 1H), 4.51-4.43 (m, 2H), 3.69-3.66 (m, 2H), 3.49 (s, 2H), 3.41-3.36 (m, 2H), 2.84-2.80 (m, 1H), 2.03-1.99 (m, 1H), 1.80-1.74 (m, 2H), 1.58-1.50 (m, 4H), 1.24-1.19 (m, 4H), 1.07 (s, 3H); MS (ESI) m/z 624.2 (M+H)$^+$ Example 50. $N^2$-(2-(1-(Cyclopropylsulfonyl)-1H-pyrazol-4-yl)pyrimidin-4-yl)-$N^4$-(4-((dimethylamino)methyl)benzyl)-5-((1-methyl-1H-pyrazol-4-yl)ethynyl)pyridine-2,4-diamine Step 1. 2-Chloro-N-(4-((dimethylamino)methyl)benzyl)-5-((1-methyl-1H-pyrazol-4-yl)ethynyl)pyridin-4-amine The title compound as a solid (118 mg) was prepared in the same fashion as Step 2 in Example 1 except that 2-chloro-N-(4-((dimethylamino)methyl)benzyl)-5-iodopyridin-4-amine (250 mg, 0.622 mmol) prepared in Reference Example 13 was used instead of 1-(2-chloro-5-iodopyridin-4-yl)-4-methylpiperazine. MS (ESI) m/z=380.2 (M+H)$^+$ Step 2. $N^2$-(2-(1-(Cyclopropylsulfonyl)-1H-pyrazol-4-yl)pyrimidin-4-yl)-$N^4$-(4-((dimethylamino)methyl)benzyl)-5-((1-methyl-1H-pyrazol-4-yl)ethynyl)pyridine-2,4-diamine The title compound as a solid (13 mg) was prepared in the same fashion as Step 3 in Example 1 except that 2-chloro-N-(4-((dimethylamino)methyl)benzyl)-5-((1-methyl-1H-pyrazol-4-yl)ethynyl)pyridin-4-amine (118 mg, 0.311 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.61 (s, 1H), 8.47 (s, 2H), 8.38 (d, 1H), 8.22 (s, 1H), 7.61 (d, 1H), 7.47 (s, 1H), 7.41-7.32 (m, 4H), 7.08 (d, 1H), 5.76 (t, 1H), 4.63 (d, 2H), 3.92 (s, 4H), 3.86 (s, 2H), 2.82-2.80 (m, 1H), 2.54-2.49 (m, 6H), 1.49-1.43 (m, 2H), 1.22-1.18 (m, 2H); MS (ESI) m/z=609.2 (M+H)$^+$ Example 51. $N^2$-(2-(1-(Cyclopropylsulfonyl)-1H-pyrazol-4-yl)pyrimidin-4-yl)-$N^4$-(4-((dimethylamino)methyl)benzyl)-5-((1-(2-fluoroethyl)-1H-pyrazol-4-yl)ethynyl)pyridine-2,4-diamine Step 1. 2-Chloro-N-(4-((dimethylamino)methyl)benzyl)-5-((1-(2-fluoroethyl)-1H-pyrazol-4-yl)ethynyl)pyridin-4-amine The title compound as a solid (135 mg) was prepared in the same fashion as Step 2 in Example 1 except that 4-ethynyl-1-(2-fluoroethyl)pyrazole (103 mg, 0.747 mmol) and 2-chloro-N-(4-((dimethylamino)methyl)benzyl)-5-iodopyridin-4-amine (250 mg, 0.622 mmol) prepared in Reference Example 13 were used instead of 4-ethynyl-1-methylpyrazole and 1-(2-chloro-5-iodopyridin-4-yl)-4-methylpiperazine. MS (ESI) m/z=412.2 (M+H)$^+$ Step 2. $N^2$-(2-(1-(Cyclopropylsulfonyl)-1H-pyrazol-4-yl)pyrimidin-4-yl)-$1V$-(4-((dimethylamino)methyl)benzyl)-5-((1-(2-fluoroethyl)-1H-pyrazol-4-yl)ethynyl)pyridine-2,4-diamine The title compound as a solid (20 mg) was prepared in the same fashion as Step 3 in Example 1 except that 2-chloro-N-(4-((dimethylamino)methyl)benzyl)-5-((1-(2-fluoroethyl)-1H-pyrazol-4-yl)ethynyl)pyridin-4-amine (135 mg, 0.328 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.62 (s, 1H), 8.47 (s, 1H), 8.40 (d, 1H), 8.29 (s, 1H), 7.69 (d, 2H), 7.37-7.35 (m, 5H), 7.12 (d, 1H), 5.69 (t, 1H), 4.81 (t, 1H), 4.73 (t, 1H), 4.62 (d, 2H), 4.45 (t, 1H), 4.41 (t, 1H), 3.77 (s, 2H), 2.82-2.78 (m, 1H), 2.47 (s, 6H), 1.49-1.46 (m, 2H), 1.26-1.18 (m, 2H); MS (ESI) m/z=642.2 (M+H)$^+$ Example 52. $N^2$-(2-(1-(Cyclopropylsulfonyl)-1H-pyrazol-4-yl)pyrimidin-4-yl)-5-((1-(2,2-di fluoroethyl)-1H-pyrazol-4-yl)ethynyl)-$N^4$-(4-((dimethylamino)methyl)benzyl)pyridine-2,4-diamine Step 1. 2-Chloro-5-((1-(2,2-difluoroethyl)-1H-pyrazol-4-yl)ethynyl)-N-(4-((dimethylamino)methyl)benzyl)pyridin-4-amine The title compound as a solid (134 mg) was prepared in the same fashion as Step 2 in Example 1 except that 4-ethynyl-1-(2,2-difluoroethyl)pyrazole (117 mg, 0.747 mmol) and 2-chloro-N-(4-((dimethylamino)methyl)benzyl)-5-iodopyridin-4-amine (250 mg, 0.622 mmol) prepared in Reference Example 13 were used instead of 4-ethynyl-1-methylpyrazole and 1-(2-chloro-5-iodopyridin-4-yl)-4-methylpiperazine. MS (ESI) m/z=430.2 (M+H)$^+$ Step 2. $N^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-$N^4$-(4-((dimethylamino)methyl)benzyl)pyridine-2,4-diamine The title compound as a solid (31 mg) was prepared in the same fashion as Step 3 in Example 1 except that 2-chloro-5-((1-(2,2-difluoroethyl)-1H-pyrazol-4-yl)ethynyl)-N-(4-((dimethylamino)methyl)benzyl)pyridin-4-amine (134 mg, 0.312 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.63 (s, 1H), 8.38 (s, 1H), 8.36 (d, 1H), 8.18 (s, 1H), 7.69 (s, 2H), 7.33-7.31 (m, 5H), 7.17 (s, 1H), 6.89 (s, 1H), 6.19-5.99 (m, 1H), 5.50 (t, 1H), 4.54 (d, 2H), 4.49-4.45 (m, 2H), 3.43 (s, 2H), 2.81-2.76 (m, 1H), 2.17 (s, 6H), 1.49-1.46 (m, 2H), 1.28-1.15 (m, 2H); MS (ESI) m/z=659.2 (M+H)$^+$ Example 53. $N^2$-(2-(1-(Cyclopropylsulfonyl)-1H-pyrazol-4-yl)pyrimidin-4-yl)-$IV^4$-(((1 r,4r)-4-((dimethylamino)methyl)cyclohexyl)methyl)-5-((1-methyl-1H-pyrazol-4-yl)ethynyl)pyridine-2,4-diamine Step 1. tert-Butyl (((1r,4r)-4-(((2-chloro-5-iodopyridin-4-yl)amino)methyl)cyclohexyl)methyl)carbamate The title compound as a solid (1.33 g) was prepared in the same fashion as Step 1 in Example 1 except that tert-butyl (((1r,4r)-4-(aminomethyl)cyclohexyl)methyl)carbamate (1.06 g, 4.381 mmol) was used instead of 1-methylpiperazine. MS (ESI) m/z=480.1 (M+H)⁺

Step 2. 2-Chloro-N-(((1r,4r)-4-((dimethylamino)methyl)cyclohexyl)methyl)-5-iodopyridin-4-amine The title compound as an off-white solid (600 mg) was prepared in the same fashion as Step 2 in Reference Example 16 except that tert-butyl (((1r,4r)-4-(((2-chloro-5-iodopyridin-4-yl)amino)methyl)cyclohexyl)methyl)carbamate (1.30 g, 1.975 mmol) prepared in Step 1 was used instead of tert-butyl (((1r,4r)-4-(((2-chloro-5-iodopyridin-4-yl)oxy)methyl)cyclohexyl)methyl)carbamate. MS (ESI) m/z=408.1 (M+H)⁺

Step 3. 2-Chloro-N-(((1r,4r)-4-((dimethylamino)methyl)cyclohexyl)methyl)-5-((1-methyl-1H-pyrazol-4-yl)ethynyl)pyridin-4-amine The title compound as a solid (140 mg) was prepared in the same fashion as Step 2 in Example 1 except that 2-chloro-N-(((1r,4r)-4-((dimethylamino)methyl)cyclohexyl)methyl)-5-iodopyridin-4-amine (150 mg, 0.368 mmol) prepared in step 2 was used instead of 1-(2-chloro-5-iodopyridin-4-yl)-4-methylpiperazine. MS (ESI) m/z=386.2 (M+H)⁺

Step 4. N²-(2-(1-(Cyclopropylsulfonyl)-1H-pyrazol-4-yl)pyrimidin-4-yl)-N⁴-(((1r,4r)-4-((dimethylamino)methyl)cyclohexyl)methyl)-5-((1-methyl-1H-pyrazol-4-yl)ethynyl)pyridine-2,4-diamine The title compound as a solid (32 mg) was prepared in the same fashion as Step 3 in Example 1 except that 2-chloro-N-(((1r,4r)-4-((dimethylamino)methyl)cyclohexyl)methyl)-5-((1-methyl-1H-pyrazol-4-yl)ethynyl)pyridin-4-amine (140 mg, 0.363 mmol) prepared in Step 3 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.65 (s, 1H), 8.44 (s, 1H), 8.41 (d, 1H), 8.12 (s, 2H), 7.64 (s, 1H), 7.58 (s, 1H), 7.24 (s, 1H), 6.98 (s, 1H), 5.17 (t, 1H), 3.94 (s, 3H), 3.17 (t, 2H), 2.84-2.80 (m, 1H), 2.19-2.15 (m, 5H), 2.13 (d, 1H) 2.07 (d, 2H), 1.89-1.87 (m, 4H), 1.53-1.50 (m, 2H), 1.29-1.19 (m, 2H), 1.13-1.06 (m, 2H), 0.96 (d, 2H), 0.95-0.88 (m, 2H); MS (ESI) m/z=616.3 (M+H)⁺

Example 54. 2-(1-(Cyclopropylsulfonyl)-1H-pyrazol-4-yl)-N-(4-isopropoxy-5-((1-methyl-1H-pyrazol-4-yl)ethynyl)pyridin-2-yl)pyrimidin-4-amine Step 1. 2-Chloro-4-isopropoxy-5-((1-methyl-1H-pyrazol-4-yl)ethynyl)pyridine The title compound as a solid (110 mg) was prepared in the same fashion as Step 2 in Example 1 except that 2-chloro-5-iodo-4-isopropoxypyridine (250 mg, 0.840 mmol) prepared in Reference Example 14 was used instead of 1-(2-chloro-5-iodopyridin-4-yl)-4-methylpiperazine. MS (ESI) m/z=276.1 (M+H)⁺

Step 2. 2-(1-(Cyclopropylsulfonyl)-1H-pyrazol-4-yl)-N-(4-isopropoxy-5-((1-methyl-1H-pyrazol-4-yl)ethynyl)pyridin-2-yl)pyrimidin-4-amine The title compound as a solid (9 mg) was prepared in the same fashion as Step 3 in Example 1 except that 2-chloro-4-isopropoxy-5-((1-methyl-1H-pyrazol-4-yl)ethynyl)pyridine (100 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.63 (s, 1H), 8.44 (s, 1H), 8.43 (d, 1H), 8.25 (s, 1H), 8.14 (s, 1H), 7.72 (s, 1H), 7.66 (s, 1H), 7.58 (s, 1H), 7.01 (d, 1H), 4.85-4.81 (m, 1H), 3.93 (s, 3H), 2.86-2.80 (m, 1H), 1.55-1.49 (m, 9H), 1.29-1.17 (m, 3H); MS (ESI) m/z=505.2 (M+H)⁺

Example 55. 2-(1-(Cyclopropylsulfonyl)-1H-pyrazol-4-yl)-N-(5-((1-(2-fluoroethyl)-1H-pyrazol-4-yl)ethynyl)-4-isopropoxypyridin-2-yl)pyrimidin-4-amine Step 1. 2-Chloro-5-((1-(2-fluoroethyl)-1H-pyrazol-4-yl)ethynyl)-4-isopropoxypyridine The title compound as a solid (183 mg) was prepared in the same fashion as Step 2 in Example 1 except that 4-ethynyl-1-(2-fluoroethyl)pyrazole (139 mg, 1.008 mmol) and 2-chloro-5-iodo-4-isopropoxypyridine (200 mg, 0.672 mmol) prepared in Reference Example 14 were used instead of 4-ethynyl-1-methylpyrazole and 1-(2-chloro-5-iodopyridin-4-yl)-4-methylpiperazine. MS (ESI) m/z=318.1 (M+H)⁺

Step 2. 2-(1-(Cyclopropylsulfonyl)-1H-pyrazol-4-yl)-N-(5-((1-(2-fluoroethyl)-1H-pyrazol-4-yl)ethynyl)-4-isopropoxypyridin-2-yl)pyrimidin-4-amine The title compound as a solid (2.6 mg) was prepared in the same fashion as Step 3 in Example 1 except that 2-chloro-5-((1-(2-fluoroethyl)-1H-pyrazol-4-yl)ethynyl)-4-isopropoxypyridine (111 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.64 (s, 1H), 8.45 (s, 1H), 8.42 (d, 1H), 8.26 (s, 1H), 8.13 (s, 1H), 7.73 (s, 1H), 7.68 (s, 1H), 7.60 (s, 1H), 7.00 (d, 1H), 4.97 (d, 1H), 4.86-4.80 (m, 2H), 4.45 (t, 1H) 4.26 (t, 1H), 2.86-2.80 (m, 1H), 1.56-1.50 (m, 8H), 1.28-1.18 (m, 2H); MS (ESI) m/z=537.2 (M+H)⁺

Example 56. N-(4-(sec-Butoxy)-5-((1-methyl-1H-pyrazol-4-yl)ethynyl)pyridin-2-yl)-2-(1-(cyclopropylsulfonyl)-1H-pyrazol-4-yl)pyrimidin-4-amine Step 1. 4-(sec-Butoxy)-2-chloro-5-((1-methyl-1H-pyrazol-4-yl)ethynyl)pyridine The title compound as a solid (166 mg) was prepared in the same fashion as Step 2 in example 1 except that 4-(sec-butoxy)-2-chloro-5-iodopyridine(230 mg, 0.738 mmol) prepared in Reference Example 15 was used instead of 1-(2-chloro-5-iodopyridin-4-yl)-4-methylpiperazine. MS (ESI) m/z=290.1 (M+H)⁺

Step 2. N-(4-(sec-Butoxy)-5-((1-methyl-1H-pyrazol-4-yl)ethynyl)pyridin-2-yl)-2-(1-(cyclopropylsulfonyl)-1H-pyrazol-4-yl)pyrimidin-4-amine The title compound as a solid (6 mg) was prepared in the same fashion as Step 3 in Example 1 except that 4-(sec-butoxy)-2-chloro-5-((1-methyl-1H-pyrazol-4-yl)ethynyl)pyridine (105 mg, 0.362 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 600 MHz) δ 8.63 (s, 1H), 8.40 (s, 2H), 8.25 (s, 1H), 8.19 (s, 1H), 7.67 (s, 1H), 7.64 (s, 1H), 7.56 (s, 1H), 7.06 (d, 1H), 4.62-4.59 (m, 1H), 3.93 (s, 3H), 3.66-3.64 (m, 1H), 2.85-2.81 (m, 1H), 1.88-1.73 (m, 3H), 1.55-1.51 (m, 3H), 1.48 (d, 3H), 1.23-1.20 (m, 3H), 1.13 (d, 3H), 1.06 (t, 3H); MS (ESI) m/z=519.2 (M+H)$^+$

Example 57. N-(4-(sec-Butoxy)-5-((1-isopropyl-1H-pyrazol-4-yl)ethynyl)pyridin-2-yl)-2-(1-(cyclopropylsulfonyl)-1H-pyrazol-4-yl)pyrimidin-4-amine

Step 1. 4-(sec-Butoxy)-2-chloro-5-((1-isopropyl-1H-pyrazol-4-yl)ethynyl)pyridine The title compound as a solid (158 mg) was prepared in the same fashion as Step 2 in Example 1 except that 4-ethynyl-1-isopropylpyrazole (129 mg, 0.963 mmol) and 4-(sec-butoxy)-2-chloro-5-iodopyridine (230 mg, 0.738 mmol) prepared in Reference Example 15 were used instead of 4-ethynyl-1-methylpyrazole and 1-(2-chloro-5-iodopyridin-4-yl)-4-methylpiperazine. MS (ESI) m/z=318.1 (M+H)$^+$

Step 2. N-(4-(sec-Butoxy)-5-((1-isopropyl-1H-pyrazol-4-yl)ethynyl)pyridin-2-yl)-2-(1-(cyclopropylsulfonyl)-1H-pyrazol-4-yl)pyrimidin-4-amine The title compound as a solid (95.2 mg) was prepared in the same fashion as Step 3 in Example 1 except that 4-(sec-butoxy)-2-chloro-5-((1-isopropyl-1H-pyrazol-4-yl)ethynyl)pyridine (115 mg, 0.362 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 9.19 (s, 1H), 8.64 (s, 1H), 8.44 (s, 1H), 8.41 (d, 1H), 8.31 (d, 1H), 7.72 (s, 1H), 7.67 (s, 1H), 7.65 (s, 1H), 7.03 (s, 1H), 4.62-4.59 (m, 1H), 4.54-4.49 (m, 1H), 2.86-2.82 (m, 1H), 1.90-1.81 (m, 2H), 1.54-1.50 (m, 8H), 1.48 (d, 3H), 1.25-1.20 (m, 2H), 1.06 (t, 3H); MS (ESI) m/z=547.2 (M+H)$^+$

Example 58. 2-(1-(Cyclopropylsulfonyl)-1H-pyrazol-4-yl)-N-(4-(((1r,4r)-4-((dimethylamino)methyl)cyclohexyl)methoxy)-5-((1-methyl-1H-pyrazol-4-yl)ethynyl)pyridin-2-yl)pyrimidin-4-amine

Step 1. 1-((1r,4r)-4-(((2-Chloro-5-((1-methyl-1H-pyrazol-4-yl)ethynyl)pyridin-4-yl)oxy)methyl)cyclohexyl)-N,N-dimethylmethanamine The title compound as a solid (129 mg) was prepared in the same fashion as Step 2 in Example 1 except that 1-((1r,4r)-4-(((2-chloro-5-iodopyridin-4-yl)oxy)methyl)cyclohexyl)-N,N-dimethylmethanamine (180 mg, 0.440 mmol) prepared in Reference Example 16 was used instead of 1-(2-chloro-5-iodopyridin-4-yl)-4-methylpiperazine. MS (ESI) m/z=387.2 (M+H)$^+$

Step 2. 2-(1-(Cyclopropylsulfonyl)-1H-pyrazol-4-yl)-N-(4-(((1r,4r)-4-((dimethylamino)methyl)cyclohexyl)methoxy)-5-((1-methyl-1H-pyrazol-4-yl)ethynyl)pyridin-2-yl)pyrimidin-4-amine The title compound as a solid (5 mg) was prepared in the same fashion as Step 3 in Example 1 except that 1-((1r,4r)-4-(((2-chloro-5-((1-methyl-1H-pyrazol-4-yl)ethynyl)pyridin-4-yl)oxy)methyl)cyclohexyl)-N,N-dimethylmethanamine (140 mg, 0.362 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.63 (s, 1H), 8.44 (d, 1H), 8.42 (s, 1H), 8.25 (s, 1H), 7.79 (s, 1H), 7.64-7.62 (m, 3H), 7.05 (s, 1H), 4.01 (d, 2H), 3.96 (s, 3H), 2.85 (s, 3H), 2.82 (s, 6H), 2.16 (d, 2H), 2.06 (d, 2H), 1.52 (s, 3H), 0.88-0.84 (m, 8H); MS (ESI) m/z=616.3 (M+H)$^+$

Example 59. 2-(1-(Cyclopropylsulfonyl)-1H-pyrazol-4-yl)-N-(4-(((1r,4r)-4-((dimethylamino)methyl)cyclohexyl)methoxy)-5-((1-isopropyl-1H-pyrazol-4-yl)ethynyl)pyridin-2-yl)pyrimidin-4-amine

Step 1. 1-((1r,4r)-4-(((2-Chloro-5-((1-isopropyl-1H-pyrazol-4-yl)ethynyl)pyridin-4-yl)oxy)methyl)cyclohexyl)-N,N-dimethylmethanamine The title compound as a solid (170 mg) was prepared in the same fashion as Step 2 in Example 1 except that 4-ethynyl-1-isopropylpyrazole (89 mg, 0.661 mmol) and 1-((1 r,4r)-4-(((2-chloro-5-iodopyridin-4-yl)oxy)methyl)cyclohexyl)-N,N-dimethylmethanamine (180 mg, 0.440 mmol) prepared in Reference Example 16 were used instead of 4-ethynyl-1-methylpyrazole and 1-(2-chloro-5-iodopyridin-4-yl)-4-methylpiperazine. MS (ESI) m/z=415.2 (M+H)$^+$

Step 2. 2-(1-(Cyclopropylsulfonyl)-1H-pyrazol-4-yl)-N-(4-(((1r,4r)-4-((dimethylamino)methyl)cyclohexyl)methoxy)-5-((1-isopropyl-1H-pyrazol-4-yl)ethynyl)pyridin-2-yl)pyrimidin-4-amine The title compound as a solid (37 mg) was prepared in the same fashion as Step 3 in Example 1 except that 1-((1r,4r)-4-(((2-chloro-5-((1-isopropyl-1H-pyrazol-4-yl)ethynyl)pyridin-4-yl)oxy)methyl)cyclohexyl)-N,N-dimethylmethanamine (150 mg, 0.362 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.65 (s, 1H), 8.44 (s, 2H), 8.26 (s, 1H), 7.98 (s, 1H), 7.67 (s, 1H), 7.65 (s, 1H), 7.48 (s, 1H), 7.17 (s, 1H), 4.51 (t, 1H), 4.00 (d, 2H), 2.84-2.82 (m, 1H), 2.22 (s, 6H), 2.12 (d, 2H), 2.00 (d, 3H), 1.91 (d, 4H), 1.54-1.52 (m, 9H), 1.24-1.22 (m, 4H), 1.02-0.98 (m, 2H); MS (ESI) m/z=644.3 (M+H)$^+$

Example 60. N-(5-((1-Cyclopropyl-1H-pyrazol-4-yl)ethynyl)-4-(((1r,4r)-4-((dimethylamino)methyl)cyclohexyl)methoxy)pyridin-2-yl)-2-(1-(cyclopropylsulfonyl)-1H-pyrazol-4-yl)pyrimidin-4-amine

Step 1. 1-((1r,4r)-4-(((2-Chloro-5-((1-cyclopropyl-1H-pyrazol-4-yl)ethynyl)pyridin-4-yl)oxy)methyl)cyclohexyl)-N,N-dimethylmethanamine The title compound as a solid (163 mg) was prepared in the same fashion as Step 2 in Example 1 except that 1-cyclopropyl-4-ethynyl-1H-pyrazole (87 mg, 0.661 mmol) and 1 ((1 r,4r)-4-(((2-chloro-5-iodopyridin-4-yl)oxy)methyl)cyclohexyl)-N,N-dimethylmethanamine (180 mg, 0.440 mmol) prepared in Reference Example 16 were used instead of 4-ethynyl-1-methylpyrazole and 1-(2-chloro-5-iodopyridin-4-yl)-4-methylpiperazine. MS (ESI) m/z=413.2 (M+H)$^+$

Step 2. N-(5-((1-Cyclopropyl-1H-pyrazol-4-yl)ethynyl)-4-(((1r,4r)-4-((dimethylamino)methyl)cyclohexyl)methoxy)pyridin-2-yl)-2-(1-(cyclopropylsulfonyl)-1H-pyrazol-4-yl)pyrimidin-4-amine The title compound as a solid (24 mg) was prepared in the same fashion as Step 3 in Example 1 except that 1-((1r,4r)-

4-(((2-chloro-5-((1-cyclopropyl-1H-pyrazol-4-yl)ethynyl) pyridin-4-yl)oxy)methyl)cyclohexyl)-N,N-dimethylmethanamine (149 mg, 0.362 mmol) prepared in Step 1 was used instead of 1-(2-chloro-5-((1-methyl-1H-pyrazol-4-yl)ethynyl)pyridin-4-yl)-4-methylpiperazine. $^1$H-NMR (solvent, 600 MHz) δ 12.01 (d, 1H), 8.47 (s, 1H), 8.42 (s, 1H), 8.22 (s, 1H), 7.82 (s, 1H), 7.72 (s, 1H), 7.61 (s, 1H), 7.12 (s, 1H), 4.05 (s, 2H), 3.67 (s, 1H), 2.88 (s, 2H), 2.83 (s, 6H), 2.16 (s, 2H), 2.05 (s, 2H), 1.96 (s, 1H), 1.17 (s, 3H), 1.07 (s, 2H), 0.88-0.84 (m, 4H); MS (ESI) m/z=642.3 (M+H)$^+$ Example 61. 2-(1-(Cyclopropylsulfonyl)-1H-pyrazol-4-yl)-N-(4-(((1r,4r)-4-((dimethylamino)methyl) cyclohexyl)methoxy)-5-((1-(2-fluoroethyl)-1H-pyrazol-4-yl)ethynyl)pyridin-2-yl)pyrimidin-4-amine Step 1. 1-((1 r,4r)-4-(((2-Chloro-5-((1-(2-fluoroethyl)-1H-pyrazol-4-yl)ethynyl)pyridin-4-yl)oxy) methyl)cyclohexyl)-N,N-dimethylmethanamine The title compound as a solid (170 mg) was prepared in the same fashion as Step 2 in Example 1 except that 4-ethynyl-1-(2-fluoroethyl)-pyrazole (127 mg, 0.918 mmol) and 1-((1r,4r)-4-(((2-chloro-5-iodopyridin-4-yl)oxy)methyl) cyclohexyl)-N,N-dimethylmethanamine (250 mg, 0.612 mmol) prepared in Reference Example 16 were used instead of 4-ethynyl-1-methylpyrazole and 1-(2-chloro-5-iodopyridin-4-yl)-4-methylpiperazine. MS (ESI) m/z=419.2 (M+H)$^+$ Step 2. 2-(1-(Cyclopropylsulfonyl)-1H-pyrazol-4-yl)-N-(4-(((1r,4r)-4-((dimethylamino)methyl)cyclohexyl)methoxy)-5-((1-(2-fluoroethyl)-1H-pyrazol-4-yl)ethynyl)pyridin-2-yl)pyrimidin-4-amine The title compound as a solid (46 mg) was prepared in the same fashion as Step 3 in Example 1 except that 1-((1r,4r)-4-(((2-chloro-5-((1-(2-fluoroethyl)-1H-pyrazol-4-yl)ethynyl)pyridin-4-yl)oxy)methyl)cyclohexyl)-N,N-dimethylmethanamine (170 mg, 0.405 mmol) prepared in Step 1 was used instead of 1-(2-chloro-5-((1-methyl-1H-pyrazol-4-yl) ethynyl)pyridin-4-yl)-4-methylpiperazine. $^1$H-NMR (CDCl$_3$, 600 MHz) δ 8.65 (s, 1H), 8.43 (s, 2H), 8.26 (s, 1H), 8.02 (s, 1H), 7.68 (s, 2H), 7.50 (s, 1H), 7.17 (s, 1H), 4.82 (t, 1H), 4.74 (t, 1H), 4.46 (t, 1H), 4.41 (t, 1H), 4.00 (d, 2H), 2.84-2.81 (m, 1H), 2.21 (s, 6H), 2.12 (d, 2H), 2.00 (d, 3H), 1.91 (d, 3H), 1.54-1.51 (m, 2H), 1.24-1.20 (m, 4H); MS (ESI) m/z=648.3 (M+H)$^+$ Example 62. 2-(1-(Cyclopropylsulfonyl)-1H-pyrazol-4-yl)-N-(4-(((I r,4r)-4-((dimethylamino)methyl) cyclohexyl)methoxy)-5-(pyridin-3-ylethynyl)pyridin-2-yl)pyrimidin-4-amine Step 1. 1-((1r,4r)-4-(((2-Chloro-5-(pyridin-3-ylethynyl)pyridin-4-yl)oxy)methyl)cyclohexyl)-N,N-dimethylmethanamine The title compound as a solid (155 mg) was prepared in the same fashion as Step 2 in Example 1 except that 3-ethynylpyridine (95 mg, 0.918 mmol) and 1-((1 r,4r)-4-(((2-chloro-5-iodopyridin-4-yl)oxy)methyl)cyclohexyl)-N,N-dimethylmethanamine (250 mg, 0.612 mmol) prepared in Reference Example 16 were used instead of 4-ethynyl-1-methylpyrazole and 1-(2-chloro-5-iodopyridin-4-yl)-4-methylpiperazine. MS (ESI) m/z=384.2 (M+H)$^+$ Step 2. 2-(1-(Cyclopropylsulfonyl)-1H-pyrazol-4-yl)-N-(4-(((1r,4r)-4-((dimethylamino)methyl)cyclohexyl)methoxy)-5-(pyridin-3-ylethynyl)pyridin-2-yl) pyrimidin-4-amine The title compound as a solid (36.9 mg) was prepared in the same fashion as Step 3 in Example 1 except that 1-((1r,4r)-4-(((2-chloro-5-(pyridin-3-ylethynyl)pyridin-4-yl)oxy)methyl)cyclohexyl)-N,N-dimethylmethanamine (155 mg, 0.405 mmol) prepared in Step 1 was used instead of 1-(2-chloro-5-((1-methyl-1H-pyrazol 4-yl)ethynyl)pyridin-4-yl)-4-methylpiperazine. $^1$H-NMR (CDCl$_3$, 600 MHz) δ 8.72 (s, 1H), 8.62 (s, 1H), 8.52 (d, 1H), 8.43 (d, 1H), 8.40 (s, 110, 8.30 (s, 1H), 7.94 (s,1H), 7.76 (d, 1H), 7.51 (s, 1H), 7.28-7.24 (m, 1H), 7.14 (s,1H), 3.99 (d, 2H), 2.82-2.78 (m, 1H), 2.19 (s, 6H), 2.09 (d, 2H), 1.98 (d, 3H), 1.91-1.89 (m, 6H), 1.51-1.49 (m, 2H), 1.26-1.18 (m, 5H), 1.00-0.95 (m, 2H); MS (ESI) m/z=613.3 (M+H)$^+$ Example 63. N-(1-(2-((2-(1-(Cyclopropylsulfonyl)-1H-pyrazol-4-yl)pyrimidin-4-yl)amino)-5-((l-methyl-1H-pyrazol-4-yl)ethynyl)pyridin-4-yl)piperidin-4-yl)methanesulfonamide The 20% TFA in DCM solution (5 mL) of tert-butyl (1-(2-((2-(1-(cyclopropylsulfonyl)-1H-pyrazol-4-yl)pyrimidin-4-yl)amino)-5-((1-methyl-1H-pyrazol-4-yl)ethynyl) pyridin-4-yl)piperidin-4-yl)carbamate (100 mg, 0.155 mmol) prepared in Reference Example 17 was stirred at room temperature overnight. The reaction mixture was quenched with sat. NaHCO$_3$ soln., extracted with DCM, dried over MgSO$_4$, and then concentrated. After the residue was re-dissolved with DCM (5 mL), methanesulfonyl chloride (0.04 mL, 0.465 mmol) and TMA (0.06 mL, 0.465 mmol) were added. After being stirred at room temperature for 3 hours, the reaction mixture was diluted in DCM, washed by water, dried over MgSO$_4$, and then concentrated. The crude product was purified by column chromatography (MeOH/DCM=0-10%) to yield N-(1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanesulfonamide (3 mg) as a yellow solid. $^1$H-NMR (CDCl$_3$, 600 MHz) δ 8.68 (s, 1H), 8.45 (s, 1H), 8.42 (d, 1H), 8.23 (s, 1H), 7.80 (s, 1H), 7.77 (s, 1H), 7.62 (s, 1H), 7.54 (s, 1H), 6.89 (d, 1H), 4.61 (d, 1H), 3.95-3.92 (m, 5H), 3.65-3.61 (m, 1H), 3.18 (t, 2H), 3.17 (s, 3H), 2.88-2.84 (m, 1H), 2.24-2.21 (m, 2H), 2.04-2.00 (m, 1H), 1.85-1.79 (m, 2H), 1.57-1.54 (m, 2H), 1.16-0.83 (m, 2H); MS (ESI) m/z=623.2 (M+H)$^+$ Example 64. 2-(1-(Cyclopropylsulfonyl)-1H-pyrazol-4-yl)-N-(4-(4-(isopropylamino)piperidin-1-yl)-5-((1-methyl-1H-pyrazol-4-yl)ethynyl)pyridin-2-yl) pyrimidin-4-amine The 20% TFA in DCM solution (5 mL) of tert-butyl (1-(2-((2-(1-(cyclopropylsulfonyl)-1H-pyrazol-4-yl)pyrimidin-4-yl)amino)-5-((1-methyl-1H-pyrazol-4-yl)ethynyl) pyridin-4-yl)piperidin-4-yl)carbamate (100 mg, 0.155 mmol) prepared in Reference Example 17 was stirred at room temperature overnight. The reaction mixture was quenched with sat. NaHCO$_3$soln., extracted with DCM, dried over MgSO$_4$, and then concentrated. After the residue was re-dissolved with DMF (5 mL), 2-iodopropane (0.08 mL, 0.775 mmol) and TMA (0.11 mL, 0.775 mmol) were added. After being stirred at 60° C. for 3 hours, the reaction mixture was diluted in EA, washed by water, dried over MgSO₄, and then concentrated. The crude product was purified by column chromatography (MeOH/DCM=0-20%) to yield 2-(1-(cyclopropylsulfonyl)-1H-pyrazol-4-yl)-N-(4-(4-(isopropylamino)piperidin-1-yl)-5-((l-methyl-1H-pyrazol-4-yl)ethynyl)pyridin-2-yl)pyrimidin-4-amine (5 mg) as a light yellow solid. $^1$H-NMR (CDCl₃, 600 MHz) δ 8.66 (s, 1H), 8.44 (s, 1H), 8.41 (d, 1H), 8.18 (s, 1H), 8.12 (s, 1H), 7.91 (s, 1H), 7.67 (s, 1H), 7.64 (s, 1H), 6.97 (s, 1H), 4.09 (d, 2H), 3.92 (s, 3H), 3.63 (t, 1H), 3.49 (d, 1H), 2.90-2.86 (m, 3H), 2.42-2.40 (m, 2H), 2.29-2.28 (m, 2H), 2.02-2.00 (m, 2H), 1.54-1.47 (m, 7H), 1.38 (s, 2H), 0.89-0.84 (m, 2H); MS (ESI) m/z=587.3 (M+H)⁺

Example 65. 2-(1-(Cyclopropylsulfonyl)-1H-pyrazol-4-yl)-N-(5-((1-methyl-1H-pyrazol-4-yl)ethynyl)-4-(4-(trifluoromethyl)piperidin-1-yl)pyridin-2-yl)pyrimidin-4-amine Step 1. 2-Chloro-5-((1-methyl-1H-pyrazol-4-yl)ethynyl)-4-(4-(trifluoromethyl)piperidin-1-yl)pyridine The suspension of 2-chloro-4-fluoro-5-((1-methyl-1H-pyrazol-4-yl)ethynyl)pyridine (150 mg, 0.637 mmol) prepared in Reference Example 18, 4-(trifluoromethyl)piperidine HCl (181.05 mg, 0.955 mmol), and DIPEA (0.44 mL, 2.546 mmol) in DMA (4 mL) was stirred at 50° C. overnight. After being cooled, the reaction mixture was diluted in EA, washed by water, dried over MgSO₄, and then concentrated. The crude product was purified by column chromatography (MeOH/DCM=0-5%) to yield 2-chloro-5-((1-methyl-1H-pyrazol-4-yl)ethynyl)-4-(4-(trifluoromethyl)piperidin-1-yl)pyridine (170 mg) as a yellow solid. MS (ESI) m/z=369.1 (M+H)⁺

Step 2. 2-(1-(Cyclopropylsulfonyl)-1H-pyrazol-4-yl)-N-(5-((1-methyl-1H-pyrazol-4-yl)ethynyl)-4-(4-(trifluoromethyl)piperidin-1-yl)pyridin-2-yl)pyrimidin-4-amine The title compound as a solid (23 mg) was prepared in the same fashion as Step 3 in Example 1 except that 2-chloro-5-((1-methyl-1H-pyrazol-4-yl)ethynyl)-4-(4-(trifluoromethyl)piperidin-1-yl)pyridine (168 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl₃, 400 MHz) δ 8.65 (s, 1H), 8.42 (s, 1H), 8.39 (d, 1H), 8.24 (s, 1H), 8.20 (s, 1H), 7.61 (s, 1H), 7.53 (s, 1H), 6.99 (d, 1H), 4.17 (d, 2H), 3.93 (s, 3H), 2.90-2.79 (m, 3H), 2.32-2.27 (m, 1H), 2.13-2.00 (m, 3H), 1.87-1.77 (m, 3H), 1.53-1.49 (m, 2H), 1.28-1.19 (m, 4H); MS (ESI) m/z=598.1 (M+H)⁺

Example 66. 2-(1-(Cyclopropylsulfonyl)-1H-pyrazol-4-yl)-N-(4-(4-fluoro-4-(trifluoromethyl)piperidin-1-yl)-5-((1-methyl-1H-pyrazol-4-yl)ethynyl)pyridin-2-yl)pyrimidin-4-amine Step 1. 2-Chloro-4-(4-fluoro-4-(trifluoromethyl)piperidin-1-yl)-5-((1-methyl-1H-pyrazol-4-yl)ethynyl)pyridine The title compound as a solid (180 mg) was prepared in the same fashion as Step 1 in Example 65 except that 4-fluoro-4-(trifluoromethyl)piperidine HCl (198 mg, 0.955 mmol) was used instead of 4-(trifluoromethyl)piperidine HCl. MS (ESI) m/z=387.0 (M+H)⁺

Step 2. 2-(1-(Cyclopropylsulfonyl)-1H-pyrazol-4-yl)-N-(4-(4-fluoro-4-(trifluoromethyl)piperidin-1-yl)-5-((1-methyl-1H-pyrazol-4-yl)ethynyl)pyridin-2-yl)pyrimidin-4-amine The title compound as a solid (23 mg) was prepared in the same fashion as Step 3 in Example 1 except that 2-chloro-4-(4-fluoro-4-(trifluoromethyl)piperidin-1-yl)-5-((1-methyl-1H-pyrazol-4-yl)ethynyl)pyridine (176 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl₃, 400 MHz) δ 8.64 (s, 1H), 8.43 (s, 1H), 8.42 (d, 1H), 8.28 (s, 1H), 8.00 (s, 1H), 7.62 (d, 1H), 7.55 (s, 1H), 7.07 (d, 1H), 4.07 (d, 2H), 3.94 (s, 3H), 3.19 (t, 2H), 2.87-2.81 (m, 1H), 2.26-2.14 (m, 3H), 2.12-2.04 (m, 1H), 1.55-1.51 (m, 2H), 1.25-1.18 (m, 3H); MS (ESI) m/z=616.1 (M+H)⁺

Example 67. 2-(1-(Cyclopropylsulfonyl)-1H-pyrazol-4-yl)-N-(5-((1-methyl-1H-pyrazol-4-yl)ethynyl)-4-(4-(trifluoromethoxy)piperidin-1-yl)pyridin-2-yl)pyrimidin-4-amine Step 1. 2-Chloro-5-((1-methyl-1H-pyrazol-4-yl)ethynyl)-4-(4-(trifluoromethoxy)piperidin-1-yl)pyridine The title compound as a solid (181 mg) was prepared in the same fashion as Step 1 in Example 65 except that 4-(trifluoromethoxy)piperidine HCl (196 mg, 0.955 mmol) was used instead of 4-(trifluoromethyl)piperidine HCl. MS (ESI) m/z=385.1 (M+H)⁺

Step 2. 2-(1-(Cyclopropylsulfonyl)-1H-pyrazol-4-yl)-N-(5-((1-methyl-1H-pyrazol-4-yl)ethynyl)-4-(4-(trifluoromethoxy)piperidin-1-yl)pyridin-2-yl)pyrimidin-4-amine The title compound as a solid (26 mg) was prepared in the same fashion as Step 3 in Example 1 except that 2-chloro-5-((1-methyl-1H-pyrazol-4-yl)ethynyl)-4-(4-(trifluoromethoxy)piperidin-1-yl)pyridine (176 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl₃, 400 MHz) δ 8.64 (s, 1H), 8.43 (s, 1H), 8.41 (d, 1H), 8.25 (s, 1H), 8.12 (s, 1H), 7.62 (s, 1H), 7.55 (s, 1H), 7.01 (d, 1H), 4.54-4.50 (m, 1H), 3.93 (s, 3H), 3.78-3.75 (m, 2H), 3.39-3.34 (m, 2H), 2.85-2.80 (m, 2H), 2.19-2.16 (m, 2H), 2.08-2.02 (m, 2H), 1.54-1.50 (m, 2H), 1.27-1.19 (m, 3H); MS (ESI) m/z=614.1 (M+H)⁺

Example 68. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-difluoropiperidin-4-ol Step 1. 1-(2-Chloro-5-((1-methyl-1H-pyrazol-4-yl)ethynyl)pyridin-4-yl)-3,3-difluoropiperidin-4-ol The title compound as a solid (165 mg) was prepared in the same fashion as Step 1 in Example 65 except that 3,3-difluoropiperidin-4-ol HCl (166 mg, 0.955 mmol) was used instead of 4-(trifluoromethyl)piperidine HCl. MS (ESI) m/z=353.1 (M+H)⁺

Step 2. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-difluoropiperidin-4-ol The title compound as a solid (84 mg) was prepared in the same fashion as Step 3 in Example 1 except that 1-(2-chloro-5-((1-methyl-1H-pyrazol-4-yl)ethynyl)pyridin-4-yl)-3,3-difluoropiperidin-4-ol (161 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 600 MHz) δ 10.29 (s, 1H), 8.68 (s, 1H), 8.47 (s, 1H), 8.46 (d, 1H), 8.21 (s, 1H), 8.01 (s, 1H), 7.64 (s, 2H), 7.46 (s, 1H), 4.07-4.01 (m, 1H), 3.92-3.88 (m, 1H), 3.87 (s, 3H), 3.67-3.62 (m, 2H), 3.39-3.37 (m, 1H), 3.29-3.25 (m, 1H), 2.03 (s, 1H), 1.84 (d, 1H), 1.37-1.34 (m, 2H), 1.27-1.23 (m, 2H); MS (ESI) m/z=574.1 (M+H)$^+$

Example 69. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-dimethylpiperidin-4-ol

Step 1. 1-(2-Chloro-5-((1-methyl-1H-pyrazol-4-yl)ethynyl)pyridin-4-yl)-3,3-dimethylpiperidin-4-ol The title compound as a solid (172 mg) was prepared in the same fashion as Step 1 in Example 65 except that 3,3-dimethylpiperidin-4-ol HCl (158 mg, 0.955 mmol) was used instead of 4-(trifluoromethyl)piperidine HCl. MS (ESI) m/z=345.1 (M+H)$^+$

Step 2. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-dimethylpiperidin-4-ol The title compound as a solid (18 mg) was prepared in the same fashion as Step 3 in Example 1 except that 1-(2-chloro-5-((1-methyl-1H-pyrazol-4-yl)ethynyl)pyridin-4-yl)-3,3-dimethylpiperidin-4-ol (157 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 600 MHz) δ 10.22 (s, 1H), 8.66 (s, 1H), 8.44 (s, 2H), 8.15 (s, 1H), 8.01 (s, 1H), 7.63 (s, 2H), 7.38 (s, 1H), 4.70 (d, 1H), 3.87 (s, 3H), 3.72 (d, 1H), 3.63 (d, 1H), 3.32-3.24 (m, 2H), 3.03 (t, 1H), 2.77 (d, 1H), 1.85-1.82 (m, 1H), 1.72-1.67 (m, 1H), 1.36-1.34 (m, 2H), 1.26-1.25 (m, 2H), 0.93 (d, 6H); MS (ESI) m/z=582.1 (M+H)$^+$

Example 70. 2-(1-(Cyclopropylsulfonyl)-1H-pyrazol-4-yl)-N-(4-(3-fluoropiperidin-1-yl)-5-((1-methyl-1H-pyrazol-4-yl)ethynyl)pyridin-2-yl)pyrimidin-4-amine

Step 1. 2-Chloro-4-(3-fluoropiperidin-1-yl)-5-((1-methyl-1H-pyrazol-4-yl)ethynyl)pyridine The title compound as a solid (154 mg) was prepared in the same fashion as Step 1 in Example 65 except that 3-fluoropiperidine HCl (124 mg, 0.891 mmol) was used instead of 4-(trifluoromethyl)piperidine HCl. MS (ESI) m/z=319.1 (M+H)$^+$

Step 2. 2-(1-(Cyclopropylsulfonyl)-1H-pyrazol-4-yl)-N-(4-(3-fluoropiperidin-1-yl)-5-((1-methyl-1H-pyrazol-4-yl)ethynyl)pyridin-2-yl)pyrimidin-4-amine The title compound as a solid (26.2 mg) was prepared in the same fashion as Step 3 in Example 1 except that 2-chloro-4-(3-fluoropiperidin-1-yl)-5-((1-methyl-1H-pyrazol-4-yl)ethynyl)pyridine (145 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44 (s, 1H), 8.39 (d, 1H), 8.24 (s, 1H), 7.64 (s, 1H), 7.60 (s, 1H), 7.57 (s, 1H), 7.00 (d, 1H), 4.92-4.78 (m, 1H), 3.92 (s, 3H), 3.84-3.76 (m, 1H), 3.68-3.62 (m, 1H), 3.51-3.42 (m, 2H), 2.84-2.79 (m, 1H), 2.10 (s, 1H), 1.99-1.90 (m, 4H), 1.78-1.74 (m, 1H), 1.54-1.50 (m, 2H), 1.23-1.19 (m, 2H); MS (ESI) m/z=548.1 (M+H)$^+$

Example 71. 2-(1-(Cyclopropylsulfonyl)-1H-pyrazol-4-yl)-N-(5-((1-methyl-1H-pyrazol-4-yl)ethynyl)-4-(3-(trifluoromethyl)piperidin-1-yl)pyridin-2-yl)pyrimidin-4-amine

Step 1. 2-Chloro-5-((1-methyl-1H-pyrazol-4-yl)ethynyl)-4-(3-(trifluoromethyl)piperidin-1-yl)pyridine The title compound as a solid (172 mg) was prepared in the same fashion as Step 1 in Example 65 except that 3-(trifluoromethyl)piperidine HCl (169 mg, 0.891 mmol) was used instead of 4-(trifluoromethyl)piperidine HCl. MS (ESI) m/z=369.1 (M+H)$^+$

Step 2. 2-(1-(Cyclopropylsulfonyl)-1H-pyrazol-4-yl)-N-(5-((1-methyl-1H-pyrazol-4-yl)ethynyl)-4-(3-(trifluoromethyl)piperidin-1-yl)pyridin-2-yl)pyrimidin-4-amine The title compound as a solid (24.6 mg) was prepared in the same fashion as Step 3 in Example 1 except that 2-chloro-5-((1-methyl-1H-pyrazol-4-yl)ethynyl)-4-(3-(trifluoromethyl)piperidin-1-yl)pyridine (168.2 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 4.48 (d, 1H), 3.92 (s, 3H), 3.83 (d, 1H), 2.91 (t, 1H), 2.85-2.73 (m, 2H), 2.57-2.55 (m, 1H), 2.13 (d, 1H), 2.03 (d, 1H), 1.62-1.52 (m, 3H), 1.25-1.17 (d, 2H); MS (ESI) m/z=598.2 (M+H)$^+$

Example 72. 2-(1-(Cyclopropylsulfonyl)-1H-pyrazol-4-yl)-N-(4-(3-(fluoromethyl)piperidin-1-yl)-5-((1-methyl-1H-pyrazol-4-yl)ethynyl)pyridin-2-yl)pyrimidin-4-amine

Step 1. 2-Chloro-4-(3-(fluoromethyl)piperidin-1-yl)-5-((1-methyl-1H-pyrazol-4-yl)ethynyl)pyridine The title compound as a solid (165 mg) was prepared in the same fashion as Step 1 in Example 65 except that 3-(fluoromethyl)piperidine HCl (137 mg, 0.891 mmol) was used instead of 4-(trifluoromethyl)piperidine HCl. MS (ESI) m/z=333.1 (M+H)$^+$

Step 2. 2-(1-(Cyclopropylsulfonyl)-1H-pyrazol-4-yl)-N-(4-(3-(fluoromethyl)piperidin-1-yl)-5-((1-methyl-1H-pyrazol-4-yl)ethynyl)pyridin-2-yl)pyrimidin-4-amine The title compound as a solid (36 mg) was prepared in the same fashion as Step 3 in Example 1 except that 2-chloro- 4-(3-(fluoromethyl)piperidin-1-yl)-5-((1-methyl-1H-pyrazol-4-yl)ethynyl)pyridine (152 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 400 MHz) S 10.22 (s, 1H), 8.65 (s, 1H), 8.42 (d, 1H), 8.16 (s, 1H), 7.97 (s, 1H), 7.63 (s, 1H), 7.61 (s, 1H), 7.37 (d, 1H), 4.49-4.29 (m, 2H), 4.04 (d, 1H), 3.83 (s, 3H), 3.77 (d, 1H), 3.25-3.19 (m, 1H), 2.92 (t, 1H), 2.72 (t, 1H), 2.10 (s, 1H), 1.85-1.85 (m, 2H), 1.69-1.63 (m, 1H), 1.34-1.28 (m, 2H), 1.25-1.20 (m, 3H); MS (ESI) m/z=562.1 (M+H)$^+$ Example 73. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol Step 1. (1-(2-Chloro-5-((1-methyl-1H-pyrazol-4-yl)ethynyl)pyridin-4-yl)-4-fluoropiperidin-4-yl)methanol The title compound as a solid (167 mg) was prepared in the same fashion as Step 1 in Example 65 except that (4-fluoropiperidin-4-yl)methanol HCl (151 mg, 0.891 mmol) was used instead of 4-(trifluoromethyl)piperidine HCl. MS (ESI) m/z=348.9 (M+H)$^+$ Step 2. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol The title compound as a solid (32 mg) was prepared in the same fashion as Step 3 in Example 1 except that (1-(2-chloro-5-((1-methyl-1H-pyrazol-4-yl)ethynyl)pyridin-4-yl)-4-fluoropiperidin-4-yl)methanol (159 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.43 (s, 1H), 8.41 (d, 1H), 8.25 (s, 1H), 7.86 (s, 1H), 7.61 (s, 1H), 7.54 (s, 1H), 7.07 (d, 1H), 3.95-3.93 (m, 5H), 3.70 (d, 2H), 3.28 (t, 2H), 2.85-2.80 (m, 1H), 2.14 (t, 2H), 2.04-1.81 (m, 3H), 1.55-1.51 (m, 2H), 1.29-1.19 (m, 2H); MS (ESI) m/z=578.1 (M+H)$^+$ Example 74. N$^2$-(2-(1-(Cyclopropylsulfonyl)-1H-pyrazol-4-yl)pyrimidin-4-yl)-N$^4$-(3-fluorocyclohexyl)-5-((1-methyl-1H-pyrazol-4-yl)ethynyl)pyridine-2,4-diamine Step 1. 2-Chloro-N-(3-fluorocyclohexyl)-5-((1-methyl-1H-pyrazol-4-yl)ethynyl)pyridin-4-amine The title compound as a solid (200 mg) was prepared in the same fashion as Step 1 in Example 65 except that 3-fluorocyclohexan-1-amine HCl (147 mg, 0.955 mmol) was used instead of 4-(trifluoromethyl)piperidine HCl. MS (ESI) m/z=333.2 (M+H)$^+$ Step 2. N$^2$-(2-(1-(Cyclopropylsulfonyl)-1H-pyrazol-4-yl)pyrimidin-4-yl)-N$^4$-(3-fluorocyclohexyl)-5-((1-methyl-1H-pyrazol-4-yl)ethynyl)pyridine-2,4-diamine The title compound as a solid (18 mg) was prepared in the same fashion as Step 3 in Example 1 except that 2-chloro-N-(3-fluorocyclohexyl)-5-((1-methyl-1H-pyrazol-4-yl)ethynyl)pyridin-4-amine (188 mg, 0.565 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (d, 1H), 8.41 (d, 1H), 8.09 (d, 1H), 7.64 (d, 1H), 7.58 (s, 1H), 7.32 (s, 1H), 4.91 (d, 1H), 3.87 (s, 3H), 2.85-2.78 (m, 1H), 2.27-2.12 (m, 4H), 1.93-1.87 (m, 2H), 1.83-1.62 (m, 2H), 1.27 (s, 2H), 1.24-1.18 (m, 2H); MS (ESI) m/z=562.0 (M+H)$^+$ Example 75. (1R,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol Step 1 (1R,3S)-3-((2-Chloro-5-((1-methyl-1H-pyrazol-4-yl)ethynyl)pyridin-4-yl)amino)cyclohexan-1-ol The title compound as a solid (102 mg) was prepared in the same fashion as Step 1 in Example 65 except that (1R,3S)-3-aminocyclohexanol (147 mg, 1.273 mmol) was used instead of 4-(trifluoromethyl)piperidine HCl. MS (ESI) m/z=331.0 (M+H)$^+$ Step 2 (1R,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol The title compound as a solid (9 mg) was prepared in the same fashion as Step 3 in Example 1 except that (1R,3S)-3-((2-chloro-5-((1-methyl-1H-pyrazol-4-yl)ethynyl)pyridin-4-yl)amino)cyclohexan-1-ol (66 mg, 0.198 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.43 (s, 1H), 8.38 (s, 1H), 8.36 (s. 1H), 8.07 (s, 1H), 7.63 (s, 1H), 7.57 (s, 1H), 7.17 (s, 1H), 7.05 (s, 1H), 6.16 (s, 1H), 4.01 (s, 1H), 3.90 (s, 3H), 3.72-3.69 (m, 1H), 2.84-2.78 (m, 1H), 2.23-2.20 (m, 2H), 2.03-1.99 (m, 1H), 1.92-1.83 (m, 3H), 1.71-1.59 (m, 2H), 1.56-1.50 (m, 3H), 1.44-1.40 (m, 1H), 1.39-1.18 (m, 3H); MS (ESI) m/z=560.1 (M+H)$^+$ Example 76. (1R,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol Step 1. (1R,3R)-3-((2-Chloro-5-((1-methyl-1H-pyrazol-4-yl)ethynyl)pyridin-4-yl)amino)cyclohexan-1-ol The title compound as a solid (107 mg) was prepared in the same fashion as Step 1 in Example 65 except that (1R,3R)-3-aminocyclohexan-1-ol HCl (193 mg, 1.273 mmol) was used instead of 4-(trifluoromethyl)piperidine HCl. MS (ESI) m/z=331.0 (M+H)$^+$ Step 2. (1R,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol The title compound as a solid (13 mg) was prepared in the same fashion as Step 3 in Example 1 except that (1R,3R)-3-((2-chloro-5-((1-methyl-1H-pyrazol-4-yl)ethynyl)pyridin-4-yl)amino)cyclohexan-1-ol (102 mg, 0.310 mmol) prepared in Step 1 was used instead of 1-(2-chloro-5-((1- methyl-1H-pyrazol-4-yl)ethynyl)pyridin-4-yl)-4-methylpiperazine. $^1$H-NMR (CDCl$_3$, 400 MHz) δ 8.65 (s, 1H), 8.48 (s, 1H), 8.38 (s, 1H), 8.36 (s, 1H), 8.10 (s, 1H), 7.64 (s, 1H), 7.58 (s, 1H), 7.14 (s, 1H), 4.99 (d, 1H), 4.15 (s, 1H), 3.99-3.96 (m, 1H), 3.93 (s, 3H), 2.86-2.82 (m, 1H), 2.10-2.00 (m, 3H), 1.88-1.84 (m, 1H), 1.68-1.60 (m, 4H), 1.53-1.49 (m, 2H), 1.48-1.43 (m, 2H), 1.22-1.20 (m, 2H); MS (ESI) m/z=560.0 (M+H)$^+$ Example 77. 1-(2-((2-(1-(Cyclopropylsulfonyl)-1H-pyrazol-4-yl)pyrimidin-4-yl)amino)-5-((l-methyl-1H-pyrazol-4-yl)ethynyl)pyridin-4-yl)azepan-4-ol Step 1. 1-(2-Chloro-5-((1-methyl-1H-pyrazol-4-yl)ethynyl)pyridin-4-yl)azepan-4-ol The title compound as a solid (125 mg) was prepared in the same fashion as Step 1 in Example 65 except that azepan-4-ol HCl (77 mg, 0.509 mmol) was used instead of 4-(trifluoromethyl)piperidine HCl. $^1$H-NMR (CDCl$_3$, 600 MHz) δ 8.16 (s, 1H), 7.58 (s, 1H), 7.52 (s, 1H), 6.55 (s, 1H), 4.02-4.00 (m, 1H), 3.91 (s, 3H), 3.86-3.82 (m, 1H), 3.75-3.66 (m, 2H), 3.57-3.54 (m, 1H), 2.18-2.08 (m, 2H), 1.99-1.96 (m, 1H), 1.91-1.85 (m, 2H), 1.84-1.79 (m, 2H)

Step 2. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-ol The title compound as a solid (47 mg) was prepared in the same fashion as Step 3 in Example 1 except that 1-(2-chloro-5-((1-methyl-1H-pyrazol-4-yl)ethynyl)pyridin-4-yl)azepan-4-ol (112 mg, 0.339 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.42 (s, 1H), 8.38 (d, 1H), 8.18 (s, 1H), 7.89 (s, 1H), 7.59 (s, 1H), 7.52 (s, 1H), 7.31 (s, 1H), 7.00 (d, 1H), 4.02-3.93 (m, 1H), 3.91-3.89 (m, 4H), 3.80-3.72 (m, 2H), 3.69-3.63 (m, 1H), 2.83-2.79 (m, 1H), 2.23-2.14 (m, 2H), 2.12-1.99 (m, 1H), 1.93-1.73 (m, 4H), 1.54-1.49 (m, 2H), 1.29-1.18 (m, 2H); MS (ESI) m/z=560.2 (M+H)$^+$ Example 78. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-yl)methanol Step 1. (1-(2-Chloro-5-((1-methyl-1H-pyrazol-4-yl)ethynyl)pyridin-4-yl)azepan-4-yl)methanol The title compound as a solid (122 mg) was prepared in the same fashion as Step 1 in Example 65 except that (azepan-4-yl)methanol (66 mg, 0.509 mmol) was used instead of 4-(trifluoromethyl)piperidine HCl. $^1$H-NMR (CDCl$_3$, 600 MHz) δ 8.12 (s, 1H), 7.57 (s, 1H), 6.54 (s, 1H), 3.99-3.92 (m, 2H), 3.91 (s, 3H), 3.74 (s, 1H), 3.62-3.53 (m, 2H), 3.47-3.46 (m, 2H), 2.77 (s, 3H), 2.15-2.11 (m, 1H), 2.05-2.02 (m, 1H), 1.91 (d, 1H), 1.83-1.81 (m, 1H), 1.69-1.67 (m, 1H), 1.58-1.55 (m, 1H), 1.23-1.20 (m, 1H)

Step 2. (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-yl)methanol The title compound as a solid (40.4 mg) was prepared in the same fashion as Step 3 in Example 1 except that (1-(2-chloro-5-((1-methyl-1H-pyrazol-4-yl)ethynyl)pyridin-4-yl)azepan-4-yl)methanol (117 mg, 0.339 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (s, 1H), 8.39 (d, 1H), 8.12 (s, 1H), 7.80 (s, 1H), 7.60 (s, 1H), 7.53 (s, 1H), 7.29 (s, 1H), 7.05 (d, 1H), 4.07-4.00 (m, 2H), 3.93 (s, 3H), 3.72-3.62 (m, 2H), 3.52-3.50 (m, 2H), 2.85-2.81 (m, 1H), 2.17-2.09 (m, 2H), 1.93-1.89 (m, 2H), 1.74-1.61 (m, 5H), 1.55-1.51 (m, 2H), 1.29-1.19 (m, 2H); MS (ESI) m/z=574.2 (M+H)$^+$ Example 79. 8-(2-((2-(1-(Cyclopropylsulfonyt)-1H-pyrazol-4-yl)pyrimidin-4-yl)amino)-5-((1-methyl-1H-pyrazol-4-yl)ethynyl)pyridin-4-yl)-2,8-diazaspiro[4.5]decan-1-one Step 1. 8-(2-Chloro-5-((1-methyl-1H-pyrazol-4-yl)ethynyl)pyridin-4-yl)-2,8-diazaspiro[4.5]decan-1-one The title compound as a solid (116 mg) was prepared in the same fashion as Step 1 in Example 65 except that 2,8-diazaspiro[4.5]decan-1-one HCl (121 mg, 0.637 mmol) was used instead of 4-(trifluoromethyl)piperidine HCl. MS (ESI) m/z=370.1 (M+H)$^+$ Step 2. 8-(2-((2-(1-(Cyclopropylsulfonyt)-1H-pyrazol-4-yl)pyrimidin-4-yl)amino)-5-((1-methyl-1H-pyrazol-4-yl)ethynyl)pyridin-4-yl)-2,8-diazaspiro[4.5]decan-1-one The title compound as a solid (9 mg) was prepared in the same fashion as Step 3 in Example 1 except that 8-(2-chloro-5-((1-methyl-1H-pyrazol-4-yl)ethynyl)pyridin-4-yl)-2,8-diazaspiro[4.5]decan-1-one (98 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.65 (s, 1H), 8.44 (s, 1H), 8.41-8.40 (m, 2H), 8.23 (s, 1H), 7.70 (s, 1H), 7.63 (s, 1H), 7.56 (s, 1H), 7.00 (s, 1H), 6.03 (s, 1H), 4.14-4.07 (m, 2H), 3.92 (s, 4H), 3.42-3.35 (m, 2H), 3.18-3.13 (m, 2H), 2.85-2.82 (m, 1H), 2.22-2.17 (m, 4H), 2.14-2.10 (m, 2H), 1.78-1.68 (m, 3H), 1.55-1.51 (m, 2H), 1.27-1.23 (m, 3H); MS (ESI) m/z=599.2 (M+H)$^+$ Example 80. N$^{N}$-(2-(1-(Cyclopropylsulfonyt)-1H-pyrazol-4-yl)pyrimidin-4-yl)-N$^4$-((1s,4s)-4-((2-fluoroethyl)amino)cyclohexyl)-5-((1-methyl-1H-pyrazol-4-yl)ethynyl)pyridine-2,4-diamine Step 1. (1s,4s)-N$^4$-(2-Chloro-5-((1-methyl-1H-pyrazol-4-yl)ethynyl)pyridin-4-yl)-N$^4$-(2-fluoroethyl)cyclohexane-1,4-diamine The title compound as a solid (130 mg) was prepared in the same fashion as Step 1 in Example 65 except that (1s,4s)-N$^4$-(2-fluoroethyl)cyclohexane-1,4-diamine (102 mg, 0.637 mmol) was used instead of 4-(trifluoromethyl)piperidine HCl. MS (ESI) m/z=376.1 (M+H)$^+$ Step 2. N$^2$-(2-(1-(Cyclopropylsulfonyt)-1H-pyrazol-4-yl)pyrimidin-4-yl)-N$^4$-((1s,4s)-4-((2-fluoroethyl)amino)cyclohexyl)-5-((1-methyl-1H-pyrazol-4-yl)ethynyl)pyridine-2,4-diamine The title compound as a solid (2 mg) was prepared in the same fashion as Step 3 in Example 1 except that (1s,4s)-

N[4]-(2-chloro-5-((1-methyl-1H-pyrazol-4-yl)ethynyl)pyridin-4-yl)-N[4]-(2-fluoroethyl)cyclohexane-1,4-diamine (128 mg, 0.339 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.06 (s, 1H), 8.62 (s, 1H), 8.43 (s, 1H), 8.42 (s, 1H), 8.21 (s, 1H), 8.10 (s, 1H), 7.83 (s, 1H), 7.47 (s, 1H), 7.26 (s, 1H), 5.39 (d, 1H), 4.49 (t, 1H), 4.37 (t, 1H), 3.90 (s, 3H), 3.62 (s, 2H), 2.81 (t, 1H), 2.74 (t, 1H), 2.64 (s, 2H), 1.95-1.92 (m, 2H), 1.77-1.66 (m, 6H), 1.65-1.61 (m, 3H), 1.46-1.44 (m, 1H), 1.32-1.24 (m, 1H); MS (ESI) m/z=605.2 (M+H)$^+$

Example 81. (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-1-methylcyclohexan-1-ol

Step 1. (1s, 4s)-4-((2-Chloro-5-((1-methyl-1H-pyrazol-4-yl)ethynyl)pyridin-4-yl)amino)-1-methylcyclohexan-1-ol The title compound as a solid (226 mg) was prepared in the same fashion as Step 1 in Example 65 except that cis-4-amino-1-methylcyclohexanol (150 mg, 1.161 mmol) was used instead of 4-(trifluoromethyl)piperidine HCl. MS (ESI) m/z=345.0 (M+H)$^+$

Step 2. (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-1-methylcyclohexan-1-ol The title compound as a solid (187 mg) was prepared in the same fashion as Step 3 in Example 1 except that (1s,4s)-4-((2-chloro-5-((1-methyl-1H-pyrazol-4-yl)ethynyl)pyridin-4-yl)amino)-1-methylcyclohexan-1-ol (195 mg, 0.565 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.02 (s, 1H), 8.63 (s, 1H), 8.44 (s, 1H), 8.41 (d, 1H), 8.06 (s, 1H), 8.01 (s, 1H), 7.68 (s, 1H), 7.49 (s, 1H), 7.21 (s, 1H), 5.38 (d, 1H), 4.13 (s, 1H), 3.84 (s, 3H), 3.33-3.22 (m, 1H), 1.76-1.74 (m, 2H), 1.71-1.50 (m, 2H), 1.56 (d, 2H), 1.42-1.39 (m, 2H), 1.34-1.32 (m, 2H), 1.23-1.21 (m, 2H), 1.11 (s, 3H); MS (ESI) m/z=574.2 (M+H)$^+$

Example 82. 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol

Step 1. 1-(2-Chloro-5-((1-(2,2-difluorocyclopropyl)-1H-pyrazol-4-yl)ethynyl)pyridin-4-yl)piperidin-4-ol The title compound as a solid (168 mg) was prepared in the same fashion as Step 1 in Example 65 except that 4-hydroxypiperidine (76 mg, 0.756 mmol) and 2-chloro-5-((1-(2,2-difluorocyclopropyl)-1H-pyrazol-4-yl)ethynyl)-4-fluoropyridine (150 mg, 0.504 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=379.1 (M+H)$^+$

Step 2. 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol The title compound as a solid (93 mg) was prepared in the same fashion as Step 3 in Example 1 except that 1-(2-chloro-5-((1-(2,2-difluorocyclopropyl)-1H-pyrazol-4-yl)ethynyl)pyridin-4-yl)piperidin-4-ol (157 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s,1H), 8.45 (s, 1H), 8.42 (d, 1H), 8.24 (s, 1H), 7.98 (s, 1H), 7.70 (s, 1H), 7.68 (d, 1H), 6.98 (d, 1H), 4.12 (q, 1H), 4.04-4.00 (m, 1H), 3.88-3.84 (m, 2H), 3.28 (t, 1H), 2.87-2.81 (m, 1H), 2.29-2.23 (m, 1H), 2.22-2.09 (m, 3H), 1.85-1.76 (m, 6H), 1.56-1.52 (m, 2H), 1.26-1.21 (m, 2H); MS (ESI) m/z=608.1 (M+H)$^+$

Example 83. (1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)methanol

Step 1. (1-(2-Chloro-5-((1-(2,2-difluorocyclopropyl)-1H-pyrazol-4-yl)ethynyl)pyridin-4-yl)piperidin-4-yl)methanol The title compound as a solid (175 mg) was prepared in the same fashion as Step 1 in Example 65 except that 4-piperidinemethanol (87 mg, 0.756 mmol) and 2-chloro-5-((1-(2,2-difluorocyclopropyl)-1H-pyrazol-4-yl)ethynyl)-4-fluoropyridine (150 mg, 0.504 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=393.1 (M+H)$^+$

Step 2. (1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)methanol The title compound as a solid (28 mg) was prepared in the same fashion as Step 3 in Example 1 except that (1-(2-chloro-5-((1-(2,2-difluorocyclopropyl)-1H-pyrazol-4-yl)ethynyl)pyridin-4-yl)piperidin-4-yl)methanol (163 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.40 (d, 1H), 8.23 (s, 1H), 8.09 (s, 1H), 7.69 (s, 2H), 7.57 (s, 1H), 7.02 (d, 1H), 4.16-4.09 (m, 3H), 3.60 (d, 2H), 2.95 (t, 2H), 2.87-2.81 (m, 1H), 2.30-2.23 (m, 1H), 2.22-2.10 (m, 1H), 1.95 (d, 2H), 1.79 (s, 5H), 1.55-1.48 (m, 4H), 1.26-1.20 (m, 2H); MS (ESI) m/z=622.1 (M+H)$^+$

Example 84. 2-(1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)ethan-1-ol

Step 1. 2-(1-(2-Chloro-5-((1-(2,2-difluorocyclopropyl)-1H-pyrazol-4-yl)ethynyl)pyridin-4-yl)piperidin-4-yl)ethan-1-ol The title compound as a solid (183 mg) was prepared in the same fashion as Step 1 in Example 65 except that 4-piperidineethanol (98 mg, 0.756 mmol) and 2-chloro-5-((1-(2,2-difluorocyclopropyl)-1H-pyrazol-4-yl)ethynyl)-4-fluoropyridine (150 mg, 0.504 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=407.2 (M+H)$^+$ Step 2. 2-(1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)ethan-1-ol The title compound as a solid (24 mg) was prepared in the same fashion as Step 3 in Example 1 except that 2-(1-(2-chloro-5-((1-(2,2-difluorocyclopropyl)-1H-pyrazol-4-yl)ethynyl)pyridin-4-yl)piperidin-4-yl)ethan-1-ol (169 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44 (s, 1H), 8.40 (d, 1H), 8.22 (s, 1H), 8.06 (s, 1H), 7.68 (s, 2H), 7.57 (s, 1H), 7.01 (d, 1H), 4.15-4.08 (m, 3H), 3.76 (t, 2H), 2.91 (t, 2H), 2.85-2.81 (m, 1H), 2.28-2.21 (m, 1H), 2.18-2.10 (m, 1H), 1.91 (d, 2H), 1.63-1.58 (m, 2H), 1.54-1.47 (m, 4H), 1.37-1.19 (m, 4H); MS (ESI) m/z=636.2 (M+H)$^+$ Example 85. (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol Step 1. (1s,4s)-4-((2-Chloro-5-((1-(2,2-difluorocyclopropyl)-1H-pyrazol-4-yl)ethynyl)pyridin-4-yl)amino)cyclohexan-1-ol The title compound as a solid (171 mg) was prepared in the same fashion as Step 1 in Example 65 except that (1s,4s)-4-aminocyclohexan-1-ol HCl (382 mg, 2.520 mmol) and 2-chloro-5-((1-(2,2-difluorocyclopropyl)-1H-pyrazol-4-yl)ethynyl)-4-fluoropyridine (150 mg, 0.504 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=393.2 (M+H)$^+$ Step 2. (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol The title compound as a solid (82 mg) was prepared in the same fashion as Step 3 in Example 1 except that (1s,4s)-4-((2-chloro-5-((1-(2,2-difluorocyclopropyl)-1H-pyrazol-4-yl)ethynyl)pyridin-4-yl)amino)cyclohexan-1-ol (163 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.43 (s, 1H), 8.39 (d, 1H), 8.12 (s, 1H), 7.97 (s, 1H), 7.73 (d, 1H), 7.26 (s, 1H), 7.14-7.11 (m, 2H), 5.16 (d, 1H), 4.14 (q, 1H), 3.95 (s, 1H), 3.64 (s, 1H), 2.85-2.79 (m, 1H), 2.30-2.21 (m, 1H), 2.18-2.08 (m, 1H), 1.88 (d, 4H), 1.83-1.54 (m, 8H), 1.52-1.50 (m, 2H), 1.25-1.23 (m, 2H); MS (ESI) m/z=622.1 (M+H)$^+$ Example 86. 1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-ol Step 1. 1-(2-Chloro-5-((5-cyclopropyl-1-methyl-1H-pyrazol-4-yl)ethynyl)pyridin-4-yl)piperidin-4-ol The title compound as a solid (157 mg) was prepared in the same fashion as Step 1 in Example 65 except that 2-chloro-5-((5-cyclopropyl-1-methyl-1H-pyrazol-4-yl)ethynyl)-4-fluoropyridine (150 mg, 0.544 mmol) prepared in Reference Example 20 and 4-hydroxypiperidine (83 mg, 0.816 mmol) were used instead of 2-chloro-4-fluoro-5-((1-methyl-1H-pyrazol-4-yl)ethynyl)pyridine and 4-(trifluoromethyl)piperidine HCl; MS (ESI) m/z=357.2 (M+H)$^+$ Step 2. 1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-ol The title compound as a solid (13 mg) was prepared in the same fashion as Step 3 in Example 1 except that 1-(2-chloro-5-((5-cyclopropyl-1-methyl-1H-pyrazol-4-yl)ethynyl)pyridin-4-yl)piperidin-4-ol (148 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.44 (s, 1H), 8.39 (d, 1H), 8.22 (s, 1H), 8.00 (s, 1H), 7.64 (s, 1H), 7.48 (s, 1H), 7.00 (d, 1H), 4.02-3.98 (m, 1H), 3.90-3.84 (m, 5H), 3.27 (t, 2H), 2.85-2.81 (m, 1H), 2.10-2.02 (m, 3H), 1.81-1.75 (m, 8H), 1.34-1.21 (m, 4H), 1.15-1.11 (m, 2H), 1.10-1.08 (m, 2H); MS (ESI) m/z=586.1 (M+H)$^+$ Example 87. 2-(1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-yl)ethan-1-ol Step 1. 2-(1-(2-Chloro-5-((5-cyclopropyl-1-methyl-1H-pyrazol-4-yl)ethynyl)pyridin-4-yl)piperidin-4-yl)ethan-1-ol The title compound as a solid (170 mg) was prepared in the same fashion as Step 1 in Example 65 except that 2-chloro-5-((5-cyclopropyl-1-methyl-1H-pyrazol-4-yl)ethynyl)-4-fluoropyridine (150 mg, 0.544 mmol) prepared in Reference Example 20 and 4-piperidineethanol (105 mg, 0.816 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=385.2 (M+H)$^+$ Step 2. 2-(1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-yl)ethan-1-ol The title compound as a solid (20 mg) was prepared in the same fashion as Step 3 in Example 1 except that 2-(1-(2-chloro-5-((5-cyclopropyl-1-methyl-1H-pyrazol-4-yl)ethynyl)pyridin-4-yl)piperidin-4-yl)ethan-1-ol (160 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.40 (d, 1H), 8.22-1H), 8.05 (s, 1H), 7.55 (s, 1H), 7.49 (s, 1H), 7.04 (d, 1H), 4.12 (d, 2H), 3.91 (s, 3H), 3.76-2H), 2.91 (t, 2H), 2.86-2.81 (m, 1H), 2.03 (d, 2H), 1.80-1.75 (m, 8H), 1.60 (q, 2H), 1.55-1.48 (m, 2H), 1.26-1.21 (m, 3H), 1.20-1.17 (m, 2H), 1.15-1.14 (m, 2H); MS (ESI) m/z=614.1 (M+H)$^+$ Example 88. (1s,4s)-4-((5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)amino)cyclohexan-1-ol Step 1. (1s,4s)-4-((2-Chloro-5-((5-cyclopropyl-1-methyl-1H-pyrazol-4-yl)ethynyl)pyridin-4-yl)amino)cyclohexan-1-ol The title compound as a solid (159 mg) was prepared in the same fashion as Step 1 in Example 65 except that 2-chloro-5-((5-cyclopropyl-1-methyl-1H-pyrazol-4-yl)ethynyl)-4-fluoropyridine (150 mg, 0.544 mmol) prepared in Reference Example 20 and (1s,4s)-4-aminocyclohexan-1-ol HCl (412 mg, 2.720 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=371.1 (M+H)$^+$ Step 2. (1s,4s)-4-((5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)amino)cyclohexan-1-ol The title compound as a solid (82 mg) was prepared in the same fashion as Step 3 in Example 1 except that (1s,4s)-4-((2-chloro-5-((5-cyclopropyl-1-methyl-1H-pyrazol-4-yl)ethynyl)pyridin-4-yl)amino)cyclohexan-1-ol (154 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.05 (s, 1H), 8.64 (s, 1H), 8.44 (d, 1H), 8.42 (s, 1H), 8.03 (s, 1H), 7.55 (s, 1H), 7.49 (s, 1H), 7.25 (s, 1H), 5.28 (d, 1H), 4.60 (d, 1H), 3.84 (s, 3H), 3.26-3.21 (m, 1H), 1.98-1.95 (m, 1H), 1.78-1.75 (m, 4H), 1.63-1.52 (m, 4H), 1.36-1.32 (m, 2H), 1.29-1.22 (m, 2H), 1.06 (s, 4H); MS (ESI) m/z=600.1 (M+H)$^+$ Example 89. 1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-ol Step 1. 1-(2-Chloro-5-((1-methyl-3-(trifluoromethyl)-1H-pyrazol-4-yl)ethynyl)pyridin-4-yl)piperidin-4-ol The title compound as a solid (160 mg) was prepared in the same fashion as Step 1 in Example 65 except that 2-chloro-4-fluoro-5-(2-(1-methyl-3-(trifluoromethyl)pyrazol-4-yl)ethynyl)pyridine (150 mg, 0.494 mmol) prepared in Reference Example 21 and 4-hydroxypiperidine (75 mg, 0.741 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=385.1 (M+H)$^+$ Step 2. 1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-ol The title compound as a solid (60 mg) was prepared in the same fashion as Step 3 in Example 1 except that 1-(2-chloro-5-((1-methyl-3-(trifluoromethyl)-1H-pyrazol-4-yl)ethynyl)pyridin-4-yl)piperidin-4-ol (160 mg, 0.415 mmol) prepared in Step 1 was used instead of 1-(2-chloro-5-((1-methyl-1H-pyrazol-4-yl)ethynyl)pyridin-4-yl)-4-methylpiperazine.

$^1$H-NMR (DMSO-d$_6$, 400 MHz) δ 10.27 (s, 1H), 8.66 (s, 1H), 8.43 (d, 1H), 8.26 (s, 1H), 8.16 (s, 1H), 7.68 (s, 1H), 7.35 (d, 1H), 4.84 (d, 1H), 3.94 (s, 3H), 3.81 (d, 1H), 3.69-3.67 (m, 1H), 3.26-3.22 (m, 1H), 3.09 (t, 2H), 1.88 (d, 2H), 1.51 (q, 2H), 1.36-1.32 (m, 2H), 1.29-1.21 (m, 2H); MS (ESI) m/z=614.1 (M+H)$^+$

Example 90. (1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)methanol Step 1. (1-(2-Chloro-5-((1-methyl-3-(trifluoromethyl)-1H-pyrazol-4-yl)ethynyl)pyridin-4-yl)piperidin-4-yl)methanol The title compound as a solid (168 mg) was prepared in the same fashion as Step 1 in Example 65 except that 2-chloro-4-fluoro-5-(2-(1-methyl-3-(trifluoromethyl)pyrazol-4-yl)ethynyl)pyridine (150 mg, 0.494 mmol) prepared in Reference Example 21 and 4-piperidinemethanol (85 mg, 0.741 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=399.1 (M+H)$^+$ Step 2. (1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)methanol The title compound as a solid (53 mg) was prepared in the same fashion as Step 3 in Example 1 except that (1-(2-chloro-5-((1-methyl-3-(trifluoromethyl)-1H-pyrazol-4-yl)ethynyl)pyridin-4-yl)piperidin-4-yl)methanol (165 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.26 (s, 1H), 8.65 (s, 1H), 8.43 (d, 1H), 8.24 (s, 1H), 8.14 (s, 1H), 7.68 (s, 1H), 7.34 (s, 1H), 4.56 (t, 1H), 4.01 (d, 2H), 3.92 (s, 3H), 3.32-3.28 (m, 2H), 3.26-3.21 (m, 1H), 2.86 (t, 2H), 1.78 (d, 2H), 1.59 (s, 1H), 1.32-1.30 (m, 2H), 1.28-1.23 (m, 4H); MS (ESI) m/z=628.2 (M+H)$^+$ Example 91. 2-(1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)ethan-1-ol Step 1. 2-(1-(2-Chloro-5-((1-methyl-3-(trifluoromethyl)-1H-pyrazol-4-yl)ethynyl)pyridin-4-yl)piperidin-4-yl)ethan-1-ol The title compound as a solid (174 mg) was prepared in the same fashion as Step 1 in Example 65 except that 2-chloro-4-fluoro-5-(2-(1-methyl-3-(trifluoromethyl)pyrazol-4-yl)ethynyl)pyridine (150 mg, 0.494 mmol) prepared in Reference Example 21 and 4-piperidineethanol (96 mg, 0.741 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=413.1 (M+H)$^+$ Step 2. 2-(1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)ethan-1-ol The title compound as a solid (61 mg) was prepared in the same fashion as Step 3 in Example 1 except that 2-(1-(2- chloro-5-((1-methyl-3-(trifluoromethyl)-1H-pyrazol-4-yl)ethynyl)pyridin-4-yl)piperidin-4-yl)ethan-1-ol (171 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 400 MHz) δ 10.26 (s, 1H), 8.65 (s, 1H), 8.43 (d, 1H), 8.26 (s, 1H), 8.15 (s, 1H), 7.69 (s, 1H), 7.34 (d, 1H), 4.45 (t, 2H), 3.99 (d, 2H), 3.94 (s, 3H), 3.26-3.22 (m, 1H), 2.86 (t, 2H), 1.79 (d, 2H), 1.40 (q, 2H), 1.33-1.31 (m, 2H), 1.28-1.23 (m, 2H); MS (ESI) m/z=642.1 (M+H)$^+$ Example 92. (1s,4s)-4-((2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)amino)cyclohexan-1-ol Step 1. (1s,4s)-4-((2-Chloro-5-((1-methyl-3-(trifluoromethyl)-1H-pyrazol-4-yl)ethynyl)pyridin-4-yl)amino)cyclohexan-1-ol The title compound as a solid (167 mg) was prepared in the same fashion as Step 1 in Example 65 except that 2-chloro-4-fluoro-5-(2-(1-methyl-3-(trifluoromethyl)pyrazol-4-yl)ethynyl)pyridine (150 mg, 0.494 mmol) prepared in Reference Example 21 and (1s,4s)-4-aminocyclohexan-1-ol HCl (375 mg, 2.470 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=399.1 (M+H)$^+$ Step 2. (1s,4s)-4-((2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)amino)cyclohexan-1-ol The title compound as a solid (11 mg) was prepared in the same fashion as Step 3 in Example 1 except that (1 s,4s)-4-((2-chloro-5-((1-methyl-3-(trifluoromethyl)-1H-pyrazol-4-yl)ethynyl)pyridin-4-yl)amino)cyclohexan-1-ol (165 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44 (s, 1H) 8.40 (d, 1H), 8.12 (s, 1H), 7.82 (s, 1H), 7.65 (s, 1H), 7.16 (d, 1H), 7.06 (s, 1H), 5.19 (d, 1H), 3.98 (s, 3H), 3.95 (s, 1H), 3.59 (d, 1H), 2.84-2.80 (m, 1H), 2.04-2.02 (m, 1H), 1.88-1.81 (m, 4H), 1.76-1.72 (m, 4H), 1.54-1.50 (m, 2H), 1.31-1.20 (m, 4H); MS (ESI) m/z=628.2 (M+H)$^+$ Example 93. 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one Step 1. 1-(2-Chloro-5-((1-(tetrahydro-2H-pyran-4-yl)-1H-pyrazol-4-yl)ethynyl)pyridin-4-yl)piperidin-4-one The title compound as a solid (88 mg) was prepared in the same fashion as Step 1 in Example 65 except that piperidin-4-one HCl hydrate (60 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=385.1 (M+H)$^+$ Step 2. 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one The title compound as a solid (175 mg) was prepared in the same fashion as Step 3 in Example 1 except that 1-(2-chloro-5-((1-(tetrahydro-2H-pyran-4-yl)-1H-pyrazol-4-yl)ethynyl)pyridin-4-yl)piperidin-4-one (264 mg, 0.686 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=614.1 (M+H)$^+$ Example 94. (1s,4s)-4-((2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)amino)cyclohexan-1-ol Step 1. (1s,4s)-4-((2-Chloro-5-((1-(tetrahydro-2H-pyran-4-yl)-1H-pyrazol-4-yl)ethynyl)pyridin-4-yl)amino)cyclohexan-1-ol The title compound as a solid (50.3 mg) was prepared in the same fashion as Step 1 in Example 65 except that (1s,4s)-4-aminocyclohexan-1-ol HCl (60 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=401.1 (M+H)$^+$ Step 2. (1s,4s)-4-((2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)amino)cyclohexan-1-ol The title compound as a solid (10 mg) was prepared in the same fashion as Step 3 in Example 1 except that (1s,4s)-4-((2-chloro-5-((1-(tetrahydro-2H-pyran-4-yl)-1H-pyrazol-4-yl)ethynyl)pyridin-4-yl)amino)cyclohexan-1-ol (50 mg, 0.125 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 600 MHz) δ 10.05 (s, 1H), 8.63 (s, 1H), 8.44 (s, 2H), 8.21 (s, 1H), 8.04 (s, 1H), 7.74 (s, 1H), 7.73 (s, 1H), 7.54 (s, 1H), 7.26 (s, 1H), 5.42 (d, 1H), 4.52 (d, 1H), 4.46-4.42 (m, 2H), 3.96 (d, 3H), 3.71 (s, 1H), 3.48-3.44 (m, 3H), 3.27-3.24 (m, 1H), 2.08-1.91 (m, 7H), 1.80-1.71 (m, 6H), 1.59-1.55 (m, 5H), 1.37-1.33 (m, 3H), 1.28-1.23 (m, 6H); MS (ESI) m/z=630.1 (M+H)$^+$ Example 95. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-methylpiperidin-4-yl)methanol Step 1. (1-(2-Chloro-5-((1-(tetrahydro-2H-pyran-4-yl)-1H-pyrazol-4-yl)ethynyl)pyridin-4-yl)-4-methylpiperidin-4-yl)methanol The title compound as a solid (89 mg) was prepared in the same fashion as Step 1 in Example 65 except that (4-methylpiperidin-4-yl)methanol (51 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=415.1 (M+H)+

Step 2. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-methylpiperidin-4-yl)methanol The title compound as a solid (35 mg) was prepared in the same fashion as Step 3 in Example 1 except that (1-(2-chloro-5-((1-(tetrahydro-2H-pyran-4-yl)-1H-pyrazol-4-yl)ethynyl)pyridin-4-yl)-4-methylpiperidin-4-yl)methanol (89 mg, 0.213 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.21 (s, 1H), 8.63 (s, 1H), 8.43 (s, 1H), 8.42 (d, 1H), 8.13 (s, 1H), 8.10 (s, 1H), 7.69 (s, 1H), 7.66 (s, 1H), 7.35 (s. 1H), 4.57 (t, 1H), 4.44-4.40 (m, 1H), 3.95-3.93 (m, 2H), 3.69-3.67 (m, 2H), 3.46-3.42 (m, 2H), 3.26-3.20 (m, 5H), 2.06-1.92 (m, 5H), 1.67-1.63 (m, 2H), 1.38 (d, 2H), 1.34-1.31 (m, 2H), 1.26-1.22 (m, 2H), 0.95 (s, 3H); MS (ESI) m/z=644.1 (M+H)+

Example 96. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-fluoropiperidin-4-yl)methanol Step 1. (1-(2-Chloro-5-((1-(tetrahydro-2H-pyran-4-yl)-1H-pyrazol-4-yl)ethynyl)pyridin-4-yl)-4-fluoropiperidin-4-yl)methanol The title compound as a solid (64 mg) was prepared in the same fashion as Step 1 in Example 65 except that (4-fluoropiperidin-4-yl)methanol HCl (53 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=419.1 (M+H)+

Step 2. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-fluoropiperidin-4-yl)methanol The title compound as a solid (26 mg) was prepared in the same fashion as Step 3 in Example 1 except that (1-(2-chloro-5-((1-(tetrahydro-2H-pyran-4-yl)-1H-pyrazol-4-yl)ethynyl)pyridin-4-yl)-4-fluoropiperidin-4-yl)methanol (64 mg, 0.153 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.26 (s, 1H), 8.65 (s, 1H), 8.45 (s, 2H), 8.19 (s, 1H), 8.15 (s, 1H), 7.71 (s, 2H), 7.41 (s, 1H), 5.05 (t, 1H), 4.46-4.42 (m, 1H), 3.96 (d, 2H), 3.88 (d, 2H), 3.51-3.44 (m, 4H), 3.28-3.25 (m, 1H), 3.15 (t, 2H), 1.98-1.80 (m, 10H), 1.35-1.33 (m, 2H), 1.27-1.22 (m, 41=1); MS (ESI) m/z=648.1 (M+H)+

Example 97. 2-(1-(Cyclopropylsulfonyl)-1H-pyrazol-4-yl)-N-(4-(4-fluoropiperidin-1-yl)-5-((1-(tetrahydro-2H-pyran-4-yl)-1H-pyrazol-4-yl)ethynyl)pyridin-2-yl)pyrimidin-4-amine Step 1. 2-Chloro-4-(4-fluoropiperidin-1-yl)-5-((1-(tetrahydro-2H-pyran-4-yl)-1H-pyrazol-4-yl)ethynyl)pyridine The title compound as a solid (99 mg) was prepared in the same fashion as Step 1 in Example 65 except that 4-fluoropiperidine (40 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=389.1 (M+H)+

Step 2. 2-(1-(Cyclopropylsulfonyl)-1H-pyrazol-4-yl)-N-(4-(4-fluoropiperidin-1-yl)-5-((1-(tetrahydro-2H-pyran-4-yl)-1H-pyrazol-4-yl)ethynyl)pyridin-2-yl)pyrimidin-4-amine The title compound as a solid (81 mg) was prepared in the same fashion as Step 3 in Example 1 except that 2-chloro-4-(4-fluoropiperidin-1-yl)-5-((1-(tetrahydro-2H-pyran-4-yl)-1H-pyrazol-4-yl)ethynyl)pyridine (88 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.27 (s, 1H), 8.66 (s, 1H), 8.45 (s, 2H), 8.18 (s, 1H), 8.16 (s, 1H), 7.71 (s, 2H), 7.38 (s, 1H), 4.96-4.87 (m, 1H), 4.45-4.42 (m, 1H), 3.97-3.95 (m, 2H), 3.57-3.54 (m, 2H), 3.48-3.42 (m, 4H), 3.29-3.25 (m, 1H), 2.12-2.04 (m, 2H), 1.98-1.91 (m, 6H), 1.36-1.34 (m, 2H), 1.28-1.21 (m, 2H); MS (ESI) m/z=618.1 (M+H)+

Example 98. 2-(1-(Cyclopropylsulfonyl)-1H-pyrazol-4-yl)-N-(4-(4-methoxypiperidin-1-yl)-5-((1-(tetrahydro-2H-pyran-4-yl)-1H-pyrazol-4-yl)ethynyl)pyridin-2-yl)pyrimidin-4-amine Step 1. 2-Chloro-4-(4-methoxypiperidin-1-yl)-5-((1-(tetrahydro-2H-pyran-4-yl)-1H-pyrazol-4-yl)ethynyl)pyridine The title compound as a solid (102 mg) was prepared in the same fashion as Step 1 in Example 65 except that 4-methoxypiperidine (45 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=401.1 (M+H)+

Step 2. 2-(1-(Cyclopropylsulfonyl)-1H-pyrazol-4-yl)-N-(4-(4-methoxypiperidin-1-yl)-5-((1-(tetrahydro-2H-pyran-4-yl)-1H-pyrazol-4-yl)ethynyl)pyridin-2-yl)pyrimidin-4-amine The title compound as a solid (38 mg) was prepared in the same fashion as Step 3 in Example 1 except that 2-chloro-4-(4-methoxypiperidin-1-yl)-5-((1-(tetrahydro-2H-pyran-4-yl)-1H-pyrazol-4-yl)ethynyl)pyridine (91 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.25 (s, 1H), 8.66 (s, 1H), 8.45 (s, 2H), 8.19 (s, 2H), 7.74 (s, 1H), 7.68 (s, 1H), 7.36 (s, 1H), 4.47-4.42 (m, 1H), 3.96 (d, 2H), 3.75-3.73 (m, 2H), 3.47-3.41 (m, 3H), 3.29-3.25 (m, 3H), 3.19-3.12 (m, 2H), 2.08-2.03 (m, 2H), 1.98-1.91 (m, 6H), 1.65-1.60 (m, 2H), 1.36-1.30 (m, 2H), 1.29-1.24 (m, 2H); MS (ESI) m/z=630.1 (M+H)+

Example 99. 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-ol

Step 1. 1-(2-Chloro-5-((1-(tetrahydro-2H-pyran-4-yl)-1H-pyrazol-4-yl)ethynyl)pyridin-4-yl)piperidin-3-ol The title compound as a solid (72 mg) was prepared in the same fashion as Step 1 in Example 65 except that 3-hydroxypiperidine (40 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=387.2 (M+H)$^+$

Step 2. 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-ol The title compound as a solid (47 mg) was prepared in the same fashion as Step 3 in Example 1 except that 1-(2-chloro-5-((1-(tetrahydro-2H-pyran-4-yl)-1H-pyrazol-4-yl)ethynyl)pyridin-4-yl)piperidin-3-ol (88 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.22 (s, 1H), 8.67 (s, 1H), 8.45 (s, 1H), 8.44 (s, 1H), 8.15 (s, 1H), 8.13 (s, 1H), 7.71 (s, 1H), 7.60 (s, 1H), 7.44 (s, 1H), 4.90 (d, 1H), 4.46-4.41 (m, 1H), 4.03 (d, 1H), 3.96 (d, 2H), 3.69 (d, 2H), 3.46 (t, 2H), 3.29-3.25 (m, 1H), 2.94 (t, 1H), 2.71 (t, 1H), 2.08-1.91 (m, 5H), 1.62-1.59 (m, 1H), 1.37-1.33 (m, 3H), 1.27-1.21 (m, 2H); MS (ESI) m/z=616.1 (M+H)$^+$

Example 100. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-yl)methanol

Step 1. (1-(2-Chloro-5-((1-(tetrahydro-2H-pyran-4-yl)-1H-pyrazol-4-yl)ethynyl)pyridin-4-yl)piperidin-3-yl)methanol The title compound as a solid (98 mg) was prepared in the same fashion as Step 1 in Example 65 except that 3-piperidinemethanol (45 mg, 0.393 mmol) and 2-chloro-4-fluoro-5-((1-(tetrahydro-2H-pyran-4-yl)-1H-pyrazol-4-yl)ethynyl)pyridine (80 mg, 0.262 mmol) prepared in Reference Example 22 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=401.1 (M+H)$^+$

Step 2. (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-yl)methanol The title compound as a solid (26 mg) was prepared in the same fashion as Step 3 in Example 1 except that (1-(2-chloro-5-((1-(tetrahydro-2H-pyran-4-yl)-1H-pyrazol-4-yl)ethynyl)pyridin-4-yl)piperidin-3-yl)methanol (91 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.23 (s, 1H), 8.66 (s, 1H), 8.45 (s, 2H), 8.16 (s, 2H), 7.72 (s, 1H), 7.67 (s, 1H), 7.42 (s, 1H), 4.60 (s, 1H), 4.45-4.41 (m, 1H), 4.14 (d, 1H), 3.96 (d, 2H), 3.81 (d, 1H), 3.46 (t, 2H), 3.29-3.26 (m, 1H), 2.91 (t, 1H), 2.58 (t, 1H), 1.99-1.80 (m, 6H), 1.78-1.62 (m, 4H), 1.36-1.33 (m, 2H), 1.28-1.22 (m, 2H); MS (ESI) m/z=630.1 (M+H)$^+$

Example 101. (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol The title compound as a solid (20 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (88 mg, 0.221 mmol) prepared in Reference Example 53 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.43 (s, 1H), 8.40 (d, 1H), 8.22 (s, 1H), 8.04 (s, 1H), 7.96 (s, 1H), 7.84 (s, 1H), 7.63 (s, 1H), 6.95 (d, 1H), 3.74-3.65 (m, 2H), 3.47-3.41 (m, 3H), 3.40-3.36 (m, 2H), 2.85-2.79 (m, 1H), 1.81-1.75 (m, 3H), 1.58-1.49 (m, 4H), 1.30-1.19 (m, 3H), 1.07 (s, 3H); MS (ESI) m/z=628.0 (M+H)$^+$

Example 102. (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol

Step 1. (1s,4s)-4-((2-Chloro-5-((1-(trifluoromethyl)-1H-pyrazol-4-yl)ethynyl)pyridin-4-yl)amino)cyclohexan-1-ol The title compound as a solid (96 mg) was prepared in the same fashion as Step 1 in Example 65 except that (1s,4s)-4-aminocyclohexan-1-ol HCl (63 mg, 0.414 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=385.0 (M+H)$^+$

Step 2. (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol The title compound as a solid (5 mg) was prepared in the same fashion as Step 3 in Example 1 except that (1s,4s)-4-((2-chloro-5-((1-(trifluoromethyl)-1H-pyrazol-4-yl)ethynyl)pyridin-4-yl)amino)cyclohexan-1-ol (85 mg, 0.221 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.43 (s, 1H), 8.42 (s, 1H), 8.09 (s, 1H), 8.04 (s, 1H), 7.90 (s, 1H), 7.33 (s, 1H), 7.10 (s, 1H), 5.16 (d, 2H), 3.98 (s, 1H), 3.67 (s, 1H), 2.83 (s, 1H), 1.73-1.61 (m, 8H), 1.54-1.49 (m, 2H), 1.27-1.20 (m, 2H); MS (ESI) m/z=614.1 (M+H)$^+$ Example 103. (1S,3S)-3-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol Step 1. (1S,3S)-3-((2-Chloro-5-((1-(trifluoromethyl)-1H-pyrazol-4-yl)ethynyl)pyridin-4-yl)amino)cyclohexan-1-ol The title compound as a solid (345 mg) was prepared in the same fashion as Step 1 in Example 65 except that (1S,3S)-3-aminocyclohexan-1-ol HCl (204 mg, 1.347 mmol) and 2-chloro-4-fluoro-5-((1-(trifluoromethyl)-1H-pyrazol-4-yl)ethynyl)pyridine (300 mg, 1.036 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=385.0 (M+H)$^+$ Step 2. (1S,3S)-3-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol The title compound as a solid (65 mg) was prepared in the same fashion as Step 3 in Example 1 except that (1S,3S)-3-((2-chloro-5-((1-(trifluoromethyl)-1H-pyrazol-4-yl)ethynyl)pyridin-4-yl)amino)cyclohexan-1-ol (290 mg, 0.754 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.66 (s, 1H), 8.49 (s, 1H), 8.40 (d, 1H), 8.13 (s, 1H), 8.01 (s, 2H), 7.88 (s, 1H), 7.14 (d, 2H), 4.90 (d, 2H), 4.18 (s, 1H), 4.02-3.98 (m, 1H), 2.87-2.82 (m, 1H), 2.13-2.11 (m, 1H), 2.05-2.00 (m, 1H), 1.89-1.87 (m, 2H), 1.68-1.61 (m, 4H), 1.54-1.51 (m, 2H), 1.46-1.41 (m, 1H), 1.22-1.19 (m, 2H); MS (ESI) m/z=614.1 (M+H)$^+$ Example 104. 7-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-2-methyl-7-azaspiro[3.5]nonan-2-ol Step 1. 7-(2-Chloro-5-((1-(trifluoromethyl)-1H-pyrazol-4-yl)ethynyl)pyridin-4-yl)-2-methyl-7-azaspiro[3.5]nonan-2-ol The title compound as a solid (401 mg) was prepared in the same fashion as Step 1 in Example 65 except that 2-methyl-7-azaspiro[3.5]nonan-2-ol (209 mg, 1.347 mmol) and 2-chloro-4-fluoro-5-((1-(trifluoromethyl)-1H-pyrazol-4-yl)ethynyl)pyridine (300 mg, 1.036 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=424.9 (M+H)$^+$ Step 2. 7-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-2-methyl-7-azaspiro[3.5]nonan-2-ol The title compound as a solid (72 mg) was prepared in the same fashion as Step 3 in Example 1 except that 7-(2-chloro-5-((1-(trifluoromethyl)-1H-pyrazol-4-yl)ethynyl)pyridin-4-yl)-2-methyl-7-azaspiro[3.5]nonan-2-ol (320 mg, 0.754 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 600 MHz) δ 8.65 (s, 1H), 8.45 (s, 1H), 8.42 (d, 1H), 8.23 (s, 1H), 7.97 (s, 1H), 7.92 (s, 1H), 7.86 (s, 1H), 7.77 (s, 1H), 7.60 (s, 1H), 6.99 (d, 1H), 3.46-3.42 (m, 4H), 2.87-2.83 (m, 1H), 2.09-2.00 (m, 4H), 1.92 (t, 2H), 1.80 (t, 2H), 1.69 (s, 1H), 1.55 (s, 1H), 1.55-1.50 (m, 2H), 1.44 (s, 3H), 1.28-1.21 (m, 2H); MS (ESI) m/z=654.2 (M+H)$^+$ Example 105. (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)-1-methylcyclohexan-1-ol Step 1. (1s,4s)-4-((2-Chloro-5-((1-(trifluoromethyl)-1H-pyrazol-4-yl)ethynyl)pyridin-4-yl)amino)-1-methylcyclohexan-1-ol The title compound as a solid (330 mg) was prepared in the same fashion as Step 1 in Example 65 except that cis-4-amino-1-methylcyclohexanol (150 mg, 1.161 mmol) and 2-chloro-4-fluoro-5-((1-(trifluoromethyl)-1H-pyrazol-4-yl)ethynyl)pyridine (150 mg, 1.161 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=398.9 (M+H)$^+$ Step 2. (1s, 4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)-1-methylcyclohexan-1-ol The title compound as a solid (178 mg) was prepared in the same fashion as Step 3 in Example 1 except that (1s,4s)-4-((2-chloro-5-((1-(trifluoromethyl)-1H-pyrazol-4-yl)ethynyl)pyridin-4-yl)amino)-1-methylcyclohexan-1-ol (225 mg, 0.565 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.07 (s, 1H), 8.93 (s, 1H), 8.66 (s, 1H), 8.45 (d, 1H), 8.44 (s, 1H), 8.24 (s, 1H), 8.07 (s, 1H), 7.52 (s, 1H), 7.24 (s, 1H), 5.61 (d, 1H), 3.26-3.22 (m, 2H), 1.75 (s, 4H), 1.60-1.57 (m, 2H), 1.43-1.38 (m, 2H), 1.36-1.33 (m, 2H), 1.26-1.23 (m, 2H), 1.13 (s, 3H); MS (ESI) m/z=628.2 (M+H)$^+$ Example 106. (1s,4s)-4-((2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)amino)cyclohexan-1-ol Step 1. (1s,4s)-4-((2-Chloro-5-((1-methyl-1H-pyrazol-3-yl)ethynyl)pyridin-4-yl)amino)cyclohexan-1-ol The title compound as a solid (99 mg) was prepared in the same fashion as Step 1 in Example 65 except that (1s,4s)-4-aminocyclohexan-1-ol HCl (193 mg, 1.273 mmol) and 2-chloro-4-fluoro-5-((1-methyl-1H-pyrazol-3-yl)ethynyl)pyridine (100 mg, 0.424 mmol) prepared in Reference Example 24 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=331.0 (M+H)$^+$ Step 2. (1s,4s)-4-((2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)amino)cyclohexan-1-ol The title compound as a solid (26 mg) was prepared in the same fashion as Step 3 in Example 1 except that (1s,4s)-4-((2-chloro-5-((1-methyl-1H-pyrazol-3-yl)ethynyl)pyridin-4-yl)amino)cyclohexan-1-ol (99 mg, 0.300 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.09 (s, 1H), 8.63 (s, 1H), 8.44 (s, 1H), 8.43 (s, 1H), 8.09 (s, 1H), 7.78 (s, 1H), 7.51 (s, 1H), 7.27 (s, 1H), 6.53 (s, 1H), 5.39 (d, 1H), 4.52 (s, 1H), 3.87 (s, 3H), 3.69 (s, 1H), 3.55 (s, 1H), 3.27-3.23 (m, 1H), 1.90-1.70 (m, 4H), 1.62-1.57 (m, 4H), 1.34-1.27 (m, 2H), 1.25-1.22 (m, 2H); MS (ESI) m/z=560.0 (M+H)$^+$ Example 107. (1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)-4-methylpiperidin-4-yl)methanol Step 1. (1-(2-Chloro-5-((1-methyl-1H-pyrazol-3-yl)ethynyl)pyridin-4-yl)-4-methylpiperidin-4-yl)methanol The title compound as a solid (80.1 mg) was prepared in the same fashion as Step 1 in Example 65 except that (4-methylpiperidin-4-yl)methanol (164 mg, 1.273 mmol) and 2-chloro-4-fluoro-5-((1-methyl-1H-pyrazol-3-yl)ethynyl)pyridine (100 mg, 0.424 mmol) prepared in Reference Example 24 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=345.1 (M+H)$^+$ Step 2. (1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)-4-methylpiperidin-4-yl)methanol The title compound as a solid (26 mg) was prepared in the same fashion as Step 3 in Example 1 except that (1-(2-chloro-5-((1-methyl-1H-pyrazol-3-yl)ethynyl)pyridin-4-yl)-4-methylpiperidin-4-yl)methanol (80 mg, 0.232 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.24 (s, 1H), 8.63 (s, 1H), 8.44 (s, 1H), 8.42 (s, 1H), 8.18 (s, 1H), 7.75 (s, 1H), 7.70 (s, 1H), 7.35 (s, 1H), 6.44 (s, 1H), 4.56 (t, 1H), 4.43 (s, 1H), 3.85 (s, 3H), 3.69 (d, 2H), 3.38 (s, 2H), 3.32-3.16 (m, 6H), 1.65 (t, 2H), 1.39-1.31 (m, 4H), 1.28-1.20 (m, 2H), 0.94 (s, 3H); MS (ESI) m/z=574.1 (M+H)$^+$ Example 108. 1-(5-((1-(1-Acetylpiperidin-4-yl)-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-one Step 1. 1-(5-((1-(1-Acetylpiperidin-4-yl)-1H-pyrazol-4-yl)ethynyl)-2-chloropyridin-4-yl)piperidin-4-one The title compound as a solid (90 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and piperidin-4-one HCl hydrate (53 mg, 0.346) were used instead of 2-chloro-4-fluoro-5-((1-methyl-1H-pyrazol-4-yl)ethynyl)pyridine and 4-(trifluoromethyl)piperidine HCl. MS (ESI) m/z=426.1 (M+H)$^+$ Step 2. 1-(5-((1-(1-Acetylpiperidin-4-yl)-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-one The title compound as a solid (51 mg) was prepared in the same fashion as Step 3 in Example 1 except that 1-(5-((1-(1-acetylpiperidin-4-yl)-1H-pyrazol-4-yl)ethynyl)-2-chloropyridin-4-yl)piperidin-4-one (293 mg, 0.688 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=655.1 (M+H)$^+$ Example 109. 1-(4-(4-((6-((2-(1-(Cyclopropylsulfonyl)-1H-pyrazol-4-yl)pyrimidin-4-yl)amino)-4-(((1s, 4s)-4-hydroxycyclohexyl)amino)pyridin-3-yl)ethynyl)-1H-pyrazol-1-yl)piperidin-1-yl)ethan-1-one Step 1. 1-(4-(4-((6-Chloro-4-(((1s,4s)-4-hydroxycyclohexyl)amino)pyridin-3-yl)ethynyl)-1H-pyrazol-1-yl)piperidin-1-yl)ethan-1-one The title compound as a solid (81 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and (1s,4s)-4-aminocyclohexan-1-ol HCl (52 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=442.1 (M+H)$^+$ Step 2. 1-(4-(4-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)-1H-pyrazol-1-yl)piperidin-1-yl)ethan-1-one -1H-1H The title compound as a solid (23.1 mg) was prepared in the same fashion as Step 3 in Example 1 except that 1-(4-(4-((6-chloro-4-(((1s,4s)-4-hydroxycyclohexyl)amino)pyridin-3-yl)ethynyl)-1H-pyrazol-1-yl)piperidin-1-yl)ethan-1 one (81 mg, 0.184 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.04 (s, 1H), 8.62 (s, 1H), 8.43 (s, 1H), 8.41 (s, 1H), 8.18 (s, 1H), 8.03 (s, 1H), 7.73 (s, 1H), 7.51 (s, 1H), 7.22 (s, 1H), 5.39 (d, 1H), 4.50 (s, 1H), 4.46-4.43 (m, 2H), 3.91 (d, 1H), 3.70 (s, 1H), 3.51 (s, 1H), 3.24-3.16 (m, 2H), 2.70 (t, 2H), 2.00 (s, 6H), 1.92-1.85 (m, 2H), 1.77-1.72 (m, 6H), 1.57 (m, 4H), 1.32 (s, 2H), 1.24-1.13 (m, 6H); MS (ESI) m/z=671.1 (M+H)$^+$ Example 110. 1-(4-(4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-1H-pyrazol-1-yl)piperidin-1-yl)ethan-1-one Step 1. 1-(4-(4-((6-Chloro-4-(4-(hydroxymethyl)-4-methylpiperidin-1-yl)pyridin-3-yl)ethynyl)-1H-pyrazol-1-yl)piperidin-1-yl)ethan-1-one The title compound as a solid (73 mg) was prepared in the same fashion as Step 1 in Example 65 except that 1-(4-(4-

((6-chloro-4-fluoropyridin-3-yl)ethynyl)-1H-pyrazol-1-yl)piperidin-1-yl)ethan-1-one (80 mg, 0.231 mmol) prepared in Reference Example 25 and (4-methylpiperidin-4-yl)methanol (44 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=456.2 (M+H)$^+$ Step 2. 1-(4-(4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-1H-pyrazol-1-yl)piperidin-1-yl)ethan-1-one The title compound as a solid (28 mg) was prepared in the same fashion as Step 3 in Example 1 except that 1-(4-(4-((6-chloro-4-(4-(hydroxymethyl)-4-methylpiperidin-1-yl)pyridin-3-yl)ethynyl)-1H-pyrazol-1-yl)piperidin-1-yl)ethan-1-one (73 mg, 0.16 mmol) was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.23 (s, 1H), 8.65 (s, 1H), 8.45 (s, 1H), 8.43 (s, 1H), 8.15 (s, 1H), 8.12 (s, 1H), 7.67 (s, 2H), 7.27 (s, 1H), 4.59 (t, 1H), 4.48-4.44 (m, 2H), 3.92 (d, 1H), 3.71-3.69 (m, 2H), 3.29-3.18 (m, 7H), 2.69 (t, 1H), 2.07-2.00 (m, 4H), 1.78-1.73 (m, 2H), 1.69-1.64 (m, 2H), 1.39 (d, 2H), 1.35-1.32 (m, 4H), 1.27-1.25 (m, 2H), 1.24-1.18 (m, 3H), 0.99 (s, 3H); MS (ESI) m/z=685.1 (M+H)$^+$ Example 111. 1-(4-(4-((6-((2-(1-(Cyclopropylsulfonyl)-1H-pyrazol-4-yl)pyrimidin-4-yl)amino)-4-(4-fluoro-4-(hydroxymethyl)piperidin-1-yl)pyridin-3-yl)ethynyl)-1H-pyrazol-1-yl)piperidin-1-yl)ethan-1-one Step 1. 1-(4-(4-((6-Chloro-4-(4-fluoro-4-(hydroxymethyl)piperidin-1-yl)pyridin-3-yl)ethynyl)-1H-pyrazol-1-yl)piperidin-1-yl)ethan-1-one The title compound as a solid (46 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and (4-fluoropiperidin-4-yl)methanol HCl (46 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=430.1 (M+H)$^+$ Step 2. 1-(4-(4-((6-((2-(1-(Cyclopropylsulfonyl)-1H-pyrazol-4-yl)pyrimidin-4-yl)amino)-4-(4-fluoro-4-(hydroxymethyl)piperidin-1-yl)pyridin-3-yl)ethynyl)-1H-pyrazol-1-yl)piperidin-1-yl)ethan-1-one The title compound as a solid (19 mg) was prepared in the same fashion as Step 3 in Example 1 except that 1-(4-(4-((6-chloro-4-(4-fluoro-4-(hydroxymethyl)piperidin-1-yl)pyridin-3-yl)ethynyl)-1H-pyrazol-1-yl)piperidin-1-yl)ethan-1-one (47 mg, 0.102 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.26 (s, 1H), 8.65 (s, 1H), 8.46 (s, 2H), 8.18 (s, 1H), 8.14 (s, 1H), 7.70 (s, 2H), 7.41 (s, 1H), 5.04 (t, 1H), 4.48-4.44 (m, 2H), 3.93-3.87 (m, 3H), 3.51-3.47 (m, 2H), 3.27-3.22 (m, 1H), 3.20-3.13 (m, 3H), 2.71 (t, 1H), 2.08-1.97 (m, 5H), 1.95-1.72 (m, 6H), 1.36-1.32 (m, 3H), 1.28-1.22 (m, 9H); MS (ESI) m/z=689.1 (M+H)$^+$ Example 112. 1-(4-(4-((6-((2-(1-(Cyclopropylsulfonyl)-1H-pyrazol-4-yl)pyrimidin-4-yl)amino)-4-(4-fluoropiperidin-1-yl)pyridin-3-yl)ethynyl)-1H-pyrazol-1-yl)piperidin-1-yl)ethan-1-one Step 1. 1-(4-(4-((6-Chloro-4-(4-fluoropiperidin-1-yl)pyridin-3-yl)ethynyl)-1H-pyrazol-1-yl)piperidin-1-yl)ethan-1-one The title compound as a solid (89 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and 4-fluoropiperidine (36 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=430.1 (M+H)$^+$ Step 2. 1-(4-(4-((6-((2-(1-(Cyclopropylsulfonyl)-1H-pyrazol-4-yl)pyrimidin-4-yl)amino)-4-(4-fluoropiperidin-1-yl)pyridin-3-yl)ethynyl)-1H-pyrazol-1-yl)piperidin-1-yl)ethan-1-one The title compound as a solid (52 mg) was prepared in the same fashion as Step 3 in Example 1 except that 1-(4-(4-((6-chloro-4-(4-fluoropiperidin-1-yl)pyridin-3-yl)ethynyl)-1H-pyrazol-1-yl)piperidin-1-yl)ethan-1-one (97 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.27 (s, 1H), 8.66 (s, 1H), 8.45 (s, 2H), 8.19 (s, 1H), 8.15 (s, 1H), 7.69 (s, 2H), 7.39 (s, 1H), 4.94-4.83 (m, 1H), 4.48-4.44 (m, 2H), 3.92 (d, 1H), 3.57-3.54 (m, 2H), 3.46-3.43 (m, 2H), 3.29-3.26 (m, 1H), 3.22-3.17 (m, 1H), 2.70 (t, 14), 2.10-2.00 (m, 5H), 1.93-1.87 (m, 4H), 1.76-1.74 (m, 1H), 1.36-1.34 (m, 2H), 1.27-1.24 (m, 2H); MS (ESI) m/z=659.1 (M+H)$^+$ Example 113. 1-(4-(4-((6-((2-(1-(Cyclopropylsulfonyl)-1H-pyrazol-4-yl)pyrimidin-4-yl)amino)-4-(4-methoxypiperidin-1-yl)pyridin-3-yl)ethynyl)-1H-pyrazol-1-yl)piperidin-1-yl)ethan-1-one Step 1. 1-(4-(4-((6-Chloro-4-(4-methoxypiperidin-1-yl)pyridin-3-yl)ethynyl)-1H-pyrazol-1-yl)piperidin-1-yl)ethan-1-one The title compound as a solid (72 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and 4-methoxypiperidine (40 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=442.1 (M+H)$^+$ Step 2. 1-(4-(4-((6-((2-(1-(Cyclopropylsulfonyl)-1H-pyrazol-4-yl)pyrimidin-4-yl)amino)-4-(4-methoxypiperidin-1-yl)pyridin-3-yl)ethynyl)-1H-pyrazol-1-yl)piperidin-1-yl)ethan-1-one The title compound as a solid (38 mg) was prepared in the same fashion as Step 3 in Example 1 except that 1-(4-(4-((6-chloro-4-(4-methoxypiperidin-1-yl)pyridin-3-yl)ethynyl)-1H-pyrazol-1-yl)piperidin-1-yl)ethan-1-one (100 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ

10.25 (s, 1H), 8.65 (s, 1H), 8.45 (s, 1H), 8.43 (s, 1H), 8.16 (s, 1H), 8.13 (s, 1H), 7.71 (s, 1H), 7.68 (s, 1H), 7.36 (s, 1H), 4.48-4.45 (m, 2H), 3.92 (d, 1H), 3.75-3.72 (m, 2H), 3.29-3.25 (m, 4H), 3.19-3.15 (m, 2H), 2.70 (t, 1H), 1.97 (s, 6H), 1.88-1.79 (m, 1H), 1.77-1.71 (m, 1H), 1.63-1.59 (m, 1H), 1.34 (s, 1H), 1.27-1.17 (m, 3H); MS (ESI) m/z=671.1 (M+H)$^+$

Example 114. 1-(4-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)-1H-pyrazol-1-yl)piperidin-1-yl)ethan-1-one Step 1. 1-(4-(4-((6-Chloro-4-(3-hydroxypiperidin-1-yl)pyridin-3-yl)ethynyl)-1H-pyrazol-1-yl)piperidin-1-yl)ethan-1-one The title compound as a solid (88 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and 3-hydroxypiperidine (35 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=428.1 (M+H)$^+$ Step 2. 1-(4-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)-1H-pyrazol-1-yl)piperidin-1-yl)ethan-1-one The title compound as a solid (26 mg) was prepared in the same fashion as Step 3 in Example 1 except that 1-(4-(4-((6-chloro-4-(3-hydroxypiperidin-1-yl)pyridin-3-yl)ethynyl)-1H-pyrazol-1-yl)piperidin-1-yl)ethan-1-one (97 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.21 (s, 1H), 8.66 (s, 1H), 8.44 (s, 1H), 8.43 (s, 1H), 8.14 (s, 1H), 8.11 (s, 1H), 7.69 (s, 1H), 7.59 (s, 1H), 7.43 (s, 1H), 4.88 (d, 1H), 4.47-4.41 (m, 2H), 4.01 (d, 1H), 3.90 (d, 1H), 3.69-3.66 (d, 2H), 3.27-3.22 (m, 1H), 3.18 (t, 1H), 2.96 (t, 1H), 2.69 (t, 2H), 2.03 (s, 4H), 1.92-1.89 (m, 3H), 1.88-1.72 (m, 2H), 1.77-1.69 (m, 2H), 1.39-1.33 (m, 3H), 1.29-1.20 (m. 4H); MS (ESI) m/z=657.1 (M+H)$^+$ Example 115. 1-(4-(4-((6-((2-(1-(Cyclopropylsulfonyl)-1H-pyrazol-4-yl)pyrimidin-4-yl)amino)-4-(3-(hydroxymethyl)piperidin-1-yl)pyridin-3-yl)ethynyl)-1H-pyrazol-1-yl)piperidin-1-yl)ethan-1-one Step 1. 1-(4-(4-((6-Chloro-4-(3-(hydroxymethyl)piperidin-1-yl)pyridin-3-yl)ethynyl)-1H-pyrazol-1-yl)piperidin-1-yl)ethan-1-one The title compound as a solid (75 mg) was prepared in the same fashion as Step 1 in Example 65 except that 1-(4-(4-((6-chloro-4-fluoropyridin-3-yl)ethynyl)-1H-pyrazol-1-yl)piperidin-1-yl)ethan-1-one (80 mg, 0.231 mmol) prepared in Reference Example 25 and 3-piperidinemethanol (40 mg, 0.346 mmol) were used instead of 2-chloro-4-fluoro-5-((1-methyl-1H-pyrazol-4-yl)ethynyl)pyridine and 4-(trifluoromethyl)piperidine HCl. MS (ESI) m/z=442.1 (M+H)$^+$ Step 2. 1-(4-(4-((6-((2-(1-(Cyclopropylsulfonyl)-1H-pyrazol-4-yl)pyrimidin-4-yl)amino)-4-(3-(hydroxymethyl)piperidin-1-yl)pyridin-3-yl)ethynyl)-1H-pyrazol-1-yl)piperidin-1-yl)ethan-1-one The title compound as a solid (21 mg) was prepared in the same fashion as Step 3 in Example 1 except that 1-(4-(4-((6-chloro-4-(3-(hydroxymethyl)piperidin-1-yl)pyridin-3-yl)ethynyl)-1H-pyrazol-1-yl)piperidin-1-yl)ethan-1-one (100 mg, 0.226 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.23 (s, 1H), 8.66 (s, 1H), 8.45 (s, 2H), 8.16 (s, 1H), 8.14 (s, 1H), 7.71 (s, 1H), 7.63 (s, 1H), 7.41 (s, 1H), 4.60 (t, 1H), 4.47-4.45 (m, 2H), 4.13 (d, 1H), 3.92 (d, 1H), 3.38 (d, 1H), 3.28-3.26 (m, 1H), 3.20 (t, 1H), 2.91 (t, 1H), 2.71 (t, 1H), 2.58 (t, 1H), 2.08-2.00 (m, 4H), 1.94-1.73 (m, 8H), 1.62 (s, 1H), 1.36-1.32 (m, 4H), 1.28-1.22 (m, 8H); MS (ESI) m/z=671.2 (M+H)$^+$ Example 116. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-methylpiperidin-4-yl)methanol Step 1. (1-(2-Chloro-5-((1-(2-(dimethylamino)ethyl)-1H-pyrazol-4-yl)ethynyl)pyridin-4-yl)-4-methylpiperidin-4-yl)methanol The title compound as a solid (89 mg) was prepared in the same fashion as Step 1 in Example 65 except that (4-methylpiperidin-4-yl)methanol (106 mg, 0.82 mmol) and 2-(4-((6-chloro-4-fluoropyridin-3-yl)ethynyl)-1H-pyrazol-1-yl)-N,N-dimethylethan-1-amine (80 mg, 0.273 mmol) prepared in Reference Example 26 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=402.1 (M+H)$^+$ Step 2. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-methylpiperidin-4-yl)methanol The title compound as a solid (22 mg) was prepared in the same fashion as Step 3 in Example 1 except that (1-(2-chloro-5-((1-(2-(dimethylamino)ethyl)-1H-pyrazol-4-yl)ethynyl)pyridin-4-yl)-4-methylpiperidin-4-yl)methanol (89 mg, 0.222 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.65 (s, 1H), 8.44 (s, 1H), 8.38 (s, 1H), 8.21 (s, 1H), 7.69 (s, 1H), 7.63 (s, 1H), 7.62 (s, 1H), 6.96 (d, 1H), 4.28 (t, 2H), 3.71-3.68 (m, 2H), 3.48 (d, 2H), 3.24 (t, 2H), 3.04-3.00 (m, 1H), 2.84 (t, 2H), 2.31 (s, 6H), 1.77-1.70 (m, 2H), 1.50-1.47 (m, 2H), 1.44-1.41 (m, 2H), 1.26-1.22 (m, 2H), 1.02 (s, 3H); MS (ESI) m/z=632.1 (M+H)$^+$ Example 117. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-fluoropiperidin-4-yl)methanol Step 1. (1-(2-Chloro-5-((1-(2-(dimethylamino)ethyl)-1H-pyrazol-4-yl)ethynyl)pyridin-4-yl)-4-fluoropiperidin-4-yl)methanol The title compound as a solid (98 mg) was prepared in the same fashion as Step 1 in Example 65 except that (4-fluoropiperidin-4-yl)methanol HCl (139 mg, 0.820 mmol) and 2-(4-((6-chloro-4-fluoropyridin-3-yl)ethynyl)-1H-pyrazol-1-yl)-N,N-dimethylethan-1-amine (80 mg, 0.273 mmol) prepared in Reference Example 26 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=406.1 (M+H)$^+$ Step 2. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-fluoropiperidin-4-yl)methanol The title compound as a solid (16 mg) was prepared in the same fashion as Step 3 in Example 1 except that (1-(2-chloro-5-((1-(2-(dimethylamino)ethyl)-1H-pyrazol-4-yl)ethynyl)pyridin-4-yl)-4-fluoropiperidin-4-yl)methanol (98 mg, 0.242 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.61 (s, 1H), 8.36 (s, 1H), 8.28 (s, 1H), 8.06 (s, 1H), 7.88 (s, 1H), 7.62 (s, 1H), 7.45 (s, 1H), 7.26 (s, 1H), 4.29 (t, 2H), 3.84 (d, 2H), 3.58 (d, 2H), 3.14 (t, 2H), 3.02-3.00 (m, 2H), 2.85 (t, 2H), 2.31 (s, 6H), 2.00-1.94 (m, 2H), 1.91-1.82 (m, 2H), 1.42 (d, 1H), 1.28-1.25 (m, 2H); MS (ESI) m/z=636.1 (M+H)$^+$ Example 118. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)piperidin-3-yl)methanol Step 1. (1-(2-Chloro-5-((1-(2-(dimethylamino)ethyl)-1H-pyrazol-4-yl)ethynyl)pyridin-4-yl)piperidin-3-yl)methanol The title compound as a solid (92 mg) was prepared in the same fashion as Step 1 in Example 65 except that 3-piperidinemethanol (94 mg, 0.820 mmol) and 2-(4-((6-chloro-4-fluoropyridin-3-yl)ethynyl)-1H-pyrazol-1-yl)-N,N-dimethylethan-1-amine (80 mg, 0.273 mmol) prepared in Reference Example 26 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=388.1 (M+H)$^+$ Step 2. (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)piperidin-3-yl)methanol The title compound as a solid (34 mg) was prepared in the same fashion as Step 3 in Example 1 except that (1-(2-chloro-5-((1-(2-(dimethylamino)ethyl)-1H-pyrazol-4-yl)ethynyl)pyridin-4-yl)piperidin-3-yl)methanol (92 mg, 0.236 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.64 (s, 1H), 8.36 (s, 1H), 8.27 (s, 1H), 8.16 (s, 1H), 8.03 (s, 1H), 7.65 (s, 1H), 7.38 (s, 1H), 7.27 (s, 1H), 4.32 (t, 2H), 4.12 (d, 1H), 3.79 (d, 1H), 3.51-3.44 (m, 2H), 3.34 (s, 2H), 3.03-3.01 (m, 1H), 2.99 (t, 2H), 2.93 (t, 1H), 2.58 (t, 1H), 2.38 (s, 6H), 1.87-1.85 (m, 2H), 1.42 (s, 1H), 1.26-1.21 (m, 3H); MS (ESI) m/z=618.0 (M+H)$^+$ Example 119. (1s,4s)-4-((2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)amino)cyclohexan-1-ol Step 1. (1s,4s)-4-((2-Chloro-5-((1-(2-(dimethylamino)ethyl)-1H-pyrazol-4-yl)ethynyl)pyridin-4-yl)amino)cyclohexan-1-ol The title compound as a solid (82 mg) was prepared in the same fashion as Step 1 in Example 65 except that (1s,4s)-4-aminocyclohexan-1-ol HCl (124 mg, 0.82 mmol) and 2-(4-((6-chloro-4-fluoropyridin-3-yl)ethynyl)-1H-pyrazol-1-yl)-N,N-dimethylethan-1-amine (80 mg, 0.273 mmol) prepared in Reference Example 26 were used instead of 4-(trifluoromethyl)piperidine HCl and 2-chloro-4-fluoro-5-((1-methyl-1H-pyrazol-4-yl)ethynyl)pyridine, respectively. MS (ESI) m/z=388.1 (M+H)$^+$ Step 2. (1 s,4s)-4-((2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)amino)cyclohexan-1-ol The title compound as a solid (5 mg) was prepared in the same fashion as Step 3 in Example 1 except that (1s,4s)-4-((2-chloro-5-((1-(2-(dimethylamino)ethyl)-1H-pyrazol-4-yl)ethynyl)pyridin-4-yl)amino)cyclohexan-1-ol (82 mg, 0.212 mmol) was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (s, 1H), 8.40 (d, 1H), 8.12 (s, 1H), 7.98 (s, 1H), 7.73 (s, 1H), 7.67 (s, 1H), 7.14 (d, 2H), 5.20 (d, 1H), 4.24 (t, 2H), 3.97-3.94 (m, 1H), 3.64-3.63 (m, 1H), 2.84-2.80 (m, 1H), 2.78 (t, 2H), 2.29 (s, 6H), 2.05-2.03 (m, 1H), 1.91-1.87 (m, 4H), 1.84-1.68 (m, 7H), 1.55-1.51 (m, 2H), 1.24-1.22 (m, 2H); MS (ESI) m/z=618.2 (M+H)$^+$ Example 120. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-methylpiperidin-4-yl)methanol Step 1. (1-(2-Chloro-5-((1-(3-(dimethylamino)propyl)-1H-pyrazol-4-yl)ethynyl)pyridin-4-yl)-4-methylpiperidin-4-yl)methanol The title compound as a solid (90 mg) was prepared in the same fashion as Step 1 in Example 65 except that 3-(4-((6-chloro-4-fluoropyridin-3-yl)ethynyl)-1H-pyrazol-1-yl)-N,N-dimethylpropan-1-amine (90 mg, 0.293 mmol) prepared in Reference Example 27 and (4-methylpiperidin-4-yl)methanol (114 mg, 0.880 mmol) were used instead of 2-chloro-4-fluoro-5-((1-methyl-1H-pyrazol-4-yl)ethynyl)pyridine and 4-(trifluoromethyl)piperidine HCl, respectively. MS (ESI) m/z=416.0 (M+H)$^+$ Step 2. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-methylpiperidin-4-yl)methanol The title compound as a solid (6 mg) was prepared in the same fashion as Step 3 in Example 1 except that (1-(2-chloro-5-((1-(3-(dimethylamino)propyl)-1H-pyrazol-4-yl)ethynyl)pyridin-4-yl)-4-methylpiperidin-4-yl)methanol (90 mg, 0.217 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.45 (s,1H), 8.41 (d, 1H), 8.22 (s, 1H), 7.91 (s, 1H), 7.64-7.61 (m, 3H), 6.99 (d, 1H), 4.20 (t, 2H), 3.72-3.69 (m, 2H), 3.49 (s, 2H), 3.39 (t, 2H), 3.24 (t, 1H), 2.84 (quintet, 1H), 2.27-2.18 (m, 12H), 2.05-2.03 (m, 6H), 1.82-1.73 (m, 4H), 1.59-1.47 (m, 5H), 1.31-1.22 (m, 6H), 1.09-1.06 (m, 4H); MS (ESI) m/z=646.1 (M+H)$^+$

Example 121. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-fluoropiperidin-4-yl)methanol

Step 1. (1-(2-Chloro-5-((1-(3-(dimethylamino)propyl)-1H-pyrazol-4-yl)ethynyl)pyridin-4-yl)-4-fluoropiperidin-4-yl)methanol The title compound as a solid (90 mg) was prepared in the same fashion as Step 1 in Example 65 except that 3-(4-((6-chloro-4-fluoropyridin-3-yl)ethynyl)-1H-pyrazol-1-yl)-N,N-dimethylpropan-1-amine (90 mg, 0.293 mmol) prepared in Reference Example 27 and (4-fluoropiperidin-4-yl)methanol HCl (149 mg, 0.88 mmol) were used instead of 2-chloro-4-fluoro-5-((1-methyl-1H-pyrazol-4-yl)ethynyl)pyridine and 4-(trifluoromethyl)piperidine HCl, respectively. MS (ESI) m/z=420.1 (M+H)$^+$

Step 2. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-fluoropiperidin-4-yl)methanol The title compound as a solid (15 mg) was prepared in the same fashion as Step 3 in Example 1 except that (1-(2-chloro-5-((1-(3-(dimethylamino)propyl)-1H-pyrazol-4-yl)ethynyl)pyridin-4-yl)-4-fluoropiperidin-4-yl)methanol (90 mg, 0.215 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.65 (s, 1H), 8.38 (s, 1H), 8.31 (d, 1H), 8.09 (s, 1H), 7.88 (s, 1H), 7.64 (s, 1H), 7.45 (s, 1H), 7.33 (d, 1H), 4.23 (t, 2H), 3.88 (d, 2H), 3.60 (d, 2H), 3.17 (t, 2H), 3.04-3.00 (m, 1H), 2.60 (t, 2H), 2.46 (s, 6H), 2.17-2.11 (m, 2H), 2.05-1.88 (m, 3H), 1.44-1.42 (m, 2H), 1.27-1.23 (m, 2H), 0.92-0.89 (m, 1H), 0.81-0.78 (m, 1H); MS (ESI) m/z=650.1 (M+H)$^+$

Example 122. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)piperidin-3-yl)methanol

Step 1. (1-(2-Chloro-5-((1-(3-(dimethylamino)propyl)-1H-pyrazol-4-yl)ethynyl)pyridin-4-yl)piperidin-3-yl)methanol The title compound as a solid (96 mg) was prepared in the same fashion as Step 1 in Example 65 except that 3-(4-((6-chloro-4-fluoropyridin-3-yl)ethynyl)-1H-pyrazol-1-yl)-N,N-dimethylpropan-1-amine (90 mg, 0.293 mmol) prepared in Reference Example 27 and 3-piperidinemethanol (101 mg, 0.880 mmol) were used instead of 2-chloro-4-fluoro-5-((1-methyl-1H-pyrazol-4-yl)ethynyl)pyridine and 4-(trifluoromethyl)piperidine HCl, respectively. MS (ESI) m/z=402.1 (M+H)$^+$

Step 2. (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)piperidin-3-yl)methanol The title compound as a solid (27 mg) was prepared in the same fashion as Step 3 in Example 1 except that (1-(2-chloro-5-((1-(3-(dimethylamino)propyl)-1H-pyrazol-4-yl)ethynyl)pyridin-4-yl)piperidin-3-yl)methanol (96 mg, 0.239 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.47 (s, 1H), 8.39 (d, 1H), 8.22 (d, 1H), 7.75 (s, 1H), 7.68 (s, 1H), 7.65 (s, 1H), 7.56 (s, 1H), 6.99 (d, 1H), 4.20-4.17 (m, 3H), 3.92 (d, 1H), 3.64-3.60 (m, 2H), 2.97-2.91 (m, 1H), 2.85-2.81 (m, 1H), 2.75-2.69 (m, 1H), 2.22 (s, 7H), 2.06-1.99 (m, 4H), 1.92-1.83 (m, 2H), 1.80-1.74 (m, 2H), 1.55-1.50 (m, 2H), 1.22-1.18 (m, 2H); MS (ESI) m/z=632.1 (M+H)$^+$

Example 123. (1s,4s)-4-((2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)amino)cyclohexan-1-ol

Step 1. (1s,4s)-4-((2-Chloro-5-((1-(3-(dimethylamino)propyl)-1H-pyrazol-4-yl)ethynyl)pyridin-4-yl)amino)cyclohexan-1-ol The title compound as a solid (95 mg) was prepared in the same fashion as Step 1 in Example 65 except that 3-(4-((6-chloro-4-fluoropyridin-3-yl)ethynyl)-1H-pyrazol-1-yl)-N,N-dimethylpropan-1-amine (90 mg, 0.293 mmol) prepared in Reference Example 27 and (1s,4s)-4-aminocyclohexan-1-ol HCl (133 mg, 0.880 mmol) were used instead of 2-chloro-4-fluoro-5-((1-methyl-1H-pyrazol-4-yl)ethynyl)pyridine and 4-(trifluoromethyl)piperidine HCl, respectively. MS (ESI) m/z=402.1 (M+H)$^+$

Step 2. (1s,4s)-4-((2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)amino)cyclohexan-1-ol The title compound as a solid (33 mg) was prepared in the same fashion as Step 3 in Example 1 except that (1s,4s)-4-((2-chloro-5-((1-(3-(dimethylamino)propyl)-1H-pyrazol-4-yl)ethynyl)pyridin-4-yl)amino)cyclohexan-1-ol (95 mg, 0.237 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43 (s, 1H), 8.37 (d, 1H), 8.10 (s, 1H), 7.68 (s, 1H), 7.67 (s, 1H), 7.21 (s, 1H), 7.09 (d, 1H), 5.24 (d, 1H), 4.20 (t, 2H), 3.91 (s, 1H), 3.64 (d, 1H), 2.85-2.78 (m, 1H), 2.31-2.27 (m, 2H), 2.25 (s, 6H), 2.09-2.02 (m, 2H), 1.89-1.86 (m, 3H), 1.79-1.66 (m, 5H), 1.53-1.48 (m, 2H), 1.26-1.17 (m, 2H); MS (ESI) m/z=632.1 (M+H)$^+$

Example 124. N-(4-(4-((Cyclopropylmethyl)amino)piperidin-1-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine The suspension of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one (40 mg, 0.074 mmol) prepared in Example 7, cyclopropylmethanamine HCl (79 mg, 0.736 mmol), NaBH(OAc)$_3$ (468 mg, 2.208 mmol), and TEA (0.11 mL, 0.773 mmol) in DCM (1 mL) and MeOH (1 mL) was stirred at room temperature overnight. The reaction mixture was quenched with sat. NaHCO$_3$ soln., extracted with DCM, dried over MgSO$_4$, and then concentrated. The crude product was purified by column chromatography (MeOH/DCM=0-20%) to yield N-(4-(4-((cyclopropylmethyl)amino)piperidin-1-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine (7 mg) as an off-white solid. $^1$H-NMR (MeOD, 600 MHz) δ 8.76 (s, 1H), 8.44 (s, 1H), 8.38 (d, 1H), 8.18 (s, 1H), 7.87 (s, 1H), 7.74 (s, 1H), 7.65 (s, 1H), 7.27 (s, 1H), 4.09 (d, 2H), 3.93 (s, 3H), 2.99 (t, 2H), 2.85-2.76 (m, 3H), 2.56 (d, 2H), 2.09-2.05 (m, 2H), 1.68-1.57 (m, 3H), 1.54-1.51 (m, 2H), 1.09-1.08 (m, 2H), 0.92-0.88 (m, 3H), 0.87-0.83 (m, 4H), 0.52 (d, 2H), 0.16 (d, 2H); MS (ESI) m/z=599.2 (M+H)$^+$ Example 125. 2-(1-(Cyclopropylsulfonyl)-1H-pyrazol-4-yl)-N-(4-(4-(isopentylamino)piperidin-1-yl)-5-((1-methyl-1H-pyrazol-4-yl)ethynyl)pyridin-2-yl)pyrimidin-4-amine The title compound as a solid (2 mg) was prepared in the same fashion as Example 124 except that isoamyl amine (0.07 mL, 0.644 mmol) was used instead of cyclopropylmethanamine HCl. $^1$H-NMR (CDCl$_3$, 600 MHz) δ 8.66 (s, 1H), 8.44 (s, 1H), 8.41 (d, 1H), 8.18 (s, 1H), 7.62 (s, 1H), 7.61 (s, 1H), 7.01 (s, 1H), 6.98 (s, 1H), 4.10 (d, 2H), 3.93 (s, 3H), 2.98 (t, 2H), 2.84-2.82 (m, 4H), 2.17 (d, 2H), 1.64-1.59 (m, 2H), 1.55-1.49 (m, 2H), 1.26-1.20 (m, 2H), 0.92 (d, 6H), 0.89-0.87 (m, 4H); MS (ESI) m/z=615.3 (M+H)$^+$ Example 126. 2-(1-(Cyclopropylsulfonyl)-1H-pyrazol-4-yl)-N-(4-(4-((2,2-difluoroethyl)amino)piperidin-1-yl)-5-((1-methyl-1H-pyrazol-4-yl)ethynyl)pyridin-2-yl)pyrimidin-4-amine The title compound as a solid (14 mg) was prepared in the same fashion as Example 124 except that 2,2-difluoroethylamine (0.04 mL, 0.644 mmol) was used instead of cyclopropylmethanamine HCl. $^1$H-NMR (CDCl$_3$, 600 MHz) δ 8.66 (s, 1H), 8.45 (s, 1H), 8.41 (d, 1H), 8.25 (s, 1H), 8.24 (s, 1H), 7.66 (s, 1H), 7.63 (s, 1H), 7.56 (s, 1H), 6.96 (s, 1H), 5.98-5.78 (m, 1H), 4.05 (d, 2H), 3.94 (s, 3H), 3.09-3.02 (m, 4H), 2.86-2.79 (m, 2H), 2.09 (d, 2H), 1.63-1.58 (m, 2H), 1.54-1.52 (m, 2H), 1.25-1.22 (m, 2H); MS (ESI) m/z=609.2 (M+H)$^+$ Example 127. 2-(1-(Cyclopropylsulfonyl)-1H-pyrazol-4-yl)-N-(5-((1-methyl-1H-pyrazol-4-yl)ethynyl)-4-(4-((3,3,3-trifluoropropyl)amino)piperidin-1-yl)pyridin-2-yl)pyrimidin-4-amine The title compound as a solid (11 mg) was prepared in the same fashion as Example 124 except that 3,3,3-trifluoropropan-1-amine HCl (96 mg, 0.644 mmol) was used instead of cyclopropylmethanamine HCl. $^1$H-NMR (CDCl$_3$, 600 MHz) δ 8.67 (s, 1H), 8.45 (s, 1H), 8.41 (d, 1H), 8.23 (s, 1H), 7.93 (s, 1H), 7.64 (s, 1H), 7.63 (s, 1H), 7.55 (s, 1H), 6.97 (s, 1H), 4.06 (d, 2H), 3.93 (s, 3H), 3.03 (t, 2H), 2.97 (t, 2H), 2.85-2.81 (m, 1H), 2.78-2.75 (m, 1H), 2.38-2.30 (m, 2H), 2.09 (d, 2H), 1.54-1.50 (m, 2H), 1.24-1.20 (m, 2H); MS (ESI) m/z=641.3 (M+H)$^+$ Example 128. 2-(1-(Cyclopropylsulfonyl)-1H-pyrazol-4-yl)-N-(4-(4-(3,3-difluoroazetidin-1-yl)piperidin-1-yl)-5-((1-methyl-1H-pyrazol-4-yl)ethynyl)pyridin-2-yl)pyrimidin-4-amine The title compound as a solid (24 mg) was prepared in the same fashion as Example 124 except that 3,3-difluoroazetidine HCl (83 mg, 0.644 mmol) was used instead of cyclopropylmethanamine HCl. $^1$H-NMR (CDCl$_3$, 600 MHz) δ 8.65 (s, 1H), 8.45 (s, 1H), 8.44 (s, 1H), 8.40 (d, 1H), 8.24 (s, 1H), 7.70 (s, 1H), 7.62 (s, 1H), 7.55 (s, 1H), 6.93 (s, 1H), 3.95-3.93 (m, 5H), 3.62 (t, 4H), 3.11 (t, 2H), 2.86-2.82 (m, 1H), 2.41-2.40 (m, 1H), 1.94-1.91 (m, 2H), 1.64-1.59 (m, 2H), 1.54-1.52 (m, 2H), 1.28-1.22 (m, 2H); MS (ESI) m/z=621.2 (M+H)$^+$ Example 129. 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine The title compound as a solid (23 mg) was prepared in the same fashion as Example 124 except that 2-fluoroethylamine HCl (348 mg, 3.495 mmol) was used instead of cyclopropylmethanamine HCl. $^1$H-NMR (CDCl$_3$, 600 MHz) δ 8.67 (s, 1H), 8.45 (s, 1H), 8.41 (d, 1H), 8.23 (s, 1H), 7.89 (d, 1H), 7.62 (s, 1H), 7.61 (s, 1H), 7.55 (s, 1H), 7.00 (s, 1H), 4.63 (t, 1H), 4.55 (t, 1H), 4.07 (d, 2H), 3.93 (s, 3H), 3.04-2.98 (m, 3H), 2.97 (t, 1H), 2.85-2.80 (m, 1H), 2.79-2.78 (m, 1H), 2.09 (m, 2H), 2.01 (m, 1H), 1.65-1.59 (m, 3H), 1.55-1.49 (m, 2H), 1.24-1.21 (m, 2H), 0.89-0.87 (m, 1H); MS (ESI) m/z=591.2 (M+H)$^+$ Example 130. 2-(1-(Cyclopropylsulfonyl)-1H-pyrazol-4-yl)-N-(5-((1-methyl-1H-pyrazol-4-yl)ethynyl)-4-(4-(methylamino)piperidin-1-yl)pyridin-2-yl)pyrimidin-4-amine The title compound as a solid (11 mg) was prepared in the same fashion as Example 124 except that methylamine HCl (174 mg, 2.575 mmol) was used instead of cyclopropylmethanamine HCl. $^1$H-NMR (CDCl$_3$, 400 MHz) δ 8.66 (s, 1H), 8.45 (s, 1H), 8.41 (d, 1H), 8.35 (s, 1H), 8.22 (s, 1H), 7.87 (s, 1H), 7.63 (s, 1H), 7.57 (s, 1H), 7.02 (s, 2H), 4.88 (s, 1H), 4.82 (d, 1H), 4.08-4.05 (m, 2H), 4.01-3.92 (m, 4H), 3.03-2.96 (m, 3H), 2.87-2.81 (m, 1H), 2.69-2.63 (m, 1H), 2.50 (s, 2H), 2.12-2.06 (m, 2H), 2.04-2.00 (m, 4H), 1.61 (m, 2H), 1.22-1.20 (m, 4H), 0.90-0.83 (m, 3H); MS (ESI) m/z=559.1 (M+H)$^+$ Example 131. 2-((1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)amino)ethan-1-ol The title compound as a solid (19 mg) was prepared in the same fashion as Example 124 except that ethanolamine (0.08 mL, 1.288 mmol) was used instead of cyclopropylmethanamine HCl. $^1$H-NMR (DMSO-d$_6$, 400 MHz) δ 10.22 (s, 1H), 8.65 (s, 1H), 8.44 (s, 1H), 8.41 (d, 1H), 8.14 (s, 1H), 7.99 (s, 1H), 7.68 (s, 1H), 7.63 (s, 1H), 7.33 (d, 1H), 3.93 (d, 2H), 3.85 (s, 3H), 3.27-3.21 (m, 1H), 2.93 (t, 2H), 2.64 (t, 2H), 1.99-1.92 (m, 2H), 1.45-1.35 (m, 2H), 1.33-1.31 (m, 2H), 1.29-1.22 (m, 2H); MS (ESI) m/z=589.1 (M+H)$^+$ Example 132. 2-(1-(Cyclopropylsulfonyl)-1H-pyrazol-4-yl)-N-(4-(4-((2-methoxyethyl)amino)piperidin-1-yl)-5-((1-methyl-1H-pyrazol-4-yl)ethynyl)pyridin-2-yl)pyrimidin-4-amine The title compound as a solid (33 mg) was prepared in the same fashion as Example 124 except that 2-methoxyethylamine (0.11 mL, 1.288 mmol) was used instead of cyclopropylmethanamine HCl. $^1$H-NMR (CDCl$_3$, 400 MHz) δ

8.75 (s, 1H), 8.65 (s, 1H), 8.43 (s, 1H), 8.37 (d, 1H), 8.18 (s, 1H), 7.68 (s, 1H), 7.61 (s, 1H), 7.60 (s, 1H), 6.98 (d, 1H), 4.08 (d, 2H), 3.92 (s, 3H), 3.54 (t, 2H), 3.37 (s, 3H), 2.99 (t, 2H), 2.88 (t, 2H), 2.10-2.02 (m, 2H), 1.67-1.58 (m, 2H), 1.54-1.49 (m, 2H), 1.25-1.19 (m, 2H); MS (ESI) m/z=603.1 (M+H)$^+$

Example 133. N$^1$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-N$^2$,N$^2$-dimethylethane-1,2-diamine The title compound as a solid (36 mg) was prepared in the same fashion as Example 124 except that N$^1$,N$^4$-dimethylethane-1,2-diamine (0.14 mL, 1.288 mmol) was used instead of cyclopropylmethanamine HCl. $^1$H-NMR (CDCl$_3$, 400 MHz) δ 8.66 (s, 1H), 8.44 (s, 1H), 8.38 (d, 1H), 8.22 (s, 1H), 7.62 (s, 1H), 7.58 (s, 1H), 7.55 (s, 1H), 6.99 (d, 1H), 4.07 (d, 2H), 3.92 (s, 3H), 2.98 (t, 2H), 2.85-2.81 (m, 1H), 2.80 (t, 2H), 2.44 (t, 2H), 2.23 (s, 6H), 2.09-2.04 (m, 611), 1.64-1.56 (m, 2H), 1.54-1.49 (m, 2H), 1.25-1.19 (m, 4H); MS (ESI) m/z=616.2 (M+H)$^+$ Example 134. N$^4$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-N$^2$,N$^2$,2-trimethylpropane-1,2-diamine The title compound as a solid (27 mg) was prepared in the same fashion as Example 124 except that (1-amino-2-methylpropan-2-yl)dimethylamine (75 mg, 0.644 mmol) was used instead of cyclopropylmethanamine HCl. $^1$H-NMR (DMSO-d$_6$, 400 MHz) δ 10.26 (s, 1H), 8.65 (s, 1H), 8.45 (s, 1H), 8.43 (s, 1H), 8.15 (s, 1H), 8.02 (s, 1H), 7.75 (s, 1H), 7.63 (s, 1H), 7.33 (s, 1H), 3.91 (d, 2H), 3.85 (s, 3H), 3.29-3.26 (m, 1H), 2.97 (t, 2H), 2.49 (s, 6H), 1.97 (d, 2H), 1.42-1.40 (m, 3H), 1.32-1.31 (m, 2H), 1.26-1.21 (m, 2H), 0.94 (s, 6H); MS (ESI) m/z=644.3 (M+H)$^+$ Example 135. 2-(1-(Cyclopropylsulfonyl)-1H-pyrazol-4-yl)-N-(5-((1-methyl-1H-pyrazol-4-yl)ethynyl)-4-(4-((2,2,2-trifluoroethyl)amino)piperidin-1-yl)pyridin-2-yl)pyrimidin-4-amine The title compound as a solid (6 mg) was prepared in the same fashion as Example 124 except that 2,2,2-trifluoroethylamine HCl (125 mg, 0.920 mmol) was used instead of cyclopropylmethanamine HCl. $^1$H-NMR (CDCl$_3$, 400 MHz) δ 8.64 (s, 1H), 8.44 (s, 1H), 8.40 (d, 1H), 8.18 (s, 1H), 7.80 (s, 1H), 7.60 (s, 1H), 7.54 (s, 1H), 7.04 (d, 1H), 4.07-4.00 (m, 2H), 3.93 (s, 3H), 3.72-3.64 (m, 2H), 3.63-3.50 (m, 2H), 2.85-2.81 (m, 1H), 2.21-2.17 (m, 2H), 1.93-1.89 (m, 2H), 1.74-1.61 (m, 4H), 1.55-1.51 (m, 2H), 1.27-1.19 (m, 2H); MS (ESI) m/z=627.2 (M+H)$^+$ Example 136. 2-(1-(Cyclopropylsulfonyl)-1H-pyrazol-4-yl)-N-(4-(4-((2-fluoroethyl)amino)piperidin-1-yl)-5-((1-(tetrahydro-2H-pyran-4-yl)-1H-pyrazol-4-yl)ethynyl)pyridin-2-yl)pyrimidin-4-amine The title compound as a solid (36 mg) was prepared in the same fashion as Example 124 except that 1-(2-((2-(1-(cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one (55 mg, 0.090 mmol) prepared in Example 93 and 2-fluoroethylamine HCl (89 mg, 0.896 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. $^1$H-NMR (DMSO-d$_6$, 600 MHz) δ 10.24 (s, 1H), 8.66 (s, 1H), 8.45 (s, 1H), 8.44 (d, 1H), 8.16 (s, 1H), 8.14 (s, 1H), 7.73 (s, 1H), 7.68 (s, 1H), 7.35 (s, 1H), 4.51 (t, 1H), 4.45-4.42 (m, 2H), 3.95 (t, 4H), 3.46 (td, 2H), 3.33-3.26 (m, 2H), 2.97 (t, 2H), 2.89 (t, 1H), 2.84 (t, 1H), 2.66 (quintet, 1H), 2.00-1.95 (m, 6H), 1.44-1.42 (m, 2H), 1.36-1.33 (m, 2H), 1.28-1.25 (m, 2H); MS (ESI) m/z=661.1 (M+H)$^+$ Example 137. 2-((1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)amino)ethan-1-ol The title compound as a solid (28 mg) was prepared in the same fashion as Example 124 except that 1-(2-((2-(1-(cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one (55 mg, 0.090 mmol) prepared in Example 93 and ethanolamine (0.05 mL, 0.896 mmol) were used instead of 1-(2-((2-(1-(cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one and cyclopropylmethanamine HCl. $^1$H-NMR (DMSO-d$_6$, 600 MHz) δ 10.24 (s, 1H), 8.66 (s, 1H), 8.45 (s, 1H), 8.43 (s, 1H), 8.15 (s, 1H), 7.72 (s, 1H), 7.68 (s, 1H), 7.35 (s, 1H), 4.52-4.41 (m, 1H), 3.97-3.90 (m, 4H), 3.48-3.42 (m, 4H), 3.29-3.25 (m, 2H), 2.95 (t, 2H), 2.68-2.63 (m, 3H), 2.00-1.92 (m, 6H), 1.46-1.41 (m, 2H), 1.36-1.30 (m, 2H), 1.28-1.26 (m, 2H); MS (ESI) m/z=659.1 (M+H)$^+$ Example 138. N$^4$-(1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)-N$^2$,N$^2$-dimethylethane-1,2-diamine The title compound as a solid (31 mg) was prepared in the same fashion as Example 124 except that 1-(2-((2-(1-(cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one (55 mg, 0.090 mmol) prepared in Example 93 and N$^1$,N$^1$-dimethylethane-1,2-diamine (0.1 mL, 0.896 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. $^1$H-NMR (DMSO-d$_6$, 400 MHz) δ 10.24 (s, 1H), 8.65 (s, 1H), 8.45 (s, 1H), 8.43 (s, 1H), 8.15 (s, 1H), 8.12 (s, 1H), 7.72 (s, 1H), 7.67 (s, 1H), 7.35 (s, 1H), 4.47-4.40 (m, 1H), 3.97-3.92 (m, 4H), 3.48-3.42 (m, 2H), 2.96 (t, 2H), 2.65 (t, 3H), 2.31 (t, 2H), 2.13 (s, 6H), 1.45-1.40 (m, 2H), 1.38-1.29 (m, 2H), 1.27-1.21 (m, 3H); MS (ESI) m/z=686.1 (M+H)$^+$ Example 139. 1-(4-(4-((6-((2-(1-(Cyclopropylsulfonyl)-1H-pyrazol-4-yl)pyrimidin-4-yl)amino)-4-(4-((2-(dimethylamino)ethyl)amino)piperidin-1-yl)pyridin-3-yl)ethynyl)-1H-pyrazol-1-yl)piperidin-1-yl)ethan-1-one The title compound as a solid (18 mg) was prepared in the same fashion as Example 124 except that 1-(5-((1-(1-acetylpiperidin-4-yl)-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-one (48 mg, 0.073 mmol)

prepared in Example 108 and N¹,N¹-dimethylethane-1,2-diamine (0.08 mL, 0.733 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. ¹H-NMR (DMSO-$d_6$, 400 MHz) δ 10.24 (s, 1H), 8.65 (s, 1H), 8.45 (s, 1H), 8.42 (s, 1H), 8.15 (s, 1H), 8.12 (s, 1H), 7.77 (s, 1H), 7.67 (s, 1H), 7.35 (s, 1H), 4.47-4.44 (m, 2H), 3.93-3.91 (m, 3H), 3.26-3.22 (m, 1H), 2.97 (t, 2H), 2.70 (t, 1H), 2.64-2.61 (m, 3H), 2.31-2.26 (m, 2H), 2.12 (s, 6H), 2.08-1.93 (m, 4H), 1.78-1.72 (m, 1H), 1.43-1.17 (m, 7H); MS (ESI) m/z=364.0 (M+H)⁺/2

Example 140. 2-(1-(Cyclopropylsulfonyl)-1H-pyrazol-4-yl)-N-(5-((1-methyl-1H-pyrazol-3-yl)ethynyl)-4-(4-(methylamino)piperidin-1-yl)pyridin-2-yl)pyrimidin-4-amine The title compound as a solid (21 mg) was prepared in the same fashion as Example 124 except that 1-(2-((2-(1-(cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-one (40 mg, 0.074 mmol) prepared in Reference Example 28 and methylamine HCl (50 mg, 0.736 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. ¹H-NMR (DMSO-$d_6$, 400 MHz) δ 10.28 (s, 1H), 8.66 (s. 1H), 8.45 (s, 2H), 8.20 (s, 1H), 7.77 (s, 1H), 7.73 (s, 1H), 7.37 (s, 1H), 6.45 (s, 1H), 3.94 (d, 1H), 3.87 (s, 3H), 3.00 (t, 2H), 2.27 (s, 3H), 1.97-1.94 (m, 3H), 1.44-1.39 (m, 2H), 1.33 (s, 2H), 1.30-1.25 (m, 4H); MS (ESI) m/z=559.0 (M+H)⁺

Example 141. 2-(1-(Cyclopropylsulfonyl)-1H-pyrazol-4-yl)-N-(4-(4-((2-fluoroethyl)amino)piperidin-1-yl)-5-((1-methyl-1H-pyrazol-3-yl)ethynyl)pyridin-2-yl)pyrimidin-4-amine The title compound as a solid (36 mg) was prepared in the same fashion as Example 124 except that 1-(2-((2-(1-(cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-one (40 mg, 0.074 mmol) prepared in Reference Example 28 and 2-fluoroethylamine HCl (73 mg, 0.736 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. ¹H-NMR (DMSO-$d_6$, 400 MHz) δ 10.28 (s, 1H), 8.66 (s, 1H), 8.45 (s, 2H), 8.29 (s, 1H), 8.20 (s, 1H), 7.77 (s, 1H), 7.73 (s, 1H), 7.36 (d, 1H), 6.46 (s, 1H), 4.52 (t, 1H), 4.40 (t, 1H), 3.95 (d, 2H), 3.87 (s, 3H), 2.98 (s, 2H), 2.88 (t, 2H), 2.82 (t, 2H), 2.63 (brs, 1H), 2.00-1.97 (m, 2H), 1.46-1.41 (m, 2H), 1.39-1.33 (m, 2H), 1.28-1.23 (m, 2H); MS (ESI) m/z=591.0 (M+H)⁺

Example 142. N⁴-(1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-yl)-N²,N²-dimethylethane-1,2-diamine The title compound as a solid (22 mg) was prepared in the same fashion as Example 124 except that 1-(2-((2-(1-(cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-one (40 mg, 0.074 mmol) prepared in Reference Example 28 and N¹,N⁴-dimethylethane-1,2-diamine (0.08 mL, 0.736 mmol) were used instead of 1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one and cyclopropylmethanamine HCl. ¹H-NMR (DMSO-$d_6$, 400 MHz) δ 10.28 (s, 1H), 8.66 (s, 1H), 8.45 (s, 2H), 8.20 (s, 1H), 7.77 (s, 1H), 7.75 (s, 1H), 7.36 (s, 1H), 6.45 (s, 1H), 3.94 (d, 2H), 3.86 (s, 3H), 2.99 (t, 3H), 2.64-2.61 (m, 3H), 2.30 (t, 2H), 2.12 (s, 6H), 1.94 (s, 3H), 1.42-1.39 (m, 2H), 1.33 (s, 2H), 1.25-1.23 (m, 41-1); MS (ESI) m/z=617.1 (M+H)⁺

Example 143. N¹-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)-N²,N²-dimethylethane-1,2-diamine Step 1. 1-(2-Chloro-5-((1-(trifluoromethyl)-1H-pyrazol-4-yl)ethynyl)pyridin-4-yl)piperidin-4-one The title compound as a solid (235 mg) was prepared in the same fashion as Step 1 in Reference Example 28 except that 2-chloro-4-fluoro-5-((1-(trifluoromethyl)-1H-pyrazol-4-yl)ethynyl)pyridine (200 mg, 0.691 mmol) prepared in Reference Example 23 was used instead of 2-chloro-4-fluoro-5-((1-methyl-1H-pyrazol-3-yl)ethynyl)pyridine. MS (ESI) m/z=369.0 (M+H)⁺

Step 2. N⁴-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)-N²,N²-dimethylethane-1,2-diamine The suspension of 2-(1-cyclopropylsulfonylpyrazol-4-yl)pyrimidin-4-amine (160 mg, 0.603 mmol), 1-(2-chloro-5-((1-(trifluoromethyl)-1H-pyrazol-4-yl)ethynyl)pyridin-4-yl)piperidin-4-one (222 mg, 0.603 mmol) prepared in Step 1, Cs₂CO₃ (393 mg, 1.206 mmol), XPhos (58 mg, 0.121 mmol), and Pd₂(dba)₃ (55 mg, 0.060 mmol) in 1,4-dioxane (6 mL) was stirred at 90° C. overnight. The reaction mixture was cooled, filtered through Celite, and then concentrated. After the residue was dissolved with DCM (2 mL) and MeOH (2 mL), N¹,N⁴-dimethylethane-1,2-diamine (532 mg, 6.031 mmol) and NaBH(OAc)₃ (2.55 g, 12.060 mmol) were added. After being stirred at room temperature overnight, the reaction mixture was quenched by sat. NaHCO₃ soln., extracted with DCM, dried over MgSO₄, and then concentrated. The crude product was purified by column chromatography (MeOH/DCM=0-25%) to yield N¹-(1-(2-((2-(1-(cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)-N²,N²-dimethylethane-1,2-diamine (35 mg) as an off-white solid. ¹H-NMR (DMSO-$d_6$, 400 MHz) δ 10.30 (s, 1H), 8.90 (s, 1H), 8.66 (s, 1H), 8.46 (s, 1H), 8.45 (s, 1H), 8.20 (s, 1H), 8.19 (s, 1H), 7.77 (s, 1H), 7.35 (s, 1H), 6.96-6.91 (m, 1H), 3.92 (d, 2H), 3.00 (t, 2H), 2.62 (t, 2H), 2.28 (t, 2H), 2.12 (s, 6H), 1.98 (d, 2H), 1.41-1.32 (m, 4H), 1.29-1.22 (m, 3H); MS (ESI) m/z=670.2 (M+H)⁺

Example 144. 2-(1-(Cyclopropylsulfonyl)-1H-pyrazol-4-yl)-N-(5-((1-(2-(dimethylamino)ethyl)-1H-pyrazol-4-yl)ethynyl)-4-(4-((2-fluoroethyl)amino)piperidin-1-yl)pyridin-2-yl)pyrimidin-4-amine Step 1. 1-(2-Chloro-5-((1-(2-(dimethylamino)ethyl)-1H-pyrazol-4-yl)ethynyl)pyridin-4-yl)piperidin-4-one The title compound as a solid (115 mg) was prepared in the same fashion as Step 1 in Reference Example 28 except that 2-(4-((6-chloro-4-fluoropyridin-3-yl)ethynyl)-1H-pyrazol-1-yl)-N,N-dimethylethan-1-amine (251 mg, 1.640 mmol) prepared in Reference Example 26 was used instead of 2-chloro-4-fluoro-5-((1-methyl-1H-pyrazol-3-yl)ethynyl) pyridine. MS (ESI) m/z=372.1 (M+H)$^+$

Step 2. 2-(1-(Cyclopropylsulfonyl)-1H-pyrazol-4-yl)-N-(5-((1-(2-(dimethylamino)ethyl)-1H-pyrazol-4-yl)ethynyl)-4-(4-((2-fluoroethyl)amino)piperidin-1-yl)pyridin-2-yl)pyrimidin-4-amine The title compound as an off-white solid (22 mg) was prepared in the same fashion as Step 2 in Example 143 except that 1-(2-chloro-5-((1-(2-(dimethylamino)ethyl)-1H-pyrazol-4-yl)ethynyl)pyridin-4-yl)piperidin-4-one (110 mg, 0.710 mmol) prepared in Step 1 and 2-fluoroethylamine HCl (82.69 mg, 0.831 mmol) were used instead of 1-(2-chloro-5-((1-(trifluoromethyl)-1H-pyrazol-4-yl)ethynyl)pyridin-4-yl)piperidin-4-one and N,N-dimethylaminoethylamine. $^1$H-NMR (MeOD, 400 MHz) δ 8.68 (s, 1H), 8.39 (s, 1H), 8.30 (d, 1H), 8.10 (s, 1H), 7.93 (s, 1H), 7.65 (s, 1H), 7.59 (s, 1H), 7.23 (s, 1H), 7.02 (s, 2H), 4.71 (t, 1H), 4.60 (t, 1H), 4.32 (t, 2H), 4.09 (d, 1H), 3.30-3.15 (m, 3H), 3.07-3.02 (m, 2H), 2.94-2.88 (m, 3H), 2.37 (s, 6H), 2.20 (d, 2H), 2.01 (d, 1H), 1.72-1.70 (m, 2H), 1.46-1.43 (m, 2H), 1.32-1.25 (m, 4H); MS (ESI) m/z=649.1 (M+H)$^+$

Example 145. 2-(1-(Cyclopropylsulfonyl)-1H-pyrazol-4-yl)-N-(5-((1-(3-(dimethylamino)propyl)-1H-pyrazol-4-yl)ethynyl)-4-(4-((2-fluoroethyl)amino)piperidin-1-yl)pyridin-2-yl)pyrimidin-4-amine

Step 1. 1-(2-Chloro-5-((1-(3-(dimethylamino)propyl)-1H-pyrazol-4-yl)ethynyl)pyridin-4-yl)piperidin-4-one The title compound as a solid (165 mg) was prepared in the same fashion as Step 1 in Reference Example 28 except that 3-(4-((6-chloro-4-fluoropyridin-3-yl)ethynyl)-1H-pyrazol-1-yl)-N,N-dimethylpropan-1-amine (270 mg, 1.76 mmol) prepared in Reference Example 27 was used instead of 2-chloro-4-fluoro-5-((1-methyl-1H-pyrazol-3-yl)ethynyl) pyridine. MS (ESI) m/z=386.1 (M+H)$^+$

Step 2. 2-(1-(Cyclopropylsulfonyl)-1H-pyrazol-4-yl)-N-(5-((1-(3-(dimethylamino)propyl)-1H-pyrazol-4-yl)ethynyl)-4-(4-((2-fluoroethyl)amino)piperidin-1-yl)pyridin-2-yl)pyrimidin-4-amine The title compound as a solid (19 mg) was prepared in the same fashion as Step 2 in Example 143 except that 1-(2-chloro-5-((1-(3-(dimethylamino)propyl)-1H-pyrazol-4-yl) ethynyl)pyridin-4-yl)piperidin-4-one (160 mg, 0.415 mmol) prepared in Step 1 and 2-fluoroethylamine HCl (69 mg, 0.695 mmol) were used instead of 1-(2-chloro-5-((1-(trifluoromethyl)-1H-pyrazol-4-yl)ethynyl)pyridin-4-yl)piperidin-4-one and N,N-dimethylaminoethylamine. $^1$H-NMR (MeOD, 400 MHz) δ 8.65 (s, 1H), 8.37 (s, 1H), 8.28 (s, 1H), 8.06 (s, 1H), 7.85 (s, 1H), 7.62 (s, 1H), 7.54 (s, 1H), 7.20 (d, 1H), 7.00 (s, 1H), 4.59 (t, 1H), 4.47 (t, 1H), 4.18 (t, 2H), 4.03 (d, 2H), 3.58 (s, 2H), 3.04-2.98 (m, 2H), 2.92-2.84 (m, 3H), 2.73 (s, 1H), 2.32 (t, 2H), 2.25 (s, 6H), 2.09-1.99 (m, 4H), 1.56-1.54 (m, 2H), 1.44-1.40 (m, 2H), 1.25-1.22 (m, 3H); MS (ESI) m/z=663.1 (M+H)$^+$

Example 146. 2-(1-(Cyclopropylsulfonyl)-1H-pyrazol-4-yl)-N-(5-((1-methyl-1H-pyrazol-4-yl)ethynyl)-4-(4-methyl-4-((methylamino)methyl)piperidin-1-yl)pyridin-2-yl)pyrimidin-4-amine The DCM (4 mL) solution of (1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol (110 mg, 0.192 mmol) prepared in Example 12, tetrabromomethane (95 mg, 0.288 mmol), PPh$_3$ (75 mg, 0.288 mmol) was stirred at room temperature for 6 hours. The reaction mixture was concentrated and the residue was dissolved with MeCN (4 mL). Methylamine HCl (26 mg, 0.383 mmol) and TEA (0.11 mL, 0.767 mmol) were added and the reaction mixture was stirred at 60° C. overnight. The solvent was removed under the reduced pressure and the crude product was purified by column chromatography (MeOH/DCM=0-30%) to yield 2-(1-(cyclopropylsulfonyl)-1H-pyrazol-4-yl)-N-(5-((1-methyl-1H-pyrazol-4-yl)ethynyl)-4-(4-methyl-4-((methylamino) methyl)piperidin-1-yl)pyridin-2-yl)pyrimidin-4-amine (19 mg) as an off-white solid. $^1$H-NMR (MeOD, 600 MHz) δ 8.68 (s, 1H), 8.40 (s, 1H), 8.28 (d, 1H), 7.97 (s, 1H), 7.80 (s, 1H), 7.58 (s, 1H), 7.27 (s, 1H), 7.15 (s, 1H), 7.14 (s, 1H), 3.90 (s, 3H), 3.84 (t, 2H), 3.60 (q, 2H), 3.16-3.12 (m, 1H), 3.09-3.04 (m, 2H), 2.73 (s, 3H), 1.93-1.86 (m, 4H), 1.45-1.43 (m, 2H), 1.30-1.26 (m, 2H), 1.19 (s, 3H); MS (ESI) m/z=587.2 (M+H)$^+$

Example 147. (1-(2-((2-(1-(Cyclopropylsulfonyl)-1H-pyrazol-4-yl)pyrimidin-4-yl)amino)-5-((1-(1-methylpiperidin-4-yl)-1H-pyrazol-4-yl)ethynyl)pyridin-4-yl)-4-methylpiperidin-4-yl)methanol

Step 1. tert-Butyl 4-(4-((6-chloro-4-(4-(hydroxymethyl)-4-methylpiperidin-1-yl)pyridin-3-yl)ethynyl)-1H-pyrazol-1-yl)piperidine-1-carboxylate The title compound as a solid (360 mg) was prepared in the same fashion as Step 2 in Example 1 except that tert-butyl 4-(4-ethynyl-1H-pyrazol-1-yl)piperidine-1-carboxylate (270 mg, 0.982 mmol) and (1-(2-chloro-5-iodopyridin-4-yl)-4-methylpiperidin-4-yl)methanol (300 mg, 0.818 mmol) prepared in Reference Example 12 were used instead of 4-ethynyl-1-methylpyrazole and 1-(2-chloro-5-iodopyridin-4-yl)-4-methylpiperazine. MS (ESI) m/z=514.2 (M+H)$^+$

Step 2. (1-(2-Chloro-5-((1-(1-methylpiperidin-4-yl)-1H-pyrazol-4-yl)ethynyl)pyridin-4-yl)-4-methylpiperidin-4-yl)methanol The DCM (7 mL) solution of tert-butyl 4-(4-((6-chloro-4-(4-(hydroxymethyl)-4-methylpiperidin-1-yl)pyridin-3-yl) ethynyl)-1H-pyrazol-1-yl)piperidine-1-carboxylate (250 mg, 0.486 mmol) prepared in Step 1 and TFA (3 mL) was stirred at room temperature overnight. The mixture was concentrated, quenched with aqueous sat. NaHCO$_3$ soln., extracted with DCM, dried over MgSO$_4$, and then concentrated. After the residue was dissolved with MeOH (5 mL), paraformaldehyde (146 mg, 4.863 mmol) and sodium cyanoborohydride (305.61 mg, 4.863 mmol) were added. After being stirred at 50° C. for 6 hours, the reaction mixture was cooled and concentrated. The residue was diluted with DCM, washed with water, dried over MgSO$_4$, and then concentrated. The crude product was purified by column chromatography (MeOH/DCM=0-20%) to yield (1-(2- chloro-5-((1-(1-methylpiperidin-4-yl)-1H-pyrazol-4-yl)ethynyl)pyridin-4-yl)-4-methylpiperidin-4-yl)methanol (190 mg) as an off-white solid. MS (ESI) m/z=429.0 (M+H)$^+$ Step 3. (1-(2-((2-(1-(Cyclopropylsulfonyl)-1H-pyrazol-4-yl)pyrimidin-4-yl)amino)-5-((1-(1-methylpiperidin-4-yl)-1H-pyrazol-4-yl)ethynyl)pyridin-4-yl)-4-methylpiperidin-4-yl)methanol The title compound as a solid (101 mg) was prepared in the same fashion as Step 3 in Example 1 except that (1-(2-chloro-5-((1-(1-methylpiperidin-4-yl)-1H-pyrazol-4-yl)ethynyl)pyridin-4-yl)-4-methylpiperidin-4-yl)methanol (177 mg, 0.415 mmol) prepared in Step 2 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.24 (s, 1H), 8.65 (s, 1H), 8.45 (s, 1H), 8.44 (d, 1H), 8.14 (s, 1H), 8.11 (s, 1H), 7.71 (s,1H), 7.60 (s, 1H), 7.36 (s, 1H), 4.60 (t, 1H), 4.19-4.15 (m, 1H), 3.70-3.68 (m, 2H), 3.29-3.25 (m, 2H), 3.23-3.19 (m, 4H), 2.90 (d, 2H), 2.25 (s, 3H), 2.12 (s, 2H), 2.00-1.94 (m, 4H), 1.69-1.64 (m, 2H), 1.39 (d, 2H), 1.35-1.32 (m, 2H), 1.30-1.25 (m, 2H), 0.96 (s, 3H); MS (ESI) m/z=657.2 (M+H)$^+$ Example 148. (1-(2-((2-(1-(Cyclopropylsulfonyl)-1H-pyrazol-4-yl)pyrimidin-4-yl)amino)-5-((1-(1-methylazetidin-3-yl)-1H-pyrazol-4-yl)ethynyl)pyridin-4-yl)-4-methylpiperidin-4-yl)methanol Step 1. tert-Butyl 3-(4-ethynyl-1H-pyrazol-1-yl)azetidine-1-carboxylate The title compound as an oil (734 mg) was prepared in the same fashion as Step 1 in Reference Example 26 except that 1-boc-3-iodoazetidine (1.6 g, 5.646 mmol) was used instead of 2-iodo-N,N-dimethylethan-1-amine HCl. MS (ESI) m/z=192.0 (M+H)$^+$ Step 2. tert-Butyl 3-(4-((6-chloro-4-(4-(hydroxymethyl)-4-methylpiperidin-1-yl)pyridin-3-yl)ethynyl)-1H-pyrazol-1-yl)azetidine-1-carboxylate The title compound as a solid (340 mg) was prepared in the same fashion as Step 2 in Example 1 except that tert-butyl 3-(4-ethynyl-1H-pyrazol-1-yl)azetidine-1-carboxylate (243 mg, 0.982 mmol) prepared in Step 1 and (1-(2-chloro-5-iodopyridin-4-yl)-4-methylpiperidin-4-yl)methanol (300 mg, 0.818 mmol) prepared in Reference Example 12 were used instead of 4-ethynyl-1-methylpyrazole and 1-(2-chloro-5-iodopyridin-4-yl)-4-methylpiperazine. MS (ESI) m/z=486.0 (M+H)$^+$ Step 3. (1-(2-Chloro-5-((1-(1-methylazetidin-3-yl)-1H-pyrazol-4-yl)ethynyl)pyridin-4-yl)-4-methylpiperidin-4-yl)methanol The title compound as a solid (75 mg) was prepared in the same fashion as Step 2 in Example 147 except that tert-butyl 3-(4-((6-chloro-4-(4-(hydroxymethyl)-4-methylpiperidin-1-yl)pyridin-3-yl)ethynyl)-1H-pyrazol-1-yl)azetidine-1-carboxylate (250 mg, 0.514 mmol) prepared in Step 2 was used instead of tert-butyl 4-(4-((6-chloro-4-(4-(hydroxymethyl)-4-methylpiperidin-1-yl)pyridin-3-yl)ethynyl)-1H-pyrazol-1-yl)piperidine-1-carboxylate-1H. MS (ESI) m/z=400.0 (M+H)$^+$ Step 4. (1-(2-((2-(1-(Cyclopropylsulfonyl)-1H-pyrazol-4-yl)pyrimidin-4-yl)amino)-5-((1-(1-methylazetidin-3-yl)-1H-pyrazol-4-yl)ethynyl)pyridin-4-yl)-4-methylpiperidin-4-yl)methanol The title compound as a solid (20 mg) was prepared in the same fashion as Step 3 in Example 1 except that (1-(2-chloro-5-((1-(1-methylazetidin-3-yl)-1H-pyrazol-4-yl)ethynyl)pyridin-4-yl)-4-methylpiperidin-4-yl)methanol (75 mg, 0.188 mmol) prepared in Step 3 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 10.25 (s, 1H), 8.65 (s, 1H), 8.45 (s, 1H), 8.44 (d, 1H), 8.19 (s, 1H), 7.73 (s, 1H), 7.71 (s, 1H), 7.33 (s, 1H), 4.97 (quintet, 1H), 4.60 (s, 1H), 3.70-3.68 (m, 4H), 3.29-3.27 (m, 2H), 3.25-3.22 (m, 4H), 2.12 (s, 3H), 1.68-1.64 (m, 2H), 1.38 (d, 2H), 1.35-1.32 (m, 2H), 1.27-1.25 (m, 2H), 1.21 (s, 3H); MS (ESI) m/z=629.2 (M+H)$^+$ Example 149. (1-(2-((2-(1-(Cyclopropylsulfonyl)-1H-pyrazol-4-yl)pyrimidin-4-yl)amino)-5-((4,5,6,7-tetrahydropyrazolo[1,5-a]pyrazin-3-yl)ethynyl)pyridin-4-yl)-4-methylpiperidin-4-yl)methanol The title compound as a solid (12 mg) was prepared in the same fashion as Step 3 in Example 1 except that (1-(2-chloro-5-((4,5,6,7-tetrahydropyrazolo[1,5-a]pyrazin-3-yl)ethynyl)pyridin-4-yl)-4-methylpiperidin-4-yl)methanol (145 mg, 0.377 mmol) prepared in Reference Example 29 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 10.24 (s, 1H), 8.64 (s, 1H), 8.45 (s, 1H), 8.43 (d, 1H), 8.15 (s, 1H), 7.72 (s, 1H), 7.60 (s, 1H), 7.33 (s, 1H), 4.59 (t, 1H), 3.97 (s, 2H), 3.94 (s, 2H), 3.68 (d, 3H), 3.10 (s, 2H), 1.65 (t, 2H), 1.39-1.36 (m, 4H), 1.33-1.27 (m, 2H), 0.95 (s, 3H); MS (ESI) m/z=615.2 (M+H)$^+$ Example 150. (1-(2-((2-(1-(Cyclopropylsulfonyl)-1H-pyrazol-4-yl)pyrimidin-4-yl)amino)-5-((5-methyl-4,5,6,7-tetrahydropyrazolo[1,5-a]pyrazin-3-yl)ethynyl)pyridin-4-yl)-4-methylpiperidin-4-yl)methanol Step 1. (1-(2-Chloro-5-((5-methyl-4,5,6,7-tetrahydropyrazolo[1,5-a]pyrazin-3-yl)ethynyl)pyridin-4-yl)-4-methylpiperidin-4-yl)methanol The suspension of (1-(2-Chloro-5-((4,5,6,7-tetrahydropyrazolo[1,5-a]pyrazin-3-yl)ethynyl)pyridin-4-yl)-4-methylpiperidin-4-yl)methanol (150 mg, 0.389 mmol) prepared in Reference Example 29, paraformaldehyde (116 mg, 3.887 mmol), and sodium cyanoborohydride (256 mg, 4.081 mmol) in MeOH (3 mL) was stirred at 50° C. overnight. After the reaction mixture was cooled, the residue was quenched by sat. NaHCO$_3$soln., extracted with DCM, dried over MgSO$_4$, and then concentrated. The crude product was purified by column chromatography (MeOH/DCM=0-20%) to yield (1-(2-chloro-5-((5-methyl-4,5,6,7-tetrahydropyrazolo[1,5-a]pyrazin-3-yl)ethynyl)pyridin-4-yl)-4-methylpiperidin-4-yl)methanol (77 mg) as an off-white solid. MS (ESI) m/z=400.2 (M+H)$^+$ Step 2. (1-(2-((2-(1-(Cyclopropylsulfonyl)-1H-pyrazol-4-yl)pyrimidin-4-yl)amino)-5-((5-methyl-4,5,6,7-tetrahydropyrazolo[1,5-a]pyrazin-3-yl)ethynyl)pyridin-4-yl)-4-methylpiperidin-4-yl)methanol The title compound as a solid (4 mg) was prepared in the same fashion as Step 3 in Example 1 except that (1-(2- chloro-5-((5-methyl-4,5,6,7-tetrahydropyrazolo[1,5-a]pyrazin-3-yl)ethynyl)pyridin-4-yl)-4-methylpiperidin-4-yl)methanol (75 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 600 MHz) δ 10.23 (s, 1H), 8.65 (s, 1H), 8.45 (s, 1H), 8.42 (d, 1H), 8.16 (s, 1H), 7.70 (s, 1H), 7.62 (s, 1H), 7.31 (s, 1H), 4.70 (s, 1H), 4.10 (t, 2H), 3.24-3.19 (m, 4H), 2.86 (t, 2H), 2.41 (s, 3H), 1.67-1.63 (m, 2H), 1.38 (d, 2H), 1.33-1.31 (m, 2H), 1.27-1.24 (m, 2H), 1.22-1.20 (m, 2H), 0.94 (s, 3H); MS (ESI) m/z=629.0 (M+H)$^+$ Example 151. (1-(2-((2-(1-(Cyclopropylsulfonyl)-1H-pyrazol-4-yl)pyrimidin-4-yl)amino)-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol Step 1. (1-(2-Chloro-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol The suspension of (1-(2-chloro-5-((4,5,6,7-tetrahydropyrazolo[1,5-a]pyrazin-3-yl)ethynyl)pyridin-4-yl)-4-methylpiperidin-4-yl)methanol (150 mg, 0.389 mmol) prepared in Reference Example 29, 1,1-difluoro-2-iodoethane (112 mg, 0.583 mmol), and Cs$_2$CO$_3$ (253 mg, 0.777 mmol) in DMA (4 mL) was stirred at 80° C. overnight. The reaction mixture was cooled, diluted in EA, washed by water, dried over MgSO$_4$, and then concentrated. The crude product was purified by column chromatography (MeOH/DCM=0-20%) to yield (1-(2-chloro-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol (139 mg) as a light yellow solid. MS (ESI) m/z=494.2 (M+H)$^+$ Step 2. (1-(2-((2-(1-(Cyclopropylsulfonyl)-1H-pyrazol-4-yl)pyrimidin-4-yl)amino)-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol The title compound as a solid (17 mg) was prepared in the same fashion as Step 3 in Example 1 except that (1-(2-chloro-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol (136 mg, 0.302 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 600 MHz) δ 10.24 (s, 1H), 8.64 (s, 1H), 8.44 (s, 1H), 8.42 (d, 1H), 8.16 (s, 1H), 7.69 (s, 1H), 7.32 (s, 1H), 6.27 (td, 1H), 4.74 (d, 2H), 4.35 (t, 2H), 4.16 (t, 2H), 3.91 (s, 3H), 3.24-20 (m, 5H), 1.66-1.61 (m, 2H), 1.39 (d, 2H), 1.34-1.31 (m, 2H), 1.27-1.23 (m, 2H), 0.91 (s, 3H)

Example 152. 7-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-2-methyl-7-azaspiro[3.5]nonan-2-ol Step 1. 7-(2-Chloro-5-((1-(3-(dimethylamino)propyl)-1H-pyrazol-4-yl)ethynyl)pyridin-4-yl)-2-methyl-7-azaspiro[3.5]nonan-2-ol The title compound as a solid (280 mg) was prepared in the same fashion as Step 2 in Example 1 except that 7-(2-chloro-5-iodopyridin-4-yl)-2-methyl-7-azaspiro[3.5]nonan-2-ol (500 mg, 1.273 mmol) prepared in Step 1 in Example 13 and 3-(4-ethynylpyrazol-1-yl)-N,N-dimethylpropan-1-amine (271 mg, 1.528 mmol) prepared in Step 1 of Reference Example 27 were used instead of 1-(2-chloro-5-iodopyridin-4-yl)-4-methylpiperazine and 4-ethynyl-1-methylpyrazole. $^1$H-NMR (CDCl$_3$, 600 MHz) δ 8.21 (s, 1H), 7.63 (s, 1H), 7.59 (s, 1H), 6.70 (s, 1H), 4.20 (t, 2H), 3.38-3.35 (m, 4H), 2.25-2.23 (m, 2H), 2.22 (s, 6H), 2.04-1.97 (m, 6H), 1.97-1.85 (m, 2H), 1.73-1.72 (m, 2H), 1.42 (s, 3H)

Step 2. 7-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-2-methyl-7-azaspiro[3.5]nonan-2-ol The title compound as a solid (95 mg) was prepared in the same fashion as Step 3 in Example 1 except that 7-(2-chloro-5-((1-(3-(dimethylamino)propyl)-1H-pyrazol-4-yl)ethynyl)pyridin-4-yl)-2-methyl-7-azaspiro[3.5]nonan-2-ol (250 mg, 0.565 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-$d_6$, 400 MHz) δ 10.24 (s, 1H), 8.64 (s, 1H), 8.45 (s, 1H), 8.43 (d, 1H), 8.15 (s, 1H), 8.04 (s, 1H), 7.72 (s, 1H), 7.65 (s, 1H), 7.32 (s, 1H), 4.77 (s, 1H), 4.14 (t, 2H), 3.35 (s, 2H), 2.17-2.12 (m, 7H), 1.94-1.85 (m, 6H), 1.73 (d, 4H), 1.34-1.25 (m, 4H); MS (ESI) m/z=671.3 (M+H)$^+$ Example 153. 2-(1-(Cyclopropylsulfonyl)-1H-pyrazol-4-yl)-N-(5-((1-methyl-1H-pyrazol-4-yl)ethynyl)-4-(4-(2-(methylamino)ethyl)piperidin-1-yl)pyridin-2-yl)pyrimidin-4-amine Step 1. tert-Butyl (2-(1-(2-chloro-5-((1-methyl-1H-pyrazol-4-yl)ethynyl)pyridin-4-yl)piperidin-4-yl)ethyl)(methyl)carbamate The title compound as a solid (160 mg) was prepared in the same fashion as Step 1 in Example 65 except that tert-butyl methyl(2-(piperidin-4-yl)ethyl)carbamate (123 mg, 0.509 mmol) was used instead of 4-(trifluoromethyl)piperidine HCl. $^1$H-NMR (CDCl$_3$, 600 MHz) δ 8.22 (s, 1H), 7.61 (s, 1H), 7.55 (s, 1H), 6.69 (s, 1H), 4.05 (d, 2H), 3.93 (s, 3H), 3.29 (s, 2H), 2.84-2.80 (m, 5H), 1.86 (d, 2H), 1.53-1.48 (m, 2H), 1.46 (s, 9H), 1.43-1.37 (m, 2H)

Step 2. 2-(1-(Cyclopropylsulfonyl)-1H-pyrazol-4-yl)-N-(5-((1-methyl-1H-pyrazol-4-yl)ethynyl)-4-(4-(2-(methylamino)ethyl)piperidin-1-yl)pyridin-2-yl)pyrimidin-4-amine The suspension of 2-(1-cyclopropylsulfonylpyrazol-4-yl)pyrimidin-4-amine (90 mg, 0.339 mmol), tert-butyl (2-(1-(2-chloro-5-((1-methyl-1H-pyrazol-4-yl)ethynyl)pyridin-4-yl)piperidin-4-yl)ethyl)(methyl)carbamate (155 mg, 0.339 mmol) prepared in Step 1, Cs$_2$CO$_3$ (221 mg, 0.679 mmol), XPhos (32.35 mg, 0.068 mmol), and Pd$_2$(dba)$_3$ (31.07 mg, 0.034 mmol) in 1,4-dioxane (3 mL) was stirred at 90° C. overnight. The reaction mixture was cooled, filtered through Celite, and then concentrated. After the residue was dissolved with 20% TFA in DCM (5 mL), the reaction mixture was stirred at room temperature overnight. The mixture was quenched by sat. NaHCO$_3$ soln., extracted with DCM, dried over MgSO$_4$, and then concentrated. The crude product was purified by column chromatography (MeOH/DCM=0-30%) to yield 2-(1-(cyclopropylsulfonyl)-1H-pyrazol-4-yl)-N-(5-

((1-methyl-1H-pyrazol-4-yl)ethynyl)-4-(4-(2-(methylamino)ethyl)piperidin-1-yl)pyridin-2-yl)pyrimidin-4-amine (7.6 mg) as an off-white solid. $^1$H-NMR (MeOD, 400 MHz) δ 8.72 (s, 1H), 8.42 (s, 1H), 8.34 (d, 1H), 8.12 (s, 1H), 7.81 (s, 1H), 7.63 (s, 1H), 7.59 (s, 1H), 7.24 (s, 1H), 7.22 (s, 1H), 4.10 (d, 2H), 3.90 (s, 3H), 3.09-3.04 (m, 4H), 2.87 (t, 2H), 2.72 (s, 3H), 2.02-1.98 (m, 2H), 1.94-1.91 (m, 2H), 1.70-1.66 (m, 2H), 1.28-1.11 (m, 2H); MS (ESI) m/z=587.2 (M+H)$^+$ Example 154. 2-(1-(Cyclopropylsulfonyl)-1H-pyrazol-4-yl)-N-(5-((1-methyl-1N-pyrazol-4-yl)ethynyl)-4-(2,8-diazaspiro[4.5]decan-2-yl)pyridin-2-yl)pyrimidin-4-amine Step 1. tert-Butyl 2-(2-chloro-5-((1-methyl-1H-pyrazol-4-yl)ethynyl)pyridin-4-yl)-2,8-diazaspiro[4.5]decane-8-carboxylate The title compound as a solid (155 mg) was prepared in the same fashion as Step 1 in Example 65 except that tert-butyl 2,8-diazaspiro[4.5]decane-8-carboxylate (122 mg, 0.509 mmol) was used instead of 4-(trifluoromethyl)piperidine HCl. $^1$H-NMR (CDCl$_3$, 600 MHz) δ 8.12 (s, 1H), 7.58 (s, 1H), 7.51 (s, 1H), 6.38 (s, 1H), 3.92 (s, 3H), 3.77 (t, 2H), 3.50 (s, 2H), 3.49-3.47 (m, 2H), 3.39-3.35 (m, 2H), 1.87 (t, 2H), 1.57-1.53 (m, 4H), 1.47 (s, 9H)

Step 2. 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-2-yl)pyridin-2-yl)pyrimidin-4-amine The title compound as a solid (3 mg) was prepared in the same fashion as Step 2 in Example 153 except that tert-butyl 2-(2-chloro-5-((1-methyl-1H-pyrazol-4-yl)ethynyl)pyridin-4-yl)-2,8-diazaspiro[4.5]decane-8-carboxylate (133 mg, 0.302 mmol) was used instead of tert-butyl (2-(1-(2-chloro-5-((1-methyl-1H-pyrazol-4-yl)ethynyl)pyridin-4-yl)piperidin-4-yl)ethyl)(methyl)carbamate. $^1$1-NMR (MeOD, 600 MHz) δ 8.71 (s, 1H), 8.42 (s, 1H), 8.31 (d, 1H), 8.00 (s, 1H), 7.79 (s, 1H), 7.59 (s, 1H), 7.25 (s, 1H), 7.22 (d, 2H), 3.91 (s, 3H), 3.78-3.75 (m, 4H), 3.05-3.03 (m, 1H), 2.91-2.87 (m, 2H), 2.81-2.77 (m, 2H), 1.94 (t, 2H), 1.64-1.60 (m, 4H), 1.45-1.41 (m, 2H), 1.27-1.25 (m, 2H); MS (ESI) m/z=585.1 (M+H)$^+$ Example 155. 2-(1-(Cyclopropylsulfonyl)-1H-pyrazol-4-yl)-N-(5-((1-methyl-1H-pyrazol-4-yl)ethynyl)-4-(2,7-diazaspiro[3.5]nonan-2-yl)pyridin-2-yl)pyrimidin-4-amine Step 1. tert-Butyl 2-(2-chloro-5-((1-methyl-1H-pyrazol-4-yl)ethynyl)pyridin-4-yl)-2,7-diazaspiro[3.5]nonane-7-carboxylate The title compound as a solid (160 mg) was prepared in the same fashion as Step 1 in Example 65 except that tert-butyl 2,7-diazaspiro[3.5]nonane-7-carboxylate HCl (134 mg, 0.509 mmol) was used instead of 4-(trifluoromethyl)piperidine HCl. $^1$H-NMR (CDCl$_3$, 600 MHz) δ 8.06 (s, 1H), 7.59 (s, 1H), 7.52 (s, 1H), 6.18 (s, 1H), 3.99 (s, 2H), 3.93 (s, 3H), 3.39 (t, 4H), 1.78 (t, 4H), 1.46 (s, 9H)

Step 2. 2-(1-(Cyclopropylsulfonyl)-1H-pyrazol-4-yl)-N-(5-((1-methyl-1H-pyrazol-4-yl)ethynyl)-4-(2,7-diazaspiro[3.5]nonan-2-yl)pyridin-2-yl)pyrimidin-4-amine The title compound as a solid (2 mg) was prepared in the same fashion as Step 2 in Example 153 except that tert-butyl 2-(2-chloro-5-((1-methyl-1H-pyrazol-4-yl)ethynyl)pyridin-4-yl)-2,7-diazaspiro[3.5]nonane-7-carboxylate (138 mg, 0.302 mmol) was used instead of tert-butyl (2-(1-(2-chloro-5-((1-methyl-1H-pyrazol-4-yl)ethynyl)pyridin-4-yl)piperidin-4-yl)ethyl)(methyl)carbamate. $^1$H-NMR (DMSO-d$_6$, 600 MHz) δ 10.14 (s, 1H), 8.65 (s, 1H), 8.46 (d, 1H), 8.41 (s, 1H), 8.41 (d, 1H), 8.02 (d, 2H), 7.99 (d, 1H), 7.64 (s, 1H), 7.30 (s, 1H), 7.20 (s, 1H), 3.99-3.97 (m, 2H), 3.85 (s, 3H), 3.28-3.25 (m, 3H), 2.64 (s, 3H), 1.68 (s, 3H), 1.35-1.30 (m, 2H), 1.28-1.25 (m, 2H); MS (ESI) m/z=571.0 (M+H)$^+$ Example 156. 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-8-yl)pyridin-2-yl)pyrimidin-4-amine Step 1. tert-Butyl 8-(2-chloro-5-((1-methyl-1H-pyrazol-4-yl)ethynyl)pyridin-4-yl)-2,8-diazaspiro[4.5]decane-2-carboxylate The title compound as a solid (151 mg) was prepared in the same fashion as Step 1 in Example 65 except that tert-butyl 2,8-diazaspiro[4.5]decane-2-carboxylate (122 mg, 0.509 mmol) was used instead of 4-(trifluoromethyl)piperidine HCl. $^1$H-NMR (CDCl$_3$, 600 MHz) δ 8.24 (s, 1H), 7.61 (s, 1H), 7.55 (s, 1H), 6.72 (d, 1H), 3.94 (s, 3H), 3.56-3.33 (m, 8H), 1.80-1.76 (m, 2H), 1.74-1.70 (m, 4H), 1.47 (s, 9H)

Step 2. 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-8-yl)pyridin-2-yl)pyrimidin-4-amine The title compound as a solid (7 mg) was prepared in the same fashion as Step 2 in Example 153 except that tert-butyl 8-(2-chloro-5-((1-methyl-1H-pyrazol-4-yl)ethynyl)pyridin-4-yl)-2,8-diazaspiro[4.5]decane-2-carboxylate (138 mg, 0.302 mmol) prepared in Step 1 was used instead of tert-butyl (2-(1-(2-chloro-5-((1-methyl-1H-pyrazol-4-yl)ethynyl)pyridin-4-yl)piperidin-4-yl)ethyl)(methyl)carbamate. $^1$H-NMR (MeOD, 600 MHz) δ 8.71 (s, 1H), 8.41 (s, 1H), 8.33 (d, 1H), 8.12 (s, 1H), 7.84 (s, 1H), 7.75 (s, 1H), 7.61 (s, 1H), 7.17 (d, 1H), 3.91 (s, 3H), 3.61-3.58 (m, 2H), 3.47-3.41 (m, 4H), 3.21 (s, 2H), 3.07-3.04 (m, 1H), 2.14 (s, 2H), 2.06 (t, 2H), 1.91-1.84 (m, 4H), 1.46-1.41 (m, 2H), 1.29-1.25 (m, 2H); MS (ESI) m/z=585.1 (M+H)$^+$ Example 157. (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol Step 1. (1s,4s)-4-((2-Chloro-5-((4-(morpholinomethyl)phenyl)ethynyl)pyridin-4-yl)amino)cyclohexan-1-ol The suspension of 4-(4-(((6-chloro-4-fluoropyridin-3-yl)ethynyl)benzyl)morpholine (500 mg, 1.512 mmol) prepared in Reference Example 30, cis-4-aminocyclohexanol HCl (298 mg, 1.965 mmol) and DIPEA (0.53 mL, 3.023 mmol) in DMF (10 mL) was stirred at 80° C. overnight. The reaction mixture was cooled, diluted in EA, washed by water, dried over MgSO$_4$, and then concentrated. The crude product was purified by column chromatography (EA/n-Hex=0-100%) to yield (1s,4s)-4-((2-chloro-5-((4-(morpholinomethyl)phenyl)ethynyl)pyridin-4-yl)amino)cyclohexan-1-ol (561 mg) as a pale yellow solid. $^1$H-NMR (CDCl$_3$, 400 MHz) δ 8.15 (s, 1H), 7.48-7.46 (d, 2H), 7.37-7.35 (d, 2H), 6.49 (s, 1H), 5.19-5.17 (d, 1H), 4.00 (s, 1H), 3.74-3.71 (t, 4H), 3.52 (s, 2H), 3.47 (s, 1H), 2.46 (s, 4H), 1.84-1.81 (m, 2H), 1.77 (s, 4H); MS (ESI) m/z=426.1 (M+H)$^+$ Step 2. (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol The title compound as a solid (144 mg) was prepared in the same fashion as Step 3 in Example 1, except that (1s,4s)-4-((2-chloro-5-((4-(morpholinomethyl)phenyl)ethynyl)pyridin-4-yl)amino)cyclohexan-1-ol (561 mg, 1.32 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.50 (brs, 1H), 8.43 (s, 1H), 8.38-8.37 (d, 1H), 8.16 (s, 1H), 7.48-7.46 (d, 2H), 7.35-7.33 (d, 2H), 7.22 (s, 1H), 7.09-7.07 (d, 1H), 5.27-5.25 (d, 1H), 3.93-3.92 (t, 1H), 3.74-3.70 (q, 4H), 3.66-3.64 (d, 1H), 3.51 (s, 2H), 2.81-2.80 (m, 1H), 2.46-2.44 (t, 4H), 2.02 (s, 1H), 1.92-1.87 (q, 4H), 1.82-1.78 (q, 2H), 1.73-1.70 (t, 2H), 1.51-1.50 (q, 2H), 1.27-1.22 (q, 2H); MS (ESI) m/z=656.1 (M+H)$^+$ Example 158. (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)-1-methylcyclohexan-1-ol Step 1. (1s,4S)-4-((2-Chloro-5-((4-(morpholinomethyl)phenyl)ethynyl)pyridin-4-yl)amino)-1-methylcyclohexan-1-ol The title compound as a solid (395 mg) was prepared in the same fashion as Step 1 in Example 157 except that cis-4-amino-1-methylcyclohexanol (186 mg, 1.44 mmol) was used instead of cis-4-aminocyclohexanol HCl. MS (ESI) m/z=441.1 (M+H)$^+$ Step 2. (1s, 4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)-1-methylcyclohexan-1-ol The title compound (102 mg) was prepared in the same fashion as Step 3 in Example 1, except that (1s,4S)-4-((2-chloro-5-((4-(morpholinomethyl)phenyl)ethynyl)pyridin-4-yl)amino)-1-methylcyclohexan-1-ol (395 mg, 0.898 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.85 (brs, 1H), 8.63 (s, 1H), 8.43-8.42 (d, 1H), 8.36-8.34 (d, 1H), 7.64 (s, 1H), 7.47-7.42 (q, 3H), 7.32-7.30 (d, 3H), 7.14-7.13 (d, 1H), 5.11-5.09 (d, 1H), 3.70-3.68 (t, 4H), 3.60 (s, 3H), 2.81-2.77 (m, 1H), 2.43 (s, 4H), 1.72-1.66 (q, 2H), 1.59-1.53 (t, 2H), 1.50-1.46 (m, 2H), 1.21-1.16 (q, 2H) Example 159. (1R, 3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol Step 1. (1R,3S)-3-((2-Chloro-5-((4-(morpholinomethyl)phenyl)ethynyl)pyridin-4-yl)amino)cyclohexan-1-ol The title compound as a solid (252 mg) was prepared in the same fashion as Step 1 in Example 157 except that (1R,3S)-3-aminocyclohexanol HCl (119 mg, 0.786 mmol) was used instead of cis-4-aminocyclohexanol HCl. $^1$H-NMR (CDCl$_3$, 400 MHz) δ 7.95 (s, 1H), 7.38-7.36 (d, 2H), 7.19-7.17 (d, 2H), 3.90 (brs, 2H), 3.57-3.55 (t, 4H), 3.48 (s, 1H), 3.35 (s, 2H), 2.29 (s, 3H), 1.99-1.91 (t, 1H), 1.81-1.79 (d, 1H), 1.71-1.65 (t, 2H), 1.59-1.54 (q, 1H), 1.45 (s, 2H), 1.29-1.28 (d, 2H); MS (ESI) m/z=426.1 (M+H)$^+$ Step 2. (1R,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol The title compound (45 mg) was prepared in the same fashion as Step 3 in Example 1, except that (1R,3S)-3-((2-chloro-5-((4-(morpholinomethyl)phenyl)ethynyl)pyridin-4-yl)amino)cyclohexan-1-ol (252 mg, 0.592 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.85 (brs, 1H), 8.62 (s, 1H), 8.43 (s, 1H), 8.38-8.35 (t, 1H), 8.13-8.11 (d, 1H), 7.48-7.45 (t, 2H), 7.31-7.29 (d, 2H), 7.15 (s, 1H), 7.08 (s, 1H), 6.25 (brs, 1H), 4.02 (s, 1H), 3.69 (s, 4H), 3.48 (s, 3H), 2.87-2.80 (m, 1H), 2.43 (s, 4H), 1.90-1.83 (t, 4H), 1.62-1.60 (d, 2H), 1.52-1.48 (m, 2H), 1.23-1.18 (q, 2H); MS (ESI) m/z=656.1 (M+H)$^+$ Example 160. (1S,3R)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol Step 1. (1S,3R)-3-((2-Chloro-5-((4-(morpholinomethyl)phenyl)ethynyl)pyridin-4-yl)amino)cyclohexan-1-ol The title compound as a solid (246 mg) was prepared in the same fashion as Step 1 in Example 157 except that (1S,3R)-3-aminocyclohexanol (102 mg, 0.786 mmol) was used instead of cis-4-aminocyclohexanol HCl. $^1$H-NMR (CDCl$_3$, 400 MHz) δ 7.93 (s, 1H), 7.37-7.35 (d, 2H), 7.17-7.15 (d, 2H), 6.29 (brs, 2H), 3.98-3.88 (m, 1H), 3.55-3.53 (t, 4H), 3.47 (s, 1H), 3.33 (s, 3H), 2.27 (s, 3H), 1.97-1.94 (d, 1H), 1.80-1.75 (m, 1H), 1.69-1.63 (t, 2H), 1.58-1.53 (q, 2H), 1.44 (s, 2H), 1.29-1.26 (d, 2H); MS (ESI) m/z=426.1 (M+H)$^+$ Step 2. (1S,3R)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol The title compound (63.6 mg) was prepared in the same fashion as Step 3 in Example 1, except that (1S,3R)-3-((2-chloro-5-((4-(morpholinomethyl)phenyl)ethynyl)pyridin-4-yl)amino)cyclohexan-1-ol (246 mg, 0.578 mmol) prepared in Step 1 was used instead of 1-(2-chloro-5-((1-methyl-1H- pyrazol-4-yl)ethynyl)pyridin-4-yl)-4-methylpiperazine. ¹H-NMR (CDCl₃, 400 MHz) δ 8.62-8.60 (d, 1H), 8.43 (s, 1H), 8.38-8.35 (t, 1H), 8.13-8.10 (d, 1H), 7.48-7.45 (t, 2H), 7.30-7.28 (d, 3H), 7.17 (s, 1H), 7.07 (s, 1H), 6.42 (brs, 1H), 4.02 (s, 1H), 3.70-3.68 (t, 4H), 3.48 (s, 2H), 2.87-2.79 (m, 1H), 2.42 (s, 4H), 2.24-2.21 (d, 1H), 1.89-1.83 (t, 4H), 1.70-1.66 (t, 2H), 1.62-1.60 (d, 2H), 1.52-1.48 (q, 2H), 1.26-1.20 (q, 2H); MS (ESI) m/z=656.1 (M+H)⁺

Example 161. (1 S,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol Step 1. (1S,3S)-3-((2-Chloro-5-((4-(morpholinomethyl)phenyl)ethynyl)pyridin-4-yl)amino)cyclohexan-1-ol The title compound as a solid (243 mg) was prepared in the same fashion as Step 1 in Example 157 except that (1S,3S)-3-aminocyclohexanol HCl (119 mg, 0.786 mmol) was used instead of cis-4-aminocyclohexanol HCl. ¹H-NMR (CDCl₃, 400 MHz) δ 8.03 (s, 1H), 7.39-7.38 (d, 2H), 7.28-7.26 (d, 2H), 6.49 (s, 1H), 5.02-5.00 (d, 1H), 4.11 (brs, 1H), 3.81 (brs, 2H), 3.64 (s, 4H), 3.44 (s, 2H), 2.37 (s, 4H), 2.02-1.91 (q, 2H), 1.63-1.32 (m, 4H); MS (ESI) m/z=426.1 (M+H)⁺

Step 2. (1S,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol The title compound (43 mg) was prepared in the same fashion as Step 3 in Example 1, except that (1S,3S)-3-((2-chloro-5-((4-(morpholinomethyl)phenyl)ethynyl)pyridin-4-yl)amino)cyclohexan-1-ol (243 mg, 0.570 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.65 (s, 1H), 8.47 (s, 1H), 8.39-8.36 (t, 2H), 8.14 (s, 1H), 7.46-7.45 (d, 2H), 7.35-7.33 (d, 3H), 7.16-7.13 (t, 2H), 5.07-5.05 (d, 1H), 4.01-4.00 (d, 1H), 3.72-3.70 (t, 4H), 3.51 (s, 2H), 2.88-2.82 (m, 1H), 2.45 (s, 4H), 2.07-2.01 (q, 2H), 1.90-1.87 (t, 1H), 1.74-1.63 (t, 4H), 1.53-1.45 (q, 41-1), 1.21-1.18 (t, 2H); MS (ESI) m/z=656.1 (M+H)⁺

Example 162. 2-((1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexyl)propan-2-ol Step 1. 2-((1s,4s)-4-((2-Chloro-5-((4-(morpholinomethyl)phenyl)ethynyl)pyridin-4-yl)amino)cyclohexyl)propan-2-ol The title compound as a solid (263 mg) was prepared in the same fashion as Step 1 in Example 157 except that 2-((1s,4s)-4-aminocyclohexyl)propan-2-ol (124 mg, 0.786 mmol) was used instead of cis-4-aminocyclohexanol HCl. ¹H-NMR (CDCl₃, 400 MHz) δ 7.98 (s, 1H), 7.85 (s, 1H), 7.34-7.32 (d, 2H), 7.21-7.19 (d, 2H), 6.34 (s, 1H), 5.39-5.38 (d, 1H), 3.65 (s, 1H), 3.57-3.55 (t, 4H), 3.36 (s, 1H), 2.80 (s, 3H), 2.72 (s, 3H), 2.30 (s, 4H), 1.89-1.83 (t, 2H), 1.68-1.65 (d, 2H), 1.54-1.47 (t, 2H), 1.15-1.12 (d, 2H), 1.02 (s, 6H); MS (ESI) m/z=468.1 (M+H)⁺

Step 2. 2-((1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexyl)propan-2-ol The title compound (45 mg) was prepared in the same fashion as Step 3 in Example 1, except that 2-((1s,4s)-4-((2-chloro-5-((4-(morpholinomethyl)phenyl)ethynyl)pyridin-4-yl)amino)cyclohexyl)propan-2-ol (263 mg, 0.562 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.65 (s, 1H), 8.43 (s, 1H), 8.38-8.36 (d, 2H), 8.15-8.14 (d, 1H), 7.47-7.41 (m, 2H), 7.33-7.31 (m, 3H), 6.97-6.95 (d, 1H), 5.52-5.50 (d, 1H), 3.96 (s, 1H), 3.72-3.70 (t, 4H), 3.50 (s, 2H), 2.87-2.81 (m, 1H), 2.44 (s, 4H), 2.11-2.08 (d, 2H), 1.81-1.78 (d, 4H), 1.54-1.50 (m, 2H), 1.47-1.31 (m, 4H), 1.27-1.22 (q, 2H), 1.20-1.15 (q, 6H); MS (ESI) m/z=698.1 (M+H)⁺

Example 163. (1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexan-1-ol Step 1. (1s,4S)-4-((2-Chloro-5-((4-((4-methylpiperazin-1-yl)methyl)phenyl)ethynyl)pyridin-4-yl)amino)cyclohexan-1-ol The title compound (405 mg) was prepared in the same fashion as Step 1 in Example 157, except that 1-(4-((6-chloro-4-fluoropyridin-3-yl)ethynyl)benzyl)-4-methylpiperazine (350 mg, 1.018 mmol) prepared in Reference Example 31 was used instead of 4-(4-((6-chloro-4-fluoropyridin-3-yl)ethynyl)benzyl)morpholine. MS (ESI) m/z=439.2 (M+H)⁺

Step 2. (1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexan-1-ol The title compound (45 mg) was prepared in the same fashion as Step 3 in Example 1, except that (1 s, 4s)-4-((2-chloro-5-((4-((4-methylpiperazin-1-yl)methyl)phenyl)ethynyl)pyridin-4-yl)amino)cyclohexan-1-ol (405 mg, 0.923 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.34-8.32 (d, 1H), 8.15-8.13 (d, 1H), 8.05 (s, 1H), 7.47-7.45 (d, 2H), 7.33-7.31 (d, 2H), 7.22 (s, 1H), 7.00-6.99 (d, 1H), 5.22-5.20 (d, 1H), 3.95 (s, 4H), 3.62 (m, 2H), 3.52 (s, 2H), 3.47 (s, 3H), 2.47 (brs, 2H), 2.28 (s, 4H), 2.10 (brs, 2H), 1.90-1.86 (q, 4H), 1.80-1.74 (m, 4H)

Example 164. (1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-yl)methanol Step 1. (1-(2-Chloro-5-((4-((4-methylpiperazin-1-yl)methyl)phenyl)ethynyl)pyridin-4-yl)-4-methylpiperidin-4-yl)methanol The title compound as a solid (263 mg) was prepared in the same fashion as Step 1 in Example 157 except that (4-methylpiperidin-4-yl)methanol (125 mg, 0.971 mmol) and 1-(4-((6-chloro-4-fluoropyridin-3-yl)ethynyl)benzyl)-4-methylpiperazine (206 mg, 0.599 mmol) prepared in Reference Example 31 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.16 (s, 1H), 6.69 (s, 1H), 3.77-3.74 (t, 4H), 3.68-3.66 (t, 2H), 3.65-3.63 (t, 2H), 3.56 (s, 2H), 3.22-3.15 (m, 2H), 2.64-2.62 (t, 4H), 1.75-1.68 (m, 2H), 1.45-1.41 (m, 2H), 1.05 (s, 3H)

Step 2. (1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-yl)methanol The title compound (19.6 mg) was prepared in the same fashion as Step 3 in Example 1, except that (1-(2-chloro-5-((4-((4-methylpiperazin-1-yl)methyl)phenyl)ethynyl)pyridin-4-yl)-4-methylpiperidin-4-yl)methanol (263 mg, 0.581 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.40-8.38 (d, 1H), 8.27 (s, 1H), 7.63 (s, 1H), 7.45-7.43 (d, 2H), 7.33-7.31 (d, 2H), 6.98-6.96 (d, 1H), 3.75-3.71 (q, 2H), 3.52-3.49 (d, 2H), 3.48-3.45 (d, 2H), 3.45-3.39 (q, 2H), 2.85-2.81 (m, 1H), 2.49 (brs, 6H), 2.30 (s, 3H), 2.10 (brs, 2H), 1.83-1.77 (m, 2H), 1.61-1.58 (q, 2H), 1.57-1.50 (m, 2H), 1.23-1.21 (q, 2H), 1.08-1.07 (d, 3H); MS (ESI) m/z=683.3 (M+H)$^+$ Example 165. (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)cyclohexan-1-ol Step 1. (1s,4s)-4-((2-Chloro-5-(3-morpholinoprop-1-yn-1-yl)pyridin-4-yl)amino)cyclohexan-1-ol The title compound (304 mg) was prepared in the same fashion as Step 1 in Example 157, except that 4-(3-(6-chloro-4-fluoropyridin-3-yl)prop-2-yn-1-yl)morpholine (245 mg, 0.962 mmol) prepared in Reference Example 32 was used instead of 4-(4-((6-chloro-4-fluoropyridin-3-yl)ethynyl)benzyl)morpholine. MS (ESI) m/z=350.1 (M+H)$^+$ Step 2. (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)cyclohexan-1-ol The title compound (183 mg) was prepared in the same fashion as Step 3 in Example 1, except that (1s,4s)-4-((2-chloro-5-(3-morpholinoprop-1-yn-1-yl)pyridin-4-yl)amino)cyclohexan-1-ol (304 mg, 0.869 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=580.1 (M+H)$^+$ Example 166. (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)-1-methylcyclohexan-1-ol Step 1. (1s,4s)-4-((2-Chloro-5-(3-morpholinoprop-1-yn-1-yl)pyridin-4-yl)amino)-1-methylcyclohexan-1-ol The title compound as a solid (221 mg) was prepared in the same fashion as Step 1 in Example 157 except that cis-4-amino-1-methylcyclohexanol (93 mg, 0.723 mmol) and 4-(3-(6-chloro-4-fluoropyridin-3-yl)prop-2-yn-1-yl)morpholine (242 mg, 0.948 mmol) prepared in Reference Example 32 were used instead of cis-4-aminocyclohexanol HCl and 4-(4-((6-chloro-4-fluoropyridin-3-yl)ethynyl)benzyl)morpholine. MS (ESI) m/z=364.0 (M+H)$^+$ Step 2. (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)-1-methylcyclohexan-1-ol The title compound (9 mg) was prepared in the same fashion as Step 3 in Example 1, except that (1s,4s)-4-((2-chloro-5-(3-morpholinoprop-1-yn-1-yl)pyridin-4-yl)amino)-1-methylcyclohexan-1-ol (221 mg, 0.607 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.63 (s, 1H), 8.43-8.40 (t, 2H), 7.96 (s, 1H), 7.37 (s, 1H), 7.12-7.11 (d, 1H), 5.27-5.25 (d, 1H), 3.79-3.77 (t, 5H), 3.60-3.58 (d, 4H), 3.51-3.49 (t, 2H), 2.83-2.79 (m, 1H), 2.66-2.64 (t, 4H), 1.98-1.95 (d, 2H), 1.74-1.69 (t, 2H), 1.63-1.60 (t, 2H), 1.56-1.50 (m, 2H), 1.21 (s, 3H)

Example 167. (1s,4s)-4-((2-((2-(1-(Cyclopropylsulfonyl)-1H-pyrazol-4-yl)pyrimidin-4-yl)amino)-5-((1-methyl-1,2,4-triazol-3-yl)ethynyl)pyridin-4-yl)amino)cyclohexan-1-ol Step 1. 2-Chloro-4-fluoro-5-((1-methyl-1H-1,2,4-triazol-3-yl)ethynyl)pyridine The title compound as a solid (669 mg) was prepared in the same fashion as Reference Example 18 except that 3-ethynyl-1-methyl-1,2,4-triazole (563 mg, 5.257 mmol) was used instead of 4-ethynyl-1-methylpyrazole. MS (ESI) m/z=237.0 (M+H)$^+$ Step 2. (1s,4s)-4-((2-Chloro-5-((1-methyl-1H-1,2,4-triazol-3-yl)ethynyl)pyridin-4-yl)amino)cyclohexan-1-ol The title compound (243 mg) was prepared in the same fashion as Step 1 in Example 157, except that 2-chloro-4-fluoro-5-((1-methyl-1H-1,2,4-triazol-3-yl)ethynyl)pyridine (300 mg, 1.142 mmol) prepared in Step 1 was used instead of 4-(4-((6-chloro-4-fluoropyridin-3-yl)ethynyl)benzyl)morpholine. MS (ESI) m/z=332.1 (M+H)$^+$ Step 3. (1s,4s)-4-((2-((2-(1-(Cyclopropylsulfonyl)-1H-pyrazol-4-yl)pyrimidin-4-yl)amino)-5-((1-methyl-1H-1,2,4-triazol-3-yl)ethynyl)pyridin-4-yl)amino)cyclohexan-1-ol The title compound (46 mg) was prepared in the same fashion as Step 3 in Example 1, except that (1s,4s)-4-((2-chloro-5-((1-methyl-1H-1,2,4-triazol-3-yl)ethynyl)pyridin-4-yl)amino)cyclohexan-1-ol (223 mg, 0.671 mmol) prepared in Step 2 was used instead of 1-(2-chloro-5-((1-methyl-1H-pyrazol-4-yl)ethynyl)pyridin-4-yl)-4-methylpiperazine. MS (ESI) m/z=561.0 (M+H)$^+$ Example 168. (1S,3R)-3-((2-((2-(1-(Cyclopropylsulfonyl)-1H-pyrazol-4-yl)pyrimidin-4-yl)amino)-5-((5-ethylthiazol-2-yl)ethynyl)pyridin-4-yl)amino)cyclohexan-1-ol Step 1. 2-((6-Chloro-4-fluoropyridin-3-yl)ethynyl)-5-ethylthiazole The title compound as a solid (343 mg) was prepared in the same fashion as Reference Example 18 except that 5-ethyl-2-ethynyl-1,3-thiazole (460 mg, 3.351 mmol) was used instead of 4-ethynyl-1-methylpyrazole. MS (ESI) m/z=266.9 (M+H)⁺

Step 2. (1S,3R)-3-((2-Chloro-5-((5-ethylthiazol-2-yl)ethynyl)pyridin-4-yl)amino)cyclohexan-1-ol The title compound as a solid (102 mg) was prepared in the same fashion as Step 1 in Example 157 except that (1S,3R)-3-aminocyclohexanol (72 mg, 0.556 mmol) and 2-((6-chloro-4-fluoropyridin-3-yl)ethynyl)-5-ethylthiazole (114 mg, 0.427 mmol) prepared in Step 1 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ7.98 (s, 1H), 7.34 (s, 1H), 6.57 (brs, 1H), 6.29 (s, 1H), 4.25 (s, 1H), 4.01-3.93 (m, 2H), 3.51 (s, 1H), 2.75-2.69 (q, 1H), 1.80-1.74 (m, 1H), 1.64-1.59 (t, 3H), 1.49 (s, 2H), 1.28-1.26 (d, 1H), 1.19-1.16 (q, 3H)

Step 3. (1S,3R)-3-((2-((2-(1-(Cyclopropylsulfonyl)-1H-pyrazol-4-yl)pyrimidin-4-yl)amino)-5-((5-ethylthiazol-2-yl)ethynyl)pyridin-4-yl)amino)cyclohexan-1-ol The title compound as an off-white solid (21 mg) was prepared in the same fashion as Step 3 in Example 1, except that (1S,3R)-3-((2-chloro-5-((5-ethylthiazol-2-yl)ethynyl)pyridin-4-yl)amino)cyclohexan-1-ol (102 mg, 0.280 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.62-8.60 (d, 1H), 8.42-8.36 (q, 31-1), 8.24-8.22 (s, 1H), 7.48 (s, 1H), 7.27 (s, 1H), 7.05 (s, 1H), 6.31 (d, 1H), 5.03 (s, 2H), 3.86 (s, 1H), 2.87-2.78 (m, 4H), 1.78-1.77 (d, 4H), 1.52-1.48 (m, 4H), 1.34-1.31 (t, 2H), 1.27-1.24 (t, 3H), 1.20-1.17 (q, 2H)

Example 169. (1 S,3R)-3-((5-((3-Aminophenyl)ethynyl)-2-((2-(1-(cyclopropylsulfonyl)-1/1 pyrazol-4-yl)pyrimidin-4-yl)amino)pyridin-4-yl)amino)cyclohexan-1-ol Step 1. 3-((4-Chloro-6-fluoropyridin-3-yl)ethynyl)aniline The title compound as an off-white solid (1.66 g) was prepared in the same fashion as Reference Example 18 except that 3-ethynylaniline (1.44 mL, 12.804 mmol) was used instead of 4-ethynyl-1-methylpyrazole. MS (ESI) m/z=247.0 (M+H)⁺

Step 2. (1 S,3R)-3-((5-((3-Aminophenyl)ethynyl)-2-fluoropyridin-4-yl)amino)cyclohexan-1-ol The title compound as a yellow solid (228 mg) was prepared in the same fashion as Step 1 in Example 157 except that (1S,3R)-3-aminocyclohexanol HCl (160 mg, 1.054 mmol) and 3-((4-chloro-6-fluoropyridin-3-yl)ethynyl)aniline (200 mg, 0.811 mmol) prepared in Step 1 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.10-8.01 (d, 1H), 7.07-7.03 (m, 1H), 6.86-6.84 (d, 1H), 6.79 (s, 1H), 6.60-6.58 (d, 1H), 6.36 (s, 1H), 6.15 (brs, 1H), 3.91 (s, 1H), 3.82-3.77 (d, 2H), 3.48 (s, 1H), 2.05-2.02 (d, 1H), 1.83-1.73 (q, 31-1), 1.56-1.54 (d, 1H), 1.45 (s, 2H), 1.33-1.31 (t, 1H); MS (ESI) m/z=342.1 (M+H)⁺

Step 3. (1 S,3R)-3-((5-((3-Aminophenyl)ethynyl)-2-((2-(1-(cyclopropylsulfonyl)-1H-pyrazol-4-yl)pyrimidin-4-yl)amino)pyridin-4-yl)amino)cyclohexan-1-ol The title compound as an off-white solid (18 mg) was prepared in the same fashion as Step 3 in Example 1, except that (1S,3R)-3-((5-((3-aminophenyl)ethynyl)-2-fluoropyridin-4-yl)amino)cyclohexan-1-ol (228 mg, 0.662 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.63-8.61 (d, 2H), 8.44 (s, 1H), 8.40-8.38 (t, 2H), 8.25-8.24 (d, 1H), 8.14 (s, 1H), 7.14-7.11 (t, 2H), 6.94-6.92 (d, 1H), 6.87-6.86 (d, 1H), 6.67-6.65 (t, 1H), 6.32-6.31 (d, 1H), 4.98 (s, 2H), 4.09 (s, 1H), 3.71 (brs, 2H), 2.82-2.80 (m, 2H), 2.30-2.20 (d, 1H), 1.91-1.88 (t, 2H), 1.54-1.50 (m, 4H), 1.20-1.17 (q, 2H)

Example 170. (1 S,3R)-3-((2-((2-(1-(Cyclopropylsulfonyl)-1H-pyrazol-4-yl)pyrimidin-4-yl)amino)-5-((5-methylpyrazin-2-yl)ethynyl)pyridin-4-yl)amino)cyclohexan-1-ol Step 1. 2-((6-Chloro-4-fluoropyridin-3-yl)ethynyl)-5-methylpyrazine The title compound as an off-white solid (821 mg) was prepared in the same fashion as Reference Example 18 except that 2-ethynyl-5-methylpyrazine (480 mg, 4.059 mmol) was used instead of 4-ethynyl-1-methylpyrazole. ¹H-NMR (CDCl₃, 400 MHz) δ 8.63 (s, 1H), 8.56-8.54 (d, 1H), 8.45 (s, 1H), 7.16-7.14 (d, 1H), 2.57 (s, 3H)

Step 2. (1S,3R)-3-((2-Chloro-5-((5-methylpyrazin-2-yl)ethynyl)pyridin-4-yl)amino)cyclohexan-1-ol The title compound as a yellow solid (142 mg) was prepared in the same fashion as Step 1 in Example 157 except that (1S,3R)-3-aminocyclohexanol HCl (95 mg, 0.630 mmol) and 2-((6-chloro-4-fluoropyridin-3-yl)ethynyl)-5-methylpyrazine (120 mg, 0.485 mmol) prepared in Step 1 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.51 (s, 1H), 8.25 (s, 1H), 8.00 (s, 1H), 7.86 (s, 1H), 6.71 (brs, 1H), 6.30 (s, 1H), 4.21 (s, 1H), 3.60-3.55 (d, 1H), 2.42 (s, 3H), 1.82-1.79 (q, 1H), 1.69-1.64 (d, 2H), 1.61-1.53 (q, 2H), 1.30-1.27 (q, 2H); MS (ESI) m/z=343.1 (M+H)⁺

Step 3. (1 S,3R)-3-((2-((2-(1-(Cyclopropylsulfonyl)-1H-pyrazol-4-yl)pyrimidin-4-yl)amino)-5-((5-methylpyrazin-2-yl)ethynyl)pyridin-4-yl)amino)cyclohexan-1-ol The title compound as an off-white solid (6 mg) was prepared in the same fashion as Step 3 in Example 1, except that (1S,3R)-3-((2-chloro-5-((5-methylpyrazin-2-yl)ethynyl)pyridin-4-yl)amino)cyclohexan-1-ol (142 mg, 0.414 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.66-8.61 (d, 2H), 8.44-8.40 (m, 3H), 8.20 (s, 1H), 8.00 (brs, 1H), 7.23 (s, 1H), 7.05-7.04 (d, 1H), 6.83 (s, 1H), 4.17 (s, 1H), 3.80 (s, 1H), 2.85-2.81 (m, 1H), 2.59 (s, 3H), 2.12-2.10 (d, 1H), 2.02-1.90 (d, 2H), 1.82-1.79 (q, 2H), 1.78-1.56 (m, 2H), 1.55-1.51 (m, 3H), 1.50-1.40 (m, 2H), 1.28-1.20 (s, 2H); MS (ESI) m/z=572.1 (M+H)⁺

Example 171. (1s,4s)-4-((2-((2-(1-(Cyclopropylsulfonyl)-1H-pyrazol-4-yl)pyrimidin-4-yl)amino)-5-(3-(pyrrolidin-1-yl)prop-1-yn-1-yl)pyridin-4-yl)amino)cyclohexan-1-ol

Step 1. 2-Chloro-4-fluoro-5-(3-(pyrrolidin-1-yl)prop-1-yn-1-yl)pyridine

The title compound as an off-white solid (525 mg) was prepared in the same fashion as Reference Example 18 except that 1-(2-propyn-1-yl)pyrrolidine (500 mg, 4.583 mmol) was used instead of 4-ethynyl-1-methylpyrazole. $^1$H-NMR (CDCl$_3$, 400 MHz) δ 8.44-8.41 (d, 1H), 7.11-7.09 (d, 1H), 3.68 (s, 2H), 2.71-2.67 (m, 4H), 1.86-1.82 (m, 4H)

Step 2. (1s,4s)-4-((2-Chloro-5-(3-(pyrrolidin-1-yl)prop-1-yn-1-yl)pyridin-4-yl)amino)cyclohexan-1-ol The title compound as a yellow solid (175 mg) was prepared in the same fashion as Step 1 in Example 157 except that 2-chloro-4-fluoro-5-(3-(pyrrolidin-1-yl)prop-1-yn-1-yl)pyridine (180 mg, 0.754 mmol) prepared in Step 1 was used instead of 4-(4-((6-chloro-4-fluoropyridin-3-yl)ethynyl)benzyl)morpholine. $^1$H-NMR (CDCl$_3$, 400 MHz) δ 7.94 (s, 1H), 6.37 (s, 1H), 5.14-5.12 (d, 1H), 3.87 (s, 1H), 3.70 (s, 1H), 3.62 (s, 2H), 3.36-3.33 (d, 1H), 2.62 (s, 4H), 1.77-1.74 (t, 4H), 1.70-1.63 (m, 8H); MS (ESI) m/z=334.1 (M+H)$^+$

Step 3. (1s,4s)-4-((2-((2-(1-(Cyclopropylsulfonyl)-1H-pyrazol-4-yl)pyrimidin-4-yl)amino)-5-(3-(pyrrolidin-1-yl)prop-1-yn-1-yl)pyridin-4-yl)amino)cyclohexan-1-ol The title compound as an off-white solid (9 mg) was prepared in the same fashion as Step 3 in Example 1, except that (1s,4s)-4-((2-chloro-5-(3-(pyrrolidin-1-yl)prop-1-yn-1-yl)pyridin-4-yl)amino)cyclohexan-1-ol (175 mg, 0.524 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43 (s, 1H), 8.39-8.38 (d, 1H), 8.06 (brs, 2H), 7.12 (s, 2H), 5.22-5.20 (d, 1H), 3.93-3.91 (t, 1H), 3.73 (s, 2H), 3.63 (s, 1H), 2.84-2.80 (m, 1H), 2.72 (s, 3H), 1.87-1.85 (t, 8H), 1.80-1.78 (t, 2H), 1.73-1.72 (d, 2H), 1.54-1.50 (m, 2H), 1.28-1.20 (d, 2H); MS (ESI) m/z=564.2 (M+H)$^+$

Example 172. (1s,4s)-4-((2-((2-(1-(Cyclopropylsulfonyl)-1H-pyrazol-4-yl)pyrimidin-4-yl)amino)-5-((4-((2-morpholinoethyl)amino)phenyl)ethynyl)pyridin-4-yl)amino)cyclohexan-1-ol

Step 1. 4-((6-Chloro-4-fluoropyridin-3-yl)ethynyl)aniline

The title compound as a solid (1.18 g) was prepared in the same fashion as Reference Example 18 except that 4-ethynylaniline (800 mg, 6.829 mmol) was used instead of 4-ethynyl-1-methylpyrazole. MS (ESI) m/z=247.0 (M+H)$^+$

Step 2. 4-((6-Chloro-4-fluoropyridin-3-yl)ethynyl)-N-(2-morpholinoethyl)aniline The suspension of 4-((6-chloro-4-fluoropyridin-3-yl)ethynyl)aniline (1.18 g, 4.784 mmol) prepared in Step 1, 4-(chloroethyl)morpholine HCl (935 mg, 5.023 mmol) and DIPEA (2.50 mL, 14.351 mmol) in NMP (20 mL) was stirred at 160° C. overnight. The reaction mixture was cooled, diluted in EA, washed by water, dried over MgSO$_4$, and then concentrated. The crude product was purified by column chromatography (EA/n-Hex=0-100% & MeOH/DCM=0-30%) to yield 4-((6-chloro-4-fluoropyridin-3-yl)ethynyl)-N-(2-morpholinoethyl)aniline (985 mg) as a white solid. MS (ESI) m/z=361.1 (M+H)$^+$

Step 3. (1s,4S)-4-((2-Chloro-5-((4-((2-morpholinoethyl)amino)phenyl)ethynyl)pyridin-4-yl)amino)cyclohexan-1-ol The title compound (124 mg) was prepared in the same fashion as Step 1 in Example 157, except that 4-((6-chloro-4-fluoropyridin-3-yl)ethynyl)-N-(2-morpholinoethyl)aniline (400 mg, 1.112 mmol) prepared in Step 2 was used instead of 4-(4-((6-chloro-4-fluoropyridin-3-yl)ethynyl)benzyl)morpholine. MS (ESI) m/z=457.1 (M+H)$^+$

Step 4. (1 s, 4s)-4-((2-((2-(1-(Cyclopropylsulfonyl)-1H-pyrazol-4-yl)pyrimidin-4-yl)amino)-5-((4-((2-morpholinoethyl)amino)phenyl)ethynyl)pyridin-4-yl)amino)cyclohexan-1-ol The title compound (16 mg) was prepared in the same fashion as Step 3 in Example 1, except that (1s,4s)-4-((2-chloro-5-((4-((2-morpholinoethyl)amino)phenyl)ethynyl)pyridin-4-yl)amino)cyclohexan-1-ol (124 mg, 0.273 mmol) prepared in Step 3 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44 (s, 1H), 8.39-8.38 (m, 1H), 8.12 (d, 1H), 7.38-7.32 (m, 3H), 7.23-7.10 (brs, 2H), 6.68-6.66 (d, 1H), 6.60-6.58 (d, 1H), 5.29 (m, 1H), 4.20 (m, 1H), 3.95 (d, 1H), 3.74-3.70 (q, 2H), 3.66-3.65 (d, 2H), 3.48 (s, 1H), 3.20-3.19 (d, 1H), 2.84-2.82 (t, 2H), 2.66-2.62 (m, 1H), 2.52-2.48 (q, 1H), 2.45 (q, 4H), 1.91-1.90 (d, 2H), 1.81-1.79 (t, 2H), 1.73-1.70 (t, 2H), 1.52-1.51 (q, 2H), 1.26-1.20 (q, 2H)

Example 173. (1s,4s)-4-((2-((2-(1-(Cyclopropylsulfonyl)-1H-pyrazol-4-yl)pyrimidin-4-yl)amino)-5-((3-((2-morpholinoethyl)amino)phenyl)ethynyl)pyridin-4-yl)amino)cyclohexan-1-ol

Step 1. 3-((6-Chloro-4-fluoropyridin-3-yl)ethynyl)aniline

The title compound as a solid (1.66 g) was prepared in the same fashion as Reference Example 18 except that 3-ethynylaniline (1.44 mL, 12.804 mmol) was used instead of 4-ethynyl-1-methylpyrazole. MS (ESI) m/z=247.0 (M+H)$^+$

Step 2. 3-((6-Chloro-4-fluoropyridin-3-yl)ethynyl)-N-(2-morpholinoethyl)aniline The title compound as a white solid (153 mg) was prepared in the same fashion as Step 2 in Example 172 except that 3-((6-chloro-4-fluoropyridin-3-yl)ethynyl)aniline (1.06 g, 4.281 mmol) prepared in Step 1 was used instead of 4-((4-chloro-6-fluoropyridin-3-yl)ethynyl)aniline. MS (ESI) m/z=360.1 (M+H)$^+$

Step 3. (1s,4s)-4-((2-Chloro-5-((3-((2-morpholinoethyl)amino)phenyl)ethynyl)pyridin-4-yl)amino)cyclohexan-1-ol The title compound (161 mg) was prepared in the same fashion as Step 1 in Example 157, except that 3-((6-chloro- 4-fluoropyridin-3-yl)ethynyl)-N-(2-morpholinoethyl)aniline (135 mg, 0.375 mmol) prepared in Step 2 was used instead of 4-(4-(((6-chloro-4-fluoropyridin-3-yl)ethynyl)benzyl) morpholine. MS (ESI) m/z=456.1 (M+H)$^+$ Step 4. (1s,4s)-4-((2-((2-(1-(Cyclopropylsulfonyl)-1H-pyrazol-4-yl)pyrimidin-4-yl)amino)-5-((3-((2-morpholinoethyl)amino)phenyl)ethynyl)pyridin-4-yl)amino)cyclohexan-1-ol The title compound (27 mg) was prepared in the same fashion as Step 3 in Example 1, except that (1s,4s)-4-((2-chloro-5-((3-((2-morpholinoethyl)amino)phenyl)ethynyl) pyridin-4-yl)amino)cyclohexan-1-ol (161 mg, 0.354 mmol) prepared in Step 3 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44 (s, 1H), 8.39-8.38 (d, 1H), 8.16-8.13 (d, 1H), 7.19-7.17 (d, 1H), 7.15 (s, 1H), 6.87-6.86 (d, 1H), 6.80 (s, 1H), 6.64-6.62 (q, 1H), 5.33-5.30 (m, 1H), 3.97 (s, 1H), 3.74-3.73 (d, 4H), 3.72 (s, 1H), 3.22-3.19 (t, 2H), 2.82 (m, 1H), 2.66-2.63 (t, 2H), 2.49 (s, 4H), 1.91-1.88 (t, 2H), 1.81 (s, 2H), 1.74-1.73 (d, 2H), 1.52-1.51 (q, 2H), 1.21-1.19 (t, 2H); MS (ESI) m/z=564.2 (M+H)$^+$ Example 174. 1-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)cyclohexan-1-ol Step 1. 1-((6-Chloro-4-(((1s,4s)-4-hydroxycyclohexyl)amino)pyridin-3-yl)ethynyl)cyclohexan-1-ol The title compound as a pale yellow solid (169 mg) was prepared in the same fashion as Step 1 in Example 157, except that 1-((6-chloro-4-fluoropyridin-3-yl)ethynyl)cyclohexan-1-ol (150 mg, 0.591 mmol) prepared in Reference Example 33 was used instead of 4-(4-(((6-chloro-4-fluoropyridin-3-yl)ethynyl)benzyl)morpholine. $^1$H-NMR (CDCl$_3$, 400 MHz) δ 8.08 (s, 1H), 6.42 (s, 2H), 5.19 (s, 1H), 3.92 (s, 1H), 3.43 (s, 1H), 2.04-1.99 (d, 2H), 1.75-1.70 (m, 8H), 1.56 (s, 4H), 1.27-1.25 (d, 4H); MS (ESI) m/z=349.1 (M+H)$^+$ Step 2. 1-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)cyclohexan-1-ol The title compound as an off-white solid (15 mg) was prepared in the same fashion as Step 3 in Example 1, except that 1-((6-chloro-4-(((1s,4s)-4-hydroxycyclohexyl)amino) pyridin-3-yl)ethynyl)cyclohexan-1-ol (169 mg, 0.484 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.44 (s, 1H), 8.38-8.37 (d, 1H), 8.09 (s, 1H), 7.18 (s, 1H), 7.03-7.00 (t, 2H), 5.22-5.20 (d, 1H), 3.89 (s, 1H), 3.52 (s, 1H), 2.88-2.81 (q, 1H), 1.85-1.83 (t, 3H), 1.80-1.74 (q, 4H), 1.71-1.61 (m, 4H), 1.58-1.55 (t, 4H), 1.53-1.49 (m, 4H); MS (ESI) m/z=578.2 (M+H)$^+$ Example 175. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl) ethynyl)cyclohexan-1-ol Step 1. 1-((6-Chloro-4-(4-(hydroxymethyl)-4-methylpiperidin-1-yl)pyridin-3-yl)ethynyl)cyclohexan-1-ol The title compound as a solid (175 mg) was prepared in the same fashion as Step 1 in Example 157 except that (4-methylpiperidin-4-yl)methanol (92 mg, 0.709 mmol) and 1-((6-chloro-4-fluoropyridin-3-yl)ethynyl)cyclohexan-1-ol (150 mg, 0.591 mmol) prepared in Reference Example 33 were used instead of cis-4-aminocyclohexanol HCl and 4-(4-(((6-chloro-4-fluoropyridin-3-yl)ethynyl)benzyl)morpholine. $^1$H-NMR (CDCl$_3$, 400 MHz) δ 8.14 (s, 1H), 6.62 (s, 1H), 4.12-4.07 (m, 1H), 3.68-3.65 (d, 2H), 3.39 (s, 2H), 3.19-3.14 (t, 2H), 2.81 (brs, 1H), 2.02 (s, 1H), 1.93-1.92 (d, 2H), 1.70-1.65 (t, 6H), 1.53-1.51 (d, 3H), 1.41-1.37 (d, 2H), 1.25-1.22 (t, 3H); MS (ESI) m/z=363.1 (M+H)$^+$ Step 2. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl) cyclohexan-1-ol The title compound (6 mg) was prepared in the same fashion as Step 3 in Example 1, except that 1-((6-chloro-4-(4-(hydroxymethyl)-4-methylpiperidin-1-yl)pyridin-3-yl) ethynyl)cyclohexan-1-ol (175 mg, 0.482 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64-8.61 (d, 1H), 8.45 (s, 1H), 8.40-8.39 (d, 1H), 8.16 (s, 1H), 6.98-6.95 (d, 1H), 6.33-6.31 (d, 1H), 4.94 (s, 1H), 3.49 (s, 1H), 3.36 (s, 2H), 2.83-2.81 (t, 1H), 2.00-1.98 (d, 2H), 1.78-1.72 (q, 81-1), 1.69-1.62 (q, 8H), 1.22-1.18 (m, 2H), 1.06 (s, 3H)

Example 176. (1s,4s)-4-((2-((2-(1-(Cyclopropylsulfonyl)-1H-pyrazol-4-yl)pyrimidin-4-yl)amino)-5-((1-hydroxycyclopentyl)ethynyl)pyridin-4-yl)amino) cyclohexan-1-ol Step 1. (1s, 4s)-4-((2-Chloro-5-((1-hydroxycyclopentyl)ethynyl)pyridin-4-yl)amino)cyclohexan-1-ol The title compound as a solid (206 mg) was prepared in the same fashion as Step 1 in Example 157 except that 1-((6-chloro-4-fluoropyridin-3-yl)ethynyl)cyclopentan-1-ol (150 mg, 0.626 mmol) prepared in Reference Example 34 was used instead of 4-(4-(((6-chloro-4-fluoropyridin-3-yl) ethynyl)benzyl)morpholine. $^1$H-NMR (CDCl$_3$, 400 MHz) δ 8.04 (s, 1H), 6.39 (s, 1H), 5.22-5.20 (d, 1H), 4.50 (s, 1H), 3.87 (s, 1H), 3.43 (s, 1H), 2.84 (s, 1H), 1.90-1.85 (m, 4H), 1.80-1.70 (m, 10H); MS (ESI) m/z=335.1 (M+H)$^+$ Step 2. (1s,4s)-4-((2-((2-(1-(Cyclopropylsulfonyl)-1H-pyrazol-4-yl)pyrimidin-4-yl)amino)-5-((1-hydroxycyclopentyl)ethynyl)pyridin-4-yl)amino)cyclohexan-1-ol The title compound as an off-white solid (14 mg) was prepared in the same fashion as Step 3 in Example 1, except that (1s,4s)-4-((2-chloro-5-((1-hydroxycyclopentyl)ethynyl) pyridin-4-yl)amino)cyclohexan-1-ol (206 mg, 0.615 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62-8.61 (d, 1H), 8.44-8.40 (d, 1H), 8.38-8.37 (d, 2H), 8.25-8.23 (d, 1H), 7.24 (s, 1H), 7.07-7.05 (d, 1H), 5.21-5.19 (d, 1H), 4.99 (s, 1H), 3.90 (s, 1H), 3.78-3.62 (d, 1H), 2.82-2.80 (t, 1H), 2.09-2.05 (m, 2H), 1.92-1.83 (m, 2H), 1.80-1.79 (d, 2H), 1.69 (s, 4H), 1.67-1.65 (d, 4H), 1.52-1.50 (q, 2H), 1.18-1.17 (d, 2H); MS (ESI) m/z=564.2 (M+H)$^+$

Example 177. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclopentan-1-ol

Step 1. 1-((6-Chloro-4-(4-(hydroxymethyl)-4-methylpiperidin-1-yl)pyridin-3-yl)ethynyl)cyclopentan-1-ol The title compound as a solid (180 mg) was prepared in the same fashion as Step 1 in Example 157 except that (4-methylpiperidin-4-yl)methanol (97 mg, 0.751 mmol) and 1-((6-chloro-4-fluoropyridin-3-yl)ethynyl)cyclopentan-1-ol (150 mg, 0.626 mmol) prepared in Reference Example 34 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.17 (s, 1H), 6.62 (s, 1H), 4.29 (s, 1H), 3.68-3.65 (q, 2H), 3.39 (s, 2H), 3.19-3.13 (t, 2H), 2.74 (brs, 1H), 2.07-2.06 (d, 2H), 2.03-1.93 (m, 4H), 1.89-1.86 (q, 4H), 1.42-1.38 (d, 2H), 1.03 (s, 3H); MS (ESI) m/z=349.2 (M+H)$^+$

Step 2. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclopentan-1-ol The title compound (3 mg) was prepared in the same fashion as Step 3 in Example 1, except that 1-((6-chloro-4-(4-(hydroxymethyl)-4-methylpiperidin-1-yl)pyridin-3-yl)ethynyl)cyclopentan-1-ol (180 mg, 0.516 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65-8.61 (d, 1H), 8.41-8.40 (m, 2H), 8.26-8.25 (d, 1H), 7.36 (s, 1H), 6.33-6.31 (d, 1H), 4.91 (s, 1H), 3.50 (s, 2H), 3.36 (m, 4H), 2.83-2.81 (t, 1H), 1.92-1.91 (d, 2H), 1.80-1.76 (m, 4H), 1.56-1.51 (m, 6H), 1.21-1.18 (q, 4H), 1.08-1.05 (t, 3H); MS (ESI) m/z=578.2 (M+H)$^+$

Example 178. (1s,4s)-4-((2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)amino)cyclohexan-1-ol

Step 1. (1s,4s)-4-((2-Chloro-5-((tetrahydro-2H-pyran-4-yl)ethynyl)pyridin-4-yl)amino)cyclohexan-1-ol The title compound as a solid (160 mg) was prepared in the same fashion as Step 1 in Example 157 except that 2-chloro-4-fluoro-5-((tetrahydro-2H-pyran-4-yl)ethynyl)pyridine (145 mg, 0.605 mmol) prepared in Reference Example 35 was used instead of 4-(4-((6-chloro-4-fluoropyridin-3-yl)ethynyl)benzyl)morpholine. $^1$H-NMR (CDCl$_3$, 400 MHz) δ 7.99 (s, 1H), 6.41 (s, 1H), 5.07-5.05 (d, 1H), 3.94-3.90 (m, 3H), 3.56-3.51 (t, 2H), 3.40 (s, 1H), 2.89-2.88 (d, 1H), 2.22 (s, 1H), 1.93-1.90 (d, 2H), 1.75-1.72 (d, 8H); MS (ESI) m/z=335.1 (M+H)$^+$

Step 2. (1s,4s)-4-((2-((2-(1-(Cyclopropylsulfonyl)-1H-pyrazol-4-yl)pyrimidin-4-yl)amino)-S-((tetrahydro-2H-pyran-4yl)ethynyl)pyridin-4-yl)amino)cyclohexan-1-ol The title compound as an off-white solid (3 mg) was prepared in the same fashion as Step 3 in Example 1, except that (1s,4s)-4-((2-chloro-5-((tetrahydro-2H-pyran-4-yl)ethynyl)pyridin-4-yl)amino)cyclohexan-1-ol (160 mg, 0.478 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.44-8.43 (d, 2H), 7.85-7.82 (d, 2H), 7.02-7.01 (d, 1H), 5.61-5.59 (d, 1H), 3.99-3.94 (m, 3H), 3.72 (s, 1H), 3.60-3.55 (m, 4H), 2.94-2.93 (d, 1H), 2.84-2.83 (d, 1H), 1.98-1.97 (d, 4H), 1.94-1.76 (m, 4H), 1.69-1.66 (t, 2H), 1.54-1.53 (q, 1H), 1.25-1.22 (q, 2H); MS (ESI) m/z=564.2 (M+H)$^+$

Example 179. (1-(2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)-4-methylpiperidin-4-yl)methanol

Step 1. (1-(2-Chloro-5-((tetrahydro-2H-pyran-4-yl)ethynyl)pyridin-4-yl)-4-methylpiperidin-4-yl)methanol The title compound as a solid (159 mg) was prepared in the same fashion as Step 1 in Example 157 except that (4-methylpiperidin-4-yl)methanol (94 mg, 0.726 mmol) and 2-chloro-4-fluoro-5-((tetrahydro-2H-pyran-4-yl)ethynyl)pyridine (145 mg, 0.605 mmol) prepared in Reference Example 35 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.10 (s, 1H), 6.66 (s, 1H), 3.92-3.90 (q, 2H), 3.64-3.61 (d, 2H), 3.53-3.48 (q, 2H), 3.41 (s, 2H), 3.21-3.15 (t, 2H), 2.86-2.85 (d, 1H), 1.90-1.87 (d, 2H), 1.76-1.64 (m, 4H), 1.45-1.42 (d, 2H), 1.05 (s, 3H); MS (ESI) m/z=349.1 (M+H)$^+$

Step 2. (1-(2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)-4-methylpiperidin-4-yl)methanol The title compound (7 mg) was prepared in the same fashion as Step 3 in Example 1, except that (1-(2-chloro-5-((tetrahydro-2H-pyran-4-yl)ethynyl)pyridin-4-yl)-4-methylpiperidin-4-yl)methanol (159 mg, 0.456 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.45-8.41 (t, 2H), 7.99-7.98 (d, 2H), 6.95-6.93 (d, 1H), 3.99-3.94 (m, 2H), 3.77-3.75 (t, 1H), 3.58-3.47 (m, 5H), 2.84 (m, 2H), 1.94-1.91 (q, 2H), 1.81-1.75 (m, 4H), 1.56-1.53 (m, 4H), 1.26-1.23 (q, 2H), 1.07 (s, 3H); MS (ESI) m/z=578.2 (M+H)$^+$

Example 180. (1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methylpiperidin-4-yl)methanol

Step 1. (1-(2-Chloro-5-((1-methylpyrrolidin-3-yl)ethynyl)pyridin-4-yl)-4-methylpiperidin-4-yl)methanol The title compound as a white solid (67 mg) was prepared in the same fashion as Step 1 in Example 157 except that (4-methylpiperidin-4-yl)methanol (44 mg, 0.337 mmol) and 2-chloro-4-fluoro-5-((1-methylpyrrolidin-3-yl)ethynyl)pyridine (67 mg, 0.281 mmol) prepared in Reference Example 36 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.12 (s, 1H), 6.67 (s, 1H), 3.66-3.61 (m, 2H), 3.43 (s, 2H), 3.26-3.15 (m, 3H), 2.99-2.95 (t, 1H), 2.71-2.68 (q, 1H), 2.57-2.49 (m, 2H), 2.38 (s, 3H), 2.13 (m, 1H), 1.96 (m, 1H), 1.74-1.67 (m, 2H), 1.47-1.42 (m, 2H), 1.04 (s, 3H)

Step 2. (1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methylpiperidin-4-yl)methanol The title compound as an off-white solid (7 mg) was prepared in the same fashion as Step 3 in Example 1, except that (1-(2-chloro-5-((1-methylpyrrolidin-3-yl)ethynyl)pyridin-4-yl)-4-methylpiperidin-4-yl)methanol (67 mg, 0.193 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.44 (s, 1H), 8.39-8.38 (d, 1H), 8.13 (s, 1H), 8.09 (s, 1H), 7.57 (s, 1H), 6.96-6.95 (d, 1H), 3.65-3.61 (t, 2H), 3.37-3.28 (m, 3H), 3.04-3.00 (t, 1H), 2.84-2.82 (t, 1H), 2.75-2.61 (m, 1H), 2.59-2.54 (m, 2H), 2.41 (s, 3H), 2.40-2.30 (q, 2H), 2.01 (s, 1H), 1.78-1.75 (q, 2H), 1.57-1.52 (m, 4H), 1.25-1.21 (q, 2H), 1.07 (s, 3H); MS (ESI) m/z=578.2 (M+H)⁺

Example 181. (1s,4s)-4-((2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)amino)cyclohexan-1-ol Step 1. (1s,4s)-4-((2-Chloro-5-((1-methylpyrrolidin-3-yl)ethynyl)pyridin-4-yl)amino)cyclohexan-1-ol The title compound as a solid (63 mg) was prepared in the same fashion as Step 1 in Example 157 except that 2-chloro-4-fluoro-5-((1-methylpyrrolidin-3-yl)ethynyl)pyridine (67 mg, 0.281 mmol) prepared in Reference Example 36 was used instead of 4-(4-((6-chloro-4-fluoropyridin-3-yl)ethynyl)benzyl)morpholine. ¹H-NMR (CDCl₃, 400 MHz) δ 8.00 (s, 1H), 6.42 (s, 1H), 5.16-5.14 (d, 1H), 3.93 (s, 1H), 3.43 (s, 1H), 3.26-3.22 (m, 1H), 2.94-2.90 (q, 1H), 2.66-2.57 (m, 3H), 2.36 (s, 3H), 2.35-2.30 (m, 1H), 2.28-2.22 (d, 1H), 1.99-1.94 (m, 1H), 1.79-1.77 (d, 8H)

Step 2. (1s,4s)-4-((2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)amino)cyclohexan-1-ol The title compound (14 mg) was prepared in the same fashion as Step 3 in Example 1, except that (1s,4s)-4-((2-chloro-5-((1-methylpyrrolidin-3-yl)ethynyl)pyridin-4-yl)amino)cyclohexan-1-ol (63 mg, 0.189 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.62 (s, 1H), 8.42 (s, 1H), 8.38-8.37 (d, 1H), 8.20 (brs, 1H), 8.02 (s, 1H), 7.14 (s, 1H), 7.08-7.07 (d, 1H), 5.24-5.22 (d, 1H), 3.88 (s, 1H), 3.48 (s, 1H), 3.31-3.29 (t, 1H), 3.01-2.97 (t, 1H), 2.83-2.80 (q, 1H), 2.74-2.66 (m, 3H), 2.43 (s, 3H), 2.42 (m, 1H), 2.05-2.01 (m, 1H), 1.90-1.81 (m, 6H), 1.69-1.66 (t, 2H), 1.52-1.51 (q, 2H), 1.22-1.19 (q, 2 1-1); MS (ESI) m/z=563.2 (M+H)⁺

Example 182. (1-(2-((2-(1-(Cyclopropylsulfonyl)-1H-pyrazol-4-yl)pyrimidin-4-yl)amino)-5-((1-methylpiperidin-4-yl)ethynyl)pyridin-4-yl)-4-methylpiperidin-4-yl)methanol Step 1. 2-Chloro-4-fluoro-5-((1-methylpiperidin-4-yl)ethynyl)pyridine The title compound as an off-white solid (118 mg) was prepared in the same fashion as Reference Example 18 except that 4-ethynyl-1-methylpiperidine HCl (250 mg, 1.566 mmol) was used instead of 4-ethynyl-1-methylpyrazole. ¹H-NMR (CDCl₃, 400 MHz) δ 8.41-8.38 (d, 1H), 7.10-7.08 (d, 1H), 2.70 (brs, 3H), 2.30 (brs, 5H), 2.00-1.95 (m, 2H), 1.85-1.78 (m, 21-1); MS (ESI) m/z=253.1 (M+H)⁺

Step 2. (1-(2-Chloro-5-((1-methylpiperidin-4-yl)ethynyl)pyridin-4-yl)-4-methylpiperidin-4-yl)methanol The title compound as an off-white solid (86 mg) was prepared in the same fashion as Step 1 in Example 157 except that (4-methylpiperidin-4-yl)methanol (40 mg, 0.309 mmol) and 2-chloro-4-fluoro-5-((1-methylpiperidin-4-yl)ethynyl)pyridine (65 mg, 0.257 mmol) prepared in Step 1 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.13 (s, 1H), 6.67 (s, 1H), 3.69-3.64 (m, 2H), 3.42 (s, 2H), 3.20-3.14 (m, 2H), 2.74 (brs, 2H), 2.60 (s, 1H), 2.28 (s, 5H), 1.98-1.93 (m, 2H), 1.81-1.77 (m, 2H), 1.76-1.69 (m, 2H), 1.47-1.37 (q, 2H), 1.02(s, 3H)

Step 3. (1-(2-((2-(1-(Cyclopropylsulfonyl)-1H-pyrazol-4-yl)pyrimidin-4-yl)amino)-5-((1-methylpiperidin-4-yl)ethynyl)pyridin-4-yl)-4-methylpiperidin-4-yl)methanol The title compound as an off-white solid (23 mg) was prepared in the same fashion as Step 3 in Example 1, except that (1-(2-chloro-5-((1-methylpiperidin-4-yl)ethynyl)pyridin-4-yl)-4-methylpiperidin-4-yl)methanol (86 mg, 0.238 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.63 (s, 1H), 8.43 (s, 1H), 8.37-8.34 (t, 2H), 8.13 (s, 1H), 7.56 (s, 1H), 6.96-6.95 (d, 1H), 3.69-3.65 (q, 2H), 3.33-3.27 (m, 2H), 2.84-2.79 (m, 3H), 2.31 (s, 3H), 2.01-1.98 (q, 2H), 1.85-1.80 (m, 4H), 1.76-1.73 (q, 4H), 1.54-1.51 (q, 2H), 1.06 (s, 3H); MS (ESI) m/z=592.3 (M+H)⁺

Example 183. (1-(2-((2-(1-(Cyclopropylsulfonyl)-1H-pyrazol-4-yl)pyrimidin-4-yl)amino)-5-((4-methyltetrahydro-2H-pyran-4-yl)ethynyl)pyridin-4-yl)-4-methylpiperidin-4-yl)methanol Step 1. 2-Chloro-4-fluoro-5-((4-methyltetrahydro-2H-pyran-4-yl)ethynyl)pyridine The title compound as an off-white solid (431 mg) was prepared in the same fashion as Reference Example 18 except that 4-ethynyl-4-methyltetrahydro-2H-pyran (500 mg, 4.029 mmol) was used instead of 4-ethynyl-1-methylpyrazole. ¹H-NMR (CDCl₃, 400 MHz) δ 8.42-8.39 (d, 1H), 7.12-7.10 (d, 1H), 3.90-3.86 (m, 2H), 3.84-3.71 (m, 2H), 1.68-1.52 (m, 4H), 1.34 (s, 3H)

Step 2. (1-(2-Chloro-5-((4-methyltetrahydro-2H-pyran-4-yl)ethynyl)pyridin-4-yl)-4-methylpiperidin-4-yl)methanol The title compound as an off-white solid (227 mg) was prepared in the same fashion as Step 1 in Example 157 except that (4-methylpiperidin-4-yl)methanol (128 mg, 0.993 mmol) and 2-chloro-4-fluoro-5-((4-methyltetrahydro-2H-pyran-4-yl)ethynyl)pyridine (210 mg, 0.828 mmol) prepared in Step 1 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.13 (s, 1H), 6.68 (s, 1H), 3.87-3.84 (q, 2H), 3.77 (d, 2H), 3.75-3.63 (m, 2H), 3.43-3.42 (d, 2H), 3.23-3.17 (m, 2H), 1.73 (s, 2H), 1.69-1.61 (m, 4H), 1.59-1.57 (d, 2H), 1.36 (s, 3H), 1.07 (s, 3H)

Step 3. (1-(2-((2-(1-(Cyclopropylsulfonyl)-1H-pyrazol-4-yl)pyrimidin-4-yl)amino)-5-((4-methyltetrahydro-2H-pyran-4-yl)ethynyl)pyridin-4-yl)-4-methylpiperidin-4-yl)methanol The title compound as an off-white solid (2 mg) was prepared in the same fashion as Step 3 in Example 1, except that (1-(2-chloro-5-((4-methyltetrahydro-2H-pyran-4-yl)ethynyl)pyridin-4-yl)-4-methylpiperidin-4-yl)methanol (227 mg, 0.626 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68-8.64 (d, 1H), 8.49-8.40 (q, 2H), 8.13-8.09 (d, 1H), 7.78-7.75 (d, 1H), 7.31 (s, 1H), 7.00-6.97 (d, 1H), 3.91-3.73 (m, 7H), 3.55-3.47 (t, 4H), 2.84-2.83 (d, 1H), 1.76-1.73 (d, 4H), 1.68-1.65 (d, 2H), 1.57-1.55 (d, 4H), 1.42-1.38 (d, 3H), 1.27-1.23 (t, 2H), 1.08 (s, 3H); MS (ESI) m/z=592.2 (M+H)$^+$

Example 184. (1s,4s)-4-((2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)amino)cyclohexan-1-ol

Step 1. (1s,4s)-4-((2-Chloro-5-((5-(morpholinomethyl)pyridin-2-yl)ethynyl)pyridin-4-yl)amino)cyclohexan-1-ol The title compound as an off-white solid (179 mg) was prepared in the same fashion as Step 1 in Example 157, except that 4-((6-((6-chloro-4-fluoropyridin-3-yl)ethynyl)pyridin-3-yl)methyl)morpholine (233 mg, 0.702 mmol) prepared in Reference Example 38 was used instead of 4-(4-((6-chloro-4-fluoropyridin-3-yl)ethynyl)benzyl)morpholine. $^1$H-NMR (MeOD, 400 MHz) δ 8.54 (s, 1H), 8.08 (s, 1H), 7.86 (d, 1H), 7.63 (s, 1H), 6.70 (s, 1H), 4.90 (brs, 4H), 3.92 (s, 1H), 3.69-3.58 (d, 6H), 2.47 (s, 3H), 1.77 (s, 6H); MS (ESI) m/z=427.1 (M+H)$^+$

Step 2. (1s,4s)-4-((2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)amino)cyclohexan-1-ol The title compound as an off-white solid (9 mg) was prepared in the same fashion as Step 3 in Example 1, except that (1s,4s)-4-((2-chloro-5-((5-(morpholinomethyl)pyridin-2-yl)ethynyl)pyridin-4-yl)amino)cyclohexan-1-ol (171 mg, 0.401 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.57 (s, 1H), 8.44-8.41 (t, 2H), 8.23 (s, 1H), 8.05 (s, 1H), 7.72-7.70 (q, 1H), 7.50-7.48 (d, 1H), 7.22 (s, 1H), 7.13-7.11 (d, 1H), 5.45-5.43 (d, 1H), 3.94-3.90 (t, 1H), 3.75-3.71 (q, 6H), 3.53 (s, 2H), 2.84-2.81 (t, 1H), 2.52 (s, 1H), 2.48-2.47 (d, 4H), 1.94-1.84 (m, 2H), 1.79-1.74 (q, 2H), 1.53-1.50 (q, 2H), 1.26-1.21 (q, 2H); MS (ESI) m/z=656.2 (M+H)$^+$

Example 185. (1-(2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)-4-methylpiperidin-4-yl)methanol

Step 1. (1-(2-Chloro-5-((5-(morpholinomethyl)pyridin-2-yl)ethynyl)pyridin-4-yl)-4-methylpiperidin-4-yl)methanol The title compound as a solid (233 mg) was prepared in the same fashion as Step 1 in Example 157 except that (4-methylpiperidin-4-yl)methanol (109 mg, 0.843 mmol) and 4-((6-((6-chloro-4-fluoropyridin-3-yl)ethynyl)pyridin-3-yl)methyl)morpholine (233 mg, 0.702 mmol) prepared in Reference Example 38 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.47 (d, 1H), 8.24-8.23 (d, 1H), 7.66-7.63 (q, 1H), 7.40-7.38 (d, 1H), 6.64 (s, 1H), 3.74-3.69 (m, 2H), 3.66-3.63 (t, 4H), 3.46 (s, 2H), 3.39-3.37 (d, 4H), 3.29-3.28 (d, 1H), 3.26 (d, 1H), 3.23-3.22 (d, 1H), 2.40-2.38 (t, 4H), 1.75-1.68 (m, 2H), 1.43-1.39 (q, 2H), 1.01 (s, 3H); MS (ESI) m/z=441.1 (M+H)$^+$

Step 2. (1-(2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)-4-methylpiperidin-4-yl)methanol The title compound as an off-white solid (26 mg) was prepared in the same fashion as Step 3 in Example 1, except that (1-(2-chloro-5-((5-(morpholinomethyl)pyridin-2-yl)ethynyl)pyridin-4-yl)-4-methylpiperidin-4-yl)methanol (223 mg, 0.506 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64-8.63 (d, 2H), 8.54 (d, 1H), 8.42 (s, 1H), 8.38-8.37 (d, 1H), 8.32 (s, 1H), 7.70-7.67 (q, 1H), 7.64 (s, 1H), 7.45-7.43 (d, 1H), 6.95 (d, 1H), 4.12-4.10 (d, 2H), 3.78-3.70 (m, 4H), 3.52-3.43 (m, 6H), 2.83 (s, 1H), 2.47-2.44 (t, 4H), 1.83 (s, 2H), 1.58-1.50 (m, 4H), 1.27-1.20 (m, 2H), 1.07 (s, 3H); MS (ESI) m/z=670.2 (M+H)$^+$

Example 186. (1s,4s)-4-((2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)amino)cyclohexan-1-ol

Step 1. (1s,4S)-4-((2-Chloro-5-((6-(morpholinomethyl)pyridin-3-yl)ethynyl)pyridin-4-yl)amino)cyclohexan-1-ol The title compound as an off-white solid (104 mg) was prepared in the same fashion as Step 1 in Example 157, except that 4-((5-((6-chloro-4-fluoropyridin-3-yl)ethynyl)pyridin-2-yl)methyl)morpholine (220 mg, 0.663 mmol) prepared in Reference Example 39 was used instead of 4-(4-((6-chloro-4-fluoropyridin-3-yl)ethynyl)benzyl)morpholine.

¹H-NMR (CDCl₃, 400 MHz) δ 8.69 (s, 1H), 8.16 (s, 1H), 7.78-7.76 (q, 1H), 7.47-7.45 (d, 1H), 6.49 (s, 1H), 5.13-5.12 (d, 1H), 4.01-3.99 (t, 1H), 3.76-3.73 (t, 6H), 3.48-3.47 (d, 2H), 2.53-2.51 (t, 4H), 1.85-1.74 (m, 8H); MS (ESI) m/z=427.1 (M+H)⁺

Step 2. (1s,4s)-4-((2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)amino)cyclohexan-1-ol The title compound as an off-white solid (1 mg) was prepared in the same fashion as Step 3 in Example 1, except that (1s,4s)-4-((2-chloro-5-((6-(morpholinomethyl)pyridin-3-yl)ethynyl)pyridin-4-yl)amino)cyclohexan-1-ol (104 mg, 0.244 mmol) prepared in Step 1 was used instead of 1-(2-chloro-5-((1-methyl-1H-pyrazol-4-yl)ethynyl)pyridin-4-yl)-4-methylpiperazine. ¹H-NMR (DMSO-d₆, 400 MHz) δ 10.11 (s, 1H), 8.69 (s, 1H), 8.65-8.63 (d, 1H), 8.45-8.43 (t, 2H), 8.29 (s, 1H), 8.13 (s, 1H), 7.97-7.95 (d, 1H), 7.51-7.49 (d, 2H), 7.26 (s, 1H), 5.70-5.68 (d, 1H), 3.78 (s, 2H), 3.71-3.58 (m, 6H), 3.53-3.51 (d, 2H), 2.32 (s, 4H), 1.89 (s, 2H), 1.85-1.83 (d, 2H), 1.73-1.72 (d, 3H), 1.58-1.57 (d, 2H), 1.27-1.25 (t, 2H); MS (ESI) m/z=657.3 (M+H)⁺

Example 187. (1-(2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)-4-methylpiperidin-4-yl)methanol Step 1. (1-(2-Chloro-5-((6-(morpholinomethyl)pyridin-3-yl)ethynyl)pyridin-4-yl)-4-methylpiperidin-4-yl)methanol The title compound as a solid (220 mg) was prepared in the same fashion as Step 1 in Example 157 except that (4-methylpiperidin-4-yl)methanol (103 mg, 0.796 mmol) and 4-((5-((6-chloro-4-fluoropyridin-3-yl)ethynyl)pyridin-2-yl)methyl)morpholine (220 mg, 0.663 mmol) prepared in Reference Example 39 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.65 (s, 1H), 8.19 (s, 1H), 7.70-7.68 (d, 1H), 7.59-7.56 (t, 1H), 7.41-7.37 (t, 1H), 6.66 (s, 1H), 3.74 (s, 4H), 3.68-3.64 (d, 2H), 3.60-3.55 (q, 2H), 2.45 (s, 4H), 1.69-1.66 (d, 2H), 1.45-1.41 (d, 2H), 1.24-1.20 (t, 2H), 0.99 (s, 3H); MS (ESI) m/z=441.2 (M+H)⁺

Step 2. (1-(2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)-4-methylpiperidin-4-yl)methanol The title compound (14 mg) was prepared in the same fashion as Step 3 in Example 1, except that (1-(2-chloro-5-((6-(morpholinomethyl)pyridin-3-yl)ethynyl)pyridin-4-yl)-4-methylpiperidin-4-yl)methanol (101 mg, 0.229 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.71-8.70 (d, 1H), 8.66 (s, 1H), 8.45-8.42 (t, 2H), 8.28 (s, 1H), 7.82 (s, 1H), 7.77-7.74 (q, 1H), 7.64 (s, 1H), 7.45-7.43 (d, 1H), 7.00-6.99 (d, 1H), 3.77-3.72 (q, 4H), 3.70-3.68 (d, 4H), 3.46-3.42 (t, 2H), 2.84 (s, 1H), 2.54-2.52 (t, 4H), 1.81-1.78 (q, 2H), 1.62-1.60 (t, 2H), 1.55-1.52 (m, 2H), 1.28-1.21 (m, 4H), 1.09-1.06 (d, 3H)

Example 188. (1s,4s)-4-((2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)amino)cyclohexan-1-ol Step 1. (1s,4S)-4-((2-Chloro-5-((2-(morpholinomethyl)thiazol-4-yl)ethynyl)pyridin-4-yl)amino)cyclohexan-1-ol The title compound as an off-white solid (244 mg) was prepared in the same fashion as Step 1 in Example 157, except that 4-((4-((6-chloro-4-fluoropyridin-3-yl)ethynyl)thiazol-2-yl)methyl)morpholine (245 mg, 0.725 mmol) prepared in Reference Example 40 was used instead of 4-(4-((6-chloro-4-fluoropyridin-3-yl)ethynyl)benzyl)morpholine. ¹H-NMR (CDCl₃, 400 MHz) δ 7.97 (s, 1H), 7.84 (s, 1H), 7.43 (s, 1H), 6.43 (s, 1H), 5.20-5.17 (t, 1H), 3.79 (s, 2H), 3.69 (s, 4H), 3.60-3.52 (m, 2H), 3.31-3.28 (t, 1H), 2.47-2.45 (t, 4H), 1.69-1.53 (m, 61-1); MS (ESI) m/z=433.1 (M+H)⁺

Step 2. (1s,4s)-4-((2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)amino)cyclohexan-1-ol The title compound (1 mg) was prepared in the same fashion as Step 3 in Example 1, except that (1s,4S)-4-((2-chloro-5-((2-(morpholinomethyl)thiazol-4-yl)ethynyl)pyridin-4-yl)amino)cyclohexan-1-ol (244 mg, 0.564 mmol) prepared in Step 1 was used instead of 1-(2-chloro-5-((1-methyl-1H-pyrazol-4-yl)ethynyl)pyridin-4-yl)-4-methylpiperazine. ¹H-NMR (DMSO-d₆, 400 MHz) δ 10.10 (s, 1H), 8.63 (s, 1H), 8.45-8.43 (t, 2H), 8.25 (s, 2H), 8.11 (s, 1H), 8.02 (s, 1H), 7.52 (s, 1H), 7.25 (s, 1H), 5.55-5.53 (d, 1H), 3.84 (s, 2H), 3.70-3.68 (d, 2H), 3.62-3.59 (t, 4H), 3.53 (s, 2H), 1.82-1.77 (q, 4H), 1.74-1.73 (d, 2H), 1.69 (s, 2H), 1.58-1.57 (d, 2H), 1.33-1.30 (d, 2H)

Example 189. (1-(2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)-4-methylpiperidin-4-yl)methanol Step 1. (1-(2-Chloro-5-((2-(morpholinomethyl)thiazol-4-yl)ethynyl)pyridin-4-yl)-4-methylpiperidin-4-yl)methanol The title compound as a solid (298 mg) was prepared in the same fashion as Step 1 in Example 157 except that (4-methylpiperidin-4-yl)methanol (112 mg, 0.87 mmol) and 4-((4-((6-chloro-4-fluoropyridin-3-yl)ethynyl)thiazol-2-yl)methyl)morpholine (245 mg, 0.725 mmol) prepared in Reference Example 40 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.07 (s, 1H), 7.81 (s, 1H), 7.35 (s, 1H), 6.52 (s, 1H), 3.72 (s, 1H), 3.67 (s, 2H), 3.59-3.55 (q, 6H), 3.24 (s, 2H), 3.15-3.10 (q, 2H), 2.44-2.42 (t, 4H), 1.61-1.60 (d, 2H), 1.58-1.54 (q, 2H), 0.86 (s, 3H); MS (ESI) m/z=447.1 (M+H)⁺

Step 2. (1-(2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)-4-methylpiperidin-4-yl)methanol The title compound (23 mg) was prepared in the same fashion as Step 3 in Example 1, except that (1-(2-chloro-5-

((2-(morpholinomethyl)thiazol-4-yl)ethynyl)pyridin-4-yl)-4-methylpiperidin-4-yl)methanol (298 mg, 0.667 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.60 (s, 1H), 8.44 (s, 1H), 8.40-8.39 (t, 2H), 7.63 (s, 1H), 7.44 (s, 1H), 6.97-6.96 (d, 1H), 3.86 (s, 2H), 3.76-3.72 (q, 6H), 3.49-3.39 (m, 4H), 2.83 (s, 1H), 2.63-2.61 (t, 4H), 1.81-1.78 (q, 2H), 1.58-1.49 (m, 4H), 1.27-1.17 (m, 2H), 1.07 (s, 3H); MS (ESI) m/z=678.2 (M+H)$^+$ Example 190. (1s,4s)-4-((2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)amino)cyclohexan-1-ol Step 1. (1s,4s)-4-((2-Chloro-5-((5-(morpholinomethyl)thiophen-2-yl)ethynyl)pyridin-4-yl)amino)cyclohexan-1-ol The title compound as an off-white solid (162 mg) was prepared in the same fashion as Step 1 in Example 157, except that 4-((5-((6-chloro-4-fluoropyridin-3-yl)ethynyl)thiophen-2-yl)methyl)morpholine (130 mg, 0.386 mmol) prepared in Reference Example 37 was used instead of 4-(4-((6-chloro-4-fluoropyridin-3-yl)ethynyl)benzyl)morpholine. $^1$H-NMR (CDCl$_3$, 400 MHz) δ 8.03 (s, 1H), 7.94 (s, 1H), 7.08-7.07 (d, 1H), 6.78-6.77 (d, 1H), 6.42 (s, 1H), 5.08-5.06 (d, 1H), 4.06-4.04 (d, 1H), 3.91-3.65 (m, 4H), 3.62 (s, 2H), 2.46-2.45 (d, 4H), 1.77-1.74 (t, 4H), 1.71-1.64 (m, 4H); MS (ESI) m/z=432.1 (M+H)$^+$ Step 2. (1s,4s)-4-((2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)amino)cyclohexan-1-ol The title compound (30 mg) was prepared in the same fashion as Step 3 in Example 1, except that (1s,4s)-4-((2-chloro-5-((5-(morpholinomethyl)thiophen-2-yl)ethynyl)pyridin-4-yl)amino)cyclohexan-1-ol (172 mg, 0.398 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43 (s, 1H), 8.39 (s, 1H), 8.38 (s, 1H), 8.14 (s, 1H), 7.19 (s, 1H), 7.13-7.12 (d, 1H), 7.09-7.07 (d, 1H), 6.84-6.83 (d, 1H), 5.18-5.16 (d, 1H), 3.93 (s, 1H), 3.74-3.72 (t, 4H), 3.69 (s, 2H), 2.81-2.80 (d, 1H), 2.52-2.51 (d, 4H), 1.91-1.87 (q, 4H), 1.83-1.80 (q, 2H), 1.78-1.70 (m, 2H), 1.52-1.50 (q, 2H), 1.21-1.19 (q, 2H); MS (ESI) m/z=661.2 (M+H)$^+$ Example 191. (1-(2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)-4-methylpiperidin-4-yl)methanol Step 1. (1-(2-Chloro-5-((5-(morpholinomethyl)thiophen-2-yl)ethynyl)pyridin-4-yl)-4-methylpiperidin-4-yl)methanol The title compound as a solid (169 mg) was prepared in the same fashion as Step 1 in Example 157 except that (4-methylpiperidin-4-yl)methanol (60 mg, 0.463 mmol) and 4-((5-((6-chloro-4-fluoropyridin-3-yl)ethynyl)thiophen-2-yl)methyl)morpholine (130 mg, 0.386 mmol) prepared in Reference Example 37 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.14 (s, 1H), 7.94 (s, 1H), 7.03 (d, 1H), 6.77-6.76 (d, 1H), 6.64 (s, 1H), 3.66-3.65 (d, 4H), 3.64-3.61 (d, 4H), 3.38 (s, 2H), 3.25-3.19 (m, 2H), 2.44 (s, 4H), 1.71-1.64 (m, 2H), 1.45-1.42 (d, 2H), 0.99 (s, 3H); MS (ESI) m/z=446.1 (M+H)$^+$ Step 2. (1-(2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)-4-methylpiperidin-4-yl)methanol The title compound (5 mg) was prepared in the same fashion as Step 3 in Example 1, except that (1-(2-chloro-5-((5-(morpholinomethyl)thiophen-2-yl)ethynyl)pyridin-4-yl)-4-methylpiperidin-4-yl)methanol (169 mg, 0.379 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.46-8.45 (d, 2H), 8.27-8.25 (d, 3H), 8.00 (s, 1H), 7.13-7.12 (d, 1H), 6.95-6.91 (q, 2H), 3.93-3.87 (t, 4H), 3.80-3.79 (d, 4H), 3.60-3.52 (q, 4H), 2.85-2.84 (d, 1H), 2.69 (s, 4H), 1.87-1.82 (t, 2H), 1.63-1.60 (t, 2H), 1.54 (s, 2H), 1.27-1.25 (d, 2H), 1.11 (s, 3H); MS (ESI) m/z=677.2 (M+H)$^+$ Example 192. (1-(2-((2-(1-(Cyclopropylsulfonyl)-1H-pyrazol-4-yl)pyrimidin-4-yl)amino)-5-((2-(morpholinomethyl)thiazol-5-yl)ethynyl)pyridin-4-yl)-4-methylpiperidin-4-yl)methanol Step 1. 4-((5-Ethynylthiazol-2-yl)methyl)morpholine The title compound as an off-white solid (1.45 g) was prepared in the same fashion as Step 1 in Reference Example 38, except that 5-ethynylthiazole-2-carbaldehyde (1.00 g, 7.291 mmol) was used instead of 6-ethynylpyridine-3-carbaldehyde. $^1$H-NMR (CDCl$_3$, 400 MHz) δ 7.82 (s, 1H), 3.81 (s, 2H), 3.75-3.73 (t, 4H), 2.61-2.59 (t, 4H); MS (ESI) m/z=209.1 (M+H)$^+$ Step 2. 4-((5-((6-Chloro-4-fluoropyridin-3-yl)ethynyl)thiazol-2-yl)methyl)morpholine The title compound as an off-white solid (427 mg) was prepared in the same fashion as Reference Example 18 except that 4-((5-ethynylthiazol-2-yl)methyl)morpholine (450 mg, 2.161 mmol) prepared in Step 1 was used instead of 4-ethynyl-1-methylpyrazole. $^1$H-NMR (CDCl$_3$, 400 MHz) δ 8.50-8.48 (d, 1H), 7.89 (s, 1H), 7.16-7.14 (d, 1H), 3.83-3.80 (d, 2H), 3.74-3.72 (t, 4H), 2.61-2.59 (t, 4H); MS (ESI) m/z=338.1 (M+H)$^+$ Step 3. (1-(2-Chloro-5-((2-(morpholinomethyl)thiazol-5-yl)ethynyl)pyridin-4-yl)-4-methylpiperidin-4-yl)methanol The title compound as a solid (119 mg) was prepared in the same fashion as Step 1 in Example 157 except that (4-methylpiperidin-4-yl)methanol (55 mg, 0.426 mmol) and 4-((5-((6-chloro-4-fluoropyridin-3-yl)ethynyl)thiazol-2-yl)methyl)morpholine (120 mg, 0.335 mmol) prepared in Step 2 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.18 (s, 1H), 7.78-7.76 (d, 1H), 6.68 (s, 1H), 3.80-3.79 (d, 2H), 3.72-3.62 (m, 6H), 3.41 (s, 2H), 3.28-3.22 (m, 2H), 2.59-2.57 (t, 4H), 1.73-1.66 (m, 2H), 1.48-1.43 (m, 2H), 1.02-1.01 (d, 3H)

Step 4. (1-(2-((2-(1-(Cyclopropylsulfonyl)-1H-pyrazol-4-yl)pyrimidin-4-yl)amino)-5-((2-(morpholinomethyl)thiazol-5-yl)ethynyl)pyridin-4-yl)-4-methylpiperidin-4-yl)methanol The title compound as an off-white solid (3 mg) was prepared in the same fashion as Step 3 in Example 1, except that (1-(2-chloro-5-((2-(morpholinomethyl)thiazol-5-yl)ethynyl)pyridin-4-yl)-4-methylpiperidin-4-yl)methanol (119 mg, 0.266 mmol) prepared in Step 3 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.46-8.45 (t, 2H), 8.25 (s, 1H), 8.15 (brs, 2H), 8.04 (s, 1H), 7.83 (s, 1H), 6.93-6.92 (d, 1H), 3.88-3.84 (t, 2H), 3.79-3.77 (t, 2H), 3.61-3.60 (d, 4H), 3.59-3.55 (q, 2H), 3.53 (s, 2H), 2.87-2.83 (q, 1H), 2.67-2.65 (t, 4H), 1.86-1.80 (m, 2H), 1.63-1.58 (m, 2H), 1.56-1.53 (q, 2H), 1.27-1.25 (t, 2H), 1.17-1.11 (d, 3H); MS (ESI) m/z=676.2 (M+H)$^+$ Example 193. (1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-yl)methanol Step 1. (1-(2-Chloro-5-((5-(morpholinomethyl)pyrimidin-2-yl)ethynyl)pyridin-4-yl)-4-methylpiperidin-4-yl)methanol The title compound as a solid (255 mg) was prepared in the same fashion as Step 1 in Example 157 except that (4-methylpiperidin-4-yl)methanol (130 mg, 1.010 mmol) and 4-((2-((6-chloro-4-fluoropyridin-3-yl)ethynyl)pyrimidin-5-yl)methyl)morpholine (280 mg, 0.841 mmol) prepared in Reference Example 41 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.68 (s, 2H), 8.35 (s, 1H), 6.70 (s, 1H), 3.83-3.80 (q, 2H), 3.79-3.78 (d, 4H), 3.71 (s, 2H), 3.70-3.69 (d, 4H), 2.47-2.44 (t, 4H), 1.80-1.73 (m, 2H), 1.49-1.45 (d, 2H), 1.04 (s, 3H)

Step 2. (1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-yl)methanol The title compound as an off-white solid (23 mg) was prepared in the same fashion as Step 3 in Example 1, except that (1-(2-chloro-5-((5-(morpholinomethyl)pyrimidin-2-yl)ethynyl)pyridin-4-yl)-4-methylpiperidin-4-yl)methanol (255 mg, 0.577 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.69 (s, 2H), 8.63 (s, 1H), 8.52 (s, 1H), 8.42-8.35 (m, 3H), 7.66 (s, 1H), 6.97-6.95 (d, 1H), 3.82-3.79 (t, 2H), 3.74-3.70 (q, 4H), 3.51 (s, 2H), 3.48-3.44 (q, 4H), 2.83 (s, 1H), 2.48-2.46 (t, 4H), 1.86-1.84 (q, 2H), 1.58-1.50 (m, 4H), 1.07-1.03 (d, 3H); MS (ESI) m/z=671.2 (M+H)$^+$ Example 194. (1s,4s)-4-((2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)amino)cyclohexan-1-ol Step 1. (1s,4s)-4-((2-Chloro-5-((5-(morpholinomethyl)pyrimidin-2-yl)ethynyl)pyridin-4-yl)amino) cyclohexan-1-ol The title compound as a solid (143 mg) was prepared in the same fashion as Step 1 in Example 157 except that 4-((2-(((6-chloro-4-fluoropyridin-3-yl)ethynyl)pyrimidin-5-yl)methyl)morpholine (280 mg, 0.841 mmol) prepared in Reference Example 41 was used instead of 4-(4-((6-chloro-4-fluoropyridin-3-yl)ethynyl)benzyl)morpholine. $^1$H-NMR (CDCl$_3$, 400 MHz) δ 8.66 (s, 2H), 8.21 (s, 1H), 6.47 (s, 1H), 5.58-5.56 (d, 1H), 3.92 (s, 2H), 3.69-3.68 (d, 4H), 2.59 (s, 2H), 2.45-2.44 (d, 4H), 1.85-1.71 (m, 8H)

Step 2. (1s,4s)-4-((2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)amino)cyclohexan-1-ol The title compound (1 mg) was prepared in the same fashion as Step 3 in Example 1, except that (1s,4s)-4-((2-chloro-5-((5-(morpholinomethyl)pyrimidin-2-yl)ethynyl)pyridin-4-yl)amino)cyclohexan-1-ol (143 mg, 0.334 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.71 (s, 1H), 8.63 (s, 1H), 8.45 (s, 1H), 8.34 (s, 1H), 8.20 (s, 1H), 7.50-7.47 (d, 1H), 7.15-7.13 (d, 1H), 5.78-5.70 (d, 1H), 3.93 (s, 1H), 3.75-3.72 (t, 5H), 3.54 (s, 2H), 2.83 (s, 1H), 2.49 (s, 4H), 1.93-1.85 (m, 8H), 1.52-1.50 (d, 2H), 1.24-1.20 (d, 2H); MS (ESI) m/z=657.2 (M+H)$^+$ Example 195. 4-((6-((2-(1-(cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-4-ol Step 1. (1-(2-Chloro-5-((tetrahydro-2H-pyran-4-yl)ethynyl)pyridin-4-yl)-4-methylpiperidin-4-yl)methanol The title compound as a solid (257 mg) was prepared in the same fashion as Step 1 in Example 157 except that (4-methylpiperidin-4-yl)methanol (130 mg, 1.009 mmol) and 4-((6-chloro-4-fluoropyridin-3-yl)ethynyl)tetrahydro-2H-pyran-4-ol (215 mg, 0.841 mmol) prepared in Reference Example 42 were used instead of cis-4-aminocyclohexanol HCl and 4-(4-((6-chloro-4-fluoropyridin-3-yl)ethynyl)benzyl)morpholine. $^1$H-NMR (CDCl$_3$, 400 MHz) δ 8.18 (s, 1H), 6.66 (s, 1H), 4.63 (s, 1H), 3.95-3.90 (m, 2H), 3.71-3.65 (m, 4H), 3.40 (s, 2H), 3.22-3.16 (q, 2H), 2.01-1.98 (q, 2H), 1.93-1.90 (q, 2H), 1.88-1.87 (t, 2H), 1.43-1.35 (q, 2H), 1.06 (s, 3H)

Step 2. 4-((6-((2-(1-(cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-4-ol The title compound as off-white solid (2 mg) was prepared in the same fashion as Step 3 in Example 1, except that (1-(2-chloro-5-((tetrahydro-2H-pyran-4-yl)ethynyl)pyridin-4-yl)-4-methylpiperidin-4-yl)methanol (257 mg, 0.704 mmol) prepared in Step 1 was used instead of 1-(2-chloro-5-((1-methyl-1H-pyrazol-4-yl)ethynyl)pyridin-4-yl)-

4-methylpiperazine. ¹H-NMR (CDCl₃, 400 MHz) δ 8.62 (s, 1H), 8.44-8.42 (t, 2H), 8.27 (s, 1H), 8.02-8.00 (d, 2H), 6.93-6.92 (d, 1H), 3.98-3.93 (m, 2H), 3.77-3.70 (m, 4H), 3.51-3.47 (q, 4H), 2.84-2.82 (t, 1H), 2.07-2.04 (t, 2H), 1.95-1.92 (q, 2H), 1.79-1.76 (q, 2H), 1.59-1.54 (m, 4H), 1.26-1.24 (q, 2H), 1.09 (s, 3H); MS (ESI) m/z=594.2 (M+H)⁺

Example 196. 4-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)tetrahydro-2H-pyran-4-ol Step 1. 4-((6-Chloro-4-(((1s,4s)-4-hydroxycyclohexyl)amino)pyridin-3-yl)ethynyl)tetrahydro-2H-pyran-4-ol The title compound as a solid (290 mg) was prepared in the same fashion as Step 1 in Example 157 except that 4-((6-chloro-4-fluoropyridin-3-yl)ethynyl)tetrahydro-2H-pyran-4-ol (215 mg, 0.841 mmol) prepared in Reference Example 42 was used instead of 4-(4-((6-chloro-4-fluoropyridin-3-yl)ethynyl)benzyl)morpholine. ¹H-NMR (CDCl₃, 400 MHz) δ8.09 (s, 2H), 6.43 (s, 1H), 5.16-5.14 (d, 1H), 5.01 (s, 1H), 3.98-3.92 (m, 3H), 3.70-3.64 (m, 2H), 3.43 (s, 1H), 2.03-1.89 (m, 3H), 1.75-1.67 (m, 8H)

Step 2. 4-((6-((2-(1-(Cyclopropylsulfonyl)-1H-pyrazol-4-yl)pyrimidin-4-yl)amino)-4-(((1 s, 4s)-4-hydroxycyclohexyl)amino)pyridin-3-yl)ethynyl)tetrahydro-2H-pyran-4-ol 1s,4s-1H The title compound (158 mg) was prepared in the same fashion as Step 3 in Example 1, except that 4-((6-chloro-4-(((1s,4s)-4-hydroxycyclohexyl)amino)pyridin-3-yl)ethynyl)tetrahydro-2H-pyran-4-ol (290 mg, 0.827 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.57 (s, 1H), 8.37 (s, 1H), 8.29-8.28 (d, 1H), 8.02 (s, 1H), 7.23 (s, 1H), 6.93-6.91 (d, 1H), 5.16-5.14 (d, 1H), 3.92-3.89 (t, 2H), 3.80 (s, 1H), 3.68-3.64 (t, 2H), 3.57 (s, 1H), 2.80-2.76 (q, 1H), 1.91-1.85 (m, 2H), 1.75-1.72 (d, 4H), 1.57-1.55 (d, 2H), 1.45-1.42 (m, 4H), 1.14 (d, 2H); MS (ESI) m/z=580.2 (M+H)⁺

Example 197. (1-(2-((2-(1-(Cyclopropylsulfonyl)-1H-pyrazol-4-yl)pyrimidin-4-yl)amino)-5-((tetrahydrofuran-3-yl)ethynyl)pyridin-4-yl)-4-methylpiperidin-4-yl)methanol Step 1. (1-(2-Chloro-5-((tetrahydrofuran-3-yl)ethynyl)pyridin-4-yl)-4-methylpiperidin-4-yl)methanol The title compound as a solid (334 mg) was prepared in the same fashion as Step 1 in Example 157 except that (4-methylpiperidin-4-yl)methanol (172 mg, 1.329 mmol) and 2-chloro-4-fluoro-5-((tetrahydrofuran-3-yl)ethynyl) pyridine (250 mg, 1.108 mmol) prepared in Reference Example 43 were used instead of cis-4-aminocyclohexanol HCl and 4-(4-((6-chloro-4-fluoropyridin-3-yl)ethynyl)benzyl)morpholine. ¹H-NMR (CDCl₃, 400 MHz) δ 8.04 (s, 1H), 6.61 (s, 1H), 4.07-4.00 (m, 2H), 3.98-3.78 (m, 2H), 3.68-3.64 (t, 2H), 3.22-3.07 (m, 4H), 2.27-2.18 (m, 1H), 1.65-1.60 (t, 2H), 1.40-1.36 (d, 2H), 0.97 (s, 3H)

Step 2. (1-(2-((2-(1-(Cyclopropylsulfonyl)-1H-pyrazol-4-yl)pyrimidin-4-yl)amino)-5-((tetrahydrofuran-3-yl)ethynyl)pyridin-4-yl)-4-methylpiperidin-4-yl)methanol The title compound (12 mg) was prepared in the same fashion as Step 3 in Example 1, except that (1-(2-chloro-5-((tetrahydrofuran-3-yl)ethynyl)pyridin-4-yl)-4-methylpiperidin-4-yl)methanol (334 mg, 0.997 mmol) prepared in Step 1 was used instead of 1-(2-chloro-5-((1-methyl-1H-pyrazol-4-yl)ethynyl)pyridin-4-yl)-4-methylpiperazine 1s,4s. ¹H-NMR (CDCl₃, 400 MHz) δ 8.61 (s, 1H), 8.43-8.41 (t, 3H), 8.14 (s, 1H), 7.91 (s, 1H), 6.93-6.91 (d, 1H), 4.09-4.05 (t, 1H), 3.98-3.89 (m, 2H), 3.81-3.72 (m, 4H), 3.54 (s, 3H), 3.52-3.46 (m, 1H), 3.28-3.24 (t, 2H), 2.84 (s, 1H), 2.39 (s, 1H), 2.09-2.07 (q, 1H), 1.79-1.77 (t, 2H), 1.58-1.53 (m, 4H), 1.26-1.23 (q, 2H), 1.09 (s, 3H)

Example 198. (1s,4s)-4-((2-((2-(1-(Cyclopropylsulfonyl)-1H-pyrazol-4-yl)pyrimidin-4-yl)amino)-5-((tetrahydrofuran-3-yl)ethynyl)pyridin-4-yl)amino)cyclohexan-1-ol Step 1. (1s,4S)-4-((2-Chloro-5-((tetrahydrofuran-3-yl)ethynyl)pyridin-4-yl)amino)cyclohexan-1-ol The title compound as a solid (275 mg) was prepared in the same fashion as Step 1 in Example 157 except that 2-chloro-4-fluoro-5-((tetrahydrofuran-3-yl)ethynyl)pyridine (250 mg, 1.108 mmol) prepared in Reference Example 43 was used instead of 4-(4-((6-chloro-4-fluoropyridin-3-yl) ethynyl)benzyl)morpholine. ¹H-NMR (CDCl₃, 400 MHz) δ 7.99 (s, 1H), 6.42 (s, 1H), 5.10-5.08 (d, 1H), 3.99-3.85 (m, 3H), 3.78-3.75 (q, 1H), 3.43 (s, 1H), 3.29-3.23 (q, 1H), 2.36-2.27 (m, 2H), 1.82-1.63 (m, 8H)

Step 2. (1s,4s)-4-((2-((2-(1-(Cyclopropylsulfonyl)-1H-pyrazol-4-yl)pyrimidin-4-yl)amino)-5-((tetrahydrofuran-3-yl)ethynyl)pyridin-4-yl)amino)cyclohexan-1-ol The title compound (6 mg) was prepared in the same fashion as Step 3 in Example 1, except that (1s,4s)-4-((2-chloro-5-((tetrahydrofuran-3-yl)ethynyl)pyridin-4-yl) amino)cyclohexan-1-ol (275 mg, 0.857 mmol) prepared in Step 1 was used instead of (I s,4s)-4-((2-fluoro-54(1-hydroxycyclopentyl)ethynyi)pyridin-4-yl)amino)cyclohexan-1-ol. ¹H-NMR (CDCl₃, 400 MHz) δ 8.60 (s, 1H), 8.45-8.42 (t, 2H), 8.33 (s, 1H), 7.88 (s, 1H), 7.80 (d, 1H), 7.02-7.00 (t, 1H), 6.73-6.69 (d, 1H), 4.08-4.02 (m, 2H), 3.93-3.83 (m, 3H), 3.82 (s, 1H), 3.34-3.24 (t, 1H), 2.83 (s, 1H), 1.93-1.86 (m, 6H), 1.65-1.63 (d, 2H), 1.55-1.53 (q, 2H), 1.25-1.22 (q, 2H)

Example 199. $N^2$-(2-(1-(Cyclopropylsulfonyl)-1H-pyrazol-4-yl)pyrimidin-4-yl)-$N^4$-isopropyl-5-((2-methylthiazol-4-yl)ethynyl)pyridine-2,4-diamine Step 1. 2-Chloro-N-isopropyl-5-(2-(2-methylthiazol-4-yl)ethynyl)pyridin-4-amine The reaction mixture of 4-ethynyl-2-methyl-thiazole (88.85 mg, 0.72 1 mmol), Pd(PPh₃)₄ (37 mg, 0.060 mmol), CuI (23 mg, 0.12 mmol), TEA (0.17 mL, 1.202 mmol) and 5-bromo-2-chloro-N-isopropyl-pyridin-4-amine (150 mg, 0.601 mmol) prepared in Reference Example 44 in DMF (5 mL) was stirred at 90° C. overnight. The reaction mixture was cooled to room temperature, and quenched with water, then extracted with DCM. The organic layer was dried over MgSO$_4$, filtered, and concentrated. (EA/n-Hex=0-50%) to yield 2-chloro-N-isopropyl-5-(2-(2-methylthiazol-4-yl)ethynyl)pyridin-4-amine (121 mg) as pale yellow solid. MS (ESI) m/z=292.1 (M+H)$^+$ Step 2. N$^2$-(2-(1-(Cyclopropylsulfonyl)-1H-pyrazol-4-yl)pyrimidin-4-yl)-N$^4$-isopropyl-5-((2-methylthiazol-4-yl)ethynyl)pyridine-2,4-diamine The title compound as a pale yellow solid (11 mg) was prepared in the same fashion as Step 3 in Example 1 except that 2-chloro-N-isopropyl-5-(2-(2-methylthiazol-4-yl)ethynyl)pyridin-4-amine (28 mg, 0.094 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.41 (d, 1H), 8.16 (s, 1H), 8.00 (s, 1H), 7.40 (s, 1H), 7.33 (s, 1H), 7.07 (d, 1H), 5.09 (d, 1H), 3.91-3.83 (m, 1H), 2.88-2.83 (m, 1H), 2.77 (s, 3H), 1.56-1.52 (m, 2H), 1.39 (d, 6H), 1.26-1.21 (m, 2H)

Example 200. N$^2$-(2-(1-(cyclopropylsulfonyl)-1H-pyrazol-4-yl)pyrimidin-4-yl)-5-((2-(fluoromethyl)thiazol-4-yl)ethynyl)-N$^4$-isopropylpyridine-2,4-diamine Step 1. 2-Chloro-5-(2-(2-(fluoromethyl)thiazol-4-yl)ethynyl)-N-isopropyl-pyridin-4-amine The title compound (301 mg) was prepared in the same fashion as Step 1 in Example 199, except that 4-ethynyl-2-(fluoromethyl)thiazole (204 mg, 1.443 mmol) was used instead of 4-ethynyl-2-methyl-thiazole. MS (ESI) m/z=250.9 (M+H)$^+$ Step 2. N$^2$-(2-(1-(cyclopropylsulfonyl)-1H-pyrazol-4-yl)pyrimidin-4-yl)-5-((2-(fluoromethyl)thiazol-4-yl)ethynyl)-N$^4$-isopropylpyridine-2,4-diamine The title compound as a pale yellow solid (9 mg) was prepared in the same fashion as Step 3 in Example 1 except that 2-chloro-5-(2-(2-(fluoromethyl)thiazol-4-yl)ethynyl)-N-isopropyl-pyridin-4-amine (58 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.42 (d, 1H), 8.19 (s, 1H), 7.77 (s, 1H), 7.62 (s, 1H), 7.30 (s, 1H), 7.06 (d, 1H), 5.72 (s, 1H), 5.60 (s, 1H), 5.02 (d, 1H), 3.91-3.83 (m, 1H), 2.87-2.81 (m, 1H), 1.56-1.52 (m, 2H), 1.39 (d, 6H), 1.25-1.19 (m, 2H); MS (ESI) m/z=539.1 (M+H)$^+$ Example 201. 4-(3-(6-((2-(1-(Cyclopropylsulfonyl)-1H-pyrazol-4-yl)pyrimidin-4-yl)amino)-4-(isopropylamino)pyridin-3-yl)prop-2-yn-1-yl)thiomorpholine 1,1-dioxide Step 1. 2-Chloro-5-iodo-N-isopropyl-pyridin-4-amine The reaction mixture of 2,4-dichloro-5-iodo-pyridine (2.00 g, 7.302 mmol), isopropylamine (1.25 mL, 14.604 mmol) and DIPEA (3.82 mL, 21.907 mmol) in DMA (20 mL) was stirred at 100° C. for 5 hours. The reaction mixture was cooled to room temperature, diluted in DCM, washed by water, dried over MgSO$_4$, and then concentrated. The crude product was purified by column chromatography (EA/n-Hex=0-50%) to yield 2-chloro-5-iodo-N-isopropylpyridin-4-amine (1.32 g) as pale yellow liquid. MS (ESI) m/z=296.9 (M+H)$^+$ Step 2. 2-Chloro-5-(3-(1,1-dioxo-1,4-thiazinan-4-yl)prop-1-ynyl)-N-isopropyl-pyridin-4-amine The title compound (194 mg) was prepared in the same fashion as Step 1 in Example 199, except that 4-propargyl-thiomorpholine 1,1-dioxide (1402 mg, 0.809 mmol) and 2-chloro-5-iodo-N-isopropylpyridin-4-amine (200 mg, 0.674 mmol) prepared in Step 1 were used instead of 4-ethynyl-2-methyl-thiazole and 5-bromo-2-chloro-N-isopropyl-pyridin-4-amine. MS (ESI) m/z=342.0 (M+H)$^+$ Step 3. 4-(3-(6-((2-(1-(Cyclopropylsulfonyl)-1H-pyrazol-4-yl)pyrimidin-4-yl)amino)-4-(isopropylamino)pyridin-3-yl)prop-2-yn-1-yl)thiomorpholine 1,1-dioxide The title compound as a pale yellow solid (21 mg) was prepared in the same fashion as Step 3 in Example 1 except that 2-chloro-5-(3-(1,1-dioxo-1,4-thiazinan-4-yl)prop-1-ynyl)-N-isopropyl-pyridin-4-amine (64 mg, 0.188 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.41 (d, 1H), 8.07 (s, 1H), 7.59 (s, 1H), 7.25 (s, 1H), 7.05 (d, 1H), 4.84 (d, 1H), 3.76 (s, 2H), 3.68-3.62 (m, 1H), 3.17 (brs, 8H), 2.87-2.81 (m, 1H), 1.56-1.51 (m, 2H), 1.38 (d, 6H), 1.25-1.20 (m, 2H)

Example 202. N$^2$-(2-(1-(Cyclopropylsulfonyl)-1H-pyrazol-4-yl)pyrimidin-4-yl)-N$^4$-isopropyl-5-(3-morpholinoprop-1-yn-1-yl)pyridine-2,4-diamine Step 1. 2-Chloro-N-isopropyl-5-(3-morpholinoprop-1-ynyl)pyridin-4-amine The title compound (155 mg) was prepared in the same fashion as Step 1 in Example 199, except that 4-prop-2-ynylmorpholine (101 mg, 0.809 mmol) was used instead of 4-ethynyl-2-methyl-thiazole. MS (ESI) m/z=294.0 (M+H)$^+$ Step 2. N$^2$-(2-(1-(Cyclopropylsulfonyl)-1H-pyrazol-4-yl)pyrimidin-4-yl)-N$^4$-isopropyl-5-(3-morpholinoprop-1-yn-1-yl)pyridine-2,4-diamine The title compound as a pale yellow solid (18 mg) was prepared in the same fashion as Step 3 in Example 1 except that 2-chloro-N-isopropyl-5-(3-morpholinoprop-1-ynyl)pyridin-4-amine (55 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.40 (d, 1H), 8.07 (s, 1H), 7.84 (s, 1H), 7.25 (s, 1H), 7.03 (d, 1H), 4.93 (d, 1H), 3.81 (t, 4H), 3.62 (s, 2H), 2.86-2.80 (m, 1H), 2.67 (t, 4H), 1.55-1.51 (m, 2H), 1.37 (d, 6H), 1.25-1.20 (m, 2H)

Example 203. N$^2$-(2-(1-(Cyclopropylsulfonyl)-1H-pyrazol-4-yl)pyrimidin-4-yl)-N$^1$-isopropyl-5-(3-(pyrrolidin-1-yl)prop-1-yn-1-yl)pyridine-2,4-diamine Step 1. 2-Chloro-N-isopropyl-5-(3-pyrrolidin-1-ylprop-1-ynyl)pyridin-4-amine The title compound (122 mg) was prepared in the same fashion as Step 1 in Example 199, except that 1-prop-2- ynylpyrrolidine (88 mg, 0.809 mmol) was used instead of 4-ethynyl-2-methyl-thiazole. MS (ESI) m/z=278.1 (M+H)+

Step 2. N²-(2-(1-(Cyclopropylsulfonyl)-1H-pyrazol-4-yl)pyrimidin-4-yl)-N⁴-isopropyl-5-(3-(pyrrolidin-1-yl)prop-1-yn-1-yl)pyridine-2,4-diamine The title compound as a pale yellow solid (25 mg) was prepared in the same fashion as Step 3 in Example 1 except that 2-chloro-N-isopropyl-5-(3-pyrrolidin-1-ylprop-1-ynyl) pyridin-4-amine (52 mg, 0.188 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.40 (d, 1H), 8.06 (s, 1H), 7.72 (s, 1H), 7.22 (s, 1H), 7.05 (d, 1H), 4.96 (d, 1H), 3.87-3.80 (m, 1H), 3.73 (s, 2H), 2.87-2.80 (m, 1H), 2.72 (brs, 4H), 1.89-1.85 (m, 4H), 1.55-1.51 (m, 2H), 1.36 (d, 6H), 1.25-1.20 (m, 2H)

Example 204. 4-(6-((2-(1-(Cyclopropylsulfonyl)-1H-pyrazol-4-yl)pyrimidin-4-yl)amino)-4-(isopropylamino)pyridin-3-yl)-2-methylbut-3-yn-2-ol Step 1. 4-(6-Chloro-4-(isopropylamino)-3-pyridyl)-2-methyl-but-3-yn-2-ol The title compound (155 mg) was prepared in the same fashion as Step 1 in Example 199, except that 3-methyl-1-butyn-3-ol (62 mg, 0.742 mmol) was used instead of 4-ethynyl-2-methyl-thiazole. MS (ESI) m/z=253.1 (M+H)+

Step 2. 4-(6-((2-(1-(Cyclopropylsulfonyl)-1H-pyrazol-4-yl)pyrimidin-4-yl)amino)-4-(isopropylamino)pyridin-3-yl)-2-methylbut-3-yn-2-ol The title compound as a pale yellow solid (5 mg) was prepared in the same fashion as Step 3 in Example 1 except that 4-(6-chloro-4-(isopropylamino)-3-pyridyl)-2-methyl-but-3-yn-2-ol (48 mg, 0.188 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.46 (s, 1H), 8.41 (d, 1H), 8.06 (s, 1H), 7.55 (s, 1H), 7.22 (s, 1H), 7.04 (d, 1H), 4.89 (d, 1H), 3.86-3.78 (m, 1H), 2.87-2.81 (m, 1H), 1.68 (s, 6H), 1.56-1.52 (m, 2H), 1.37 (d, 6H), 1.25-1.20 (m, 2H)

Example 205. N²-(2-(1-(Cyclopropylsulfonyl)-1H-pyrazol-4-yl)pyrimidin-4-yl)-5-((2-cyclopropylthiazol-4-yl)ethynyl)-N⁴-isopropylpyridine-2,4-diamine Step 1. 2-Chloro-5-(2-(2-cyclopropylthiazol-4-yl)ethynyl)-N-isopropyl-pyridin-4-amine The title compound (98 mg) was prepared in the same fashion as Step 1 in Example 199, except that 2-cyclopropyl-4-ethynyl-thiazole (55 mg, 0.371 mmol) was used instead of 4-ethynyl-2-methyl-thiazole. MS (ESI) m/z=318.1 (M+H)+

Step 2. N²-(2-(1-(Cyclopropylsulfonyl)-1H-pyrazol-4-yl)pyrimidin-4-yl)-5-((2-cyclopropylthiazol-4-yl)ethynyl)-N⁴-isopropylpyridine-2,4-diamine The title compound as a pale yellow solid (5 mg) was prepared in the same fashion as Step 3 in Example 1 except that 2-chloro-5-(2-(2-cyclopropylthiazol-4-yl)ethynyl)-N-isopropyl-pyridin-4-amine (30 mg, 0.094 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=547.1 (M+H)+

Example 206. N²-(2-(1-(Cyclopropylsulfonyl)-1H-pyrazol-4-yl)pyrimidin-4-yl)-N⁴-isopropyl-5-((tetrahydro-2H-pyran-4-yl)ethynyl)pyridine-2,4-diamine Step 1. 2-Chloro-N-isopropyl-5-(2-tetrahydropyran-4-ylethynyl)pyridin-4-amine The title compound (247 mg) was prepared in the same fashion as Step 1 in Example 199, except that 4-ethynyltetrahydropyran (123 mg, 1.113 mmol) was used instead of 4-ethynyl-2-methyl-thiazole. MS (ESI) m/z=279.1 (M+H)+

Step 2. N²-(2-(1-(Cyclopropylsulfonyl)-1H-pyrazol-4-yl)pyrimidin-4-yl)-N⁴-isopropyl-5-((tetrahydro-2H-pyran-4-yl)ethynyl)pyridine-2,4-diamine The title compound as a pale yellow solid (2 mg) was prepared in the same fashion as Step 3 in Example 1 except that 2-chloro-N-isopropyl-5-(2-tetrahydropyran-4-ylethynyl)pyridin-4-amine (53 mg, 0.188 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=508.2 (M+H)+

Example 207. N-(5-(6-((2-(1-(Cyclopropylsulfonyl)-1H-pyrazol-4-yl)pyrimidin-4-yl)amino)-4-(isopropylamino)pyridin-3-yl)pent-4-yn-1-yl)morpholine-4-carboxamide Step 1. N-(5-(6-Chloro-4-(isopropylamino)-3-pyridyl)pent-4-ynyl)morpholine-4-carboxamide The title compound (307 mg) was prepared in the same fashion as Step 1 in Example 199, except that N-pent-4-ynylmorpholine-4-carboxamide (218 mg, 1.113 mmol) was used instead of 4-ethynyl-2-methyl-thiazole. MS (ESI) m/z=365.2 (M+H)+

Step 2. N-(5-(6-((2-(1-(Cyclopropylsulfonyl)-1H-pyrazol-4-yl)pyrimidin-4-yl)amino)-4-(isopropylamino)pyridin-3-yl)pent-4-yn-1-yl)morpholine-4-carboxamide The title compound as a pale yellow solid (6 mg) was prepared in the same fashion as Step 3 in Example 1 except that N-(5-(6-chloro-4-(isopropylamino)-3-pyridyl)pent-4-ynyl)morpholine-4-carboxamide (69 mg, 0.188 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=594.3 (M+H)+

Example 208. 6-(6-((2-(1-(Cyclopropylsulfonyl)-1H-pyrazol-4-yl)pyrimidin-4-yl)amino)-4-(isopropyl amino)pyridin-3-yl)-1-morpholinohex-5-yn-1-one Step 1. 6-(6-Chloro-4-(isopropylamino)-3-pyridyl)-1-morpholino-hex-5-yn-1-one The title compound (211 mg) was prepared in the same fashion as Step 1 in Example 199, except that 1-morpholino-hex-5-yn-1-one (202 mg, 1.113 mmol) was used instead of 4-ethynyl-2-methyl-thiazole. MS (ESI) m/z=350.2 (M+H)+

Step 2. 6-(6-((2-(1-(Cyclopropylsulfonyl)-1H-pyrazol-4-yl)pyrimidin-4-yl)amino)-4-(isopropylamino)pyridin-3-yl)-1-morpholinohex-5-yn-1-one The title compound as a pale yellow solid (6 mg) was prepared in the same fashion as Step 3 in Example 1 except that 6-(6-chloro-4-(isopropylamino)-3-pyridyl)-1-morpholino-hex-5-yn-1-one (66 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.39 (d, 1H), 8.01 (s, 1H), 7.63 (s, 1H), 7.19 (s, 1H), 7.06 (d, 1H), 4.97 (d, 1H), 3.86-3.78 (m, 1H), 3.70-3.64 (m, 6H), 3.51 (t, 2H), 2.87-2.80 (m, 1H), 2.61 (t, 2H), 2.52 (t, 2H), 2.04-1.97 (m, 2H), 1.55-1.51 (m, 2H), 1.36 (d, 6H), 1.25-1.19 (m, 2H); MS (ESI) m/z=579.2 (M+H)$^+$ Example 209. N-(6-(6-((2-(1-(Cyclopropylsulfonyl)-1H-pyrazol-4-yl)pyrimidin-4-yl)amino)-4-(isopropylamino)pyridin-3-yl)hex-5-yn-1-yl)morpholine-4-carboxamide Step 1. N-(6-(6-Chloro-4-(isopropylamino)-3-pyridyl)hex-5-ynyl)morpholine-4-carboxamide The title compound (297 mg) was prepared in the same fashion as Step 1 in Example 199, except that N-hex-5-ynylmorpholine-4-carboxamide (234 mg, 1.113 mmol) was used instead of 4-ethynyl-2-methyl-thiazole. MS (ESI) m/z=379.2 (M+H)$^+$ Step 2. N-(6-(6-((2-(1-(Cyclopropylsulfonyl)-1H-pyrazol-4-yl)pyrimidin-4-yl)amino)-4-(isopropylamino)pyridin-3-yl)hex-5-yn-1-yl)morpholine-4-carboxamide The title compound as a pale yellow solid (22 mg) was prepared in the same fashion as Step 3 in Example 1 except that N-(6-(6-chloro-4-(isopropylamino)-3-pyridyl)hex-5-ynyl)morpholine-4-carboxamide (79 mg, 0.207 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.40 (d, 1H), 8.01 (s, 1H), 7.57 (s, 1H), 7.20 (s, 1H), 7.06 (d, 1H), 4.92 (d, 1H), 4.81 (s, 1H), 3.86-3.78 (m, 1H), 3.69 (t, 4H), 3.35 (t, 6H), 2.87-2.80 (m, 1H), 2.55 (t, 2H), 1.74-1.68 (m, 4H), 1.56-1.52 (m, 2H), 1.37 (d, 6H), 1.25-1.20 (m, 2H); MS (ESI) m/z=608.3 (M+H)$^+$ Example 210. 7-(6-((2-(1-(Cyclopropylsulfonyl)-1H-pyrazol-4-yl)pyrimidin-4-yl)amino)-4-(isopropylamino)pyridin-3-yl)-1-morpholinohept-6-yn-1-one Step 1. 7-(6-Chloro-4-(isopropylamino)-3-pyridyl)-1-morpholino-hept-6-yn-1-one The title compound (367 mg) was prepared in the same fashion as Step 1 in Example 199, except that 1-morpholinohept-6-yn-1-one (217 mg, 1.113 mmol) was used instead of 4-ethynyl-2-methyl-thiazole. MS (ESI) m/z=364.2 (M+H)$^+$ Step 2. 7-(6-((2-(1-(Cyclopropylsulfonyl)-1H-pyrazol-4-yl)pyrimidin-4-yl)amino)-4-(isopropylamino)pyridin-3-yl)-1-morpholinohept-6-yn-1-one The title compound as a pale yellow solid (35 mg) was prepared in the same fashion as Step 3 in Example 1 except that 7-(6-chloro-4-(isopropylamino)-3-pyridyl)-1-morpholino-hept-6-yn-1-one (75 mg, 0.207 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.39 (d, 1H), 8.02 (s, 1H), 7.72 (s, 1H), 7.19 (s, 1H), 7.08 (d, 1H), 4.94 (d, 1H), 3.86-3.76 (m, 1H), 3.67-3.63 (m, 6H), 3.50-3.47 (m, 2H), 2.86-2.80 (m, 1H), 2.55 (t, 2H), 2.40 (t, 2H), 1.89-1.82 (m, 2H), 1.75-1.68 (m, 2H), 1.55-1.51 (m, 2H), 1.36 (d, 6H), 1.24-1.19 (m, 2H); MS (ESI) m/z=593.3 (M+H)$^+$ Example 211. 1-(2-((2-(1-(Cyclopropylsulfonyl)-1H-pyrazol-4-yl)pyrimidin-4-yl)amino)-5-((2-methylthiazol-4-yl)ethynyl)pyridin-4-yl)piperidin-4-ol Step 1. 1-(2-Chloro-5-(2-(2-methylthiazol-4-yl)ethynyl)-4-pyridyl)piperidin-4-ol The title compound as a pale yellow solid (134 mg) was prepared in the same fashion as Step 1 in Example 199, except that 1-(2-chloro-5-iodopyridin-4-yl)piperidin-4-ol (200 mg, 0.591 mmol) prepared in Reference Example 2 was used instead of 5-bromo-2-chloro-N-isopropyl-pyridin-4-amine. MS (ESI) m/z=334.1 (M+H)$^+$ Step 2. 1-(2-((2-(1-(Cyclopropylsulfonyl)-1H-pyrazol-4-yl)pyrimidin-4-yl)amino)-5-((2-methylthiazol-4-yl)ethynyl)pyridin-4-yl)piperidin-4-ol The title compound as a pale yellow solid (21 mg) was prepared in the same fashion as Step 3 in Example 1 except that 1-(2-chloro-5-(2-(2-methylthiazol-4-yl)ethynyl)-4-pyridyl)piperidin-4-ol (63 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.44 (s, 1H), 8.41 (d, 1H), 8.32 (s, 1H), 8.19 (s, 1H), 7.65 (s, 1H), 7.34 (s, 1H), 6.99 (d, 1H), 4.05-3.99 (m, 1H), 3.93-3.87 (m, 2H), 3.34-3.28 (m, 2H), 2.86-2.80 (m, 1H), 2.75 (s, 3H), 2.15-2.10 (m, 2H), 1.87-1.79 (m, 2H), 1.56-1.52 (m, 2H), 1.25-1.20 (m, 2H); MS (ESI) m/z=563.1 (M+H)$^+$ Example 212. 1-(2-((2-(1-(Cyclopropylsulfonyl)-1H-pyrazol-4-yl)pyrimidin-4-yl)amino)-5-((2-(fluoromethyl)thiazol-4-yl)ethynyl)pyridin-4-yl)piperidin-4-ol Step 1. 1-(2-Chloro-5-(2-(2-(fluoromethyl)thiazol-4-yl)ethynyl)-4-pyridyl)piperidin-4-ol The title compound as a pale yellow solid (118 mg) was prepared in the same fashion as Step 1 in Example 199, except that 1-(2-chloro-5-iodopyridin-4-yl)piperidin-4-ol (200 mg, 0.591 mmol) prepared in Reference Example 2 and 4-ethynyl-2-(fluoromethyl)thiazole (92 mg, 0.650 mmol) were used instead of 5-bromo-2-chloro-N-isopropyl-pyridin-4-amine and 4-ethynyl-2-methyl-thiazole. MS (ESI) m/z=352.1 (M+H)$^+$ Step 2. 1-(2-((2-(1-(Cyclopropylsulfonyl)-1H-pyrazol-4-yl)pyrimidin-4-yl)amino)-5-((2-(fluoromethyl)thiazol-4-yl)ethynyl)pyridin-4-yl)piperidin-4-ol The title compound as a pale yellow solid (14 mg) was prepared in the same fashion as Step 3 in Example 1 except that 1-(2-chloro-5-(2-(2-(fluoromethyl)thiazol-4-yl)ethynyl)-4-pyridyl)piperidin-4-ol (66 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.42 (d, 1H), 8.32 (s, 1H), 8.16 (s, 1H), 7.67 (s, 1H), 7.56 (s, 1H), 6.99 (d, 1H), 5.71 (s, 1H), 5.59 (s, 1H), 4.04-4.01 (m, 1H), 3.92-3.87 (m, 2H), 3.35-3.28 (m, 2H), 2.87-2.81 (m, 1H), 2.15-2.10 (m, 2H), 1.97-1.87 (m, 2H), 1.79-1.75 (m, 2H), 1.56-1.52 (m, 2H), 1.24-1.20 (m, 2H); MS (ESI) m/z=581.1 (M+H)$^+$ Example 213. 1-(2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)piperidin-4-ol Step 1. 1-(2-Chloro-5-(2-(1-methylimidazol-4-yl)ethynyl)-4-pyridyl)piperidin-4-ol The title compound as a pale yellow solid (123 mg) was prepared in the same fashion as Step 1 in Example 199, except that 1-(2-chloro-5-iodopyridin-4-yl)piperidin-4-ol (300 mg, 0.886 mmol) prepared in Reference Example 2 and 4-ethynyl-1-methyl-imidazole (103 mg, 0.975 mmol) were used instead of 5-bromo-2-chloro-N-isopropyl-pyridin-4-amine and 4-ethynyl-2-methyl-thiazole. MS (ESI) m/z=317.2 (M+H)$^+$ Step 2. 1-(2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)piperidin-4-ol The title compound as a pale yellow solid (15 mg) was prepared in the same fashion as Step 3 in Example 1 except that 1-(2-chloro-5-(2-(1-methylimidazol-4-yl)ethynyl)-4-pyridyl)piperidin-4-ol (60 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.44 (s, 1H), 8.40 (d, 1H), 8.30 (s, 1H), 8.17 (s, 1H), 7.58 (s, 1H), 7.44 (s, 1H), 7.13 (s, 1H), 7.03 (d, 1H), 4.02-3.98 (m, 1H), 3.91-3.87 (m, 2H), 3.72 (s, 3H), 3.31-3.26 (m, 2H), 2.86-2.79 (m, 1H), 2.13-2.10 (m, 2H), 1.87-1.79 (m, 2H), 1.55-1.51 (m, 2H), 1.25-1.20 (m, 2H); MS (ESI) m/z=546.2 (M+H)$^+$ Example 214. 1-(2-((2-(1-(Cyclopropylsulfonyl)-1H-pyrazol-4-yl)pyrimidin-4-yl)amino)-5-((1-methyl-1H-1,2,4-triazol-3-yl)ethynyl)pyridin-4-yl)piperidin-4-ol Step 1. 1-(2-Chloro-5-(2-(1-methyl-1,2,4-triazol-3-yl)ethynyl)-4-pyridyl)piperidin-4-ol The title compound as a pale yellow solid (72 mg) was prepared in the same fashion as Step 1 in Example 199, except that 1-(2-chloro-5-iodopyridin-4-yl)piperidin-4-ol (300 mg, 0.886 mmol) prepared in Reference Example 2 and 3-ethynyl-1-methyl-1,2,4-triazole (104 mg, 0.975 mmol) were used instead of 5-bromo-2-chloro-N-isopropyl-pyridin-4-amine and 4-ethynyl-2-methyl-thiazole. MS (ESI) m/z=318.1 (M+H)$^+$ Step 2. 1-(2-((2-(1-(Cyclopropylsulfonyl)-1H-pyrazol-4-yl)pyrimidin-4-yl)amino)-5-((1-methyl-1H-1,2,4-triazol-3-yl)ethynyl)pyridin-4-yl)piperidin-4-ol The title compound as a pale yellow solid (13 mg) was prepared in the same fashion as Step 3 in Example 1 except that 1-(2-chloro-5-(2-(1-methyl-1,2,4-triazol-3-yl)ethynyl)-4-pyridyl)piperidin-4-ol (60 mg, 0.188 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=547.1 (M+H)$^+$ Example 215. 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-4-ol Step 1. 1-(2-Chloro-5-(2-(6-morpholino-3-pyridyl)ethynyl)-4-pyridyl)piperidin-4-ol The title compound as a pale yellow solid (276 mg) was prepared in the same fashion as Step 1 in Example 199, except that 1-(2-chloro-5-iodopyridin-4-yl)piperidin-4-ol (299 mg, 0.885 mmol) prepared in Reference Example 2 and 4-(5-ethynyl-2-pyridyl)morpholine (185 mg, 0.983 mmol) were used instead of 5-bromo-2-chloro-N-isopropyl-pyridin-4-amine and 4-ethynyl-2-methyl-thiazole. MS (ESI) m/z=399.0 (M+H)$^+$ Step 2. 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-4-ol The title compound as a pale yellow solid (19 mg) was prepared in the same fashion as Step 3 in Example 1 except that 1-(2-chloro-5-(2-(6-morpholino-3-pyridyl)ethynyl)-4-pyridyl)piperidin-4-ol (165 mg, 0.415 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.46 (s, 1H), 8.42 (d, 1H), 8.36 (d, 1H), 8.27 (s, 1H), 7.81 (s, 1H), 7.67 (s, 1H), 7.60 (dd, 1H), 6.99 (d, 1H), 6.62 (d, 1H), 4.05-3.99 (m, 1H), 3.90-3.82 (m, 6H), 3.59-3.57 (m, 4H), 3.32-3.26 (m, 2H), 2.87-2.81 (m, 1H), 2.15-2.10 (m, 2H), 1.88-1.80 (m, 2H), 1.57-1.52 (m, 2H), 1.25-1.21 (m, 2H); MS (ESI) m/z=628.0 (M+H)$^+$ Example 216. (1s,4s)-4-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclohexan-1-ol Step 1. (1s,4s)-4-((2-Chloro-5-(2-(1-methylimidazol-4-yl)ethynyl)-4-pyridyl)amino)cyclohexanol The title compound as a pale yellow solid (104 mg) was prepared in the same fashion as Step 1 in Example 199, except that (1s,4s)-4-((2-chloro-5-iodopyridin-4-yl)amino)cyclohexan-1-ol (200 mg, 0.567 mmol) prepared in Reference Example 9 and 4-ethynyl-1-methyl-imidazole (66 mg, 0.624 mmol) were used instead of 5-bromo-2-chloro-N-isopropyl-pyridin-4-amine and 4-ethynyl-2-methyl-thiazole. MS (ESI) m/z=331.1 (M+H)$^+$ Step 2. (1s,4s)-4-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclohexan-1-ol The title compound as a pale yellow solid (12 mg) was prepared in the same fashion as Step 3 in Example 1 except that (1s,4s)-4-((2-chloro-5-(2-(1-methylimidazol-4-yl)ethynyl)-4-pyridyl)amino)cyclohexanol (62 mg, 0.188 mmol)

prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.44 (s, 1H), 8.40 (d, 1H), 8.15 (s, 1H), 7.83 (s, 1H), 7.44 (s, 1H), 7.17 (s, 1H), 7.14 (s, 2H), 5.43 (d, 1H), 3.85 (brs, 1H), 3.73 (s, 3H), 3.71 (brs, 1H), 2.86-2.80 (m, 1H), 1.92-1.81 (m, 6H), 1.78-1.73 (m, 2H), 1.55-1.51 (m, 2H), 1.24-1.19 (m, 2H)

Example 217. (1s,4s)-4-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol Step 1. (1s,4S)-4-((2-Chloro-5-(thiophen-3-ylethynyl)pyridin-4-yl)amino)cyclohexan-1-ol The title compound as a pale yellow solid (145 mg) was prepared in the same fashion as Step 1 in Example 199, except that (1s,4s)-4-((2-chloro-5-iodopyridin-4-yl)amino)cyclohexan-1-ol (200 mg, 0.567 mmol) prepared in Reference Example 9 and 3-ethynylthiophene (67 mg, 0.624 mmol) were used instead of 5-bromo-2-chloro-N-isopropyl-pyridin-4-amine and 4-ethynyl-2-methyl-thiazole. MS (ESI) m/z=333.1 (M+H)⁺

Step 2. (1s,4s)-4-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol The title compound as a pale yellow solid (49 mg) was prepared in the same fashion as Step 3 in Example 1 except that (1s,4s)-4-((2-chloro-5-(thiophen-3-ylethynyl)pyridin-4-yl)amino)cyclohexan-1-ol (104 mg, 0.311 mmol) prepared in Step 1 was used instead of 1-(2-chloro-5-((1-methyl-1H-pyrazol-4-yl)ethynyl)pyridin-4-yl)-4-methylpiperazine. ¹H-NMR (DMSO-d₆, 400 MHz) δ 8.63 (s, 1H), 8.44 (s, 1H), 8.43 (s, 1H), 8.09 (s, 1H), 7.89 (s, 1H), 7.68-7.64 (m, 1H), 7.52 (s, 1H), 7.29 (d, 1H), 7.26 (s, 1H), 5.51 (d, 1H), 4.50 (d, 1H), 3.71-3.69 (m, 1H), 3.56-3.52 (m, 3H), 3.28-3.22 (m, 1H), 1.85-1.78 (m, 2H), 1.74-1.70 (m, 2H), 1.63-1.57 (m, 4H), 1.36-1.32 (m, 2H), 1.26-1.22 (m, 2H); MS (ESI) m/z=562.2 (M+H)⁺

Example 218. (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)cyclohexan-1-ol Step 1. (1s,4s)-4-((2-Chloro-5-((1-((tetrahydro-2H-pyran-4-yl)methyl)-1H-pyrazol-4-yl)ethynyl)pyridin-4-yl)amino)cyclohexan-1-ol The title compound as a pale yellow solid (253 mg) was prepared in the same fashion as Step 1 in Example 199, except that (1s,4s)-4-((2-chloro-5-iodopyridin-4-yl)amino)cyclohexan-1-ol (253 mg, 0.717 mmol) prepared in Reference Example 9 and 4-ethynyl-1-(tetrahydropyran-4-ylmethyl)pyrazole (150 mg, 0.788 mmol) were used instead of 5-bromo-2-chloro-N-isopropyl-pyridin-4-amine and 4-ethynyl-2-methyl-thiazole. MS (ESI) m/z=415.1 (M+H)⁺

Step 2. (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)cyclohexan-1-ol The title compound as a pale yellow solid (27 mg) was prepared in the same fashion as Step 3 in Example 1 except that (1s,4s)-4-((2-chloro-5-((1-((tetrahydro-2H-pyran-4-yl)methyl)-1H-pyrazol-4-yl)ethynyl)pyridin-4-yl)amino)cyclohexan-1-ol (156 mg, 0.377 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.42 (d, 1H), 8.12 (s, 1H), 7.69 (s, 1H), 7.60 (s, 1H), 7.46 (s, 1H), 7.17 (d, 1H), 7.09 (s, 1H), 5.18 (d, 1H), 4.03-3.98 (m, 4H), 3.66-3.62 (m, 1H), 3.42-3.36 (m, 2H), 2.86-2.80 (m, 1H), 2.23-2.18 (m, 1H), 1.90-1.87 (m, 3H), 1.84-1.71 (m, 5H), 1.56-1.53 (m, 2H), 1.44-1.34 (m, 2H), 1.25-1.20 (m, 2H)

Example 219. (1s,4s)-4-((2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)amino)cyclohexan-1-ol Step 1. (1s,4s)-4-((2-Chloro-5-((1-(2-morpholinoethyl)-1H-pyrazol-4-yl)ethynyl)pyridin-4-yl)amino)cyclohexan-1-ol The title compound as a pale yellow solid (167 mg) was prepared in the same fashion as Step 1 in Example 199, except that (1s,4s)-4-((2-chloro-5-iodopyridin-4-yl)amino)cyclohexan-1-ol (200 mg, 0.567 mmol) prepared in Reference Example 9 and 4-(2-(4-ethynylpyrazol-1-yl)ethyl)morpholine (128 mg, 0.624 mmol) were used instead of 5-bromo-2-chloro-N-isopropyl-pyridin-4-amine and 4-ethynyl-2-methyl-thiazole. MS (ESI) m/z=430.1 (M+H)⁺

Step 2. (1s,4s)-4-((2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)amino)cyclohexan-1-ol The title compound as a pale yellow solid (27 mg) was prepared in the same fashion as Step 3 in Example 1 except that (1s,4s)-4-((2-chloro-5-((1-(2-morpholinoethyl)-1H-pyrazol-4-yl)ethynyl)pyridin-4-yl)amino)cyclohexan-1-ol (156 mg, 0.377 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.41 (d, 1H), 8.13 (s, 1H), 7.75 (s, 1H), 7.73 (s, 1H), 7.67 (s, 1H), 7.15 (s, 1H), 7.13 (s, 1H), 5.19 (d, 1H), 4.26 (t, 2H), 3.98-3.94 (m, 1H), 3.76-3.71 (m, 4H), 3.67-3.62 (m, 1H), 2.86-2.81 (m, 3H), 2.52-2.50 (m, 4H), 1.92-1.89 (m, 4H), 1.84-1.69 (m, 4H), 1.56-1.51 (m, 2H), 1.25-1.19 (m, 2H)

Example 220. (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)-1-methylcyclohexan-1-ol Step 1. (1s,4s)-4-((2-Chloro-5-((1-((tetrahydro-2H-pyran-4-yl)methyl)-1H-pyrazol-4-yl)ethynyl)pyridin-4-yl)amino)-1-methylcyclohexan-1-ol The title compound as a pale yellow solid (253 mg) was prepared in the same fashion as Step 1 in Example 199, except that (1s,4s)-4-((2-chloro-5-iodopyridin-4-yl)amino)-1-methylcyclohexan-1-ol (263 mg, 0.717 mmol) prepared in Reference Example 45 and 4-ethynyl-1-(tetrahydropyran-4-ylmethyl)pyrazole (150 mg, 0.788 mmol) were used instead of 5-bromo-2-chloro-N-isopropyl-pyridin-4-amine and 4-ethynyl-2-methyl-thiazole. MS (ESI) m/z=429.1 (M+H)$^+$ Step 2. (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)-1-methylcyclohexan-1-ol The title compound as a pale yellow solid (29 mg) was prepared in the same fashion as Step 3 in Example 1 except that (1s,4s)-4-((2-chloro-5-((1-((tetrahydro-2H-pyran-4-yl)methyl)-1H-pyrazol-4-yl)ethynyl)pyridin-4-yl)amino)-1-methylcyclohexan-1-ol (162 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.43 (d, 1H), 8.10 (s, 1H), 8.03 (s, 1H), 7.72 (s, 1H), 7.52 (s, 1H), 7.22 (s, 1H), 5.75 (s, 1H), 5.42 (d, 1H), 4.12 (s, 1H), 4.02 (d, 2H), 3.83 (d, 2H), 3.39 (s, 1H), 3.28-3.22 (m, 3H), 2.09-2.03 (m, 1H), 1.75-1.66 (m, 4H), 1.59-1.56 (m, 2H), 1.45-1.33 (m, 6H), 1.28-1.18 (m, 4H), 1.13 (s, 3H)

Example 221. 2-(4-((6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)ethynyl)-1H-pyrazol-1-yl)-N,N-dimethylacetamide Step 1. 2-(4-((6-Chloro-4-(((1s,4s)-4-hydroxy-4-methylcyclohexyl)amino)pyridin-3-yl)ethynyl)-1H-pyrazol-1-yl)-N,N-dimethylacetamide The title compound as a pale yellow solid (185 mg) was prepared in the same fashion as Step 1 in Example 199, except that (1s,4s)-4-((2-chloro-5-iodopyridin-4-yl)amino)-1-methylcyclohexan-1-ol (200 mg, 0.546 mmol) prepared in Reference Example 45 and 2-(4-ethynylpyrazol-1-yl)-N,N-dimethyl-acetamide (106 mg, 0.600 mmol) were used instead of 5-bromo-2-chloro-N-isopropyl-pyridin-4-amine and 4-ethynyl-2-methyl-thiazole. MS (ESI) m/z=416.1 (M+H)$^+$ Step 2. 2-(4-((6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)ethynyl)-1H-pyrazol-1-yl)-N,N-dimethylacetamide The title compound as a pale yellow solid (18 mg) was prepared in the same fashion as Step 3 in Example 1 except that 2-(4-((6-chloro-4-(((1s,4s)-4-hydroxy-4-methylcyclohexyl)amino)pyridin-3-yl)ethynyl)-1H-pyrazol-1-yl)-N,N-dimethylacetamide (110 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.46 (s, 1H), 8.41 (d, 1H), 8.09 (s, 1H), 7.77 (s, 1H), 7.69 (s, 1H), 7.25 (s, 1H), 7.24 (s, 1H), 7.02 (s, 1H), 5.08 (d, 1H), 5.01 (s, 2H), 3.48-3.44 (m, 1H), 3.03 (s, 6H), 2.86-2.79 (m, 1H), 2.01-1.96 (m, 2H), 1.76-1.71 (m, 2H), 1.68-1.56 (m, 2H), 1.56-1.51 (m, 2H), 1.29 (s, 3H), 1.29-1.26 (m, 2H), 1.24-1.18 (m, 2H)

Example 222. (1S,3S)-3-((2-((2-(1-(Cyclopropylsulfonyl)-1H-pyrazol-4-yl)pyrimidin-4-yl)amino)-5-((2-methylthiazol-4-yl)ethynyl)pyridin-4-yl)amino)cyclopentan-1-ol Step 1. (1S,3S)-3-((2-Chloro-5-iodopyridin-4-yl)amino)cyclopentan-1-ol The title compound as a pale yellow solid (330 mg) was prepared in the same fashion as Reference Example 2 except that (1S,3S)-3-aminocyclopentan-1-ol HCl (226 mg, 1.643 mmol) was used instead of 4-hydroxypiperidine. MS (ESI) m/z=339.0 (M+H)$^+$ Step 2. (1S,3S)-3-((2-Chloro-5-((2-methylthiazol-4-yl)ethynyl)pyridin-4-yl)amino)cyclopentan-1-ol The title compound as a pale yellow solid (231 mg) was prepared in the same fashion as Step 1 in Example 199, except that (1S,3S)-3-((2-chloro-5-iodopyridin-4-yl)amino)cyclopentan-1-ol (330 mg, 0.975 mmol) prepared in Step 1 was used instead of 4-ethynyl-2-methyl-thiazole. MS (ESI) m/z=334.1 (M+H)$^+$ Step 3. (1S,3S)-3-((2-((2-(1-(Cyclopropylsulfonyl)-1H-pyrazol-4-yl)pyrimidin-4-yl)amino)-5-((2-methylthiazol-4-yl)ethynyl)pyridin-4-yl)amino)cyclopentan-1-ol The title compound as a pale yellow solid (24 mg) was prepared in the same fashion as Step 3 in Example 1 except that (1S,3S)-3-((2-chloro-5-((2-methylthiazol-4-yl)ethynyl)pyridin-4-yl)amino)cyclopentan-1-ol (63 mg, 0.188 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.49 (s, 1H), 8.42 (d, 1H), 8.18 (s, 1H), 7.89 (s, 1H), 7.39 (s, 1H), 7.21 (s, 1H), 7.10 (d, 1H), 5.15 (d, 1H), 4.52-4.50 (m, 1H), 4.33-4.24 (m, 1H), 2.88-2.82 (m, 1H), 2.76 (s, 3H), 2.49-2.40 (m, 1H), 2.31-2.26 (m, 1H), 2.17-2.08 (m, 1H), 1.84-1.73 (m, 2H), 1.67-1.56 (m, 1H), 1.56-1.52 (m, 2H), 1.24-1.19 (m, 2H); MS (ESI) m/z=563.1 (M+H)$^+$ Example 223. (1S,3R)-3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclopentan-1-ol Step 1. (1S,3R)-3-((2-Chloro-5-iodopyridin-4-yl)amino)cyclopentan-1-ol The title compound as a pale yellow solid (604 mg) was prepared in the same fashion as Reference Example 2 except that (1S,3R)-3-aminocyclopentan-1-ol HCl (401 mg, 2.913 mmol) was used instead of 4-hydroxypiperidine. MS (ESI) m/z=339.0 (M+H)$^+$ Step 2. (1S,3R)-3-((2-Chloro-5-((1-methyl-1H-imidazol-4-yl)ethynyl)pyridin-4-yl)amino)cyclopentan-1-ol The title compound as a pale yellow solid (163 mg) was prepared in the same fashion as Step 1 in Example 199, except that (1S,3R)-3-((2-chloro-5-iodopyridin-4-yl)amino)cyclopentan-1-ol (200 mg, 0.591 mmol) prepared in Step 1 and 4-ethynyl-1-methyl-imidazole (69 mg, 0.650 mmol) were used instead of 5-bromo-2-chloro-N-isopropyl-pyridin-4-amine and 4-ethynyl-2-methyl-thiazole. MS (ESI) m/z=317.1 (M+H)$^+$ Step 3. (1S,3R)-3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclopentan-1-ol The title compound as a pale yellow solid (15 mg) was prepared in the same fashion as Step 3 in Example 1 except that (1S,3R)-3-((2-chloro-5-((1-methyl-1H-imidazol-4-yl)ethynyl)pyridin-4-yl)amino)cyclopentan-1-ol (60 mg, 0.188 mmol) prepared in Step 2 was used instead of 1-(2-chloro-5-((1-methyl-1H-pyrazol-4-yl)ethynyl)pyridin-4-yl)-4-methylpiperazine. MS (ESI) m/z=546.2 (M+H)$^+$ Example 224. 3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)-2,2-dimethylpropan-1-ol Step 1. 3-((2-Chloro-5-iodo-4-pyridyl)amino)-2,2-dimethyl-propan-1-ol The title compound as a pale yellow solid (573 mg) was prepared in the same fashion as Reference Example 2 except that 3-amino-2,2-dimethyl-1-propanol (301 mg, 2.913 mmol) was used instead of 4-hydroxypiperidine. MS (ESI) m/z=341.0 (M+H)$^+$ Step 2. 3-((2-Chloro-5-(2-(1-methylimidazol-4-yl)ethynyl)-4-pyridyl)amino)-2,2-dimethyl-propan-1-ol The title compound as a pale yellow solid (193 mg) was prepared in the same fashion as Step 1 in Example 199, except that 3-((2-chloro-5-iodo-4-pyridyl)amino)-2,2-dimethyl-propan-1-ol (300 mg, 0.881 mmol) prepared in Step 1 and 4-ethynyl-1-methyl-imidazole (103 mg, 0.969 mmol) were used instead of 5-bromo-2-chloro-N-isopropyl-pyridin-4-amine and 4-ethynyl-2-methyl-thiazole. MS (ESI) m/z=319.1 (M+H)$^+$ Step 3. 3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)-2,2-dimethylpropan-1-ol The title compound as a pale yellow solid (24 mg) was prepared in the same fashion as Step 3 in Example 1 except that 3-((2-chloro-5-(2-(1-methylimidazol-4-yl)ethynyl)-4-pyridyl)amino)-2,2-dimethyl-propan-1-ol (99 mg, 0.311 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.46 (s, 1H), 8.38 (d, 1H), 8.07 (s, 1H), 8.02 (s, 1H), 7.39 (s, 1H), 7.19 (d, 1H), 7.10 (s, 1H), 7.03 (s, 1H), 6.72 (s, 1H), 3.70 (s, 3H), 3.60 (s, 2H), 3.24 (d, 2H), 2.85-2.80 (m, 1H), 1.52 (s, 2H), 1.21-1.19 (m, 2H), 1.05 (s, 6H); MS (ESI) m/z=548.2 (M+H)$^+$ Example 225. (1 S,3S)-3-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol Step 1. (1S,3S)-3-((2-Chloro-5-iodopyridin-4-yl)amino)cyclohexan-1-ol The title compound as a pale yellow solid (986 mg) was prepared in the same fashion as Reference Example 2 except that (1S,3S)-3-aminocyclohexanol HCl (883 mg, 5.827 mmol) was used instead of 4-hydroxypiperidine. MS (ESI) m/z=353.0 (M+H)$^+$ Step 2. (1S,3S)-3-((2-Chloro-5-(thiophen-3-ylethynyl)pyridin-4-yl)amino)cyclohexan-1-ol The title compound as a pale yellow solid (281 mg) was prepared in the same fashion as Step 1 in Example 199, except that (1S,3S)-3-((2-chloro-5-iodopyridin-4-yl)amino)cyclohexan-1-ol (350 mg, 0.993 mmol) prepared in Step 1 and 3-ethynylthiophene (118 mg, 1.092 mmol) were used instead of 5-bromo-2-chloro-N-isopropyl-pyridin-4-amine and 4-ethynyl-2-methyl-thiazole. MS (ESI) m/z=333.1 (M+H)$^+$ Step 3. (1 S,3S)-3-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol The title compound as a pale yellow solid (25 mg) was prepared in the same fashion as Step 3 in Example 1 except that (1S,3S)-3-((2-chloro-5-(thiophen-3-ylethynyl)pyridin-4-yl)amino)cyclohexan-1-ol (76 mg, 0.226 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.50 (s, 1H), 8.40 (d, 1H), 8.15 (s, 1H), 7.94 (s, 1H), 7.53 (dd, 1H), 7.35 (dd, 1H), 7.20 (d, 1H), 7.19 (d, 1H), 7.11 (s, 1H), 5.03 (d, 1H), 4.17 (s, 1H), 4.04-3.98 (m, 1H), 2.87-2.82 (m, 1H), 2.12-2.01 (m, 2H), 1.92-1.83 (m, 2H), 1.74-1.64 (m, 3H), 1.55-1.51 (m, 2H), 1.51-1.43 (m, 1H), 1.23-1.18 (m, 2H); MS (ESI) m/z=562.1 (M+H)$^+$ Example 226. 2-(1-(Cyclopropylsulfonyl)-1H-pyrazol-4-yl)-N-(4-(4-(4-methylpiperazin-1-yl)piperidin-1-yl)-5-(thiophen-3-ylethynyl)pyridin-2-yl)pyrimidin-4-amine Step 1. 1-(1-(2-Chloro-5-iodopyridin-4-yl)piperidin-4-yl)-4-methylpiperazine The title compound as a pale yellow solid (703 mg) was prepared in the same fashion as Reference Example 2 except that 1-methyl-4-(piperidin-4-yl)piperazine HCl (640 mg, 2.913 mmol) was used instead of 4-hydroxypiperidine. MS (ESI) m/z=421.0 (M+H)$^+$ Step 2. 1-(1-(2-Chloro-5-(thiophen-3-ylethynyl)pyridin-4-yl)piperidin-4-yl)-4-methylpiperazine The title compound as a pale yellow solid (223 mg) was prepared in the same fashion as Step 1 in Example 199, except that 1-(1-(2-chloro-5-iodopyridin-4-yl)piperidin-4-yl)-4-methylpiperazine (300 mg, 0.692 mmol) prepared in Step 1 and 3-ethynylthiophene (82 mg, 0.761 mmol) were used instead of 5-bromo-2-chloro-N-isopropyl-pyridin-4-amine and 4-ethynyl-2-methyl-thiazole. MS (ESI) m/z=401.2 (M+H)$^+$ Step 3. 2-(1-(Cyclopropylsulfonyl)-1H-pyrazol-4-yl)-N-(4-(4-(4-methylpiperazin-1-yl)piperidin-1-yl)-5-(thiophen-3-ylethynyl)pyridin-2-yl)pyrimidin-4-amine The title compound as a pale yellow solid (13 mg) was prepared in the same fashion as Step 3 in Example 1 except that 1-(1-(2-chloro-5-(thiophen-3-ylethynyl)pyridin-4-yl)piperidin-4-yl)-4-methylpiperazine (76 mg, 0.188 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.42 (d, 1H), 8.26 (s, 1H), 7.85 (s, 1H), 7.54 (s, 1H), 7.49 (d, 1H), 7.34 (d, 1H), 7.18 (d, 1H), 7.05 (d, 1H), 4.21 (d, 2H), 2.96-2.90 (m, 2H), 2.86-2.81 (m, 1H), 2.67 (brs, 4H), 2.52-2.49 (m, 4H), 2.31 (s, 3H), 2.09-2.05

(m, 2H), 1.78-1.73 (m, 2H), 1.55-1.51 (m, 2H), 1.24-1.22 (m, 2H); MS (ESI) m/z=630.2 (M+H)+

Example 227. 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-3-ol Step 1. 1-(2-Chloro-5-iodo-4-pyridyl)piperidin-3-ol The title compound as a pale yellow solid (751 mg) was prepared in the same fashion as Reference Example 2 except that 3-hydroxypiperidine (442 mg, 4.370 mmol) was used instead of 4-hydroxypiperidine. MS (ESI) m/z=339.0 (M+H)+

Step 2. 1-(2-Chloro-5-((6-morpholinopyridin-3-yl)ethynyl)pyridin-4-yl)piperidin-3-ol The title compound as a pale yellow solid (261 mg) was prepared in the same fashion as Step 1 in Example 199, except that 1-(2-chloro-5-iodo-4-pyridyl)piperidin-3-ol (299 mg, 0.885 mmol) prepared in Step 1 and 4-(5-ethynyl-2-pyridyl)morpholine (185 mg, 0.983 mmol) were used instead of 5-bromo-2-chloro-N-isopropyl-pyridin-4-amine and 4-ethynyl-2-methyl-thiazole. MS (ESI) m/z=399.0 (M+H)+

Step 3. 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-3-ol The title compound as a pale yellow solid (19 mg) was prepared in the same fashion as Step 3 in Example 1 except that 1-(2-chloro-5-((6-morpholinopyridin-3-yl)ethynyl)pyridin-4-yl)piperidin-3-ol (165 mg, 0.415 mmol) prepared in Step 2 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.69 (s, 1H), 8.47 (s, 1H), 8.43 (d, 1H), 8.40 (d, 1H), 8.28 (s, 1H), 7.67 (d, 1H), 7.65 (d, 1H), 7.57 (s, 1H), 6.98 (d, 1H), 6.62 (d, 1H), 4.03 (brs, 1H), 3.85-3.82 (m, 4H), 3.65-3.60 (m, 1H), 3.59-3.57 (m, 5H), 3.45-3.41 (m, 1H), 3.35-3.29 (m, 1H), 2.86-2.82 (m, 1H), 2.03-1.93 (m, 2H), 1.80-1.62 (m, 2H), 1.58-1.54 (m, 2H), 1.25-1.21 (m, 2H); MS (ESI) m/z=628.0 (M+H)+

Example 228. (S)-1-(2-((2-(1-(Cyclopropylsulfonyl)-1H-pyrazol-4-yl)pyrimidin-4-yl)amino)-5-(thiophen-3-ylethynyl)pyridin-4-yl)piperidin-3-ol Step 1. (S)-1-(2-Chloro-5-(thiophen-3-ylethynyl)pyridin-4-yl)piperidin-3-ol The title compound as a pale yellow liquid (273 mg) was prepared in the same fashion as Step 1 in Example 65 except that (S)-3-hydroxypiperidine HCl (217 mg, 1.578 mmol) and 2-chloro-4-fluoro-5-(2-(3-thienyl)ethynyl)pyridine prepared in Reference Example 46 were used instead of 4-(trifluoromethyl)piperidine HCl and 2-chloro-4-fluoro-5-((1-methyl-1H-pyrazol-4-yl)ethynyl)pyridine. MS (ESI) m/z=319.0 (M+H)+

Step 2. (S)-1-(2-((2-(1-(Cyclopropylsulfonyl)-1H-pyrazol-4-yl)pyrimidin-4-yl)amino)-5-(thiophen-3-ylethynyl)pyridin-4-yl)piperidin-3-ol The title compound as a pale yellow solid (10 mg) was prepared in the same fashion as Step 3 in Example 1 except that (S)-1-(2-chloro-5-(thiophen-3-ylethynyl)pyridin-4-yl)piperidin-3-ol (36 mg, 0.113 mmol) prepared in Step 1 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.69 (s, 1H), 8.47 (s, 1H), 8.42 (d, 1H), 8.29 (s, 1H), 7.81 (s, 1H), 7.67 (s, 1H), 7.58 (d, 1H), 7.33 (dd, 1H), 7.25 (d, 1H), 6.98 (d, 1H), 4.06-4.04 (m, 1H), 3.69-3.62 (m, 1H), 3.57-3.52 (m, 1H), 3.49-3.44 (m, 1H), 3.37-3.31 (m, 1H), 2.88-2.82 (m, 1H), 2.09-2.01 (m, 1H), 1.99-1.93 (m, 1H), 1.85-1.78 (m, 1H), 1.75-1.69 (m, 1H), 1.58-1.53 (m, 2H), 1.27-1.21 (m, 2H); MS (ESI) m/z=548.1 (M+H)+

Example 229. 1-(2-((2-(1-(Cyclopropylsulfonyl)-1H-pyrazol-4-yl)pyrimidin-4-yl)amino)-5-(thiophen-3-ylethynyl)pyridin-4-yl)-3,3-dimethylpiperidin-4-ol Step 1. 1-(2-Chloro-5-(thiophen-3-ylethynyl)pyridin-4-yl)-3,3-dimethylpiperidin-4-ol The title compound as a pale yellow liquid (256 mg) was prepared in the same fashion as Step 1 in Example 65 except that 3,3-dimethylpiperidin-4-ol (204 mg, 1.578 mmol) and 2-chloro-4-fluoro-5-(2-(3-thienyl)ethynyl)pyridine (250 mg, 1.052 mmol) prepared in Reference Example 46 were used instead of 4-(trifluoromethyl)piperidine HCl and 2-chloro-4-fluoro-5-((1-methyl-1H-pyrazol-4-yl)ethynyl)pyridine. MS (ESI) m/z=347.1 (M+H)+

Step 2. 1-(2-((2-(1-(Cyclopropylsulfonyl)-1H-pyrazol-4-yl)pyrimidin-4-yl)amino)-5-(thiophen-3-ylethynyl)pyridin-4-yl)-3,3-dimethylpiperidin-4-ol The title compound as a pale yellow solid (19 mg) was prepared in the same fashion as Step 3 in Example 1 except that 1-(2-chloro-5-(thiophen-3-ylethynyl)pyridin-4-yl)-3,3-dimethylpiperidin-4-ol (39 mg, 0.113 mmol) prepared in Step 1 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.68 (s, 1H), 8.46 (s, 1H), 8.43 (d, 1H), 8.27 (s, 1H), 7.66 (s, 1H), 7.53 (s, 2H), 7.35 (d, 1H), 7.20 (d, 110, 7.10 (s, 1H), 3.86-3.83 (m, 1H), 3.66-3.63 (m, 1H), 3.57-3.55 (m, 1H), 3.25-3.20 (m, 1H), 3.03-3.00 (m, 1H), 2.85-2.82 (m, 1H), 2.10-2.06 (m, 1H), 1.95-1.89 (m, 1H), 1.55-1.54 (m, 2H), 1.27-1.22 (m, 2H), 1.09 (d, 6H); MS (ESI) m/z=576.2 (M+H)+

Example 230. (1s,4s)-4-((2-((2-(1-(Cyclopropylsulfonyl)-1H-pyrazol-4-yl)pyrimidin-4-yl)amino)-5-(3-methyl-3-morpholinobut-1-yn-1-yl)pyridin-4-yl)amino)cyclohexan-1-ol Step 1. 4-(3-(6-Chloro-4-fluoro-3-pyridyl)-1,1-dimethyl-prop-2-ynyl)morpholine The title compound as a pale yellow solid (1.01 g) was prepared in the same fashion as Reference Example 18 except that 4-(1,1-dimethylprop-2-ynyl)morpholine (1.96 g, 12.819 mmol) was used instead of 4-ethynyl-1-methylpyrazole. MS (ESI) m/z=283.1 (M+H)+

Step 2. (1s,4s)-4-((2-Chloro-5-(3-methyl-3-morpholinobut-1-yn-1-yl)pyridin-4-yl)amino)cyclohexan-1-ol The title compound as a pale yellow liquid (327 mg) was prepared in the same fashion as Step 1 in Example 65 except that cis-4-aminocyclohexanol HCl (201 mg, 1.326 mmol) and 4-(3-(6-chloro-4-fluoro-3-pyridyl)-1,1-dimethyl-prop-2-ynyl)morpholine (250 mg, 0.884 mmol) prepared in Step 1 were used instead of 4-(trifluoromethyl)piperidine HCl and 2-chloro-4-fluoro-5-((1-methyl-1H-pyrazol-4-yl)ethynyl)pyridine. MS (ESI) m/z=378.1 (M+H)$^+$ Step 3. (1s,4s)-4-((2-((2-(1-(Cyclopropylsulfonyl)-1H-pyrazol-4-yl)pyrimidin-4-yl)amino)-5-(3-methyl-3-morpholinobut-1-yn-1-yl)pyridin-4-yl)amino)cyclohexan-1-ol The title compound as a pale yellow solid (17 mg) was prepared in the same fashion as Step 3 in Example 1 except that (1s,4s)-4-((2-chloro-5-(3-methyl-3-morpholinobut-1-yn-1-yl)pyridin-4-yl)amino)cyclohexan-1-ol (142 mg, 0.377 mmol) prepared in Step 2 was used instead of 1-(2-chloro-5-((1-methyl-1H-pyrazol-4-yl)ethynyl)pyridin-4-yl)-4-methylpiperazine. MS (ESI) m/z=607.1 (M+H)$^+$ Example 231. (1-(2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)-4-methylpiperidin-4-yl)methanol Step 1. 2-Chloro-4-fluoro-5-(2-(1-(tetrahydropyran-4-ylmethyl)pyrazol-4-yl)ethynyl)pyridine The title compound as a pale yellow solid (1.01 g) was prepared in the same fashion as Reference Example 18 except that 4-ethynyl-1-(tetrahydropyran-4-ylmethyl)pyrazole (813 mg, 4.273 mmol) was used instead of 4-ethynyl-1-methylpyrazole. MS (ESI) m/z=320.0 (M+H)$^+$ Step 2. (1-(2-Chloro-5-(2-(1-(tetrahydropyran-4-ylmethyl)pyrazol-4-yl)ethynyl)-4-pyridyl)-4-methyl-4-piperidyl)methanol The title compound as a pale yellow liquid (300 mg) was prepared in the same fashion as Step 1 in Example 65 except that (4-methylpiperidin-4-yl)methanol (152 mg, 1.173 mmol) and 2-chloro-4-fluoro-5-(2-(1-(tetrahydropyran-4-ylmethyl)pyrazol-4-yl)ethynyl)pyridine (250 mg, 0.782 mmol) prepared in Step 1 were used instead of 4-(trifluoromethyl)piperidine HCl and 2-chloro-4-fluoro-5-((1-methyl-1H-pyrazol-4-yl)ethynyl)pyridine. MS (ESI) m/z=429.1 (M+H)$^+$ Step 3. (1-(2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)-4-methylpiperidin-4-yl)methanol The title compound as a pale yellow solid (15 mg) was prepared in the same fashion as Step 3 in Example 1 except that (1-(2-chloro-5-(2-(1-(tetrahydropyran-4-ylmethyl)pyrazol-4-yl)ethynyl)-4-pyridyl)-4-methyl-4-piperidyl)methanol (162 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.46 (s, 1H), 8.42 (d, 1H), 8.22 (s, 1H), 7.66 (s, 1H), 7.61 (s, 2H), 7.55 (s, 1H), 6.99 (d, 1H), 4.02-3.98 (m, 4H), 3.71-3.67 (m, 2H), 3.43-3.36 (m, 4H), 2.87-2.81 (m, 1H), 2.22-2.16 (m, 1H), 1.83-1.76 (m, 2H), 1.57-1.51 (m, 4H), 1.43-1.33 (m, 2H), 1.27-1.22 (m, 2H), 1.09 (d, 3H); MS (ESI) m/z=673.1 (M+H)$^+$ Example 232. (1-(2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)-4-methylpiperidin-4-yl)methanol Step 1. 4-(2-(4-(2-(6-Chloro-4-fluoro-3-pyridyl)ethynyl)pyrazol-1-yl)ethyl)morpholine The title compound as a pale yellow solid (608 mg) was prepared in the same fashion as Reference Example 18 except that 4-(2-(4-ethynylpyrazol-1-yl)ethyl)morpholine (439 mg, 2.137 mmol) was used instead of 4-ethynyl-1-methylpyrazole. MS (ESI) m/z=335.0 (M+H)$^+$ Step 2. (1-(2-Chloro-5-((1-(2-morpholinoethyl)-1H-pyrazol-4-yl)ethynyl)pyridin-4-yl)-4-methylpiperidin-4-yl)methanol The title compound as a pale yellow liquid (168 mg) was prepared in the same fashion as Step 1 in Example 65 except that (4-methylpiperidin-4-yl)methanol (87 mg, 0.672 mmol) and 4-(2-(4-(2-(6-chloro-4-fluoro-3-pyridyl)ethynyl)pyrazol-1-yl)ethyl)morpholine (150 mg, 0.448 mmol) prepared in Step 1 were used instead of 4-(trifluoromethyl)piperidine HCl and 2-chloro-4-fluoro-5-((1-methyl-1H-pyrazol-4-yl)ethynyl)pyridine. MS (ESI) m/z=444.1 (M+H)$^+$ Step 3. (1-(2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)-4-methylpiperidin-4-yl)methanol-1H-1H The title compound as a pale yellow solid (11 mg) was prepared in the same fashion as Step 3 in Example 1 except that (1-(2-chloro-5-((1-(2-morpholinoethyl)-1H-pyrazol-4-yl)ethynyl)pyridin-4-yl)-4-methylpiperidin-4-yl)methanol (167 mg, 0.377 mmol) prepared in Step 2 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.46 (s, 1H), 8.42 (d, 1H), 8.23 (s, 1H), 7.68-7.60 (m, 4H), 7.01 (d, 1H), 4.26 (t, 2H), 3.73-3.67 (m, 5H), 3.43-3.37 (m, 2H), 2.85-2.82 (m, 3H), 2.51-2.49 (m, 4H), 1.83-1.72 (m, 2H), 1.61-1.52 (m, 2H), 1.27-1.23 (m, 4H), 1.09 (s, 3H); MS (ESI) m/z=674.1 (M+H)$^+$ Example 233. 2-(1-(Cyclopropylsulfonyl)-1H-pyrazol-4-yl)-N-(4-(1-methyl-1H-pyrazol-4-yl)-5-((1-methyl-1H-pyrazol-4-yl)ethynyl)pyridin-2-yl)pyrimidin-4-amine Step 1. 2-Chloro-4-(1-methylpyrazol-4-yl)-5-(2-(1-methylpyrazol-4-yl)ethynyl)pyridine The reaction mixture of 4-ethynyl-1-methyl-1H-pyrazole (61 mg, 0.572 mmol), Pd(PPh$_3$)$_4$ (25 mg, 0.022 mmol), CuI (8 mg, 0.044 mmol), TEA (0.12 mL, 0.881 mmol) and 5-bromo-2-chloro-4-(1-methylpyrazol-4-yl)pyridine (120 mg, 0.440 mmol) prepared in Reference Example 48 in DMF (2 mL) was stirred at 90° C. overnight. The reaction mixture was cooled to room temperatureroom temperature, and quenched with water, then extracted with DCM. The organic layer was dried over MgSO$_4$, filtered, and concentrated. (EA/n-Hex=0-50%) to yield room temperature2-chloro-4-(1-methylpyrazol-4-yl)-5-(2-(1-methylpyrazol-4-yl)ethynyl)pyridine (47 mg) as a pale yellow solid. MS (ESI) m/z=298.1 (M+H)$^+$

Step 2. 2-(1-(Cyclopropylsulfonyl)-1H-pyrazol-4-yl)-N-(4-(1-methyl-1H-pyrazol-4-yl)-5-((1-methyl-1H-pyrazol-4-yl)ethynyl)pyridin-2-yl)pyrimidin-4-amine The title compound as a pale yellow solid (3 mg) was prepared in the same fashion as Step 3 in Example 1 except that 2-chloro-4-(1-methylpyrazol-4-yl)-5-(2-(1-methylpyrazol-4-yl)ethynyl)pyridine (45 mg, 0.151 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.53-8.43 (m, 3H), 8.22 (s, 1H), 8.19 (d, 1H), 8.09 (s, 1H), 7.68 (s, 1H), 7.62 (s, 1H), 7.16 (d, 1H), 4.03 (s, 3H), 3.96 (s, 3H), 2.87-2.83 (m, 1H), 1.56-1.53 (m, 2H), 1.04-1.01 (m, 2H)

Example 234. 2-(1-(Cyclopropylsulfonyl)-1H-pyrazol-4-yl)-N-(5-((1-(2-fluoroethyl)-1H-pyrazol-4-yl)ethynyl)-4-(1-methyl-1H-pyrazol-4-yl)pyridin-2-yl)pyrimidin-4-amine

Step 1. 2-chloro-5-(2-(1-(2-fluoroethyl)pyrazol-4-yl)ethynyl)-4-(1-methylpyrazol-4-yl)pyridine The title compound (82 mg) was prepared in the same fashion as Step 1 in Example 233, except that 4-ethynyl-1-(2-fluoroethyl)pyrazole (79 mg, 0.572 mmol) was used instead of 4-ethynyl-1-methyl-1H-pyrazole. MS (ESI) m/z=330.1 (M+H)$^+$

Step 2. 2-(1-(Cyclopropylsulfonyl)-1H-pyrazol-4-yl)-N-(5-((1-(2-fluoroethyl)-1H-pyrazol-4-yl)ethynyl)-4-(1-methyl-1H-pyrazol-4-yl)pyridin-2-yl)pyrimidin-4-amine The title compound as a pale yellow solid (5 mg) was prepared in the same fashion as Step 3 in Example 1 except that 2-chloro-5-(2-(1-(2-fluoroethyl)pyrazol-4-yl)ethynyl)-4-(1-methylpyrazol-4-yl)pyridine (50 mg, 0.151 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.48-8.45 (m, 3H), 8.20 (s, 2H), 8.10 (s, 1H), 8.09 (d, 1H), 7.74 (s, 2H), 7.21 (d, 1H), 4.86 (t, 1H), 4.75 (t, 1H), 4.50 (t, 1H), 4.43 (t, 1H), 4.03 (s, 3H), 2.88-2.84 (m, 1H), 1.57-1.55 (m, 2H), 1.25-1.23 (m, 2H)

Example 235. N-(4-(1-Cyclopropyl-1H-pyrazol-4-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine

Step 1. 2-Chloro-4-(1-cyclopropylpyrazol-4-yl)-5-(2-(1-methylpyrazol-4-yl)ethynyl)pyridine The title compound (53 mg) was prepared in the same fashion as Step 1 in Example 233, except that 5-bromo-2-chloro-4-(1-cyclopropylpyrazol-4-yl)pyridine (110 mg, 0.368 mmol) prepared in Reference Example 47 was used instead of 5-bromo-2-chloro-4-(1-methylpyrazol-4-yl)pyridine. MS (ESI) m/z=324.1 (M+H)$^+$

Step 2. N-(4-(1-Cyclopropyl-1H-pyrazol-4-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine The title compound as a pale yellow solid (5 mg) was prepared in the same fashion as Step 3 in Example 1 except that 2-chloro-4-(1-cyclopropylpyrazol-4-yl)-5-(2-(1-methylpyrazol-4-yl)ethynyl)pyridine (37 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.49-8.46 (m, 3H), 8.24 (s, 1H), 8.13 (s, 1H), 7.84 (s, 1H), 7.69 (s, 1H), 7.65 (s, 1H), 7.62 (s, 1H), 7.37 (d, 1H), 3.97 (s, 3H), 3.74-3.72 (m, 1H), 2.86-2.84 (m, 1H), 1.57-1.55 (m, 2H), 1.27-1.22 (m, 4H), 1.11-1.09 (m, 2H)

Example 236. N-(4-(1-cyclopropyl-1H-pyrazol-4-yl)-5-((1-isopropyl-1H-pyrazol-4-yl)ethynyl)pyridin-2-yl)-2-(1-(cyclopropylsulfonyl)-1H-pyrazol-4-yl)pyrimidin-4-amine

Step 1. 2-Chloro-4-(1-cyclopropylpyrazol-4-yl)-5-(2-(1-isopropylpyrazol-4-yl)ethynyl)pyridine The title compound (72 mg) was prepared in the same fashion as Step 1 in Example 233, except that 4-ethynyl-1-isopropyl-pyrazole (64 mg, 0.479 mmol) and 5-bromo-2-chloro-4-(1-cyclopropylpyrazol-4-yl)pyridine (110 mg, 0.368 mmol) prepared in Reference Example 47 was used instead of 4-ethynyl-1-methyl-1H-pyrazole and 5-bromo-2-chloro-4-(1-methylpyrazol-4-yl)pyridine. MS (ESI) m/z=352.2 (M+H)$^+$

Step 2. N-(4-(1-cyclopropyl-1H-pyrazol-4-yl)-5-((1-isopropyl-1H-pyrazol-4-yl)ethynyl)pyridin-2-yl)-2-(1-(cyclopropylsulfonyl)-1H-pyrazol-4-yl)pyrimidin-4-amine The title compound as a pale yellow solid (5 mg) was prepared in the same fashion as Step 3 in Example 1 except that 2-chloro-4-(1-cyclopropylpyrazol-4-yl)-5-(2-(1-isopropylpyrazol-4-yl)ethynyl)pyridine (40 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.46-8.45 (m, 3H), 8.24 (s, 1H), 8.13 (s, 1H), 7.81 (s, 1H), 7.70 (s, 1H), 7.67 (s, 1H), 7.60 (s, 1H), 7.36 (d, 1H), 4.55-4.52 (m, 1H), 3.72-3.71 (m, 1H), 2.84-2.83 (m, 1H), 1.57-1.55 (m, 8H), 1.25-1.20 (m, 4H), 1.11-1.09 (m, 2H)

Example 237. N-(4-(1-Cyclopropyl-1H-pyrazol-4-yl)-5-((1-(2-fluoroethyl)-1H-pyrazol-4-yl)ethynyl)pyridin-2-yl)-2-(1-(cyclopropylsulfonyl)-1H-pyrazol-4-yl)pyrimidin-4-amine

Step 1. 2-Chloro-4-(1-cyclopropylpyrazol-4-yl)-5-(2-(1-(2-fluoroethyl)pyrazol-4-yl)ethynyl)pyridine The title compound (84 mg) was prepared in the same fashion as Step 1 in Example 233, except that 4-ethynyl-1-(2-fluoroethyl)pyrazole (66 mg, 0.479 mmol) and 5-bromo-2-chloro-4-(1-cyclopropylpyrazol-4-yl)pyridine (110 mg, 0.368 mmol) prepared in Reference Example 47 was used instead of 4-ethynyl-1-methyl-1H-pyrazole and 5-bromo-2-chloro-4-(1-methylpyrazol-4-yl)pyridine. MS (ESI) m/z=356.1 (M+H)$^+$

Step 2. N-(4-(1-Cyclopropyl-1H-pyrazol-4-yl)-5-((1-(2-fluoroethyl)-1H-pyrazol-4-yl)ethynyl)pyridin-2-yl)-2-(1-(cyclopropylsulfonyl)-1H-pyrazol-4-yl)pyrimidin-4-amine The title compound as a pale yellow solid (10 mg) was prepared in the same fashion as Step 3 in Example 1 except that 2-chloro-4-(1-cyclopropylpyrazol-4-yl)-5-(2-(1-(2-fluoroethyl)pyrazol-4-yl)ethynyl)pyridine (40 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.47-8.46 (m, 3H), 8.23 (s, 1H), 8.11 (s, 1H), 7.81 (s, 1H), 7.73 (s, 2H), 7.64 (s, 1H), 7.37 (d, 1H), 4.86 (t, 1H), 4.74 (t, 1H), 4.50 (t, 1H), 4.42 (t, 1H), 3.71-3.68 (m, 1H), 2.86-2.84 (m, 1H), 1.56-1.54 (m, 2H), 1.25-1.20 (m, 4H), 1.12-1.08 (m, 2H)

Example 238. 2-(1-(Cyclopropylsulfonyl)-1H-pyrazol-4-yl)-N-(4-(((1r,4r)-4-((dimethylamino)methyl)cyclohexyl)methoxy)-5-((2-methylthiazol-4-yl)ethynyl)pyridin-2-yl)pyrimidin-4-amine Step 1. 1-((1r,4r)-4-(((2-Chloro-5-((2-methylthiazol-4-yl)ethynyl)pyridin-4-yl)oxy)methyl)cyclohexyl)-N,N-dimethylmethanamine The reaction mixture of 1-((1r,4r)-4-(((2-chloro-5-iodopyridin-4-yl)oxy)methyl)cyclohexyl)-N,N-dimethylmethanamine (200 mg, 0.489 mmol) prepared in Reference Example 16, 4-ethynyl-2-methyl-thiazole (66 mg, 0.538 mmol), PdCl$_2$(PPh$_3$)$_2$ (17 mg, 0.024 mmol), CuI (19 mg, 0.098 mmol) and TEA (0.14 mL, 0.979 mmol) in DMF (2 mL) was stirred at 70° C. for 2 hours. The reaction mixture was cooled to room temperature, quenched with water, and then extracted with DCM. The organic layer was dried over MgSO$_4$, filtered, and concentrated. (MeOH/DCM=0-20%) to yield room temperature1-((1 r,4r)-4-(((2-chloro-5-((2-methylthiazol-4-yl)ethynyl)pyridin-4-yl)oxy)methyl)cyclohexyl)-N,N-dimethylmethanamine (126 mg) as pale yellow solid. MS (ESI) m/z=404.1 (M+H)$^+$ Step 2. 2-(1-(Cyclopropylsulfonyl)-1H-pyrazol-4-yl)-N-(4-(((1 r,4r)-4-((dimethylamino)methyl)cyclohexyl)methoxy)-5-((2-methylthiazol-4-yl)ethynyl)pyridin-2-yl)pyrimidin-4-amine The title compound as a yellow oil (23 mg) was prepared in the same fashion as Step 3 in Example 1 except that 1-((1r,4r)-4-(((2-chloro-5-((2-methylthiazol-4-yl)ethynyl)pyridin-4-yl)oxy)methyl)cyclohexyl)-N,N-dimethylmethanamine (46 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.47 (d, 1H), 8.44 (s, 1H), 8.35 (s, 1H), 7.60 (s, 1H), 7.44 (s, 1H), 7.33 (s, 1H), 7.23 (d, 1H), 4.01 (d, 2H), 2.87-2.80 (m, 1H), 2.21 (s, 6H), 2.11 (d, 2H), 2.03-1.99 (m, 2H), 1.94-1.90 (m, 2H), 1.56-1.49 (m, 3H), 1.30-1.20 (m, 5H), 1.04-0.94 (m, 2H); MS (ESI) m/z=627.2 (M+H)$^+$ Example 239. 4-(3-(6-((2-(1-(Cyclopropylsulfonyl)-1H-pyrazol-4-yl)pyrimidin-4-yl)amino)-4-(((1 r,4r)-4-((dimethylamino)methyl)cyclohexyl)methoxy)pyridin-3-yl)prop-2-yn-1-yl)thiomorpholine 1,1-dioxide Step 1. 4-(3-(6-Chloro-4-(((1r,4r)-4-((dimethylamino)methyl)cyclohexyl)methoxy)pyridin-3-yl)prop-2-yn-1-yl)thiomorpholine 1,1-dioxide The title compound (143 mg) was prepared in the same fashion as Step 1 in Example 238, except that 4-propargyl-thiomorpholine 1,1-dioxide (93 mg, 0.538 mmol) was used instead of 4-ethynyl-2-methyl-thiazole. MS (ESI) m/z=454.1 (M+H)$^+$ Step 2. 4-(3-(6-((2-(1-(Cyclopropylsulfonyl)-1H-pyrazol-4-yl)pyrimidin-4-yl)amino)-4-(((1 r,4r)-4-((dimethylamino)methyl)cyclohexyl)methoxy)pyridin-3-yl)prop-2-yn-1-yl)thiomorpholine 1,1-dioxide The title compound as a yellow oil (17.1 mg) was prepared in the same fashion as Step 3 in Example 1 except that 4-(3-(6-chloro-4-(((1r,4r)-4-((dimethylamino)methyl)cyclohexyl)methoxy)pyridin-3-yl)prop-2-yn-1-yl)thiomorpholine 1,1-dioxide (51 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.46 (d, 1H), 8.43 (s, 1H), 8.22 (s, 1H), 7.60 (s, 1H), 7.42 (s, 1H), 7.27 (s, 1H), 7.21 (d, 1H), 3.97 (d, 2H), 3.71 (s, 2H), 3.19-3.14 (m, 8H), 2.87-2.80 (m, 1H), 2.22 (s, 6H), 2.12-2.10 (m, 2H), 1.99-1.90 (m, 5H), 1.56-1.52 (m, 2H), 1.50-1.44 (m, 1H), 1.25-1.20 (m, 2H), 1.19-1.12 (m, 2H), 1.02-0.96 (m, 2H)

Example 240. 2-(1-(Cyclopropylsulfonyl)-1H-pyrazol-4-yl)-N-(4-(((1 r,4r)-4-((dimethylamino)methyl)cyclohexyl)methoxy)-5-(3-(pyrrolidin-1-yl)prop-1-yn-1-yl)pyridin-2-yl)pyrimidin-4-amine Step 1. 1-((1r,4r)-4-(((2-Chloro-5-(3-(pyrrolidin-1-yl)prop-1-yn-1-yl)pyridin-4-yl)oxy)methyl)cyclohexyl)-N,N-dimethylmethanamine The title compound (107 mg) was prepared in the same fashion as Step 1 in Example 238, except that 1-prop-2-ynylpyrrolidine (59 mg, 0.538 mmol) prepared in Step 1 was used instead of 4-ethynyl-2-methyl-thiazole. MS (ESI) m/z=390.1 (M+H)$^+$ Step 2. 2-(1-(Cyclopropylsulfonyl)-1H pyrazol-4-yl)-N-(4-(((1r,4r)-4-((dimethylamino)methyl)cyclohexyl)methoxy)-5-(3-(pyrrolidin-1-yl)prop-1-yn-1-yl)pyridin-2-yl)pyrimidin-4-amine The title compound as a yellow oil (8 mg) was prepared in the same fashion as Step 3 in Example 1 except that 1-((1r,4r)-4-(((2-chloro-5-(3-(pyrrolidin-1-yl)prop-1-yn-1-yl)pyridin-4-yl)oxy)methyl)cyclohexyl)-N,N-dimethylmethanamine (44.1 mg, 0.113 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (d, 1H), 8.42 (s, 1H), 8.23 (s, 1H), 7.67 (s, 1H), 7.43 (s, 1H), 7.18 (d, 1H), 3.96 (d, 2H), 3.73 (s, 2H), 2.87-2.80 (m, 1H), 2.75 (s, 4H), 2.28 (s, 6H), 2.19-2.18 (m, 2H), 2.05-1.86 (m, 5H), 1.85 (brs, 4H), 1.55-1.51 (m, 3H), 1.26-1.20 (m, 4H), 1.04-0.95 (m, 2H)

Example 241. (1-(2-((2-(1-(Cyclopropylsulfonyl)-1H-pyrazol-4-yl)pyrimidin-4-yl)amino)-5-((1-((tetrahydro-2H-pyran-3-yl)methyl)-1H-pyrazol-4-yl)ethynyl)pyridin-4-yl)-4-methylpiperidin-4-yl)methanol Step 1. (1-(2-Chloro-5-((1-((tetrahydro-2H-pyran-3-yl)methyl)-1H-pyrazol-4-yl)ethynyl)pyridin-4-yl)-4-methylpiperidin-4-yl)methanol The title compound as a solid (70 mg) was prepared in the same fashion as Step 2 in Example 1 except that (1-(2- chloro-5-iodopyridin-4-yl)-4-methylpiperidin-4-yl)methanol (100 mg, 0.273 mmol) prepared in Reference Example 12 and 4-ethynyl-1-(tetrahydropyran-3-ylmethyl)pyrazole (78 mg, 0.409 mmol) were used instead of 1-(2-chloro-5-iodopyridin-4-yl)-4-methylpiperazine and 4-ethynyl-1-methylpyrazole, respectively. MS (ESI) m/z=430.2 (M+H)$^+$ Step 2. (1-(2-((2-(1-(Cyclopropylsulfonyl)-1H-pyrazol-4-yl)pyrimidin-4-yl)amino)-5-((1-((tetrahydro-2H-pyran-3-yl)methyl)-1H-pyrazol-4-yl)ethynyl) pyridin-4-yl)-4-methylpiperidin-4-yl)methanol The title compound as a solid (6 mg) was prepared in the same fashion as Step 3 in Example 1 except that (1-(2-chloro-5-((1-((tetrahydro-2H-pyran-3-yl)methyl)-1H-pyrazol-4-yl)ethynyl)pyridin-4-yl)-4-methylpiperidin-4-yl) methanol (81 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.46 (s, 1H), 8.42-8.41 (m, 1H), 8.23 (s, 1H), 7.84 (s, 1H), 7.65-7.56 (m, 3H), 7.01 (d, 1H), 4.09-4.06 (m, 2H), 3.78-3.69 (m, 4H), 3.53-3.39 (m, 4H), 3.30-3.25 (m, 2H), 2.86-2.82 (m, 1H), 2.26-2.22 (m, 1H), 1.82-1.52 (m, 14H), 1.27-1.22 (m, 6H), 1.09 (s, 3H); MS (ESI) m/z=658.8 (M+H)$^+$ Example 242. (1-(5-((1-((1,4-Dioxan-2-yl)methyl)-1H-pyrazol-4-yl)ethynyl)-2-((2-(1-(cyclopropylsulfonyl)-1H-pyrazol-4-yl)pyrimidin-4-yl)amino) pyridin-4-yl)-4-methylpiperidin-4-yl)methanol Step 1. (1-(5-((1-((1,4-Dioxan-2-yl)methyl)-1H-pyrazol-4-yl)ethynyl)-2-chloropyridin-4-yl)-4-methylpiperidin-4-yl)methanol The title compound as a solid (85 mg) was prepared in the same fashion as Step 2 in Example 1 except that (1-(2-chloro-5-iodopyridin-4-yl)-4-methylpiperidin-4-yl)methanol (100 mg, 0.273 mmol) prepared in Reference Example 12 and 1-(1,4-dioxan-2-ylmethyl)-4-ethynyl-pyrazole (79 mg, 0.409 mmol) were used instead of 1-(2-chloro-5-iodopyridin-4-yl)-4-methylpiperazine and 4-ethynyl-1-methylpyrazole, respectively. MS (ESI) m/z=432.0 (M+H)$^+$ Step 2. (1-(5-((1-((1,4-Dioxan-2-yl)methyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a solid (14 mg) was prepared in the same fashion as Step 3 in Example 1 except that (1-(5-((1-((1,4-dioxan-2-yl)methyl)-1H-pyrazol-4-yl)ethynyl)-2-chloropyridin-4-yl)-4-methylpiperidin-4-yl)methanol (81 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.45 (s, 1H), 8.40 (d, 1H), 8.23 (s, 1H), 7.66-7.63 (m, 3H), 7.01 (d, 1H), 4.18-4.16 (m, 2H), 4.01-3.90 (m, 1H), 3.82-3.58 (m, 5H), 3.51 (s, 2H), 3.43-3.41 (m, 2H), 3.32-3.27 (m, 2H), 2.87-2.81 (m, 1H), 1.92-1.76 (m, 3H), 1.60-1.53 (m, 4H), 1.24-1.22 (m, 2H), 1.09 (s, 3H); MS (ESI) m/z=660.1 (M+H)$^+$ Example 243. (1-(2-((2-(1-(Cyclopropylsulfonyl)-1H-pyrazol-4-yl)pyrimidin-4-yl)amino)-5-((1-((tetrahydrofuran-3-yl)methyl)-1H-pyrazol-4-yl)ethynyl) pyridin-4-yl)-4-methylpiperidin-4-yl)methanol Step 1. (1-(2-Chloro-5-((1-((tetrahydrofuran-3-yl) methyl)-1H-pyrazol-4-yl)ethynyl)pyridin-4-yl)-4-methylpiperidin-4-yl)methanol The title compound as a solid (88 mg) was prepared in the same fashion as Step 2 in Example 1 except that (1-(2-chloro-5-iodopyridin-4-yl)-4-methylpiperidin-4-yl)methanol (100 mg, 0.273 mmol) prepared in Reference Example 12 and 4-ethynyl-1-((tetrahydrofuran-3-yl)methyl)-1H-pyrazole (72 mg, 0.409 mmol) were used instead of 1-(2-chloro-5-iodopyridin-4-yl)-4-methylpiperazine and 4-ethynyl-1-methylpyrazole, respectively. MS (ESI) m/z=415.9 (M+H)$^+$ Step 2. (1-(2-((2-(1-(Cyclopropylsulfonyl)-1H-pyrazol-4-yl)pyrimidin-4-yl)amino)-5-((1-((tetrahydrofuran-3-yl)methyl)-1H-pyrazol-4-yl)ethynyl)pyridin-4-yl)-4-methylpiperidin-4-yl)methanol The title compound as a solid (7 mg) was prepared in the same fashion as Step 3 in Example 1 except that (1-(2-chloro-5-((1-((tetrahydrofuran-3-yl)methyl)-1H-pyrazol-4-yl)ethynyl)pyridin-4-yl)-4-methylpiperidin-4-yl)methanol (78 mg, 0.188 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.39 (d, 2H), 8.23 (s, 1H), 7.65-7.63 (m, 2H), 7.59 (s, 1H), 6.95 (d, 1H), 4.12 (d, 2H), 3.93-3.91 (m, 1H), 3.81-3.68 (m, 4H), 3.61-3.58 (m, 1H), 3.50 (s, 2H), 3.41-3.39 (m, 2H), 2.86-2.82 (m, 2H), 2.09-2.04 (m, 2H), 1.79-1.77 (m, 2H), 1.59-1.52 (m, 4H), 1.24-1.21 (m, 2H), 1.08 (s, 3H); MS (ESI) m/z=645.0 (M+H)$^+$ Example 244. (1-(2-((2-(1-(Cyclopropylsulfonyl)-1H-pyrazol-4-yl)pyrimidin-4-yl)amino)-5-((1-(tetrahydrofuran-3-yl)-1H-pyrazol-4-yl)ethynyl)pyridin-4-yl)-4-methylpiperidin-4-yl)methanol Step 1. (1-(2-Chloro-5-((1-(tetrahydrofuran-3-yl)-1H-pyrazol-4-yl)ethynyl)pyridin-4-yl)-4-methylpiperidin-4-yl)methanol The title compound as a solid (85 mg) was prepared in the same fashion as Step 2 in Example 1 except that (1-(2-chloro-5-iodopyridin-4-yl)-4-methylpiperidin-4-yl)methanol (100 mg, 0.273 mmol) prepared in Reference Example 12 and 4-ethynyl-1-(tetrahydrofuran-3-yl)-1H-pyrazole (22 mg, 0.136 mmol were used instead of 1-(2-chloro-5-iodopyridin-4-yl)-4-methylpiperazine and 4-ethynyl-1-methylpyrazole, respectively. MS (ESI) m/z=401.1 (M+H)$^+$ Step 2. (1-(2-((2-(1-(Cyclopropylsulfonyl)-1H-pyrazol-4-yl)pyrimidin-4-yl)amino)-5-((1-(tetrahydrofuran-3-yl)-1H-pyrazol-4-yl)ethynyl)pyridin-4-yl)-4-methylpiperidin-4-yl)methanol The title compound as a solid (5 mg) was prepared in the same fashion as Step 3 in Example 1 except that (1-(2-chloro-5-((1-((tetrahydrofuran-3-yl)-1H-pyrazol-4-yl)ethynyl)pyridin-4-yl)-4-methylpiperidin-4-yl)methanol (76 mg, 0.188 mmol) prepared in Step 1 was used instead of 1-(2-chloro-5-((1-methyl-1H-pyrazol-4-yl)ethynyl)pyridin-4-yl)-

4-methylpiperazine. ¹H-NMR (CDCl₃, 400 MHz) δ 8.66 (s, 1H), 8.46 (s, 1H), 8.42 (d, 2H), 8.23 (s, 1H), 7.74-7.60 (m, 4H), 7.00 (d, 1H), 5.00 (s, 1H), 4.16-4.04 (m, 4H), 3.97-3.96 (m, 1H), 3.71-3.68 (m, 2H), 3.51 (s, 2H), 3.42-3.40 (m, 2H), 2.87-2.83 (m, 1H), 2.49-2.47 (m, 1H), 2.40-2.31 (m, 1H), 1.82-1.52 (m, 7H), 1.26-1.23 (m, 3H), 1.09 (s, 3H); MS (ESI) m/z=630.7 (M+H)⁺

Example 245. (1-(2-((2-(1-(Cyclopropylsulfonyl)-1H-pyrazol-4-yl)pyrimidin-4-yl)amino)-5-((1-(oxetan-3-yl)-1H-pyrazol-4-yl)ethynyl)pyridin-4-yl)-4-methylpiperidin-4-yl)methanol Step 1. (1-(2-Chloro-5-((1-(oxetan-3-yl)-1H-pyrazol-4-yl)ethynyl)pyridin-4-yl)-4-methylpiperidin-4-yl)methanol The title compound as a solid (80 mg) was prepared in the same fashion as Step 2 in Example 1 except that (1-(2-chloro-5-iodopyridin-4-yl)-4-methylpiperidin-4-yl)methanol (100 mg, 0.273 mmol) prepared in Reference Example 12 and 4-ethynyl-1-(oxetan-3-yl)-1H-pyrazole (20 mg, 0.136 mmol) were used instead of 1-(2-chloro-5-iodopyridin-4-yl)-4-methylpiperazine and 4-ethynyl-1-methylpyrazole, respectively. MS (ESI) m/z=387.1 (M+H)⁺

Step 2. (1-(2-((2-(1-(Cyclopropylsulfonyl)-1H-pyrazol-4-yl)pyrimidin-4-yl)amino)-5-((1-(oxetan-3-yl)-1H-pyrazol-4-yl)ethynyl)pyridin-4-yl)-4-methylpiperidin-4-yl)methanol The title compound as a solid (5 mg) was prepared in the same fashion as Step 3 in Example 1 except that (1-(2-chloro-5-((1-(oxetan-3-yl)-1H-pyrazol-4-yl)ethynyl)pyridin-4-yl)-4-methylpiperidin-4-yl)methanol (73 mg, 0.188 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.66 (s, 1H), 8.46 (s, 1H), 8.42 (d, 2H), 8.23 (s, 1H), 7.77-7.62 (m, 4H), 6.99 (d, 1H), 5.49-5.46 (m, 1H), 5.11-5.05 (m, 5H), 3.70-3.67 (m, 2H), 3.51 (s, 2H), 3.44-3.39 (m, 2H), 2.87-2.83 (m, 1H), 2.05-2.03 (m, 2H), 1.83-1.52 (m, 9H), 1.26-1.23 (m, 4H), 1.09 (s, 3H); MS (ESI) m/z=616.2 (M+H)⁺

Example 246. (1-(2-((2-(1-(Cyclopropylsulfonyl)-1H-pyrazol-4-yl)pyrimidin-4-yl)amino)-5-((trimethylsilyl)ethynyl)pyridin-4-yl)-4-methylpiperidin-4-yl)methanol Step 1. (1-(2-Chloro-5-((trimethylsilyl)ethynyl)pyridin-4-yl)-4-methylpiperidin-4-yl)methanol (1-(2-chloro-5-iodopyridin-4-yl)-4-methylpiperidin-4-yl)methanol (8.90 g, 24.280 mmol) prepared in Reference Example 12, CuI (2.08 g, 10.920 mmol) and PPh₃ (2.10 g, 8.010 mmol) were dissolved in TEA (80 mL, 24.280 mmol), stirred at room temperature for 20 minutes, and then added dropwise with trimethylsilylacetylene (4.04 mL, 29.130 mmol). The reaction mixture was heated to 60° C. and stirred for 12 hours. Then, the reaction mixture was cooled to room temperature and filtered through Celite. The filtrate thus obtained was concentrated under reduced pressure to obtain a compound as brown oil. The residue was diluted with ethyl acetate, washed with aqueous ammonia, water and brine, in sequence, which was then dried over MgSO₄ and filtered. After the filtrate was concentrated under reduced pressure, the residue thus obtained was purified by silica gel column chromatography (EA/n-Hex=0-50%) to yield (1-(2-chloro-5-((1-(oxetan-3-yl)-1H-pyrazol-4-yl)ethynyl)pyridin-4-yl)-4-methylpiperidin-4-yl)methanol (7.50 g) as an off-light yellow solid. ¹H-NMR (CDCl₃, 400 MHz) δ 8.19 (s, 1H), 6.67 (s, 1H), 3.72-3.66 (m, 2H), 3.46 (d, 2H), 3.28-3.21 (m, 2H), 1.73-1.66 (m, 3H), 1.5-1.44 (m, 2H), 1.05 (s, 3H), 0.25 (s, 9H); MS (ESI) m/z=337.1 (M+H)⁺

Step 2. (1-(2-((2-(1-(Cyclopropylsulfonyl)-1H-pyrazol-4-yl)pyrimidin-4-yl)amino)-5-((trimethylsilyl)ethynyl)pyridin-4-yl)-4-methylpiperidin-4-yl)methanol The title compound as an off-white solid (7.10 g) was prepared in the same fashion as Step 3 in Example 1 except that (1-(2-chloro-5-((trimethylsilyl)ethynyl)pyridin-4-yl)-4-methylpiperidin-4-yl)methanol (7.47 g, 22.164 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.65 (s, 1H), 8.45 (s, 1H), 8.41 (d, 1H), 8.21 (s, 1H), 7.72 (s, 1H), 7.60 (s, 1H), 6.96 (d, 1H), 3.68-3.64 (m, 2H), 3.52 (s, 2H), 3.43 (dt, 2H), 2.84-2.82 (m, 1H), 1.78-1.73 (m, 2H), 1.60-1.52 (m, 2H), 1.26-1.22 (m, 2H), 1.09 (s, 3H), 0.27 (s, 9H); MS (ESI) m/z=566.3 (M+H)⁺

Example 247. (1-(2-((2-(1-(Cyclopropylsulfonyl)-1H-pyrazol-4-yl)pyrimidin-4-yl)amino)-5-ethynylpyridin-4-yl)-4-methylpiperidin-4-yl)methanol The reaction mixture of (1-(2-((2-(1-(cyclopropylsulfonyl)-1H-pyrazol-4-yl)pyrimidin-4-yl)amino)-5-((trimethylsilyl)ethynyl)pyridin-4-yl)-4-methylpiperidin-4-yl)methanol (5.00 g, 8.838 mmol) prepared in Example 246, and 1.0M tetrabutylammonium fluoride in THF (9.72 mL, 9.721 mmol) in DCM (150 mL) was stirred at room temperature for 1 hour. The reaction mixture was diluted in DCM, washed by water, dried over MgSO₄, and then concentrated. The crude product was purified by column chromatography (MeOH/DCM=0-10%) to yield (1-(2-((2-(1-(cyclopropylsulfonyl)-1H-pyrazol-4-yl)pyrimidin-4-yl)amino)-5-ethynylpyridin-4-yl)-4-methylpiperidin-4-yl)methanol (4.60 g) as an off-white solid. ¹H-NMR (CDCl₃, 400 MHz) δ 8.65 (s, 1H), 8.45 (s, 1H), 8.41 (d, 1H), 8.24 (s, 1H), 8.08 (br, 1H), 7.60 (br, 1H), 6.98 (d, 1H), 3.70-3.65 (m, 2H), 3.50 (s, 2H), 3.46 (s, 1H), 3.38 (td, 2H), 2.85-2.82 (m, 1H), 1.80-1.73 (m, 2H), 1.57-1.51 (m, 4H), 1.26-1.18 (m, 2H), 1.09 (s, 3H); MS (ESI) m/z=494.1 (M+H)⁺

Example 248. (1-(2-((2-(1-(Cyclopropylsulfonyl)-1H-pyrazol-4-yl)pyrimidin-4-yl)amino)-5-((5-((3,3-difluoroazetidin-1-yl)methyl)-1-(2,2-difluoroethyl)-1H-pyrrol-3-yl)ethynyl)pyridin-4-yl)-4-methylpiperidin-4-yl)methanol The reaction mixture of (1-(2-((2-(1-(cyclopropylsulfonyl)-1H-pyrazol-4-yl)pyrimidin-4-yl)amino)-5-ethynylpyridin-4-yl)-4-methylpiperidin-4-yl)methanol (50 mg, 0.101 mmol) prepared in Example 247, 2-((3,3-difluoroazetidin-1-yl)methyl)-1-(2,2-difluoroethyl)-4-iodo-1H-pyrrole (73 mg, 0.202 mmol), PdCl₂(PPh₃)₂ (14 mg, 0.020 mmol), CuI (12 mg, 0.061 mmol) and TEA (0.07 mL, 0.507 mmol) in DMF (1.00 mL) was stirred at 80° C. overnight. The reaction mixture was cooled, diluted in EA, washed by water and sat. NH₄Cl soln., dried over MgSO₄, and then concentrated. The crude product was purified by column chromatography (MeOH/DCM=0-10%) to yield (1-(2-((2-(1-(cyclopropylsulfonyl)-1H-pyrazol-4-yl)pyrimidin-4-yl)amino)-5-((5-((3,3-difluoroazetidin-1-yl)methyl)-1-(2,2-difluoroethyl)-1H-pyrrol-3-yl)ethynyl)pyridin-4-yl)-4-methylpiperidin-4-yl)methanol (60 mg). $^1$H-NMR (CDCl$_3$, 400 MHz) δ 8.64 (s, 1H), 8.48-8.43 (m, 4H), 8.17 (s, 1H), 7.98 (s, 1H), 6.96 (d, 2H), 6.21 (s, 1H), 4.39-4.32 (m, 3H), 3.88-3.87 (m, 2H), 3.70-3.53 (m, 11H), 2.86-2.83 (m, 1H), 1.85-1.80 (m, 2H), 1.62-1.55 (m, 5H), 1.27-1.25 (m, 2H), 1.11 (s, 3H); MS (ESI) m/z=651.2 (M+H)$^+$ Example 249. (1-(2-((2-(1-(Cyclopropylsulfonyl)-1H-pyrazol-4-yl)pyrimidin-4-yl)amino)-5-((1-(2,2-difluoroethyl)-1H-pyrrolo[3,2-c]pyridin-3-yl)ethynyl)pyridin-4-yl)-4-methylpiperidin-4-yl)methanol The title compound as an off-white solid (1 mg) was prepared in the same fashion as Example 248 except that 1-(2,2-difluoroethyl)-3-iodo-1H-pyrrolo[3,2-c]pyridine (37 mg, 0.122 mmol) was used instead of 2-((3,3-difluoroazetidin-1-yl)methyl)-1-(2,2-difluoroethyl)-4-iodo-1H-pyrrole. MS (ESI) m/z=674.2 (M+H)$^+$ Example 250. (1-(5-(Cyclopropylethynyl)-2-((2-(1-(cyclopropylsulfonyl)-1H-pyrazol-4-yl)pyrimidin-4-yl)amino)pyridin-4-yl)-4-methylpiperidin-4-yl)methanol Step 1. (1-(2-Chloro-5-(cyclopropylethynyl)pyridin-4-yl)-4-methylpiperidin-4-yl)methanol The title compound as a yellow oil (40 mg) was prepared in the same fashion as Step 2 in Example 1 except that (1-(2-chloro-5-iodopyridin-4-yl)-4-methylpiperidin-4-yl)methanol (70 mg, 0.19 mmol) prepared in Reference Example 12 and cyclopropylacetylene (15 mg, 0.23 mmol) were used instead of 1-(2-chloro-5-iodopyridin-4-yl)-4-methylpiperazine and 4-ethynyl-1-methylpyrazole, respectively. $^1$H-NMR (CDCl$_3$, 400 MHz) δ 8.13 (s, 1H), 6.67 (s, 1H), 3.66-3.61 (dt, 2H), 3.46 (d, 2H), 3.17 (td, 2H), 1.69 (td, 2H), 1.52-1.44 (m, 3H), 1.04 (s, 3H), 0.94-0.89 (m, 2H), 0.82-0.78 (m, 2H); MS (ESI) m/z=305.1 (M+H)$^+$ Step 2. (1-(5-(Cyclopropylethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a clear oil (11 mg) was prepared in the same fashion as Step 3 in Example 1 except that (1-(2-chloro-5-(cyclopropylethynyl)pyridin-4-yl)-4-methylpiperidin-4-yl)methanol (40 mg, 0.130 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 9.02 (br, 1H), 8.64 (s, 1H), 8.44 (s, 1H), 8.40 (d, 1H), 8.04 (s, 1H), 7.76 (s, 1H), 6.95 (d, 1H), 3.70-3.65 (m, 2H), 3.52 (s, 2H), 3.43-3.38 (td, 2H), 2.83 (m, 1H), 1.74 (td, 2H), 1.60-1.50 (m, 4H), 1.26-1.22 (m, 2H), 1.09 (s, 3H), 0.93-0.89 (m, 2H), 0.82-0.80 (m, 2H); MS (ESI) m/z=534.2 (M+H)$^+$ Example 251. (1-(5-(Cyclopentylethynyl)-2-((2-(1-(cyclopropylsulfonyl)-1H-pyrazol-4-yl)pyrimidin-4-yl)amino)pyridin-4-yl)-4-methylpiperidin-4-yl)methanol Step 1. (1-(2-Chloro-5-(cyclopentylethynyl)pyridin-4-yl)-4-methylpiperidin-4-yl)methanol The title compound as a yellow oil (40 mg) was prepared in the same fashion as Step 2 in Example 1 except that (1-(2-chloro-5-iodopyridin-4-yl)-4-methylpiperidin-4-yl)methanol (70 mg, 0.190 mmol) prepared in Reference Example 12 and cyclopentylacetylene (22 mg, 0.230 mmol) were used instead of 1-(2-chloro-5-iodopyridin-4-yl)-4-methylpiperazine and 4-ethynyl-1-methylpyrazole, respectively. $^1$H-NMR (CDCl$_3$, 400 MHz) δ 8.13 (s, 1H), 6.67 (s, 1H), 3.66-3.62 (dt, 2H), 3.45 (d, 2H), 3.19 (td, 2H), 2.88-2.84 (m, 1H), 2.04-1.98 (m, 2H), 1.78-1.60 (m, 9H), 1.50-1.45 (m, 2H), 1.04 (s, 3H); MS (ESI) m/z=333.2 (M+H)$^+$ Step 2. (1-(5-(Cyclopentylethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a clear oil (5 mg) was prepared in the same fashion as Step 3 in Example 1 except that (1-(2-chloro-5-(cyclopentylethynyl)pyridin-4-yl)-4-methylpiperidin-4-yl)methanol (40 mg, 0.120 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (d, 1H), 8.40 (d, 1H), 8.08 (s, 1H), 7.70 (s, 1H), 6.98 (d, 1H), 3.70-3.65 (m, 2H), 3.52 (s, 2H), 3.42 (td, 2H), 2.89-2.84 (m, 3H), 2.03-2.01 (m, 2H), 1.80-1.53 (m, 11H), 1.26-1.23 (m, 2H), 1.09 (s, 3H); MS (ESI) m/z=562.3 (M+H)$^+$ Example 252. (1-(5-(Cyclohexylethynyl)-2-((2-(1-(cyclopropylsulfonyl)-1H-pyrazol-4-yl)pyrimidin-4-yl)amino)pyridin-4-yl)-4-methylpiperidin-4-yl)methanol Step 1. (1-(2-Chloro-5-(cyclohexylethynyl)pyridin-4-yl)-4-methylpiperidin-4-yl)methanol The title compound as a yellow oil (40 mg) was prepared in the same fashion as Step 2 in Example 1 except that (1-(2-chloro-5-iodopyridin-4-yl)-4-methylpiperidin-4-yl)methanol (70 mg, 0.190 mmol) prepared in Reference Example 12 and cyclohexylacetylene (25 mg, 0.230 mmol) were used instead of 1-(2-chloro-5-iodopyridin-4-yl)-4-methylpiperazine and 4-ethynyl-1-methylpyrazole, respectively. $^1$H-NMR (CDCl$_3$, 400 MHz) δ 8.65 (s, 1H), 8.45 (s, 1H), 8.41 (d, 1H), 8.17 (br, 1H), 8.10 (s, 1H), 7.65 (s, 1H), 6.98 (d, 1H), 3.71-3.66 (m, 2H), 3.52 (s, 2H), 3.41 (dt, 2H), 2.85-2.81 (m, 1H), 2.64 (m, 1H), 1.94-1.91 (m, 2H), 1.79-1.74 (m, 4H), 1.60-1.52 (m, 6H), 1.39-1.35 (m, 4H), 1.26-1.22 (m, 2H), 1.09 (s, 3H); MS (ESI) m/z=347.2 (M+H)$^+$ Step 2. (1-(5-(Cyclohexylethynyl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a clear oil (2 mg) was prepared in the same fashion as Step 3 in Example 1 except that (1-(2-chloro-5-(cyclohexylethynyl)pyridin-4-yl)-4-methylpiperidin-4-yl)methanol (40 mg, 0.115 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.41 (d, 1H), 8.17 (br, 1H), 8.10 (s, 1H), 7.65 (s, 1H), 6.98 (d, 1H), 3.71-3.66 (m, 2H), 3.52 (s, 2H), 3.41 (dt, 2H), 2.85-2.81 (m, 1H), 2.64 (m, 1H), 1.94-1.91 (m, 2H), 1.79-1.74 (m, 4H), 1.60-1.52 (m, 6H), 1.39-1.35 (m, 4H), 1.26-1.22 (m, 2H), 1.09 (s, 3H); MS (ESI) m/z=576.3 (M+H)$^+$

Example 253. (1-(2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol Step 1. 4-(4-Iodobenzyl)morpholine To a solution of 1-(bromomethyl)-4-iodobenzene (500 mg, 1.680 mmol) in DCM (5 mL) was added DIPEA (379 mg, 3.70 mmol) and morpholine (191 mg, 2.190 mmol) and the reaction mixture was stirred at room temperature overnight. The reaction mixture was diluted with DCM, washed with water and brine, dried over MgSO$_4$, then concentrated to provide 4-(4-iodobenzyl)morpholine (480 mg) as a beige solid. $^1$H-NMR (CDCl$_3$, 400 MHz) δ 7.65 (d, 2H), 7.10 (d, 2H), 3.98 (t, 4H), 3.46 (s, 2H), 2.45 (br, 4H); MS (ESI) m/z=304.0 (M+H)$^+$ Step 2. (1-(2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol To the reaction mixture of 4-(4-iodobenzyl)morpholine (27 mg, 0.087 mmol) prepared in Step 1, CuI (7 mg, 0.037 mmol), PdCl$_2$(PPh$_3$)$_2$ (6 mg, 0.008 mmol), and PPh$_3$ (7 mg, 0.027 mmol) in TEA (2 mL) was added (1-(2-((2-(1-(cyclopropylsulfonyl)-1H-pyrazol-4-yl)pyrimidin-4-yl)amino)-5-ethynylpyridin-4-yl)-4-methylpiperidin-4-yl)methanol (41 mg, 0.083 mmol) prepared in Example 247 in DMF (1 mL), then the mixture was stirred at 60° C. overnight. The reaction mixture was cooled, diluted in DCM, and filtered with Celite filter. The filtrate was evaporated in vacuo, and then concentrated. The crude product was purified by column chromatography (MeOH/DCM=0-15%) to yield (1-(2-((2-(1-(cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol (5 mg) as a clear oil. $^1$H-NMR (CDCl$_3$, 400 MHz) δ 8.64 (s, 1H), 8.46 (m, 2H), 8.28 (br, 1H), 8.25 (s, 1H), 8.05 (s, 1H), 7.47 (d, 2H), 7.39 (d, 2H), 6.95 (d, 1H), 3.95-3.92 (m, 2H), 3.83-3.80 (br, 4H), 3.74 (s, 2H), 3.62-3.60 (m, 2H), 3.53 (s, 2H), 2.85-2.82 (m, 1H), 2.69 (br, 4H), 1.88-1.84 (m, 2H), 1.64-1.54 (m, 4H), 1.26-1.18 (m, 2H), 1.12 (s, 3H); MS (ESI) m/z=669.3 (M+H)$^+$

Example 254. (1-(2-((2-(1-(Cyclopropylsulfonyl)-1H-pyrazol-4-yl)pyrimidin-4-yl)amino)-5-((4-((dimethylamino)methyl)phenyl)ethynyl)pyridin-4-yl)-4-methylpiperidin-4-yl)methanol Step 1. 1-(4-Iodophenyl)-N,N-dimethylmethanamine The title compound as a beige solid (400 mg) was prepared in the same fashion as Step 1 in Example 253 except that 2.0M dimethylamine in MeOH (1.09 mL, 2.19 mmol) was used instead of morpholine. $^1$H-NMR (CDCl$_3$, 400 MHz) δ 7.65 (d, 2H), 7.06 (d, 2H), 3.36 (s, 2H), 2.23 (s, 6H); MS (ESI) m/z=262.0 (M+H)$^+$ Step 2. (1-(2-((2-(1-(Cyclopropylsulfonyl)-1H-pyrazol-4-yl)pyrimidin-4-yl)amino)-5-((4-((dimethylamino)methyl)phenyl)ethynyl)pyridin-4-yl)-4-methylpiperidin-4-yl)methanol The title compound as a clear oil (5 mg) was prepared in the same fashion as Step 2 in Example 253 except that 1-(4-iodophenyl)-N,N-dimethylmethanamine (23 mg, 0.087 mmol) prepared in Step 1 was used instead of 4-(4-iodobenzyl)morpholine. $^1$H-NMR (CDCl$_3$, 400 MHz) δ 8.64 (s, 1H), 8.47-8.45 (m, 2H), 8.28 (m, 2H), 8.05 (s, 1H), 7.53 (d, 2H), 7.47 (d, 2H), 6.95 (d, 1H), 4.16 (s, 2H), 3.98-3.96 (m, 2H), 3.60 (t, 2H), 3.52 (s, 2H), 2.87-2.84 (m, 1H), 2.75 (s, 6H), 1.89-1.85 (m, 2H), 1.64-1.55 (m, 4H), 1.28-1.18 (m, 2H), 1.12 (s, 3H); MS (ESI) m/z=627.3 (M+H)$^+$

Example 255. (1-(2-((2-(1-(Cyclopropylsulfonyl)-1H-pyrazol-4-yl)pyrimidin-4-yl)amino)-5-((3-((dimethylamino)methyl)phenyl)ethynyl)pyridin-4-yl)-4-methylpiperidin-4-yl)methanol Step 1. 1-(3-Iodophenyl)-N,N-dimethylmethanamine The title compound as a beige solid (320 mg) was prepared in the same fashion as Step 1 in Example 253 except that 1-(bromomethyl)-3-iodobenzene (400 mg, 1.350 mmol) was used instead of 1-(bromomethyl)-4-iodobenzene. $^1$H-NMR (CDCl$_3$, 400 MHz) δ 7.69 (s, 1H), 7.60 (d, 1H), 7.27 (d, 1H), 7.06 (t, 1H), 3.36 (s, 2H), 2.24 (s, 6H); MS (ESI) m/z=262.0 (M+H)$^+$ Step 2. (1-(2-((2-(1-(Cyclopropylsulfonyl)-1H-pyrazol-4-yl)pyrimidin-4-yl)amino)-5-((3-((dimethylamino)methyl)phenyl)ethynyl)pyridin-4-yl)-4-methylpiperidin-4-yl)methanol The title compound as a clear oil (5 mg) was prepared in the same fashion as Step 2 in Example 253 except that 1-(3-iodophenyl)-N,N-dimethylmethanamine (23 mg, 0.087 mmol) prepared in Step 1 was used instead of 4-(4-iodobenzyl)morpholine. $^1$H-NMR (CDCl$_3$, 400 MHz) δ 8.65 (s, 1H), 8.47-8.45 (m, 2H), 8.30-8.27 (m, 2H), 8.06 (s, 1H), 7.66 (s, 1H), 7.55 (d, 1H), 7.45 (t, 1H), 7.37 (d, 1H), 6.96 (d, 1H), 4.16 (s, 2H), 4.05-4.02 (m, 2H), 3.55-3.50 (m, 4H), 2.87-2.83 (m, 1H), 2.74 (s, 6H), 1.95 (t, 2H), 1.61-1.54 (m, 4H), 1.26-1.18 (m, 2H), 1.11 (s, 3H); MS (ESI) m/z=627.3 (M+H)$^+$

Example 256. (1-(2-((2-(1-(Cyclopropylsulfonyl)-1H-pyrazol-4-yl)pyrimidin-4-yl)amino)-5-(phenylethynyl)pyridin-4-yl)-4-methylpiperidin-4-yl)methanol The title compound as a clear oil (5 mg) was prepared in the same fashion as Step 2 in Example 253 except that iodobenzene (17 mg, 0.087 mmol) was used instead of 4-(4-iodobenzyl)morpholine. $^1$H-NMR (CDCl$_3$, 400 MHz) δ 8.66 (s, 1H), 8.46 (s, 1H), 8.42 (d, 1H), 8.35 (br, 1H), 8.24 (s, 1H), 7.73 (br, 1H), 7.52-7.50 (m, 2H), 7.40-7.36 (m, 3H), 6.97 (d, 1H), 3.78-3.74 (m, 2H), 3.52 (s, 2H), 3.51-3.45 (m, 2H), 2.85-2.83 (m, 1H), 1.83-1.79 (m, 2H), 1.65-1.60 (m, 2H), 1.56-1.54 (m, 2H), 1.26-1.23 (m, 2H), 1.11 (s, 3H); MS (ESI) m/z=570.2 (M+H)$^+$

Example 257. (1-(2-((2-(1-(Cyclopropylsulfonyl)-1H-pyrazol-4-yl)pyrimidin-4-yl)amino)-5-((2-fluorophenyl)ethynyl)pyridin-4-yl)-4-methylpiperidin-4-yl)methanol The title compound as a clear oil (2 mg) was prepared in the same fashion as Step 2 in Example 253 except that 2-fluoroiodobenzene (19 mg, 0.087 mmol) was used instead of 4-(4-iodobenzyl)morpholine. $^1$H-NMR (CDCl$_3$, 400

MHz) δ 8.67 (s, 1H), 8.46 (s, 1H), 8.43 (d, 1H), 8.27 (s, 1H), 7.96 (br, 1H), 7.68 (s, 1H), 7.50 (t, 1H), 7.30 (m, 1H), 7.17-7.10 (m, 2H), 7.00 (d, 1H), 3.80-3.76 (m, 2H), 3.52 (s, 2H), 3.51-3.46 (m, 2H), 2.85-2.83 (m, 1H), 1.85-1.78 (m, 2H), 1.63-1.58 (m, 2H), 1.55-1.54 (m, 2H), 1.26-1.22 (m, 2H), 1.10 (s, 3H); MS (ESI) m/z=588.2 (M+H)$^+$

Example 258. (1-(2-((2-(1-(Cyclopropylsulfonyl)-1H-pyrazol-4-yl)pyrimidin-4-yl)amino)-5-(pyridin-4-ylethynyl)pyridin-4-yl)-4-methylpiperidin-4-yl)methanol The title compound as a clear oil (8 mg) was prepared in the same fashion as Step 2 in Example 253 except that 4-iodopyridine (18 mg, 0.087 mmol) was used instead of 4-(4-iodobenzyl)morpholine. $^1$H-NMR (CDCl$_3$, 400 MHz) δ 8.64-8.63 (m, 3H), 8.46 (s, 1H), 8.45 (d, 1H), 8.27 (br, 1H), 8.18 (s, 1H), 8.12 (s, 1H), 7.36 (d, 2H), 6.92 (d, 1H), 3.90-3.84 (m, 2H), 3.62-3.54 (m, 4H), 2.87-2.83 (m, 1H), 1.89-1.83 (m, 2H), 1.65-1.61 (m, 2H), 1.56-1.53 (m, 2H), 1.26-1.18 (m, 2H), 1.13 (s, 3H); MS (ESI) m/z=571.2 (M+H)$^+$ Example 259. (1-(2-((2-(1-(Cyclopropylsulfonyl)-1H-pyrazol-4-yl)pyrimidin-4-yl)amino)-5-(pyridin-2-ylethynyl)pyridin-4-yl)-4-methylpiperidin-4-yl)methanol The title compound as a clear oil (6 mg) was prepared in the same fashion as Step 2 in Example 253 except that 2-iodopyridine (17 mg, 0.081 mmol) was used instead of 4-(4-iodobenzyl)morpholine. $^1$H-NMR (CDCl$_3$, 400 MHz) δ 8.65 (s, 2H), 8.46 (s, 1H), 8.44 (d, 1H), 8.30 (s, 1H), 8.15-8.14 (m, 2H), 7.71 (t, 1H), 7.48 (d, 1H), 7.30-7.27 (m, 1H), 6.93 (d, 1H), 3.92-3.89 (m, 2H), 3.59 (td, 2H), 3.52 (s, 2H), 2.86-2.83 (m, 1H), 1.90-1.85 (m, 2H), 1.64-1.54 (m, 4H), 1.26-1.24 (m, 2H), 1.11 (s, 3H); MS (ESI) m/z=571.2 (M+H)$^+$ Example 260. (1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-yl)methanol The title compound as a clear oil (11 mg) was prepared in the same fashion as Step 2 in Example 253 except that 3-iodopyridine (17 mg, 0.081 mmol) was used instead of 4-(4-iodobenzyl)morpholine. $^1$H-NMR (CDCl$_3$, 400 MHz) δ 8.75 (s, 1H), 8.66 (s, 1H), 8.55 (d, 1H), 8.46 (s, 1H), 8.42 (d, 1H), 8.28 (br, 1H), 8.27 (s, 1H), 7.78 (m, 2H), 7.32 (dd, 1H), 6.96 (d, 1H), 5.64 (d, 1H), 3.98-3.96 (m, 2H), 3.52 (s, 2H), 3.46 (td, 2H), 2.86-2.83 (m, 1H), 1.90-1.85 (m, 2H), 1.63-1.53 (m, 4H), 1.25-1.23 (m, 2H), 1.10 (s, 3H); MS (ESI) m/z=571.2 (M+H)$^+$ Example 261. (3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone Step 1. (3-Iodophenyl)(morpholino)methanone To a solution of 3-iodobenzoyl chloride (350 mg, 1.310 mmol) in DCM (5 mL) was added morpholine (0.15 mL, 1.710 mmol) and the reaction mixture was stirred at room temperature overnight. The reaction mixture was diluted with DCM, washed with water and brine, dried over MgSO$_4$, then concentrated. The crude product was purified by column chromatography (EA/n-Hex=0-100%) to yield (3-iodophenyl)(morpholino)methanone (320 mg, yield=77%) as a clear oil. $^1$H-NMR (CDCl$_3$, 400 MHz) δ 7.77 (m, 2H), 7.36 (d, 1H), 7.16 (t, 1H), 3.83-3.40 (m, 8H); MS (ESI) m/z=318.0 (M+H)$^+$ Step 2. (3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone The title compound as a white solid (32 mg) was prepared in the same fashion as Step 2 in Example 253 except that (3-iodophenyl)(morpholino)methanone (64 mg, 0.203 mmol) prepared in Step 1 was used instead of 4-(4-iodobenzyl)morpholine. $^1$H-NMR (CDCl$_3$, 400 MHz) δ 8.65 (s, 1H), 8.44 (s, 1H), 8.41-8.39 (m, 2H), 8.26 (s, 1H), 7.65 (br, 1H), 7.56 (s, 1H), 7.54 (d, 1H), 7.41 (t, 1H), 7.36 (d, 1H), 6.99 (d, 1H), 3.90-3.58 (m, 10H), 3.49 (s, 2H), 3.44-3.38 (m, 2H), 2.86-2.82 (m, 1H), 1.86-1.79 (m, 2H), 1.58-1.51 (m, 4H), 1.26-1.21 (m, 2H), 1.08 (s, 3H); MS (ESI) m/z=683.3 (M+H)$^+$ Example 262. 4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylbenzamide Step 1. 4-Iodo-N,N-dimethylbenzamide To a solution of 4-iodobenzoic acid (1.00 g, 4.030 mmol) in DCM (10 mL) was added 2.0M dimethylamine in MeOH (3.02 mL, 6.050 mmol), DIPEA (782 mg, 6.050 mmol), and HATU (2.30 g, 6.050 mmol) and the reaction mixture was stirred at room temperature overnight. The reaction mixture was diluted with DCM, washed with water and brine, dried over MgSO$_4$ then concentrated. The crude product was purified by column chromatography (EA/n-Hex=0-100%) to yield 4-iodo-N,N-dimethylbenzamide (950 mg) as a white solid. $^1$H-NMR (CDCl$_3$, 400 MHz) δ 7.75 (d, 2H), 7.16 (d, 2H), 3.09 (s, 3H), 2.97 (s, 3H); MS (ESI) m/z=276.0 (M+H)$^+$ Step 2. 4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylbenzamide The title compound as a white solid (40 mg) was prepared in the same fashion as Step 2 in Example 253 except that 4-iodo-N,N-dimethylbenzamide (45 mg, 0.162 mmol) prepared in Step 1 was used instead of 4-(4-iodobenzyl)morpholine. $^1$H-NMR (CDCl$_3$, 400 MHz) δ 8.66 (s, 1H), 8.45 (s, 1H), 8.41 (d, 1H), 8.27 (s, 1H), 8.06 (br, 1H), 7.63 (br, 1H), 7.52 (d, 2H), 7.42 (d, 2H), 7.01 (d, 1H), 3.75 (m, 2H), 3.51 (s, 2H), 3.46-3.43 (dt, 2H), 3.12 (br, 3H), 3.01 (br, 3H), 2.84-2.82 (m, 1H), 1.81-1.78 (m, 2H), 1.61-1.52 (m, 4H), 1.26-1.22 (m, 2H), 1.09 (s, 3H); MS (ESI) m/z=641.3 (M+H)$^+$ Example 263. (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone Step 1. (4-Iodophenyl)(morpholino)methanone The title compound as a white solid (1.05 g) was prepared in the same fashion as Step 1 in Example 262 except that morpholine (0.53 mL, 6.05 mmol) was used instead of dimethylamine. ¹H-NMR (CDCl₃, 400 MHz) δ 7.77 (d, 2H), 7.16 (d, 2H), 3.74-3.44 (br, 8H); MS (ESI) m/z=318.0 (M+H)⁺

Step 2. (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone The title compound as a white solid (25 mg) was prepared in the same fashion as Step 2 in Example 253 except that (4-iodophenyl)(morpholino)methanone (51 mg, 0.162 mmol) prepared in Step 1 was used instead of 4-(4-iodobenzyl)morpholine. ¹H-NMR (CDCl₃, 400 MHz) δ 8.65 (s, 1H), 8.44 (s, 1H), 8.41 (d, 1H), 8.27 (s, 1H), 7.92 (br, 1H), 7.62 (br, 1H), 7.53 (d, 2H), 7.41 (d, 2H), 7.05 (d, 1H), 3.90-3.63 (m, 10H), 3.50 (s, 2H), 3.46-3.43 (dt, 2H), 2.84-2.82 (m, 1H), 1.81-1.78 (m, 2H), 1.61-1.56 (m, 2H), 1.52-1.48 (m, 2H), 1.26-1.22 (m, 2H), 1.09 (s, 3H); MS (ESI) m/z=683.3 (M+H)⁺

Example 264. 6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylpicolinamide Step 1. 6-Bromo-N,N-dimethylpicolinamide The title compound as a clear oil (850 mg) was prepared in the same fashion as Step 1 in Example 262 except that 6-bromopicolinic acid (1.00 g, 4.950 mmol) was used instead of 4-iodobenzoic acid. ¹H-NMR (CDCl₃, 400 MHz) δ 7.65 (t, 1H), 7.61 (t, 1H), 7.52 (d, 1H), 3.09 (d, 6H); MS (ESI) m/z=229.0 (M+H)⁺

Step 2. 6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylpicolinamide The title compound as a clear oil (8 mg) was prepared in the same fashion as Step 2 in Example 253 except that 6-bromo-N,N-dimethylpicolinamide (38 mg, 0.162 mmol) prepared in Step 1 was used instead of 4-(4-iodobenzyl) morpholine. ¹H-NMR (CDCl₃, 400 MHz) δ 8.67 (s, 1H), 8.46 (s, 1H), 8.43 (d, 1H), 8.34 (s, 1H), 7.80 (t, 1H), 7.64 (br, 2H), 7.56 (d, 1H), 7.51 (d, 1H), 7.00 (d, 1H), 3.78-3.74 (m, 2H), 3.51 (s, 2H), 3.50-3.43 (td, 2H), 3.14 (d, 611), 2.85-2.83 (m, 1H), 1.87-1.81 (m, 2H), 1.60-1.54 (m, 4H), 1.26-1.22 (m, 2H), 1.10 (s, 3H); MS (ESI) m/z=642.3 (M+H)⁺

Example 265. (6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyridin-2-yl)(morpholino)methanone Step 1. (6-Bromopyridin-2-yl)(morpholino)methanone The title compound as a clear oil (770 mg) was prepared in the same fashion as Step 1 in Example 262 except that 6-bromopicolinic acid (1.00 g, 4.950 mmol) and morpholine (0.53 mL, 6.050 mmol) were used instead of 4-iodobenzoic acid and dimethylamine. ¹H-NMR (CDCl₃, 400 MHz) δ 7.69-7.64 (m, 2H), 7.53 (d, 1H), 3.78 (s, 4H), 3.69-3.64 (dd, 4H); MS (ESI) m/z=271.0 (M+H)⁺

Step 2. (6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyridin-2-yl)(morpholino)methanone The title compound as a white solid (11 mg) was prepared in the same fashion as Step 2 in Example 253 except that (6-bromopyridin-2-yl)(morpholino)methanone (44 mg, 0.162 mmol) prepared in Step 1 was used instead of 4-(4-iodobenzyl)morpholine. ¹H-NMR (CDCl₃, 400 MHz) δ 8.66 (s, 1H), 8.46 (s, 1H), 8.43 (d, 1H), 8.33 (s, 1H), 7.84 (br, 1H), 7.81 (t, 1H), 7.67 (br, 1H), 7.59 (d, 1H), 7.52 (d, 1H), 7.01 (d, 1H), 3.83-3.68 (m, 10H), 3.51 (s, 2H), 3.48 (td, 2H), 2.86-2.83 (m, 1H), 1.86-1.82 (m, 2H), 1.60-1.53 (m, 4H), 1.26-1.22 (m, 2H), 1.10 (s, 3H); MS (ESI) m/z=684.3 (M+H)⁺

Example 266. 2-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutyl)propan-2-ol Step 1. 2-(3-((6-Chloro-4-(4-(hydroxymethyl)-4-methylpiperidin-1-yl)pyridin-3-yl)ethynyl)cyclobutyl)propan-2-ol The title compound as a solid (209 mg) was prepared in the same fashion as Reference Example 18 except that 2-(3-ethynylcyclobutyl)propan-2-ol (210 mg, 1.500 mmol) and (1-(2-chloro-5-iodopyridin-4-yl)-4-methylpiperidin-4-yl)methanol (500 mg, 1.364 mmol) prepared in Reference Example 12 were used instead of 4-ethynyl-1-methylpyrazole and 2-chloro-4-fluoro-5-iodopyridine. ¹H-NMR (CDCl₃, 400 MHz) δ 8.13 (d, 1H), 6.70 (d, 1H), 3.68 (m, 2H), 3.43 (m, 2H), 3.23-3.04 (m, 3H), 2.66 (m, 1H), 2.30 (m, 3H), 2.14 (m, 2H), 1.83-1.58 (m, 2H), 1.45-1.41 (m, 3H), 1.13 (d, 6H), 1.04 (d, 3H); MS (ESI) m/z=377.2 (M+H)⁺

Step 2. 2-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutyl)propan-2-ol The title compound as a solid (53 mg) was prepared in the same fashion as Step 3 in Reference Example 17 except that 2-(3-((6-chloro-4-(4-(hydroxymethyl)-4-methylpiperidin-1-yl)pyridin-3-yl)ethynyl)cyclobutyl)propan-2-ol (104 mg, 0.276 mmol) prepared in Step 1 was used instead of tert-butyl (1-(2-chloro-5-((1-methyl-1H-pyrazol-4-yl)ethynyl)pyridin-4-yl)piperidin-4-yl)carbamate. ¹H-NMR (MeOD, 400 MHz) δ 8.70 (s, 1H), 8.43 (s, 1H), 8.35 (d, 1H), 8.05-8.02 (d, 1H), 7.49 (m, 1H), 7.32 (m, 1H), 3.70 (m, 2H), 3.39 (s, 2H), 3.25-3.13 (m, 3H), 3.06 (m, 1H), 2.44 (m, 1H), 2.30 (m, 2H), 2.14 (m, 2H), 1.77 (m, 2H), 1.54 (m, 2H), 1.44 (m, 2H), 1.26 (m, 2H), 1.12 (d, 6H), 1.06 (s, 3H); MS (ESI) m/z=606.3 (M+H)⁺

Example 267. (1-(2-((2-(1-(2,2-Difluoroethyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol Step 1. 2-(1-(2,2-Difluoroethyl)-1H-pyrazol-4-yl)pyrimidin-4-amine The reaction mixture of 2-bromo-4-pyrimidinamine (150 mg, 0.862 mmol), 1-(2,2-difluoroethyl)-4-(4,4,5,5-tetramethyl-1,3,2-dioxaborolan-2-yl)pyrazole (222 mg, 0.862 mmol), PdCl₂(PPh₃)₂ (61 mg, 0.086 mmol), and 3 M K₂CO₃ solution (0.86 mL, 2.586 mmol) in 1,4-dioxane (8 mL) was stirred at 90° C. for 10 hours. The reaction mixture was cooled, diluted in DCM, washed by water, dried over MgSO₄, and then concentrated. The crude product was purified by column chromatography (MeOH/DCM=0-20%) to yield 2-(1-(2,2-difluoroethyl)-1H-pyrazol-4-yl)pyrimidin-4-amine (70 mg). ¹H-NMR (CDCl₃, 400 MHz) δ 8.23 (d, 1H), 8.18 (s, 1H), 8.12 (s, 1H), 6.26 (d, 1H), 6.13 (tt, 1H), 4.82 (s, 2H), 4.50 (td, 2H); MS (ESI) m/z=226.1 (M+H)⁺

Step 2. (1-(2-((2-(1-(2,2-Difluoroethyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol The title compound as a solid (15 mg) was prepared in the same fashion as Step 3 in Reference Example 17 except that 2-(1-(2,2-difluoroethyl)-1H-pyrazol-4-yl)pyrimidin-4-amine (32 mg, 0.142 mmol) prepared in Step 1 and (1-(2-chloro-5-((1-(trifluoromethyl)-1H-pyrazol-4-yl)ethynyl)pyridin-4-yl)-4-methylpiperidin-4-yl)methanol (62 mg, 0.156 mmol) prepared in Reference Example 53 were used instead of 2-(1-cyclopropylsulfonylpyrazol-4-yl)pyrimidin-4-amine and tert-butyl (1-(2-chloro-5-((1-methyl-1H-pyrazol-4-yl)ethynyl)pyridin-4-yl)piperidin-4-yl)carbamate. ¹H-NMR (CDCl₃, 400 MHz) δ 8.40 (d, 1H), 8.25-8.17 (m, 2H), 7.98 (s, 1H), 7.86 (s, 2H), 7.47 (s, 1H), 7.03 (d, 1H), 6.14 (t, 1H), 4.52 (td, 2H), 3.76-3.71 (m, 2H), 3.49 (s, 2H), 3.33 (t, 2H), 1.81-1.76 (m, 2H), 1.62-1.52 (m, 2H), 1.28-1.25 (m, 1H), 1.09 (s, 3H); MS (ESI) m/z=588.2 (M+H)⁺

Example 268. (4-Methyl-1-(2-((2-(1-(methylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)methanol Step 1. 2-(1-(Methylsulfonyl)-1H-pyrazol-4-yl)pyrimidin-4-amine The title compound as an off white solid (210 mg) was prepared in the same fashion as Reference Example 49, except that (1-(methylsulfonyl)-4-pyrazolyl)boronic acid (330 mg, 1.74 mmol) was used instead of N,N-dimethyl-4-(4,4,5,5-tetramethyl-1,3,2-dioxaborolan-2-yl)pyrazole-1-sulfonamide. ¹H-NMR (CDCl₃, 400 MHz) δ 8.66 (s, 1H), 8.41 (s, 1H), 8.25 (d, 1H), 6.33 (d, 1H), 4.95 (brs, 2NH), 3.35 (s, 3H); MS (ESI) m/z=239.8 (M+H)⁺

Step 2. (4-Methyl-1-(2-((2-(1-(methylsulfonyl)-1H-pyrazol-4-yl)pyrimidin-4-yl)amino)-5-((1-(trifluoromethyl)-1H-pyrazol-4-yl)ethynyl)pyridin-4-yl) piperidin-4-yl)methanol The title compound as a white solid (1.2 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (50 mg, 0.125 mmol) prepared in Reference Example 53 and 2-(1-(methylsulfonyl)-1H-pyrazol-4-yl)pyrimidin-4-amine (20 mg, 0.084 mmol) prepared in Step 1 were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. ¹H-NMR (CDCl₃, 400 MHz) δ 8.70 (s, 1H), 8.44 (m, 3H), 8.18 (s, 1H), 7.98 (s, 1H), 7.87 (s, 1H), 7.79 (s, 1H), 6.99 (d, 1H), 3.74 (m, 2H), 3.52 (s, 2H), 3.47 (m, 2H), 3.43 (s, 3H), 1.81-1.76 (m, 2H), 1.59 (m, 2H), 1.11 (s, 3H); MS (ESI) m/z 602.2 (M+H)⁺

Example 269. (1-(2-((2-(6-Fluoropyridin-3-yl)pyrimidin-4-yl)amino)-5-((1-(trifluoromethyl)-1H-pyrazol-4-yl)ethynyl)pyridin-4-yl)-4-methylpiperidin-4-yl)methanol Step 1. 2-(6-Fluoropyridin-3-yl)pyrimidin-4-amine The title compound as an off white solid (168 mg) was prepared in the same fashion as Reference Example 49, except that 6-fluoropyridine-3-boronic acid (261 mg, 1.853 mmol) was used instead of N,N-dimethyl-4-(4,4,5,5-tetramethyl-1,3,2-dioxaborolan-2-yl)pyrazole-1-sulfonamide. ¹H-NMR (CDCl₃, 400 MHz) δ 9.19 (s, 1H), 8.73 (t, 1H), 8.33 (d, 1H), 6.99 (d, 1H), 6.39 (d, 1H), 5.02 (brs, 2NH); MS (ESI) m/z=190.8 (M+H)⁺

Step 2. (1-(2-((2-(6-Fluoropyridin-3-yl)pyrimidin-4-yl)amino)-5-((1-(trifluoromethyl)-1H-pyrazol-4-yl) ethynyl)pyridin-4-yl)-4-methylpiperidin-4-yl)methanol The title compound as a white solid (8.0 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (94 mg, 0.237 mmol) prepared in Reference Example 53 and 2-(6-fluoropyridin-3-yl)pyrimidin-4-amine (30 mg, 0.158 mmol) prepared in Step 1 were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. ¹H-NMR (CDCl₃, 400 MHz) δ 9.28 (s, 1H), 8.79 (t, 1H), 8.52 (d, 1H), 8.25 (s, 1H), 7.98 (s, 1H), 7.87 (s, 1H), 7.61 (s, 1H), 7.49 (s, 1H), 7.20 (d, 1H), 7.04 (d, 1H), 3.78 (m, 2H), 3.50 (d, 2H), 3.36 (m, 2H), 1.99 (brs, 1H), 1.80 (m, 2H), 1.52 (m, 2H), 1.10 (s, 3H); MS (ESI) m/z=553.2 (M+H)⁺

Example 270. (4-Methyl-1-(5-((1-methyl-1H-pyrazol-4-yl)ethynyl)-2-((2-((2-(methylsulfonyl)phenyl) amino)pyrimidin-4-yl)amino)pyridin-4-yl)piperidin-4-yl)methanol The title compound as a white solid (65.8 mg) was prepared in the same fashion as Step 3 in Example 1 except that (1-(2-chloro-5-((1-methyl-1H-pyrazol-4-yl)ethynyl)pyridin-4-yl)-4-methylpiperidin-4-yl)methanol (100 mg, 0.291 mmol) prepared in Step 2 of Example 12 and N²-(2-(methylsulfonyl)phenyl)pyrimidine-2,4-diamine were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. ¹H-NMR (DMSO-d₆, 600 MHz) δ 9.14 (s, 1H), 8.76 (d, 1H), 8.22 (d, 1H), 8.12 (s, 1H), 7.99 (s, 1H), 7.84 (d, 1H), 7.69 (t, 1H), 7.62 (s, 1H), 7.53 (s, 1H), 7.20 (t, 1H), 7.07 (d, 1H), 4.60 (t, 1H), 3.85 (s, 3H), 3.57-3.54 (m, 2H), 3.25 (s, 3H), 3.20 (d, 2H), 3.19-3.10 (m, 2H), 1.64-1.58 (m, 2H), 1.35-1.31 (m, 2H); MS (ESI) m/z=573.2 (M+H)⁺

Example 271. (1-(5-((1-(Difluoromethyl)-1H-pyrazol-4-yl)ethynyl)-2-((2-((2-(methylsulfonyl)phenyl) amino)pyrimidin-4-yl)amino)pyridin-4-yl)-4-methylpiperidin-4-yl)methanol Step 1. (1-(2-Chloro-5-((1-(difluoromethyl)-1H-pyrazol-4-yl)ethynyl)pyridin-4-yl)-4-methylpiperidin-4-yl)methanol The title compound as a white solid (125.8 mg) was prepared in the same fashion as Step 2 in Example 1 except that (1-(2-chloro-5-iodopyridin-4-yl)-4-methylpiperidin-4-yl)methanol (150 mg, 0.409 mmol) prepared in Reference Example 12 and 1-(difluoromethyl)-4-ethynyl-1H-pyrazole (64 mg, 0.45 mmol) were used instead of 1-(2-chloro-5-iodopyridin-4-yl)-4-methylpiperazine and 4-ethynyl-1-methyl-1H-pyrazole. MS (ESI) m/z=381.1 (M+H)$^+$ Step 2. (1-(5-((1-(Difluoromethyl)-1H-pyrazol-4-yl)ethynyl)-2-((2-((2-(methylsulfonyl)phenyl)amino)pyrimidin-4-yl)amino)pyridin-4-yl)-4-methylpiperidin-4-yl)methanol The title compound as a white solid (58.7 mg) was prepared in the same fashion as Step 3 in Example 1 except that (1-(2-chloro-5-((1-(difluoromethyl)-1H-pyrazol-4-yl)ethynyl)pyridin-4-yl)-4-methylpiperidin-4-yl)methanol (111 mg, 0.291 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 600 MHz) δ 9.15 (s, 1H), 8.77 (d, 1H), 8.57 (s, 1H), 8.23 (d, 1H), 8.16 (s, 1H), 8.00 (s, 1H), 7.85 (d, 1H), 7.82 (t, 1H), 7.68 (d, 1H), 7.55 (s, 1H), 7.20 (t, 1H), 7.08 (d, 1H), 4.60 (t, 1H), 3.58-3.55 (m, 2H), 3.25 (s, 3H), 3.20 (d, 2H), 3.19-3.10 (m, 2H), 1.64-1.59 (m, 2H), 1.35-1.32 (m, 2H); MS (ESI) m/z=609. 2 (M+H)$^+$ Example 272. 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N,3-trimethyl-1H-pyrazole-1-sulfonamide The title compound as a white solid (39.2 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (78 mg, 0.195 mmol) prepared in Reference Example 53 and 4-(4-aminopyrimidin-2-yl)-N,N,3-trimethyl-1H-pyrazole-1-sulfonamide (50 mg, 0.177 mmol) prepared in Reference Example 50 were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. $^1$H-NMR (DMSO-d$_6$, 400 MHz) δ 10.14 (s, 1H), 8.86 (s, 1H), 8.53 (s, 1H), 8.45 (d, 1H), 8.18 (d, 2H), 7.53 (s, 1H), 7.41 (d, 1H), 6.85 (s, 1H), 4.59 (t, 1H), 3.68-3.65 (m, 2H), 3.25-3.15 (m, 4H), 2.89 (s, 6H), 2.60 (s, 3H), 1.67-1.61 (m, 2H), 1.39-1.35 (m, 2H), 0.94 (s, 3H); MS (ESI) m/z=645.2 (M+H)$^+$ Example 273. 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N-dimethyl-1H-pyrazole-1-sulfonamide The title compound as a white solid (50.2 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (82 mg, 0.205 mmol) prepared in Reference Example 53 and 4-(4-aminopyrimidin-2-yl)-N,N-dimethyl-1H-pyrazole-1-sulfonamide (50 mg, 0.186 mmol) prepared in Reference Example 49 were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. $^1$H-NMR (MeOD, 400 MHz) δ 8.61 (s, 1H), 8.42 (s, 1H), 8.32 (s, 1H), 8.30 (d, 1H), 8.10 (s, 1H), 7.95 (s, 1H), 7.51 (s, 1H), 7.27 (d, 1H), 3.73-3.70 (m, 2H), 3.37 (s, 2H), 3.27-3.21 (m, 2H), 2.90 (s, 6H), 1.79-1.72 (m, 2H), 1.51-1.48 (m, 2H), 1.04 (s, 3H); MS (ESI) m/z=631.2 (M+H)$^+$ Example 274. 4-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol Step 1. 4-(6-Chloro-4-fluoro-3-pyridyl)but-3-yn-1-ol The title compound as a light yellow oil (500 mg) was prepared in the same fashion as Reference Example 18 except that 3-butyn-1-ol (450 mg, 6.41 mmol) was used instead of 4-ethynyl-1-methylpyrazole. $^1$H-NMR (CDCl$_3$, 400 MHz) δ 8.42 (d, 1H), 7.11 (d, 1H), 3.87 (m, 2H), 2.76 (t, 2H), 1.89 (m, 1H)

Step 2. 4-(6-Chloro-4-(4-(hydroxymethyl)-4-methyl-1-piperidyl)-3-pyridyl)but-3-yn-1-ol The title compound as a light beige solid (140 mg) was prepared in the same fashion as Reference Example 2 except that (4-methylpiperidin-4-yl)methanol (157 mg, 1.21 mmol) and 4-(6-chloro-4-fluoro-3-pyridyl)but-3-yn-1-ol (220 mg, 1.10 mmol) prepared in Step 1 were used instead of 4-hydroxypiperidine and 2,4-dichloro-5-iodopyridine. $^1$H-NMR (CDCl$_3$, 400 MHz) δ 8.17 (s, 1H), 6.71 (s, 1H), 3.84 (br, 2H), 3.66 (dt, 2H), 3.45 (s, 2H), 3.20 (td, 2H), 2.76 (t, 2H), 1.81 (br, 1H), 1.72 (m, 2H), 1.46 (m, 2H), 1.05 (s, 3H); MS (ESI) m/z=309.0 (M+H)$^+$ Step 3. 4-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol The suspension of 2-(1-(cyclopropylsulfonyl)-1H-pyrazol-4-yl)pyrimidin-4-amine (103 mg, 0.39 mmol), Cs$_2$CO$_3$ (380 mg, 1.17 mmol), Xphos (37 mg, 0.078 mmol), 4-(6-chloro-4-(4-(hydroxymethyl)-4-methyl-1-piperidyl)-3-pyridyl)but-3-yn-1-ol (120 mg, 0.39 mmol) prepared in Step 2 and tris(dibenzylideneacetone)dipalladium(0) (36 mg, 0.04 mmol) in 1,4-dioxane (2 mL) was bubbled with nitrogen gas for 5 mins. The reaction mixture was stirred at room temperature for 30 mins, then stirred at MW (600 W, 120° C.) for 1 hour. The mixture was diluted in DCM and THF, filtered through Celite, and then concentrated. The crude product was purified by column chromatography (MeOH/DCM=0-7%) to provide 4-(6-((2-(1-(cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol (2.8 mg) as a clear oil. $^1$H-NMR (CDCl$_3$, 400 MHz) δ 8.65 (s, 1H), 8.45 (s, 1H), 8.41 (d, 1H), 8.15 (s, 1H), 7.68 (br, 1H), 7.59 (s, 1H), 6.99 (d, 1H), 4.90 (br, 1H), 3.85 (t, 2H), 3.64 (m, 2H), 3.50 (s, 2H), 3.31 (td, 2H), 2.83 (m, 1H), 2.79 (t, 2H), 1.80-1.74 (m, 2H), 1.56-1.52 (m, 2H), 1.28-1.21 (m, 4H), 1.08 (s, 3H); MS (ESI) m/z=538.2 (M+H)$^+$ Example 275. (1-(2-((2-(1-(Cyclopropylsulfonyl)-1H-pyrazol-4-yl)pyrimidin-4-yl)amino)-5-(4,4,4-trifluorobut-1-yn-1-yl)pyridin-4-yl)-4-methylpiperidin-4-yl)methanol To a stirred solution of (1-(2-((2-(1-(cyclopropylsulfonyl)-1H-pyrazol-4-yl)pyrimidin-4-yl)amino)-5-ethynylpyridin-4-yl)-4-methylpiperidin-4-yl)methanol (100 mg, 0.203 mmol) prepared in Example 247 in toluene (3 mL), were added 1,1,1-trifluoro-2-iodoethane (85 mg, 0.405 mmol) at room temperature. This mixture was degassed with $N_2$ and was added $Pd_2(dba)_3$ (9 mg, 0.01 mmol) followed by DPEphos (22 mg, 0.041 mmol) and DABCO (5 mg, 0.041 mmol). The reaction mixture was heated at 80° C. for 7 days. The reaction mixture was diluted with water and extracted with EA. The combined organic extracts were washed with water, brine, and concentrated under vacuum. The crude product was purified by HPLC (reverse phase, ACN/water=10-95%) to afford (1-(2-((2-(1-(cyclopropylsulfonyl)-1H-pyrazol-4-yl)pyrimidin-4-yl)amino)-5-(4,4,4-trifluorobut-1-yn-1-yl)pyridin-4-yl)-4-methylpiperidin-4-yl)methanol (0.2 mg). $^1$H-NMR ($CDCl_3$, 400 MHz) δ 8.65 (s, 1H), 8.45 (s, 1H), 8.43 (d, 1H), 8.13 (s, 1H), 7.71 (s, 1H), 6.98 (d, 1H), 3.69 (m, 2H), 3.51 (s, 2H), 3.42 (m, 2H), 3.35 (m, 2H), 2.84 (m, 1H), 2.23 (m, 2H), 1.80-1.60 (m, 4H), 1.09 (s, 3H), 0.89 (m, 4H); MS (ESI) m/z=576.2 $(M+H)^+$ Example 276. (1-(2-((2-(1-(Cyclopropylsulfonyl)-1H-pyrazol-4-yl)pyrimidin-4-yl)amino)-5-(4-fluorobut-1-yn-1-yl)pyridin-4-yl)-4-methylpiperidin-4-yl)methanol Step 1. 2-Chloro-4-fluoro-5-(4-fluorobut-1-ynyl)pyridine To a solution of 4-(6-chloro-4-fluoro-3-pyridyl)but-3-yn-1-ol (480 mg, 2.40 mmol) prepared in Step 1 of Example 274 in DCM (10 mL) at −10° C. was added (diethylamino)sulfur trifluoride (775 mg, 4.81 mmol) in a portionwise manner. The reaction mixture was stirred at −10° C. for 2 hours, and then stirred at room temperature overnight.

The reaction mixture was quenched with water, extracted with EA, and washed with brine. The organic phase was evaporated in vacuo, then the residue was purified by column chromatography (EA/n-Hex=0-12%) to provide 2-chloro-4-fluoro-5-(4-fluorobut-1-ynyl)pyridine (135 mg) as a light yellow oil. $^1$H-NMR ($CDCl_3$, 400 MHz) δ 8.42 (d, 1H), 7.10 (d, 1H), 4.61 (dt, 2H), 2.90 (dt, 2H)

Step 2. (1-(2-Chloro-5-(4-fluorobut-1-yn-1-yl)pyridin-4-yl)-4-methylpiperidin-4-yl)methanol The title compound as a light beige solid (82 mg) was prepared in the same fashion as Reference Example 2 except that (4-methylpiperidin-4-yl)methanol (95 mg, 0.737 mmol) and 2-chloro-4-fluoro-5-(4-fluorobut-1-ynyl)pyridine (135 mg, 0.67 mmol) prepared in Step 1 were used instead of 4-hydroxypiperidine and 2,4-dichloro-5-iodopyridine. $^1$H-NMR ($CDCl_3$, 400 MHz) δ 8.16 (s, 1H), 6.69 (s, 1H), 4.59 (dt, 2H), 3.66 (dt, 2H), 3.45 (s, 2H), 3.22 (td, 2H), 2.89 (dt, 2H), 1.69 (m, 2H), 1.52-1.44 (m, 2H), 1.09 (s, 3H); MS (ESI) m/z=547.3 $(M+H)^+$ Step 3. (1-(2-((2-(1-(Cyclopropylsulfonyl)-1H-pyrazol-4-yl)pyrimidin-4-yl)amino)-5-(4-fluorobut-1-yn-1-yl)pyridin-4-yl)-4-methylpiperidin-4-yl)methanol The title compound as a light beige solid (2.8 mg) was prepared in the same fashion as Step 3 in Example 274 except that (1-(2-chloro-5-(4-fluorobut-1-yn-1-yl)pyridin-4-yl)-4-methylpiperidin-4-yl)methanol (81 mg, 0.259 mmol) prepared in Step 2 was used instead of 4-(6-chloro-4-(4-(hydroxymethyl)-4-methyl-1-piperidyl)-3-pyridyl)but-3-yn-1-ol. $^1$H-NMR ($CDCl_3$, 400 MHz) δ 8.64 (s, 1H), 8.45 (s, 1H), 8.41 (t, 1H), 8.09 (s, 1H), 7.74 (br, 1H), 6.98 (d, 1H), 4.62 (dt, 2H), 3.70 (dt, 2H), 3.51 (s, 2H), 3.41 (td, 2H), 2.91 (dt, 2H), 2.83 (m, 1H), 1.87 (m, 2H), 1.59-1.52 (m, 4H), 1.25 (m, 2H), 1.09 (s, 3H); MS (ESI) m/z=540.2 $(M+H)^+$ Example 277. (1-(5-(But-3-en-1-yn-1-yl)-2-((2-(1-(cyclopropylsulfonyl)-1H-pyrazol-4-yl)pyrimidin-4-yl)amino)pyridin-4-yl)-4-methylpiperidin-4-yl)methanol The title compound as a clear oil (4.6 mg) was prepared in the same fashion as Step 3 in Example 274 except that (1-(2-chloro-5-(4-fluorobut-1-yn-1-yl)pyridin-4-yl)-4-methylpiperidin-4-yl)methanol (81 mg, 0.259 mmol) prepared in Step 2 of Example 276 was used instead of 4-(6-chloro-4-(4-(hydroxymethyl)-4-methyl-1-piperidyl)-3-pyridyl)but-3-yn-1-ol. $^1$H-NMR ($CDCl_3$, 400 MHz) δ 8.65 (s, 1H), 8.45 (s, 1H), 8.41 (d, 1H), 8.13 (s, 1H), 7.73 (br, 1H), 6.97 (d, 1H), 6.08 (dd, 1H), 5.62 (dd, 2H), 3.70 (m, 2H), 3.51 (s, 2H), 3.42 (td, 2H), 2.84 (m, 1H), 1.78 (m, 2H), 1.60-1.52 (m, 4H), 1.25 (m, 2H), 1.09 (s, 3H); MS (ESI) m/z=520.1 $(M+H)^+$ Example 278. (1-(2-((2-(1-(Cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol Step 1. (5-Iodo-2-pyridyl)methanol To a solution of 5-iodopyridine-2-carboxylic acid (2.0 g, 8.03 mmol) in MeOH (50 mL) was added thionyl chloride (1.2 mL, 16.5 mmol) at ambient temperature. After the addition, the reaction mixture was heated to reflux for 3 hours. Methanol was removed and EA was added to the residue and was adjusted pH to 7.0 by addition of sat. $NaHCO_3$ soln. The organic phase was separated and dried over magnesium sulfate. The organic solvent was removed to provide methyl 5-iodopyridine-2-carboxylate (1.2 g) as a white solid which was used for the next step of the reaction without further purification. To the solution of methyl 5-iodopyridine-2-carboxylate (1.0 g, 3.80 mmol) in MeOH (20 mL) was added sodium borohydride (360 mg, 9.51 mmol) at 0° C. and the reaction mixture was stirred at room temperature for 3 hours. Methanol was removed and EA was added to the residue. After being quenched with brine, the organic phase was separated and dried over $MgSO_4$. The organic solvent was removed to provide product (5-iodo-2-pyridyl)methanol (900 mg) as a white solid. MS (ESI) m/z=235.9 $(M+H)^+$ Step 2. 2-(Chloromethyl)-5-iodo-pyridine hydrochloride To a solution of (5-iodo-2-pyridyl)methanol (900 mg, 3.80 mmol) prepared in Step 1 in toluene (20 mL) was added thionyl chloride (912 mg, 7.66 mmol) at ambient temperature and the reaction mixture was stirred at room temperature for 8 hours. Residual thionyl chloride and excess solvent were removed by evaporation and IPE was added to the residue and was triturated to provide 2-(chloromethyl)-5-iodo-pyridine hydrochloride (900 mg) as a white solid. MS (ESI) m/z=253.7 $(M+H)^+$ Step 3. 1-(5-Iodo-2-pyridyl)-N,N-dimethyl-methanamine To a solution of 2-(chloromethyl)-5-iodo-pyridine hydrochloride (250 mg, 0.86 mmol) prepared in Step 2 in DCM (5 mL) was added DIPEA (368 mg, 2.85 mmol) and dimethylamine (2.0M in MeOH) (0.56 mL, 1.12 mmol) and the reaction mixture was stirred at room temperature overnight. The reaction mixture was diluted with DCM, washed with water and brine, dried over $MgSO_4$, then concentrated to provide 1-(5-iodo-2-pyridyl)-N,N-dimethyl-methanamine (100 mg) as a beige solid. MS (ESI) m/z=262.8 $(M+H)^+$ Step 4. (1-(2-((2-(1-(Cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol To the reaction mixture of 1-(5-iodo-2-pyridyl)-N,N-dimethyl-methanamine (22 mg, 0.081 mmol) prepared in step 3, CuI (7 mg, 0.036 mmol), $Pd(PPh_3)_2C_1$ (6 mg, 0.008 mmol), and triphenylphosphine (7 mg, 0.027 mmol) in TEA (2 mL) was added (1-(2-((2-(1-(cyclopropylsulfonyl)-1H-pyrazol-4-yl)pyrimidin-4-yl)amino)-5-ethynylpyridin-4-yl)-4-methylpiperidin-4-yl)methanol (40 mg, 0.081 mmol) prepared in Example 247 in DMF (1 mL), then the mixture was stirred at 60° C. overnight. The reaction mixture was cooled, diluted in DCM, and filtered with Celite filter. The filtrate was evaporated in vacuo, and then concentrated. The crude product was purified by column chromatography (MeOH/DCM=0-12%) (1-(2-((2-(1-(cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol (4.8 mg) as a clear oil. $^1$H-NMR ($CDCl_3$, 400 MHz) δ 8.71 (s, 1H), 8.67 (s, 1H), 8.46 (s, 1H), 8.43 (d, 1H), 7.80-7.67 (m, 3H), 7.50 (m, 1H), 7.01 (d, 1H), 3.71 (m, 4H), 3.51 (s, 2H), 3.44 (m, 2H), 2.84 (m, 1H), 2.39 (s, 6H), 1.85-1.52 (m, 8H), 1.10 (s, 3H); MS (ESI) m/z=628.2 $(M+H)^+$ Example 279. (1-(2-((2-(1-(Cyclopropylsulfonyl)-1H-pyrazol-4-yl)pyrimidin-4-yl)amino)-5-((6-((4-methylpiperazin-1-yl)methyl)pyridin-3-yl)ethynyl)pyridin-4-yl)-4-methylpiperidin-4-yl)methanol Step 1. 1-((5-Iodo-2-pyridyl)methyl)-4-methyl-piperazine The title compound as a beige solid (120 mg) was prepared in the same fashion as Step 3 of Example 278 except that 1-methylpiperazine (113 mg, 1.12 mmol) was used instead of dimethylamine. MS (ESI) m/z=318.0 $(M+H)^+$ Step 2. (1-(2-((2-(1-(Cyclopropylsulfonyl)-1H-pyrazol-4-yl)pyrimidin-4-yl)amino)-5-((6-((4-methylpiperazin-1-yl)methyl)pyridin-3-yl)ethynyl)pyridin-4-yl)-4-methylpiperidin-4-yl)methanol The title compound as a clear oil (2.4 mg) was prepared in the same fashion as Step 4 in Example 278 except that 1-((5-iodo-2-pyridyl)methyl)-4-methyl-piperazine (32 mg, 0.101 mmol) prepared in Step 1 was used instead of 1-(5-iodo-2-pyridyl)-N,N-dimethyl-methanamine. $^1$H-NMR ($CDCl_3$, 400 MHz) δ 8.73 (s, 1H), 8.66 (s, 1H), 8.46 (s, 1H), 8.43 (d, 1H), 8.26 (s, 1H) 7.76 (d, 1H), 7.70 (s, 1H), 7.35 (d, 1H), 6.99 (d, 1H), 3.78 (s, 2H), 3.74 (m, 2H), 3.51 (s, 2H), 3.44 (td, 2H), 3.08 (br, 4H), 2.92 (br, 4H), 2.82 (m, 1H), 1.84-1.55 (m, 8H), 1.12 (s, 3H); MS (ESI) m/z=683.3 $(M+H)^+$ Example 280. 1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-ol Step 1. 2-Chloro-4-fluoro-5-((trimethylsilyl)ethynyl)pyridine The title compound as a clear oil (2.0 g) was prepared in the same fashion as Reference Example 18 except that trimethylsilylacetylene (1.24 g, 12.62 mmol) was used instead of 4-ethynyl-1-methylpyrazole. MS (ESI) m/z=227.9 $(M+H)^+$ Step 2. 2-Chloro-5-ethynyl-4-fluoro-pyridine To a solution of 2-chloro-4-fluoro-5-((trimethylsilyl)ethynyl)pyridine (2.0 g, 8.782 mmol) prepared in Step 1 in DCM (3 mL) at 0° C. was added tetrabutylammonium fluoride solution (1.0 M in THF) (8.78 mL, 8.782 mmol) in dropwise manner. The reaction mixture was stirred at 0° C. for 1 hour. The reaction mixture was added water, extracted with DCM, washed with water, dried over $MgSO_4$, and then concentrated. The crude product was purified by column chromatography (EA/n-Hex=0-20%) to yield 2-chloro-5-ethynyl-4-fluoro-pyridine (1.5 g) as light yellow oil. MS (ESI) m/z=159.9 $(M+H)^+$ Step 3. 2-Chloro-4-fluoro-5-(2-(3-pyridyl)ethynyl)pyridine The reaction mixture of 3-iodopyridine (2.17 g, 10.61 mmol), CuI (826 mg, 4.34 mmol), $Pd(PPh_3)_2C_1$ (787 mg, 0.96 mmol), and triphenylphosphine (834 mg, 3.18 mmol) in TEA (35 mL) was added 2-chloro-5-ethynyl-4-fluoro-pyridine (1.5 g, 9.64 mmol) prepared in Step 2, then the mixture was stirred at 60° C. overnight. The reaction mixture was cooled, diluted in EA, filtered with Celite filter. The filtrate was evaporated in vacuo, then the crude product was purified by column chromatography (EA/n-Hex=0-30%) to provide 2-chloro-4-fluoro-5-(2-(3-pyridyl)ethynyl)pyridine (0.6 g) as a light yellow oil. MS (ESI) m/z=232.8 $(M+H)^+$ Step 4. 1-(2-Chloro-5-(2-(3-pyridyl)ethynyl)-4-pyridyl)-4-methyl-piperidin-4-ol The title compound as a clear oil (100 mg) was prepared in the same fashion as Reference Example 2 except that 4-methylpiperidin-4-ol (55 mg, 0.473 mmol) and 2-chloro-4-fluoro-5-(2-(3-pyridyl)ethynyl)pyridine (100 mg, 0.43 mmol) prepared in Step 3 were used instead of 4-hydroxypiperidine and 2,4-dichloro-5-iodopyridine. MS (ESI) m/z=328.0 $(M+H)^+$ Step 5. 1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-ol To a solution of 2-(1-(cyclopropylsulfonyl)-1H-pyrazol-4-yl)pyrimidin-4-amine (40 mg, 0.15 mmol) in 1,4-dioxane (2 mL) was added 1-(2-chloro-5-(2-(3-pyridyl)ethynyl)-4-pyridyl)-4-methyl-piperidin-4-ol (50 mg, 0.150 mmol) prepared in Step 4, $Cs_2CO_3$ (149 mg, 0.46 mmol), BrettPhos (17 mg, 0.030 mmol), BrettPhos Pd GI methyl t-butyl ether adduct (12 mg, 0.020 mmol). The reaction mixture was stirred at 100° C. for 3 hrs. The mixture was cooled to room temperature, then was filtered through phase separator. The filtrate was evaporated in vacuo, then purified by column chromatography (MeOH/DCM=0-10%) to provide 1-(2-((2-(1-(cyclopropylsulfonyl)-1H-pyrazol-4-yl)pyrimidin-4-yl)amino)-5-(pyridin-3-ylethynyl)pyridin-4-yl)-4-methylpiperidin-4-ol (12.2 mg) as a clear oil. $^1$H-NMR (CDCl$_3$, 400 MHz) δ 8.75 (s, 1H), 8.69 (s, 1H), 8.55 (d, 1H), 8.46 (s, 1H), 8.41 (d, 1H), 8.30 (s, 1H), 8.16 (br, 1H), 7.80 (s, 1H), 7.77 (d, 1H), 7.32 (m, 1H), 6.97 (d, 1H), 3.82 (dt, 2H), 3.42 (td, 2H), 2.83 (m, 1H), 1.93-1.82 (m, 4H), 1.54 (m, 2H), 1.37 (s, 3H), 1.25 (m, 2H); MS (ESI) m/z=557.2 (M+H)$^+$ Example 281. 2-(1-(Cyclopropylsulfonyl)-1H-pyrazol-4-yl)-N-(4-(4-methoxy-4-methylpiperidin-1-yl)-5-(pyridin-3-ylethynyl)pyridin-2-yl)pyrimidin-4-amine Step 1. 2-Chloro-4-(4-methoxy-4-methylpiperidin-1-yl)-5-(pyridin-3-ylethynyl)pyridine The title compound as a light beige solid (123 mg) was prepared in the same fashion as Reference Example 2 except that 4-methoxy-4-methyl-piperidine (61 mg, 0.473 mmol) and 2-chloro-4-fluoro-5-(2-(3-pyridyl)ethynyl)pyridine (100 mg, 0.43 mmol) prepared in Step 3 in Example 280 were used instead of 4-hydroxypiperidine and 2,4-dichloro-5-iodopyridine. MS (ESI) m/z=342.0 (M+H)$^+$ Step 2. 2-(1-(Cyclopropylsulfonyl)-1H-pyrazol-4-yl)-N-(4-(4-methoxy-4-methylpiperidin-1-yl)-5-(pyridin-3-ylethynyl)pyridin-2-yl)pyrimidin-4-amine The title compound as a clear oil (19.2 mg) was prepared in the same fashion as Step 5 in Example 280 except that 2-chloro-4-(4-methoxy-4-methylpiperidin-1-yl)-5-(pyridin-3-ylethynyl)pyridine (35 mg, 0.102 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) 8.75 (s, 1H), 8.64 (s, 1H), 8.55 (d, 1H), 8.46 (s, 1H), 8.44 (d, 1H), 8.30 (s, 1H), 8.06 (s, 1H), 7.79 (d, 1H), 7.48 (s, 1H), 7.31 (dd, 1H), 7.11 (d, 1H), 3.79 (dd, 2H), 3.34 (td, 2H), 3.23 (s, 3H), 2.95 (m, 1H), 2.02 (dd, 2H), 1.73 (td, 2H), 1.54 (m, 2H), 1.28 (s, 3H), 1.22 (m, 2H); MS (ESI) m/z=571.2 (M+H)$^+$ Example 282. 2-(1-(Cyclopropylsulfonyl)-1H-pyrazol-4-yl)-N-(5-(pyridin-3-ylethynyl)-4-(1-oxa-8-azaspiro[4.5]decan-8-yl)pyridin-2-yl)pyrimidin-4-amine Step 1. 8-(2-Chloro-5-(2-(3-pyridyl)ethynyl)-4-pyridyl)-1-oxa-8-azaspiro[4.5]decane The title compound as a light beige solid (112 mg) was prepared in the same fashion as Reference Example 2 except that 1-oxa-8-azaspiro[4.5]decane HCl salt (58 mg, 0.32 mmol) and 2-chloro-4-fluoro-5-(2-(3-pyridyl)ethynyl)pyridine (75 mg, 0.32 mmol) prepared in Step 3 in Example 280 were used instead of 4-hydroxypiperidine and 2,4-dichloro-5-iodopyridine. MS (ESI) m/z=354.0 (M+H)$^+$ Step 2. 2-(1-(Cyclopropylsulfonyl)-1H-pyrazol-4-yl)-N-(5-(pyridin-3-ylethynyl)-4-(1-oxa-8-azaspiro[4.5]decan-8-yl)pyridin-2-yl)pyrimidin-4-amine The title compound as a clear oil (19.6 mg) was prepared in the same fashion as Step 5 in Example 280 except that 8-(2-chloro-5-(2-(3-pyridyl)ethynyl)-4-pyridyl)-1-oxa-8-azaspiro[4.5]decane (35 mg, 0.099 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.75 (d, 1H), 8.65 (s, 1H), 8.55 (d, 1H), 8.45 (s, 1H), 8.43 (d, 1H), 8.30 (s, 1H), 8.11 (s, 1H), 7.78 (d, 1H), 7.54 (s, 1H), 7.30 (dd, 1H), 7.08 (d, 1H), 3.89 (t, 2H), 3.69 (m, 2H), 3.55 (m, 2H), 2.83 (m, 1H), 2.04-1.78 (m, 8H), 1.53 (m, 2H), 1.22 (m, 2H); MS (ESI) m/z=583.2 (M+H)$^+$ Example 283. 2-(1-(Cyclopropylsulfonyl)-1H-pyrazol-4-yl)-N-(5-(pyridin-3-ylethynyl)-4-(1-oxa-7-azaspiro[3.5]nonan-7-yl)pyridin-2-yl)pyrimidin-4-amine Step 1. 7-(2-Chloro-5-(2-(3-pyridyl)ethynyl)-4-pyridyl)-1-oxa-7-azaspiro[3.5]nonane The title compound as a light beige solid (106 mg) was prepared in the same fashion as Reference Example 2 except that 1-oxa-7-azaspiro[3.5]nonane (41 mg, 0.32 mmol) and 2-chloro-4-fluoro-5-(2-(3-pyridyl)ethynyl)pyridine (75 mg, 0.32 mmol) prepared in Step 3 of Example 280 were used instead of 4-hydroxypiperidine and 2,4-dichloro-5-iodopyridine. MS (ESI) m/z=339.9 (M+H)$^+$ Step 2. 2-(1-(Cyclopropylsulfonyl)-1H-pyrazol-4-yl)-N-(5-(pyridin-3-ylethynyl)-4-(1-oxa-7-azaspiro[3.5]nonan-7-yl)pyridin-2-yl)pyrimidin-4-amine The title compound as a clear oil (10.1 mg) was prepared in the same fashion as Step 5 in Example 280 except that 7-(2-chloro-5-(2-(3-pyridyl)ethynyl)-4-pyridyl)-1-oxa-7-azaspiro[3.5]nonane (35 mg, 0.103 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.75 (d, 1H), 8.66 (s, 1H), 8.57 (d, 1H), 8.45 (s, 1H), 8.43 (d, 1H), 8.30 (s, 1H), 7.90 (s, 1H), 7.79 (d, 1H), 7.56 (s, 1H), 7.31 (dd, 1H), 7.08 (d, 1H), 4.60 (t, 2H), 3.59-3.53 (m, 4H), 2.85 (m, 1H), 2.51 (t, 2H), 2.21-2.08 (m, 4H), 1.55 (m, 2H), 1.22 (m, 2H); MS (ESI) m/z=569.1 (M+H)$^+$ Example 284. 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)-2-methylpent-4-yn-2-ol Step 1. 5-(6-Chloro-4-(4-(hydroxymethyl)-4-methylpiperidin-1-yl)pyridin-3-yl)-2-methylpent-4-yn-2-ol The title compound as a light yellow oil (151 mg) was prepared in the same fashion as Step 1 in Example 246 except that 2-methylpent-4-yn-2-ol (81 mg, 0.82 mmol) was used instead of trimethylsilylacetylene. $^1$H-NMR (MeOD, 400 MHz) δ 8.06 (s, 1H), 6.85 (s, 1H), 3.75 (td, 2H), 3.35 (s, 2H), 3.26 (m, 2H), 2.64 (s, 2H), 1.69 (td, 2H), 1.44 (dt, 2H), 1.35 (s, 6H), 1.03 (s, 3H); MS (ESI) m/z=337.0 (M+H)$^+$ Step 2. 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)-2-methylpent-4-yn-2-ol The title compound as a clear oil (26.6 mg) was prepared in the same fashion as Step 5 in Example 280 except that 5-(6-chloro-4-(4-(hydroxymethyl)-4-methylpiperidin-1-yl)pyridin-3-yl)-2-methylpent-4-yn-2-ol (35 mg, 0.104 mmol)

prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.63 (s, 1H), 8.46 (br, 1H), 8.43 (s, 1H), 8.35 (d, 1H), 8.12 (s, 1H), 7.61 (s, 1H), 6.91 (dd, 1H), 3.61 (m, 2H), 3.45 (s, 2H), 3.29 (td, 2H), 2.83 (m, 1H), 2.68 (s, 2H), 1.71 (td, 2H), 1.51 (m, 4H), 1.39 (s, 6H), 1.22 (m, 2H), 1.04 (s, 3H); MS (ESI) m/z=566.3 (M+H)$^+$ Example 285. (1-(2-((2-(1-(Cyclopropylsulfonyl)-1H-pyrazol-4-yl)pyrimidin-4-yl)amino)-5-(4-morpholinobut-1-yn-1-yl)pyridin-4-yl)-4-methylpiperidin-4-yl)methanol Step 1. (1-(2-Chloro-5-(4-morpholinobut-1-yn-1-yl)pyridin-4-yl)-4-methylpiperidin-4-yl)methanol To a solution of 4-bromo-1-butyne (1.0 g, 7.52 mmol) and potassium carbonate (3.12 g, 22.56 mmol) in ACN (30 mL) was added morpholine (721 mg, 8.27 mmol) and the reaction mixture was stirred at room temperature overnight. The reaction mixture was diluted with EA, washed with brine, and then the organic phase was filtered through a phase separator. The organic phase was evaporated in vacuo to provide product 4-but-3-ynylmorpholine (300 mg) as a yellow oil which was used for the next step of the reaction without further purification. To the reaction mixture of (1-(2-chloro-5-iodopyridin-4-yl)-4-methylpiperidin-4-yl)methanol (120 mg, 0.327 mmol) prepared in Reference Example 12, CuI (28 mg, 0.147 mmol), Pd(PPh$_3$)$_2$C$_1$ (23 mg, 0.033 mmol), and triphenylphosphine (29 mg, 0.108 mmol) in TEA (2 mL) was added 4-but-3-ynylmorpholine (46 mg, 0.327 mmol), and then the mixture was stirred at 60° C. overnight. The reaction mixture was cooled, diluted in EA, filtered through Celite. The filtrate was evaporated in vacuo, and the crude product was purified by column chromatography (EA/n-Hex=0-60%) to provide (1-(2-chloro-5-(4-morpholinobut-1-yn-1-yl)pyridin-4-yl)-4-methylpiperidin-4-yl)methanol (24 mg) as a light yellow oil. $^1$H-NMR (CDCl$_3$, 400 MHz) δ 8.13 (s, 1H), 6.68 (s, 1H), 3.74 (br, 4H), 3.65 (dt, 2H), 3.44 (s, 2H), 3.20 (td, 2H), 2.66 (s, 4H), 2.52 (br, 4H), 1.71 (td, 2H), 1.47 (td, 2H), 1.05 (s, 3H); MS (ESI) m/z=378.0 (M+H)$^+$ Step 2. (1-(2-((2-(1-(Cyclopropylsulfonyl)-1H-pyrazol-4-yl)pyrimidin-4-yl)amino)-5-(4-morpholinobut-1-yn-1-yl)pyridin-4-yl)-4-methylpiperidin-4-yl)methanol The title compound as a clear oil (6.6 mg) was prepared in the same fashion as Step 5 in Example 280 except that (1-(2-chloro-5-(4-morpholinobut-1-yn-1-yl)pyridin-4-yl)-4-methylpiperidin-4-yl)methanol (24 mg, 0.064 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.65 (s, 1H), 8.45 (s, 1H), 8.41 (d, 1H), 8.13 (s, 1H), 7.60 (d, 2H), 6.98 (d, 1H), 3.75 (m, 4H), 3.63 (m, 2H), 3.51 (s, 2H), 3.37 (td, 2H), 2.84 (m, 1H), 2.69 (s, 4H), 2.54 (m, 4H), 1.79 (dt, 2H), 1.58-1.52 (m, 4H), 1.26 (m, 2H), 1.09 (s, 3H); MS (ESI) m/z=607.3 (M+H)$^+$ Example 286. 3-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)oxetan-3-ol Step 1. 3-(3-(6-Chloro-4-(4-(hydroxymethyl)-4-methylpiperidin-1-yl)pyridin-3-yl)prop-2-yn-1-yl)oxetan-3-ol The title compound as a light yellow oil (66 mg) was prepared in the same fashion as Step 1 in Example 246 except that 3-prop-2-ynyloxetan-3-ol (44 mg, 0.393 mmol) was used instead of trimethylsilylacetylene. $^1$H-NMR (CDCl$_3$, 400 MHz) δ 8.15 (s, 1H), 6.68 (s, 1H), 4.63 (dd, 4H), 4.02 (s, 1H), 3.67 (dd, 2H), 3.42 (s, 2H), 3.17 (td, 2H), 3.05 (s, 2H), 2.29 (s, 1H), 1.71 (td, 2H), 1.42 (dd, 2H), 1.02 (s, 3H); MS (ESI) m/z=351.0 (M+H)$^+$ Step 2. 3-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)oxetan-3-ol The title compound as a clear oil (4 mg) was prepared in the same fashion as Step 5 in Example 280 except that 3-(3-(6-chloro-4-(4-(hydroxymethyl)-4-methylpiperidin-1-yl)pyridin-3-yl)prop-2-yn-1-yl)oxetan-3-ol (33 mg, 0.094 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.64 (s, 1H), 8.45 (s, 1H), 8.39 (d, 1H), 8.13 (s, 1H), 7.94 (br, 1H), 7.61 (s, 1H), 6.94 (d, 1H), 4.65 (dd, 4H), 3.67 (dd, 2H), 3.47 (s, 2H), 3.33 (td, 2H), 3.09 (s, 2H), 2.84 (m, 1H), 1.75 (td, 2H), 1.53 (m, 2H), 1.22 (m, 4H), 1.09 (s, 3H); MS (ESI) m/z=580.2 (M+H)$^+$ Example 287. 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)pent-4-yn-2-ol Step 1. 5-(6-Chloro-4-(4-(hydroxymethyl)-4-methylpiperidin-1-yl)pyridin-3-yl)pent-4-yn-2-ol The title compound as a light yellow oil (55 mg) was prepared in the same fashion as Step 1 in Example 246 except that 4-pentyn-2-ol (33 mg, 0.393 mmol) was used instead of trimethylsilylacetylene. $^1$H-NMR (CDCl$_3$, 400 MHz) δ 8.11 (s, 1H), 6.65 (s, 1H), 4.03 (m, 1H), 3.64 (dd, 2H), 3.38 (s, 2H), 3.15 (td, 2H), 2.60 (d, 2H), 2.33 (br, 1H), 1.70 (td, 2H), 1.40 (dd, 2H), 1.29 (d, 3H), 1.00 (s, 3H); MS (ESI) m/z=323.0 (M+H)$^+$ Step 2. 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)pent-4-yn-2-ol The title compound as a clear oil (6.3 mg) was prepared in the same fashion as Step 5 in Example 280 except that 5-(6-chloro-4-(4-(hydroxymethyl)-4-methylpiperidin-1-yl)pyridin-3-yl)pent-4-yn-2-ol (33 mg, 0.102 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.64 (s, 1H), 8.45 (s, 1H), 8.39 (d, 1H), 8.14 (s, 1H), 7.90 (br, 1H), 7.59 (s, 1H), 6.96 (d, 1H), 4.06 (m, 1H), 3.64 (dd, 2H), 3.49 (s, 2H), 3.33 (td, 2H), 2.84 (m, 1H), 2.66 (m, 2H), 1.75 (td, 2H), 1.53 (m, 4H), 1.35 (d, 3H), 1.22 (m, 2H), 1.07 (s, 3H); MS (ESI) m/z=555.2 (M+H)$^+$ Example 288. N-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)-2,2,2-trifluoroacetamide Step 1. N-(3-(6-Chloro-4-(4-(hydroxymethyl)-4-methylpiperidin-1-yl)pyridin-3-yl)prop-2-yn-1-yl)-2,2,2-trifluoroacetamide The title compound as a light yellow oil (53 mg) was prepared in the same fashion as Step 1 in Example 246 except that 2,2,2-trifluoro-N-prop-2-ynyl-acetamide (59 mg, 0.393 mmol) was used instead of trimethylsilylacetylene. $^1$H-NMR (CDCl$_3$, 400 MHz) δ 8.17 (s, 1H), 6.70 (s, 1H), 4.40 (d, 2H), 3.64 (d, 2H), 3.43 (s, 2H), 3.20 (td, 2H), 1.42 (d, 2H), 1.04 (s, 3H); MS (ESI) m/z=390.0 (M+H)$^+$ Step 2. N-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)-2,2,2-trifluoroacetamide The title compound as a clear oil (1.6 mg) was prepared in the same fashion as Step 5 in Example 280 except that N-(3-(6-chloro-4-(4-(hydroxymethyl)-4-methylpiperidin-1-yl)pyridin-3-yl)prop-2-yn-1-yl)-2,2,2-trifluoroacetamide (33 mg, 0.085 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.64 (s, 1H), 8.45 (s, 1H), 8.41 (d, 1H), 8.14 (s, 1H), 7.91 (br, 1H), 7.60 (s, 1H), 6.97 (d, 1H), 4.45 (d, 2H), 3.64 (dd, 2H), 3.49 (s, 2H), 3.32 (td, 2H), 2.83 (m, 1H), 1.75 (td, 2H), 1.53 (m, 4H), 1.22 (m, 2H), 1.07 (s, 3H); MS (ESI) m/z=619.2 (M+H)$^+$ Example 289. 4-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)thiomorpholine 1,1-dioxide Step 1. 4-(3-(6-Chloro-4-(4-(hydroxymethyl)-4-methylpiperidin-1-yl)pyridin-3-yl)prop-2-yn-1-yl)thiomorpholine 1,1-dioxide The title compound as a light yellow oil (77 mg) was prepared in the same fashion as Step 1 in Example 246 except that 4-propargylthiomorpholine 1,1-dioxide (68 mg, 0.393 mmol) was used instead of trimethylsilylacetylene. $^1$H-NMR (CDCl$_3$, 400 MHz) δ 8.16 (s, 1H), 6.71 (s, 1H), 3.72 (s, 2H), 3.69 (m, 2H), 3,41 (s, 2H), 3.18 (td, 2H), 3.14 (s, 8H), 1.78 (td, 2H), 1.40 (d, 2H), 1.02 (s, 3H); MS (ESI) m/z=412.0 (M+H)$^+$ Step 2. 4-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)thiomorpholine 1,1-dioxide The title compound as a clear oil (2.3 mg) was prepared in the same fashion as Step 5 in Example 280 except that 4-(3-(6-chloro-4-(4-(hydroxymethyl)-4-methylpiperidin-1-yl)pyridin-3-yl)prop-2-yn-1-yl)thiomorpholine 1,1-dioxide (33 mg, 0.080 mmol) prepared in Step 1 was used instead of 1-(2-chloro-5-(2-(3-pyridyl)ethynyl)-4-pyridyl)-4-methyl-piperidin-4-ol. $^1$H-NMR (CDCl$_3$, 400 MHz) δ 8.65 (s, 1H), 8.45 (s, 1H), 8.42 (d, 1H), 8.15 (s, 1H), 7.89 (d, 1H), 7.64 (br, 1H), 7.00 (d, 1H), 3.75 (s, 2H), 3.71 (m, 2H), 3.48 (s, 2H), 3.32 (td, 2H), 3.16 (s, 8H), 2.83 (m, 1H), 1.75 (td, 2H), 1.53 (m, 4H), 1.22 (m, 2H), 1.07 (s, 3H); MS (ESI) m/z=641.2 (M+H)$^+$ Example 290. (1-(2-((2-(1-(Cyclopropylsulfonyl)-1H-pyrazol-4-yl)pyrimidin-4-yl)amino)-5-((3-(trifluoromethyl)-1H-pyrazol-5-yl)ethynyl)pyridin-4-yl)-4-methylpiperidin-4-yl)methanol The title compound as an off-white solid (1 mg) was prepared in the same fashion as Example 248 except that 5-iodo-3-(trifluoromethyl)-1H-pyrazole (106 mg, 0.405 mmol) was used instead of 2-((3,3-difluoroazetidin-1-yl)methyl)-1-(2,2-difluoroethyl)-4-iodo-1H-pyrrole. $^1$H-NMR (MeOD, 400 MHz) δ 8.75 (s, 1H), 8.46 (s, 1H), 8.40 (d, 1H), 8.25 (s, 1H), 7.62 (s, 1H), 7.40 (d, 1H), 6.84 (s, 1H), 3.81-3.78 (m, 2H), 3.04-3.03 (m, 1H), 1.83-1.80 (m, 2H), 1.77-1.76 (m, 1H), 1.70-1.65 (m, 2H), 1.55-1.40 (m, 3H), 1.30-1.26 (m, 2H), 1.08-1.02 (m, 4H); MS (ESI) m/z=628.2 (M+H)$^+$ Example 291. (1-(2-((2-(1-(Cyclopropylsulfonyl)-1H-pyrazol-4-yl)pyrimidin-4-yl)amino)-5-((4-(trifluoromethyl)thiazol-2-yl)ethynyl)pyridin-4-yl)-4-methylpiperidin-4-yl)methanol The title compound as an off-white solid (1 mg) was prepared in the same fashion as Example 248 except that 2-iodo-4-(trifluoromethyl)thiazole (34 mg, 0.122 mmol) was used instead of 2-((3,3-difluoroazetidin-1-yl)methyl)-1-(2,2-difluoroethyl)-4-iodo-1H-pyrrole. $^1$H-NMR (CDCl$_3$, 400 MHz) δ 8.66 (s, 1H), 8.45 (d, 2H), 8.28 (s, 1H), 8.15 (bs, 1H), 7.78 (s, 2H), 6.98 (d, 1H), 3.80-3.76 (m, 2H), 3.52-3.47 (m, 4H), 2.92-2.82 (m, 1H), 1.56-1.55 (m, 6H), 1.27-1.24 (m, 3H), 1.11 (s, 3H); MS (ESI) m/z=645.1 (M+H)$^+$ Example 292. (1-(2-((2-(1-(Cyclopropylsulfonyl)-1H-pyrazol-4-yl)pyrimidin-4-yl)amino)-5-((2-(trifluoromethyl)thiazol-5-yl)ethynyl)pyridin-4-yl)-4-methylpiperidin-4-yl)methanol The title compound as an off-white solid (2 mg) was prepared in the same fashion as Example 248 except that 5-iodo-2-(trifluoromethyl)thiazole (34 mg, 0.122 mmol) was used instead of 2-((3,3-difluoroazetidin-1-yl)methyl)-1-(2,2-difluoroethyl)-4-iodo-1H-pyrrole. $^1$H-NMR (CDCl$_3$, 400 MHz) δ 8.66 (s, 1H), 8.45 (d, 2H), 8.24 (s, 1H), 8.15 (bs, 1H), 8.00 (s, 1H), 7.77 (s, 1H), 6.97 (d, 1H), 3.75-3.69 (m, 2H), 3.52-3.43 (m, 4H), 2.87-2.83 (m, 1H), 1.85-1.78 (m, 2H), 1.62-1.53 (m, 4H), 1.28-1.27 (m, 2H), 1.11 (s, 3H); MS (ESI) m/z=645.1 (M+H)$^+$ Example 293. 2-(1-(Cyclopropylsulfonyl)-1H-pyrazol-4-yl)-N-(4-(4-((dimethylamino)methyl)-4-fluoropiperidin-1-yl)-5-((1-methyl-1H-pyrazol-4-yl)ethynyl)pyridin-2-yl)pyrimidin-4-amine formate Step 1. 1-(1-(2-Chloro-5-((1-methyl-1H-pyrazol-4-yl)ethynyl)pyridin-4-yl)-4-fluoropiperidin-4-yl)-N,N-dimethylmethanamine The title compound as a solid (227 mg) was prepared in the same fashion as Step 1 in Example 65 except that 1-(4-fluoro-4-piperidyl)-N,N-dimethyl-methanamine HCl (83 mg, 0.424 mmol) was used instead of 4-(trifluoromethyl)piperidine HCl. $^1$H-NMR (CDCl$_3$, 400 MHz) δ 8.22 (s, 1H), 7.59 (s, 1H), 7.54 (s, 1H), 7.27 (s, 1H), 6.73 (s, 1H), 3.92 (s, 3H), 3.83 (d, 2H), 3.24 (t, 2H), 2.47 (d, 2H), 2.31 (s, 6H), 1.87-1.71 (m, 2H); MS (ESI) m/z=376.1 (M+H)$^+$ Step 2. 2-(1-(Cyclopropylsulfonyl)-1H-pyrazol-4-yl)-N-(4-(4-((dimethylamino)methyl)-4-fluoropiperidin-1-yl)-5-((1-methyl-1H-pyrazol-4-yl)ethynyl)pyridin-2-yl)pyrimidin-4-amine formate The title compound as a solid (1 mg) was prepared in the same fashion as Step 3 in Example 1 except that 1-(1-(2-chloro-5-((1-methyl-1H-pyrazol-4-yl)ethynyl)pyridin-4-yl)-4-fluoropiperidin-4-yl)-N,N-dimethylmethanamine (141 mg, 0.377 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (DMSO-$d_6$, 400 MHz) δ 10.28 (s, 1H), 8.65 (s, 1H), 8.46-8.44 (m, 2H), 8.37 (bs, 1H), 8.18 (s, 1H), 8.04 (s, 1H), 7.72 (bs, 1H), 7.65 (s, 1H), 7.39 (bs, 1H), 3.85 (s, 3H), 3.32-3.21 (m, 7H), 2.22 (s, 6H), 2.04-1.79 (m, 6H), 1.34-1.23 (m, 4H); MS (ESI) m/z=605.2 (M+H)$^{+}$ Example 294. 2-(1-(Cyclopropylsulfonyl)-1H-pyrazol-4-yl)-N-(4-(4-(2-(dimethylamino)ethyl)piperidin-1-yl)-5-((1-methyl-1H pyrazol-4-yl)ethynyl)pyridin-2-yl)pyrimidin-4-amine formate Step 1. 2-(1-(2-Chloro-5-((1-methyl-1H-pyrazol-4-yl)ethynyl)pyridin-4-yl)piperidin-4-yl)-N,N-dimethylethan-1-amine The title compound as a solid (170 mg) was prepared in the same fashion as Step 1 in Example 65 except that N,N-dimethyl-2-(4-piperidyl)ethanamine (66 mg, 0.424 mmol) was used instead of 4-(trifluoromethyl)piperidine HCl. $^{1}$H-NMR (CDCl$_3$, 400 MHz) δ 8.21 (s, 1H), 7.61 (s, 1H), 7.54 (s, 1H), 6.68 (s, 1H), 4.03 (d, 2H), 3.93 (s, 3H), 2.83 (t, 2H), 2.42-2.29 (m, 2H), 2.25 (s, 6H), 1.81 (d, 2H), 1.59-1.40 (m, 5H); MS (ESI) m/z=372.1 (M+H)$^{+}$ Step 2. 2-(1-(Cyclopropylsulfonyl)-1H-pyrazol-4-yl)-N-(4-(4-(2-(dimethylamino)ethyl)piperidin-1-yl)-5-((1-methyl-1H-pyrazol-4-yl)ethynyl)pyridin-2-yl)pyrimidin-4-amine formate The title compound as a solid (4 mg) was prepared in the same fashion as Step 3 in Example 1 except that 2-(1-(2-chloro-5-((1-methyl-1H-pyrazol-4-yl)ethynyl)pyridin-4-yl)piperidin-4-yl)-N,N-dimethylethan-1-amine (140 mg, 0.377 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (DMSO-$d_6$, 400 MHz) δ 10.26 (s, 1H), 8.66 (s, 1H), 8.44 (d, 2H), 8.25 (s, 3H), 8.18 (s, 1H), 8.02 (s, 1H), 7.73 (bs, 1H), 7.64 (s, 1H), 7.34 (bs, 1H), 4.00 (d, 2H), 3.86 (s, 3H) 3.30-3.25 (m, 1H), 2.87-2.82 (m, 2H), 2.31 (s, 6H), 1.85-1.82 (m, 2H), 1.53-1.46 (m, 3H), 1.36-1.25 (m, 61-1); MS (ESI) m/z=601.3 (M+H)$^{+}$ Example 295. 2-(1-(Cyclopropylsulfonyl)-1H-pyrazol-4-yl)-N-(4-(4-((dimethylamino)methyl)piperidin-1-yl)-5-((1-methyl-1H-pyrazol-4-yl)ethynyl)pyridin-2-yl)pyrimidin-4-amine Step 1. 1-(1-(2-Chloro-5-((1-methyl-1H-pyrazol-4-yl)ethynyl)pyridin-4-yl)piperidin-4-yl)-N, N-dimethylmethanamine The title compound as a solid (124 mg) was prepared in the same fashion as Step 1 in Example 65 except that N,N-dimethyl-1-(4-piperidyl)methanamine HCl (66 mg, 0.424 mmol) was used instead of 4-(trifluoromethyl)piperidine HCl. $^{1}$H-NMR (CDCl$_3$, 400 MHz) δ 8.23 (s, 1H), 7.62 (s, 1H), 7.55 (s, 1H), 6.71 (s, 1H), 4.06 (d, 2H), 3.93 (s, 3H), 2.86 (t, 2H), 2.24 (s, 6H), 2.18 (d, 2H), 1.88 (d, 2H), 1.74-1.67 (m, 1H), 1.42-1.33 (m, 2H); MS (ESI) m/z=358.2 (M+H)$^{+}$ Step 2. 2-(1-(Cyclopropylsulfonyl)-1H-pyrazol-4-yl)-N-(4-(4-((dimethylamino)methyl)piperidin-1-yl)-5-((1-methyl-1H-pyrazol-4-yl)ethynyl)pyridin-2-yl)pyrimidin-4-amine The title compound as a solid (17 mg) was prepared in the same fashion as Step 3 in Example 1 except that 1-(1-(2-chloro-5-((1-methyl-1H-pyrazol-4-yl)ethynyl)pyridin-4-yl)piperidin-4-yl)-N,N-dimethylmethanamine (135 mg, 0.377 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (CDCl$_3$, 400 MHz) δ 8.67 (s, 1H), 8.44 (s, 1H), 8.40 (d, 1H), 8.34 (brs, 1H), 8.24 (s, 1H), 7.63 (s, 1H), 7.57-7.56 (m, 2H), 7.03 (d, 1H), 4.13 (d, 2H), 3.93 (s, 3H), 2.92-2.81 (m, 3H), 2.27-2.22 (m, 8H), 1.96 (d, 2H), 1.79-1.73 (m, 1H), 1.54-1.38 (m, 4H), 1.25-1.19 (m, 2H); MS (ESI) m/z=587.2 (M+H)$^{+}$ Example 296. 2-(1-(Cyclopropylsulfonyl)-1H-pyrazol-4-yl)-N-(4-(4-((dimethylamino)methyl)-4-methylpiperidin-1-yl)-5-((1-methyl-1H-pyrazol-4-yl)ethynyl)pyridin-2-yl)pyrimidin-4-amine Step 1. 1-(1-(2-Chloro-5-((1-methyl-1H-pyrazol-4-yl)ethynyl)pyridin-4-yl)-4-methylpiperidin-4-yl)-N,N-dimethylmethanamine The title compound as a solid (233 mg) was prepared in the same fashion as Step 1 in Example 65 except that N,N-dimethyl-1-(4-methyl-4-piperidyl)methanamine HCl (82 mg, 0.424 mmol) was used instead of 4-(trifluoromethyl)piperidine HCl. $^{1}$H-NMR (CDCl$_3$, 400 MHz) δ 8.14 (s, 1H), 7.55 (s, 1H), 7.50 (s, 1H), 6.65 (s, 1H), 3.87 (s, 3H), 3.64-3.58 (m, 2H), 3.41 (s, 1H), 2.26 (s, 6H), 2.14 (s, 2H), 1.68-1.61 (m, 2H), 1.43-1.38 (m, 2H), 0.98 (s, 3H); MS (ESI) m/z=372.1 (M+H)$^{+}$ Step 2. 2-(1-(Cyclopropylsulfonyl)-1H-pyrazol-4-yl)-N-(4-(4-((dimethylamino)methyl)-4-methylpiperidin-1-yl)-5-((1-methyl-1H-pyrazol-4-yl)ethynyl)pyridin-2-yl)pyrimidin-4-amine The title compound as a solid (12 mg) was prepared in the same fashion as Step 3 in Example 1 except that 1-(1-(2-chloro-5-((1-methyl-1H-pyrazol-4-yl)ethynyl)pyridin-4-yl)-4-methylpiperidin-4-yl)-N,N-dimethylmethanamine (140 mg, 0.377 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (CDCl$_3$, 400 MHz) δ 8.65 (s, 1H), 8.44 (s, 1H), 8.41 (d, 1H), 8.23 (s, 1H), 8.13 (brs, 1H), 7.63 (s, 1H), 7.55 (s, 1H), 7.44 (brs, 1H), 7.27 (s, 1H), 7.09 (d, 1H), 3.93 (s, 3H), 3.77-3.71 (m, 2H), 3.33-3.26 (m, 2H), 2.86-2.82 (m, 1H), 2.33 (s, 6H), 2.22 (s, 2H), 1.80-1.74 (m, 2H), 1.55-1.50 (m, 4H), 1.28-1.21 (m, 3H), 1.07 (s, 3H); MS (ESI) m/z=601.3 (M+H)$^{+}$ Example 297. 2-(1-(Cyclopropylsulfonyl)-1H-pyrazol-4-yl)-N-(5-((1-methyl-1H-pyrazol-4-yl)ethynyl)-4-(2-methyl-2,8-diazaspiro[4.5]decan-8-yl)pyridin-2-yl)pyrimidin-4-amine formate Step 1. 8-(2-Chloro-5-((1-methyl-1H-pyrazol-4-yl)ethynyl)pyridin-4-yl)-2-methyl-2,8-diazaspiro[4.5]decane The title compound as a solid (140 mg) was prepared in the same fashion as Step 1 in Example 65 except that 2-methyl-2,8-diazaspiro[4.5]decane HCl (81 mg, 0.424 mmol) was used instead of 4-(trifluoromethyl)piperidine HCl. $^{1}$H-NMR (CDCl$_3$, 400 MHz) δ 8.17 (s, 1H), 7.57 (s, 1H), 7.52 (s, 1H), 6.66 (s, 1H), 3.89 (s, 3H), 3.46-3.30 (m, 7H), 2.63-2.55 (m, 4H), 2.41 (s, 2H), 2.31 (s, 3H), 1.77-1.66 (m, 6H); MS (ESI) m/z=370.2 (M+H)$^{+}$ Step 2. 2-(1-(Cyclopropylsulfonyl)-1H-pyrazol-4-yl)-N-(5-(((1-methyl-1H-pyrazol-4-yl)ethynyl)-4-(2-methyl-2,8-diazaspiro[4.5]decan-8-yl)pyridin-2-yl)pyrimidin-4-amine formate The title compound as a solid (10 mg) was prepared in the same fashion as Step 3 in Example 1 except that 8-(2-chloro-5-((1-methyl-1H-pyrazol-4-yl)ethynyl)pyridin-4-yl)-2-methyl-2,8-diazaspiro[4.5]decane (140 mg, 0.377 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (DMSO-d$_6$, 400 MHz) δ 10.24 (s, 1H), 8.64 (s, 1H), 8.44-8.41 (m, 2H), 8.24 (s, 2H), 8.14 (d, 1H), 7.99 (s, 1H), 7.73 (brs, 1H), 7.61 (s, 1H), 7.32 (brs, 1H), 3.48-3.24 (m, 7H), 2.75-2.68 (m, 3H), 1.76-1.65 (m, 9H), 1.34-1.25 (m, 4H); MS (ESI) m/z=599.3 (M+H)$^+$ Example 298. N-(5-((1-Cyclopropyl-1H-pyrazol-4-yl)ethynyl)-4-(4-((dimethylamino)methyl)piperidin-1-yl)pyridin-2-yl)-2-(1-(cyclopropylsulfonyl)-1H-pyrazol-4-yl)pyrimidin-4-amine Step 1. 1-(1-(2-Chloro-5-((1-cyclopropyl-1H-pyrazol-4-yl)ethynyl)pyridin-4-yl)piperidin-4-yl)-N,N-dimethylmethanamine The title compound as a solid (72 mg) was prepared in the same fashion as Step 1 in Example 65 except that N,N-dimethyl-1-(4-piperidyl)methanamine HCl (76 mg, 0.424 mmol) and 2-chloro-5-((1-cyclopropyl-1H-pyrazol-4-yl)ethynyl)-4-fluoropyridine (111 mg, 0.424 mmol) prepared in Reference Example 51 were used instead of 4-(trifluoromethyl)piperidine HCl and 2-chloro-4-fluoro-5-((1-methyl-1H-pyrazol-4-yl)ethynyl)pyridine. $^{1}$H-NMR (CDCl$_3$, 400 MHz) δ 8.18 (s, 1H), 7.61 (s, 1H), 7.56 (s, 1H), 6.67 (s, 1H), 4.02 (d, 2H), 3.61-3.56 (m, 1H), 2.84-2.78 (m, 2H), 2.24 (s, 6H), 2.21 (d, 2H), 1.85 (d, 2H), 1.70-1.63 (m, 1H), 1.38-1.23 (m, 2H), 1.15-1.00 (m, 4H); MS (ESI) m/z=384.1 (M+H)$^+$ Step 2. N-(5-((1-Cyclopropyl-1H-pyrazol-4-yl)ethynyl)-4-(4-((dimethylamino)methyl)piperidin-1-yl)pyridin-2-yl)-2-(1-(cyclopropylsulfonyl)-1H-pyrazol-4-yl)pyrimidin-4-amine The title compound as a solid (4 mg) was prepared in the same fashion as Step 3 in Example 1 except that 1-(1-(2-chloro-5-((1-cyclopropyl-1H-pyrazol-4-yl)ethynyl)pyridin-4-yl)piperidin-4-yl)-N,N-dimethylmethanamine (72 mg, 0.188 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (CDCl$_3$, 400 MHz) δ 8.68 (s, 1H), 8.45 (s, 1H), 8.41 (d, 1H), 8.22 (s, 1H), 7.77 (brs, 1H), 7.62 (d, 2H), 7.52 (brs, 1H), 7.27 (s, 1H), 7.09 (d, 1H), 3.93 (s, 3H), 3.77-3.71 (m, 2H), 3.33-3.26 (m, 2H), 2.86-2.82 (m, 1H), 2.33 (s, 6H), 2.22 (s, 2H), 1.80-1.74 (m, 2H), 1.55-1.50 (m, 4H), 1.28-1.21 (m, 3H), 1.07 (s, 3H); MS (ESI) m/z=601.3 (M+H)$^+$ Example 299. N-(5-((1-Cyclopropyl-1H-pyrazol-4-yl)ethynyl)-4-(4-((dimethylamino)methyl)-4-methylpiperidin-1-yl)pyridin-2-yl)-2-(1-(cyclopropylsulfonyl)-1H-pyrazol-4-yl)pyrimidin-4-amine Step 1. 1-(1-(2-Chloro-5-((1-cyclopropyl-1H-pyrazol-4-yl)ethynyl)pyridin-4-yl)-4-methylpiperidin-4-yl)-N, N-dimethylmethanamine The title compound as a solid (120 mg) was prepared in the same fashion as Step 1 in Example 65 except that N,N-dimethyl-1-(4-methyl-4-piperidyl)methanamine HCl (82 mg, 0.424 mmol) and 2-chloro-5-((1-cyclopropyl-1H-pyrazol-4-yl)ethynyl)-4-fluoropyridine (111 mg, 0.424 mmol) prepared in Reference Example 51 were used instead of 4-(trifluoromethyl)piperidine HCl and 2-chloro-4-fluoro-5-((1-methyl-1H-pyrazol-4-yl)ethynyl)pyridine. $^{1}$H-NMR (CDCl$_3$, 400 MHz) δ 7.95 (s, 1H), 7.46 (s, 1H), 7.35 (s, 1H), 6.49 (s, 1H), 5.13 (s, 1H), 3.48-3.38 (m, 3H), 3.11-3.01 (m, 2H), 2.10 (s, 6H), 1.52-1.46 (m, 2H), 1.25-1.22 (m, 2H), 0.93-0.90 (m, 4H); MS (ESI) m/z=398.1 (M+H)$^+$ Step 2. N-(5-((1-Cyclopropyl-1H-pyrazol-4-yl)ethynyl)-4-(4-((dimethylamino)methyl)-4-methylpiperidin-1-yl)pyridin-2-yl)-2-(1-(cyclopropylsulfonyl)-1H-pyrazol-4-yl)pyrimidin-4-amine The title compound as a solid (1 mg) was prepared in the same fashion as Step 3 in Example 1 except that 1-(1-(2-chloro-5-((1-cyclopropyl-1H-pyrazol-4-yl)ethynyl)pyridin-4-yl)-4-methylpiperidin-4-yl)-N,N-dimethylmethanamine (75 mg, 0.188 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (CDCl$_3$, 400 MHz) δ 8.66 (s, 1H), 8.45-8.42 (m, 2H), 8.21 (s, 1H), 7.63-7.59 (m, 3H), 7.40 (brs, 1H), 7.14 (d, 1H), 3.64-3.60 (m, 1H), 3.29 (t, 2H), 2.86-2.82 (m, 1H), 2.34 (s, 6H), 2.23 (s, 2H), 1.81-1.74 (m, 2H), 1.56-1.51 (m, 4H), 1.26-1.04 (m, 11H); MS (ESI) m/z=627.2 (M+H)$^+$ Example 300. N-(5-((1-Cyclopropyl-1H-pyrazol-4-yl)ethynyl)-4-(4-((dimethylamino)methyl)-4-fluoropiperidin-1-yl)pyridin-2-yl)-2-(1-(cyclopropylsulfonyl)-1H-pyrazol-4-yl)pyrimidin-4-amine Step 1. 1-(1-(2-Chloro-5-((1-cyclopropyl-1H-pyrazol-4-yl)ethynyl)pyridin-4-yl)-4-fluoropiperidin-4-yl)-N, N-dimethylmethanamine The title compound as a solid (140 mg) was prepared in the same fashion as Step 1 in Example 65 except that 1-(4-fluoro-4-piperidyl)-N,N-dimethyl-methanamine HCl (83 mg, 0.424 mmol) and 2-chloro-5-((1-cyclopropyl-1H-pyrazol-4-yl)ethynyl)-4-fluoropyridine (111 mg, 0.424 mmol) prepared in Reference Example 51 were used instead of 4-(trifluoromethyl)piperidine HCl and 2-chloro-4-fluoro-5-((1-methyl-1H-pyrazol-4-yl)ethynyl)pyridine. $^{1}$H-NMR (CDCl$_3$, 400 MHz) δ 7.96 (s, 1H), 7.46 (s, 1H), 7.33 (s, 1H), 6.50 (s, 1H), 3.61 (d, 2H), 3.44-3.37 (m, 1H), 3.01-2.98 (m, 2H), 2.25 (d, 2H), 2.08 (s, 6H), 1.79-1.50 (m, 2H), 0.99-0.79 (m, 4H); MS (ESI) m/z=402.1 (M+H)$^+$ Step 2. N-(5-((1-Cyclopropyl-1H-pyrazol-4-yl)ethynyl)-4-(4-((dimethylamino)methyl)-4-fluoropiperidin-1-yl)pyridin-2-yl)-2-(1-(cyclopropylsulfonyl)-1H-pyrazol-4-yl)pyrimidin-4-amine The title compound as a solid (7 mg) was prepared in the same fashion as Step 3 in Example 1 except that 1-(1-(2-chloro-5-((1-cyclopropyl-1H-pyrazol-4-yl)ethynyl)pyridin-4-yl)-4-fluoropiperidin-4-yl)-N,N-dimethylmethanamine (76 mg, 0.188 mmol) prepared in Step 1 was used instead of 1-(2-chloro-5-((1-methyl-1H-pyrazol-4-yl)ethynyl)pyridin-4-yl)-4-methylpiperazine. $^{1}$H-NMR (CDCl$_3$, 400 MHz) δ 8.65 (s, 1H), 8.44-8.42 (m, 2H), 8.25 (s, 1H), 7.82 (brs, 1H), 7.62 (d, 1H), 7.43 (brs, 1H), 7.15 (brs, 1H), 3.91-3.88 (m, 2H), 3.64-3.61 (m, 1H), 3.27 (t, 2H), 2.87-2.83 (m, 1H), 2.52

(d, 2H), 2.34 (s, 6H), 2.18-2.12 (m, 2H), 1.56-1.52 (m, 2H), 1.26-1.04 (m, 8H); MS (ESI) m/z=632.2 (M+H)+

Example 301. 2-(1-(Cyclopropylsulfonyl)-1H-pyrazol-4-yl)-N-(5-((1-(2,2-di fluoroethyl)-1H-pyrazol-4-yl)ethynyl)-4-(4-((dimethylamino)methyl)piperidin-1-yl)pyridin-2-yl)pyrimidin-4-amine Step 1. 1-(1-(2-Chloro-5-((1-(2,2-difluoroethyl)-1H-pyrazol-4-yl)ethynyl)pyridin-4-yl)piperidin-4-yl)-N, N-dimethylmethanamine The title compound as a solid (75 mg) was prepared in the same fashion as Step 1 in Example 65 except that N,N-dimethyl-1-(4-piperidyl)methanamine HCl (47 mg, 0.263 mmol) and 2-chloro-5-((1-(2,2-difluoroethyl)-1H-pyrazol-4-yl)ethynyl)-4-fluoropyridine (75 mg, 0.263 mmol) prepared in Reference Example 52 were used instead of 4-(trifluoromethyl)piperidine HCl and 2-chloro-4-fluoro-5-((1-methyl-1H-pyrazol-4-yl)ethynyl)pyridine. MS (ESI) m/z=408.2 (M+H)+

Step 2. 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)piperidin-1-yl)pyridin-2-yl)pyrimidin-4-amine The title compound as a solid (25 mg) was prepared in the same fashion as Step 3 in Example 1 except that 1-(1-(2-chloro-5-((1-(2,2-difluoroethyl)-1H-pyrazol-4-yl)ethynyl)pyridin-4-yl)piperidin-4-yl)-N,N-dimethylmethanamine (75 mg, 0.188 mmol) prepared in Step 1 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.67 (s, 1H), 8.45 (s, 1H), 8.41 (d, 1H), 8.27 (brs, 1H), 8.25 (s, 1H), 7.70 (d, 2H), 7.55 (brs, 1H), 7.03 (d, 1H), 6.12 (t, 1H), 4.53-4.46 (m, 2H), 4.12 (d, 2H), 2.93-2.82 (m, 3H), 2.26-2.21 (m, 8H), 2.09-1.95 (m, 4H), 1.80-1.74 (m, 1H), 1.53-1.50 (m, 2H), 1.44-1.40 (m, 2H), 1.25-1.21 (m, 2H); MS (ESI) m/z=637.3 (M+H)+

Example 302. 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)-4-methylpiperidin-1-yl)pyridin-2-yl)pyrimidin-4-amine Step 1. 1-(1-(2-Chloro-5-((1-(2,2-difluoroethyl)-1H-pyrazol-4-yl)ethynyl)pyridin-4-yl)-4-methylpiperidin-4-yl)-N, N-dimethylmethanamine The title compound as a solid (159 mg) was prepared in the same fashion as Step 1 in Example 65 except that N,N-dimethyl-1-(4-methyl-4-piperidyl)methanamine HCl (51 mg, 0.263 mmol) and 2-chloro-5-((1-(2,2-difluoroethyl)-1H-pyrazol-4-yl)ethynyl)-4-fluoropyridine (75 mg, 0.263 mmol) prepared in Reference Example 52 were used instead of 4-(trifluoromethyl)piperidine HCl and 2-chloro-4-fluoro-5-((1-methyl-1H-pyrazol-4-yl)ethynyl)pyridine. MS (ESI) m/z=422.2 (M+H)+

Step 2. 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)-4-methylpiperidin-1-yl)pyridin-2-yl)pyrimidin-4-amine The title compound as a solid (14 mg) was prepared in the same fashion as Step 3 in Example 1 except that 1-(1-(2-chloro-5-((1-(2,2-difluoroethyl)-1H-pyrazol-4-yl)ethynyl)pyridin-4-yl)-4-methylpiperidin-4-yl)-N,N-dimethylmethanamine (78 mg, 0.188 mmol) prepared in Step 1 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.65 (s, 1H), 8.44 (s, 1H), 8.41 (d, 1H), 8.25-8.24 (m, 2H), 7.69 (d, 2H), 7.46 (brs, 1H), 7.08 (d, 1H), 6.10 (t, 1H), 4.52-4.45 (m, 2H), 3.77-3.74 (m, 2H), 3.32-3.26 (m, 2H), 2.85-2.82 (m, 1H), 2.32 (s, 6H), 2.22 (s, 2H), 1.87 (brs, 1H), 1.80-1.74 (m, 2H), 1.54-1.50 (m, 4H), 1.23-1.21 (m, 2H), 1.07 (s, 3H); MS (ESI) m/z=651.2 (M+H)+

Example 303. 2-(1-(Cyclopropylsulfonyl)-1H-pyrazol-4-yl)-N-(5-((1-(2,2-difluoroethyl)-1H-pyrazol-4-yl)ethynyl)-4-(4-(2-(dimethylamino)ethyl)piperidin-1-yl)pyridin-2-yl)pyrimidin-4-amine Step 1. 2-(1-(2-Chloro-5-((1-(2,2-difluoroethyl)-1H-pyrazol-4-yl)ethynyl)pyridin-4-yl)piperidin-4-yl)-N, N-dimethylethan-1-amine The title compound as a solid (159 mg) was prepared in the same fashion as Step 1 in Example 65 except that N,N-dimethyl-2-(4-piperidyl)ethanamine (41 mg, 0.263 mmol) and 2-chloro-5-((1-(2,2-difluoroethyl)-1H-pyrazol-4-yl)ethynyl)-4-fluoropyridine (75 mg, 0.263 mmol) prepared in Reference Example 52 were used instead of 4-(trifluoromethyl)piperidine HCl and 2-chloro-4-fluoro-5-((1-methyl-1H-pyrazol-4-yl)ethynyl)pyridine. MS (ESI) m/z=422.2 (M+H)+

Step 2. 2-(1-(Cyclopropylsulfonyl)-1H-pyrazol-4-yl)-N-(5-((1-(2,2-difluoroethyl)-1H-pyrazol-4-yl)ethynyl)-4-(4-(2-(dimethylamino)ethyl)piperidin-1-yl)pyridin-2-yl)pyrimidin-4-amine The title compound as a solid (9 mg) was prepared in the same fashion as Step 3 in Example 1 except that 2-(1-(2-chloro-5-((1-(2,2-difluoroethyl)-1H-pyrazol-4-yl)ethynyl)pyridin-4-yl)piperidin-4-yl)-N,N-dimethylethan-1-amine (78 mg, 0.188 mmol) prepared in Step 1 was used instead of 1-(2-chloro-5-((1-methyl-1H-pyrazol-4-yl)ethynyl)pyridin-4-yl)-4-methylpiperazine. 1H-NMR (CDCl3, 400 MHz) δ 8.66 (s, 1H), 8.45 (s, 1H), 8.41 (d, 1H), 8.24 (s, 1H), 8.03 (brs, 1H), 7.70 (s, 2H), 7.54 (brs, 1H), 7.04 (d, 1H), 6.12 (t, 1H), 4.55-4.47 (m, 2H), 4.10 (d, 2H), 2.94-2.83 (m, 2H), 2.53-2.49 (m, 2H), 2.37 (s, 6H), 1.91 (d, 2H), 1.61-1.46 (m, 7H), 1.26-1.20 (m, 2H); MS (ESI) m/z=651.3 (M+H)+

Example 304. (1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)-1-(hydroxymethyl)cyclohexan-1-ol Step 1. (1s,4s)-4-((2-Chloro-5-iodopyridin-4-yl)amino)-1-(hydroxymethyl)cyclohexan-1-ol The suspension of 2-chloro-4-fluoro-5-iodopyridine (500 mg, 1.942 mmol), (1s,4s)-4-amino-1-(hydroxymethyl)cyclohexan-1-ol (282 mg, 1.942 mmol), and DIPEA (0.68 mL, 3.885 mmol) in DMA (8 mL) was stirred at 60° C. overnight. After being cooled, the reaction mixture was diluted in EA, washed by water, dried over MgSO4, and then concentrated. The crude product was purified by column chromatography (MeOH/DCM=0-15%) to yield (1s,4s)-4-((2-chloro-5-iodopyridin-4-yl)amino)-1-(hydroxymethyl)cyclohexan-1-ol (580 mg). MS (ESI) m/z=383.2 (M+H)⁺

Step 2. (1s,4s)-4-((2-Chloro-5-((1-(difluoromethyl)-1H-pyrazol-4-yl)ethynyl)pyridin-4-yl)amino)-1-(hydroxymethyl)cyclohexan-1-ol The title compound as a solid (230 mg) was prepared in the same fashion as Step 2 in Example 1 except that (1s,4s)-4-((2-chloro-5-iodopyridin-4-yl)amino)-1-(hydroxymethyl)cyclohexan-1-ol (215 mg, 0.563 mmol) prepared in Step 1 and 1-(difluoromethyl)-4-ethynyl-1H-pyrazole (80 mg, 0.563 mmol) were used instead of 1-(2-chloro-5-iodopyridin-4-yl)-4-methylpiperazine and 4-ethynyl-1-methyl-1H-pyrazole. MS (ESI) m/z=397.0 (M+H)⁺

Step 3. (1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)-1-(hydroxymethyl)cyclohexan-1-ol The title compound as a solid (80 mg) was prepared in the same fashion as Step 3 in Example 1 except that (1s,4s)-4-((2-chloro-5-((1-(difluoromethyl)-1H-pyrazol-4-yl)ethynyl)pyridin-4-yl)amino)-1-(hydroxymethyl)cyclohexan-1-ol (165 mg, 0.415 mmol) prepared in Step 2 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.71 (s, 1H), 8.45 (s, 1H), 8.36-8.34 (m, 2H), 8.04 (s, 1H), 7.91 (s, 1H), 7.52 (t, 1H), 7.44 (d, 1H), 7.10 (s, 1H), 3.52-3.47 (m, 1H), 3.40 (s, 2H), 3.06-3.03 (m, 1H), 1.99-1.96 (m, 2H), 1.78-1.70 (m, 4H), 1.62-1.55 (m, 2H), 1.47-1.44 (m, 2H), 1.29-1.26 (m, 2H); MS (ESI) m/z=626.2 (M+H)⁺

Example 305. (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol Step 1. (1-(2-Chloro-5-((1-(difluoromethyl)-1H-pyrazol-4-yl)ethynyl)pyridin-4-yl)-4-methylpiperidin-4-yl)methanol The title compound as a solid (130 mg) was prepared in the same fashion as Step 2 in Example 1 except that (1-(2-chloro-5-iodopyridin-4-yl)-4-methylpiperidin-4-yl)methanol (188 mg, 0.511 mmol) prepared in Reference Example 12 and 1-(difluoromethyl)-4-ethynyl-1H-pyrazole (80 mg, 0.563 mmol) were used instead of 1-(2-chloro-5-iodopyridin-4-yl)-4-methylpiperazine and 4-ethynyl-1-methyl-1H-pyrazole. MS (ESI) m/z=381.0 (M+H)⁺

Step 2. (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol The title compound as a solid (3 mg) was prepared in the same fashion as Step 3 in Example 1 except that (1-(2-chloro-5-((1-(difluoromethyl)-1H-pyrazol-4-yl)ethynyl)pyridin-4-yl)-4-methylpiperidin-4-yl)methanol (57 mg, 0.151 mmol) prepared in Step 1 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.71 (s, 1H), 8.43 (s, 1H), 8.36 (d, 1H), 8.30 (s, 1H), 8.16 (s, 1H), 7.86 (s, 1H), 7.56 (s, 1H), 7.52 (t, 1H), 7.37-7.34 (m, 1H), 3.78-3.74 (m, 2H), 3.39 (s, 2H), 3.07-3.01 (m, 1H), 1.82-1.76 (m, 2H), 1.54-1.42 (m, 4H), 1.29-1.23 (m, 3H); MS (ESI) m/z=610.2 (M+H)⁺

Example 306. (1R,3S)-3-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclopentan-1-ol Step 1. (1R,3S)-3-(((2-Chloro-5-iodopyridin-4-yl)amino)methyl)cyclopentan-1-ol The title compound (490 mg) was prepared in the same fashion as Step 1 in Example 304 except that (1R,3S)-3-(aminomethyl)cyclopentan-1-ol (224 mg, 1.942 mmol) was used instead of (1s,4s)-4-amino-1-(hydroxymethyl)cyclohexan-1-ol. MS (ESI) m/z=352.9 (M+H)⁺

Step 2. (1R,3S)-3-(((2-Chloro-5-((1-(difluoromethyl)-1H-pyrazol-4-yl)ethynyl)pyridin-4-yl)amino)methyl)cyclopentan-1-ol The title compound as a solid (220 mg) was prepared in the same fashion as Step 2 in Example 1 except that (1R,3S)-3-(((2-chloro-5-iodopyridin-4-yl)amino)methyl)cyclopentan-1-ol (198 mg, 0.563 mmol) prepared in Step 1 and 1-(difluoromethyl)-4-ethynyl-1H-pyrazole (80 mg, 0.563 mmol) were used instead of 1-(2-chloro-5-iodopyridin-4-yl)-4-methylpiperazine and 4-ethynyl-1-methyl-1H-pyrazole. MS (ESI) m/z=367.0 (M+H)⁺

Step 3. (1R,3S)-3-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclopentan-1-ol The title compound as a solid (2.2 mg) was prepared in the same fashion as Step 3 in Example 1 except that (1R,3S)-3-(((2-chloro-5-((1-(difluoromethyl)-1H-pyrazol-4-yl)ethynyl)pyridin-4-yl)amino)methyl)cyclopentan-1-ol (152 mg, 0.415 mmol) prepared in Step 2 prepared in Step 2 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.77 (s, 1H), 8.47 (s, 1H), 8.39 (d, 1H), 8.37 (s, 1H), 8.26 (s, 1H), 8.07 (s, 1H), 7.93 (s, 1H), 7.53 (t, 1H), 7.37 (d, 1H), 7.09 (s, 1H), 4.63 (brs, 1H), 4.29-4.27 (m, 1H), 3.07-3.03 (m, 1H), 2.52-2.48 (m, 1H), 2.14-2.08 (m, 1H), 1.87-1.66 (m, 4H), 1.48-1.44 (m, 3H), 1.29-1.25 (m, 2H); MS (ESI) m/z=596.2 (M+H)⁺

Example 307. (1r,4r)-4-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclohexan-1-ol Step 1. (1r,4r)-4-(((2-Chloro-5-iodopyridin-4-yl)amino)methyl)cyclohexan-1-ol The title compound (510 mg) was prepared in the same fashion as Step 1 in Example 304 except that (1r,4r)-4-(aminomethyl)cyclohexan-1-ol (224 mg, 1.942 mmol) was used instead of (1s,4s)-4-amino-1-(hydroxymethyl)cyclohexan-1-ol. MS (ESI) m/z=366.9 (M+H)⁺

Step 2. (1 r,4r)-4-(((2-Chloro-5-((1-(difluoromethyl)-1H-pyrazol-4-yl)ethynyl)pyridin-4-yl)amino)methyl)cyclohexan-1-ol The title compound as a solid (190 mg) was prepared in the same fashion as Step 2 in Example 1 except that (1 r,4r)-4-(((2-chloro-5-iodopyridin-4-yl)amino)methyl)cyclohexan-1-ol (206 mg, 0.563 mmol) prepared in Step 1 and 1-(difluoromethyl)-4-ethynyl-1H-pyrazole (80 mg, 0.563 mmol) were used instead of 1-(2-chloro-5-iodopyridin-4-yl)-4-methylpiperazine and 4-ethynyl-1-methyl-1H-pyrazole. MS (ESI) m/z=381.0 (M+H)$^+$ Step 3. (1 r,4r)-4-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclohexan-1-ol The title compound as a solid (2.3 mg) was prepared in the same fashion as Step 3 in Example 1 except that (1 r,4r)-4-(((2-chloro-5-((1-(difluoromethyl)-1H-pyrazol-4-yl)ethynyl)pyridin-4-yl)amino)methyl)cyclohexan-1-ol (158 mg, 0.415 mmol) prepared in Step 2 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 8.66 (s, 1H), 8.62 (s, 1H), 8.50-8.44 (m, 2H), 8.06 (d, 1H), 7.86 (t, 1H), 7.67 (brs, 1H), 7.04 (brs, 1H), 6.31-6.28 (m, 1H), 4.49-4.48 (m, 1H), 3.10-3.08 (m, 2H), 1.82-1.70 (m, 4H), 1.34-1.22 (m, 5H), 1.09-1.00 (m, 5H); MS (ESI) m/z=610.2 (M+H)$^+$ Example 308. ((1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)cyclohexyl)methanol Step 1. ((1s,4s)-4-((2-Chloro-5-iodopyridin-4-yl)amino)cyclohexyl)methanol The title compound (470 mg) was prepared in the same fashion as Step 1 in Example 304 except that ((1s,4s)-4-aminocyclohexyl)methanol (251 mg, 1.942 mmol) was used instead of (1s,4s)-4-amino-1-(hydroxymethyl)cyclohexan-1-ol. MS (ESI) m/z=366.9 (M+H)$^+$ Step 2. ((1s,4S)-4-((2-Chloro-5-((1-(difluoromethyl)-1H-pyrazol-4-yl)ethynyl)pyridin-4-yl)amino)cyclohexyl)methanol The title compound as a solid (180 mg) was prepared in the same fashion as Step 2 in Example 1 except that ((1s,4s)-4-((2-chloro-5-iodopyridin-4-yl)amino)cyclohexyl)methanol (206 mg, 0.563 mmol) prepared in Step 1 and 1-(difluoromethyl)-4-ethynyl-1H-pyrazole (80 mg, 0.563 mmol) were used instead of 1-(2-chloro-5-iodopyridin-4-yl)-4-methylpiperazine and 4-ethynyl-1-methyl-1H-pyrazole. MS (ESI) m/z=381.0 (M+H)$^+$ Step 3. ((1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)cyclohexyl)methanol The title compound as a solid (3.3 mg) was prepared in the same fashion as Step 3 in Example 1 except that ((1s,4s)-4-((2-chloro-5-((1-(difluoromethyl)-1H-pyrazol-4-yl)ethynyl)pyridin-4-yl)amino)cyclohexyl)methanol (158 mg, 0.415 mmol) prepared in Step 2 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 8.64 (s, 1H), 8.63 (s, 1H), 8.45 (s, 1H), 8.43 (s, 1H), 8.09 (s, 1H), 8.06 (s, 1H), 7.86 (t, 1H), 7.40 (d, 2H), 5.50 (d, 1H), 3.73 (brs, 1H), 1.82-1.67 (m, 4H), 1.60-1.51 (m, 3H), 1.34-1.23 (m, 6H); MS (ESI) m/z=610.2 (M+H)$^+$ Example 309. 5-((1-(Cyclopropylmethyl)-1H-pyrazol-4-yl)ethynyl)-N$^2$-(2-(1-(cyclopropylsulfonyl)-1H-pyrazol-4-yl)pyrimidin-4-yl)-N$^4$-((1s,4s)-4-((dimethylamino)methyl)cyclohexyl)pyridine-2,4-diamine Step 1. 2-Chloro-N-((1s, 4S)-4-((dimethylamino)methyl)cyclohexyl)-5-iodopyridin-4-amine The title compound (590 mg) was prepared in the same fashion as Step 1 in Example 304 except that (1s,4s)-4-((dimethylamino)methyl)cyclohexan-1-amine (1.21 g, 7.769 mmol) was used instead of (1s,4s)-4-amino-1-(hydroxymethyl)cyclohexan-1-ol. MS (ESI) m/z=393.9 (M+H)$^+$ Step 2. 2-Chloro-5-((1-(cyclopropylmethyl)-1H-pyrazol-4-yl)ethynyl)-N-((1s, 4s)-4-((dimethylamino)methyl)cyclohexyl)pyridin-4-amine The title compound as a solid (116 mg) was prepared in the same fashion as Step 2 in Example 1 except that 2-chloro-N-((1s,4s)-4-((dimethylamino)methyl)cyclohexyl)-5-iodopyridin-4-amine (150 mg, 0.381 mmol) prepared in Step 1 and 1-(cyclopropylmethyl)-4-ethynyl-1H-pyrazole (56 mg, 0.381 mmol) were used instead of 1-(2-chloro-5-iodopyridin-4-yl)-4-methylpiperazine and 4-ethynyl-1-methyl-1H-pyrazole. MS (ESI) m/z=412.0 (M+H)$^+$ Step 3. 5-((1-(Cyclopropylmethyl)-1H-pyrazol-4-yl)ethynyl)-N$^2$-(2-(1-(cyclopropylsulfonyl)-1H-pyrazol-4-yl)pyrimidin-4-yl)-N$^4$-((1s,4s)-4-((dimethylamino)methyl)cyclohexyl)pyridine-2,4-diamine The title compound as a solid (5.6 mg) was prepared in the same fashion as Step 3 in Example 1 except that 2-chloro-5-((1-(cyclopropylmethyl)-1H-pyrazol-4-yl)ethynyl)-N-((1s,, 4s)-4-((dimethylamino)methyl)cyclohexyl)pyridin-4-amine (116 mg, 0.283 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 8.64 (s, 1H), 8.63 (s, 1H), 8.44-8.42 (m, 2H), 8.14 (s, 1H), 8.05 (s, 1H), 7.70 (s, 1H), 7.47 (brs, 1H), 7.31 (brs, 1H), 5.45 (d, 1H), 3.99 (d, 1H), 3.33 (s, 1H), 3.28-3.25 (m, 1H), 2.10 (s, 6H), 1.76-1.60 (m, 7H), 1.36-1.23 (m, 7H), 0.56-0.54 (m, 2H), 0.41-0.37 (m, 2H); MS (ESI) m/z=641.3 (M+H)$^+$ Example 310. N$^2$-(2-(1-(Cyclopropylsulfonyl)-1H-pyrazol-4-yl)pyrimidin-4-yl)-5-((1-(difluoromethyl)-1H-pyrazol-4-yl)ethynyl)-N$^4$-((1s,4s)-4-((dimethylamino)methyl)cyclohexyl)pyridine-2,4-diamine Step 1. 2-Chloro-5-((1-(difluoromethyl)-1H-pyrazol-4-yl)ethynyl)-N-((1s,4s)-4-((dimethylamino)methyl)cyclohexyl)pyridin-4-amine The title compound as a solid (115 mg) was prepared in the same fashion as Step 2 in Example 1 except that 2-chloro-N-((1s,4S)-4-((dimethylamino)methyl)cyclohexyl)-5-iodopyridin-4-amine (150 mg, 0.381 mmol) prepared in Step 1 of Example 309 and 1-(difluoromethyl)-4-ethynyl-1H-pyrazole (59 mg, 0.381 mmol) were used instead of 1-(2-chloro-5-iodopyridin-4-yl)-4-methylpiperazine and 4-ethynyl-1-methyl-1H-pyrazole. MS (ESI) m/z=408.1 (M+H)$^+$ Step 2. N$^2$-(2-(1-(Cyclopropylsulfonyl)-1H-pyrazol-4-yl)pyrimidin-4-yl)-5-((1-(difluoromethyl)-1H-pyrazol-4-yl)ethynyl)-N$^4$-((1s, 4s)-4-((dimethylamino)methyl)cyclohexyl)pyridine-2,4-diamine The title compound as a solid (5.2 mg) was prepared in the same fashion as Step 3 in Example 1 except that 2-chloro-5-((1-(difluoromethyl)-1H-pyrazol-4-yl)ethynyl)-N-((1s,4s)-4-((dimethylamino)methyl)cyclohexyl)pyridin-4-amine (115 mg, 0.283 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 8.64 (d, 2H), 8.43 (d, 2H), 8.11 (d, 2H), 7.86 (t, 1H), 7.49 (brs, 1H), 7.30 (brs, 1H), 5.52 (d, 1H), 3.68 (brs, 1H), 3.30-3.24 (m, 1H), 2.19 (s, 6H), 1.73-1.57 (m, 7H), 1.36-1.26 (m, 7H); MS (ESI) m/z=637.3 (M+H)$^+$ Example 311. N$^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N$^4$-((1s,4s)-4-((dimethylamino)methyl)cyclohexyl)pyridine-2,4-diamine Step 1. 2-Chloro-5-((1-(2,2-difluoroethyl)-1H-pyrazol-4-yl)ethynyl)-N-((1s,4s)-4-((dimethylamino)methyl)cyclohexyl)pyridin-4-amine The title compound as a solid (119 mg) was prepared in the same fashion as Step 2 in Example 1 except that 2-chloro-N-((1s,4s)-4-((dimethylamino)methyl)cyclohexyl)-5-iodopyridin-4-amine (150 mg, 0.381 mmol) prepared in Step 1 of Example 309 and 1-(2,2-difluoroethyl)-4-ethynyl-1H-pyrazole (54 mg, 0.381 mmol) were used instead of 1-(2-chloro-5-iodopyridin-4-yl)-4-methylpiperazine and 4-ethynyl-1-methyl-1H-pyrazole. MS (ESI) m/z=422.1 (M+H)$^+$ Step 2. N$^2$-(2-(1-(Cyclopropylsulfonyl)-1H-pyrazol-4-yl)pyrimidin-4-yl)-5-((1-(2,2-difluoroethyl)-1H pyrazol-4-yl)ethynyl)-N$^4$-((1s,4s)-4-((dimethylamino)methyl)cyclohexyl)pyridine-2,4-diamine The title compound as a solid (8.9 mg) was prepared in the same fashion as Step 3 in Example 1 except that 2-chloro-5-((1-(2,2-difluoroethyl)-1H-pyrazol-4-yl)ethynyl)-N-((1s,4s)-4-((dimethylamino)methyl)cyclohexyl)pyridin-4-amine (119 mg, 0.283 mmol) prepared in Step 1 was used instead of 1-(2-chloro-5-((1-methyl-1H-pyrazol-4-yl)ethynyl)pyridin-4-yl)-4-methylpiperazine. $^1$H-NMR (DMSO-d$_6$, 400 MHz) δ 8.63 (s, 1H), 8.44-8.42 (m, 1H), 8.16 (s, 1H), 8.06 (s, 1H), 7.80 (s, 1H), 7.47 (brs, 1H), 7.30 (brs, 1H), 6.39 (t, 1H), 5.47 (d, 1H), 4.68 (t, 1H), 3.69 (brs, 1H), 2.10 (s, 8H), 1.76-1.59 (m, 8H), 1.34-1.24 (m, 6H); MS (ESI) m/z=651.3 (M+H)$^+$ Example 312. N$^2$-(2-(1-(Cyclopropylsulfonyl)-1H-pyrazol-4-yl)pyrimidin-4-yl)-N$^2$-((1s, 4s)-4-((dimethylamino)methyl)cyclohexyl)-5-((1-methyl-1H-pyrazol-4-yl)ethynyl)pyridine-2,4-diamine Step 1. 2-Chloro-N-((1s,4S)-4-((dimethylamino)methyl)cyclohexyl)-5-((1-methyl-1H-pyrazol-4-yl)ethynyl)pyridin-4-amine The title compound as a solid (98 mg) was prepared in the same fashion as Step 2 in Example 1 except that 2-chloro-N-((1s,4s)-4-((dimethylamino)methyl)cyclohexyl)-5-iodopyridin-4-amine (150 mg, 0.381 mmol) prepared in Step 1 of Example 309 and 4-ethynyl-1-methyl-1H-pyrazole (40 mg, 0.381 mmol) were used instead of 1-(2-chloro-5-iodopyridin-4-yl)-4-methylpiperazine and 4-ethynyl-1-methyl-1H-pyrazole. MS (ESI) m/z=372.0 (M+H)$^+$ Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-((1-methyl-1H-pyrazol-4-yl)ethynyl)pyridine-2,4-diamine The title compound as a solid (6.7 mg) was prepared in the same fashion as Step 3 in Example 1 except that 2-chloro-N-((1s,4s)-4-((dimethylamino)methyl)cyclohexyl)-5-((1-methyl-1H-pyrazol-4-yl)ethynyl)pyridin-4-amine (98 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.69 (s, 1H), 8.42 (s, 1H), 8.33 (d, 1H), 8.00 (s, 1H), 7.88 (s, 1H), 7.65 (s, 1H), 7.31-7.28 (m, 2H), 3.92 (s, 3H), 3.88-3.87 (m, 1H), 3.06-3.03 (m, 1H), 2.28-2.21 (m, 9H), 1.95-1.72 (m, 9H), 1.46-1.43 (m, 2H), 1.29-1.26 (m, 4H); MS (ESI) m/z=601.2 (M+H)$^+$ Example 313. 5-((1-Cyclopropyl-1H-pyrazol-4-yl)ethynyl)-N$^2$-(2-(1-(cyclopropylsulfonyl)-1H-pyrazol-4-yl)pyrimidin-4-yl)-N$^4$-((1s,4s)-4-((dimethylamino)methyl)cyclohexyl)pyridine-2,4-diamine Step 1. 2-Chloro-5-((1-cyclopropyl-1H-pyrazol-4-yl)ethynyl)-N-((1s,4s)-4-((dimethylamino)methyl)cyclohexyl)pyridin-4-amine The title compound as a solid (105 mg) was prepared in the same fashion as Step 2 in Example 1 except that 2-chloro-N-((1s,4s)-4-((dimethylamino)methyl)cyclohexyl)-5-iodopyridin-4-amine (150 mg, 0.381 mmol) prepared in Step 1 of Example 309 and 1-cyclopropyl-4-ethynyl-1H-pyrazole (50 mg, 0.381 mmol) were used instead of 1-(2-chloro-5-iodopyridin-4-yl)-4-methylpiperazine and 4-ethynyl-1-methyl-1H-pyrazole. MS (ESI) m/z=398.0 (M+H)$^+$ Step 2. 5-((1-Cyclopropyl-1H-pyrazol-4-yl)ethynyl)-N$^2$-(2-(1-(cyclopropylsulfonyl)-1H-pyrazol-4-yl)pyrimidin-4-yl)-N$^4$-((1s,4s)-4-((dimethylamino)methyl)cyclohexyl)pyridine-2,4-diamine The title compound as a solid (12.1 mg) was prepared in the same fashion as Step 3 in Example 1 except that 2-chloro-5-((1-cyclopropyl-1H-pyrazol-4-yl)ethynyl)-N-((1s,4s)-4-((dimethylamino)methyl)cyclohexyl)pyridin-4-amine (105 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.66 (s, 1H), 8.40 (s, 1H), 8.31 (d, 1H), 7.96 (d, 2H), 7.63 (s, 1H), 7.27-7.26 (m, 2H), 3.84 (brs, 1H), 3.72-3.66 (m, 1H), 3.08-3.01 (m, 1H), 2.26-2.19 (m, 9H), 1.93-1.70 (m, 8H), 1.47-1.43 (m, 2H), 1.29-1.09 (m, 8H); MS (ESI) m/z 627.3 (M+H)$^+$ Example 314. N²-(2-(1-(Cyclopropylsulfonyl)-1H-pyrazol-4-yl)pyrimidin-4-yl)-N²-((1s,4s)-4-((dimethylamino)methyl)cyclohexyl)-5-((1-(trifluoromethyl)-1H-pyrazol-4-yl)ethynyl)pyridine-2,4-diamine Step 1. 2-Chloro-N-((1s,4s)-4-((dimethylamino)methyl)cyclohexyl)-5-((1-(trifluoromethyl)-1H-pyrazol-4-yl)ethynyl)pyridin-4-amine The title compound as a solid (112 mg) was prepared in the same fashion as Step 2 in Example 1 except that 2-chloro-N-((1s,4S)-4-((dimethylamino)methyl)cyclohexyl)-5-iodopyridin-4-amine (150 mg, 0.381 mmol) prepared in Step 1 of Example 309 and 4-ethynyl-1-(trifluoromethyl)-1H-pyrazole (61 mg, 0.381 mmol) were used instead of 1-(2-chloro-5-iodopyridin-4-yl)-4-methylpiperazine and 4-ethynyl-1-methyl-1H-pyrazole. MS (ESI) m/z=426.1 (M+H)⁺

Step 2. N²-(2-(1-(Cyclopropylsulfonyl)-1H-pyrazol-4-yl)pyrimidin-4-yl)-N²-((1s,4s)-4-((dimethylamino)methyl)cyclohexyl)-5-((1-(trifluoromethyl)-1H-pyrazol-4-yl)ethynyl)pyridine-2,4-diamine The title compound as a solid (12.1 mg) was prepared in the same fashion as Step 3 in Example 1 except that 2-chloro-N-((1s,4s)-4-((dimethylamino)methyl)cyclohexyl)-5-((1-(trifluoromethyl)-1H-pyrazol-4-yl)ethynyl)pyridin-4-amine (112 mg, 0.264 mmol) prepared in Step 1 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.69 (s, 1H), 8.54 (s, 1H), 8.42 (s, 1H), 8.04-8.02 (m, 2H), 7.32-7.30 (m, 2H), 3.85 (brs, 1H), 3.08-3.02 (m, 1H), 2.25 (s, 6H), 1.94-1.72 (m, 8H), 1.47-1.43 (m, 2H), 1.33-1.28 (m, 5H); MS (ESI) m/z=655.3 (M+H)⁺

Example 315. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-((dimethylamino)methyl)piperidin-4-ol Step 1. 1-(2-Chloro-5-iodopyridin-4-yl)-4-((dimethylamino)methyl)piperidin-4-ol The title compound (2.17 g) was prepared in the same fashion as Step 1 in Example 304 except that 4-((dimethylamino)methyl)piperidin-4-ol (922 mg, 5.827 mmol) was used instead of (1s,4s)-4-amino-1-(hydroxymethyl)cyclohexan-1-ol. MS (ESI) m/z=395.9 (M+H)⁺

Step 2. 1-(2-Chloro-5-((1-methyl-1H-pyrazol-4-yl)ethynyl)pyridin-4-yl)-4-((dimethylamino)methyl)piperidin-4-ol The title compound as a solid (100 mg) was prepared in the same fashion as Step 2 in Example 1 except that 1-(2-chloro-5-iodopyridin-4-yl)-4-((dimethylamino)methyl)piperidin-4-ol (151 mg, 0.381 mmol) prepared in Step 1 and 4-ethynyl-1-methyl-1H-pyrazole (40 mg, 0.381 mmol) were used instead of 1-(2-chloro-5-iodopyridin-4-yl)-4-methylpiperazine and 4-ethynyl-1-methyl-1H-pyrazole. MS (ESI) m/z=374.0 (M+H)⁺

Step 3. 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-((dimethylamino)methyl)piperidin-4-ol The title compound as a solid (6.9 mg) was prepared in the same fashion as Step 3 in Example 1 except that 1-(2-chloro-5-((1-methyl-1H-pyrazol-4-yl)ethynyl)pyridin-4-yl)-4-((dimethylamino)methyl)piperidin-4-ol (99 mg, 0.264 mmol) prepared in Step 2 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.68 (s, 1H), 8.40 (s, 1H), 8.32 (s, 1H), 8.10 (s, 1H), 7.82 (s, 1H), 7.61 (s, 1H), 7.39 (s, 2H), 3.91 (s, 3H), 3.75 (s, 2H), 3.04 (brs, 1H), 2.42-2.37 (m, 8H), 1.80-1.78 (m, 4H), 1.45-1.27 (m, 4H); MS (ESI) m/z=603.3 (M+H)⁺

Example 316. 1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-((dimethylamino)methyl)piperidin-4-ol Step 1. 1-(2-Chloro-5-((1-cyclopropyl-1H-pyrazol-4-yl)ethynyl)pyridin-4-yl)-4-((dimethylamino)methyl)piperidin-4-ol The title compound as a solid (90 mg) was prepared in the same fashion as Step 2 in Example 1 except that 1-(2-chloro-5-iodopyridin-4-yl)-4-((dimethylamino)methyl)piperidin-4-ol (151 mg, 0.381 mmol) prepared in Step 1 of Example 315 and 1-cyclopropyl-4-ethynyl-1H-pyrazole (50 mg, 0.381 mmol) were used instead of 1-(2-chloro-5-iodopyridin-4-yl)-4-methylpiperazine and 4-ethynyl-1-methyl-1H-pyrazole. MS (ESI) m/z=400.0 (M+H)⁺

Step 2. 1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-((dimethylamino)methyl)piperidin-4-ol The title compound as a solid (4.8 mg) was prepared in the same fashion as Step 3 in Example 1 except that 1-(2-chloro-5-((1-cyclopropyl-1H-pyrazol-4-yl)ethynyl)pyridin-4-yl)-4-((dimethylamino)methyl)piperidin-4-ol (106 mg, 0.264 mmol) prepared in Step 1 was used instead of 1-(2-chloro-5-((1-methyl-1H-pyrazol-4-yl)ethynyl)pyridin-4-yl)-4-methylpiperazine. ¹H-NMR (MeOD, 400 MHz) δ 8.69 (s, 1H), 8.41 (s, 1H), 8.33 (s, 1H), 8.10 (s, 1H), 7.91 (s, 1H), 7.61 (s, 1H), 7.40 (s, 2H), 3.86-3.68 (m, 4H), 3.05 (brs, 1H), 2.43-2.37 (m, 10H), 1.45-1.07 (m, 10H); MS (ESI) m/z=629.3 (M+H)⁺

Example 317. 1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-((dimethylamino)methyl)piperidin-4-ol Step 1. 1-(2-Chloro-5-((1-(trifluoromethyl)-1H-pyrazol-4-yl)ethynyl)pyridin-4-yl)-4-((dimethylamino)methyl)piperidin-4-ol The title compound as a solid (110 mg) was prepared in the same fashion as Step 2 in Example 1 except that 1-(2-chloro-5-iodopyridin-4-yl)-4-((dimethylamino)methyl)piperidin-4-ol (151 mg, 0.381 mmol) prepared in Step 1 of Example 315 and 4-ethynyl-1-(trifluoromethyl)-1H-pyrazole (61 mg, 0.381 mmol) were used instead of 1-(2-chloro-5-iodopyridin-4-yl)-4-methylpiperazine and 4-ethynyl-1-methyl-1H-pyrazole. MS (ESI) m/z=428.0 (M+H)⁺

Step 2. 1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-((dimethylamino)methyl)piperidin-4-ol The title compound as a solid (2.2 mg) was prepared in the same fashion as Step 3 in Example 1 except that 1-(2-chloro- 5-((1-(trifluoromethyl)-1H-pyrazol-4-yl)ethynyl)pyridin-4-yl)-4-((dimethylamino)methyl)piperidin-4-ol (113 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.74 (s, 1H), 8.50-8.39 (m, 3H), 8.21 (s, 1H), 8.00 (s, 1H), 7.49-7.46 (m, 2H), 3.80 (s, 2H), 3.06-3.01 (m, 1H), 2.50-2.42 (m, 7H), 2.03 (s, 1H), 1.83-1.20 (m, 11H); MS (ESI) m/z=657.2 (M+H)$^+$ Example 318. 2-(1-(Cyclopropylsulfonyl)-1H-pyrazol-4-yl)-N-(5-((1-methyl-1H-pyrazol-4-yl)ethynyl)-4-(9-methyl-3,9-diazaspiro[5.5]undecan-3-yl)pyridin-2-yl)pyrimidin-4-amine Step 1. 3-(2-Chloro-5-iodopyridin-4-yl)-9-methyl-3,9-diazaspiro[5.5]undecane The title compound (2.0 g) was prepared in the same fashion as Step 1 in Example 304 except that 3-methyl-3,9-diazaspiro[5.5]undecane (980 mg, 5.827 mmol) was used instead of (1s,4s)-4-amino-1-(hydroxymethyl)cyclohexan-1-ol. MS (ESI) m/z=405.9 (M+H)$^+$ Step 2. 3-(2-Chloro-5-((1-methyl-1H-pyrazol-4-yl)ethynyl)pyridin-4-yl)-9-methyl-3,9-diazaspiro[5.5]undecane The title compound as a solid (101 mg) was prepared in the same fashion as Step 2 in Example 1 except that 3-(2-chloro-5-iodopyridin-4-yl)-9-methyl-3,9-diazaspiro[5.5]undecane (150 mg, 0.37 mmol) prepared in Step 1 and 4-ethynyl-1-methyl-1H-pyrazole (39 mg, 0.37 mmol) were used instead of 1-(2-chloro-5-iodopyridin-4-yl)-4-methylpiperazine and 4-ethynyl-1-methyl-1H-pyrazole. MS (ESI) m/z=384.0 (M+H)$^+$ Step 3. 2-(1-(Cyclopropylsulfonyl)-1H-pyrazol-4-yl)-N-(5-((1-methyl-1H-pyrazol-4-yl)ethynyl)-4-(9-methyl-3,9-diazaspiro[5.5]undecan-3-yl)pyridin-2-yl)pyrimidin-4-amine The title compound as a solid (10.2 mg) was prepared in the same fashion as Step 3 in Example 1 except that 3-(2-chloro-5-((1-methyl-1H-pyrazol-4-yl)ethynyl)pyridin-4-yl)-9-methyl-3,9-diazaspiro[5.5]undecane (101.3 mg, 0.264 mmol) prepared in Step 2 was used instead of 1-(2-chloro-5-((1-methyl-1H-pyrazol-4-yl)ethynyl)pyridin-4-yl)-4-methylpiperazine. MS (ESI) m/z=613.2 (M+H)$^+$ Example 319. N-(5-((1-Cyclopropyl-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine Step 1. 3-(2-Chloro-5-((1-cyclopropyl-1H-pyrazol-4-yl)ethynyl)pyridin-4-yl)-9-methyl-3,9-diazaspiro[5.5]undecane The title compound as a solid (108 mg) was prepared in the same fashion as Step 2 in Example 1 except that 3-(2-chloro-5-iodopyridin-4-yl)-9-methyl-3,9-diazaspiro[5.5]undecane (150 mg, 0.37 mmol) prepared in Step 1 of Example 318 and 1-cyclopropyl-4-ethynyl-1H-pyrazole (49 mg, 0.37 mmol) were used instead of 1-(2-chloro-5-iodopyridin-4-yl)-4-methylpiperazine and 4-ethynyl-1-methyl-1H-pyrazole. MS (ESI) m/z=410.0 (M+H)$^+$ Step 2. N-(5-((1-Cyclopropyl-1H-pyrazol-4-yl)ethynyl)-4-(9-methyl-3,9 diazaspiro[5.5]undecan-3-yl)pyridin-2-yl)-2-(1-(cyclopropylsulfonyl)-1H-pyrazol-4-yl)pyrimidin-4-amine The title compound as a solid (11.8 mg) was prepared in the same fashion as Step 3 in Example 1 except that 3-(2-chloro-5-((1-cyclopropyl-1H-pyrazol-4-yl)ethynyl)pyridin-4-yl)-9-methyl-3,9-diazaspiro[5.5]undecane (113 mg, 0.264 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=639.3 (M+H)$^+$ Example 320. N-(5-((1-(Cyclopropylmethyl)-1H-pyrazol-4-yl)ethynyl)-4-(9-methyl-3,9 diazaspiro[5.5]undecan-3-yl)pyridin-2-yl)-2-(1-(cyclopropylsulfonyl)-1H-pyrazol-4-yl)pyrimidin-4-amine Step 1. 3-(2-Chloro-5-((1-(cyclopropylmethyl)-1H-pyrazol-4-yl)ethynyl)pyridin-4-yl)-9-methyl-3,9-diazaspiro[5.5]undecane The title compound as a solid (103 mg) was prepared in the same fashion as Step 2 in Example 1 except that 3-(2-chloro-5-iodopyridin-4-yl)-9-methyl-3,9-diazaspiro[5.5]undecane (150 mg, 0.37 mmol) prepared in Step 1 of Example 318 and 1-(cyclopropylmethyl)-4-ethynyl-1H-pyrazole (54 mg, 0.37 mmol) were used instead of 1-(2-chloro-5-iodopyridin-4-yl)-4-methylpiperazine and 4-ethynyl-1-methyl-1H-pyrazole. MS (ESI) m/z=424.1 (M+H)$^+$ Step 2. N-(5-((1-(Cyclopropylmethyl)-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine The title compound as a solid (14.4 mg) was prepared in the same fashion as Step 3 in Example 1 except that 3-(2-chloro-5-((1-(cyclopropylmethyl)-1H-pyrazol-4-yl)ethynyl)pyridin-4-yl)-9-methyl-3,9-diazaspiro[5.5]undecane (104 mg, 0.245 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=653.3 (M+H)$^+$ Example 321. 2-(1-(Cyclopropylsulfonyl)-1H-pyrazol-4-yl)-N-(5-((1-(difluoromethyl)-1H-pyrazol-4-yl)ethynyl)-4-(9-methyl-3,9-diazaspiro[5.5]undecan-3-yl)pyridin-2-yl)pyrimidin-4-amine Step 1. 3-(2-Chloro-5-((1-(difluoromethyl)-1H-pyrazol-4-yl)ethynyl)pyridin-4-yl)-9-methyl-3,9-diazaspiro[5.5]undecane The title compound as a solid (102 mg) was prepared in the same fashion as Step 2 in Example 1 except that 3-(2-chloro-5-iodopyridin-4-yl)-9-methyl-3,9-diazaspiro[5.5]undecane (150 mg, 0.37 mmol) prepared in Step 1 of Example 318 and 1-(difluoromethyl)-4-ethynyl-1H-pyrazole (53 mg, 0.37 mmol) were used instead of 1-(2-chloro-5-iodopyridin-4-yl)-4-methylpiperazine and 4-ethynyl-1-methyl-1H-pyrazole. MS (ESI) m/z=420.0 (M+H)$^+$

Step 2. 2-(1-(Cyclopropylsulfonyl)-1H-pyrazol-4-yl)-N-(5-((1-(difluoromethyl)-1H-pyrazol-4-yl)ethynyl)-4-(9-methyl-3,9-diazaspiro[5.5]undecan-3-yl)pyridin-2-yl)pyrimidin-4-amine The title compound as a solid (17.3 mg) was prepared in the same fashion as Step 3 in Example 1 except that 3-(2-chloro-5-((1-(difluoromethyl)-1H-pyrazol-4-yl)ethynyl)pyridin-4-yl)-9-methyl-3,9-diazaspiro[5.5]undecane (103 mg, 0.245 mmol) in Step 1 was used instead of 1-(2-chloro-5-((1-methyl-1H-pyrazol-4-yl)ethynyl)pyridin-4-yl)-4-methylpiperazine. MS (ESI) m/z=663.3 (M+H)$^+$

Example 322. 2-(1-(Cyclopropylsulfonyl)-1H-pyrazol-4-yl)-N-(5-((1-(2,2-difluoroethyl)-1H-pyrazol-4-yl)ethynyl)-4-(9-methyl-3,9-diazaspiro[5.5]undecan-3-yl)pyridin-2-yl)pyrimidin-4-amine

Step 1. 3-(2-Chloro-5-((1-(2,2-difluoroethyl)-1H-pyrazol-4-yl)ethynyl)pyridin-4-yl)-9-methyl-3,9-diazaspiro[5.5]undecane The title compound as a solid (106 mg) was prepared in the same fashion as Step 2 in Example 1 except that 3-(2-chloro-5-iodopyridin-4-yl)-9-methyl-3,9-diazaspiro[5.5]undecane (150 mg, 0.37 mmol) prepared in Step 1 of Example 318 and 1-(2,2-difluoroethyl)-4-ethynyl-1H-pyrazole (58 mg, 0.37 mmol) were used instead of 1-(2-chloro-5-iodopyridin-4-yl)-4-methylpiperazine and 4-ethynyl-1-methyl-1H-pyrazole. MS (ESI) m/z=434.1 (M+H)$^+$

Step 2. 2-(1-(Cyclopropylsulfonyl)-1H-pyrazol-4-yl)-N-(5-((1-(2,2-difluoroethyl)-1H-pyrazol-4-yl)ethynyl)-4-(9-methyl-3,9-diazaspiro[5.5]undecan-3-yl)pyridin-2-yl)pyrimidin-4-amine The title compound as a solid (12.6 mg) was prepared in the same fashion as Step 3 in Example 1 except that 3-(2-chloro-5-((1-(2,2-difluoroethyl)-1H-pyrazol-4-yl)ethynyl)pyridin-4-yl)-9-methyl-3,9-diazaspiro[5.5]undecane (106 mg, 0.245 mmol) in Step 1 was used instead of 1-(2-chloro-5-((1-methyl-1H-pyrazol-4-yl)ethynyl)pyridin-4-yl)-4-methylpiperazine. MS (ESI) m/z=663.3 (M+H)$^+$

Example 323. (1s, 4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)-1-methylcyclohexan-1-ol

Step 1. (1s,4s)-4-((2-Chloro-5-((1-(2,2-difluoroethyl)-1H-pyrazol-4-yl)ethynyl)pyridin-4-yl)amino)-1-methylcyclohexan-1-ol The title compound as a solid (104 mg) was prepared in the same fashion as Step 1 in Example 65 except that cis-4-amino-1-methylcyclohexanol (45 mg, 0.35 mmol) and 2-chloro-5-((1-(2,2-difluoroethyl)-1H-pyrazol-4-yl)ethynyl)-4-fluoropyridine (100 mg, 0.35 mmol) prepared in Reference Example 52 were used instead of 4-(trifluoromethyl)piperidine HCl and 2-chloro-4-fluoro-5-((1-methyl-1H-pyrazol-4-yl)ethynyl)pyridine. MS (ESI) m/z=395.0 (M+H)$^+$

Step 2. (1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)-1-methylcyclohexan-1-ol The title compound as a solid (16.3 mg) was prepared in the same fashion as Step 3 in Example 1 except that (1s,4s)-4-((2-chloro-5-((1-(2,2-difluoroethyl)-1H-pyrazol-4-yl)ethynyl)pyridin-4-yl)amino)-1-methylcyclohexan-1-ol (104 mg, 0.264 mmol) in Step 1 was used instead of 1-(2-chloro-5-((1-methyl-1H-pyrazol-4-yl)ethynyl)pyridin-4-yl)-4-methylpiperazine. MS (ESI) m/z=624.2 (M+H)$^+$

Example 324. ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol

Step 1. ((1s,4s)-4-((2-Chloro-5-((1-(2,2-difluoroethyl)-1H-pyrazol-4-yl)ethynyl)pyridin-4-yl)amino)cyclohexyl)methanol The title compound as a solid (104 mg) was prepared in the same fashion as Step 1 in Example 65 except that cis-(4-aminocyclohexyl)methanol HCl (58 mg, 0.35 mmol) and 2-chloro-5-((1-(2,2-difluoroethyl)-1H-pyrazol-4-yl)ethynyl)-4-fluoropyridine (100 mg, 0.35 mmol) prepared in Reference Example 52 were used instead of 4-(trifluoromethyl)piperidine HCl and 2-chloro-4-fluoro-5-((1-methyl-1H-pyrazol-4-yl)ethynyl)pyridine. MS (ESI) m/z=395.0 (M+H)$^+$

Step 2. ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol The title compound as a solid (10.3 mg) was prepared in the same fashion as Step 3 in Example 1 except that ((1s,4s)-4-((2-chloro-5-((1-(2,2-difluoroethyl)-1H-pyrazol-4-yl)ethynyl)pyridin-4-yl)amino)cyclohexyl)methanol (104 mg, 0.264 mmol) in Step 1 was used instead of 1-(2-chloro-5-((1-methyl-1H-pyrazol-4-yl)ethynyl)pyridin-4-yl)-4-methylpiperazine. MS (ESI) m/z=624.3 (M+H)$^+$

Example 325. 2-((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)propan-2-ol

Step 1. 2-((1s,4s)-4-((2-Chloro-5-((1-(2,2-difluoroethyl)-1H-pyrazol-4-yl)ethynyl)pyridin-4-yl)amino)cyclohexyl)propan-2-ol The title compound as a solid (111 mg) was prepared in the same fashion as Step 1 in Example 65 except that 2-((1s,4s)-4-aminocyclohexyl)propan-2-ol (55 mg, 0.35 mmol) and 2-chloro-5-((1-(2,2-difluoroethyl)-1H-pyrazol-4-yl)ethynyl)-4-fluoropyridine (100 mg, 0.35 mmol) prepared in Reference Example 52 were used instead of 4-(trifluoromethyl)piperidine HCl and 2-chloro-4-fluoro-54(1-methyl-1H-pyrazol-4-yl)ethynyl)pyridine. MS (ESI) m/z=423.0 (M+H)$^+$

Step 2. 2-((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)propan-2-ol The title compound as a solid (5.2 mg) was prepared in the same fashion as Step 3 in Example 1 except that 2-((1s,4s)-4-((2-chloro-5-((1-(2,2-difluoroethyl)-1H-pyrazol-4-yl)ethynyl)pyridin-4-yl)amino)cyclohexyl)propan-2-ol (112 mg, 0.264 mmol) in Step 1 was used instead of 1-(2-chloro- 5-((1-methyl-1H-pyrazol-4-yl)ethynyl)pyridin-4-yl)-4-methylpiperazine. MS (ESI) m/z=652.3 (M+H)⁺

Example 326. (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)-1-methylcyclohexan-1-ol Step 1. (1s,4s)-4-((2-Chloro-5-((1-(2,2-difluorocyclopropyl)-1H-pyrazol-4-yl)ethynyl)pyridin-4-yl)amino)-1-methylcyclohexan-1-ol The title compound as a solid (60 mg) was prepared in the same fashion as Step 1 in Example 65 except that cis-4-amino-1-methylcyclohexanol (43 mg, 0.336 mmol) and 2-chloro-5-((1-(2,2-difluorocyclopropyl)-1H-pyrazol-4-yl)ethynyl)-4-fluoropyridine (100 mg, 0.336 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine. MS (ESI) m/z=407.0 (M+H)⁺

Step 2. (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)-1-methylcyclohexan-1-ol The title compound as a solid (14.1 mg) was prepared in the same fashion as Step 3 in Example 1 except that (1s,4s)-4-((2-chloro-5-((1-(2,2-difluorocyclopropyl)-1H-pyrazol-4-yl)ethynyl)pyridin-4-yl)amino)-1-methylcyclohexan-1-ol (58 mg, 0.143 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.69 (s, 1H), 8.43 (s, 1H), 8.32 (d, 1H), 8.04 (s, 1H), 7.98 (s, 1H), 7.73 (s, 1H), 7.35 (d, 1H), 7.13 (s, 1H), 4.37-4.35 (m, 1H), 3.47 (brs, 1H), 3.04-3.00 (m, 1H), 2.35-2.21 (m, 4H), 1.92-1.90 (m, 2H), 1.72-1.66 (m, 4H), 1.59-1.56 (m, 2H), 1.45-1.42 (m, 2H), 1.28-1.24 (m, 4H); MS (ESI) m/z=636.2 (M+H)⁺

Example 327. ((1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol Step 1. ((1s,4s)-4-((2-Chloro-5-((1-(2,2-difluorocyclopropyl)-1H-pyrazol-4-yl)ethynyl)pyridin-4-yl)amino)cyclohexyl)methanol The title compound as a solid (51 mg) was prepared in the same fashion as Step 1 in Example 65 except that cis-(4-aminocyclohexyl)methanol HCl (56 mg, 0.336 mmol) and 2-chloro-5-((1-(2,2-difluorocyclopropyl)-1H-pyrazol-4-yl)ethynyl)-4-fluoropyridine (100 mg, 0.336 mmol) prepared in Reference Example 19 were used instead of 4-(trifluoromethyl)piperidine HCl and 2-chloro-4-fluoro-5-((1-methyl-1H-pyrazol-4-yl)ethynyl)pyridine. MS (ESI) m/z=407.0 (M+H)⁺

Step 2. ((1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol The title compound as a solid (9.4 mg) was prepared in the same fashion as Step 3 in Example 1 except that ((1s,4s)-4-((2-chloro-5-((1-(2,2-difluorocyclopropyl)-1H-pyrazol-4-yl)ethynyl)pyridin-4-yl)amino)cyclohexyl)methanol (58 mg, 0.143 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.68 (s, 1H), 8.42 (s, 1H), 8.33 (d, 1H), 8.05 (s, 1H), 8.00 (s, 1H), 7.73 (s, 1H), 7.30-7.26 (m, 2H), 4.38-4.37 (m, 1H), 3.89-3.87 (m, 1H), 3.44-3.43 (d, 2H), 3.05-3.03 (m, 1H), 2.37-2.25 (m, 2H), 1.99-1.68 (m, 8H), 1.46-1.26 (m, 6H); MS (ESI) m/z.=636.2 (M+H)⁺

Example 328. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-ol Step 1. 1-(1-(2-Chloro-5-((1-(trifluoromethyl)-1H-pyrazol-4-yl)ethynyl)pyridin-4-yl)piperidin-4-yl)ethan-1-ol The title compound as a solid (60 mg) was prepared in the same fashion as Step 1 in Example 65 except that 1-(piperidine-4-yl)ethan-1-ol (36 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=399.0 (M+H)⁺

Step 2. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-ol The title compound as a solid (2.2 mg) was prepared in the same fashion as Step 3 in Example 1 except that 1-(1-(2-chloro-5-((1-(trifluoromethyl)-1H-pyrazol-4-yl)ethynyl)pyridin-4-yl)piperidin-4-yl)ethan-1-ol (105 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl₃, 400 MHz) δ 8.67 (s, 1H), 8.46-8.43 (m, 2H), 8.24 (s, 1H), 7.98 (s, 1H), 7.87 (s, 1H), 7.57 (d, 2H), 7.06 (d, 1H), 4.20-4.14 (m, 2H), 3.71-3.68 (m, 1H), 2.96-2.82 (m, 3H), 2.09-2.05 (m, 1H), 1.61 (brs, 1H), 1.56-1.52 (m, 4H), 1.27-1.23 (m, 6H); MS (ESI) m/z=628.2 (M+H)⁺

Example 329. 2-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)propan-2-ol Step 1. 2-(1-(2-Chloro-5-((1-(trifluoromethyl)-1H-pyrazol-4-yl)ethynyl)pyridin-4-yl)piperidin-4-yl)propan-2-ol The title compound as a solid (100 mg) was prepared in the same fashion as Step 1 in Example 65 except that 2-(piperidin-4-yl)propan-2-ol (40 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=413.0 (M+H)⁺

Step 2. 2-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)propan-2-ol The title compound as a solid (4.2 mg) was prepared in the same fashion as Step 3 in Example 1 except that 2-(1-(2-chloro-5-((1-(trifluoromethyl)-1H-pyrazol-4-yl)ethynyl)pyridin-4-yl)piperidin-4-yl)propan-2-ol (100 mg, 0.242 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.46-8.43 (m, 2H), 8.25 (s, 1H), 7.98 (s, 1H), 7.87 (s, 1H), 7.67 (s, 1H), 7.57 (s, 1H), 7.05 (d, 1H), 4.21 (d, 2H), 2.92-2.82 (m, 3H), 2.00-1.98 (d, 1H), 1.64-1.51 (m, 7H), 1.26-1.24 (m, 8H); MS (ESI) m/z=642.2 (M+H)$^+$

Example 330. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)cyclopropan-1-ol

Step 1. 1-(1-(2-Chloro-5-((1-(trifluoromethyl)-1H-pyrazol-4-yl)ethynyl)pyridin-4-yl)piperidin-4-yl)cyclopropan-1-ol The title compound as a solid (97 mg) was prepared in the same fashion as Step 1 in Example 65 except that 1-(piperidin-4-yl)cyclopropan-1-ol (39 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=411.0 (M+H)$^+$

Step 2. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)cyclopropan-1-ol The title compound as a solid (4.7 mg) was prepared in the same fashion as Step 3 in Example 1 except that 1-(1-(2-chloro-5-((1-(trifluoromethyl)-1H-pyrazol-4-yl)ethynyl)pyridin-4-yl)piperidin-4-yl)cyclopropan-1-ol (108 mg, 0.264 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45-8.42 (m, 2H), 8.24 (s, 1H), 7.99 (s, 1H), 7.88 (s, 1H), 7.75 (s, 1H), 7.62 (s, 1H), 7.01 (d, 1H), 4.22 (d, 2H), 2.94-2.82 (m, 3H), 1.95-1.52 (m, 11H), 1.28-1.22 (m, 3H), 0.82-0.79 (m, 1H), 0.57-0.54 (m, 1H); MS (ESI) m/z=640.2 (M+H)$^+$

Example 331. ((1R,5S,6r)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-6-yl)methanol

Step 1. ((1R,5S,6r)-3-(2-Chloro-5-((1-(trifluoromethyl)-1H-pyrazol-4-yl)ethynyl)pyridin-4-yl)-3-azabicyclo[3.1.0]hexan-6-yl)methanol The title compound as a solid (93 mg) was prepared in the same fashion as Step 1 in Example 65 except that ((1R,5S,6r)-3-azabicyclo[3.1.0]hexan-6-yl)methanol (31 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=383.0 (M+H)$^+$

Step 2. ((1R,5S,6r)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-6-yl)methanol The title compound as a solid (1.8 mg) was prepared in the same fashion as Step 3 in Example 1 except that ((1R,5S,6r)-3-(2-chloro-5-((1-(trifluoromethyl)-1H-pyrazol-4-yl)ethynyl)pyridin-4-yl)-3-azabicyclo[3.1.0]hexan-6-yl)methanol (93 mg, 0.242 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.69 (s, 1H), 8.46 (s, 1H), 8.24 (s, 1H), 7.99 (s, 1H), 7.88 (s, 1H), 7.75 (s, 1H), 7.62 (s, 1H), 7.01 (d, 1H), 4.22 (d, 2H), 2.94-2.82 (m, 3H), 1.95-1.52 (m, 1H11), 1.28-1.22 (m, 3H), 0.82-0.79 (m, 1H), 0.57-0.54 (m, 1H); MS (ESI) m/z=612.2 (M+H)$^+$

Example 332. ((1R,3s,5S)-8-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-8-azabicyclo[3.2.1]octan-3-yl)methanol

Step 1. ((1R,3s,5S)-8-(2-Chloro-5-((1-(trifluoromethyl)-1H-pyrazol-4-yl)ethynyl)pyridin-4-yl)-8-azabicyclo[3.2.1]octan-3-yl)methanol The title compound as a solid (100 mg) was prepared in the same fashion as Step 1 in Example 65 except that ((1R,3s,5S)-8-azabicyclo[3.2.1]octan-3-yl)methanol HCl (49 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=411.0 (M+H)$^+$

Step 2. ((1R,3s,5S)-8-(2-((2-(1-(cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-8-azabicyclo[3.2.1]octan-3-yl)methanol The title compound as a solid (6.1 mg) was prepared in the same fashion as Step 3 in Example 1 except that ((1R,3s,5S)-8-(2-chloro-5-((1-(trifluoromethyl)-1H-pyrazol-4-yl)ethynyl)pyridin-4-yl)-8-azabicyclo[3.2.1]octan-3-yl)methanol (101 mg, 0.245 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.44 (s, 1H), 8.41 (d, 1H), 8.15 (s, 1H), 8.01 (brs, 1H), 7.95 (s, 1H), 7.84 (s, 1H), 7.53 (s, 1H), 6.98 (d, 1H), 5.02 (brs, 2H), 3.47 (d, 2H), 2.86-2.82 (m, 1H), 2.25-2.21 (m, 1H), 2.14-2.12 (m, 2H), 1.93-1.88 (m, 2H), 1.56-1.52 (m, 2H), 1.29-1.21 (m, 5H), 1.03-1.00 (m, 1H); MS (ESI) m/z=640.2 (M+H)$^+$ Example 333. ((1S,5S)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-1-yl)methanol Step 1. ((1S,5S)-3-(2-Chloro-5-((1-(trifluoromethyl)-1H-pyrazol-4-yl)ethynyl)pyridin-4-yl)-3-azabicyclo[3.1.0]hexan-1-yl)methanol The title compound as a solid (93 mg) was prepared in the same fashion as Step 1 in Example 65 except that ((1S,5S)-3-azabicyclo[3.1.0]hexan-1-yl)methanol (31 mg, 0.276 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=383.0 (M+H)$^+$ Step 2. ((1 S,5S)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-1-yl)methanol The title compound as a solid (1 mg) was prepared in the same fashion as Step 3 in Example 1 except that ((1S,5S)-3-(2-chloro-5-((1-(trifluoromethyl)-1H-pyrazol-4-yl)ethynyl)pyridin-4-yl)-3-azabicyclo[3.1.0]hexan-1-yl)methanol (94 mg, 0.245 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.49 (s, 1H), 8.41 (d, 1H), 8.10 (s, 1H), 7.98 (s, 1H), 7.87 (s, 1H), 7.45 (s, 1H), 6.91 (d, 1H), 4.29-4.22 (m, 2H), 3.88-3.81 (m, 4H), 2.87-2.86 (m, 1H), 2.38-2.34 (m, 1H), 1.58-1.55 (m, 2H), 1.35-1.24 (m, 9H), 1.03-0.91 (m, 4H), 0.67-0.65 (m, 1H); MS (ESI) m/z=612.2 (M+H)$^+$ Example 334. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-one Step 1. 1-(1-(2-Chloro-5-((1-(trifluoromethyl)-1H-pyrazol-4-yl)ethynyl)pyridin-4-yl)piperidin-4-yl)ethan-1-one The title compound as a solid (121 mg) was prepared in the same fashion as Step 1 in Example 65 except that 1-(4-piperidyl)ethanone (44 mg, 0.345 mmol) and 2-chloro-4-fluoro-5-((1-(trifluoromethyl)-1H-pyrazol-4-yl)ethynyl)pyridine (80 mg, 0.276 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=397.0 (M+H)$^+$ Step 2. 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-one The title compound as a solid (7.5 mg) was prepared in the same fashion as Step 3 in Example 1 except that 1-(1-(2-chloro-5-((1-(trifluoromethyl)-1H-pyrazol-4-yl)ethynyl)pyridin-4-yl)piperidin-4-yl)ethan-1-one (97 mg, 0.245 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.42 (d, 1H), 8.25 (s, 1H), 8.05 (s, 1H), 7.99 (s, 1H), 7.87 (s, 1H), 7.67 (s, 1H), 6.98 (d, 1H), 4.14-4.08 (m, 2H), 3.02 (t, 2H), 2.86-2.81 (m, 1H), 2.65-2.59 (m, 1H), 2.24 (s, 3H), 2.11-2.08 (m, 2H), 1.90-1.80 (m, 3H), 1.56-1.52 (m, 2H), 1.28-1.21 (m, 2H); MS (ESI) m/z=626.2 (M+H)$^+$ Example 335. 2-(1-(Cyclopropylsulfonyl)-1H-pyrazol-4-yl)-N-(4-(4-(2-(dimethylamino)ethyl)piperidin-1-yl)-5-((1-(trifluoromethyl)-1H-pyrazol-4-yl)ethynyl)pyridin-2-yl)pyrimidin-4-amine Step 1. 2-(1-(2-Chloro-5-((1-(trifluoromethyl)-1H-pyrazol-4-yl)ethynyl)pyridin-4-yl)piperidin-4-yl)-N,N-dimethylethan-1-amine The title compound as a solid (55 mg) was prepared in the same fashion as Step 1 in Example 65 except that N,N-dimethyl-2-(piperidin-4-yl)ethan-1-amine (27 mg, 0.173 mmol) and 2-chloro-4-fluoro-5-((1-(trifluoromethyl)-1H-pyrazol-4-yl)ethynyl)pyridine (50 mg, 0.173 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=426.0 (M+H)$^+$ Step 2. 2-(1-(Cyclopropylsulfonyl)-1H-pyrazol-4-yl)-N-(4-(4-(2-(dimethylamino)ethyl)piperidin-1-yl)-5-((1-(trifluoromethyl)-1H-pyrazol-4-yl)ethynyl)pyridin-2-yl)pyrimidin-4-amine The title compound as a solid (4.1 mg) was prepared in the same fashion as Step 3 in Example 1 except that 2-(1-(2-chloro-5-((1-(trifluoromethyl)-1H-pyrazol-4-yl)ethynyl)pyridin-4-yl)piperidin-4-yl)-N,N-dimethylethan-1-amine (64 mg, 0.151 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45 (s, 1H), 8.43 (d, 1H), 8.24 (s, 1H), 7.98 (s, 1H), 7.87 (s, 1H), 7.67 (s, 1H), 7.49 (s, 1H), 7.09 (d, 1H), 4.09 (d, 2H), 2.93 (t, 2H), 2.88-2.81 (m, 1H), 2.40-2.36 (m, 2H), 2.27 (s, 6H), 1.92 (d, 2H), 1.63-1.61 (m, 1H), 1.54-1.40 (m, 6H), 1.28-1.24 (m, 2H); MS (ESI) m/z=655.2 (M+H)$^+$ Example 336. ((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)methanol Step 1. ((1s,4s)-4-((2-Chloro-5-((1-(trifluoromethyl)-1H-pyrazol-4-yl)ethynyl)pyridin-4-yl)amino)cyclohexyl)methanol The title compound as a solid (70 mg) was prepared in the same fashion as Step 1 in Example 65 except that cis-(4-aminocyclohexyl)methanol HCl (29 mg, 0.173 mmol) and 2-chloro-4-fluoro-5-((1-(trifluoromethyl)-1H-pyrazol-4-yl)ethynyl)pyridine (50 mg, 0.173 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=430.0 (M+H)$^+$ Step 2. ((1s, 4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)methanol The title compound as a solid (4.6 g) was prepared in the same fashion as Step 3 in Example 1 except that ((1s,4s)-

4-((2-cloro-5-((1-(trifluoromethyl)-1H-pyrazol-4-yl)ethynyl)pyridin-4-yl)amino)cyclohexyl)methanol (65 mg, 0.151 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.41 (d, 1H), 8.13 (s, 1H), 8.06 (s, 1H), 7.90 (s, 1H), 7.80 (brs, 1H), 7.31 (s, 1H), 7.04 (d, 1H), 5.32 (d, 1H), 3.93-3.91 (m, 1H), 3.56 (d, 2H), 2.86-2.81 (m, 1H), 2.00-1.97 (m, 2H), 1.88-1.81 (m, 2H), 1.75-1.66 (m, 4H), 1.56-1.52 (m, 2H), 1.43-1.34 (m, 2H), 1.29-1.20 (m, 3H); MS (ESI) m/z=628.2 (M+H)⁺

Example 337. 2-((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)propan-2-ol Step 1. 2-((1s,4s)-4-((2-Chloro-5-((1-(trifluoromethyl)-1H-pyrazol-4-yl)ethynyl)pyridin-4-yl)amino)cyclohexyl)propan-2-ol The title compound as a solid (64 mg) was prepared in the same fashion as Step 1 in Example 65 except that 2-((1s,4s)-4-aminocyclohexyl)propan-2-ol (29 mg, 0.173 mmol) and 2-chloro-4-fluoro-5-((1-(trifluoromethyl)-1H-pyrazol-4-yl)ethynyl)pyridine (50 mg, 0.173 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=430.0 (M+H)⁺

Step 2. 2-((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)propan-2-ol The title compound as a solid (3.8 mg) was prepared in the same fashion as Step 3 in Example 1 except that 2-((1s,4s)-4-((2-chloro-5-((1-(trifluoromethyl)-1H-pyrazol-4-yl)ethynyl)pyridin-4-yl)amino)cyclohexyl)propan-2-ol (64 mg, 0.151 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.41 (d, 1H), 8.13 (s, 1H), 8.08 (s, 1H), 7.90 (s, 1H), 7.76 (brs, 1H), 7.37 (brs, 1H), 7.00 (d, 1H), 5.42 (d, 1H), 3.98-3.96 (m, 1H), 2.87-2.81 (m, 1H), 2.11-2.08 (m, 2H), 1.82-1.76 (m, 5H), 1.57-1.52 (m, 2H), 1.44-1.27 (m, 7H); MS (ESI) m/z=656.3 (M+H)⁺

Example 338. (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-fluoropiperidin-4-yl)methanol Step 1. (1-(2-Chloro-5-((1-(trifluoromethyl)-1H-pyrazol-4-yl)ethynyl)pyridin-4-yl)-4-fluoropiperidin-4-yl)methanol The title compound as a solid (69 mg) was prepared in the same fashion as Step 1 in Example 65 except that (4-fluoropiperidin-4-yl)methanol HCl (29 mg, 0.173 mmol) and 2-chloro-4-fluoro-5-((1-(trifluoromethyl)-1H-pyrazol-4-yl)ethynyl)pyridine (50 mg, 0.173 mmol) prepared in Reference Example 23 were used instead of 4-(trifluoromethyl)piperidine HCl and 2-chloro-4-fluoro-5-((1-methyl-1H-pyrazol-4-yl)ethynyl)pyridine. MS (ESI) m/z=430.0 (M+H)⁺

Step 2. (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-fluoropiperidin-4-yl)methanol The title compound as a solid (4.8 mg) was prepared in the same fashion as Step 3 in Example 1 except that (1-(2-chloro-5-((1-(trifluoromethyl)-1H-pyrazol-4-yl)ethynyl)pyridin-4-yl)-4-fluoropiperidin-4-yl)methanol (61 mg, 0.151 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.66 (s, 1H), 8.46-8.45 (m, 1H), 8.27 (s, 1H), 7.98 (s, 1H), 7.86 (s, 1H), 7.58-7.51 (m, 2H), 7.10 (d, 1H), 3.94 (d, 1H), 3.74-3.67 (m, 3H), 3.41-3.30 (m, 2H), 2.86-2.83 (m, 1H), 2.19-2.13 (m, 2H), 2.05-2.03 (m, 1H), 1.96-1.81 (m, 2H), 1.26-1.23 (m, 3H); MS (ESI) m/z=632.2 (M+H)⁺

Example 339. (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol Step 1. 2-Chloro-4-fluoro-5-((1-(2,2,2-trifluoroethyl)-1H-pyrazol-4-yl)ethynyl)pyridine The title compound as a solid (890 mg) was prepared in the same fashion as Reference Example 18 except that 4-ethynyl-1-(2,2,2-trifluoroethyl)pyrazole (2.03 g, 11.654 mmol) was used instead of 4-ethynyl-1-methylpyrazole. MS (ESI) m/z=304.2 (M+H)⁺

Step 2. (1s,4s)-4-((2-Chloro-5-((1-(2,2,2-trifluoroethyl)-1H-pyrazol-4-yl)ethynyl)pyridin-4-yl)amino)cyclohexan-1-ol The title compound as a solid (60 mg) was prepared in the same fashion as Step 1 in Example 65 except that (1s,4s)-4-aminocyclohexan-1-ol HCl (50 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 were used instead of 4-(trifluoromethyl)piperidine HCl and 2-chloro-4-fluoro-5-((1-methyl-1H-pyrazol-4-yl)ethynyl)pyridine. MS (ESI) m/z=399.0 (M+H)⁺

Step 3. (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol The title compound as a solid (2.2 mg) was prepared in the same fashion as Step 3 in Example 1 except that (1s,4s)-4-((2-chloro-5-((1-(2,2,2-trifluoroethyl)-1H-pyrazol-4-yl)ethynyl)pyridin-4-yl)amino)cyclohexan-1-ol (83 mg, 0.207 mmol) prepared in Step 2 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.45 (s, 1H), 8.42 (d, 1H), 8.11 (s, 1H), 7.76 (s, 2H), 7.19 (brs, 1H), 7.13 (d, 1H), 5.20 (d, 1H), 4.74 (q, 2H), 3.97 (brs, 1H) 3.66-3.65 (m, 1H), 2.86-2.80 (m, 1H), 1.94-1.70 (m, 10H), 1.56-1.53 (m, 2H), 1.31-1.21 (m, 2H); MS (ESI) m/z=628.2 (M+H)⁺

Example 340. ((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)methanol

Step 1. ((1s,4s)-4-((2-Chloro-5-((1-(2,2,2-trifluoroethyl)-1H-pyrazol-4-yl)ethynyl)pyridin-4-yl)amino)cyclohexyl)methanol The title compound as a solid (92 mg) was prepared in the same fashion as Step 1 in Example 65 except that ((1s,4s)-4-aminocyclohexyl)methanol HCl (55 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=413.0 (M+H)$^+$

Step 2. ((1s, 4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)methanol The title compound as a solid (5.2 mg) was prepared in the same fashion as Step 3 in Example 1 except that ((1s,4s)-4-((2-chloro-5-((1-(2,2,2-trifluoroethyl)-1H-pyrazol-4-yl)ethynyl)pyridin-4-yl)amino)cyclohexyl)methanol (86 mg, 0.207 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.45 (s, 1H), 8.41 (d, 1H), 8.11 (s, 1H), 8.06 (s, 1H), 7.76 (d, 2H), 7.32 (brs, 1H), 7.04 (d, 1H), 5.38 (d, 1H), 4.74 (q, 2H), 3.93-3.91 (m, 1H), 3.54 (d, 2H), 2.85-2.82 (m, 1H), 2.00-1.67 (m, 8H), 1.54-1.51 (m, 2H), 1.41-1.20 (m, 2H); MS (ESI) m/z=642.3 (M+H)$^+$

Example 341. (1 S,3S)-3-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol

Step 1. (1S,3S)-3-((2-Chloro-5-((1-(2,2,2-trifluoroethyl)-1H-pyrazol-4-yl)ethynyl)pyridin-4-yl)amino)cyclohexan-1-ol The title compound as a solid (92 mg) was prepared in the same fashion as Step 1 in Example 65 except that (1S,3S)-3-aminocyclohexan-1-ol HCl (50 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=399.0 (M+H)$^+$

Step 2. (1S,3S)-3-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol The title compound as a solid (3.1 mg) was prepared in the same fashion as Step 3 in Example 1 except that (1S,3S)-3-((2-chloro-5-((1-(2,2,2-trifluoroethyl)-1H-pyrazol-4-yl)ethynyl)pyridin-4-yl)amino)cyclohexan-1-ol (83 mg, 0.207 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.50 (s, 1H), 8.41 (d, 1H), 8.10 (s, 1H), 7.74 (s, 1H), 7.18-7.14 (m, 3H), 4.99 (d, 1H), 4.74 (q, 2H), 4.17-4.16 (m, 1H), 2.86-2.83 (m, 1H), 1.72-1.62 (m, 4H), 1.56-1.45 (m, 2H), 1.29-1.19 (m, 4H); MS (ESI) m/z=628.2 (M+H)$^+$

Example 342. (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-fluoropiperidin-4-yl)methanol

Step 1. (1-(2-Chloro-5-((1-(2,2,2-trifluoroethyl)-1H-pyrazol-4-yl)ethynyl)pyridin-4-yl)-4-fluoropiperidin-4-yl)methanol The title compound as a solid (100 mg) was prepared in the same fashion as Step 1 in Example 65 except that (4-fluoropiperidin-4-yl)methanol (44 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=417.0 (M+H)$^+$

Step 2. (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-fluoropiperidin-4-yl)methanol The title compound as a solid (1.2 mg) was prepared in the same fashion as Step 3 in Example 1 except that (1-(2-chloro-5-((1-(2,2,2-trifluoroethyl)-1H-pyrazol-4-yl)ethynyl)pyridin-4-yl)-4-fluoropiperidin-4-yl)methanol (86 mg, 0.207 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44 (s, 2H), 8.25 (s, 1H), 7.70 (d, 2H), 7.58 (s, 1H), 7.10 (d, 1H), 4.74 (q, 2H), 3.96 (d, 2H), 3.73 (d, 2H), 3.32 (t, 1H), 2.86-2.83 (m, 1H), 2.16 (t, 1H), 1.75-1.56 (m, 4H), 1.30-1.21 (m, 4H); MS (ESI) m/z=646.2 (M+H)$^+$

Example 343. 1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)piperidin-3-ol

Step 1. 1-(2-Chloro-5-((1-(2,2,2-trifluoroethyl)-1H-pyrazol-4-yl)ethynyl)pyridin-4-yl)piperidin-3-ol The title compound as a solid (87 mg) was prepared in the same fashion as Step 1 in Example 65 except that piperidin-3-ol (33 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=385.0 (M+H)$^+$

Step 2. 1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)piperidin-3-ol The title compound as a solid (2.4 mg) was prepared in the same fashion as Step 3 in Example 1 except that 1-(2-chloro-5-((1-(2,2,2-trifluoroethyl)-1H-pyrazol-4-yl)ethynyl)pyridin-4-yl)piperidin-3-ol (80 mg, 0.207 mmol) prepared in Step 1 was used instead of 1-(2-chloro-5-((1-methyl-1H-pyrazol-4-yl)ethynyl)pyridin-4-yl)-4-methylpiperazine.
$^1$H-NMR (CDCl$_3$, 400 MHz) δ 8.69 (s, 1H), 8.47 (s, 1H), 8.43 (s, 1H), 7.80-7.70 (m, 3H), 6.98 (d, 1H), 4.73 (q, 2H), 4.04 (brs, 1H), 3.56-3.48 (m, 3H), 3.36-3.34 (m, 1H), 2.87-2.83 (m, 1H), 1.82-1.63 (m, 4H), 1.29-1.21 (m, 4H); MS (ESI) m/z=614.1 (M+H)$^+$ Example 344. (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)-1-methylcyclohexan-1-ol Step 1. (1s,4s)-4-((2-Chloro-5-((1-(2,2,2-trifluoroethyl)-1H-pyrazol-4-yl)ethynyl)pyridin-4-yl)amino)-1-methylcyclohexan-1-ol The title compound as a solid (155 mg) was prepared in the same fashion as Step 1 in Example 65 except that cis-4-amino-1-methylcyclohexanol (43 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=413.0 (M+H)$^+$ Step 2. (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)-1-methylcyciohexan-1-ol The title compound as a solid (1.7 mg) was prepared in the same fashion as Step 3 in Example 1 except that (1s,4s)-4-((2-chloro-5-((1-(2,2,2-trifluoroethyl)-1H-pyrazol-4-yl)ethynyl)pyridin-4-yl)amino)-1-methylcyclohexan-1-ol (155 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.46 (s, 1H), 8.42 (d, 1H), 8.06 (s, 1H), 7.75 (s, 2H), 7.20-7.18 (m, 2H), 5.12-5.10 (m, 1H), 4.74 (q, 2H), 3.50 (brs, 1H), 2.84-2.79 (m, 1H), 1.87-1.83 (m, 3H), 1.75-1.53 (m, 4H), 1.32 (s, 3H), 1.28-1.21 (m, 41-1); MS (ESI) m/z=642.2 (M+H)$^+$ Example 345. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-((1-(2,2,2-trifluoroethyl)-1H-pyrazol-4-yl)ethynyl)pyridine-2,4-diamine Step 1. (1s,4s)-N$^4$-(2-Chloro-5-((1-(2,2,2-trifluoroethyl)-1H-pyrazol-4-yl)ethynyl)pyridin-4-yl)-N$^a$-(2-fluoroethyl)cyclohexane-1,4-diamine The title compound as a solid (167 mg) was prepared in the same fashion as Step 1 in Example 65 except that (1s,4s)-N$^r$-(2-fluoroethyl)cyclohexane-1,4-diamine (53 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=444.0 (M+H)$^+$ Step 2. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-((1-(2,2,2-trifluoroethyl)-1H-pyrazol-4-yl)ethy-nyl)pyridine- The title compound as a solid (8.1 mg) was prepared in the same fashion as Step 3 in Example 1 except that (1s,4s)-N$^4$-(2-chloro-5-((1-(2,2,2-trifluoroethyl)-1H-pyrazol-4-yl)ethynyl)pyridin-4-yl)-N$^4$-(2-fluoroethyl)cyclohexane-1,4-diamine (167 mg, 0.377 mmol) prepared in Step 1 was used instead of 1-(2-chloro-5-((1-methyl-1H-pyrazol-4-yl)ethynyl)pyridin-4-yl)-4-methylpiperazine.2,4-diamine.
$^1$H-NMR (CDCl$_3$, 400 MHz) δ 8.59 (s, 1H), 8.46-8.43 (m, 2H), 8.30 (s, 2H), 8.01 (s, 1H), 7.95 (s, 1H), 7.90 (s, 1H), 7.80 (s, 1H), 6.98 (d, 1H), 5.76 (d, 1H), 4.80-4.61 (m, 3H), 3.93 (brs, 1H), 3.19-3.11 (m, 2H), 2.99 (brs, 1H), 2.85-2.81 (m, 1H), 2.10-1.91 (m, 6H), 1.74-1.69 (m, 2H), 1.54 (s, 2H), 1.26-1.23 (m, 2H); MS (ESI) m/z=673.2 (M+H)$^+$ Example 346. 2-((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)propan-2-ol Step 1. 2-((1s,4s)-4-((2-Chloro-5-((1-(2,2,2-trifluoroethyl)-1H-pyrazol-4-yl)ethynyl)pyridin-4-yl)amino)cyclohexyl)propan-2-ol The title compound as a solid (166 mg) was prepared in the same fashion as Step 1 in Example 65 except that 2-((1s,4s)-4-aminocyclohexyl)propan-2-ol (52 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=441.0 (M+H)$^+$ Step 2. 2-((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)propan-2-ol The title compound as a solid (2.8 mg) was prepared in the same fashion as Step 3 in Example 1 except that 2-((1s,4s)-4-((2-chloro-5-((1-(2,2,2-trifluoroethyl)-1H-pyrazol-4-yl)ethynyl)pyridin-4-yl)amino)cyclohexyl)propan-2-ol (166 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.54 (s, 1H), 8.37-8.35 (m, 2H), 7.92 (s, 1H), 7.85 (s, 2H), 7.75 (s, 1H), 6.94 (d, 1H), 5.94 (d, 1H), 4.74 (q, 2H), 3.98 (brs, 1H), 3.06-2.82 (m, 3H), 2.12-2.09 (m, 1H), 1.84-1.81 (m, 4H), 1.54-1.17 (m, 12H); MS (ESI) m/z 670.2 (M+H)$^+$ Example 347. 7-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-2-methyl-7-azaspiro[3.5]nonan-2-ol Step 1. 7-(2-Chloro-5-((1-(2,2,2-trifluoroethyl)-1H-pyrazol-4-yl)ethynyl)pyridin-4-yl)-2-methyl-7-azaspiro[3.5]nonan-2-ol The title compound as a solid (165 mg) was prepared in the same fashion as Step 1 in Example 65 except that 2-methyl-7-azaspiro[3.5]nonan-2-ol (51 mg, 0.329 mmol) and 2-chloro-4-fluoro-5-((1-(2,2,2-tri fluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=441.0 (M+H)+

Step 2. 7-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-2-methyl-7-azaspiro[3.5]nonan-2-ol The title compound as a solid (3.4 mg) was prepared in the same fashion as Step 3 in Example 1 except that 7-(2-chloro-5-((1-(2,2,2-trifluoroethyl)-1H-pyrazol-4-yl)ethynyl)pyridin-4-yl)-2-methyl-7-azaspiro[3.5]nonan-2-ol (165 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.41 (s, 1H), 8.36 (d, 1H), 8.08 (s, 1H), 7.80 (s, 1H), 7.70 (d, 2H), 6.95 (d, 1H), 4.74 (q, 2H), 3.50-3.47 (m, 4H), 3.06-2.83 (m, 3H), 2.06-1.80 (m, 8H), 1.54-1.23 (m, 7H); MS (ESI) m/z=668.2 (M+H)+

Example 348. (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-methylpiperidin-4-yl)methanol Step 1. (1-(2-Chloro-5-((1-(2,2,2-trifluoroethyl)-1H-pyrazol-4-yl)ethynyl)pyridin-4-yl)-4-methylpiperidin-4-yl)methanol The title compound as a solid (155 mg) was prepared in the same fashion as Step 1 in Example 65 except that (4-methylpiperidin-4-yl)methanol (43 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=413.0 (M+H)+

Step 2. (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-methylpiperidin-4-yl)methanol The title compound as a solid (1.9 mg) was prepared in the same fashion as Step 3 in Example 1 except that (1-(2-chloro-5-((1-(2,2,2-trifluoroethyl)-1H-pyrazol-4-yl)ethynyl)pyridin-4-yl)-4-methylpiperidin-4-yl)methanol (156 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.57 (s, 1H), 8.38 (s, 1H), 8.32 (d, 1H), 8.02 (s, 1H), 7.90 (s, 1H), 7.71 (s, 2H), 6.90 (d, 1H), 4.74 (q, 2H), 3.81-3.77 (m, 2H), 3.67-3.45 (m, 4H), 3.28-2.82 (m, 3H), 1.83-1.78 (m, 2H), 1.56-1.54 (m, 4H), 1.28-1.27 (m, 3H), 1.11 (s, 3H); MS (ESI) m/z=642.2 (M+H)+

Example 349. 2-(1-(Cyclopropylsulfonyl)-1H-pyrazol-4-yl)-N-(4-(4-(2-(dimethylamino)ethyl)piperidin-1-yl)-5-((1-(2,2,2-trifluoroethyl)-1H-pyrazol-4-yl)ethynyl)pyridin-2-yl)pyrimidin-4-amine Step 1. 2-(1-(2-Chloro-5-((1-(2,2,2-trifluoroethyl)-1H-pyrazol-4-yl)ethynyl)pyridin-4-yl)piperidin-4-yl)-N,N-dimethylethan-1-amine The title compound as a solid (165 mg) was prepared in the same fashion as Step 1 in Example 65 except that N,N-dimethyl-2-(piperidin-4-yl)ethan-1-amine (51 mg, 0.329 mmol) and 2-chloro-4-fluoro-5-((1-(2,2,2-trifluoroethyl)-1H-pyrazol-4-yl)ethynyl)pyridine (100 mg, 0.329 mmol) prepared in Step 1 of Example 339 were used instead of 4-(trifluoromethyl)piperidine HCl and 2-chloro-4-fluoro-5-((1-methyl-1H-pyrazol-4-yl)ethynyl)pyridine. MS (ESI) m/z=413.0 (M+H)+

Step 2. 2-(1-(Cyclopropylsulfonyl)-1H-pyrazol-4-yl)-N-(4-(4-(2-(dimethylamino)ethyl)piperidin-1-yl)-5-((1-(2,2,2-trifluoroethyl)-1H-pyrazol-4-yl)ethynyl)pyridin-2-yl)pyrimidin-4-amine The title compound as a solid (3.9 mg) was prepared in the same fashion as Step 3 in Example 1 except that 2-(1-(2-chloro-5-((1-(2,2,2-trifluoroethyl)-1H-pyrazol-4-yl)ethynyl)pyridin-4-yl)piperidin-4-yl)-N,N-dimethylethan-1-amine (166 mg, 0.377 mmol) prepared in Step 1 was used instead of 1-(2-chloro-5-((1-methyl-1H-pyrazol-4-yl)ethynyl)pyridin-4-yl)-4-methylpiperazine. $^1$H-NMR (MeOD, 400 MHz) δ 8.75 (s, 1H), 8.51 (brs, 1H), 8.45 (s, 1H), 8.37 (d, 1H), 8.18 (s, 1H), 8.01 (s, 1H), 7.74-7.71 (m, 2H), 7.27 (d, 1H), 4.74 (q, 2H), 4.13 (d, 2H), 3.19-3.15 (m, 2H), 3.07-3.04 (m, 1H), 2.98-2.87 (m, 2H), 1.97 (s, 6H), 1.94 (d, 2H), 1.78-1.43 (m, 6H), 1.31-1.27 (m, 2H); MS (ESI) m/z=669.3 (M+H)+

Example 350. (1s,4s)-4-((2-((2-(1-(Cyclopropylsulfonyl)-1H-pyrazol-4-yl)pyrimidin-4-yl)amino)-5-((3-methyloxetan-3-yl)ethynyl)pyridin-4-yl)amino)cyclohexan-1-ol Step 1. (1s,4S)-4-((2-Chloro-5-((3-methyloxetan-3-yl)ethynyl)pyridin-4-yl)amino)cyclohexan-1-ol The title compound as a solid (126 mg) was prepared in the same fashion as Step 1 in Example 157 except that 2-chloro-4-fluoro-5-((3-methyloxetan-3-yl)ethynyl)pyridine (0.20 g, 0.886 mmol) prepared in Reference Example 54 was used instead of 4-(4-((6-chloro-4-fluoropyridin-3-yl)ethynyl)benzyl)morpholine. $^1$H-NMR (CDCl$_3$, 400 MHz) δ 8.01 (s, 1H), 6.43 (s, 1H), 5.05-5.03 (d, 1H), 4.87-4.86 (d, 2H), 4.51-4.49 (d, 2H), 3.94 (s, 1H), 3.43-3.40 (t, 1H), 1.79-1.75 (t, 4H), 1.72-1.71 (d, 7H)

Step 2. (1s,4s)-4-((2-((2-(1-(Cyclopropylsulfonyl)-1H-pyrazol-4-yl)pyrimidin-4-yl)amino)-5-((3-methyloxetan-3-yl)ethynyl)pyridin-4-yl)amino)cyclohexan-1-ol The title compound (1.5 mg) was prepared in the same fashion as Step 3 in Example 1, except that (1s,4S)-4-((2-chloro-5-((3-methyloxetan-3-yl)ethynyl)pyridin-4-yl)amino)cyclohexan-1-ol (126 mg, 0.393 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.41-8.38 (t, 2H), 8.14-8.07 (m, 3H), 7.82 (s, 1H), 6.92-6.91 (d, 1H), 6.10-6.05 (m, 1H), 5.65-5.64 (d, 2H), 5.40-5.25 (m, 3H), 4.91-4.90 (d, 3H), 4.82-4.81 (d, 2H), 4.57-4.55 (d, 2H), 3.98 (s, 1H), 3.81 (s, 2H), 1.93-1.92 (d, 7H), 1.87-1.84 (t, 6H)

Example 351. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutan-1-ol

Step 1. 1-((6-Chloro-4-(4-(hydroxymethyl)-4-methylpiperidin-1-yl)pyridin-3-yl)ethynyl)cyclobutan-1-ol The title compound as a solid (273 mg) was prepared in the same fashion as Step 1 in Example 157 except that 1-((6-chloro-4-fluoropyridin-3-yl)ethynyl)cyclobutan-1-ol (0.20 g, 0.886 mmol) prepared in Reference Example 55 and (4-methylpiperidin-4-yl)methanol (137 mg, 1.064 mmol) were used instead of 4-(4-((6-chloro-4-fluoropyridin-3-yl)ethynyl)benzyl)morpholine and cis-4-aminocyclohexanol HCl. $^1$H-NMR (MeOD, 400 MHz) δ 8.05 (s, 1H), 6.82 (s, 1H), 4.10-4.07 (t, 2H), 3.77-3.71 (m, 2H), 3.36-3.31 (q, 2H), 3.29-3.28 (d, 3H), 2.48-2.44 (m, 2H), 2.36-2.28 (m, 2H), 1.90-1.84 (m, 2H), 1.74-1.69 (m, 2H), 1.56-1.52 (q, 2H), 1.03 (d, 2H)

Step 2. 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutan-1-ol The title compound (1.1 mg) was prepared in the same fashion as Step 3 in Example 1, except that 1-((6-chloro-4-(4-(hydroxymethyl)-4-methylpiperidin-1-yl)pyridin-3-yl)ethynyl)cyclobutan-1-ol (273 mg, 0.815 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.45-8.42 (t, 1H), 8.25 (s, 2H), 7.99 (s, 1H), 6.93-6.92 (d, 1H), 4.91-4.90 (d, 1H), 3.82-3.77 (q, 2H), 3.55-3.44 (m, 4H), 2.54-2.53 (d, 2H), 2.50 (d, 2H), 1.92-1.90 (t, 4H), 1.88-1.77 (m, 4H), 1.57-1.53 (m, 2H), 1.26 (d, 3H)

Example 352. (1-(2-((2-(1-(Cyclopropylsulfonyl)-1H-pyrazol-4-yl)pyrimidin-4-yl)amino)-5-(oxetan-3-ylethynyl)pyridin-4-yl)-4-methylpiperidin-4-yl)methanol

Step 1. (1-(2-Chloro-5-(oxetan-3-ylethynyl)pyridin-4-yl)-4-methylpiperidin-4-yl)methanol The title compound as a solid (248 mg) was prepared in the same fashion as Step 1 in Example 157 except that 2-chloro-4-fluoro-5-(oxetan-3-ylethynyl)pyridine (0.20 g, 0.886 mmol) prepared in Reference Example 56 and (4-methylpiperidin-4-yl)methanol (146 mg, 1.134 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.12 (s, 1H), 6.68 (s, 1H), 4.89-4.74 (q, 2H), 4.77-4.74 (q, 2H), 3.67-3.62 (m, 2H), 3.41 (s, 2H), 3.23-3.17 (m, 2H), 1.72-1.65 (m, 2H), 1.47-1.43 (m, 2H), 1.20-1.18 (q, 2H), 1.04 (s, 3H)

Step 2. (1-(2-((2-(1-(Cyclopropylsulfonyl)-1H-pyrazol-4-yl)pyrimidin-4-yl)amino)-5-(oxetan-3-ylethynyl)pyridin-4-yl)-4-methylpiperidin-4-yl)methanol The title compound (17.1 mg) was prepared in the same fashion as Step 3 in Example 1, except that (1-(2-chloro-5-(oxetan-3-ylethynyl)pyridin-4-yl)-4-methylpiperidin-4-yl)methanol (248 mg, 0.773 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44-8.39 (m, 3H), 8.02 (s, 1H), 7.93 (s, 1H), 6.95-6.93 (d, 1H), 4.93-4.90 (q, 2H), 4.81-4.78 (q, 2H), 4.15-4.11 (q, 1H), 3.77-3.72 (m, 2H), 3.51 (s, 2H), 3.49-3.44 (m, 2H), 2.84 (m, 1H), 1.80-1.76 (q, 2H), 1.60-1.53 (m, 4H), 1.25-1.23 (t, 2H), 1.09-1.06 (d, 3H); MS (ESI) m/z=550.2 (M+H)$^+$

Example 353. (1s,4s)-4-((2-((2-(1-(Cyclopropylsulfonyl)-1H-pyrazol-4-yl)pyrimidin-4-yl)amino)-5-(oxetan-3-ylethynyl)pyridin-4-yl)amino)cyclohexan-1-ol

Step 1. (1s,4s)-4-((2-Chloro-5-(oxetan-3-ylethynyl)pyridin-4-yl)amino)cyclohexan-1-ol The title compound as a solid (241 mg) was prepared in the same fashion as Step 1 in Example 157 except that 2-chloro-4-fluoro-5-(oxetan-3-ylethynyl)pyridine (0.20 g, 0.886 mmol) prepared in Reference Example 56 was used instead of 4-(4-((6-chloro-4-fluoropyridin-3-yl)ethynyl)benzyl)morpholine. $^1$H-NMR (CDCl$_3$, 400 MHz) δ 7.98-7.95 (d, 2H), 6.41 (s, 1H), 5.03-5.01 (d, 1H), 4.89-4.86 (q, 2H), 4.75-4.72 (t, 2H), 4.12-4.04 (m, 1H), 3.93 (s, 1H), 3.39-3.38 (d, 1H), 1.74 (m, 4H), 1.70 (m, 4H)

Step 2. (1s,4s)-4-((2-((2-(1-(Cyclopropylsulfonyl)-1H-pyrazol-4-yl)pyrimidin-4-yl)amino)-5-(oxetan-3-ylethynyl)pyridin-4-yl)amino)cyclohexan-1-ol The title compound (1.8 mg) was prepared in the same fashion as Step 3 in Example 1, except that (1s,4s)-4-((2-chloro-5-(oxetan-3-ylethynyl)pyridin-4-yl)amino)cyclohexan-1-ol (241 mg, 0.784 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.48-8.41 (m, 2H), 7.94 (s, 1H), 7.51 (s, 1H), 7.08-7.06 (d, 1H), 5.36-5.34 (d, 1H), 4.97-4.94 (q, 2H), 4.81-4.79 (d, 2H), 4.17-4.13 (t, 1H), 3.97-3.96 (d, 1H), 3.70-3.68 (d, 1H), 2.85-2.80 (m, 1H), 1.91-1.86 (m, 4H), 1.82 (d, 2H), 1.71-1.67 (q, 2H), 1.56-1.53 (q, 2H), 1.25-1.19 (m, 2H); MS (ESI) m/z=536.1 (M+H)$^+$

Example 354. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)oxetan-3-ol

Step 1. 3-((6-Chloro-4-(4-(hydroxymethyl)-4-methylpiperidin-1-yl)pyridin-3-yl)ethynyl)oxetan-3-ol The title compound as a solid (252 mg) was prepared in the same fashion as Step 1 in Example 157 except that 3-((6-chloro-4-fluoropyridin-3-yl)ethynyl)oxetan-3-ol (0.20 g, 0.879 mmol) prepared in Reference Example 57 and (4-methylpiperidin-4-yl)methanol (136 mg, 1.054 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.18 (s, 1H), 6.66 (s, 1H), 6.09 (s, 1H), 4.84 (s, 4H), 3.73-3.70 (d, 2H), 3.39 (s, 2H), 3.22 (t, 2H), 1.72 (m, 2H), 1.43-1.40 (d, 2H), 1.26-1.23 (t, 1H), 1.01 (s, 3H)

Step 2. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)oxetan-3-ol The title compound (59.9 mg) was prepared in the same fashion as Step 3 in Example 1, except that 3-((6-chloro-4-

(4-(hydroxymethyl)-4-methylpiperidin-1-yl)pyridin-3-yl) ethynyl)oxetan-3-ol (252 mg, 0.748 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.57 (s, 1H), 8.38-8.30 (d, 2H), 8.05 (s, 1H), 7.63 (s, 1H), 6.88 (d, 1H), 5.28 (t, 1H), 4.87-4.80 (q, 4H), 3.63 (s, 3H), 3.22-3.20 (d, 2H), 2.83 (s, 2H), 1.73 (s, 2H), 1.48-1.44 (q, 4H), 1.21 (s, 2H), 0.99 (s, 3H); MS (ESI) m/z=566.1 (M+H)$^+$ Example 355. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl) ethynyl)tetrahydrofuran-3-ol Step 1. 3-((6-Chloro-4-(4-(hydroxymethyl)-4-methylpiperidin-1-yl)pyridin-3-yl)ethynyl)tetrahydrofuran-3-ol The title compound as a solid (272 mg) was prepared in the same fashion as Step 1 in Example 157 except that 3-((6-chloro-4-fluoropyridin-3-yl)ethynyl)tetrahydrofuran-3-ol (0.20 g, 0.828 mmol) prepared in Reference Example 58 and (4-methylpiperidin-4-yl)methanol (128 mg, 0.993 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.15 (s, 1H), 6.65 (s, 1H), 4.54 (s, 1H), 3.98-3.95 (m, 2H), 3.90 (s, 2H), 3.62 (t, 2H), 3.38 (s, 2H), 3.18 (m, 2H), 2.33-2.31 (m, 2H), 1.71-1.63 (m, 2H), 1.44-1.40 (t, 2H), 0.99 (s, 3H)

Step 2. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl) tetrahydrofuran-3-ol The title compound (1.2 mg) was prepared in the same fashion as Step 3 in Example 1, except that 3-((6-chloro-4-(4-(hydroxymethyl)-4-methylpiperidin-1-yl)pyridin-3-yl) ethynyl)tetrahydrofuran-3-ol (272 mg, 0.775 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.44-8.42 (d, 2H), 8.23 (s, 1H), 8.06 (s, 1H), 8.00 (d, 1H), 6.92-6.91 (d, 1H), 4.13-3.94 (m, 4H), 3.77-3.74 (m, 3H), 3.51-3.46 (m, 4H), 2.85-2.83 (t, 2H), 2.39-2.35 (q, 2H), 1.80-1.78 (t, 2H), 1.59-1.54 (q, 4H), 1.26-1.24 (q, 2H), 1.03 (s, 3H); MS (ESI) m/z=580.2 (M+H)$^+$ Example 356. 3-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl) tetrahydrofuran-3-ol Step 1. 3-((6-Chloro-4-(((1s,4s)-4-hydroxycyclohexyl)amino)pyridin-3-yl)ethynyl)tetrahydrofuran-3-ol The title compound as a solid (262 mg) was prepared in the same fashion as Step 1 in Example 157 except that 3-((6-chloro-4-fluoropyridin-3-yl)ethynyl)tetrahydrofuran-3-ol (0.20 g, 0.828 mmol) prepared in Reference Example 58 was used instead of 4-(4-((6-chloro-4-fluoropyridin-3-yl) ethynyl)benzyl)morpholine. $^1$H-NMR (CDCl$_3$, 400 MHz) δ 7.97-7.91 (d, 2H), 6.36 (s, 1H), 5.69 (s, 1H), 5.24-5.15 (d, 2H), 4.04-3.85 (m, 6H), 3.45-3.39 (d, 2H), 2.31 (s, 2H), 1.68 (s, 2H), 1.19-1.17 (d, 2H); MS (ESI) m/z=337.0 (M+H)$^+$ Step 2. 3-((6-((2-(1-(Cyclopropylsulfonyl)-1H-pyrazol-4-yl)pyrimidin-4-yl)amino)-4-(((1s, 4s)-4-hydroxycyclohexyl)amino)pyridin-3-yl)ethynyl)tetrahydrofuran-3-ol The title compound (1.8 mg) was prepared in the same fashion as Step 3 in Example 1, except that 3-((6-chloro-4-(((1s,4s)-4-hydroxycyclohexyl)amino)pyridin-3-yl)ethynyl) tetrahydrofuran-3-ol (262 mg, 0.778 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.57 (s, 1H), 8.46-8.44 (d, 2H), 8.39 (s, 1H), 7.90 (s, 1H), 7.85 (s, 1H), 7.00-6.98 (d, 1H), 5.66-5.65 (d, 1H), 4.15-3.97 (m, 8H), 3.91-3.89 (t, 2H), 2.84 (s, 1H), 2.44-2.40 (m, 2H), 1.92-1.84 (q, 6H), 1.65-1.62 (t, 2H), 1.55-1.53 (q, 2H), 1.25 (d, 2H); MS (ESI) m/z=566.2 (M+H)$^+$ Example 357. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl) ethynyl)tetrahydro-2H-pyran-3-ol Step 1. 3-((6-Chloro-4-(4-(hydroxymethyl)-4-methylpiperidin-1-yl)pyridin-3-yl)ethynyl)tetrahydro-2H-pyran-3-ol The title compound as a solid (213 mg) was prepared in the same fashion as Step 1 in Example 157 except that 3-((6-chloro-4-fluoropyridin-3-yl)ethynyl)tetrahydro-2H-pyran-3-ol (0.16 g, 0.606 mmol) prepared in Reference Example 59 and (4-methylpiperidin-4-yl)methanol (94 mg, 0.728 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.13 (s, 1H), 7.95 (s, 1H), 6.60 (s, 1H), 4.88 (s, 1H), 3.76-3.53 (m, 6H), 3.35 (s, 2H), 3.18-3.13 (t, 2H), 2.05-2.00 (m, 1H), 1.94-1.79 (m, 2H), 1.71-1.64 (m, 3H), 1.39-1.35 (d, 2H), 0.97 (s, 3H)

Step 2. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl) tetrahydro-2H-pyran-3-ol The title compound (4.4 mg) was prepared in the same fashion as Step 3 in Example 1, except that 3-((6-chloro-4-(4-(hydroxymethyl)-4-methylpiperidin-1-yl)pyridin-3-yl) ethynyl)tetrahydro-2H-pyran-3-ol (213 mg, 0.584 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.42-8.37 (q, 3H), 8.01 (s, 1H), 7.91 (s, 1H), 6.90-6.89 (d, 1H), 3.78-3.73 (t, 4H), 3.69-3.63 (q, 3H), 3.49 (s, 3H), 3.45-3.40 (m, 4H), 2.87-2.83 (q, 1H), 2.07-2.02 (q, 2H), 1.92-1.90 (t, 1H), 1.83-1.82 (d, 2H), 1.79-1.72 (m, 4H), 1.56-1.53 (m, 2H), 1.05 (s, 3H); MS (ESI) m/z=594.2 (M+H)$^+$ Example 358. (1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-yl)methanol Step 1. (1-(2-Chloro-5-((1-methylcyclopropyl)ethynyl)pyridin-4-yl)-4-methylpiperidin-4-yl)methanol The title compound as a solid (431 mg) was prepared in the same fashion as Step 1 in Example 157 except that 2-chloro-4-fluoro-5-((1-methylcyclopropyl)ethynyl)pyridine (0.30 g, 1.431 mmol) prepared in Reference Example 60 and (4-methylpiperidin-4-yl)methanol (221 mg, 1.717 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.06 (s, 1H), 6.63 (s, 1H), 3.62-3.57 (m, 2H), 3.42 (s, 3H), 3.19-3.13 (m, 2H), 2.37 (s, 1H), 1.70-1.63 (m, 2H), 1.49-1.42 (m, 2H), 1.33 (s, 3H), 1.07 (s, 3H), 0.94-0.90 (t, 2H), 0.79-0.76 (t, 2H)

Step 2. (1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-yl)methanol The title compound (3.9 mg) was prepared in the same fashion as Step 3 in Example 1, except that (1-(2-chloro-5-((1-methylcyclopropyl)ethynyl)pyridin-4-yl)-4-methylpiperidin-4-yl)methanol (300 mg, 1.01 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44-8.40 (t, 2H), 8.00 (s, 1H), 7.83 (s, 1H), 6.94 (s, 1H), 3.69 (s, 2H), 3.52 (s, 1H), 3.46-3.44 (d, 2H), 2.82 (s, 1H), 2.67 (brs, 4H), 1.77-1.75 (d, 1H), 1.58-1.53 (d, 4H), 1.38 (s, 3H), 1.25-1.23 (d, 2H), 1.10 (s, 3H), 1.00 (s, 2H), 0.73 (s, 2H); MS (ESI) m/z=548.2 (M+H)$^+$ Example 359. (1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexan-1-ol Step 1. (1s,4s)-4-((2-Chloro-5-((1-methylcyclopropyl)ethynyl)pyridin-4-yl)amino)cyclohexan-1-ol The title compound as a solid (390 mg) was prepared in the same fashion as Step 1 in Example 157 except that 2-chloro-4-fluoro-5-((1-methylcyclopropyl)ethynyl)pyridine (0.30 g, 1.431 mmol) prepared in Reference Example 60 was used instead of 4-(4-((6-chloro-4-fluoropyridin-3-yl)ethynyl)benzyl)morpholine. $^1$H-NMR (CDCl$_3$, 400 MHz) δ 7.95 (s, 1H), 6.38 (s, 1H), 5.09-5.07 (d, 1H), 3.95 (s, 1H), 3.39-3.36 (t, 2H), 2.29 (s, 1H), 1.77-1.76 (d, 4H), 1.74-1.73 (t, 6H), 1.35 (s, 3H), 1.00-0.97 (q, 2H), 0.73-0.72 (t, 2H)

Step 2. (1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexan-1-ol The title compound (4.4 mg) was prepared in the same fashion as Step 3 in Example 1, except that (1s,4s)-4-((2-chloro-5-((1-methylcyclopropyl)ethynyl)pyridin-4-yl)amino)cyclohexan-1-ol (250 mg, 0.82 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.44-8.42 (d, 2H), 7.91 (s, 1H), 7.75 (s, 1H), 7.01-7.00 (d, 1H), 5.72-5.70 (d, 1H), 3.95 (s, 1H), 3.72 (s, 1H), 2.83 (s, 1H), 1.93-1.92 (d, 4H), 1.87-1.83 (d, 2H), 1.79 (s, 2H), 1.69-1.64 (q, 2H), 1.52 (s, 3H), 1.40 (s, 2H), 1.24-1.22 (t, 2H), 0.79 (s, 2H); MS (ESI) m/z=534.2 (M+H)$^+$ Example 360. ((1s, 4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol Step 1. ((1s,4S)-4-((2-Chloro-5-((4-((4-methylpiperazin-1-yl)methyl)phenyl)ethynyl)pyridin-4-yl)amino)cyclohexyl)methanol The title compound as a solid (91.9 mg) was prepared in the same fashion as Step 1 in Example 157 except that 1-(4-((6-chloro-4-fluoropyridin-3-yl)ethynyl)benzyl)-4-methylpiperazine (95 mg, 0.276 mmol) prepared in Reference Example 31 and ((1s,4s)-4-aminocyclohexyl)methanol (46 mg, 0.359 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.06 (s, 1H), 7.41-7.39 (d, 2H), 7.27-7.25 (d, 2H), 6.42 (s, 1H), 5.38-5.36 (d, 1H), 3.66 (s, 2H), 3.46-3.37 (q, 4H), 2.42 (brs, 6H), 2.22 (s, 3H), 1.81-1.78 (d, 2H), 1.66-1.62 (d, 6H), 1.28-1.26 (d, 2H)

Step 2. ((1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol The title compound (0.4 mg) was prepared in the same fashion as Step 3 in Example 1, except that ((1s,4s)-4-((2-chloro-5-((4-((4-methylpiperazin-1-yl)methyl)phenyl)ethynyl)pyridin-4-yl)amino)cyclohexyl)methanol (91.9 mg, 0.203 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.44-8.41 (t, 2H), 7.98 (s, 1H), 7.82 (s, 1H), 7.52-7.48 (t, 1H), 7.35-7.33 (d, 1H), 7.02-7.00 (d, 1H), 5.81-5.79 (d, 1H), 4.01 (s, 1H), 3.52-3.50 (d, 2H), 2.84-2.82 (t, 3H), 2.77-2.63 (q, 4H), 2.50 (s, 3H), 2.06-2.03 (d, 4H), 1.93-1.86 (t, 4H), 1.80-1.76 (d, 2H), 1.71-1.70 (d, 2H), 1.54-1.52 (t, 2H), 1.33-1.29 (d, 2H); MS (ESI) m/z=683.2 (M+H)$^+$ Example 361. (1r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)cyclohexan-1-ol Step 1. (1 r,4r)-4-(((2-Chloro-5-((4-((4-methylpiperazin-1-yl)methyl)phenyl)ethynyl)pyridin-4-yl)amino)methyl)cyclohexan-1-ol The title compound as a solid (95.4 mg) was prepared in the same fashion as Step 1 in Example 157 except that 1-(4-((6-chloro-4-fluoropyridin-3-yl)ethynyl)benzyl)-4-methylpiperazine (95 mg, 0.276 mmol) prepared in Reference Example 31 and trans-4-(aminomethyl)cyclohexanol HCl (60 mg, 0.359 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.06 (s, 1H), 7.41-7.39 (d, 2H), 7.29-7.27 (d, 2H), 6.40 (s, 1H), 5.21-5.18 (t, 1H), 3.54-3.50 (m, 1H), 3.47 (s, 3H), 3.04-3.00 (t, 2H), 2.43 (brs, 6H), 2.23 (s, 3H), 1.99-1.96 (d, 2H), 1.83-1.80 (d, 2H), 1.56-1.54 (t, 1H), 1.27-1.21 (q, 2H), 1.08-1.05 (d, 2H)

Step 2. (1r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)cyclohexan-1-ol The title compound (4.8 mg) was prepared in the same fashion as Step 3 in Example 1, except that (1 r,4r)-4-(((2- chloro-5-((4-((4-methylpiperazin-1-yl)methyl)phenyl)ethynyl)pyridin-4-yl)amino)methyl)cyclohexan-1-ol (95.4 mg, 0.211 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.66 (s, 1H), 8.45-8.42 (t, 1H), 8.14 (s, 1H), 7.48-7.46 (d, 2H), 7.36-7.34 (d, 2H), 7.02 (s, 1H), 5.21 (s, 1H), 3.60 (m, 1H), 3.55 (s, 2H), 3.22-3.19 (t, 2H), 2.83 (s, 1H), 2.52 (brs, 6H), 2.32 (s, 3H), 2.06-2.04 (d, 2H), 1.94-1.91 (d, 2H), 1.54-1.53 (q, 2H), 1.33-1.30 (d, 2H), 1.23-1.20 (q, 4H); MS (ESI) m/z=682.2 (M+H)⁺

Example 362. (5s,8s)-8-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)-1-azaspiro[4.5]decan-2-one Step 1. (5s,8s)-8-((2-Chloro-5-((4-((4-methylpiperazin-1-yl)methyl)phenyl)ethynyl)pyridin-4-yl)amino)-1-azaspiro[4.5]decan-2-one The title compound as a solid (74.7 mg) was prepared in the same fashion as Step 1 in Example 157 except that 1-(4-((6-chloro-4-fluoropyridin-3-yl)ethynyl)benzyl)-4-methylpiperazine (95 mg, 0.276 mmol) prepared in Reference Example 31 and (5s,8s)-8-amino-1-azaspiro[4.5]decan-2-one HCl (74 mg, 0.359 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.58 (s, 1H), 8.09 (s, 1H), 7.47-7.45 (d, 2H), 7.29-7.27 (d, 2H), 6.42 (s, 1H), 5.25-5.23 (d, 1H), 3.48-3.47 (d, 3I), 3.17 (s, 1H), 2.43 (brs, 6H), 2.26-2.21 (d, 4H), 2.19-2.17 (d, 2H), 2.00-1.97 (d, 2H), 1.83-1.75 (q, 4H), 1.62-1.56 (t, 4H)

Step 2. (5s,8s)-8-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)-1-azaspiro[4.5]decan-2-one The title compound (2.0 mg) was prepared in the same fashion as Step 3 in Example 1, except that (5s,8s)-8-((2-chloro-5-((4-((4-methylpiperazin-1-yl)methyl)phenyl)ethynyl)pyridin-4-yl)amino)-1-azaspiro[4.5]decan-2-one (74.7 mg, 0.152 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.62 (s, 1H), 8.46-8.44 (t, 1H), 8.38 (s, 2H), 7.77 (s, 1H), 7.53-7.48 (t, 2H), 7.37-7.35 (d, 2H), 7.01-7.00 (d, 1H), 6.42 (s, 1H), 5.44-5.42 (d, 1H), 3.61 (m, 1H), 3.10-3.06 (t, 1H), 2.87-2.81 (m, 4H), 2.44-2.40 (t, 2H), 2.20-2.17 (d, 2H), 2.05-2.01 (t, 2H), 1.78-1.73 (t, 4H), 1.60-1.53 (m, 4H), 1.45-1.43 (t, 1H), 1.31-1.20 (d, 2H); MS (ESI) m/z=722.2 (M+H)⁺

Example 363. (1 r, 4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)-1-methylcyclohexan-1-ol Step 1. (1 r, 4r)-4-(((2-Chloro-5-((4-((4-methylpiperazin-1-yl)methyl)phenyl)ethynyl)pyridin-4-yl)amino)methyl)-1-methylcyclohexan-1-ol The title compound as a solid (94.1 mg) was prepared in the same fashion as Step 1 in Example 157 except that 1-(4-((6-chloro-4-fluoropyridin-3-yl)ethynyl)benzyl)-4-methylpiperazine (95 mg, 0.276 mmol) prepared in Reference Example 31 and trans-4-(aminomethyl)-1-methyl-cyclohexanol HCl (65 mg, 0.359 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.08 (s, 1H), 7.41-7.39 (d, 2H), 7.30-7.28 (d, 2H), 6.41 (s, 1H), 5.18-5.17 (d, 1H), 3.47 (s, 2H), 3.08-3.05 (t, 2H), 2.42 (brs, 6H), 2.24 (s, 3H), 1.79-1.76 (d, 2H), 1.71-1.64 (m, 3H), 1.49-1.42 (m, 2H), 1.20 (s, 3H), 1.15-1.12 (d, 2H)

Step 2. (1 r, 4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)-1-methylcyclohexan-1-ol The title compound (0.9 mg) was prepared in the same fashion as Step 3 in Example 1, except that (1 r, 4r)-4-(((2-chloro-5-((4-((4-methylpiperazin-1-yl)methyl)phenyl)ethynyl)pyridin-4-yl)amino)methyl)-1-methylcyclohexan-1-ol (94.1 mg, 0.201 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.66 (s, 1H), 8.45-8.43 (d, 2H), 8.04 (s, 1H), 7.48-7.46 (d, 2H), 7.36-7.34 (d, 2H), 7.14-7.13 (d, 1H), 5.39 (s, 1H), 3.58 (s, 2H), 3.31-3.28 (t, 2H), 2.85-2.74 (m, 4H), 2.69 (s, 3H), 1.88-1.85 (d, 2H), 1.77-1.74 (t, 3H), 1.54-1.51 (m, 4H), 1.48 (s, 2H), 1.30-1.26 (d, 4H); MS (ESI) m/z=697.2 (M+H)⁺

Example 364. 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-ol Step 1. 1-(2-Chloro-5-((5-(morpholinomethyl)pyrimidin-2-yl)ethynyl)pyridin-4-yl)-4-methylpiperidin-4-ol The title compound as a solid (98.1 mg) was prepared in the same fashion as Step 1 in Example 157 except that 4-((2-((6-chloro-4-fluoropyridin-3-yl)ethynyl)pyrimidin-5-yl)methyl)morpholine (254 mg, 0.596 mmol) prepared in Reference Example 41 and 4-methylpiperidin-4-ol (65 mg, 0.567 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.71 (s, 2H), 8.39 (s, 1H), 6.75 (s, 1H), 3.86-3.82 (q, 1H), 3.74-3.71 (t, 4H), 3.53 (s, 2H), 3.49-3.41 (m, 2H), 2.49-2.47 (t, 4H), 1.87-1.84 (q, 2H), 1.75-1.72 (d, 2H), 1.34 (s, 3H)

Step 2. 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-ol The title compound (1.9 mg) was prepared in the same fashion as Step 3 in Example 1, except that 1-(2-chloro-5-((5-(morpholinomethyl)pyrimidin-2-yl)ethynyl)pyridin-4-yl)-4-methylpiperidin-4-ol (98.1 mg, 0.229 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.72 (s, 2H), 8.69 (s, 1H), 8.45-8.44 (d, 2H), 8.26-8.22 (d, 3H), 6.93-6.91 (d, 1H), 4.04-4.01 (d, 2H), 3.75-3.73 (t, 4H), 3.60-3.50 (m, 6H), 2.84

(s, 1H), 2.50 (s, 4H), 1.96-1.92 (t, 2H), 1.88-1.85 (d, 2H), 1.56-1.55 (d, 2H), 1.38 (s, 3H), 1.26-1.24 (d, 2H)

Example 365. 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methoxypiperidin-4-ol Step 1. 1-(2-Chloro-5-((5-(morpholinomethyl)pyrimidin-2-yl)ethynyl)pyridin-4-yl)-4-methoxypiperidin-4-ol The title compound as a solid (99.3 mg) was prepared in the same fashion as Step 1 in Example 157 except that 4-((2-((6-chloro-4-fluoropyridin-3-yl)ethynyl)pyrimidin-5-yl)methyl)morpholine (254 mg, 0.596 mmol) prepared in Reference Example 41 and 4-methoxypiperidin-4-ol (73 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.71 (s, 2H), 8.39 (s, 1H), 6.73 (s, 1H), 3.85-3.81 (d, 2H), 3.74-3.71 (t, 5H), 3.53 (s, 2H), 3.36-3.30 (m, 2H), 3.23 (s, 3H), 2.49-2.47 (t, 4H), 1.93-1.90 (d, 2H), 1.77-1.73 (t, 2H), 1.62 (s, 1H), 1.26-1.22 (d, 3H)

Step 2. 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methoxypiperidin-4-ol The title compound (3.4 mg) was prepared in the same fashion as Step 3 in Example 1, except that 1-(2-chloro-5-((5-(morpholinomethyl)pyrimidin-2-yl)ethynyl)pyridin-4-yl)-4-methoxypiperidin-4-ol (99.3 mg, 0.224 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.71 (s, 2H), 8.64 (s, 1H), 8.44-8.43 (d, 2H), 8.30-8.28 (d, 2H), 7.84 (s, 1H), 7.04-7.03 (d, 1H), 3.97-3.94 (d, 2H), 3.74-3.72 (t, 4H), 3.54 (s, 2H), 3.49-3.44 (t, 2H), 3.26-3.25 (d, 3H), 2.85 (s, 1H), 2.50-2.48 (t, 4H), 2.04-2.01 (d, 2H), 1.81 (t, 2H), 1.55-1.53 (t, 2H), 1.25-1.22 (t, 5H)

Example 366. 2-(1-(Cyclopropylsulfonyl)-1H-pyrazol-4-yl)-N-(5-((5-(morpholinomethyl)pyrimidin-2-yl)ethynyl)-4-(1-oxa-8-azaspiro[4.5]decan-8-yl)pyridin-2-yl)pyrimidin-4-amine Step 1. 8-(2-Chloro-5-((5-(morpholinomethyl)pyrimidin-2-yl)ethynyl)pyridin-4-yl)-1-oxa-8-azaspiro[4.5]decane The title compound as a solid (74.1 mg) was prepared in the same fashion as Step 1 in Example 157 except that 4-((2-((6-chloro-4-fluoropyridin-3-yl)ethynyl)pyrimidin-5-yl)methyl)morpholine (254 mg, 0.596 mmol) prepared in Reference Example 41 and 1-oxa-8-azaspiro[4.5]decane (80 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.70 (s, 2H), 8.38 (s, 1H), 6.72 (s, 1H), 3.88-3.85 (t, 2H), 3.81-3.80 (d, 2H), 3.78-3.72 (m, 4H), 3.52-3.45 (m, 4H), 2.48-2.46 (t, 4H), 2.00-1.93 (m, 2H), 1.87-1.76 (m, 6H)

Step 2. 2-(1-(Cyclopropylsulfonyl)-1H-pyrazol-4-yl)-N-(5-((5-(morpholinomethyl)pyrimidin-2-yl)ethynyl)-4-(1-oxa-8-azaspiro[4.5]decan-8-yl)pyridin-2-yl)pyrimidin-4-amine The title compound (1.8 mg) was prepared in the same fashion as Step 3 in Example 1, except that 8-(2-chloro-5-((5-(morpholinomethyl)pyrimidin-2-yl)ethynyl)pyridin-4-yl)-1-oxa-8-azaspiro[4.5]decane (74.1 mg, 0.163 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.71 (s, 2H), 8.64 (s, 1H), 8.45-8.44 (d, 2H), 8.20 (s, 2H), 6.96-6.95 (d, 1H), 3.96-3.89 (m, 4H), 3.75-3.67 (m, 6H), 2.85 (s, 1H), 2.51-2.49 (t, 4H), 2.02-1.98 (t, 2H), 1.94-1.91 (t, 4H), 1.83-1.80 (t, 2H), 1.55-1.53 (q, 2H), 1.25-1.24 (d, 2H)

Example 367. 2-(1-(Cyclopropylsulfonyl)-1H-pyrazol-4-yl)-N-(5-((5-(morpholinomethyl)pyrimidin-2-yl)ethynyl)-4-(1-oxa-7-azaspiro[3.5]nonan-7-yl)pyridin-2-yl)pyrimidin-4-amine Step 1. 7-(2-Chloro-5-((5-(morpholinomethyl)pyrimidin-2-yl)ethynyl)pyridin-4-yl)-1-oxa-7-azaspiro[3.5]nonane The title compound as a solid (95.9 mg) was prepared in the same fashion as Step 1 in Example 157 except that 4-((2-((6-chloro-4-fluoropyridin-3-yl)ethynyl)pyrimidin-5-yl)methyl)morpholine (254 mg, 0.596 mmol) prepared in Reference Example 41 and 1-oxa-7-azaspiro[3.5]nonane (72 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.71 (s, 2H), 8.39 (s, 1H), 6.73 (s, 1H), 4.59-4.55 (t, 2H), 3.74-3.71 (t, 4H), 3.64-3.59 (q, 2H), 3.58-3.50 (m, 4H), 2.49-2.44 (m, 6H), 2.18-2.13 (m, 2H), 2.06-2.02 (q, 2H)

Step 2. 2-(1-(Cyclopropylsulfonyl)-1H-pyrazol-4-yl)-N-(5-((5-(morpholinomethyl)pyrimidin-2-yl)ethynyl)-4-(1-oxa-7-azaspiro[3.5]nonan-7-yl)pyridin-2-yl)pyrimidin-4-amine The title compound (2.3 mg) was prepared in the same fashion as Step 3 in Example 1, except that 7-(2-chloro-5-((5-(morpholinomethyl)pyrimidin-2-yl)ethynyl)pyridin-4-yl)-1-oxa-7-azaspiro[3.5]nonane (95.9 mg, 0.218 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.71 (d, 2H), 8.66 (s, 1H), 8.49-8.44 (m, 2H), 8.29-8.24 (m, 2H), 7.97 (d, 1H), 6.99-6.97 (d, 1H), 4.63-4.59 (t, 1H), 4.12-4.11 (d, 1H), 3.98-3.95 (t, 1H), 3.80-3.79 (d, 5H), 3.74-3.73 (d, 1H), 3.67-3.63 (q, 3H), 2.87-2.85 (q, 1H), 2.54-2.49 (q, 4H), 2.23-2.22 (d, 1H), 2.17-2.15 (t, 2H), 1.98-1.88 (t, 2H), 1.55-1.54 (d, 2H), 1.25-1.23 (d, 2H); MS (ESI) m/z=669.2 (M+H)$^+$ Example 368. 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-ol Step 1. 1-(2-Chloro-5-((4-((4-methylpiperazin-1-yl)methyl)phenyl)ethynyl)pyridin-4-yl)-4-methylpiperidin-4-ol The title compound as a solid (107.6 mg) was prepared in the same fashion as Step 1 in Example 157 except that 1-(4-((6-chloro-4-fluoropyridin-3-yl)ethynyl)benzyl)-4-methylpiperazine (205 mg, 0.596 mmol) prepared in Reference Example 31 and 4-methylpiperidin-4-ol (65 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.28 (s, 1H), 7.45-7.43 (d, 2H), 7.34-7.37 (d, 2H), 6.75 (s, 1H), 3.80-3.77 (d, 2H), 3.57 (s, 2H), 3.41-3.38 (t, 2H), 2.65 (brs, 6H), 2.46 (s, 3H), 1.84-1.80 (q, 2H), 1.76-1.72 (d, 2H), 1.35 (s, 3H)

Step 2. 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-ol The title compound (3.6 mg) was prepared in the same fashion as Step 3 in Example 1, except that 1-(2-chloro-5-((4-((4-methylpiperazin-1-yl)methyl)phenyl)ethynyl)pyridin-4-yl)-4-methylpiperidin-4-ol (107 mg, 0.245 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.69 (s, 1H), 8.45-8.41 (q, 4H), 8.16-8.13 (d, 2H), 7.46-7.44 (d, 2H), 7.33-7.31 (d, 2H), 6.94-6.92 (d, 1H), 3.98-3.94 (d, 2H), 3.60 (s, 2H), 3.54-3.48 (q, 2H), 2.86-2.82 (q, 1H), 2.73 (s, 4H), 2.62 (s, 3H), 1.91-1.87 (t, 4H), 1.56-1.55 (q, 2H), 1.38-1.35 (d, 3H), 1.27-1.24 (t, 2H)

Example 369. 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methoxypiperidin-4-ol Step 1. 1-(2-Chloro-5-((4-((4-methylpiperazin-1-yl)methyl)phenyl)ethynyl)pyridin-4-yl)-4-methoxypiperidin-4-ol The title compound as a solid (105.1 mg) was prepared in the same fashion as Step 1 in Example 157 except that 1-(4-((6-chloro-4-fluoropyridin-3-yl)ethynyl)benzyl)-4-methylpiperazine (205 mg, 0.596 mmol) prepared in Reference Example 31 and 4-methoxypiperidin-4-ol (74 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.26 (s, 1H), 7.44-7.42 (d, 2H), 7.34-7.32 (d, 2H), 6.72 (s, 1H), 3.77-3.74 (d, 2H), 3.52 (s, 2H), 3.28-3.23 (m, 5H), 2.48 (brs, 6H), 2.30 (s, 3H), 1.93-1.89 (d, 2H), 1.72-1.69 (d, 2H), 1.22 (s, 3H)

Step 2. 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methoxypiperidin-4-ol The title compound (3.0 mg) was prepared in the same fashion as Step 3 in Example 1, except that 1-(2-chloro-5-((4-((4-methylpiperazin-1-yl)methyl)phenyl)ethynyl)pyridin-4-yl)-4-methoxypiperidin-4-ol (105.1 mg, 0.231 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44-8.42 (t, 4H), 8.12 (s, 1H), 7.93 (s, 1H), 7.46-7.44 (d, 2H), 7.33-7.31 (d, 2H), 7.02-7.00 (d, 1H), 3.96-3.93 (d, 2H), 3.60 (s, 2H), 3.48-3.45 (d, 2H), 3.27 (s, 3H), 2.85 (s, 2H), 2.73 (s, 4H), 2.61 (s, 3H), 2.04-2.01 (d, 2H), 1.76 (s, 2H), 1.55-1.53 (d, 2H), 1.26-1.22 (m, 5H)

Example 370. 2-(1-(Cyclopropylsulfonyl)-1H-pyrazol-4-yl)-N-(5-((4-((4-methylpiperazin-1-yl)methyl)phenyl)ethynyl)-4-(1-oxa-7-azaspiro[3.5]nonan-7-yl)pyridin-2-yl)pyrimidin-4-amine Step 1. 7-(2-Chloro-5-((4-((4-methylpiperazin-1-yl)methyl)phenyl)ethynyl)pyridin-4-yl)-1-oxa-7-azaspiro[3.5]nonane The title compound as a solid (98.9 mg) was prepared in the same fashion as Step 1 in Example 157 except that 1-(4-((6-chloro-4-fluoropyridin-3-yl)ethynyl)benzyl)-4-methylpiperazine (205 mg, 0.596 mmol) prepared in Reference Example 31 and 1-oxa-7-azaspiro[3.5]nonane (72 mg, 0.567 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.27 (s, 1H), 7.44-7.42 (d, 2H), 7.34-7.32 (d, 2H), 6.71 (s, 1H), 4.59-4.55 (t, 2H), 3.52-3.47 (m, 6H), 2.47-2.44 (m, 8H), 2.30 (s, 3H), 2.15-2.10 (q, 2H), 2.03-1.99 (d, 2H)

Step 2. 2-(1-(Cyclopropylsulfonyl)-1H-pyrazol-4-yl)-N-(5-((4-((4-methylpiperazin-1-yl)methyl)phenyl)ethynyl)-4-(1-oxa-7-azaspiro[3.5]nonan-7-yl)pyridin-2-yl)pyrimidin-4-amine The title compound (6.3 mg) was prepared in the same fashion as Step 3 in Example 1, except that 7-(2-chloro-5-((4-((4-methylpiperazin-1-yl)methyl)phenyl)ethynyl)pyridin-4-yl)-1-oxa-7-azaspiro[3.5]nonane (98.8 mg, 0.219 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67-8.65 (d, 1H), 8.45-8.43 (d, 3H), 8.15-8.08 (m, 1H), 7.93-7.92 (d, 1H), 7.45-7.43 (t, 2H), 7.32-7.30 (m, 2H), 6.99-6.94 (q, 1H), 4.61 (t, 1H), 4.01-3.96 (q, 2H), 3.79 (s, 1H), 3.60 (s, 2H), 3.54-3.49 (t, 2H), 2.96 (s, 2H), 2.89-2.83 (m, 2H), 2.59 (s, 3H), 2.53 (s, 1H), 2.40-2.38 (d, 1H), 2.01-1.97 (d, 2H), 1.88-1.83 (q, 2H), 1.55 (s, 2H), 1.27-1.24 (t, 2H); MS (ESI) m/z=680.3 (M+H)$^+$ Example 371. 1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methoxypiperidin-4-ol Step 1. 1-(2-Chloro-5-((1-methylpyrrolidin-3-yl)ethynyl)pyridin-4-yl)-4-methoxypiperidin-4-ol The title compound as a solid (64.4 mg) was prepared in the same fashion as Step 1 in Example 157 except that 2-chloro-4-fluoro-5-((1-methylpyrrolidin-3-yl)ethynyl)pyridine (127 mg, 0.536 mmol) prepared in Reference Example 36 and 4-methoxypiperidin-4-ol (67 mg, 0.510 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.09 (s, 1H), 6.64 (s, 1H), 3.63-3.60 (d, 2H), 3.25-3.21 (m, 1H), 3.19 (s, 3H), 3.17-3.11 (q, 2H), 3.02-2.97 (t, 1H), 2.76-2.73 (m, 1H), 2.55-2.46 (m, 2H), 2.38 (s, 3H), 2.31-2.25 (m, 1H), 1.96-1.93 (q, 1H), 1.87-1.79 (d, 2H), 1.62 (d, 2H), 1.13 (s, 3H)

Step 2. 1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methoxypiperidin-4-ol The title compound (1.8 mg) was prepared in the same fashion as Step 3 in Example 1, except that 1-(2-chloro-5-

((1-methylpyrrolidin-3-yl)ethynyl)pyridin-4-yl)-4-methoxypiperidin-4-ol (64.4 mg, 0.184 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.44-8.43 (d, 2H), 8.32 (s, 3H), 8.08 (s, 1H), 7.94 (s, 1H), 6.96-6.94 (d, 1H), 3.90-3.86 (d, 2H), 3.77-3.75 (d, 1H), 3.58-3.52 (q, 4H), 3.44-3.38 (t, 2H), 3.15-3.12 (d, 2H), 2.98-2.96 (d, 2H), 2.83 (s, 3H), 2.51 (s, 1H), 2.21 (s, 1H), 2.01-1.98 (d, 2H), 1.70-1.64 (q, 3H), 1.53 (s, 2H), 1.25 (s, 3H), 1.22 (d, 2H)

Example 372. 2-(1-(Cyclopropylsulfonyl)-1H-pyrazol-4-yl)-N-(5-((1-methylpyrrolidin-3-yl)ethynyl)-4-(1-oxa-8-azaspiro[4.5]decan-8-yl)pyridin-2-yl)pyrimidin-4-amine

Step 1. 8-(2-Chloro-5-((1-methylpyrrolidin-3-yl)ethynyl)pyridin-4-yl)-1-oxa-8-azaspiro[4.5]decane The title compound as a solid (65.2 mg) was prepared in the same fashion as Step 1 in Example 157 except that 2-chloro-4-fluoro-5-((1-methylpyrrolidin-3-yl)ethynyl)pyridine (127 mg, 0.536 mmol) prepared in Reference Example 36 and 1-oxa-8-azaspiro[4.5]decane (72 mg, 0.510 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.07 (s, 1H), 6.62 (s, 1H), 3.83-3.80 (t, 2H), 3.54-3.51 (d, 2H), 3.34-3.28 (m, 2H), 3.22-3.20 (d, 2H), 3.18 (s, 1H), 2.98-2.94 (t, 1H), 2.71-2.68 (t, 1H), 2.53-2.42 (m, 2H), 2.35 (s, 3H), 2.28-2.22 (q, 1H), 1.95-1.90 (q, 3H), 1.82-1.70 (2, 6H)

Step 2. 2-(1-(Cyclopropylsulfonyl)-1H-pyrazol-4-yl)-N-(5-((1-methylpyrrolidin-3-yl)ethynyl)-4-(1-oxa-8-azaspiro[4.5]decan-8-yl)pyridin-2-yl)pyrimidin-4-amine The title compound (2.8 mg) was prepared in the same fashion as Step 3 in Example 1, except that 8-(2-chloro-5-((1-methylpyrrolidin-3-yl)ethynyl)pyridin-4-yl)-1-oxa-8-azaspiro[4.5]decane (65.2 mg, 0.181 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43-8.38 (t, 3H), 7.99 (s, 1H), 7.90 (s, 1H), 6.99-6.97 (d, 1H), 3.92-3.86 (m, 4H), 3.73-3.70 (t, 2H), 3.59-3.54 (t, 5H), 2.86-2.82 (t, 2H), 2.69-2.67 (d, 3H), 2.59-2.53 (d, 2H), 2.03-1.99 (q, 4H), 1.85-1.75 (m, 8H), 1.54-1.53 (q, 2H), 1.24-1.23 (d, 2H)

Example 373. 2-(1-(Cyclopropylsulfonyl)-1H-pyrazol-4-yl)-N-(5-((1-methylpyrrolidin-3-yl)ethynyl)-4-(1-oxa-7-azaspiro[3.5]nonan-7-yl)pyridin-2-yl)pyrimidin-4-amine

Step 1. 7-(2-Chloro-5-((1-methylpyrrolidin-3-yl)ethynyl)pyridin-4-yl)-1-oxa-7-azaspiro[3.5]nonane The title compound as a solid (64 mg) was prepared in the same fashion as Step 1 in Example 157 except that 2-chloro-4-fluoro-5-((1-methylpyrrolidin-3-yl)ethynyl)pyridine (127 mg, 0.536 mmol) prepared in Reference Example 36 and 1-oxa-7-azaspiro[3.5]nonane (65 mg, 0.510 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.10 (s, 1H), 6.63 (s, 1H), 4.55-4.51 (t, 2H), 3.39-3.36 (t, 4H), 3.24-3.20 (t, 1H), 3.00-2.96 (t, 1H), 2.73-2.72 (d, 1H), 2.54-2.52 (d, 1H), 2.49-2.37 (m, 6H), 2.30-2.27 (q, 1H), 2.06-2.02 (t, 2H), 1.94-1.91 (t, 3H)

Step 2. 2-(1-(Cyclopropylsulfonyl)-1H-pyrazol-4-yl)-N-(5-((1-methylpyrrolidin-3-yl)ethynyl)-4-(1-oxa-7-azaspiro[3.5]nonan-7-yl)pyridin-2-yl)pyrimidin-4-amine The title compound (7.4 mg) was prepared in the same fashion as Step 3 in Example 1, except that 7-(2-chloro-5-((1-methylpyrrolidin-3-yl)ethynyl)pyridin-4-yl)-1-oxa-7-azaspiro[3.5]nonane (64 mg, 0.185 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.43-8.40 (t, 3H), 8.05 (s, 1H), 7.76 (s, 1H), 7.00-6.98 (d, 1H), 4.70 (brs, 4H), 4.62-4.58 (t, 2H), 3.61-3.57 (q, 2H), 3.48-3.43 (q, 4H), 3.22 (m, 1H), 2.92-2.90 (d, 1H), 2.88-2.83 (m, 2H), 2.64 (s, 3H), 2.53-2.51 (d, 2H), 2.49-2.43 (d, 1H), 2.15-2.10 (m, 3I1), 2.08-2.05 (q, 2H), 1.55-1.53 (m, 2H), 1.25-1.22 (q, 2H); MS (ESI) m/z=575.2 (M+H)$^+$

Example 374. ((1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexyl)methanol

Step 1. ((1s,4s)-4-((2-Chloro-5-((tetrahydrofuran-2-yl)ethynyl)pyridin-4-yl)amino)cyclohexyl)methanol The title compound as a solid (95 mg) was prepared in the same fashion as Step 1 in Example 157 except that 2-chloro-4-fluoro-5-((tetrahydrofuran-2-yl)ethynyl)pyridine (130 mg, 0.576 mmol) prepared in Reference Example 61 and ((1s,4s)-4-aminocyclohexyl)methanol (97 mg, 0.749 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96 (s, 1H), 6.39 (s, 1H), 5.29-5.27 (d, 1H), 4.82-4.79 (q, 1H), 3.96-3.91 (q, 1H), 3.84-3.79 (q, 1H), 3.63-3.62 (d, 1H), 3.48-3.46 (d, 2H), 2.77 (brs, 1H), 2.25-2.19 (m, 1H), 2.08-1.88 (m, 3H), 1.78-1.74 (q, 2H), 1.66-1.59 (q, 4H), 1.32-1.26 (t, 2H)

Step 2. ((1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexyl)methanol The title compound (4.3 mg) was prepared in the same fashion as Step 3 in Example 1, except that ((1s,4s)-4-((2-chloro-5-((tetrahydrofuran-2-yl)ethynyl)pyridin-4-yl)amino)cyclohexyl)methanol (95 mg, 0.284 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.46-8.42 (m, 1H), 7.94 (s, 1H), 7.82 (s, 1H), 7.00-6.99 (d, 1H), 5.85-5.83 (d, 1H), 4.90-4.87 (q, 1H), 4.02-3.98 (t, 2H), 3.93-3.88 (m, 1H), 3.56-3.55 (d, 2H), 2.85-2.83 (t, 1H), 2.12-2.10 (t, 1H), 2.08 (m, 2H), 2.05-2.00 (t, 3H), 1.92-1.89 (t, 2H), 1.78-1.74 (t, 2H), 1.55-1.53 (q, 2H), 1.34-1.31 (d, 2H), 1.25-1.23 (t, 2H); MS (ESI) m/z=564.2 (M+H)$^+$

Example 375. (1 r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)cyclohexan-1-ol

Step 1. (1 r,4r)-4-(((2-Chloro-5-((tetrahydrofuran-2-yl)ethynyl)pyridin-4-yl)amino)methyl)cyclohexan-1-ol The title compound as a solid (97.9 mg) was prepared in the same fashion as Step 1 in Example 157 except that 2-chloro-4-fluoro-5-((tetrahydrofuran-2-yl)ethynyl)pyridine (130 mg, 0.576 mmol) prepared in Reference Example 61 and trans-4-(aminomethyl)cyclohexanol HCl (124 mg, 0.749 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.95 (s, 1H), 6.36 (s, 1H), 5.23-5.20 (t, 1H), 4.81-4.78 (q, 1H), 3.96-3.91 (q, 1H), 3.84-3.79 (q, 1H), 3.55-3.50 (m, 1H), 3.00-2.96 (t, 2H), 2.63 (brs, 1H), 2.23-2.18 (t, 1H), 2.07-1.89 (m, 5H), 1.80-1.77 (d, 2H), 1.53-1.51 (t, 1H), 1.28-1.20 (q, 2H), 1.05-0.96 (q, 2H)

Step 2. (1r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)cyclohexan-1-ol The title compound (2.9 mg) was prepared in the same fashion as Step 3 in Example 1, except that (1 r,4r)-4-(((2-chloro-5-((tetrahydrofuran-2-yl)ethynyl)pyridin-4-yl)amino)methyl)cyclohexan-1-ol (97.9 mg, 0.292 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.43-8.42 (t, 2H), 7.92 (s, 1H), 7.44 (s, 1H), 7.11-7.09 (d, 1H), 5.35 (s, 1H), 4.89-4.86 (q, 1H), 4.02-4.00 (d, 1H), 3.91-3.90 (d, 1H), 3.60 (s, 1H), 3.23-3.20 (t, 2H), 2.84-2.80 (m, 2H), 2.12-2.10 (d, 1H), 2.09-2.03 (m, 4H), 1.91-1.88 (d, 2H), 1.54-1.52 (q, 1H), 1.32-1.26 (t, 2H), 1.23-1.20 (m, 6H); MS (ESI) m/z=564.2 (M+H)$^+$

Example 376. (1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexan-1-ol

Step 1. (1s,4s)-4-((2-Chloro-5-((tetrahydrofuran-2-yl)ethynyl)pyridin-4-yl)amino)cyclohexan-1-ol The title compound as a solid (97.9 mg) was prepared in the same fashion as Step 1 in Example 157 except that 2-chloro-4-fluoro-5-((tetrahydrofuran-2-yl)ethynyl)pyridine (130 mg, 0.576 mmol) prepared in Reference Example 61 was used instead of 4-(4-((6-chloro-4-fluoropyridin-3-yl)ethynyl)benzyl)morpholine. $^1$H-NMR (CDCl$_3$, 400 MHz) δ 7.96-7.95 (d, 1H), 6.39 (s, 1H), 5.11-5.09 (d, 1H), 4.81-4.78 (q, 1H), 3.97-3.83 (m, 2H), 3.81-3.79 (d, 1H), 3.39-3.35 (q, 1H), 2.70 (brs, 1H), 2.25-2.20 (m, 1H), 2.07-1.91 (m, 3H), 1.64 (d, 8H)

Step 2. (1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexan-1-ol The title compound (2.4 mg) was prepared in the same fashion as Step 3 in Example 1, except that (1s,4s)-4-((2-chloro-5-((tetrahydrofuran-2-yl)ethynyl)pyridin-4-yl)amino)cyclohexan-1-ol (98.7 mg, 0.308 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.47-8.41 (m, 2H), 8.02 (s, 1H), 7.21-7.20 (d, 1H), 7.07 (s, 1H), 5.17 (s, 1H), 4.90-4.87 (q, 1H), 4.02-4.01 (d, 1H), 3.90-3.89 (d, 1H), 3.22-3.19 (t, 2H), 2.84-2.81 (q, 1H), 2.10-2.08 (t, 2H), 1.86-1.74 (q, 4H), 1.55-1.46 (m, 4H), 1.29 (d, 6H); MS (ESI) m/z=550.2 (M+H)$^+$

Example 377. (1r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)-1-methylcyclohexan-1-ol

Step 1. (1 r,4r)-4-(((2-Chloro-5-((tetrahydrofuran-2-yl)ethynyl)pyridin-4-yl)amino)methyl)-1-methylcyclohexan-1-ol The title compound as a solid (116.4 mg) was prepared in the same fashion as Step 1 in Example 157 except that 2-chloro-4-fluoro-5-((tetrahydrofuran-2-yl)ethynyl)pyridine (130 mg, 0.576 mmol) prepared in Reference Example 61 and trans-4-(aminomethyl)-1-methyl-cyclohexanol HCl (134 mg, 0.749 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.94-7.92 (d, 1H), 6.35 (s, 1H), 5.18-5.15 (t, 1H), 4.79-4.76 (q, 1H), 3.92-3.88 (t, 1H), 3.82-3.79 (t, 1H), 3.02-2.99 (t, 2H), 2.21-2.19 (d, 1H), 2.04-1.89 (m, 2H), 1.74-1.68 (t, 1H), 1.64-1.60 (q, 4H), 1.59-1.56 (m, 1H), 1.46-1.40 (m, 2H), 1.39 (s, 3H), 1.17-1.12 (m, 2H)

Step 2. (1r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)-1-methylcyclohexan-1-ol The title compound (2.6 mg) was prepared in the same fashion as Step 3 in Example 1, except that (1 r,4r)-4-(((2-chloro-5-((tetrahydrofuran-2-yl)ethynyl)pyridin-4-yl)amino)methyl)-1-methylcyclohexan-1-ol (116.4 mg, 0.334 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.48-8.43 (m, 2H), 8.30 (s, 2H), 7.98 (s, 1H), 7.84 (s, 1H), 7.01-7.00 (d, 1H), 5.73-5.72 (d, 1H), 4.88-4.85 (q, 1H), 4.01 (d, 1H), 3.99-3.90 (s, 1H), 3.33-3.30 (t, 2H), 2.84-2.82 (t, 1H), 2.56 (s, 1H), 2.11-2.08 (q, 3H), 1.86-1.74 (m, 4H), 1.55-1.47 (m, 4H), 1.29-1.22 (m, 6H); MS (ESI) m/z=578.2 (M+H)$^+$

Example 378. (1-(2-((2-(1-(Cyclopropylsulfonyl)-1H-pyrazol-4-yl)pyrimidin-4-yl)amino)-5-((tetrahydrofuran-2-yl)ethynyl)pyridin-4-yl)-4-methylpiperidin-4-yl)methanol

Step 1. (1-(2-Chloro-5-((tetrahydrofuran-2-yl)ethynyl)pyridin-4-yl)-4-methylpiperidin-4-yl)methanol The title compound as a solid (83.9 mg) was prepared in the same fashion as Step 1 in Example 157 except that 2-chloro-4-fluoro-5-((tetrahydrofuran-2-yl)ethynyl)pyridine (130 mg, 0.576 mmol) prepared in Reference Example 61 and (4-methylpiperidin-4-yl)methanol (113 mg, 0.749 mmol) were used instead of 4-(4-((6-chloro-4-fluoropyridin- 3-yl)ethynyl)benzyl)morpholine and cis-4-aminocyclohexanol HCl. $^1$H-NMR (CDCl$_3$, 400 MHz) δ 8.10 (s, 1H), 6.63 (s, 1H), 4.82-4.79 (q, 1H), 3.96-3.91 (q, 1H), 3.85-3.81 (q, 1H), 3.64-3.59 (m, 2H), 3.39 (s, 2H), 3.21-3.15 (q, 2H), 2.21-2.16 (q, 1H), 2.06-1.90 (m, 3H), 1.69-1.62 (m, 2H), 1.43-1.39 (d, 2H), 1.23-1.20 (t, 3H)

Step 2. (1-(2-((2-(1-(Cyclopropylsulfonyl)-1H-pyrazol-4-yl)pyrimidin-4-yl)amino)-5-((tetrahydrofuran-2-yl)ethynyl)pyridin-4-yl)-4-methylpiperidin-4-yl)methanol The title compound (4.6 mg) was prepared in the same fashion as Step 3 in Example 1, except that (1-(2-chloro-5-((tetrahydrofuran-2-yl)ethynyl)pyridin-4-yl)-4-methylpiperidin-4-yl)methanol (83.9 mg, 0.251 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66-8.62 (d, 1H), 8.48-8.40 (m, 3H), 8.05-7.98 (t, 2H), 7.31-7.26 (m, 1H), 6.93 (s, 1H), 4.87-4.86 (d, 1H), 4.00 (d, 1H), 3.89-3.80 (d, 2H), 3.55-3.51 (m, 4H), 2.84 (d, 1H), 2.09-2.00 (m, 4H), 1.79 (d, 2H), 1.58-1.55 (t, 4H), 1.25 (d, 2H), 1.13-1.09 (d, 3H); MS (EST) m/z=564.2 (M+H)$^+$ Example 379. ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol Step 1. ((1s,4s)-4-((2-Chloro-5-((1-(2-fluoroethyl)-1H-pyrazol-4-yl)ethynyl)pyridin-4-yl)amino)cyclohexyl)methanol The title compound as a solid (177 mg) was prepared in the same fashion as Step 1 in Example 157 except that 2-chloro-4-fluoro-5-((1-(2-fluoroethyl)-1H-pyrazol-4-yl)ethynyl)pyridine (130 mg, 0.486 mmol) prepared in Reference Example 62 and ((1s,4s)-4-aminocyclohexyl)methanol (82 mg, 0.631 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.98 (s, 1H), 7.68 (s, 1H), 7.61 (s, 1H), 6.38 (s, 1H), 5.30-5.28 (d, 1H), 4.75-4.73 (t, 1H), 4.64-4.61 (t, 1H), 4.39-4.36 (t, 1H), 4.32-4.30 (t, 1H), 3.61 (s, 1H), 3.45-3.43 (d, 2H), 3.23 (brs, 1H), 1.75-1.73 (d, 2H), 1.64-1.60 (d, 4H), 1.32-1.26 (t, 2H)

Step 2. ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol The title compound (6.5 mg) was prepared in the same fashion as Step 3 in Example 1, except that ((1s,4s)-4-((2-chloro-5-((1-(2-fluoroethyl)-1H-pyrazol-4-yl)ethynyl)pyridin-4-yl)amino)cyclohexyl)methanol (177 mg, 0.47 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 7.97 (s, 1H), 7.61 (s, 1H), 7.57 (s, 1H), 6.35 (s, 1H), 4.73-4.71 (t, 1H), 4.61-4.59 (t, 1H), 4.37-4.34 (t, 1H), 4.30-4.28 (t, 1H), 3.01-2.98 (t, 2H), 2.66 (s, 1H), 1.71-1.61 (m, 5H), 1.43-1.37 (m, 2H), 1.16-1.04 (m, 6H); MS (ESI) m/z=606.2 (M+H)$^+$ Example 380. (1r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)-1-methylcyclohexan-1-ol Step 1. (1 r,4r)-4-(((2-Chloro-5-((1-(2-fluoroethyl)-1H-pyrazol-4-yl)ethynyl)pyridin-4-yl)amino)methyl)-1-methylcyclohexan-1-ol The title compound as a solid (116.4 mg) was prepared in the same fashion as Step 1 in Example 157 except that 2-chloro-4-fluoro-5-((1-(2-fluoroethyl)-1H-pyrazol-4-yl)ethynyl)pyridine (130 mg, 0.486 mmol) prepared in Reference Example 62 and trans-4-(aminomethyl)-1-methyl-cyclohexanol HCl (113 mg, 0.631 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.97 (s, 1H), 7.61 (s, 1H), 7.57 (s, 1H), 6.35 (s, 1H), 4.73-4.71 (t, 1H), 4.61-4.59 (t, 1H), 4.37-4.34 (t, 1H), 4.30-4.28 (t, 1H), 3.01-2.98 (t, 2H), 2.66 (s, 1H), 1.71-1.61 (m, 5H), 1.43-1.37 (m, 2H), 1.16-1.04 (m, 6H)

Step 2. (1r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)-1-methylcyclohexan-1-ol The title compound (6.2 mg) was prepared in the same fashion as Step 3 in Example 1, except that (1 r,4r)-4-(((2-chloro-5-((1-(2-fluoroethyl)-1H-pyrazol-4-yl)ethynyl)pyridin-4-yl)amino)methyl)-1-methylcyclohexan-1-ol (189 mg, 0.485 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.48 (s, 1H), 8.45-8.43 (t, 2H), 7.93 (s, 1H), 7.72-7.71 (d, 3H), 7.07-7.06 (d, 1H), 5.49 (s, 1H), 4.87-4.84 (t, 1H), 4.75-4.73 (t, 1H), 4.50-4.48 (t, 1H), 4.43-4.41 (t, 1H), 3.33-3.30 (t, 2H), 2.82 (s, 1H), 1.86-1.82 (d, 2H), 1.76-1.72 (d, 2H), 1.54-1.49 (q, 4H), 1.28-1.22 (m, 6H); MS (ESI) m/z=620.2 (M+H)$^+$ Example 381. ((l r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)cyclohexyl)methanol Step 1. ((l r,4r)-4-(((2-Chloro-5-((1-(2-fluoroethyl)-1H-pyrazol-4-yl)ethynyl)pyridin-4-yl)amino)methyl)cyclohexyl)methanol The title compound as a solid (163 mg) was prepared in the same fashion as Step 1 in Example 157 except that 2-chloro-4-fluoro-5-((1-(2-fluoroethyl)-1H-pyrazol-4-yl)ethynyl)pyridine (130 mg, 0.486 mmol) prepared in Reference Example 62 and trans-4-(aminomethyl)cyclohexanemethanol HCl (113 mg, 0.631 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.09 (s, 1H), 7.69-7.68 (d, 2H), 6.45 (s, 1H), 5.21-5.18 (t, 1H), 4.85-4.82 (t, 1H), 4.73-4.71 (t, 1H), 4.48-4.45 (t, 1H), 4.41-4.39 (t, 1H), 3.48-3.46 (d, 2H), 3.09-3.06 (t, 2H), 1.89-1.87 (d, 4H), 1.61-1.60 (d, 2H), 1.49-1.48 (t, 1H), 1.07-0.98 (m, 41-1)

Step 2. ((1r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)cyclohexyl)methanol The title compound (2.1 mg) was prepared in the same fashion as Step 3 in Example 1, except that ((l r,4r)-4-(((2-chloro-5-((1-(2-fluoroethyl)-1H-pyrazol-4-yl)ethynyl)pyridin-4-yl)amino)methyl)cyclohexyl)methanol (163 mg, 0.419 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44-8.42 (d, 2H), 7.99 (s, 11-0,7.72-7.71 (d, 2H), 7.41 (s, 1H), 7.16-7.15 (d, 1H), 5.40 (s, 1H), 4.87-4.85 (t, 1H), 4.75-4.73 (t, 1H), 4.50-4.48 (t, 1H), 4.43-4.41 (t, 1H), 3.48-3.46 (d, 2H), 3.26-3.23 (t, 2H), 2.83 (s, 1H), 1.93-1.86 (t, 4H), 1.54-1.51 (m, 4H), 1.23-1.21 (q, 2H), 1.15-1.06 (m, 4H); MS (ESI) m/z=620.2 (M+H)$^+$ Example 382. 2-(1-(Cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine Step 1. tert-Butyl ((1-(2-chloro-5-((1-methyl-1H-pyrazol-4-yl)ethynyl)pyridin-4-yl)-4-fluoropiperidin-4-yl)methyl)carbamate The title compound as a solid (1340 mg) was prepared in the same fashion as Step 1 in Example 157 except that 2-chloro-4-fluoro-5-((1-methyl-1H-pyrazol-4-yl)ethynyl)pyridine (0.80 g, 3.395 mmol) prepared in Reference Example 18 and tert-butyl (4-fluoropiperidin-4-yl)methylcarbamate (960 mg, 4.074 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.25 (s, 1H), 7.61-7.59 (d, 2H), 6.73 (s, 1H), 4.87 (s, 1H), 3.93 (s, 3H), 3.86-3.83 (d, 2H), 3.41-3.34 (q, 2H), 3.23-3.18 (t, 2H), 1.97-1.94 (d, 4H), 1.46 (s, 9H)

Step 2. tert-Butyl ((1-(2-chloro-5-((1-methyl-1H-pyrazol-4-yl)ethynyl)pyridin-4-yl)-4-fluoropiperidin-4-yl)methyl)(methyl)carbamate The mixture of tert-butyl ((1-(2-chloro-5-((1-methyl-1H-pyrazol-4-yl)ethynyl)pyridin-4-yl)-4-fluoropiperidin-4-yl)methyl)carbamate (445 mg, 0.993 mmol) prepared in Step 1 in DMF (4 mL)/THE (4 mL) was charged nitrogen gas for 10 minutes. After NaH (48 mg, 1.192 mmol) and iodomethane (0.07 mL, 1.192 mmol) were added, the reaction mixture was stirred at room temperature for 2 hours. The reaction mixture was diluted in EA, washed by water, dried over MgSO$_4$, and then concentrated. The crude product was purified by column chromatography (MeOH/DCM=0-10%) to yield tert-butyl ((1-(2-chloro-5-((1-methyl-1H-pyrazol-4-yl)ethynyl)pyridin-4-yl)-4-fluoropiperidin-4-yl)methyl)(methyl)carbamate (456 mg) as a yellow solid. MS (ESI) m/z=462.1 (M+H)$^+$ Step 3. tert-Butyl ((1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methyl)(methyl)carbamate The title compound (89 mg) was prepared in the same fashion as Step 3 in Example 1, except that tert-butyl ((1-(2-chloro-5-((1-methyl-1H-pyrazol-4-yl)ethynyl)pyridin-4-yl)-4-fluoropiperidin-4-yl)methyl)(methyl)carbamate (456 mg, 0.988 mmol) prepared in Step 2 was used instead of 1-(2-chloro-5-((1-methyl-1H-pyrazol-4-yl)ethynyl)pyridin-4-yl)-4-methylpiperazine. MS (ESI) m/z=691.2 (M+H)$^+$ Step 4. 2-(1-(Cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine The mixture of tert-butyl ((1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methyl)(methyl)carbamate (89 mg, 0.13 mmol) prepared in Step 3 in EA (1 mL) was added 4M HCl in 1,4-dioxane (0.1 mL, 0.39 mmol). The reaction mixture was stirred at room temperature overnight. The reaction mixture was concentrated. The crude product was purified by column chromatography (MeOH/DCM=0-30%) to yield 2-(1-(cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine (4.1 mg) as a white solid. $^1$H-NMR (CDCl$_3$, 400 MHz) δ 8.64 (s, 1H), 8.43-8.42 (d, 2H), 8.21 (s, 1H), 8.11 (s, 1H), 7.93 (s, 1H), 7.62-7.60 (d, 2H), 7.07-6.97 (d, 1H), 4.06-4.03 (d, 2H), 3.95 (s, 2H), 3.50-3.32 (t, 2H), 3.02-2.96 (t, 2H), 2.87-2.84 (m, 1H), 2.62 (s, 3H), 2.35-2.32 (m, 6H), 1.95-1.92 (d, 2H), 1.54 (d, 2H); MS (ESI) m/z=591.2 (M+H)$^+$ Example 383. 2-(1-(Cyclopropylsulfonyl)-1H-pyrazol-4-yl)-N-(4-(4-fluoro-4-(((2-fluoroethyl)amino)methyl)piperidin-1-yl)-5-((1-methyl-1H-pyrazol-4-yl)ethynyl)pyridin-2-yl)pyrimidin-4-amine Step 1. tert-Butyl ((1-(2-chloro-5-((1-methyl-1H-pyrazol-4-yl)ethynyl)pyridin-4-yl)-4-fluoropiperidin-4-yl)methyl)(2-fluoroethyl)carbamate The title compound as a solid (466 mg) was prepared in the same fashion as Step 2 in Example 382 except that 1-bromo-2-fluoroethane (154 mg, 1.192 mmol) was used instead of iodomethane. MS (ESI) m/z=494.2 (M+H)$^+$ Step 2. tert-Butyl ((1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methyl)(2-fluoroethyl)carbamate The title compound (39 mg) was prepared in the same fashion as Step 3 in Example 1, except that tert-butyl ((1-(2-chloro-5-((1-methyl-1H-pyrazol-4-yl)ethynyl)pyridin-4-yl)-4-fluoropiperidin-4-yl)methyl)(2-fluoroethyl)carbamate (466 mg, 0.943 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=723.2 (M+H)$^+$ Step 3. 2-(1-(Cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine The title compound as a white solid (1.2 mg) was prepared in the same fashion as Step 4 in Example 382, except that tert-butyl ((1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methyl)(2-fluoroethyl)carbamate (39 mg, 0.055 mmol) prepared in Step 2 was used instead of tert-butyl ((1-(2-((2-(1-(cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methyl)(methyl)carbamate. $^1$H-NMR (CDCl$_3$, 400 MHz) δ 8.64 (s, 1H), 8.44-8.43 (d, 1H), 8.15-8.13 (d, 1H), 7.87 (s, 1H), 7.62 (s, 1H), 7.55-7.53 (d, 1H), 7.03-7.00 (m, 1H), 4.63-4.62 (d, 1H), 4.51-4.50 (d, 1H), 4.04-4.01 (d, 2H), 3.94 (s, 2H), 3.34 (s, 2H), 3.03-2.92 (m, 3H), 2.86-2.85 (d, 2H), 2.21-2.18 (q, 2H), 1.74 (brs, 6H), 1.57-1.53 (q, 2H), 1.25-1.22 (q, 2H); MS (ESI) m/z=623.2 (M+H)$^+$ Example 384. (S)-2-(1-(Cyclopropylsulfonyl)-1H-pyrazol-4-yl)-N-(4-(3-((dimethylamino)methyl)piperidin-1-yl)-5-((1-methyl-1H-pyrazol-4-yl)ethynyl)pyridin-2-yl)pyrimidin-4-amine Step 1. (S)-1-(1-(2-Chloro-5-((1-methyl-1H-pyrazol-4-yl)ethynyl)pyridin-4-yl)piperidin-3-yl)-N,N-dimethylmethanamine The title compound as a solid (203 mg) was prepared in the same fashion as Step 2 in Example 1 except that (S)-1-(1-(2-chloro-5-iodopyridin-4-yl)piperidin-3-yl)-N,N-dimethylmethanamine (246 mg, 0.649 mmol) prepared in Reference Example 63 was used instead of 1-(2-chloro-5-iodopyridin-4-yl)-4-methylpiperazine. MS (ESI) m/z=358.1 (M+H)$^+$ Step 2. (S)-2-(1-(Cyclopropylsulfonyl)-1H-pyrazol-4-yl)-N-(4-(3-((dimethylamino)methyl)piperidin-1-yl)-5-((1-methyl-1H-pyrazol-4-yl)ethynyl)pyridin-2-yl)pyrimidin-4-amine The title compound (10.2 mg) was prepared in the same fashion as Step 3 in Example 1, except that (S)-1-(1-(2-chloro-5-((1-methyl-1H-pyrazol-4-yl)ethynyl)pyridin-4-yl)piperidin-3-yl)-N,N-dimethylmethanamine (203 mg, 0.567 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44-8.37 (m, 4H), 8.10 (s, 1H), 7.85 (s, 1H), 7.62 (s, 2H), 7.04-7.03 (d, 1H), 4.06-4.03 (d, 1H), 3.96-3.93 (d, 4H), 3.05-2.99 (t, 1H), 2.90-2.83 (q, 4H), 2.61 (s, 6H), 2.21 (s, 1H), 2.09-2.06 (d, 1H), 1.95-1.92 (d, 1H), 1.82-1.79 (d, 1H), 1.53 (s, 2H), 1.42-1.39 (d, 1H), 1.24-1.23 (d, 2H); MS (ESI) m/z=587.2 (M+H)$^+$ Example 385. (S)-2-(1-(Cyclopropylsulfonyl)-1H-pyrazol-4-yl)-N-(4-(3-((dimethylamino)methyl)piperidin-1-yl)-5-((1-(2-fluoroethyl)-1H-pyrazol-4-yl)ethynyl)pyridin-2-yl)pyrimidin-4-amine Step 1. (S)-1-(1-(2-Chloro-5-((1-(2-fluoroethyl)-1H-pyrazol-4-yl)ethynyl)pyridin-4-yl)piperidin-3-yl)-N,N-dimethylmethanamine The title compound as a solid (214 mg) was prepared in the same fashion as Step 2 in Example 1 except that (S)-1-(1-(2-chloro-5-iodopyridin-4-yl)piperidin-3-yl)-N,N-dimethylmethanamine (246 mg, 0.649 mmol) prepared in Reference Example 63 and 4-ethynyl-1-(2-fluoroethyl)pyrazole (85 mg, 0.618 mmol) were used instead of 1-(2-chloro-5-iodopyridin-4-yl)-4-methylpiperazine and 4-ethynyl-1-methylpyrazole. MS (ESI) m/z=390.2 (M+H)$^+$ Step 2. (S)-2-(1-(Cyclopropylsulfonyl)-1H-pyrazol-4-yl)-N-(4-(3-((dimethylamino)methyl)piperidin-1-yl)-5-((1-(2-fluoroethyl)-1H-pyrazol-4-yl)ethynyl)pyridin-2-yl)pyrimidin-4-amine The title compound (13.6 mg) was prepared in the same fashion as Step 3 in Example 1, except that (S)-1-(1-(2-chloro-5-((1-(2-fluoroethyl)-1H-pyrazol-4-yl)ethynyl)pyridin-4-yl)piperidin-3-yl)-N,N-dimethylmethanamine (214 mg, 0.549 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.46-8.45 (t, 2H), 8.27 (s, 1H), 8.13 (s, 1H), 8.06 (s, 1H), 7.78 (s, 1H), 7.70 (s, 1H), 6.96-6.94 (d, 1H), 4.86-4.84 (t, 1H), 4.75-4.72 (t, 1H), 4.51-4.49 (t, 1H), 4.44-4.42 (t, 1H), 4.09-3.98 (q, 2H), 3.10-3.03 (m, 2H), 2.98-2.91 (m, 2H), 2.88-2.84 (q, 1H), 2.73 (s, 5H), 2.13 (s, 1H), 1.97 (s, 1H), 1.54 (d, 2H), 1.52-1.49 (d, 4H), 1.27-1.25 (d, 2H); MS (ESI) m/z=619.2 (M+H)$^+$ Example 386. 2-(1-(Cyclopropylsulfonyl)-1H-pyrazol-4-yl)-N-(4-(3-(2-(dimethylamino)ethyl)piperidin-1-yl)-5-((1-(2-fluoroethyl)-1H-pyrazol-4-yl)ethynyl)pyridin-2-yl)pyrimidin-4-amine Step 1. 2-(1-(2-Chloro-5-((1-(2-fluoroethyl)-1H-pyrazol-4-yl)ethynyl)pyridin-4-yl)piperidin-3-yl)-N,N-dimethylethan-1-amine The title compound as a solid (180 mg) was prepared in the same fashion as Step 2 in Example 1 except that 2-(1-(2-chloro-5-iodopyridin-4-yl)piperidin-3-yl)-N,N-dimethylethan-1-amine (243 mg, 0.618 mmol) prepared in Reference Example 64 and 4-ethynyl-1-(2-fluoroethyl)pyrazole (85 mg, 0.618 mmol) were used instead of 1-(2-chloro-5-iodopyridin-4-yl)-4-methylpiperazine and 4-ethynyl-1-methylpyrazole. $^1$H-NMR (CDCl$_3$, 400 MHz) δ 8.17 (s, 1H), 7.74 (s, 1H), 7.64 (s, 1H), 6.66 (s, 1H), 4.79 (s, 1H), 4.67 (s, 1H), 4.45 (s, 1H), 4.39 (s, 1H), 4.02-3.99 (d, 1H), 3.82-3.79 (d, 1H), 3.39-3.36 (t, 2H), 2.81-2.76 (q, 1H), 2.68-2.62 (q, 1H), 2.51-2.46 (t, 2H), 2.37-2.32 (t, 2H), 1.88-1.85 (d, 2H), 1.77-1.71 (t, 4H), 1.69-1.63 (t, 2H), 1.23-1.18 (d, 2H)

Step 2. 2-(1-(Cyclopropylsulfonyl)-1H-pyrazol-4-yl)-N-(4-(3-(2-(dimethylamino)ethyl)piperidin-1-yl)-5-((1-(2-fluoroethyl)-1H-pyrazol-4-yl)ethynyl)pyridin-2-yl)pyrimidin-4-amine The title compound (10.7 mg) was prepared in the same fashion as Step 3 in Example 1, except that 2-(1-(2-chloro-5-((1-(2-fluoroethyl)-1H-pyrazol-4-yl)ethynyl)pyridin-4-yl)piperidin-3-yl)-N,N-dimethylethan-1-amine (180 mg, 0.446 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.46-8.45 (d, 2H), 8.25-8.21 (d, 1H), 8.03 (s, 1H), 7.77 (s, 1H), 7.70 (s, 1H), 6.95-6.94 (d, 1H), 4.88-4.85 (t, 1H), 4.76-4.74 (t, 1H), 4.51-4.49 (t, 1H), 4.44-4.42 (t, 1H), 4.19 (m, 2H), 3.02-3.00 (m, 4H), 2.87 (s, 1H), 2.70 (s, 6H), 1.98 (m, 2H), 1.77-1.73 (m, 4H), 1.54-1.52 (q, 2H), 1.26-1.24 (t, 2H); MS (ESI) m/z=633.2 (M+H)$^+$

Example 387. ((1s,4s)-4-((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)cyclohexyl)methanol

Step 1. ((1s,4s)-4-((2-Chloro-5-((1-(methylsulfonyl)piperidin-4-yl)ethynyl)pyridin-4-yl)amino)cyclohexyl)methanol The title compound as a solid (174 mg) was prepared in the same fashion as Step 1 in Example 157 except that 2-chloro-4-fluoro-5-((1-(methylsulfonyl)piperidin-4-yl)ethynyl)pyridine (155 mg, 0.486 mmol) prepared in Reference Example 65 and ((1s,4s)-4-aminocyclohexyl)methanol (82 mg, 0.636 mmol) were was used instead of 4-(4-((6-chloro-4-fluoropyridin-3-yl)ethynyl)benzyl)morpholine and cis-4-aminocyclohexanol HCl. MS (ESI) m/z=426.1 (M+H)$^+$

Step 2. ((1s,4s)-4-((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)cyclohexyl)methanol The title compound (6.5 mg) was prepared in the same fashion as Step 3 in Example 1, except that ((1s,4s)-4-((2-chloro-5-((1-(methylsulfonyl)piperidin-4-yl)ethynyl)pyridin-4-yl)amino)cyclohexyl)methanol (174 mg, 0.41 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.59 (s, 1H), 8.47-8.45 (d, 1H), 8.41 (s, 1H), 8.36 (s, 1H), 8.08 (s, 1H), 7.83 (s, 1H), 7.01-7.00 (d, 1H), 5.96-5.94 (d, 1H), 3.61-3.55 (m, 4H), 3.14-3.12 (t, 2H), 3.09 (d, 1H), 2.91 (s, 3H), 2.11-2.06 (m, 4H), 2.04-2.00 (m, 4H), 1.95-1.87 (m, 3H), 1.79-1.75 (q, 2H), 1.55-1.53 (q, 2H); MS (ESI) m/z=655.2 (M+H)$^+$

Example 388. ((1r,4r)-4-(((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)methyl)cyclohexyl)methanol

Step 1. ((1r,4r)-4-(((2-Chloro-5-((1-(methylsulfonyl)piperidin-4-yl)ethynyl)pyridin-4-yl)amino)methyl)cyclohexyl)methanol The title compound as a solid (207 mg) was prepared in the same fashion as Step 1 in Example 157 except that 2-chloro-4-fluoro-5-((1-(methylsulfonyl)piperidin-4-yl)ethynyl)pyridine (155 mg, 0.49 mmol) prepared in Reference Example 65 and trans-4-(aminomethyl)cyclohexanemethanol HCl (105 mg, 0.64 mmol) were used instead of 4-(4-((6-chloro-4-fluoropyridin-3-yl)ethynyl)benzyl)morpholine and cis-4-aminocyclohexanol HCl. MS (ESI) m/z=441.2 (M+H)$^+$

Step 2. ((1r,4r)-4-(((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)methyl)cyclohexyl)methanol The title compound (6.8 mg) was prepared in the same fashion as Step 3 in Example 1, except that ((1r,4r)-4-(((2-chloro-5-((1-(methylsulfonyl)piperidin-4-yl)ethynyl)pyridin-4-yl)amino)methyl)cyclohexyl)methanol (207 mg, 0.47 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.49-8.47 (d, 1H), 8.42 (s, 114), 8.00 (s, 1H), 7.85 (s, 1H), 7.01-7.00 (d, 1H), 5.67 (s, 1H), 3.61-3.57 (q, 2H), 3.50-3.48 (d, 2H), 3.32-3.29 (t, 2H), 3.14-3.08 (m, 2H), 2.90-2.83 (m, 2H), 2.81 (s, 3H), 2.12-2.07 (m, 2H), 1.89-1.85 (m, 6H), 1.55-1.52 (q, 1H), 1.25-1.23 (d, 3H), 1.19-1.16 (t, 2H), 1.05-1.02 (d, 4H); MS (ESI) m/z=669.2 (M+H)$^+$

Example 389. (1-(2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)-4-methylpiperidin-4-yl)methanol

Step 1. (1-(2-Chloro-5-((1-(methylsulfonyl)piperidin-4-yl)ethynyl)pyridin-4-yl)-4-methylpiperidin-4-yl)methanol The title compound as a solid (184 mg) was prepared in the same fashion as Step 1 in Example 157 except that 2-chloro-4-fluoro-5-((1-(methylsulfonyl)piperidin-4-yl)ethynyl)pyridine (155 mg, 0.49 mmol) prepared in Reference Example 65 and (4-methylpiperidin-4-yl)methanol (96 mg, 0.64 mmol) were used instead of 4-(4-((6-chloro-4-fluoropyridin-3-yl)ethynyl)benzyl)morpholine and cis-4-aminocyclohexanol HCl. MS (ESI) m/z=426.1 (M+H)$^+$

Step 2. (1-(2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)-4-methylpiperidin-4-yl)methanol The title compound (9.0 mg) was prepared in the same fashion as Step 3 in Example 1, except that (1-(2-chloro-5-((1-(methylsulfonyl)piperidin-4-yl)ethynyl)pyridin-4-yl)-4-methylpiperidin-4-yl)methanol (184 mg, 0.43 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.44-8.43 (d, 2H), 8.31 (s, 1H), 8.21 (s, 1H), 7.92 (s, 1H), 6.94-6.92 (d, 1H), 3.89-3.83 (m, 3H), 3.58-3.51 (m, 6H), 3.13-3.11 (t, 2H), 2.87-2.84 (m, 5H), 2.05-2.03 (q, 2H), 1.87-1.83 (m, 4H), 1.81-1.79 (t, 4H), 1.58-1.55 (t, 2H), 1.05 (s, 3H); MS (ESI) m/z=655.2 (M+H)$^+$

Example 390. ((1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexyl)methanol

Step 1. ((1s,4s)-4-((2-Chloro-5-((1-(cyclopropylsulfonyl)piperidin-4-yl)ethynyl)pyridin-4-yl)amino)cyclohexyl)methanol The title compound as a solid (214 mg) was prepared in the same fashion as Step 1 in Example 157 except that 2-chloro-5-((1-(cyclopropylsulfonyl)piperidin-4-yl)ethynyl)-4-fluoropyridine (173 mg, 0.505 mmol) prepared in Reference Example 66 and ((1s,4s)-4-aminocyclohexyl)methanol (85 mg, 0.66 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.98 (s, 2H), 6.41 (s, 1H), 5.24-5.22 (d, 1H), 3.60-3.48 (m, 5H), 3.19-3.14 (m, 2H), 2.97 (s, 3H), 2.87-2.85 (d, 4H), 2.27 (s, 1H), 2.11 (m, 2H), 2.04-2.00 (m, 2H), 1.85-1.79 (m, 4H), 1.69-1.62 (m, 4H), 1.28-1.25 (d, 2H), 1.15-1.13 (q, 2H), 0.99-0.96 (q, 2H)

Step 2. ((1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexyl)methanol The title compound (13.5 mg) was prepared in the same fashion as Step 3 in Example 1, except that ((1s,4s)-4-((2-chloro-5-((1-(cyclopropylsulfonyl)piperidin-4-yl)ethynyl)pyridin-4-yl)amino)cyclohexyl)methanol (214 mg, 0.47 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.49-8.47 (d, 1H), 8.42 (s, 1H), 8.00 (s, 1H), 7.85 (s, 1H), 7.01-7.00 (d, 1H), 5.67 (s, 1H), 3.61-3.57 (q, 2H), 3.50-3.48 (d, 2H), 3.32-3.29 (t, 2H), 3.14-3.08 (m, 2H), 2.90-2.83 (m, 2H), 2.81 (s, 3H), 2.12-2.07 (m, 2H), 1.89-1.85 (m, 6H), 1.55-1.52 (q, 1H), 1.25-1.23 (d, 3H), 1.19-1.16 (t, 2H), 1.05-1.02 (d, 4H); MS (ESI) m/z=681.2 (M+H)$^+$

Example 391. (1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexan-1-ol

Step 1. (1s,4s)-4-((2-Chloro-5-((1-(cyclopropylsulfonyl)piperidin-4-yl)ethynyl)pyridin-4-yl)amino)cyclohexan-1-ol The title compound as a solid (212 mg) was prepared in the same fashion as Step 1 in Example 157 except that 2-chloro-5-((1-(cyclopropylsulfonyl)piperidin-4-yl)ethynyl)-4-fluoropyridine (173 mg, 0.505 mmol) prepared in Reference Example 66 was used instead of 4-(4-((6-chloro-4-fluoropyridin-3-yl)ethynyl)benzyl)morpholine. $^1$H-NMR (CDCl$_3$, 400 MHz) δ 7.98 (s, 1H), 6.42 (s, 1H), 5.03-5.01 (d, 1H), 3.94 (s, 1H), 3.57-3.52 (m, 2H), 3.22 (s, 1H), 3.21-3.16 (m, 2H), 2.93-2.85 (q, 3H), 2.29-2.25 (q, 1H), 2.04-1.99 (m, 3H), 1.84-1.71 (m, 10H), 1.15-1.13 (q, 2H), 0.99-0.96 (q, 2H)

Step 2. (1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexan-1-ol The title compound (10 mg) was prepared in the same fashion as Step 3 in Example 1, except that (1s,4s)-4-((2-chloro-5-((1-(cyclopropylsulfonyl)piperidin-4-yl)ethynyl)pyridin-4-yl)amino)cyclohexan-1-ol (212 mg, 0.48 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.44-8.43 (d, 2H), 7.84-7.82 (d, 2H), 7.01-7.00 (d, 1H), 5.63-5.62 (d, 1H), 4.00-3.98 (q, 1H), 3.62-3.60 (t, 2H), 3.23-3.22 (d, 2H), 2.83 (d, 2H), 2.09-2.05 (m, 2H), 1.93-1.82 (m, 8H), 1.66 (s, 2H), 1.54-1.53 (q, 2H), 1.24-1.19 (m, 4H), 1.03-1.01 (q, 2H); MS (ESI) m/z=667.2 (M+H)$^+$

Example 392. ((1r,4r)-4-(((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)methyl)cyclohexyl)methanol

Step 1. ((1r,4r)-4-(((2-Chloro-5-((1-(cyclopropylsulfonyl)piperidin-4-yl)ethynyl)pyridin-4-yl)amino)methyl)cyclohexyl)methanol The title compound as a solid (217 mg) was prepared in the same fashion as Step 1 in Example 157 except that 2-chloro-5-((1-(cyclopropylsulfonyl)piperidin-4-yl)ethynyl)-4-fluoropyridine (173 mg, 0.505 mmol) prepared in Reference Example 66 and trans-4-(aminomethyl)cyclohexanemethanol HCl (117.8 mg, 0.66 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.98 (s, 1H), 6.40 (s, 1H), 5.06 (s, 1H), 3.60-3.56 (m, 2H), 3.46-3.44 (d, 2H), 3.19-3.13 (m, 2H), 3.05-3.02 (t, 2H), 2.86-2.84 (d, 2H), 2.27-2.24 (q, 1H), 2.05-2.00 (m, 4H), 1.88-1.79 (m, 6H), 1.60-1.52 (d, 2H), 1.16-1.14 (q, 2H), 1.06-0.97 (m, 6H)

Step 2. ((1r,4r)-4-(((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)methyl)cyclohexyl)methanol The title compound (6.8 mg) was prepared in the same fashion as Step 3 in Example 1, except that ((1r,4r)-4-(((2-chloro-5-((1-(cyclopropylsulfonyl)piperidin-4-yl)ethynyl)pyridin-4-yl)amino)methyl)cyclohexyl)methanol (217 mg, 0.47 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.48 (s, 1H), 8.44-8.43 (d, 2H), 7.85 (s, 1H), 7.69 (s, 1H), 7.05-7.04 (d, 1H), 5.41 (s, 1H), 3.65-3.63 (d, 2H), 3.49-3.48 (d, 2H), 3.28-3.19 (m, 4H), 2.89-2.81 (q, 2H), 2.29 (s, 1H), 2.08-2.06 (q, 2H), 1.91-1.83 (m, 6H), 1.54-1.52 (q, 3H), 1.24-1.16 (m, 6H), 1.04-1.00 (m, 4H); MS (ESI) m/z=695.2 (M+H)$^+$

Example 393. ((1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexyl)methanol

Step 1. ((1s,4s)-4-((2-Chloro-5-((1-(cyclopropylsulfonyl)pyrrolidin-3-yl)ethynyl)pyridin-4-yl)amino)cyclohexyl)methanol The title compound as a solid (145 mg) was prepared in the same fashion as Step 1 in Example 157 except that 2-chloro-5-((1-(cyclopropylsulfonyl)pyrrolidin-3-yl)ethynyl)-4-fluoropyridine (160 mg, 0.49 mmol) prepared in Reference Example 67 and ((1s,4s)-4-aminocyclohexyl)methanol (82 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.00-7.99 (s, 2H), 6.43 (s, 1H), 5.26-5.24 (d, 1H), 3.73-3.69 (q, 2H), 3.61-3.48 (m, 5H), 3.38-3.35 (t, 1H), 2.38-2.30 (q, 2H), 2.15 (s, 1H), 1.90 (s, 1H), 1.84-1.81 (t, 2H), 1.70-1.65 (m, 5H), 1.35-1.32 (t, 2H), 1.20 (d, 2H), 1.09-1.02 (d, 2H)

Step 2. ((1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexyl)methanol The title compound (6.8 mg) was prepared in the same fashion as Step 3 in Example 1, except that ((1s,4s)-4-((2-chloro-5-((1-(cyclopropylsulfonyl)pyrrolidin-3-yl)ethynyl)pyridin-4-yl)amino)cyclohexyl)methanol (145 mg, 0.33 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.59 (s, 1H), 8.44-8.42 (t, 3H), 8.01 (s, 1H), 7.79 (s, 1H), 6.99-6.98

(d, 1H), 5.86-5.85 (d, 1H), 3.76-3.72 (q, 1H), 3.66-3.64 (d, 1H), 3.57-3.50 (m, 4H), 3.42-3.41 (d, 1H), 2.84 (s, 1H), 2.41-2.36 (m, 2H), 2.18 (s, 1H), 2.04-2.01 (d, 2H), 1.92-1.89 (d, 2H), 1.75-1.72 (d, 2H), 1.55-1.53 (q, 3H), 1.37-1.34 (d, 2H), 1.27-1.22 (m, 6H), 1.03-1.01 (t, 2H); MS (ESI) m/z=667.2 (M+H)$^+$

Example 394. (1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexan-1-ol Step 1. (1s,4s)-4-((2-Chloro-5-((1-(cyclopropylsulfonyl)pyrrolidin-3-yl)ethynyl)pyridin-4-yl)amino)cyclohexan-1-ol The title compound as a solid (105 mg) was prepared in the same fashion as Step 1 in Example 157 except that 2-chloro-5-((1-(cyclopropylsulfonyl)pyrrolidin-3-yl)ethynyl)-4-fluoropyridine (160 mg, 0.49 mmol) prepared in Reference Example 67 was used instead of 4-(4-((6-chloro-4-fluoropyridin-3-yl)ethynyl)benzyl)morpholine. $^1$1-NMR (CDCl$_3$, 400 MHz) δ 7.96-7.94 (d, 1H), 6.40 (s, 1H), 5.06-5.04 (d, 1H), 3.89 (s, 1H), 3.69-3.64 (q, 1H), 3.59-3.57 (t, 1H), 3.49-3.43 (m, 2H), 3.40-3.30 (m, 2H), 2.67 (brs, 1H), 2.38-2.28 (m, 2H), 2.13-2.10 (t, 1H), 1.73-1.70 (q, 8H), 1.16-1.13 (m, 2H), 0.98-0.95 (m, 2H)

Step 2. (1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexan-1-ol The title compound (3.3 mg) was prepared in the same fashion as Step 3 in Example 1, except that (1s,4s)-4-((2-chloro-5-((1-(cyclopropylsulfonyl)pyrrolidin-3-yl)ethynyl)pyridin-4-yl)amino)cyclohexan-1-ol (105 mg, 0.25 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43-8.41 (d, 2H), 8.40 (s, 1H), 7.18-7.12 (m, 2H), 5.17-5.15 (d, 1H), 3.91 (s, 1H), 3.75-3.53 (m, 5H), 3.40-3.39 (d, 1H), 2.82 (s, 1H), 2.62 (s, 3H), 2.42-2.35 (d, 2H), 2.21-2.19 (d, 2H), 1.70-1.66 (q, 2H), 1.53-1.52 (q, 2H), 1.31-1.21 (m, 8H), 1.02-1.00 (q, 2H); MS (ESI) m/z=653.2 (M+H)$^+$ Example 395. (1-(2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)-4-methylpiperidin-4-yl)methanol Step 1. (1-(2-Chloro-5-((1-(cyclopropylsulfonyl)pyrrolidin-3-yl)ethynyl)pyridin-4-yl)-4-methylpiperidin-4-yl)methanol The title compound as a solid (142 mg) was prepared in the same fashion as Step 1 in Example 157 except that 2-chloro-5-((1-(cyclopropylsulfonyl)pyrrolidin-3-yl)ethynyl)-4-fluoropyridine (160 mg, 0.49 mmol) prepared in Reference Example 67 and (4-methylpiperidin-4-yl)methanol (96 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.05 (s, 1H), 6.63 (s, 1H), 3.67-3.52 (m, 4H), 3.47-3.41 (q, 4H), 3.36-3.29 (q, 2H), 3.14-3.11 (t, 3H), 3.08 (s, 2H), 2.83 (s, 2H), 2.36-2.25 (m, 2H), 2.10-2.06 (t, 1H), 1.70-1.64 (q, 2H), 1.40-1.37 (q, 2H), 1.20-1.18 (q, 2H), 1.14-1.13 (d, 2H), 0.97-0.94 (t, 5H)

Step 2. (1-(2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)-4-methylpiperidin-4-yl)methanol The title compound (24.1 mg) was prepared in the same fashion as Step 3 in Example 1, except that (1-(2-chloro-5-((1-(cyclopropylsulfonyl)pyrrolidin-3-yl)ethynyl)pyridin-4-yl)-4-methylpiperidin-4-yl)methanol (142 mg, 0.32 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (s, 1H), 8.42-8.40 (t, 1H), 8.06 (s, 1H), 7.72 (s, 1H), 6.98-6.97 (d, 1H), 3.74-3.63 (m, 4H), 3.53-3.47 (m, 4H), 3.39-3.32 (m, 2H), 2.83 (s, 1H), 2.58 (brs, 1H), 2.42-2.32 (q, 2H), 2.16 (s, 1H), 1.81-1.78 (t, 2H), 1.55-1.51 (m, 4H), 1.24-1.20 (q, 4H), 1.07 (s, 3H), 1.05-0.99 (m, 3H); MS (ESI) m/z=667.2 (M+H)$^+$ Example 396. 2-(1-(Cyclopropylsulfonyl)-1H-pyrazol-4-yl)-N-(4-(3-(2-(dimethylamino)ethyl)piperidin-1-yl)-5-((1-methyl-1H-pyrazol-4-yl)ethynyl)pyridin-2-yl)pyrimidin-4-amine Step 1. 2-(1-(2-Chloro-5-((1-methyl-1H-pyrazol-4-yl)ethynyl)pyridin-4-yl)piperidin-3-yl)-N,N-dimethylethan-1-amine The title compound as a solid (252 mg) was prepared in the same fashion as Step 1 in Example 157 except that 2-chloro-4-fluoro-5-((1-methyl-1H-pyrazol-4-yl)ethynyl)pyridine (500 mg, 2.12 mmol) prepared in Reference Example 18 and N,N-dimethyl-2-(3-piperidinyl)-1-ethanamine (397 mg, 2.55 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.18 (s, 1H), 7.59 (s, 1H), 7.54 (s, 1H), 6.70 (s, 1H), 3.99-3.91 (t, 2H), 3.89 (s, 3H), 3.43 (s, 3H), 2.83-2.78 (q, 1H), 2.53-2.45 (q, 3H), 2.27-2.23 (t, 2H), 2.15 (s, 6H), 1.90-1.87 (d, 1H), 1.75-1.65 (m, 3H), 1.42-1.40 (d, 2H), 1.38-1.23 (t, 2H), 0.83-0.80 (d, 1H)

Step 2. 2-(1-(Cyclopropylsulfonyl)-1H-pyrazol-4-yl)-N-(4-(3-(2-(dimethylamino)ethyl)piperidin-1-yl)-5-((1-methyl-1H-pyrazol-4-yl)ethynyl)pyridin-2-yl)pyrimidin-4-amine The title compound (9.0 mg) was prepared in the same fashion as Step 3 in Example 1, except that 2-(1-(2-chloro-5-((1-methyl-1H-pyrazol-4-yl)ethynyl)pyridin-4-yl)piperidin-3-yl)-N,N-dimethylethan-1-amine (252 mg, 0.68 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45-8.42 (t, 2H), 8.06 (s, 2H), 7.65-7.62 (d, 2H), 6.96-6.94 (d, 1H), 4.14-4.11 (d, 2H), 3.95 (s, 3H), 2.99-2.96 (d, 2H), 2.93-2.85 (m, 2H), 2.74-2.69 (t, 2H), 2.65-2.63 (d, 8H), 1.96-1.92 (d, 2H), 1.80-1.72 (q, 4H), 1.52-1.51 (d, 2H), 1.28-1.23 (t, 2H); MS (ESI) m/z=601.3 (M+H)$^+$

Example 397. ((1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexyl)methanol

Step 1. ((1s,4s)-4-((2-Chloro-5-((1-(methylsulfonyl)pyrrolidin-3-yl)ethynyl)pyridin-4-yl)amino)cyclohexyl)methanol The title compound as a solid (161 mg) was prepared in the same fashion as Step 1 in Example 157 except that 2-chloro-4-fluoro-5-((1-(methylsulfonyl)pyrrolidin-3-yl)ethynyl)pyridine (180 mg, 0.59 mmol) prepared in Reference Example 68 and ((1s, 4s)-4-aminocyclohexyl)methanol (100 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.98-7.96 (t, 2H), 6.42 (s, 1H), 5.24-5.22 (d, 1H), 3.66-3.62 (q, 2H), 3.57-3.52 (m, 3H), 3.48-3.42 (m, 2H), 3.40-3.35 (m, 1H), 2.87-2.86 (d, 4H), 2.33-2.29 (q, 1H), 2.16-2.10 (m, 1H), 1.83-1.80 (q, 2H), 1.66-1.63 (d, 5H), 1.37-1.31 (t, 2H)

Step 2. ((1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexyl)methanol The title compound (11.7 mg) was prepared in the same fashion as Step 3 in Example 1, except that ((1s,4s)-4-((2-chloro-5-((1-(methylsulfonyl)pyrrolidin-3-yl)ethynyl)pyridin-4-yl)amino)cyclohexyl)methanol (161 mg, 0.39 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.59 (s, 1H), 8.47-8.46 (d, 1H), 8.41 (s, 1H), 8.31 (s, 2H), 8.07 (s, 1H), 7.85-7.84 (d, 1H), 7.01-7.00 (d, 1H), 5.97-5.95 (d, 1H), 4.01 (brs, 1H), 3.68-3.57 (m, 4H), 3.55-3.40 (m, 3H), 2.93-2.91 (d, 3H), 2.85-2.83 (d, 1H), 2.66 (s, 3H), 2.35 (s, 1H), 2.20 (s, 1H), 2.04-2.01 (d, 2H), 1.93-1.90 (d, 2H), 1.75-1.72 (d, 3H), 1.55-1.53 (q, 2H), 1.37-1.35 (d, 2H), 1.26-1.24 (d, 2H); MS (ESI) m/z=641.2 (M+H)$^+$

Example 398. (1 r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexan-1-ol

Step 1. (1 r,4r)-4-(((2-Chloro-5-((1-(methylsulfonyl)pyrrolidin-3-yl)ethynyl)pyridin-4-yl)amino)methyl)cyclohexan-1-ol The title compound as a solid (179 mg) was prepared in the same fashion as Step 1 in Example 157 except that 2-chloro-4-fluoro-5-((1-(methylsulfonyl)pyrrolidin-3-yl)ethynyl)pyridine (180 mg, 0.59 mmol) prepared in Reference Example 68 and trans-4-(aminomethyl)cyclohexanol HCl (128 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96-7.94 (d, 1H), 6.37 (s, 1H), 5.23-5.20 (t, 1H), 3.61-3.58 (t, 3H), 3.56-3.52 (m, 1H), 3.49-3.30 (m, 2H), 3.03-2.99 (t, 2H), 2.92 (s, 1H), 2.87-2.84 (d, 3H), 2.30-2.26 (q, 2H), 2.16-2.12 (q, 2H), 2.01-1.99 (d, 2H), 1.81-1.78 (d, 2H), 1.66 (s, 1H), 1.08-1.01 (q, 2H)

Step 2. (1 r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexan-1-ol The title compound (17.2 mg) was prepared in the same fashion as Step 3 in Example 1, except that (1 r,4r)-4-(((2-chloro-5-((1-(methylsulfonyl)pyrrolidin-3-yl)ethynyl)pyridin-4-yl)amino)methyl)cyclohexan-1-ol (179 mg, 0.43 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.41-8.38 (t, 2H), 7.95 (s, 1H), 7.19-7.17 (d, 1H), 7.10 (s, 1H), 5.22 (s, 1H), 3.66-3.57 (m, 4H), 3.53-3.34 (m, 2H), 3.17-3.14 (t, 2H), 2.91 (s, 3H), 2.81 (s, 1H), 2.61 (s, 8H), 2.32 (s, 1H), 2.17 (s, 1H), 2.03-2.01 (d, 2H), 1.87-1.84 (d, 2H), 1.51-1.49 (q, 1H), 1.30-1.27 (d, 2H), 1.23-1.21 (d, 2H), 1.19-1.10 (q, 4H); MS (ESI) m/z=641.2 (M+H)$^+$

Example 399. (1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexan-1-ol

Step 1. (1s,4s)-4-((2-Chloro-5-((1-(methylsulfonyl)pyrrolidin-3-yl)ethynyl)pyridin-4-yl)amino)cyclohexan-1-ol The title compound as a solid (169 mg) was prepared in the same fashion as Step 1 in Example 157 except that 2-chloro-4-fluoro-5-((1-(methylsulfonyl)pyrrolidin-3-yl)ethynyl)pyridine (180 mg, 0.59 mmol) prepared in Reference Example 68 was used instead of 4-(4-((6-chloro-4-fluoropyridin-3-yl)ethynyl)benzyl)morpholine. $^1$H-NMR (CDCl$_3$, 400 MHz) δ 7.97-7.96 (d, 1H), 6.42 (s, 1H), 5.04-5.02 (d, 1H), 3.91 (s, 1H), 3.66-3.61 (q, 1H), 3.55-3.51 (m, 1H), 3.46-3.32 (m, 4H), 2.87 (s, 3H), 2.52 (brs, 1H), 2.33-2.28 (q, 1H), 2.17-2.01 (m, 2H), 1.79-1.57 (m, 8H)

Step 2. (1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexan-1-ol The title compound (18.7 mg) was prepared in the same fashion as Step 3 in Example 1, except that (1s,4s)-4-((2-chloro-5-((1-(methylsulfonyl)pyrrolidin-3-yl)ethynyl)pyridin-4-yl)amino)cyclohexan-1-ol (169 mg, 0.42 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.41 (s, 1H), 8.38-8.37 (d, 1H), 7.99 (s, 1H), 7.19 (s, 1H), 7.10-7.09 (d, 1H), 5.13-5.11 (d, 1H), 3.89 (s, 1H), 3.70-3.56 (m, 3H), 3.50-3.47 (q, 2H), 3.39-3.36 (t, 2H), 2.90 (s, 3H), 2.83-2.79 (m, 1H), 2.61 (s, 6H), 2.57-2.52 (q, 1H), 2.20-2.15 (q, 1H), 1.87-1.84 (t, 6H), 1.79 (s, 2H), 1.69-1.66 (t, 2H), 1.21-1.19 (d, 2H); MS (ESI) m/z=627.2 (M+H)$^+$

Example 400. ((1 r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexyl)methanol

Step 1. ((1 r,4r)-4-(((2-Chloro-5-((1-(methylsulfonyl)pyrrolidin-3-yl)ethynyl)pyridin-4-yl)amino)methyl)cyclohexyl)methanol The title compound as a solid (175 mg) was prepared in the same fashion as Step 1 in Example 157 except that 2-chloro-4-fluoro-5-((1-(methylsulfonyl)pyrrolidin-3-yl)ethynyl)pyridine (180 mg, 0.59 mmol) prepared in Reference Example 68 and trans-4-(aminomethyl)cyclohexanemethanol HCl (139 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.94 (s, 1H), 6.39 (s, 1H), 5.21-5.18 (t, 1H), 3.63-3.52 (m, 2H), 3.47-3.30 (m, 5H), 3.04-3.00 (t, 2H), 2.87 (s, 3H), 2.85 (s, 1H), 2.32-2.27 (q, 1H), 2.15-2.11 (t, 3H), 1.85-1.80 (t, 4H), 1.54-1.45 (d, 2H), 1.03-0.95 (q, 4H)

Step 2. ((1r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexyl)methanol The title compound (6.3 mg) was prepared in the same fashion as Step 3 in Example 1, except that ((1r,4r)-4-(((2-chloro-5-((1-(methylsulfonyl)pyrrolidin-3-yl)ethynyl)pyridin-4-yl)amino)methyl)cyclohexyl)methanol (175 mg, 0.41 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.42-8.39 (t, 2H), 7.92 (s, 1H), 7.24 (s, 1H), 7.16-7.15 (d, 1H), 5.30 (s, 1H), 3.68-3.59 (m, 2H), 3.52-3.45 (m, 4H), 3.38-3.35 (t, 1H), 3.21-3.18 (t, 2H), 2.91 (s, 3H), 2.83-2.81 (t, 1H), 2.34-2.31 (t, 1H), 2.17 (s, 1H), 1.88-1.86 (d, 4H), 1.52 (d, 1H), 1.51-1.49 (t, 3H), 1.24-1.21 (t, 2H), 1.07-0.93 (m, 4H); MS (ESI) m/z=655.2 (M+H)$^+$ Example 401. (1-(2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)-4-methylpiperidin-4-yl)methanol Step 1. (1-(2-Chloro-5-((1-(methylsulfonyl)pyrrolidin-3-yl)ethynyl)pyridin-4-yl)-4-methylpiperidin-4-yl)methanol The title compound as a solid (156 mg) was prepared in the same fashion as Step 1 in Example 157 except that 2-chloro-4-fluoro-5-((1-(methylsulfonyl)pyrrolidin-3-yl)ethynyl)pyridine (180 mg, 0.59 mmol) prepared in Reference Example 68 and (4-methylpiperidin-4-yl)methanol (117.1 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.07 (s, 1H), 6.66 (s, 1H), 3.66-3.58 (m, 3H), 3.53-3.49 (m, 1H), 3.44-3.32 (m, 5H), 3.15-3.09 (m, 2H), 2.85 (s, 5H), 2.60 (s, 1H), 2.28-2.25 (t, 1H), 2.14-2.11 (t, 2H), 1.73-1.66 (m, 2H), 1.42-1.38 (d, 2H), 0.99 (s, 3H)

Step 2. (1-(2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)-4-methylpiperidin-4-yl)methanol The title compound (13.5 mg) was prepared in the same fashion as Step 3 in Example 1, except that (1-(2-chloro-5-((1-(methylsulfonyl)pyrrolidin-3-yl)ethynyl)pyridin-4-yl)-4-methylpiperidin-4-yl)methanol (156 mg, 0.38 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.44-8.38 (m, 2H), 8.00 (s, 1H), 7.87 (s, 1H), 6.96-6.95 (d, 1H), 3.78-3.74 (q, 2H), 3.67-3.58 (m, 2H), 3.51-3.45 (m, 4H), 3.39-3.35 (q, 3H), 2.90 (s, 3H), 2.85-2.83 (t, 1H), 2.32-2.29 (t, 1H), 2.19-2.16 (q, 1H), 1.84-1.78 (q, 2H), 1.56-1.51 (m, 4H), 1.25-1.23 (d, 2H), 1.08 (s, 3H); MS (ESI) m/z=641.2 (M+H)$^+$ Example 402. ((1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexyl)methanol Step 1. ((1s,4s)-4-((2-Chloro-5-((1-methylcyclopropyl)ethynyl)pyridin-4-yl)amino)cyclohexyl)methanol The title compound as a solid (191 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and ((1s,4s)-4-aminocyclohexyl)methanol (144 mg, 1.12 mmol) were used instead of 4-(4-((6-chloro-4-fluoropyridin-3-yl)ethynyl)benzyl)morpholine and cis-4-aminocyclohexanol HC. $^1$H-NMR (CDCl$_3$, 400 MHz) δ 7.91 (s, 1H), 6.36 (s, 1H), 5.28-5.26 (d, 1H), 3.66-3.63 (q, 1H), 3.49-3.45 (t, 2H), 2.83-2.81 (d, 1H), 1.81-1.77 (q, 2H), 1.71-1.56 (m, 6H), 1.33 (s, 3H), 1.30-1.21 (m, 3H), 0.97-0.94 (t, 2H), 0.79-0.76 (t, 2H); MS (ESI) m/z=319.1 (M+H)$^+$ Step 2. ((1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexyl)methanol The title compound (12.2 mg) was prepared in the same fashion as Step 3 in Example 1, except that ((1s,4s)-4-((2-chloro-5-((1-methylcyclopropyl)ethynyl)pyridin-4-yl)amino)cyclohexyl)methanol (191 mg, 0.60 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.42-8.38 (t, 2H), 7.84 (s, 1H), 7.00-6.98 (d, 1H), 5.68-5.66 (d, 1H), 3.95-3.94 (t, 1H), 3.55-3.53 (t, 2H), 2.83 (s, 1H), 2.02-2.01 (d, 2H), 1.99-1.98 (d, 2H), 1.89-1.76 (m, 4H), 1.54-1.51 (q, 2H), 1.39 (s, 3H), 1.30-1.22 (m, 4H), 1.04-1.01 (q, 2H), 0.79-0.76 (q, 2H); MS (ESI) m/z=548.2 (M+H)$^+$ Example 403. (1r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexan-1-ol Step 1. (1r,4r)-4-(((2-Chloro-5-((1-methylcyclopropyl)ethynyl)pyridin-4-yl)amino)methyl)cyclohexan-1-ol The title compound as a solid (153 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and trans-4-(aminomethyl)cyclohexanol HCl (185 mg, 1.12 mmol) were used instead of 4-(4-((6-chloro-4-fluoropyridin-3-yl)ethynyl)benzyl)morpholine and cis-4-aminocyclohexanol HCl. MS (ESI) m/z=319.1 (M+H)$^+$ Step 2. (1r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexan-1-ol The title compound (3.9 mg) was prepared in the same fashion as Step 3 in Example 1, except that (1r,4r)-4-(((2- chloro-5-((1-methylcyclopropyl)ethynyl)pyridin-4-yl) amino)methyl)cyclohexan-1-ol (153 mg, 0.48 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.40-8.39 (d, 2H), 7.79 (s, 1H), 7.63 (s, 1H), 7.03-7.02 (d, 1H), 5.47-5.45 (t, 1H), 3.61-3.59 (t, 1H), 3.24-3.21 (t, 2H), 2.84-2.80 (m, 1H), 2.06-2.04 (d, 2H), 1.90-1.87 (d, 2H), 1.71 (s, 1H), 1.52-1.49 (m, 2H), 1.38 (s, 3H), 1.33-1.30 (d, 2H), 1.27-1.24 (t, 4H), 1.22-1.17 (q, 2H), 0.79-0.73 (t, 2H); MS (ESI) m/z=548.2 (M+H)$^+$ Example 404. 1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-ol Step 1. 1-(2-Chloro-5-((1-methylcyclopropyl)ethynyl)pyridin-4-yl)-4-methylpiperidin-4-ol The title compound as a solid (169 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and 4-methylpiperidin-4-ol (221 mg, 1.12 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.06 (s, 1H), 6.65 (s, 1H), 3.65-3.62 (q, 2H), 3.29-3.21 (m, 3H), 2.03-2.02 (d, 2H), 1.78-1.67 (m, 4H), 1.33-1.30 (t, 7H), 1.25-1.21 (t, 2H), 0.97-0.96 (t, 2H); MS (ESI) m/z=305.1 (M+H)$^+$ Step 2. 1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-ol The title compound (8.5 mg) was prepared in the same fashion as Step 3 in Example 1, except that 1-(2-chloro-5-((1-methylcyclopropyl)ethynyl)pyridin-4-yl)-4-methylpiperidin-4-ol (169 mg, 0.55 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.44-8.38 (t, 2H), 8.01 (s, 1H), 7.97 (s, 1H), 6.91-6.90 (d, 1H), 3.85-3.82 (d, 2H), 3.41-3.35 (m, 3H), 2.83 (s, 1H), 1.85-1.82 (t, 4H), 1.55-1.53 (q, 2H), 1.37 (s, 6H), 1.26-1.22 (m, 2H), 1.01-1.00 (q, 2H), 0.74 (s, 2H); MS (ESI) m/z=534.2 (M+H)$^+$ Example 405. ((1 r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino) methyl)cyclohexyl)methanol Step 1. ((1 r,4r)-4-(((2-Chloro-5-((1-methylcyclopropyl)ethynyl)pyridin-4-yl)amino)methyl)cyclohexyl) methanol The title compound as a solid (182 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and trans-4-(aminomethyl)cyclohexanemethanol HCl (200 mg, 1.12 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96 (s, 1H), 6.38 (s, 1H), 5.12 (s, 1H), 3.48-3.47 (d, 2H), 3.05-3.02 (t, 2H), 1.89-1.86 (d, 4H), 1.67 (s, 1H), 1.58-1.50 (d, 1H), 1.49-1.48 (d, 1H), 1.36 (s, 3H), 1.07-0.98 (m, 6H), 0.75 (d, 2H); MS (ESI) m/z=333.1 (M+H)$^+$ Step 2. ((1 r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl) cyclohexyl)methanol The title compound (12.8 mg) was prepared in the same fashion as Step 3 in Example 1, except that ((1 r,4r)-4-(((2-chloro-5-((1-methylcyclopropyl)ethynyl)pyridin-4-yl) amino)methyl)cyclohexyl)methanol (182 mg, 0.55 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.43-8.39 (t, 2H), 7.88 (s, 1H), 7.35 (s, 1H), 7.12-7.10 (d, 1H), 5.34-5.30 (d, 1H), 3.50-3.48 (d, 2H), 2.84-2.82 (t, 2H), 1.92-1.89 (t, 4H), 1.53 (d, 1H), 1.52-1.50 (t, 2H), 1.39 (s, 3H), 1.23-1.02 (m, 8H), 0.74 (s, 2H); MS (ESI) m/z=562.2 (M+H)$^+$ Example 406. 2-(1-(Cyclopropylsulfonyl)-1H-pyrazol-4-yl)-N-(4-(4-((dimethylamino)methyl)-4-methylpiperidin-1-yl)-5-((1-methylcyclopropyl)ethynyl) pyridin-2-yl)pyrimidin-4-amine Step 1. 1-(1-(2-Chloro-5-((1-methylcyclopropyl) ethynyl)pyridin-4-yl)-4-methylpiperidin-4-yl)-N,N-dimethylmethanamine The title compound as a solid (203 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and N,N-dimethyl-1-(4-methylpiperidin-4-yl)methanamine 2HCl (254 mg, 1.12 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.08 (s, 1H), 6.64 (s, 1H), 3.62-3.56 (m, 2H), 3.18-3.11 (m, 2H), 2.32-2.31 (d, 7H), 1.70-1.63 (m, 2H), 1.45-1.41 (m, 2H), 1.35 (s, 3H), 1.03-1.00 (m, 5H), 0.74-0.70 (t, 2H); MS (ESI) m/z=346.1 (M+H)$^+$ Step 2. 2-(1-(Cyclopropylsulfonyl)-1H-pyrazol-4-yl)-N-(4-(4-((dimethylamino)methyl)-4-methylpiperidin-1-yl)-5-((1-methylcyclopropyl)ethynyl)pyridin-2-yl)pyrimidin-4-amine The title compound (23.1 mg) was prepared in the same fashion as Step 3 in Example 1, except that 1-(1-(2-chloro-5-((1-methylcyclopropyl)ethynyl)pyridin-4-yl)-4-methylpiperidin-4-yl)-N,N-dimethylmethanamine (203 mg, 0.59 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.58 (s, 1H), 8.40-8.38 (t, 3H), 8.06 (s, 1H), 7.88 (s, 1H), 6.91-6.89 (s, 1H), 3.89-3.86 (d, 2H), 3.38-3.36 (s, 2H), 2.84 (s, 1H), 2.76 (s, 2H), 2.69 (s, 6H), 1.78-1.74 (q, 5H), 1.53-1.51 (t, 2H), 1.35 (s, 3H), 1.27-1.23 (d, 6H), 0.99-0.97 (q, 2H), 0.74-0.72 (t, 2H); MS (ESI) m/z=575.3 (M+H)$^+$ Example 407. 2-(1-(Cyclopropylsulfonyl)-1H-pyrazol-4-yl)-N-(4-(4-(2-(dimethylamino)ethyl)piperidin-1-yl)-5-((1-methylcyclopropyl)ethynyl)pyridin-2-yl)pyrimidin-4-amine Step 1. 2-(1-(2-Chloro-5-((1-methylcyclopropyl) ethynyl)pyridin-4-yl)piperidin-4-yl)-N,N-dimethyl-ethan-1-amine The title compound as a solid (202 mg) was prepared in the same fashion as Step 1 in Example 157 except that 2-chloro-4-fluoro-5-((1-methylcyclopropyl)ethynyl)pyridine (180 mg, 0.86 mmol) prepared in Reference Example 60 and N,N-dimethyl-2-(piperidin-4-yl)ethanamine (174 mg, 1.12 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.09 (s, 1H), 6.63 (s, 1H), 3.98-3.95 (d, 2H), 2.77-2.68 (q, 2H), 2.33-2.30 (t, 2H), 2.23 (s, 6H), 1.80-1.77 (d, 2H), 1.54-1.43 (m, 4H), 1.40-1.30 (m, 5H), 1.05 (s, 2H), 0.70 (s, 2H); MS (ESI) m/z=346.1 (M+H)$^+$ Step 2. 2-(1-(Cyclopropylsulfonyl)-1H-pyrazol-4-yl)-N-(4-(4-(2-(dimethylamino)ethyl)piperidin-1-yl)-5-((1-methylcyclopropyl)ethynyl)pyridin-2-yl)pyrimidin-4-amine The title compound (18.2 mg) was prepared in the same fashion as Step 3 in Example 1, except that 2-(1-(2-chloro-5-((1-methylcyclopropyl)ethynyl)pyridin-4-yl)piperidin-4-yl)-N,N-dimethylethan-1-amine (202 mg, 0.58 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.46 (s, 2H), 8.42-8.38 (t, 2H), 7.95 (d, 2H), 6.92-6.91 (d, 1H), 4.19-4.16 (d, 2H), 2.99-2.82 (m, 5H), 2.71-2.68 (d, 6H), 1.92-1.89 (d, 2H), 1.77-1.72 (q, 3H), 1.53-1.44 (m, 5H), 1.36 (s, 3H), 1.25-1.23 (t, 2H), 1.00 (s, 2H), 0.75 (s, 2H); MS (ESI) m/z=548.2 (M+H)$^+$ Example 408. 1-(3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)pyrrolidin-1-yl)-2,2,2-trifluoroethan-1-one Step 1. 1-(3-((6-Chloro-4-(((1s,4s)-4-(hydroxymethyl)cyclohexyl)amino)pyridin-3-yl)ethynyl)pyrrolidin-1-yl)-2,2,2-trifluoroethan-1-one The title compound as a solid (116 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and ((1s,4s)-4-aminocyclohexyl)methanol (78 mg, 0.61 mmol) were used instead of 4-(4-((6-chloro-4-fluoropyridin-3-yl)ethynyl)benzyl)morpholine and cis-4-aminocyclohexanol HCl. MS (ESI) m/z=430.1 (M+H)$^+$ Step 2. 1-(3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)pyrrolidin-1-yl)-2,2,2-trifluoroethan-1-one The title compound (17.8 mg) was prepared in the same fashion as Step 3 in Example 1, except that 1-(3-((6-chloro-4-(((1s,4s)-4-(hydroxymethyl)cyclohexyl)amino)pyridin-3-yl)ethynyl)pyrrolidin-1-yl)-2,2,2-trifluoroethan-1-one (116 mg, 0.27 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.60 (s, 1H), 8.42-8.40 (d, 1H), 7.96-7.94 (d, 1H), 7.62-7.58 (d, 1H), 6.98-6.97 (d, 1H), 5.49-5.39 (d, 1H), 3.99-3.82 (m, 3H), 3.80-3.64 (m, 3H), 3.51-3.22 (m, 4H), 2.82 (d, 2H), 2.41-2.18 (m, 3H), 1.99-1.92 (d, 2H), 1.87-1.80 (d, 2H), 1.73-1.63 (m, 4H), 1.60 (s, 2H), 1.42-1.23 (m, 6H); MS (ESI) m/z=659.2 (M+H)$^+$ Example 409. 1-(3-((6-((2-(1-(Cyclopropylsulfonyl)-1H-pyrazol-4-yl)pyrimidin-4-yl)amino)-4-((((1 r,4r)-4-hydroxycyclohexyl)methyl)amino)pyridin-3-yl)ethynyl)pyrrolidin-1-yl)-2,2,2-trifluoroethan-1-one Step 1. 1-(3-((6-Chloro-4-((((1r,4r)-4-hydroxycyclohexyl)methyl)amino)pyridin-3-yl)ethynyl)pyrrolidin-1-yl)-2,2,2-trifluoroethan-1-one The title compound as a solid (134 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and trans-4-(aminomethyl)cyclohexanol HCl (100 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96 (s, 1H), 6.39 (s, 1H), 5.00-4.99 (d, 1H), 3.94-3.85 (m, 2H), 3.77-3.52 (m, 4H), 3.39-3.33 (d, 1H), 3.02-3.01 (d, 2H), 2.43-2.41 (d, 1H), 2.39-2.31 (q, 2H), 2.29-2.19 (d, 3H), 1.80-1.77 (d, 2H), 1.53 (s, 1H), 1.31-1.22 (q, 2H), 1.07-1.01 (t, 2H); MS (ESI) m/z=430.1 (M+H)$^+$ Step 2. 1-(3-((6-((2-(1-(Cyclopropylsulfonyl)-1H-pyrazol-4-yl)pyrimidin-4-yl)amino)-4-((((1 r,4r)-4-hydroxycyclohexyl)methyl)amino)pyridin-3-yl)ethynyl)pyrrolidin-1-yl)-2,2,2-trifluoroethan-1-one The title compound (3.2 mg) was prepared in the same fashion as Step 3 in Example 1, except that 1-(3-((6-chloro-4-((((1 r,4r)-4-hydroxycyclohexyl)methyl)amino)pyridin-3-yl)ethynyl)pyrrolidin-1-yl)-2,2,2-trifluoroethan-1-one (134 mg, 0.31 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44-8.42 (d, 2H), 7.92 (s, 1H), 7.43 (s, 1H), 7.10-7.09 (d, 1H), 5.16-5.13 (t, 1H), 4.13-4.12 (d, 1H), 4.01-3.92 (q, 2H), 3.75-3.59 (m, 4H), 3.45-3.39 (d, 1H), 3.22 (s, 2H), 2.83-2.81 (t, 1H), 2.14-2.05 (d, 2H), 1.89-1.86 (d, 2H), 1.66 (s, 1H), 1.53 (s, 2H), 1.35-1.15 (m, 7H); MS (ESI) m/z=659.2 (M+H)$^+$ Example 410. 1-(3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)pyrrolidin-1-yl)-2,2,2-trifluoroethan-1-one Step 1. 1-(3-((6-Chloro-4-(4-hydroxy-4-methylpiperidin-1-yl)pyridin-3-yl)ethynyl)pyrrolidin-1-yl)-2,2,2-trifluoroethan-1-one The title compound as a solid (146 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and 4-methylpiperidin-4-ol (70 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.09 (s, 1H), 6.67 (s, 1H), 3.89-3.84 (q, 1H), 3.75-3.73 (d, 1H), 3.68-3.60 (m, 4H), 3.34-3.24 (m, 2H), 2.34-2.32 (d, 1H), 2.20-2.16 (q, 2H), 1.67-1.66 (d, 4H), 1.22 (s, 3H); MS (ESI) m/z=416.1 (M+H)$^+$ Step 2. 1-(3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)pyrrolidin-1-yl)-2,2,2-trifluoroethan-1-one The title compound (5.8 mg) was prepared in the same fashion as Step 3 in Example 1, except that 1-(3-((6-chloro-4-(4-hydroxy-4-methylpiperidin-1-yl)pyridin-3-yl)ethynyl)pyrrolidin-1-yl)-2,2,2-trifluoroethan-1-one (146 mg, 0.35 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=645.2 (M+H)$^+$ Example 411. 1-(3-((6-((2-(1-(Cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)ethynyl)pyrrolidin-1-yl)-2,2,2-trifluoroethan-1-one Step 1. 1-(3-((6-Chloro-4-((((1r,4r)-4-(hydroxymethyl)cyclohexyl)methyl)amino)pyridin-3-yl)ethynyl)pyrrolidin-1-yl)-2,2,2-trifluoroethan-1-one The title compound as a solid (113 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and trans-4-(aminomethyl)cyclohexanemethanol HCl (109 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.99 (s, 1H), 6.39 (s, 1H), 5.04-5.01 (t, 1H), 3.94-3.59 (m, 4H), 3.43-3.41 (d, 2H), 3.39-3.31 (m, 1H), 3.01-2.99 (t, 2H), 2.39-2.28 (m, 2H), 2.20-2.08 (t, 1H), 1.85-1.78 (t, 4H), 1.53-1.44 (t, 2H), 1.01-0.93 (q, 4H)

Step 2. 1-(3-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)pyrrolidin-1-yl)-2,2,2-trifluoroethan-1-one The title compound (2.0 mg) was prepared in the same fashion as Step 3 in Example 1, except that 1-(3-((6-chloro-4-((((1 r,4r)-4-(hydroxymethyl)cyclohexyl)methyl)amino)pyridin-3-yl)ethynyl)pyrrolidin-1-yl)-2,2,2-trifluoroethan-1-one (113 mg, 0.25 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=673.2 (M+H)$^+$ Example 412. 1-(3-((6-((2-(1-(Cyclopropylsulfonyl)-1H-pyrazol-4-yl)pyrimidin-4-yl)amino)-4-(4-((dimethylamino)methyl)-4-methylpiperidin-1-yl)pyridin-3-yl)ethynyl)pyrrolidin-1-yl)-2,2,2-trifluoroethan-1-one Step 1. 1-(3-((6-Chloro-4-(4-((dimethylamino)methyl)-4-methylpiperidin-1-yl)pyridin-3-yl)ethynyl)pyrrolidin-1-yl)-2,2,2-trifluoroethan-1-one The title compound as a solid (140 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and N,N-dimethyl-1-(4-methylpiperidin-4-yl)methanamine 2HCl (139 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.05 (s, 1H), 6.62 (s, 1H), 3.93-3.83 (q, 2H), 3.74-3.52 (m, 3H), 3.37-3.27 (m, 1H), 3.15-3.09 (q, 2H), 2.33 (m, 1H), 2.31 (s, 6H), 2.30-2.25 (t, 3H), 1.62-1.61 (d, 2H), 1.43-1.40 (d, 2H), 0.97 (s, 3H)

Step 2. 1-(3-((6-((2-(1-(Cyclopropylsulfonyl)-1H-pyrazol-4-yl)pyrimidin-4-yl)amino)-4-(4-((dimethylamino)methyl)-4-methylpiperidin-1-yl)pyridin-3-yl)ethynyl)pyrrolidin-1-yl)-2,2,2-trifluoroethan-1-one The title compound (1.2 mg) was prepared in the same fashion as Step 3 in Example 1, except that 1-(3-((6-chloro-4-(4-((dimethylamino)methyl)-4-methylpiperidin-1-yl)pyridin-3-yl)ethynyl)pyrrolidin-1-yl)-2,2,2-trifluoroethan-1-one (140 mg, 0.31 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=686.2 (M+H)$^+$ Example 413. 1-(3-((6-((2-(1-(Cyclopropylsulfonyl)-1H-pyrazol-4-yl)pyrimidin-4-yl)amino)-4-(4-(2-(dimethylamino)ethyl)piperidin-1-yl)pyridin-3-yl)ethynyl)pyrrolidin-1-yl)-2,2,2-trifluoroethan-1-one Step 1. 1-(3-((6-Chloro-4-(4-(2-(dimethylamino)ethyl)piperidin-1-yl)pyridin-3-yl)ethynyl)pyrrolidin-1-yl)-2,2,2-trifluoroethan-1-one The title compound as a solid (124 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and N,N-dimethyl-2-(piperidin-4-yl)ethanamine (95 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.03 (s, 1H), 6.58 (s, 1H), 3.92-3.79 (m, 3H), 3.72-3.55 (m, 2H), 3.36-3.26 (m, 1H), 2.74-2.68 (t, 2H), 2.32-2.21 (m, 2H), 2.17-2.11 (q, 6H), 2.04-2.01 (t, 1H), 1.73-1.70 (d, 2H), 1.47-1.46 (d, 1H), 1.41-1.36 (q, 2H), 1.26-1.18 (q, 2H)

Step 2. 1-(3-((6-((2-(1-(Cyclopropylsulfonyl)-1H-pyrazol-4-yl)pyrimidin-4-yl)amino)-4-(4-(2-(dimethylamino)ethyl)piperidin-1-yl)pyridin-3-yl)ethynyl)pyrrolidin-1-yl)-2,2,2-trifluoroethan-1-one The title compound (2.4 mg) was prepared in the same fashion as Step 3 in Example 1, except that 1-(3-((6-chloro-4-(4-(2-(dimethylamino)ethyl)piperidin-1-yl)pyridin-3-yl)ethynyl)pyrrolidin-1-yl)-2,2,2-trifluoroethan-1-one (124 mg, 0.27 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=686.2 (M+H)$^+$ Example 414. 1-(3-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)pyrrolidin-1-yl)-2,2,2-trifluoroethan-1-one Step 1. 1-(3-((6-Chloro-4-(((1s,4s)-4-hydroxycyclohexyl)amino)pyridin-3-yl)ethynyl)pyrrolidin-1-yl)-2,2,2-trifluoroethan-1-one The title compound as a solid (129 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 was used instead of 4-(4-((6-chloro-4-fluoropyridin-3-yl)ethynyl)benzyl)morpholine. $^1$H-NMR (CDCl$_3$, 400 MHz) δ 8.00 (s, 1H), 6.44 (s, 1H), 4.97-4.92 (q, 1H), 4.12-3.98 (m, 3H), 3.93-3.66 (m, 3H), 3.43-3.40 (t, 1H), 2.40-2.32 (m, 1H), 2.25-2.22 (t, 1H), 2.14-2.06 (m, 3H), 1.76-1.72 (t, 8H); MS (ESI) m/z=416.1 (M+H)$^+$

Step 2. 1-(3-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)pyrrolidin-1-yl)-2,2,2-trifluoroethan-1-one The title compound (1.7 mg) was prepared in the same fashion as Step 3 in Example 1, except that 1-(3-((6-chloro-4-(((1s,4s)-4-hydroxycyclohexyl)amino)pyridin-3-yl)ethynyl)pyrrolidin-1-yl)-2,2,2-trifluoroethan-1-one (129 mg, 0.31 mmol) prepared in Step 1 was used instead of 1-(2-chloro-5-((1-methyl-1H-pyrazol-4-yl)ethynyl)pyridin-4-yl)-4-methylpiperazine. $^1$1-NMR (CDCl$_3$, 400 MHz) δ 8.65 (s, 1H), 8.45-8.42 (d, 2H), 8.17 (s, 1H), 7.75 (s, 1H), 7.00 (d, 1H), 3.97-3.75 (m, 6H), 3.72-3.60 (q, 2H), 3.57 (s, 3H), 3.48-3.33 (m, 2H), 2.93-2.92 (d, 1H), 2.37-2.19 (m, 4H), 1.59-1.52 (d, 4H), 1.34-1.22 (m, 5H), 1.09 (s, 2H); MS (ESI) m/z=645.2 (M+H)$^+$

Example 415. 1-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyrrolidin-1 yl)-2,2,2-trifluoroethan-1-one

Step 1. 1-(3-((6-Chloro-4-(4-(hydroxymethyl)-4-methylpiperidin-1-yl)pyridin-3-yl)ethynyl)pyrrolidin-1-yl)-2,2,2-trifluoroethan-1-one The title compound as a solid (131 mg) was prepared in the same fashion as Step 1 in Example 157 except that 1-(3-((6-chloro-4-fluoropyridin-3-yl)ethynyl)pyrrolidin-1-yl)-2,2,2-trifluoroethan-1-one (150 mg, 0.47 mmol) prepared in Reference Example 69 and (4-methylpiperidin-4-yl)methanol (92 mg, 0.61 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.07 (s, 1H), 6.65 (s, 1H), 3.91-3.80 (m, 4H), 3.75-3.55 (m, 3H), 3.41-3.31 (m, 3H), 3.15-3.10 (q, 2H), 2.33-2.17 (m, 2H), 1.65-1.61 (q, 2H), 1.40-1.34 (q, 2H), 0.98 (s, 3H); MS (ESI) m/z=430.1 (M+H)$^+$

Step 2. 1-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyrrolidin-1-yl)-2,2,2-trifluoroethan-1-one The title compound (1.0 mg) was prepared in the same fashion as Step 3 in Example 1, except that 1-(3-((6-chloro-4-(4-(hydroxymethyl)-4-methylpiperidin-1-yl)pyridin-3-yl)ethynyl)pyrrolidin-1-yl)-2,2,2-trifluoroethan-1-one (131 mg, 0.30 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.45-8.44 (d, 2H), 8.00 (s, 1H), 7.25 (s, 1H), 7.10-7.08 (d, 1H), 5.09-5.07 (d, 1H), 4.07-3.92 (m, 3H), 3.90-3.62 (m, 4H), 3.47-3.45 (d, 1H), 2.88-2.83 (d, 1H), 2.43-2.02 (m, 3H), 1.97-1.89 (m, 4H), 1.85-1.52 (m, 2H), 1.32-1.15 (m, 5H); MS (ESI) m/z=659.2 (M+H)$^+$

Example 416. ((1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexyl)methanol

Step 1. ((1s,4S)-4-((2-Chloro-5-(((2R)-2-(trifluoromethyl)tetrahydrofuran-3-yl)ethynyl)pyridin-4-yl)amino)cyclohexyl)methanol The title compound as a solid (156 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.48 mmol) prepared in Reference Example 70 and ((1s,4s)-4-aminocyclohexyl)methanol (104 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96-7.95 (d, 1H), 6.40-6.36 (d, 1H), 5.16 (s, 1H), 4.28 (d, 1H), 4.11 (s, 1H), 4.00 (s, 1H), 3.63 (s, 1H), 3.47-3.43 (d, 3H), 2.80 (brs, 1H), 2.44 (s, 1H), 2.16 (s, 1H), 1.75 (s, 2H), 1.65 (s, 6H), 1.24 (s, 3H)

Step 2. ((1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexyl)methanol The title compound (7.7 mg) was prepared in the same fashion as Step 3 in Example 1, except that ((1s,4S)-4-((2-chloro-5-(((2R)-2-(trifluoromethyl)tetrahydrofuran-3-yl)ethynyl)pyridin-4-yl)amino)cyclohexyl)methanol (156 mg, 0.39 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.43-8.40 (t, 2H), 7.96 (s, 1H), 7.49 (s, 1H), 7.01-7.00 (d, 1H), 5.39-5.37 (d, 1H), 4.37-4.34 (t, 1H), 4.18 (s, 1H), 4.08-4.06 (d, 1H), 3.93 (s, 1H), 3.55-3.49 (m, 3H), 2.83 (s, 1H), 2.49 (s, 2H), 2.39 (s, 2H), 2.25-2.23 (d, 2H), 1.99-1.95 (t, 2H), 1.87-1.84 (d, 2H), 1.76-1.72 (q, 31-1), 1.54-1.52 (q, 2H), 1.30-1.27 (d, 2H), 1.24 (d, 2H); MS (ESI) m/z=632.2 (M+H)$^+$

Example 417. 1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-ol

Step 1. 1-(2-Chloro-5-(((2R)-2-(trifluoromethyl)tetrahydrofuran-3-yl)ethynyl)pyridin-4-yl)-4-methylpiperidin-4-ol The title compound as a solid (174 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.47 mmol) prepared in Reference Example 70 and 4-methylpiperidin-4-ol (72.5 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.09 (s, 1H), 6.67 (s, 1H), 4.20 (s, 1H), 4.10-4.00 (m, 3H), 3.64-3.62 (d, 2H), 3.42 (s, 1H), 3.29 (s, 2H), 2.41 (s, 2H), 2.29 (s, 1H), 2.16 (s, 1H), 1.69 (s, 5H), 1.29 (s, 3H), 1.22 (s, 1H)

Step 2. 1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-ol The title compound (14.3 mg) was prepared in the same fashion as Step 3 in Example 1, except that 1-(2-chloro-5-(((2R)-2-(trifluoromethyl)tetrahydrofuran-3-yl)ethynyl)pyridin-4-yl)-4-methylpiperidin-4-ol (174 mg, 0.45 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.44-8.39 (t, 2H), 8.14 (s, 2H), 7.75 (s, 1H), 6.94-6.92 (d, 1H), 4.36-4.33 (t, 1H), 4.17-4.15 (d, 1H), 4.09-4.05 (t, 1H), 3.74-3.71 (d, 2H), 3.49-3.48 (d, 1H), 3.38-3.34 (t, 2H), 2.85-2.82 (q, 1H), 2.47-2.45 (d, 1H), 2.23-2.18 (q, 1H), 1.82-1.79 (q, 4H), 1.55-1.53 (q, 2H), 1.35 (s, 3H), 1.24 (d, 2H); MS (ESI) m/z=618.2 (M+H)$^+$

Example 418. 2-(1-(Cyclopropylsulfonyl)-1H-pyrazol-4-yl)-N-(4-(4-((dimethylamino)methyl)-4-methylpiperidin-1-yl)-5-(((2R)-2-(trifluoromethyl)tetrahydrofuran-3-yl)ethynyl)pyridin-2-yl)pyrimidin-4-amine

Step 1. 1-(1-(2-Chloro-5-(((2R)-2-(trifluoromethyl)tetrahydrofuran-3-yl)ethynyl)pyridin-4-yl)-4-methylpiperidin-4-yl)-N,N-dimethylmethanamine The title compound as a solid (134 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.47 mmol) prepared in Reference Example 70 and N,N-dimethyl-1-(4-methylpiperidin-4-yl)methanamine 2HCl (144 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.12 (s, 1H), 6.68 (s, 1H), 4.32 (s, 1H), 4.13-4.04 (d, 2H), 3.59 (s, 2H), 3.45 (s, 1H), 3.16 (s, 2H), 2.43 (s, 1H), 2.31 (s, 7H), 2.17 (s, 3H), 1.65 (s, 2H), 1.43 (s, 2H), 1.02 (s, 3H)

Step 2. 2-(1-(Cyclopropylsulfonyl)-1H-pyrazol-4-yl)-N-(4-(4-((dimethylamino)methyl)-4-methylpiperidin-1-yl)-5-(((2R)-2-(trifluoromethyl)tetrahydrofuran-3-yl)ethynyl)pyridin-2-yl)pyrimidin-4-amine The title compound (12.2 mg) was prepared in the same fashion as Step 3 in Example 1, except that 1-(1-(2-chloro-5-(((2R)-2-(trifluoromethyl)tetrahydrofuran-3-yl)ethynyl)pyridin-4-yl)-4-methylpiperidin-4-yl)-N,N-dimethylmethanamine (134 mg, 0.31 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43-8.40 (t, 2H), 8.01 (s, 2H), 7.85 (s, 1H), 6.98-6.97 (d, 1H), 4.36-4.32 (t, 1H), 4.16-4.15 (d, 1H), 4.08-4.05 (t, 1H), 3.83-3.80 (t, 1H), 3.48-3.46 (d, 1H), 3.33-3.27 (m, 2H), 2.85-2.83 (t, 1H), 2.52 (s, 6H), 2.49 (s, 3H), 2.48-2.45 (t, 1H), 2.22-2.20 (d, 1H), 1.77-1.73 (q, 2H), 1.64-1.60 (d, 2H), 1.54-1.52 (q, 2H), 1.25-1.22 (q, 2H), 1.17-1.13 (d, 3H); MS (ESI) m/z=659.3 (M+H)$^+$

Example 419. 2-(1-(Cyclopropylsulfonyl)-1H-pyrazol-4-yl)-N-(4-(4-(2-(dimethylamino)ethyl)piperidin-1-yl)-5-(((2R)-2-(trifluoromethyl)tetrahydrofuran-3-yl)ethynyl)pyridin-2-yl)pyrimidin-4-amine

Step 1. 2-(1-(2-Chloro-5-(((2R)-2-(trifluoromethyl)tetrahydrofuran-3-yl)ethynyl)pyridin-4-yl)piperidin-4-yl)-N,N-dimethylethan-1-amine The title compound as a solid (144 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.47 mmol) prepared in Reference Example 70 and N,N-dimethyl-2-(piperidin-4-yl)ethanamine (98 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.13 (s, 1H), 6.66 (s, 1H), 4.32-4.31 (d, 1H), 4.14-4.04 (d, 2H), 3.95 (s, 2H), 3.52-3.45 (d, 1H), 2.80 (s, 2H), 2.48-2.45 (d, 2H), 2.32 (s, 2H), 2.26 (s, 7H), 1.81 (s, 2H), 1.54-1.46 (d, 4H), 1.33 (s, 2H)

Step 2. 2-(1-(Cyclopropylsulfonyl)-1H-pyrazol-4-yl)-N-(4-(4-(2-(dimethylamino)ethyl)piperidin-1-yl)-5-(((2R)-2-(trifluoromethyl)tetrahydrofuran-3-yl)ethynyl)pyridin-2-yl)pyrimidin-4-amine The title compound (2.9 mg) was prepared in the same fashion as Step 3 in Example 1, except that 2-(1-(2-chloro-5-(((2R)-2-(trifluoromethyl)tetrahydrofuran-3-yl)ethynyl)pyridin-4-yl)piperidin-4-yl)-N,N-dimethylethan-1-amine (144 mg, 0.34 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.44-8.41 (t, 2H), 8.13 (s, 1H), 7.54 (s, 1H), 7.00-6.98 (d, 1H), 4.36-4.33 (t, 1H), 4.08 (s, 1H), 4.05-4.02 (t, 3H), 3.49-3.48 (d, 1H), 3.41 (s, 1H), 2.88-2.84 (q, 3H), 2.65-2.62 (d, 5H), 2.47-2.44 (d, 5H), 1.63-1.60 (t, 2H), 1.54-1.52 (q, 4H), 1.25-1.22 (q, 2H); MS (ESI) m/z=660.2 (M+H)$^+$

Example 420. (1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexan-1-ol

Step 1. (1s,4S)-4-((2-Chloro-5-(((2R)-2-(trifluoromethyl)tetrahydrofuran-3-yl)ethynyl)pyridin-4-yl)amino)cyclohexan-1-ol The title compound as a solid (157 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.48 mmol) prepared in Reference Example 70 was used instead of 4-(4-((6-chloro-4-fluoropyridin-3-yl)ethynyl)benzyl)morpholine. $^1$H-NMR (CDCl$_3$, 400 MHz) δ 8.02 (s, 1H), 6.44 (s, 1H), 4.99 (s, 1H), 4.32-4.31 (d, 1H), 4.16 (s, 1H), 4.10-4.06 (d, 1H), 3.99 (s, 1H), 3.46-3.41 (q, 2H), 2.49 (s, 1H), 2.22-2.21 (d, 1H), 1.75 (s, 12H), 1.26-1.25 (d, 1H)

Step 2. (1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexan-1-ol The title compound (5.1 mg) was prepared in the same fashion as Step 3 in Example 1, except that (1s,4s)-4-((2- chloro-5-(((2R)-2-(trifluoromethyl)tetrahydrofuran-3-yl) ethynyl)pyridin-4-yl)amino)cyclohexan-1-ol (157 mg, 0.40 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61 (s, 1H), 8.43-8.41 (d, 2H), 7.91 (s, 1H), 7.58 (s, 1H), 7.39-7.33 (q, 2H), 7.05-7.03 (d, 1H), 5.32-5.30 (d, 1H), 4.36-4.32 (t, 1H), 4.18-4.17 (d, 1H), 4.09-4.07 (t, 2H), 3.50 (s, 1H), 3.48 (s, 1H), 2.83-2.81 (d, 1H), 2.49 (s, 1H), 1.91 (s, 4H), 1.89-1.80 (m, 3H), 1.68 (s, 2H), 1.54-1.52 (q, 2H), 1.24-1.21 (q, 2H); MS (ESI) m/z=618.2 (M+H)$^+$ Example 421. (1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-yl)methanol Step 1. (1-(2-Chloro-5-(((2R)-2-(trifluoromethyl) tetrahydrofuran-3-yl)ethynyl)pyridin-4-yl)-4-methylpiperidin-4-yl)methanol The title compound as a solid (152.9 mg) was prepared in the same fashion as Step 1 in Example 157 except that 2-chloro-4-fluoro-5-(((2R)-2-(trifluoromethyl)tetrahydrofuran-3-yl)ethynyl)pyridine (150 mg, 0.48 mmol) prepared in Reference Example 70 and (4-methylpiperidin-4-yl) methanol (95 mg, 0.63 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.14 (s, 1H), 6.70 (s, 1H), 4.33 (s, 1H), 4.15-4.05 (d, 2H), 3.62 (s, 2H), 3.45 (s, 3H), 3.21 (s, 2H), 2.45 (s, 1H), 2.21-2.19 (d, 1H), 1.68 (s, 4H), 1.47 (s, 2H), 1.27-1.26 (d, 1H), 1.05 (s, 3H)

Step 2. (1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-yl)methanol The title compound (2.5 mg) was prepared in the same fashion as Step 3 in Example 1, except that (1-(2-chloro-5-(((2R)-2-(trifluoromethyl)tetrahydrofuran-3-yl)ethynyl) pyridin-4-yl)-4-methylpiperidin-4-yl)methanol (152 mg, 0.38 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45-8.41 (t, 2H), 8.14 (s, 1H), 7.65 (s, 1H), 7.59 (s, 1H), 6.98-6.97 (d, 1H), 4.37-4.33 (t, 1H), 4.17-4.16 (d, 1H), 4.07-4.05 (d, 1H), 3.64-3.60 (q, 2H), 3.50-3.46 (t, 3H), 3.39-3.33 (m, 2H), 2.85-2.84 (d, 1H), 2.47-2.45 (d, 1H), 2.23-2.20 (t, 1H), 1.79-1.72 (m, 3H), 1.67 (s, 9H), 1.56-1.52 (m, 4H), 1.25-1.23 (t, 2H), 1.08-1.06 (d, 3H); MS (ESI) m/z=632.2 (M+H)$^+$ Example 422. ((1s,4s)-4-((5-((7-Oxabicyclo[2.2.1] heptan-2-yl)ethynyl)-2-((2-(1-(cyclopropylsulfonyl)-1H-pyrazol-4-yl)pyrimidin-4-yl)amino)pyridin-4-yl) amino)cyclohexyl)methanol Step 1. ((1s,4s)-4-((5-((7-Oxabicyclo[2.2.1]heptan-2-yl)ethynyl)-2-chloropyridin-4-yl)amino)cyclohexyl)methanol The title compound as a solid (206 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 and ((1s,4s)-4-aminocyclohexyl)methanol (128 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.98 (s, 1H), 6.41 (s, 1H), 5.42 (s, 1H), 4.71-4.64 (d, 2H), 3.69 (s, 1H), 3.53 (s, 2H), 2.81 (s, 1H), 2.32-2.23 (t, 1H), 2.00 (s, 2H), 1.85 (s, 3H), 1.72-1.64 (d, 8H), 1.49-1.42 (t, 3H), 1.27 (s, 2H)

Step 2. ((1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl) amino)cyclohexyl)methanol The title compound (9.1 mg) was prepared in the same fashion as Step 3 in Example 1, except that ((1s,4s)-4-((5-((7-oxabicyclo[2.2.1]heptan-2-yl)ethynyl)-2-chloropyridin-4-yl)amino)cyclohexyl)methanol (206 mg, 0.55 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.59 (s, 1H), 8.52 (s, 1H), 8.42 (d, 2H), 7.96 (s, 1H), 7.74 (s, 1H), 7.01-6.98 (t, 1H), 6.02-6.00 (d, 1H), 4.75-4.73 (t, 1H), 4.67-4.66 (d, 1H), 3.99 (s, 1H), 3.57-3.52 (q, 2H), 2.85-2.82 (q, 2H), 2.08-2.01 (q, 2H), 1.91-1.85 (q, 3H), 1.80-1.77 (t, 2H), 1.72-1.62 (m, 3H), 1.54-1.51 (t, 4H), 1.49-1.47 (d, 2H), 1.29-1.23 (d, 2H); MS (ESI) m/z=590.2 (M+H)$^+$ Example 423. (1r,4r)-4-(((5-((7-Oxabicyclo[2.2.1] heptan-2-yl)ethynyl)-2-((2-(1-(cyclopropylsulfonyl)-1H-pyrazol-4-yl)pyrimidin-4-yl)amino)pyridin-4-yl) amino)methyl)cyclohexan-1-ol Step 1. (1r,4r)-4-(((5-((7-Oxabicyclo[2.2.1]heptan-2-yl)ethynyl)-2-chloropyridin-4-yl)amino)methyl)cyclohexan-1-ol The title compound as a solid (196 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 and trans-4-(aminomethyl)cyclohexanol HCl (128 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.99 (s, 1H), 6.39 (s, 1H), 5.23 (s, 1H), 4.69-4.63 (d, 2H), 3.60 (s, 1H), 3.11-3.03 (d, 2H), 2.88-2.80 (d, 1H), 2.04 (s, 3H), 1.85-1.77 (d, 7H), 1.57-1.50 (d, 3H), 1.30 (s, 2H), 1.09 (s, 2H)

Step 2. (1r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino) methyl)cyclohexan-1-ol The title compound (11.5 mg) was prepared in the same fashion as Step 3 in Example 1, except that (1r,4r)-4-(((5-((7-oxabicyclo[2.2.1]heptan-2-yl)ethynyl)-2-chloropyridin-4-yl)amino)methyl)cyclohexan-1-ol (196 mg, 0.52 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.63 (s, 1H), 8.41-8.40 (t, 2H), 7.81 (s, 1H), 7.56 (s, 1H), 7.07-7.05 (d, 1H), 5.56 (s, 1H), 4.72-4.63 (m, 2H), 3.61 (s, 1H), 3.23-3.19 (q, 2H), 2.84-2.80 (m, 2H), 2.07-2.01 (q, 3H), 1.91-1.88 (q, 3H), 1.77 (d, 2H), 1.54-1.49 (m, 4H), 1.33-1.30 (t, 2H), 1.24-1.17 (m, 4H); MS (ESI) m/z=590.2 (M+H)⁺

Example 424. 1-(5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)-4-methylpiperidin-4-ol Step 1. 1-(5-((7-Oxabicyclo[2.2.1]heptan-2-yl)ethynyl)-2-chloropyridin-4-yl)-4-methylpiperidin-4-ol The title compound as a solid (169 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 and 4-methylpiperidin-4-ol (89 mg, 0.77 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.15 (s, 1H), 6.70 (s, 1H), 4.71-4.65 (d, 2H), 3.69 (s, 2H), 3.30 (s, 2H), 2.81 (s, 1H), 2.22 (s, 1H), 2.00-1.89 (d, 2H), 1.75-1.69 (d, 8H), 1.50 (s, 2H), 1.33 (s, 4H)

Step 2. 1-(5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)-4-methylpiperidin-4-ol The title compound (9.7 mg) was prepared in the same fashion as Step 3 in Example 1, except that 1-(5-((7-oxabicyclo[2.2.1]heptan-2-yl)ethynyl)-2-chloropyridin-4-yl)-4-methylpiperidin-4-ol (169 mg, 0.49 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.65-8.64 (d, 1H), 8.43-8.41 (d, 2H), 8.29-8.28 (d, 1H), 7.88 (s, 1H), 6.93-6.91 (t, 1H), 4.73-4.71 (t, 1H), 4.65-4.63 (t, 2H), 4.00-3.96 (q, 2H), 3.51-3.48 (t, 2H), 2.84-2.79 (m, 2H), 2.00-1.98 (d, 1H), 1.89-1.83 (d, 5H), 1.78-1.76 (t, 2H), 1.55-1.48 (m, 4H), 1.36 (s, 3H), 1.30-1.28 (d, 2H); MS (ESI) m/z=576.2 (M+H)⁺

Example 425. ((1r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexyl)methanol Step 1. ((1r,4r)-4-(((5-((7-Oxabicyclo[2.2.1]heptan-2-yl)ethynyl)-2-chloropyridin-4-yl)amino)methyl)cyclohexyl)methanol The title compound as a solid (162 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 and trans-4-(aminomethyl)cyclohexanemethanol HCl (139 mg, 0.77 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.00-7.99 (d, 1H), 6.41 (s, 1H), 5.23 (s, 1H), 4.70-4.64 (d, 1H), 3.49 (s, 2H), 3.04 (s, 2H), 2.81 (s, 1H), 2.04 (s, 1H), 1.89 (s, 5H), 1.76 (s, 2H), 1.66-1.60 (d, 4H), 1.51 (s, 4H), 1.26 (s, 2H), 1.04 (s, 4H), 0.85 (s, 1H)

Step 2. ((1r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexyl)methanol The title compound (7.6 mg) was prepared in the same fashion as Step 3 in Example 1, except that ((1r,4r)-4-(((5-((7-oxabicyclo[2.2.1]heptan-2-yl)ethynyl)-2-chloropyridin-4-yl)amino)methyl)cyclohexyl)methanol (162 mg, 0.43 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.42-8.41 (t, 2H), 7.80-7.79 (d, 1H), 7.07-7.05 (d, 1H), 5.62 (s, 1H), 4.72-4.63 (q, 2H), 4.02-4.01 (d, 1H), 3.49-3.47 (d, 2H), 3.24-3.22 (t, 2H), 2.84-2.80 (q, 2H), 2.05-2.02 (t, 1H), 1.93-1.87 (t, 5H), 1.78-1.77 (d, 2H), 1.55 (s, 1H), 1.53-1.49 (m, 5H), 1.22-1.15 (m, 4H), 1.04-1.01 (t, 3H); MS (ESI) m/z=604.2 (M+H)⁺

Example 426. N-(5-((7-Oxabicyclo[2.2.1]heptan-2-yl)ethynyl)-4-(4-(2-(dimethylamino)ethyl)piperidin-1-yl)pyridin-2-yl)-2-(1-(cyclopropylsulfonyl)-1H-pyrazol-4-yl)pyrimidin-4-amine Step 1. 2-(1-(5-((7-Oxabicyclo[2.2.1]heptan-2-yl)ethynyl)-2-chloropyridin-4-yl)piperidin-4-yl)-N,N-dimethylethan-1-amine The title compound as a solid (176 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 and N,N-dimethyl-2-(piperidin-4-yl)ethanamine (121 mg, 0.77 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.11 (s, 1H), 6.64 (s, 1H), 4.70-4.63 (d, 2H), 3.99 (s, 2H), 3.52-3.46 (d, 1H), 2.78 (s, 3H), 2.41 (s, 2H), 2.33 (s, 2H), 2.16 (s, 7H), 1.98 (s, 1H), 1.87-1.78 (d, 5H), 1.48 (s, 6H), 1.36 (s, 2H)

Step 2. N-(5-((7-oxabicyclo[2.2.1]heptan-2-yl)ethynyl)-4-(4-(2-(dimethylamino)ethyl)piperidin-1-yl)pyridin-2-yl)-2-(1-(cyclopropylsulfonyl)-1H-pyrazol-4-yl)pyrimidin-4-amine The title compound (13.0 mg) was prepared in the same fashion as Step 3 in Example 1, except that 2-(1-(5-((7-oxabicyclo[2.2.1]heptan-2-yl)ethynyl)-2-chloropyridin-4-yl)piperidin-4-yl)-N,N-dimethylethan-1-amine (176 mg, 0.44 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.64 (s, 1H), 8.43-8.37 (t, 1H), 8.14-8.12 (d, 2H), 7.50 (s, 1H), 7.02 (s, 1H), 4.72-4.65 (t, 2H), 4.08-4.05 (d, 2H), 2.86-2.81 (m, 4H), 2.62 (s, 3H), 2.55-2.52 (t, 2H), 2.39-2.37 (d, 2H), 2.00-1.98 (d, 1H), 1.89-1.86 (d, 3H), 1.76-1.75 (d, 2H), 1.57-1.48 (m, 10H), 1.28-1.24 (d, 2H); MS (ESI) m/z=576.2 (M+H)⁺

Example 427. (1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexan-1-ol Step 1. (1s,4s)-4-((5-((7-Oxabicyclo[2.2.1]heptan-2-yl)ethynyl)-2-chloropyridin-4-yl)amino)cyclohexan-1-ol The title compound as a solid (138 mg) was prepared in the same fashion as Step 1 in Example 157 except that 5-((7-oxabicyclo[2.2.1]heptan-2-yl)ethynyl)-2-chloro-4-fluoropyridine (150 mg, 0.60 mmol) prepared in Reference Example 71 was used instead of 4-(4-((6-chloro-4-fluoropyridin-3-yl)ethynyl)benzyl)morpholine. $^1$H-NMR (CDCl$_3$, 400 MHz) δ 7.96 (s, 1H), 6.42 (s, 1H), 5.31 (s, 1H), 4.72 (d, 1H), 4.63 (s, 1H), 4.10 (s, 1H), 3.78 (s, 1H), 3.51 (s, 2H), 2.80 (s, 1H), 2.60 (s, 1H), 2.15 (s, 1H), 2.02 (s, 2H), 1.88 (s, 10H), 1.49 (s, 2H), 1.24 (s, 1H)

Step 2. (1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexan-1-ol The title compound (7.8 mg) was prepared in the same fashion as Step 3 in Example 1, except that (1s,4s)-4-((5-((7-oxabicyclo[2.2.1]heptan-2-yl)ethynyl)-2-chloropyridin-4-yl)amino)cyclohexan-1-ol (138 mg, 0.38 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.61-8.60 (d, 1H), 8.42-8.39 (m, 2H), 7.86 (s, 1H), 7.59 (s, 1H), 7.04-7.02 (d, 1H), 5.75-5.73 (d, 1H), 4.77 (s, 1H), 4.69-4.68 (d, 2H), 2.86-2.81 (m, 3H), 2.62 (s, 6H), 2.06-2.04 (d, 1H), 1.92-1.77 (m, 12H), 1.54-1.49 (m, 8H), 1.23-1.21 (q, 2H)

Example 428. 3-((6-((2-(1-(Cyclopropylsulfonyl)-1H-pyrazol-4-yl)pyrimidin-4-yl)amino)-4-(((1s,4S)-4-(hydroxymethyl)cyclohexyl)amino)pyridin-3-yl)ethynyl)tetrahydrothiophene 1,1-dioxide Step 1. 3-((6-Chloro-4-(((1s,4S)-4-(hydroxymethyl)cyclohexyl)amino)pyridin-3-yl)ethynyl)tetrahydrothiophene 1,1-dioxide The title compound as a solid (194 mg) was prepared in the same fashion as Step 1 in Example 157 except that 3-((6-chloro-4-fluoropyridin-3-yl)ethynyl)tetrahydrothiophene 1,1-dioxide (140 mg, 0.51 mmol) prepared in Reference Example 72 and ((1s,4s)-4-aminocyclohexyl)methanol (110 mg, 0.66 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.96 (s, 1H), 6.42 (s, 1H), 5.30-5.29 (d, 1H), 3.62-3.60 (q, 2H), 3.54-3.53 (d, 2H), 3.36-3.35 (d, 1H), 3.30 (s, 1H), 3.21-3.20 (d, 1H), 3.14 (s, 1H), 2.55 (s, 1H), 2.41-2.40 (d, 2H), 1.77-1.75 (d, 2H), 1.67-1.60 (m, 6H), 1.47-1.40 (m, 2H)

Step 2. 3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)tetrahydrothiophene 1,1-dioxide The title compound (7.8 mg) was prepared in the same fashion as Step 3 in Example 1, except that 3-((6-chloro-4-(((1s,4s)-4-(hydroxymethyl)cyclohexyl)amino)pyridin-3-yl)ethynyl)tetrahydrothiophene 1,1-dioxide (194 mg, 0.51 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.62 (s, 1H), 8.43-8.39 (t, 2H), 8.03 (s, 1H), 7.05-7.03 (d, 2H), 5.33-5.31 (d, 1H), 3.86 (s, 1H), 3.68-3.65 (m, 1H), 3.59-3.58 (d, 2H), 3.46-3.36 (m, 2H), 3.30-3.24 (q, 2H), 3.18-3.14 (d, 1H), 2.83-2.81 (d, 1H), 2.64-2.59 (t, 7H), 2.47-2.45 (d, 1H), 1.96-1.94 (d, 2H), 1.84-1.78 (t, 2H), 1.62-1.66 (q, 3H), 1.53-1.43 (m, 4H), 1.23-1.21 (q, 2H); MS (ESI) m/z=612.2 (M+H)$^+$ Example 429. 3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)tetrahydrothiophene 1,1-dioxide Step 1. 3-((6-Chloro-4-(4-hydroxy-4-methylpiperidin-1-yl)pyridin-3-yl)ethynyl)tetrahydrothiophene 1,1-dioxide The title compound as a solid (170 mg) was prepared in the same fashion as Step 1 in Example 157 except that 3-((6-chloro-4-fluoropyridin-3-yl)ethynyl)tetrahydrothiophene 1,1-dioxide (140 mg, 0.51 mmol) prepared in Reference Example 72 and 4-methylpiperidin-4-ol (77 mg, 0.66 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.11-8.10 (d, 1H), 6.69-6.68 (d, 1H), 3.65-3.56 (m, 4H), 3.42-3.38 (q, 1H), 3.32-3.28 (m, 4H), 3.13-3.09 (m, 4H), 2.59-2.57 (t, 1H), 2.35-2.33 (t, 1H), 1.88 (s, 6H), 1.28 (s, 3H)

Step 2. 3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)tetrahydrothiophene 1,1-dioxide The title compound (6.6 mg) was prepared in the same fashion as Step 3 in Example 1, except that 3-((6-chloro-4-(4-hydroxy-4-methylpiperidin-1-yl)pyridin-3-yl)ethynyl)tetrahydrothiophene 1,1-dioxide (170 mg, 0.46 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.44-8.41 (t, 2H), 8.10 (s, 1H), 7.89 (s, 1H), 6.94-6.92 (d, 1H), 3.77-3.73 (q, 2H), 3.62-3.60 (d, 1H), 3.49-3.43 (q, 2H), 3.39-3.34 (m, 2H), 3.20-3.13 (m, 2H), 2.84-2.82 (d, 1H), 2.64-2.61 (t, 1H), 2.38-2.34 (t, 2H), 1.82-1.80 (q, 4H), 1.56-1.55 (d, 2H), 1.36 (s, 3H), 1.25-1.23 (d, 2H); MS (ESI) m/z=598.2 (M+H)$^+$ Example 430. ((1s,4s)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexyl)methanol Step 1. ((1s,4s)-4-((2-Chloro-5-((2-methyltetrahydrofuran-3-yl)ethynyl)pyridin-4-yl)amino)cyclohexyl)methanol The title compound as a solid (162 mg) was prepared in the same fashion as Step 1 in Example 157 except that 2-chloro-4-fluoro-5-((2-methyltetrahydrofuran-3-yl)ethynyl)pyridine (148 mg, 0.62 mmol) prepared in Reference Example 73 and ((1s,4s)-4-aminocyclohexyl)methanol (132 mg, 0.77 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 7.99 (d, 1H), 6.41 (d, 1H), 5.23-5.22 (d, 1H), 4.00-3.96 (m, 2H), 3.91-3.80 (m, 1H), 3.68-3.66 (q, 1H), 3.51-3.50 (t, 2H), 2.72-2.71 (d, 1H), 2.41-2.33 (m, 1H), 2.09-2.07 (t, 1H), 1.93 (brs, 2H), 1.81-1.80 (d, 2H), 1.70-1.65 (q, 6H), 1.37-1.35 (t, 4H), 1.28-1.26 (d, 3H); MS (ESI) m/z=349.1 (M+H)$^+$ Step 2. ((1s,4s)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexyl)methanol The title compound (7.2 mg) was prepared in the same fashion as Step 3 in Example 1, except that ((1s,4s)-4-((2- chloro-5-((2-methyltetrahydrofuran-3-yl)ethynyl)pyridin-4-yl)amino)cyclohexyl)methanol (162 mg, 0.46 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.61 (s, 1H), 8.43-8.39 (t, 2H), 7.93-7.92 (d, 1H), 7.55 (s, 1H), 7.01 (s, 1H), 5.50 (s, 1H), 4.02-3.95 (q, 3H), 3.93-3.91 (t, 4H), 3.55-3.53 (t, 2H), 2.79-2.75 (t, 2H), 2.45 (s, 2H), 2.25-2.17 (m, 2H), 1.98-1.97 (d, 2H), 1.88-1.85 (q, 3H), 1.77-1.70 (t, 6H), 1.54-1.52 (q, 2H), 1.43-1.38 (m, 6H), 1.24-1.22 (q, 41-1); MS (ESI) m/z=578.2 (M+H)⁺

Example 431. (1 r,4r)-4-(((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)methyl)cyclohexan-1-ol

Step 1. (1 r,4r)-4-(((2-Chloro-5-((2-methyltetrahydrofuran-3-yl)ethynyl)pyridin-4-yl)amino)methyl)cyclohexan-1-ol The title compound as a solid (196 mg) was prepared in the same fashion as Step 1 in Example 157 except that 2-chloro-4-fluoro-5-((2-methyltetrahydrofuran-3-yl)ethynyl)pyridine (148 mg, 0.62 mmol) prepared in Reference Example 73 and trans-4-(aminomethyl)cyclohexanol HCl (132 mg, 0.77 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.00 (d, 1H), 6.40-6.39 (d, 1H), 5.04 (d, 1H), 4.03-4.02 (d, 2H), 3.99-3.90 (m, 1H), 3.83-3.82 (d, 1H), 3.04-3.01 (q, 2H), 2.47 (s, 1H), 2.06-2.04 (q, 1H), 2.03-2.02 (t, 2H), 1.86-1.83 (d, 2H), 1.76 (s, 3H), 1.57-1.56 (t, 3H), 1.37-1.35 (q, 3H), 1.30-1.28 (d, 2H), 1.09-1.06 (t, 2H); MS (ESI) m/z=349.1 (M+H)⁺

Step 2. (1r,4r)-4-(((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)methyl)cyclohexan-1-ol The title compound (12.5 mg) was prepared in the same fashion as Step 3 in Example 1, except that (1r,4r)-4-(((2-chloro-5-((2-methyltetrahydrofuran-3-yl)ethynyl)pyridin-4-yl)amino)methyl)cyclohexan-1-ol (196 mg, 0.56 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.63 (s, 1H), 8.42-8.41 (t, 2H), 7.87-7.85 (d, 1H), 7.59 (s, 1H), 7.05-7.04 (d, 1H), 5.34 (s, 1H), 4.07-4.01 (m, 3H), 3.99-3.84 (m, 3H), 3.60 (s, 1H), 3.24-3.22 (t, 2H), 2.82 (s, 1H), 2.75-2.73 (d, 1H), 2.42 (s, 1H), 2.08-2.03 (m, 2H), 1.91-1.87 (d, 2H), 1.53-1.51 (q, 2H), 1.40-1.39 (d, 3H), 1.33-1.26 (t, 2H), 1.23-1.17 (q, 4H); MS (ESI) m/z=578.2 (M+H)⁺

Example 432. 1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-ol

Step 1. 1-(2-Chloro-5-((2-methyltetrahydrofuran-3-yl)ethynyl)pyridin-4-yl)-4-methylpiperidin-4-ol The title compound as a solid (147 mg) was prepared in the same fashion as Step 1 in Example 157 except that 2-chloro-4-fluoro-5-((2-methyltetrahydrofuran-3-yl)ethynyl)pyridine (148 mg, 0.62 mmol) prepared in Reference Example 73 and 4-methylpiperidin-4-ol (92 mg, 0.77 mmol) were used instead of 4-(4-((6-chloro-4-fluoropyridin-3-yl)ethynyl)benzyl)morpholine and cis-4-aminocyclohexanol HCl. ¹H-NMR (CDCl₃, 400 MHz) δ 8.13 (s, 1H), 6.69 (d, 1H), 4.05-4.04 (d, 1H), 3.98-3.96 (m, 1H), 3.91-3.89 (q, 1H), 3.84-3.78 (m, 1H), 3.69-3.66 (m, 2H), 3.28 (d, 3H), 2.70-2.68 (d, 1H), 2.09-2.07 (t, 1H), 1.75-1.72 (q, 4H), 1.69 (s, 3H), 1.36-1.35 (d, 4H), 1.32-1.31 (d, 4H); MS (ESI) m/z=335.1 (M+H)⁺

Step 2. 1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-ol The title compound (11.8 mg) was prepared in the same fashion as Step 3 in Example 1, except that 1-(2-chloro-5-((2-methyltetrahydrofuran-3-yl)ethynyl)pyridin-4-yl)-4-methylpiperidin-4-ol (147 mg, 0.44 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.67 (s, 1H), 8.44-8.39 (q, 2H), 8.04-8.00 (d, 1H), 7.87 (s, 1H), 6.93-6.91 (d, 1H), 4.10-4.07 (t, 1H), 4.01-3.99 (d, 1H), 3.93-3.92 (d, 1H), 3.88-3.82 (m, 4H), 3.32-3.27 (q, 2H), 2.83 (s, 1H), 2.73-2.71 (d, 1H), 2.40 (s, 1H), 2.08-2.06 (t, 1H), 1.84-1.78 (q, 4H), 1.55-1.53 (q, 2H), 1.40-1.33 (m, 8H), 1.24-1.22 (d, 2H); MS (ESI) m/z=564.2 (M+H)⁺

Example 433. (1s,4s)-4-((2-((2-(1-(cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexan-1-ol

Step 1. (1s,4S)-4-((2-Chloro-5-((2-methyltetrahydrofuran-3-yl)ethynyl)pyridin-4-yl)amino)cyclohexan-1-ol The title compound as a solid (173 mg) was prepared in the same fashion as Step 1 in Example 157 except that 2-chloro-4-fluoro-5-((2-methyltetrahydrofuran-3-yl)ethynyl)pyridine (148 mg, 0.62 mmol) prepared in Reference Example 73 was used instead of 4-(4-((6-chloro-4-fluoropyridin-3-yl)ethynyl)benzyl)morpholine. MS (ESI) m/z=335.1 (M+H)⁺

Step 2. (1s,4S)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexan-1-ol The title compound (6.1 mg) was prepared in the same fashion as Step 3 in Example 1, except that (1s,4s)-4-((2-chloro-5-((2-methyltetrahydrofuran-3-yl)ethynyl)pyridin-4-yl)amino)cyclohexan-1-ol (173 mg, 0.52 mmol) prepared in Step 1 was used instead of 1-(2-chloro-5-((1-methyl-1H-pyrazol-4-yl)ethynyl)pyridin-4-yl)-4-methylpiperazine. ¹H-NMR (CDCl₃, 400 MHz) δ 8.61 (s, 1H), 8.42-8.41 (m, 2H), 7.90-7.88 (d, 1H), 7.58 (s, 1H), 7.05-7.04 (d, 1H), 5.45-5.43 (d, 1H), 4.03-3.88 (m, 5H), 3.75 (s, 2H), 2.82-2.74 (t, 2H), 2.56-2.48 (m, 1H), 2.26-2.22 (m, 1H), 1.90-1.82 (m, 7H), 1.69-1.66 (q, 2H), 1.54-1.52 (q, 2H), 1.42-1.39 (t, 4H), 1.23-1.21 (d, 2H); MS (ESI) m/z=564.2 (M+H)⁺

Example 434. ((1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexyl)methanol Step 1. ((1s,4s)-4-((2-Chloro-5-((3-fluorotetrahydrofuran-3-yl)ethynyl)pyridin-4-yl)amino)cyclohexyl)methanol The title compound as a solid (71 mg) was prepared in the same fashion as Step 1 in Example 157 except that 2-chloro-4-fluoro-5-((3-fluorotetrahydrofuran-3-yl)ethynyl)pyridine (130 mg, 0.53 mmol) prepared in Reference Example 74 and ((1s,4s)-4-aminocyclohexyl)methanol (114 mg, 0.69 mmol) were used instead of 4-(4-((6-chloro-4-fluoropyridin-3-yl)ethynyl)benzyl)morpholine and cis-4-aminocyclohexanol HCl. MS (ESI) m/z=353.1 (M+H)+

Step 2. ((1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexyl)methanol The title compound (2.3 mg) was prepared in the same fashion as Step 3 in Example 1, except that ((1s,4S)-4-((2-chloro-5-((3-fluorotetrahydrofuran-3-yl)ethynyl)pyridin-4-yl)amino)cyclohexyl)methanol (71 mg, 0.20 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=582.2 (M+H)+

Example 435. 1-(2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)-4-methylpiperidin-4-ol Step 1. 1-(2-Chloro-5-((3-fluorotetrahydrofuran-3-yl)ethynyl)pyridin-4-yl)-4-methylpiperidin-4-ol The title compound as a solid (71 mg) was prepared in the same fashion as Step 1 in Example 157 except that 2-chloro-4-fluoro-5-((3-fluorotetrahydrofuran-3-yl)ethynyl)pyridine (130 mg, 0.53 mmol) prepared in Reference Example 74 and 4-methylpiperidin-4-ol (80 mg, 0.69 mmol) were used instead of 4-(4-((6-chloro-4-fluoropyridin-3-yl)ethynyl)benzyl)morpholine and cis-4-aminocyclohexanol HCl. MS (ESI) m/z=339.1 (M+H)+

Step 2. 1-(2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)-4-methylpiperidin-4-ol The title compound (3.0 mg) was prepared in the same fashion as Step 3 in Example 1, except that 1-(2-chloro-5-((3-fluorotetrahydrofuran-3-yl)ethynyl)pyridin-4-yl)-4-methylpiperidin-4-ol (71 mg, 0.21 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=568.2 (M+H)+

Example 436. (1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexan-1-ol Step 1. (1s,4s)-4-((2-Chloro-5-((3-fluorotetrahydrofuran-3-yl)ethynyl)pyridin-4-yl)amino)cyclohexan-1-ol The title compound as a solid (62 mg) was prepared in the same fashion as Step 1 in Example 157 except that 2-chloro-4-fluoro-5-((3-fluorotetrahydrofuran-3-yl)ethynyl)pyridine (130 mg, 0.53 mmol) prepared in Reference Example 74 was used instead of 4-(4-((6-chloro-4-fluoropyridin-3-yl)ethynyl)benzyl)morpholine. MS (ESI) m/z=339.1 (M+H)+

Step 2. (1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexan-1-ol The title compound (3.1 mg) was prepared in the same fashion as Step 3 in Example 1, except that (1s,4s)-4-((2-chloro-5-((3-fluorotetrahydrofuran-3-yl)ethynyl)pyridin-4-yl)amino)cyclohexan-1-ol (62 mg, 0.18 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=568.2 (M+H)+

Example 437. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrothiophene 1,1-dioxide Step 1. 3-((6-Chloro-4-(4-(hydroxymethyl)-4-methylpiperidin-1-yl)pyridin-3-yl)ethynyl)tetrahydrothiophene 1,1-dioxide The title compound as a solid (242 mg) was prepared in the same fashion as Step 1 in Example 157 except that 3-((6-chloro-4-fluoropyridin-3-yl)ethynyl)tetrahydrothiophene 1,1-dioxide (152 mg, 0.95 mmol) prepared in Reference Example 72 and (4-methylpiperidin-4-yl)methanol (85 mg, 0.66 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.11 (s, 1H), 6.68 (s, 1H), 3.65-3.57 (m, 3H), 3.44 (s, 3H), 3.41-3.39 (t, 1H), 3.34-3.07 (m, 4H), 2.62-2.57 (q, 1H), 2.37-2.32 (q, 1H), 1.73-1.66 (m, 2H), 1.44-1.41 (d, 2H), 1.02 (s, 3H); MS (ESI) m/z=383.1 (M+H)+

Step 2. 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrothiophene 1,1-dioxide The title compound (7.5 mg) was prepared in the same fashion as Step 3 in Example 1, except that 3-((6-chloro-4-(4-(hydroxymethyl)-4-methylpiperidin-1-yl)pyridin-3-yl)ethynyl)tetrahydrothiophene 1,1-dioxide (242 mg, 0.63 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=612.2 (M+H)+

Example 438. (1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-yl)methanol Step 1. (1-(2-Chloro-5-((2-methyltetrahydrofuran-3-yl)ethynyl)pyridin-4-yl)-4-methylpiperidin-4-yl)methanol The title compound as a solid (124 mg) was prepared in the same fashion as Step 1 in Example 157 except that 2-chloro-4-fluoro-5-((2-methyltetrahydrofuran-3-yl)ethynyl)pyridine (148 mg, 0.62 mmol) prepared in Reference Example 73 and (4-methylpiperidin-4-yl)methanol (85 mg, 0.66 mmol) were used instead of 4-(4-((6-chloro-4-fluoro-pyridin-3-yl)ethynyl)benzyl)morpholine and cis-4-aminocyclohexanol HCl. $^1$H-NMR (CDCl$_3$, 400 MHz) δ 8.14 (s, 1H), 6.69 (s, 1H), 4.15-4.09 (q, 2H), 3.99-3.83 (m, 3H), 3.66-3.62 (m, 2H), 3.45 (s, 2H), 3.23-3.20 (t, 2H), 2.71-2.69 (d, 1H), 2.40 (s, 1H), 2.11-2.04 (t, 4H), 1.71-1.66 (m, 4H), 1.49-1.45 (q, 2H), 1.38-1.36 (d, 3H), 1.27-1.24 (t, 4H), 1.05 (s, 3H), 0.90-0.86 (t, 1H); MS (ESI) m/z=349.1 (M+H)$^+$ Step 2. (1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-yl)methanol The title compound (3.8 mg) was prepared in the same fashion as Step 3 in Example 1, except that (1-(2-chloro-5-((2-methyltetrahydrofuran-3-yl)ethynyl)pyridin-4-yl)-4-methylpiperidin-4-yl)methanol (124 mg, 0.36 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=578.2 (M+H)$^+$ Example 439. (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-3-ol Step 1. (S)-1-(2-Chloro-5-((1-(trifluoromethyl)-1H-pyrazol-4-yl)ethynyl)pyridin-4-yl)piperidin-3-ol The title compound as a solid (128 mg) was prepared in the same fashion as Step 1 in Example 157 except that 2-chloro-4-fluoro-5-((1-(trifluoromethyl)-1H-pyrazol-4-yl)ethynyl)pyridine (280 mg, 0.97 mmol) prepared in Reference Example 23 and (S)-3-hydroxypiperidine HCl (126 mg, 0.71 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.23 (s, 1H), 8.17 (s, 1H), 7.95 (s, 1H), 6.88 (s, 1H), 4.02-4.01 (d, 1H), 3.65-3.64 (d, 1H), 3.53-3.52 (d, 1H), 3.25-3.24 (d, 1H), 2.36 (brs, 1H), 1.97-1.94 (m, 2H), 1.67-1.59 (q, 3H)

Step 2. (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-3-ol The title compound (6.9 mg) was prepared in the same fashion as Step 3 in Example 1, except that (S)-1-(2-chloro-5-((1-(trifluoromethyl)-1H-pyrazol-4-yl)ethynyl)pyridin-4-yl)piperidin-3-ol (112 mg, 0.30 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.46-8.42 (t, 2H), 8.31 (s, 1H), 8.20 (s, 1H), 7.91 (s, 1H), 7.83 (s, 1H), 6.95-6.94 (d, 1H), 4.04 (d, 1H), 3.64-3.61 (d, 1H), 3.54-3.51 (t, 2H), 3.38-3.36 (d, 1H), 2.86-2.85 (d, 1H), 2.02-1.96 (t, 2H), 1.81-1.72 (m, 2H), 1.55-1.54 (d, 2H), 1.25-1.23 (d, 2H); MS (ESI) m/z=600.1 (M+H)$^+$ Example 440. (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-3-ol Step 1. (R)-1-(2-Chloro-5-((1-(2-fluoroethyl)-1H-pyrazol-4-yl)ethynyl)pyridin-4-yl)piperidin-3-ol The title compound as a solid (231 mg) was prepared in the same fashion as Step 1 in Example 157 except that 2-chloro-4-fluoro-5-((1-(2-fluoroethyl)-1H-pyrazol-4-yl)ethynyl)pyridine (200 mg, 0.75 mmol) prepared in Reference Example 62 and (R)-piperidin-3-ol HCl (98 mg, 0.71 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.18 (s, 1H), 7.70-7.67 (d, 2H), 6.70 (s, 1H), 4.78 (s, 1H), 4.67 (s, 1H), 4.41 (s, 1H), 4.35-4.34 (d, 1H), 3.92 (s, 1H), 3.67-3.64 (d, 1H), 3.47-3.44 (d, 1H), 3.27-3.22 (q, 1H), 3.18-3.13 (t, 1H), 1.92-1.89 (d, 2H), 1.67-1.59 (m, 2H)

Step 2. (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-3-ol The title compound (8.0 mg) was prepared in the same fashion as Step 3 in Example 1, except that (R)-1-(2-chloro-5-((1-(2-fluoroethyl)-1H-pyrazol-4-yl)ethynyl)pyridin-4-yl)piperidin-3-ol (231 mg, 0.66 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.43-8.34 (t, 2H), 8.19 (s, 1H), 7.81 (s, 1H), 7.74-7.72 (d, 2H), 6.96-6.95 (d, 1H), 4.85-4.83 (t, 1H), 4.74-4.71 (t, 1H), 4.48-4.46 (t, 1H), 4.41-4.39 (t, 1H), 4.05-4.03 (t, 1H), 3.65-3.50 (m, 3H), 3.36 (s, 1H), 2.86-2.81 (m, 2H), 1.95 (s, 2H), 1.85-1.80 (m, 2), 1.56-1.53 (m, 2H), 1.25-1.22 (t, 2H); MS (ESI) m/z=578.2 (M+H)$^+$ Example 441. (4-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)phenyl)(4-hydroxypiperidin-1-yl)methanone Step 1. (4-((6-Chloro-4-(((1s,4s)-4-(hydroxymethyl)cyclohexyl)amino)pyridin-3-yl)ethynyl)phenyl)(4-hydroxypiperidin-1-yl)methanone The title compound as a solid (107 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and ((1s,4s)-4-aminocyclohexyl)methanol (44 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.11 (s, 1H), 7.53-7.51 (d, 2H), 7.39-7.37 (d, 2H), 6.47 (s, 1H), 5.38-5.36 (d, 1H), 4.13-4.11 (d, 1H), 4.09-3.93 (m, 1H), 3.71-3.70 (d, 2H), 3.49-3.38 (q, 6H), 3.21 (s, 1H), 1.85-1.81 (t, 3H), 1.72-1.69 (q, 4H), 1.67-1.61 (m, 2H), 1.51 (s, 1H), 1.36-1.31 (t, 2H); MS (ESI) m/z=468.2 (M+H)$^+$ Step 2. (4-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)phenyl)(4-hydroxypiperidin-1-yl)methanone The title compound (4.4 mg) was prepared in the same fashion as Step 3 in Example 1, except that (4-((6-chloro-4-(((1s,4s)-4-(hydroxymethyl)cyclohexyl)amino)pyridin-3-yl)ethynyl)phenyl)(4-hydroxypiperidin-1-yl)methanone (107 mg, 0.23 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.64 (s, 1H), 8.44 (s, 1H), 8.41-8.40 (d, 1H), 8.15 (s, 1H), 7.56-7.54 (d, 2H), 7.43-7.41 (d, 2H), 7.05-7.04 (d, 1H), 5.43-5.41 (d, 1H), 4.02-4.00 (t, 1H), 3.94-3.92 (t, 2H), 3.54-3.52 (d, 2H), 2.84 (s, 1H), 2.62 (s, 7H), 2.02-1.99 (d, 3H), 1.87-1.80 (q, 3H), 1.56-1.51 (m, 4H), 1.36-1.33 (d, 4H), 1.25-1.22 (t, 2H); MS (ESI) m/z=697.3 (M+H)$^+$ Example 442. (4-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)phenyl)(4-hydroxypiperidin-1-yl)methanone Step 1. (4-((6-Chloro-4-(4-hydroxy-4-methylpiperidin-1-yl)pyridin-3-yl)ethynyl)phenyl)(4-hydroxypiperidin-1-yl)methanone The title compound as a solid (104 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and 4-methylpiperidin-4-ol (31 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.24 (s, 1H), 7.51-7.49 (d, 2H), 7.39-7.37 (d, 2H), 6.73 (s, 1H), 4.13-4.10 (t, 1H), 3.98-3.94 (m, 1H), 3.78-3.73 (m, 2H), 3.63 (s, 1H), 3.45 (s, 4H), 3.42-3.35 (m, 3H), 3.22 (s, 1H), 1.82-1.71 (m, 3H), 1.67-1.61 (m, 6H), 1.52-1.47 (d, 3H), 1.32 (s, 3H); MS (EST) m/z=454.1 (M+H)$^+$ Step 2. (4-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)phenyl)(4-hydroxypiperidin-1-yl)methanone The title compound (7.8 mg) was prepared in the same fashion as Step 3 in Example 1, except that (4-((6-chloro-4-(4-hydroxy-4-methylpiperidin-1-yl)pyridin-3-yl)ethynyl)phenyl)(4-hydroxypiperidin-1-yl)methanone (104 mg, 0.23 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.69 (s, 1H), 8.45-8.41 (t, 2H), 8.24 (s, 1H), 7.85 (s, 1H), 7.53-7.51 (d, 2H), 7.42-7.40 (d, 2H), 6.97-6.96 (d, 2H), 4.01-3.98 (m, 1H), 3.87-3.84 (d, 2H), 3.47-3.42 (q, 3H), 3.25 (s, 1H), 2.86-2.82 (m, 1H), 2.62 (s, 3H), 1.93-1.82 (m, 6H), 1.62-1.60 (t, 1H), 1.57-1.53 (m, 3H), 1.37-1.34 (d, 3H), 1.26-1.21 (q, 2H); MS (ESI) m/z=683.2 (M+H)$^+$ Example 443. (4-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)phenyl)(4-hydroxypiperidin-1-yl)methanone Step 1. (4-((6-Chloro-4-((((1r,4r)-4-(hydroxymethyl)cyclohexyl)methyl)amino)pyridin-3-yl)ethynyl)phenyl)(4-hydroxypiperidin-1-yl)methanone The title compound as a solid (118 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and trans-4-(aminomethyl)cyclohexanemethanol HCl (48 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.13 (s, 1H), 7.54-7.52 (d, 2H), 7.41-7.37 (d, 2H), 6.47 (s, 1H), 5.24-5.22 (d, 1H), 4.15 (brs, 1H), 4.00-3.96 (m, 1H), 3.70 (s, 1H), 3.47-3.45 (q, 7H), 3.24 (s, 1H), 3.11-3.08 (t, 2H), 1.89-1.87 (d, 6H), 1.62-1.61 (t, 3H), 1.51-1.47 (m, 2H), 1.09-0.99 (m, 4H); MS (ESI) m/z=482.2 (M+H)$^+$ Step 2. (4-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)phenyl)(4-hydroxypiperidin-1-yl)methanone The title compound (4.9 mg) was prepared in the same fashion as Step 3 in Example 1, except that (4-((6-chloro-4-((((1r,4r)-4-(hydroxymethyl)cyclohexyl)methyl)amino)pyridin-3-yl)ethynyl)phenyl)(4-hydroxypiperidin-1-yl)methanone (118 mg, 0.24 mmol) prepared in Step 1 was used instead of 1-(2-chloro-5-((1-methyl-1H-pyrazol-4-yl)ethynyl)pyridin-4-yl)-4-methylpiperazine. MS (ESI) m/z=711.3 (M+H)$^+$ Example 444. (R)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone Step 1. (R)-(4-((6-Chloro-4-(3-hydroxypiperidin-1-yl)pyridin-3-yl)ethynyl)phenyl)(4-hydroxypiperidin-1-yl)methanone The title compound as a solid (106 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and (R)-piperidin-3-ol HCl (36 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.26 (s, 1H), 7.56-7.54 (d, 2H), 7.38-7.36 (d, 2H), 6.74 (s, 1H), 4.13-4.10 (t, 1H), 3.98-3.92 (m, 2H), 3.75-3.71 (q, 1H), 3.63 (s, 1H), 3.52-3.47 (m, 1H), 3.45 (s, 4H), 3.37 (s, 1H), 3.29-3.20 (m, 3H), 1.96-1.94 (d, 4H), 1.87-1.82 (d, 1H), 1.73-1.60 (m, 4H), 1.50 (s, 1H); MS (ESI) m/z=440.1 (M+H)$^+$ Step 2. (R)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone The title compound (8.6 mg) was prepared in the same fashion as Step 3 in Example 1, except that (R)-(4-((6-chloro-4-(3-hydroxypiperidin-1-yl)pyridin-3-yl)ethynyl)phenyl)(4-hydroxypiperidin-1-yl)methanone (106 mg, 0.24 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.45 (s, 1H), 8.41-8.40 (d, 1H), 8.25 (s, 1H), 7.76 (s, 1H), 7.58-7.56 (d, 2H), 7.40-7.68 (d, 2H), 6.97-6.96 (d, 1H), 4.22 (s, 1H), 4.05-3.98 (m, 2H), 3.72-3.69 (d, 2H), 3.59-3.58 (d, 1H), 3.44-3.34 (m, 4H), 2.86-2.84 (t, 1H), 2.18 (s, 6H), 2.04-1.96 (q, 3H), 1.85-1.80 (q, 2H), 1.71-1.69 (d, 2H), 1.57-1.52 (m, 3H), 1.26-1.22 (t, 2H); MS (ESI) m/z=669.2 (M+H)$^+$ Example 445. (S)-(4-((6-((2-(1-(Cyclopropylsulfo-nyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone Step 1. (S)-(4-((6-Chloro-4-(3-hydroxypiperidin-1-yl)pyridin-3-yl)ethynyl)phenyl)(4-hydroxypiperidin-1-yl)methanone The title compound as a solid (116 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and (S)-3-hydroxypiperidine HCl (36 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.23 (s, 1H), 7.54-7.52 (d, 2H), 7.35-7.33 (d, 2H), 6.72 (s, 1H), 4.18 (s, 1H), 3.94-3.90 (m, 2H), 3.78-3.75 (q, 1H), 3.55-3.52 (t, 2H), 3.42 (s, 5H), 3.22-3.17 (q, 4H), 1.96-1.91 (t, 4H), 1.70-1.67 (d, 1H), 1.63-1.60 (d, 1H), 1.58-1.56 (d, 3H); MS (ESI) m/z=440.1 (M+H)$^+$ Step 2. (S)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone The title compound (7.1 mg) was prepared in the same fashion as Step 3 in Example 1, except that (S)-(4-((6-chloro-4-(3-hydroxypiperidin-1-yl)pyridin-3-yl)ethynyl)phenyl)(4-hydroxypiperidin-1-yl)methanone (116 mg, 0.26 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.68 (s, 1H), 8.45 (s, 1H), 8.41-8.40 (d, 1H), 8.23 (s, 1H), 7.81 (s, 1H), 7.58-7.56 (d, 2H), 7.40-7.38 (d, 2H), 6.96-6.95 (d, 1H), 4.20 (s, 1H), 4.05-3.98 (m, 2H), 3.74-3.71 (d, 2H), 3.63-3.60 (t, 1H), 3.45-3.40 (q, 3H), 3.37-3.35 (d, 1H), 2.86-2.84 (t, 1H), 2.63 (s, 6H), 2.04-1.97 (q, 3H), 1.83-1.80 (t, 2H), 1.71-1.69 (d, 2H), 1.57-1.54 (t, 3H), 1.23-1.20 (d, 2H); MS (ESI) m/z=669.2 (M+H)$^+$ Example 446. (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(4-hydroxypiperidin-1-yl)methanone Step 1. (4-((6-Chloro-4-(4-(hydroxymethyl)-4-methylpiperidin-1-yl)pyridin-3-yl)ethynyl)phenyl)(4-hydroxypiperidin-1-yl)methanone The title compound as a solid (123 mg) was prepared in the same fashion as Step 1 in Example 157 except that (4-((6-chloro-4-fluoropyridin-3-yl)ethynyl)phenyl)(4-hydroxypiperidin-1-yl)methanone (100 mg, 0.28 mmol) prepared in Reference Example 75 and (4-methylpiperidin-4-yl)methanol (34 mg, 0.26 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.23 (s, 1H), 7.50-7.48 (d, 2H), 7.38-7.36 (d, 2H), 6.71 (s, 1H), 4.18 (s, 1H), 3.95-3.94 (t, 1H), 3.75-3.70 (m, 3H), 3.44-3.41 (d, 7H), 3.31-3.24 (m, 3H), 1.75-1.69 (m, 4H), 1.49-1.45 (t, 41-1); MS (ESI) m/z=468.2 (M+H)$^+$ Step 2. (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(4-hydroxypiperidin-1-yl)methanone The title compound (8.5 mg) was prepared in the same fashion as Step 3 in Example 1, except that (4-((6-chloro-4-(4-(hydroxymethyl)-4-methylpiperidin-1-yl)pyridin-3-yl)ethynyl)phenyl)(4-hydroxypiperidin-1-yl)methanone (123 mg, 0.26 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.65 (s, 1H), 8.45 (s, 1H), 8.42-8.40 (d, 1H), 8.26 (s, 1H), 7.65 (s, 1H), 7.53-7.51 (d, 2H), 7.41-7.39 (d, 2H), 7.00-6.99 (d, 1H), 4.22 (s, 1H), 4.01-3.99 (t, 2H), 3.77-3.71 (m, 3H), 3.51-3.40 (m, 3H), 2.85-2.82 (q, 1H), 2.62 (s, 7H), 1.81 (s, 1H), 1.61-1.57 (t, 3H), 1.54-1.51 (m, 3H), 1.26-1.22 (t, 2H), 1.09 (s, 3H); MS (ESI) m/z=697.2 (M+H)$^+$ Example 447. (5)-1-(2-((2-(1-(Cyclopropylsulfo-nyl)-1H-pyrazol-4-yl)pyrimidin-4-yl)amino)-5-((1-(2-fluoroethyl)-1H-pyrazol-4-yl)ethynyl)pyridin-4-yl)-3-methylpiperidin-3-ol Step 1. (S)-1-(2-Chloro-5-((1-(2-fluoroethyl)-1H-pyrazol-4-yl)ethynyl)pyridin-4-yl)-3-methylpiperidin-3-ol The title compound as a solid (199 mg) was prepared in the same fashion as Step 1 in Example 157 except that 2-chloro-4-fluoro-5-((1-(2-fluoroethyl)-1H-pyrazol-4-yl)ethynyl)pyridine (200 mg, 0.75 mmol) prepared in Reference Example 62 and (3S)-3-methylpiperidin-3-ol HCl (107 mg, 0.71 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.23 (s, 1H), 7.76-7.71 (d, 2H), 6.75 (s, 1H), 4.80-4.78 (t, 1H), 4.69-4.66 (t, 1H), 4.43-4.41 (t, 1H), 4.36-4.34 (t, 1H), 4.09-4.08 (d, 1H), 3.80-3.77 (d, 1H), 3.60-3.57 (d, 1H), 2.86-2.83 (q, 1H), 2.80-2.74 (t, 2H), 2.01-1.94 (t, 2H), 1.77-1.69 (q, 2H), 1.49-1.42 (m, 1H), 1.26 (s, 3H)

Step 2. (5)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)-3-methylpiperidin-3-ol The title compound (37.6 mg) was prepared in the same fashion as Step 3 in Example 1, except that (S)-1-(2-chloro-5-((1-(2-fluoroethyl)-1H-pyrazol-4-yl)ethynyl)pyridin-4-yl)-3-methylpiperidin-3-ol (199 mg, 0.55 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.66 (s, 1H), 8.44-8.39 (t, 2H), 8.14 (s, 1H), 7.91 (s, 1H), 7.79-7.74 (d, 2H), 6.96-6.94 (d, 1H), 4.84-4.82 (t, 1H), 4.72-4.70 (t, 1H), 4.47-4.44 (t, 1H), 4.40-4.38 (t, 1H), 3.98-3.95 (d, 1H), 3.74-3.71 (d, 1H), 3.07-3.02 (t, 1H), 2.89-2.82 (m, 2H), 2.04-2.01 (d, 1H), 1.87-1.80 (t, 2H), 1.59-1.53 (m, 3H), 1.30 (s, 3H), 1.25-1.23 (d, 3H); MS (ESI) m/z=592.2 (M+H)$^+$ Example 448. (S)-1-(2-((2-(1-(Cyclopropylsulfo-nyl)-1H-pyrazol-4-yl)pyrimidin-4-yl)amino)-5-((1-(trifluoromethyl)-1H-pyrazol-4-yl)ethynyl)pyridin-4-yl)-3-methylpiperidin-3-ol Step 1. (S)-1-(2-Chloro-5-((1-(trifluoromethyl)-1H-pyrazol-4-yl)ethynyl)pyridin-4-yl)-3-methylpiperi-din-3-ol The title compound as a solid (109 mg) was prepared in the same fashion as Step 1 in Example 157 except that 2-chloro-4-fluoro-5-((1-(trifluoromethyl)-1H-pyrazol-4-yl)ethynyl)pyridine (300 mg, 1.03 mmol) prepared in Reference Example 23 and (3S)-3-methylpiperidin-3-ol HCl (156 mg, 1.03 mmol) were used instead of 4-(4-((6-chloro-4-fluoropyridin-3-yl)ethynyl)benzyl)morpholine and cis-4-aminocyclohexanol HCl. $^1$H-NMR (CDCl$_3$, 400 MHz) δ 8.30 (s, 1H), 8.15 (s, 1H), 7.96 (s, 1H), 6.83 (s, 1H), 3.89-3.86 (d, 1H), 3.59-3.56 (d, 1H), 2.85-2.84 (t, 2H), 2.77-2.73 (d, 1H), 1.99-1.95 (d, 1H), 1.82-1.76 (q, 2H), 1.60 (s, 2H), 1.52-1.45 (m, 1H), 1.27-1.24 (t, 6H), 0.90-0.88 (d, 1H); MS (ESI) m/z=385.1 (M+H)$^+$ Step 2. (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-methylpiperidin-3-ol The title compound (6.8 mg) was prepared in the same fashion as Step 3 in Example 1, except that (S)-1-(2-chloro-5-((1-(trifluoromethyl)-1H-pyrazol-4-yl)ethynyl)pyridin-4-yl)-3-methylpiperidin-3-ol (109 mg, 0.28 mmol) prepared in Step 1 was used instead of 1-(2-chloro-5-((1-methyl-1H-pyrazol-4-yl)ethynyl)pyridin-4-yl)-4-methylpiperazine. $^1$H-NMR (CDCl$_3$, 400 MHz) δ 8.67 (s, 1H), 8.45-8.43 (d, 2H), 8.28 (s, 1H), 8.15 (s, 1H), 7.96 (s, 1H), 7.89 (s, 1H), 7.68 (s, 1H), 7.05-7.04 (d, 1H), 3.94-3.91 (d, 1H), 3.65-3.62 (d, 1H), 3.02-2.78 (m, 2H), 2.03-2.00 (d, 2H), 1.89-1.81 (t, 2H), 1.56-1.51 (t, 3H), 1.30 (s, 4H), 1.24-1.22 (d, 3H); MS (ESI) m/z=614.1 (M+H)$^+$ Example 449. (1-(2-((2-(4-(Cyclopropylsulfonyl)piperazin-1-yl)pyrimidin-4-yl)amino)-5-((1-(trifluoromethyl)-1H-pyrazol-4-yl)ethynyl)pyridin-4-yl)-4-methylpiperidin-4-yl)methanol Step 1, tert-Butyl 4-(Cyclopropylsulfonyl)piperazine-1-carboxylate The mixture of 1-(tert-butoxycarbonyl)piperazine (1.00 g, 5.37 mmol) and TEA (1.12 mL, 8.05 mmol) in DCM (10 mL) was added cyclopropanesulfonyl chloride (0.55 mL, 5.37 mmol) and the reaction mixture was stirred at room temperature overnight. The reaction mixture was diluted in DCM, washed by water, dried over MgSO$_4$, and then concentrated. The crude product was purified by column chromatography (EA/n-Hex=0-40%) to yield tert-butyl 4-(cyclopropylsulfonyl)piperazine-1-carboxylate (1.20 g) as an off-white solid. $^1$H-NMR (CDCl$_3$, 400 MHz) δ 3.53-3.51 (t, 4H), 3.26-3.25 (d, 4H), 2.24 (s, 1H), 1.46 (s, 9H), 1.17-1.16 (d, 2H), 1.00-0.98 (d, 2H)

Step 2. 1-(Cyclopropylsulfonyl)piperazine hydrochloride

The mixture of tert-butyl 4-(cyclopropylsulfonyl)piperazine-1-carboxylate (1.20 g, 4.15 mmol) prepared in Step 1 was charged nitrogen gas for 10 minutes. After DCM (10 mL) and 4M HCl in 1,4-dioxane (11.3 mL, 8.05 mmol) were added, the reaction mixture was stirred at room temperature for 3 hours. The reaction mixture was concentrated to yield 1-(cyclopropylsulfonyl)piperazine hydrochloride (806 mg) as a colorless solid. $^1$H-NMR (CDCl$_3$, 400 MHz) δ 3.28-3.27 (t, 2H), 3.13-3.10 (t, 2H), 2.04 (s, 1H), 1.60-1.59 (t, 4H), 1.47-1.36 (m, 4H)

Step 3. 2-(4-(Cyclopropylsulfonyl)piperazin-1-yl)pyrimidin-4-amine

The mixture of 1-(cyclopropylsulfonyl)piperazine hydrochloride (806 mg, 3.55 mmol) prepared in Step 2 and 2-bromo-4-pyrimidinamine (1.00 g, 5.75 mmol), was charged nitrogen gas for 10 minutes. After DMF (10 mL) and DIPEA (1.50 mL, 8.62 mmol) were added, the reaction mixture was stirred at 90° C. for 3 hours. The reaction mixture was cooled, diluted in EA, washed by water, dried over MgSO$_4$, and then concentrated. The crude product was purified by column chromatography (EA/n-Hex=0-100%) to yield 2-(4-(cyclopropylsulfonyl)piperazin-1-yl)pyrimidin-4-amine (681 mg) as an off-white solid. $^1$H-NMR (CDCl$_3$, 400 MHz) δ 7.92-7.91 (d, 1H), 5.80-5.79 (d, 1H), 4.68 (d, 2H), 3.87 (s, 4H), 3.31 (s, 4H), 2.24 (s, 1H), 1.16 (s, 2H), 1.02-0.96 (t, 2H); MS (ESI) m/z=284.1 (M+H)$^+$ Step 4. (1-(2-((2-(4-(Cyclopropylsulfonyl)piperazin-1-yl)pyrimidin-4-yl)amino)-5-((1-(trifluoromethyl)-1H-pyrazol-4-yl)ethynyl)pyridin-4-yl)-4-methylpiperidin-4-yl)methanol The title compound as a solid (7.7 mg) was prepared in the same fashion as Step 3 in Example 1 except that (1-(2-chloro-5-((1-(trifluoromethyl)-1H-pyrazol-4-yl)ethynyl)pyridin-4-yl)-4-methylpiperidin-4-yl)methanol (90 mg, 0.23 mmol) prepared in Reference Example 53 and 2-(4-(cyclopropylsulfonyl)piperazin-1-yl)pyrimidin-4-amine (63 mg, 0.23 mmol) prepared in Step 3 were used instead of 1-(2-chloro-5-((1-methyl-1H-pyrazol-4-yl)ethynyl)pyridin-4-yl)-4-methylpiperazine and 2-(1-(cyclopropylsulfonyl)-1H-pyrazol-4-yl)pyrimidin-4-amine. $^1$H-NMR (CDCl$_3$, 400 MHz) δ 8.20 (s, 1H), 8.10-8.09 (d, 1H), 7.96 (s, 1H), 7.85 (s, 1H), 7.60 (s, 1H), 7.46 (s, 1H), 6.37-6.36 (d, 1H), 3.98-3.96 (t, 4H), 3.68-3.65 (d, 2H), 3.47 (s, 2H), 3.38-3.35 (t, 4H), 3.30-3.27 (t, 2H), 2.27 (s, 1H), 1.80-1.73 (m, 6H), 1.51-1.48 (t, 2H), 1.21-1.20 (d, 2H), 1.19 (d, 3H), 1.07-1.01 (d, 2H); MS (ESI) m/z=646.2 (M+H)$^+$ Biological Assays 1. Biochemical EGFR Inhibition Assays Biochemical EGFR kinase assays were conducted using Lance Ultra time-resolved fluorescence resonance energy transfer (TR-FRET) technology from Perkin-Elmer. Compounds of the invention were initially diluted to 20 mM in 100% DMSO for storage and made into kinase buffer solution to create a compound concentration ranging from 0.003 μM and 10 μM.

Briefly, each EGFR enzyme wildtype, double mutant [del19/C797S and L858R/C797S], triple mutant[del19/T790M/C797S and L858R/T790M/C797S], serial diluted EGFR inhibitors, substrate of ULight-poly-GT peptide (PerkinElmer; TRF0100-M) and different concentrations of ATP (Km and 100 μM final assay concentration) were mixed in kinase assay buffer (50 mM HEPES pH 7.4, 10 mM mgCl$_2$, 1 mM EGTA, 2 mM DTT and 0.01% Tween-20) and were added to a 384-well plate (Optiplate™ 384, white, PerkinElmer; 6007290).

Each kinase reactions were incubated at room temperature for 1 hour and then stopped by the addition of 4 μL of stop solution (10 mM EDTA). The specific Europium-labeled-anti-phosphopeptide antibody (PerkinElmer, AD0069) diluted in LANCE detection buffer was then added to a final concentration of 2 nM. After 60 minutes incubation at room temperature the LANCE signal was measured on an EnVision Multilabel Reader (Perkin-Elmer). Excitation wavelength was set at 320 nm and emission monitored at 615 nm (donor) and 665 nm (acceptor). The IC$_{50}$ values were determined using GraphPad prism software (GraphPad Software, Inc., San Diego, CA, USA).

The IC$_{50}$ values of compounds of formula (I) on the activity of each EGFR kinase evaluated as above are shown in Tables 3 to 17 below.

TABLE 3

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 1 | 1.3 | | | 5.4 | | 71.3 | | 34.6 | | 230.4 |
| 2 | 5.7 | | | 11.2 | | 111.9 | | 142.6 | | 880.6 |
| 3 | 6.6 | | | | | 240.3 | | | | 3829.0 |
| 4 | | 1.1 | | 12.6 | | 38.6 | | 103.2 | | >10000 |
| 5 | | 3.8 | | 44.3 | | 403.9 | | 417.8 | | >10000 |
| 6 | | 0.5 | | 4.2 | | 5.1 | | 24.1 | | 6015.0 |
| 7 | | 4.5 | | 5.0 | | 24.2 | | 143.4 | | >10000 |
| 8 | | 3.1 | | 2.2 | | 9.5 | | 33.2 | | >10000 |
| 9 | 0.7 | 1.9 | 0.4 | 1.1 | 2.8 | 3.8 | 2.2 | 27.5 | 52.8 | >10000 |
| 10 | 1.1 | 0.9 | 0.5 | 0.7 | 3.0 | 4.4 | 2.8 | 12.9 | 31.9 | >10000 |
| 11 | | 1.6 | | 1.2 | | 9.1 | | 28.5 | | >10000 |
| 12 | 0.7 | 0.8 | 0.3 | 0.6 | 1.1 | 1.9 | 0.7 | 5.1 | 6.0 | 1102.0 |
| 13 | | 1.4 | | 1.1 | | 3.3 | | 9.2 | | 3090.0 |
| 14 | | 3.9 | | 3.0 | | 21.7 | | 41.0 | | >10000 |
| 15 | | 2.6 | | 1.6 | | 6.4 | | 25.5 | | 661.0 |
| 16 | 4.5 | 3.3 | | 10.1 | 68.6 | 165.4 | | | 144.9 | >10000 |
| 17 | | 2.0 | | 6.1 | | 10.3 | | 53.3 | | >10000 |
| 18 | 2.2 | 1.6 | 3.3 | 1.1 | 35.5 | 47.3 | | | 212.9 | >10000 |
| 19 | 4.4 | 5.4 | 2.3 | 3.7 | 41.8 | 139.7 | | | 1681.0 | >10000 |
| 20 | 1.2 | 2.4 | 1.3 | 1.6 | 23.1 | 61.5 | 20.4 | | 517.1 | >10000 |
| 21 | 0.8 | | | 1.8 | | 34.3 | | | | 374.2 |
| 22 | 2.8 | | | 5.4 | | 121.9 | | | | 629.8 |
| 23 | 1.6 | | | 7.1 | | 77.7 | | 92.5 | | 906.5 |
| 24 | 2.7 | | | 4.4 | | 32.9 | | | | 462.5 |
| 25 | 6.9 | | | 6.5 | | 104.7 | | | | 915.2 |
| 26 | 3.1 | | | 3.6 | | 58.1 | | | | 545.4 |
| 27 | 0.6 | 0.6 | | 1.5 | 4.0 | 4.1 | 3.6 | 27.8 | 22.0 | >10000 |
| 28 | | 0.7 | | 2.3 | | 4.9 | | 28.1 | | >10000 |
| 29 | | 1.8 | | 2.3 | | 2.7 | | 28.1 | | 7996.0 |
| 30 | 0.9 | 1.3 | | 1.4 | 3.0 | 2.8 | 4.4 | 22.3 | 8.2 | >10000 |

TABLE 4

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 31 | | 0.7 | | 1.4 | | 6.5 | | 52.3 | | >10000 |
| 32 | 1.5 | 1.1 | | 4.8 | | 11.8 | 12.0 | 96.9 | 29.4 | >10000 |
| 33 | | 1.9 | | 3.7 | | 10.2 | | 151.9 | | >10000 |
| 34 | 2.1 | 1.8 | | 6.8 | | 11.5 | | 236.1 | 27.9 | >10000 |
| 35 | 0.9 | 1.9 | 2.4 | 2.4 | 28.0 | 27.3 | 34.2 | 53.0 | 99.6 | >10000 |
| 36 | | 2.1 | | 3.0 | | 25.5 | | 100.1 | | >10000 |
| 37 | 20.2 | | | | | 869.7 | | | 435.4 | >10000 |
| 38 | 17.6 | | | | | 464.2 | | | 367.6 | >10000 |
| 39 | | 2.6 | | 8.8 | | 53.6 | 32.3 | 203.0 | | >10000 |
| 40 | | 4.8 | | 13.1 | | 49.1 | | 278.4 | | >10000 |
| 41 | 0.5 | 0.6 | 0.2 | 0.8 | 1.3 | 2.8 | 1.5 | 10.0 | 23.8 | >10000 |
| 42 | | 1.1 | | 1.2 | | 3.2 | | 11.5 | | >10000 |
| 43 | 0.5 | 0.6 | 0.2 | 0.7 | 1.4 | 1.7 | 1.1 | 8.9 | 20.3 | >10000 |
| 44 | | 1.2 | | 1.4 | | 2.6 | | 12.7 | | 2306.0 |
| 45 | | 0.9 | | 2.3 | | 7.3 | | 46.2 | | >10000 |
| 46 | | 1.3 | | 2.9 | | 8.6 | | 59.3 | | >10000 |
| 47 | 2.1 | 2.8 | 1.4 | 3.5 | 2.6 | 1.6 | 3.3 | 7.8 | 19.6 | 1741.0 |
| 48 | 4.0 | 5.3 | 2.3 | 9.1 | 4.3 | 2.2 | 7.2 | 15.9 | 38.2 | 2915.0 |
| 49 | 1.8 | 1.8 | 1.1 | 2.9 | 2.1 | 0.9 | 2.8 | 7.2 | 14.3 | 1262.0 |
| 50 | 0.9 | | | 4.5 | | 128.5 | 130.5 | | 362.3 | |
| 51 | 0.9 | | | 3.2 | | 68.6 | 49.1 | | 262.3 | |
| 52 | 1.4 | | | 3.8 | | 76.9 | 65.6 | | 304.2 | |
| 53 | 0.4 | | | 0.3 | | 5.9 | 141.4 | | 141.6 | |
| 54 | 6.1 | | | 13.2 | | 137.9 | | | 2578.0 | |
| 55 | 7.0 | | | 19.1 | | 397.6 | | | 2626.0 | |
| 56 | 7.6 | | | 24.2 | | 290.8 | | | >10000 | |
| 57 | 13.9 | | | 26.1 | | 492.6 | | | | |

TABLE 4-continued

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 58 | 0.3 | 1.1 | 0.1 | 0.5 | 0.6 | 2.8 | 4.7 | 24.7 | 15.1 | >10000 |
| 59 | 0.6 | 1.4 | 0.1 | 0.7 | 1.1 | 2.6 | 1.7 | | 19.2 | >10000 |
| 60 | 0.5 | | 0.1 | | 0.4 | | 2.6 | | 8.8 | |

TABLE 5

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 61 | 0.5 | | 0.1 | | 0.5 | | 3.1 | | 4.2 | |
| 62 | 0.2 | | 0.1 | | 0.4 | | 4.9 | | 7.9 | |
| 63 | | 1.2 | | 2.4 | | 23.1 | | 83.4 | | >10000 |
| 64 | | 1.0 | | 2.0 | | 88.3 | | 305.6 | | >10000 |
| 65 | | 8.2 | | 39.2 | | 338.3 | | 603.8 | | >10000 |
| 66 | | 9.0 | | 31.1 | | 114.0 | | 350.5 | | >10000 |
| 67 | | 13.3 | | 27.7 | | 181.3 | | 208.6 | | >10000 |
| 68 | | 1.3 | | 8.9 | | 31.0 | | 129.9 | | >10000 |
| 69 | | 1.7 | | 13.2 | | 43.8 | | 179.4 | | >10000 |
| 70 | | 1.6 | | 10.4 | | 24.7 | | 172.5 | | >10000 |
| 71 | | 15.7 | | 52.6 | | 127.4 | | 751.3 | | >10000 |
| 72 | | 2.8 | | 16.9 | | 50.3 | | 169.9 | | >10000 |
| 73 | | 0.4 | | 1.2 | | 2.8 | | 6.6 | | 7552.0 |
| 74 | | 4.7 | | 13.6 | | 123.0 | | 181.0 | | >10000 |
| 75 | 1.8 | 1.6 | 0.8 | 1.8 | 3.8 | 5.7 | 2.6 | 103.6 | 45.6 | >10000 |
| 76 | 3.7 | 4.0 | 2.2 | 8.8 | 51.9 | 80.7 | 22.1 | 2775.0 | 667.0 | >10000 |
| 77 | 0.9 | 0.6 | 0.5 | 3.6 | 5.0 | 6.3 | 14.1 | 356.5 | 97.0 | >10000 |
| 78 | 1.6 | 1.3 | 0.7 | 5.9 | 10.4 | 12.4 | 22.1 | 562.6 | 163.4 | >10000 |
| 79 | 0.2 | 0.3 | 0.1 | 0.8 | 1.3 | 1.3 | 1.2 | 17.8 | 6.1 | 7190.0 |
| 80 | 0.5 | 0.6 | 0.5 | 1.9 | 12.3 | 16.1 | 16.4 | 137.3 | 80.1 | >10000 |
| 81 | 0.3 | 0.3 | 0.2 | 0.4 | 7.7 | 5.8 | 5.3 | 79.1 | 61.6 | >10000 |
| 82 | | 0.6 | | 1.8 | | 3.5 | | 22.8 | | >10000 |
| 83 | | 1.3 | | 2.5 | | 4.0 | | 24.4 | | >10000 |
| 84 | | 3.3 | | 6.7 | | 7.2 | | 33.0 | | >10000 |
| 85 | 1.8 | 1.8 | 1.0 | 3.5 | 3.5 | 7.0 | 3.1 | 50.8 | 114.1 | >10000 |
| 86 | | 1.4 | | 6.4 | | 23.9 | | 73.9 | | >10000 |
| 87 | | 2.3 | | 6.2 | | 26.3 | | 40.5 | | >10000 |
| 88 | | 1.6 | | 3.9 | | 15.6 | | 65.0 | | >10000 |
| 89 | | 4.3 | | 19.6 | | 63.8 | | 183.1 | | >10000 |
| 90 | | 3.6 | | 11.8 | | 28.5 | | 37.2 | | >10000 |

TABLE 6

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 91 | | 5.6 | | 13.9 | | 76.8 | | 165.7 | | >10000 |
| 92 | | 5.5 | | 11.3 | | 67.5 | | 80.7 | | >10000 |
| 93 | 1.9 | 2.2 | 2.5 | 18.2 | 43.0 | 64.8 | 18.3 | 371.8 | 260.2 | >10000 |
| 94 | 2.0 | 2.1 | 1.4 | 3.6 | 6.7 | 8.8 | 4.3 | 30.5 | 32.3 | >10000 |
| 95 | 1.5 | 1.6 | 0.9 | 2.0 | 2.7 | 2.3 | 1.4 | 4.1 | 5.0 | 1036.0 |
| 96 | 1.0 | 1.0 | 0.6 | 2.1 | 3.0 | 3.1 | 1.5 | 8.1 | 12.8 | >10000 |
| 97 | 1.8 | 1.8 | 1.7 | 5.9 | 18.3 | 25.1 | 9.2 | 162.1 | 86.5 | >10000 |
| 98 | 2.3 | 2.1 | 2.3 | 9.9 | 15.5 | 21.1 | 7.5 | 100.9 | 72.0 | >10000 |
| 99 | 0.7 | 0.7 | 0.8 | 3.0 | 10.4 | 14.0 | 4.2 | 58.1 | 41.7 | >10000 |
| 100 | 1.7 | 1.6 | 1.3 | 5.6 | 10.7 | 12.9 | 7.1 | 73.9 | 62.0 | >10000 |
| 101 | 3.5 | 3.2 | 2.4 | 4.8 | 4.3 | 7.9 | 3.0 | 103.7 | 32.0 | >10000 |

TABLE 6-continued

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 102 | 2.8 | 2.7 | 2.1 | 7.6 | 13.9 | 26.6 | 15.7 | 1030.0 | 185.9 | >10000 |
| 103 | 2.7 | 3.5 | 2.8 | 8.5 | 66.8 | 87.3 | 103.8 | 1226.0 | 1070.0 | >10000 |
| 104 | 3.1 | 4.1 | 1.1 | 3.0 | 9.7 | 12.4 | 32.3 | 119.3 | 89.4 | >10000 |
| 105 | 2.3 | 3.2 | 1.5 | 6.5 | 48.7 | 64.2 | 100.2 | 2200.0 | 2520.0 | >10000 |
| 106 | 1.0 | 1.1 | 0.6 | 1.6 | 12.5 | 15.1 | 6.1 | 274.3 | 95.5 | >10000 |
| 107 | 1.2 | 1.2 | 0.6 | 1.3 | 3.2 | 4.6 | 1.9 | 85.6 | 24.1 | >10000 |
| 108 | 1.1 | 1.2 | 1.6 | 7.8 | 25.5 | 29.8 | 8.4 | 154.4 | 126.4 | >10000 |
| 109 | 0.9 | 1.0 | 0.7 | 1.4 | 2.3 | 3.0 | 1.6 | 9.1 | 10.4 | >10000 |
| 110 | 1.1 | 1.2 | 0.6 | 1.3 | 1.8 | 1.7 | 0.8 | 2.7 | 2.8 | 295.7 |
| 111 | 0.8 | 0.9 | 0.5 | 1.3 | 2.0 | 2.0 | 1.2 | 4.7 | 6.0 | 4382.0 |
| 112 | 1.5 | 1.5 | 1.1 | 2.8 | 4.6 | 5.2 | 2.8 | 17.1 | 21.3 | >10000 |
| 113 | 1.3 | 1.3 | 0.8 | 2.9 | 3.2 | 4.0 | 2.6 | 11.3 | 12.0 | 7554.0 |
| 114 | 0.5 | 0.5 | 0.6 | 1.7 | 5.4 | 9.5 | 2.6 | 13.7 | 17.4 | >10000 |
| 115 | 0.9 | 1.2 | 0.9 | 2.3 | 5.4 | 8.1 | 2.9 | 15.6 | 19.6 | >10000 |
| 116 | 0.3 | 0.4 | 0.2 | 0.3 | 0.3 | 0.6 | 0.2 | 1.0 | 1.0 | 143.2 |
| 117 | 0.3 | 0.4 | 0.2 | 0.3 | 0.4 | 0.7 | 0.3 | 3.4 | 3.7 | 1018.0 |
| 118 | 0.5 | 0.6 | 0.2 | 0.5 | 0.7 | 0.8 | 0.6 | 8.5 | 10.2 | 2687.0 |
| 119 | 0.4 | 0.5 | 0.2 | 0.4 | 0.4 | 0.8 | 0.4 | 3.5 | 4.2 | 859.5 |
| 120 | 0.7 | 0.7 | 0.3 | 0.5 | 0.5 | 0.8 | 0.3 | 1.3 | 1.6 | 211.7 |

TABLE 7

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 121 | 0.3 | 0.3 | 0.1 | 0.3 | 0.3 | 0.5 | 0.3 | 4.1 | 3.1 | 782.8 |
| 122 | 0.4 | 0.5 | 0.2 | 0.5 | 0.6 | 0.8 | 0.5 | 11.8 | 7.8 | 2776.0 |
| 123 | 0.4 | 0.4 | 0.1 | 0.4 | 0.3 | 0.6 | 0.3 | 4.3 | 3.6 | 1085.0 |
| 124 |  | 3.0 |  | 2.6 |  | 26.3 |  | 153.7 |  | >10000 |
| 125 |  | 5.6 |  | 5.6 |  | 34.2 |  | 329.7 |  | >10000 |
| 126 | 0.6 | 1.7 | 0.3 | 0.9 | 1.4 | 1.6 | 1.8 | 11.5 | 35.0 | >10000 |
| 127 |  | 2.8 |  | 1.8 |  | 6.9 |  | 45.7 |  | >10000 |
| 128 |  | 7.1 |  | 4.8 |  | 29.5 |  | 73.0 |  | >10000 |
| 129 |  | 0.5 |  | 0.8 |  | 4.4 |  | 23.8 |  | >10000 |
| 130 |  | 1.4 |  | 5.1 |  | 107.1 |  | 68.7 |  | >10000 |
| 131 |  | 0.7 |  | 2.6 |  | 50.8 |  | 35.6 |  | >10000 |
| 132 |  | 1.3 |  | 4.2 |  | 131.1 |  | 46.4 |  | >10000 |
| 133 |  | 0.3 |  | 0.4 |  | 2.4 |  | 3.5 |  | 3839.0 |
| 134 | 0.4 | 0.4 | 0.1 | 0.9 | 1.5 | 2.3 | 5.6 | 121.0 | 40.5 | >10000 |
| 135 | 0.7 | 2.6 | 0.6 | 5.2 | 1.6 | 3.0 | 4.1 | 40.6 | 28.7 | >10000 |
| 136 | 0.3 | 0.3 | 0.3 | 1.2 | 3.3 | 4.9 | 2.7 | 30.5 | 60.2 | >10000 |
| 137 | 0.4 | 0.4 | 0.4 | 2.0 | 8.8 | 11.7 | 5.0 | 74.2 | 173.9 | >10000 |
| 138 | 0.3 | 0.3 | 0.1 | 0.4 | 1.0 | 1.3 | 0.9 | 8.7 | 7.8 | 2943.0 |
| 139 | 0.4 | 0.4 | 0.1 | 0.4 | 0.9 | 1.4 | 0.9 | 8.2 | 5.4 | 1579.0 |
| 140 | 1.3 | 1.8 | 1.3 | 6.4 | 114.5 | 175.5 | 23.2 | 887.4 | 621.6 | >10000 |
| 141 | 0.7 | 0.9 | 0.7 | 3.4 | 48.7 | 49.1 | 13.7 | 1900.0 | 256.4 | >10000 |
| 142 | 0.4 | 0.4 | 0.2 | 0.9 | 5.9 | 8.4 | 3.9 | 175.9 | 31.3 | >10000 |
| 143 | 0.5 | 0.5 | 0.3 | 0.9 | 1.2 | 1.9 | 1.8 | 83.5 | 14.3 | >10000 |
| 144 | 0.3 | 0.3 | 0.1 | 0.4 | 0.8 | 0.9 | 0.8 | 34.3 | 23.8 | >10000 |
| 145 | 0.2 | 0.2 | 0.1 | 0.3 | 0.6 | 0.7 | 0.5 | 23.4 | 14.2 | 5555.0 |
| 146 | 0.1 | 0.2 | 0.04 | 0.1 | 0.2 | 0.5 | 0.3 | 1.5 | 0.8 | 348.4 |
| 147 | 0.2 | 0.4 | 0.1 | 0.2 | 0.2 | 0.4 | 0.2 | 0.7 | 0.4 | 43.3 |
| 148 | 0.2 | 0.3 | 0.1 | 0.2 | 0.2 | 0.3 | 0.2 | 0.6 | 0.4 | 47.0 |
| 149 | 0.2 | 0.4 | 0.1 | 0.2 | 0.2 | 0.4 | 0.3 | 3.4 | 1.6 | 853.5 |
| 150 | 0.5 | 0.5 | 0.2 | 0.5 | 0.8 | 0.7 | 2.2 | 8.9 | 4.9 | 3758.0 |

TABLE 8

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 151 | 2.4 | 2.6 | 1.1 | 3.0 | 4.2 | 3.5 | 8.6 | 57.8 | 29.4 | >10000 |
| 152 | 0.2 | 0.3 | 0.1 | 0.2 | 0.1 | 0.4 | 0.2 | 0.8 | 0.6 | 195.6 |
| 153 | 0.1 | 0.1 | 0.04 | 0.1 | 0.3 | 0.3 | 1.8 | 5.1 | 1.9 | 821.6 |
| 154 | 0.4 | 1.4 | 0.3 | 4.3 | 6.0 | 12.0 | 6.4 | 145.4 | 44.4 | 6717.0 |
| 155 | 0.6 | 0.6 | 0.5 | 1.9 | 20.8 | 34.3 | 19.4 | 309.0 | 90.6 | >10000 |
| 156 | 0.1 | 0.1 | 0.04 | 0.1 | 0.3 | 0.4 | 1.2 | 9.0 | 2.6 | 2096.0 |
| 157 | 3.3 | 3.6 | 1.7 | 4.6 | 3.7 | 10.6 | 3.3 | 40.8 | 126.8 | >10000 |
| 158 | 6.2 | 6.8 | 2.5 | 8.4 | 18.3 | 131.1 | 15.3 | 809.1 | 522.8 | >10000 |
| 159 | 8.3 | 10.6 | 3.4 | 9.6 | 7.7 | 21.7 | 7.4 | 98.5 | 85.5 | >10000 |
| 160 | 5.7 | 7.3 | 2.5 | 6.2 | 4.1 | 10.1 | 3.8 | 65.6 | 64.8 | >10000 |
| 161 | 5.5 | 8.8 | 3.2 | 10.6 | 25.5 | 38.2 | 21.6 | 547.2 | 650.2 | >10000 |
| 162 | 27.6 | 22.9 | 12.2 | 26.3 | 44.8 | 58.4 | 39.9 | 618.9 | 540.0 | >10000 |
| 163 | 1.3 | 1.5 | 3.4 | 20.0 | 141.5 | 327.8 | 37.3 | >1000 | 271.7 | >10000 |
| 164 | 0.7 | 0.6 | 0.2 | 0.5 | 0.9 | 1.6 | 0.6 | 2.2 | 1.5 | 236.2 |
| 165 | 0.5 | 0.6 | 0.5 | 1.7 | 8.5 | 7.4 | 7.1 | 140.3 | 74.7 | >10000 |
| 166 | 1.4 | 1.9 | 0.9 | 3.8 | 66.5 | 51.1 | 21.9 | 193.5 | 410.6 | >10000 |
| 167 | 3.7 | 3.4 | 3.5 | 15.4 | 81.8 | 88.8 | 24.0 | 531.7 | 278.6 | >10000 |
| 168 | 11.0 | 11.8 | 9.1 | 71.2 | 67.9 | 391.3 | 783.5 | 8374.0 | 6251.0 | >10000 |
| 169 | 7.1 | 3.1 | 2.6 | 6.8 | 4.7 | 10.5 | 30.6 | 391.2 | 237.6 | >10000 |
| 170 | 0.9 | 1.0 | 0.6 | 5.7 | 4.4 | 19.9 | 23.8 | 316.2 | 285.7 | >10000 |
| 171 | 0.3 | 1.2 | 0.2 | 2.5 | 7.5 | 20.4 | 13.6 | 175.0 | 49.6 | >10000 |
| 172 | 4.6 | 6.9 | 4.8 | 14.5 | 14.1 | 32.4 | 11.5 | 124.2 | 68.4 | >10000 |
| 173 | 2.9 | 9.9 | 1.3 | 10.5 | 6.2 | 8.5 | 7.8 | 100.3 | 22.9 | >10000 |
| 174 | 0.5 | 0.9 | 1.2 | 2.1 | 11.0 | 10.8 | 30.5 | 283.5 | 149.6 | >10000 |
| 175 | 1.2 | 1.4 | 3.6 | 3.6 | 13.3 | 17.2 | 33.5 | 332.9 | 131.2 | >10000 |
| 176 | 0.5 | 0.4 | 0.3 | 0.8 | 3.0 | 3.6 | 14.2 | 103.9 | 40.1 | >10000 |
| 177 | 0.6 | 0.5 | 0.4 | 0.7 | 2.0 | 2.5 | 7.5 | 66.5 | 17.7 | 4873.0 |
| 178 | 0.3 | 0.3 | 0.2 | 0.3 | 1.1 | 2.3 | 3.0 | 27.0 | 9.5 | 8010.0 |
| 179 | 0.4 | 0.5 | 0.2 | 0.3 | 0.8 | 1.9 | 1.5 | 13.4 | 6.2 | 3877.0 |
| 180 | 0.2 | 0.1 | 0.1 | 0.1 | 0.5 | 0.3 | 0.4 | 2.7 | 2.8 | 1098.0 |

TABLE 9

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 181 | 0.1 | 0.1 | 0.05 | 0.1 | 0.7 | 0.6 | 0.6 | 6.0 | 6.1 | 2921.0 |
| 182 | 0.1 | 0.1 | 0.04 | 0.1 | 0.4 | 0.3 | 0.4 | 1.7 | 1.8 | 648.4 |
| 183 | 2.0 | 1.9 | 0.9 | 4.1 | 11.7 | 43.9 | 26.9 | 400.0 | 146.4 | >10000 |
| 184 | 0.4 | 1.5 | 0.2 | 2.1 | 2.3 | 3.5 | 3.2 | 94.1 | 11.7 | >10000 |
| 185 | 0.4 | 1.2 | 0.2 | 1.1 | 0.5 | 0.8 | 0.9 | 6.8 | 1.7 | >10000 |
| 186 | 0.7 | 0.6 | 0.7 | 1.0 | 2.1 | 1.6 | 3.4 | 70.5 | 16.1 | >10000 |
| 187 | 0.9 | 0.5 | 1.2 | 0.8 | 1.6 | 0.9 | 2.0 | 8.2 | 3.9 | 932.1 |
| 188 | 2.2 | 2.0 | 4.5 | 4.2 | 14.4 | 10.9 | 45.9 | 591.9 | 126.3 | >10000 |
| 189 | 0.7 | 0.7 | 0.6 | 0.9 | 2.1 | 1.8 | 2.8 | 40.4 | 8.4 | >10000 |
| 190 | 1.8 | 5.1 | 1.0 | 6.7 | 3.3 | 4.6 | 8.9 | 71.5 | 19.7 | >10000 |
| 191 | 3.0 | 7.0 | 1.5 | 9.8 | 2.2 | 4.3 | 3.2 | 21.7 | 8.1 | 3584.0 |
| 192 | 1.0 | 1.5 | 0.4 | 1.3 | 1.1 | 1.8 | 2.1 | 4.5 | 6.1 | 1478.0 |
| 193 | 0.5 | 0.6 | 0.2 | 0.5 | 0.4 | 0.7 | 0.9 | 6.6 | 2.2 | 1266.0 |
| 194 | 0.5 | 0.5 | 0.2 | 0.7 | 2.2 | 3.3 | 3.4 | 169.4 | 26.1 | >10000 |
| 195 | 0.3 | 0.4 | 0.1 | 0.4 | 2.4 | 2.7 | 2.3 | 14.8 | 19.6 | 8537.0 |
| 196 | 0.7 | 0.6 | 0.3 | 1.1 | 6.0 | 9.8 | 6.8 | 50.6 | 68.0 | >10000 |
| 197 | 0.3 | 0.3 | 0.1 | 0.3 | 0.6 | 0.8 | 0.8 | 8.9 | 5.6 | 1559.0 |
| 198 | 0.4 | 0.5 | 0.2 | 0.6 | 2.1 | 3.6 | 2.5 | 50.8 | 25.1 | 5984.0 |
| 199 | 5.7 | | 3.4 | | 82.0 | | 414.1 | | | |
| 200 | 12.6 | 11.3 | | | 29.8 | 349.7 | 1003.0 | | 4104.0 | >10000 |
| 201 | 1.7 | | 1.2 | | 36.7 | | 140.7 | | 292.1 | |
| 202 | 2.2 | | 1.6 | | 43.4 | | 92.7 | | 311.9 | |
| 203 | 2.2 | | 1.4 | | 68.1 | | 110.3 | | 437.2 | |
| 204 | 22.7 | | | | 186.7 | | | | 263.7 | >10000 |
| 205 | 18.3 | | | | 265.0 | | | | 587.0 | |
| 206 | 3.5 | | | | 69.1 | | | | 201.4 | |
| 207 | 2.1 | 2.9 | | | 29.1 | 76.4 | | 119.9 | 56.0 | >10000 |
| 208 | 5.1 | 3.5 | | 8.1 | 56.0 | 120.3 | | | 106.8 | >10000 |

TABLE 9-continued

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 209 |  | 2.6 |  | 4.4 |  | 119.5 |  | 112.4 |  | >10000 |
| 210 |  | 3.4 |  |  |  | 143.2 |  | 157.2 |  | >10000 |

TABLE 10

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 211 |  | 1.4 |  | 6.9 |  | 32.3 |  | 66.2 |  | >10000 |
| 212 |  | 1.5 |  | 8.9 |  | 44.8 |  | 97.6 |  | >10000 |
| 213 |  | 0.7 |  | 1.4 |  | 8.8 |  | 37.5 |  | >10000 |
| 214 |  | 1.4 |  | 4.0 |  | 108.9 |  | 274.3 |  | >10000 |
| 215 |  | 2.9 |  | 11.4 |  | 46.9 |  | 213.1 |  | >10000 |
| 216 |  | 0.7 |  | 0.8 |  | 4.9 |  | 28.0 |  | >10000 |
| 217 |  | 2.6 |  | 14.5 |  | 28.3 |  | 237.9 |  | >10000 |
| 218 | 1.3 | 1.2 | 0.6 | 2.1 | 2.1 | 3.4 | 1.7 | 8.0 | 18.9 | >10000 |
| 219 | 0.8 | 0.9 | 0.3 | 1.4 | 1.2 | 2.2 | 1.3 | 4.4 | 12.5 | 8119.0 |
| 220 | 2.1 | 2.2 | 0.8 | 4.4 | 5.6 | 12.0 | 3.9 | 32.9 | 126.8 | >10000 |
| 221 | 2.9 | 2.0 | 0.8 | 2.2 | 6.3 | 8.4 | 3.8 | 33.0 | 65.0 | >10000 |
| 222 |  | 5.2 |  | 12.2 |  | 196.6 |  |  |  | >10000 |
| 223 |  | 0.5 |  | 0.8 |  | 6.7 |  | 44.7 |  | >10000 |
| 224 |  | 1.8 |  | 26.1 |  | 37.7 |  | 285.7 |  | >10000 |
| 225 |  | 6.4 |  | 12.3 |  | 87.8 |  | 309.5 |  | >10000 |
| 226 |  | 1.1 |  | 1.1 |  | 5.1 |  | 43.4 |  | >10000 |
| 227 |  | 4.6 |  | 18.3 |  | 94.7 |  | 293.8 |  | >10000 |
| 228 |  | 6.2 |  | 21.8 |  | 273.9 |  | 494.3 |  | >10000 |
| 229 |  | 8.9 |  | 26.9 |  | 174.8 |  | 368.0 |  | >10000 |
| 230 |  | 5.9 |  | 18.2 |  | 1721.0 |  | 813.3 |  | >10000 |
| 231 | 1.7 | 1.6 | 0.9 | 1.5 | 1.3 | 3.0 | 1.1 | 4.6 | 6.1 | 967.8 |
| 232 | 0.8 | 1.3 | 0.5 | 1.3 | 0.4 | 1.1 | 0.2 | 5.9 | 0.9 | 718.5 |
| 233 | 4.5 |  | 15.5 |  | 299.3 |  |  |  | 1343.0 |  |
| 234 | 4.1 |  | 16.1 |  | 213.6 |  |  |  | 1006.0 |  |
| 235 | 4.7 |  | 13.2 |  | 310.8 |  |  |  | 2225.0 |  |
| 236 | 11.3 |  | 45.3 |  | 359.0 |  |  |  |  |  |
| 237 | 5.5 |  | 16.5 |  | 232.5 |  |  |  | 2715.0 |  |
| 238 | 0.3 | 1.2 | 0.7 | 0.8 | 9.4 | 8.1 | 5.4 |  | 17.2 | >10000 |
| 239 | 0.5 |  | 5.4 |  | 44.2 |  | 7.5 |  | 79.6 |  |
| 240 | 0.7 |  | 2.0 |  | 168.3 |  | 19.0 |  | 193.7 |  |

TABLE 11

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 241 | 2.1 | 2.5 | 0.8 | 3.9 | 1.2 | 1.7 | 2.3 | 17.5 | 9.1 | 4183.0 |
| 242 | 0.8 | 1.0 | 0.4 | 1.6 | 0.7 | 0.6 | 1.0 | 13.8 | 4.6 | 2607.0 |
| 243 | 0.9 | 1.4 | 0.4 | 1.8 | 0.8 | 0.7 | 0.9 | 14.7 | 4.7 | 2166.0 |
| 244 | 0.8 | 1.3 | 0.5 | 1.5 | 0.6 | 0.5 | 1.0 | 3.1 | 6.0 | 417.8 |
| 245 | 0.8 | 1.4 | 0.5 | 1.3 | 0.6 | 0.5 | 1.1 | 2.8 | 6.7 | 473.7 |
| 246 | 7.4 | 6.4 | 3.8 | 15.4 | 34.0 | 54.6 | 105.5 | 957.3 | 257.9 | >10000 |
| 247 | 0.1 | 0.1 | 0.1 | 0.5 | 1.3 | 1.7 | 8.1 | 42.3 | 18.7 | 8668.0 |
| 248 | 8.3 | 13.8 | 3.9 | 11.4 | 9.9 | 8.6 | 16.6 | 39.4 | 30.1 | 6598.0 |
| 249 | 3.1 | 2.6 | 1.1 | 1.9 | 6.9 | 7.5 | 4.7 | 29.7 | 23.9 | >10000 |
| 250 | 0.7 | 0.7 | 0.4 | 0.9 | 2.0 | 2.8 | 6.6 | 74.7 | 15.0 | >10000 |
| 251 | 3.0 | 3.3 | 1.4 | 5.3 | 8.7 | 15.9 | 41.5 | 397.1 | 72.6 | >10000 |
| 252 | 8.5 | 7.9 | 4.3 | 15.9 | 35.9 | 39.9 | 100.4 | 2078.0 | 234.6 | >10000 |

TABLE 11-continued

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 253 | 5.3 | 3.3 | 3.1 | 4.4 | 4.2 | 7.1 | 9.8 | 81.2 | 23.9 | >10000 |
| 254 | 0.1 | 0.2 | 0.1 | 0.2 | 0.3 | 0.4 | 2.1 | 1.3 | 0.9 | 247.8 |
| 255 | 1.3 | 0.2 | 0.1 | 0.3 | 0.3 | 0.4 | 1.4 | 1.2 | 1.0 | 375.8 |
| 256 | | 20.6 | | 17.7 | | 7.6 | | 67.3 | | >10000 |
| 257 | | 19.4 | | 23.1 | | 10.7 | | 143.3 | | >10000 |
| 258 | 0.3 | 0.5 | 0.1 | 0.5 | 0.7 | 0.5 | 1.8 | 7.7 | 5.0 | 5307.0 |
| 259 | 0.6 | 0.5 | 0.3 | 0.5 | 0.5 | 1.2 | 1.2 | 36.0 | 5.3 | 3403.0 |
| 260 | 0.5 | 0.4 | 0.2 | 0.3 | 0.3 | 0.5 | 1.0 | 10.8 | 2.1 | 832.3 |
| 261 | 1.2 | 0.6 | 0.5 | 0.6 | 1.3 | 1.0 | 1.3 | 4.2 | 6.2 | 2498.0 |
| 262 | 1.2 | 1.4 | 0.4 | 1.3 | 0.8 | 1.1 | 0.9 | 5.7 | 4.4 | >10000 |
| 263 | 1.1 | 1.5 | 0.4 | 1.2 | 0.8 | 1.3 | 0.7 | 3.2 | 3.0 | >10000 |
| 264 | 0.7 | 0.9 | 0.3 | 0.8 | 1.0 | 1.8 | 1.3 | 14.1 | 9.9 | >10000 |
| 265 | 0.8 | 0.9 | 0.3 | 0.8 | 0.8 | 1.1 | 0.9 | 9.1 | 7.6 | 6519.0 |
| 266 | 1.0 | 0.8 | 0.4 | 0.4 | 1.1 | 2.1 | 0.9 | 5.4 | 7.2 | 1225.0 |
| 267 | 1.6 | 1.9 | 0.8 | 3.1 | 24.2 | 12.4 | 4.1 | 129.8 | 252.4 | >10000 |
| 268 | 2.4 | 6.2 | 1.0 | 2.9 | 26.6 | 59.6 | 41.8 | 116.4 | 105.4 | >10000 |
| 269 | | 128.9 | | 159.8 | | 1951.0 | | 1348.0 | >10000 | >10000 |
| 270 | 0.7 | 1.2 | 1.6 | 4.8 | 27.9 | 28.0 | 72.8 | 2804.0 | 111.1 | >10000 |

TABLE 12

| | Del19/T790M/C797S (nM) | | L858R/T790M/C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 271 | 1.8 | 3.0 | 6.7 | 9.2 | 68.5 | 110.9 | 439.2 | >10000 | 411.5 | >10000 |
| 272 | 4.0 | 7.1 | 2.2 | 3.1 | 51.2 | 81.9 | 18.9 | 2121.0 | 108.2 | >10000 |
| 273 | 5.6 | 2.9 | 0.3 | 1.5 | 35.8 | 97.4 | 16.6 | 198.3 | 46.1 | >10000 |
| 274 | 0.1 | 0.2 | 0.1 | 0.2 | 0.4 | 0.6 | 1.0 | 10.8 | 4.4 | 1886.0 |
| 275 | 1.0 | 1.7 | 0.8 | 3.6 | 4.5 | 10.4 | 12.3 | 117.7 | 62.3 | >10000 |
| 276 | 0.3 | 0.7 | 0.1 | 0.5 | 0.8 | 1.3 | 1.5 | 16.5 | 7.5 | 5287.0 |
| 277 | 0.6 | 0.8 | 0.3 | 1.8 | 1.4 | 3.3 | 2.5 | 33.7 | 11.4 | >10000 |
| 278 | 0.3 | 0.6 | 0.1 | 0.3 | 0.2 | 0.6 | 0.5 | 0.5 | 0.7 | 107.9 |
| 279 | 0.6 | 0.7 | 0.1 | 0.5 | 0.2 | 0.6 | 0.6 | 0.6 | 0.6 | 111.1 |
| 280 | 0.5 | 0.3 | 0.4 | 0.6 | 0.3 | 0.5 | 0.6 | 6.3 | 3.5 | >10000 |
| 281 | 10.2 | 82.1 | | 22.0 | 17.0 | 88.5 | 6.3 | 287.2 | 192.1 | >10000 |
| 282 | 5.5 | 23.8 | | 7.1 | 8.3 | 28.6 | 4.2 | 39.2 | 50.7 | >10000 |
| 283 | 2.0 | 9.5 | | 3.0 | 3.1 | 7.9 | 1.9 | 11.2 | 16.2 | >10000 |
| 284 | 1.1 | 4.4 | | 1.7 | 2.8 | 6.8 | 1.7 | 15.9 | 12.6 | 7268.0 |
| 285 | 0.8 | 1.0 | 0.4 | 0.6 | 0.4 | 1.1 | 0.1 | 1.3 | 2.5 | 1253.0 |
| 286 | | 0.1 | | 0.4 | | 2.2 | | 13.5 | | 4295.0 |
| 287 | | 0.1 | | 0.3 | | 1.6 | | 8.9 | | 3194.0 |
| 288 | | 0.2 | | 0.2 | | 3.6 | | 21.6 | | 7822.0 |
| 289 | | 0.2 | | 0.9 | | 3.0 | | 23.1 | | 8442.0 |
| 290 | | 5.7 | | 8.6 | | 26.2 | | >10000 | | >10000 |
| 291 | 4.5 | 7.4 | 3.6 | 14.9 | 8.9 | 22.5 | 36.7 | 382.7 | 615.3 | >10000 |
| 292 | 4.9 | 2.2 | 2.4 | 4.2 | 12.2 | 10.4 | 38.7 | 145.8 | 101.4 | >10000 |
| 293 | 0.1 | 0.4 | 0.03 | 1.3 | 2.3 | 6.5 | 4.2 | 34.1 | 8.6 | >10000 |
| 294 | 0.1 | 0.1 | 0.1 | 0.1 | 0.2 | 0.2 | 0.3 | 1.6 | 0.6 | 351.5 |
| 295 | | 0.8 | | 2.4 | | 9.9 | | 68.2 | | >10000 |
| 296 | 0.1 | 0.1 | 0.1 | 0.3 | 0.6 | 0.6 | 1.4 | 9.0 | 4.4 | 3254.0 |
| 297 | 0.1 | 0.1 | 0.1 | 0.2 | 1.2 | 3.2 | 1.0 | 38.1 | 4.1 | 4182.0 |
| 298 | 0.3 | 0.4 | 0.4 | 1.5 | 5.3 | 12.0 | 18.5 | 140.2 | 23.0 | >10000 |
| 299 | 0.2 | 0.2 | 0.1 | 0.2 | 1.1 | 1.0 | 1.4 | 17.2 | 4.7 | 7513.0 |
| 300 | 0.9 | 0.9 | 1.1 | 1.5 | 3.3 | 10.3 | 13.5 | 288.1 | 26.8 | >10000 |

TABLE 13

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 301 | 0.6 | 0.7 | 0.6 | 1.4 | 7.2 | 4.9 | 11.2 | 137.8 | 22.9 | >10000 |
| 302 | 0.1 | 0.3 | 0.1 | 0.3 | 0.8 | 0.7 | 1.5 | 11.5 | 5.0 | 2688.0 |
| 303 | 0.1 | 0.3 | 0.1 | 0.2 | 0.4 | 0.3 | 0.6 | 3.4 | 1.4 | 205.7 |
| 304 |  | 2.7 |  | 5.3 |  | 64.0 |  | 103.1 |  | >10000 |
| 305 | 1.3 | 1.0 | 0.5 | 0.9 | 0.6 | 2.4 | 0.8 | 5.4 |  | 1516.0 |
| 306 | 1.0 | 1.6 | 0.4 | 3.9 | 3.4 | 4.6 | 4.3 | 6.8 | 14.6 | >10000 |
| 307 | 14.7 | 29.6 | 0.3 | 35.1 | 17.2 | 37.3 | 21.3 | 44.2 | 87.7 | >10000 |
| 308 | 4.8 | 3.5 | 3.2 | 2.3 | 1.6 | 2.8 | 3.7 | 75.0 | 39.4 | >10000 |
| 309 |  | 1.0 |  | 1.1 | 2.4 | 3.1 | 1.0 | 43.8 | 24.3 | 7632.0 |
| 310 |  | 0.8 |  | 1.3 | 2.9 | 4.2 | 1.9 | 56.3 | 44.0 | 8836.0 |
| 311 |  | 0.5 |  | 0.7 | 1.6 | 1.8 | 0.7 | 26.0 | 17.5 | 8554.0 |
| 312 | 0.3 | 0.3 | 0.1 | 0.4 | 1.1 | 2.4 | 1.1 | 12.2 | 9.6 | 6180.0 |
| 313 | 0.3 | 0.4 | 0.1 | 0.3 | 1.2 | 2.0 | 0.9 | 9.0 | 10.7 | 4691.0 |
| 314 | 0.7 | 0.9 | 0.2 | 0.2 | 5.4 | 9.9 | 3.4 | 78.4 | 52.6 | >10000 |
| 315 |  | 3.7 |  | 6.8 |  | 52.2 |  | 78.6 |  | >10000 |
| 316 |  | 4.7 |  | 5.8 |  | 56.7 |  | 72.8 |  | >10000 |
| 317 |  | 16.2 |  | 35.1 |  | 244.9 |  | 333.9 |  | >10000 |
| 318 |  | 0.3 |  | 0.4 |  | 4.2 |  | 18.4 |  | 5993.0 |
| 319 |  | 0.3 |  | 0.3 |  | 3.2 |  | 17.1 |  | 4536.0 |
| 320 |  | 1.0 |  | 0.8 |  | 10.5 |  | 44.0 |  | 5672.0 |
| 321 |  | 0.7 |  | 1.2 |  | 8.0 |  | 45.2 |  | 5846.0 |
| 322 |  | 0.5 |  | 0.4 |  | 6.0 |  | 18.0 |  | 4537.0 |
| 323 | 0.3 | 0.6 | 0.2 | 0.8 | 4.5 | 7.4 | 14.3 | 184.5 | 145.5 | >10000 |
| 324 | 0.3 | 0.3 | 0.2 | 0.5 | 1.3 | 2.0 | 3.7 | 20.9 | 16.5 | >10000 |
| 325 | 0.9 | 1.1 | 0.8 | 2.1 | 6.2 | 6.9 | 16.3 | 89.8 | 114.6 | >10000 |
| 326 | 1.9 | 1.9 | 0.6 | 2.1 | 10.3 | 19.2 | 5.3 | 145.1 | 17.6 | >10000 |
| 327 | 2.2 | 2.5 | 0.8 | 1.5 | 1.6 | 4.8 | 2.1 | 39.3 | 11.9 | >10000 |
| 328 | 5.3 | 3.1 | 1.0 | 22.7 | 36.6 | 648.0 | 25.8 | 47.4 | 161.7 | >10000 |
| 329 | 21.2 | 5.9 | 1.7 | 3.0 | 81.8 | 1085.0 | 47.6 | 124.8 | 700.5 | >10000 |
| 330 | 1.9 | 5.2 | 2.2 | 6.2 | 55.5 | 770.7 | 17.6 | 45.5 | 272.0 | >10000 |

TABLE 14

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 331 | 6.1 | 10.3 | 5.0 | 13.9 | 87.5 | 244.6 | 173.2 | 9132.0 | 309.4 | >10000 |
| 332 | 18.9 | 23.9 | 7.8 | 21.6 | 800.0 | 1731.0 | 844.5 | >10000 | 800.9 | >10000 |
| 333 | 6.8 | 17.8 | 3.5 | 13.0 | 133.0 | 255.3 | 245.4 | >10000 | 240.4 | >10000 |
| 334 | 5.6 | 8.0 | 3.3 | 14.8 | 238.7 | 1836.0 | 136.0 | 7534.0 | 275.9 | >10000 |
| 335 | 0.4 | 0.4 | 0.2 | 0.4 | 2.1 | 2.3 | 4.3 | 53.4 | 9.2 | 4971.0 |
| 336 | 2.0 | 3.9 | 1.3 | 2.4 | 26.1 | 38.2 | 50.1 | 1750.0 | 295.4 | >10000 |
| 337 | 6.0 | 8.0 | 3.3 | 10.9 | 197.1 | 325.3 |  | >10000 |  | >10000 |
| 338 | 0.3 | 0.4 | 0.2 | 0.5 | 10.8 | 17.1 | 42.8 | 9583.0 | 148.6 | >10000 |
| 339 | 1.0 | 0.9 | 0.5 | 1.0 | 3.8 | 7.5 | 4.9 | 29.7 | 18.2 | >10000 |
| 340 | 1.6 | 2.0 | 0.7 | 1.6 | 5.0 | 7.3 | 10.5 | 40.8 | 26.0 | >10000 |
| 341 | 2.5 | 3.1 | 0.9 | 4.0 | 21.4 | 34.2 | 42.4 | 128.2 | 163.3 | >10000 |
| 342 | 0.8 | 0.9 | 0.2 | 0.8 | 2.3 | 3.6 | 4.5 | 11.8 | 11.0 | >10000 |
| 343 | 2.6 | 1.9 | 0.7 | 3.1 | 11.9 | 19.2 | 19.8 | 68.1 | 55.5 | >10000 |
| 344 | 7.9 | 11.5 | 3.1 | 5.0 | 31.3 | 50.6 | 24.1 | 112.2 | 200.4 | >10000 |
| 345 | 1.5 | 2.7 | 1.3 | 2.2 | 11.0 | 27.6 | 9.3 | 45.3 | 138.4 | 7834.0 |
| 346 |  | 17.4 |  | 5.8 |  | 45.3 |  | 249.1 |  | >10000 |
| 347 | 5.4 | 6.0 | 3.2 | 1.7 | 9.2 | 8.4 | 5.9 | 11.7 | 74.3 | 7138.0 |
| 348 | 4.2 | 2.1 | 1.4 | 0.8 | 4.7 | 4.9 | 1.1 | 14.3 | 14.1 | 650.8 |
| 349 | 1.5 | 1.5 | 0.5 | 1.0 | 2.6 | 4.8 | 1.4 | 9.4 | 9.1 | 844.4 |
| 350 |  | 2.8 |  | 13.9 |  | 81.4 |  | 953.9 |  | >10000 |
| 351 | 1.6 | 1.2 | 0.8 | 1.6 | 4.9 | 3.7 | 12.8 | 77.8 | 44.2 | 7622.0 |
| 352 | 0.3 | 0.3 | 0.1 | 0.2 | 0.6 | 0.5 | 1.6 | 9.5 | 5.5 | 820.0 |
| 353 | 0.2 | 0.2 | 0.1 | 0.2 | 1.0 | 0.6 | 3.3 | 16.6 | 11.3 | >10000 |
| 354 | 0.2 | 0.2 | 0.1 | 0.2 | 0.3 | 0.5 | 0.8 | 8.6 | 5.1 | 1633.0 |
| 355 | 0.2 | 0.2 | 0.1 | 0.2 | 0.2 | 0.4 | 0.5 | 7.4 | 4.8 | 1739.0 |
| 356 | 0.2 | 0.2 | 0.1 | 0.3 | 0.6 | 0.9 | 2.0 | 24.5 | 20.1 | 5311.0 |
| 357 | 0.2 | 0.3 | 0.1 | 0.4 | 1.4 | 1.5 | 1.5 | 14.0 | 9.2 | 4709.0 |
| 358 | 1.2 | 1.7 | 0.7 | 1.6 | 1.9 | 3.7 | 3.8 | 30.2 | 22.9 | 6284.0 |

TABLE 14-continued

| | Del19/T790M/ C797S (nM) | | L858R/T790M/ C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 359 | 0.9 | 1.6 | 0.4 | 1.5 | 2.2 | 2.6 | 3.6 | 55.1 | 26.7 | >10000 |
| 360 | 0.8 | 1.1 | 0.3 | 0.9 | 2.3 | 2.7 | 2.5 | 7.7 | 3.8 | 1134.0 |

TABLE 15

| | Del19/T790M/ C797S (nM) | | L858R/T790M/ C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 361 | | 0.7 | | 1.5 | | 4.3 | | 468.3 | | >10000 |
| 362 | 0.5 | 0.7 | 0.1 | 0.6 | 1.1 | 1.7 | 0.9 | 3.2 | 10.7 | 4897.0 |
| 363 | | 1.2 | | 2.4 | | 8.2 | | 94.9 | | >10000 |
| 364 | 0.2 | 0.3 | 0.1 | 0.6 | 1.4 | 1.3 | 2.1 | 12.9 | 7.5 | 2530.0 |
| 365 | 0.4 | 0.7 | 0.1 | 1.3 | 3.3 | 3.5 | 3.9 | 46.6 | 10.5 | >10000 |
| 366 | 0.3 | 0.5 | 0.1 | 1.1 | 2.5 | 4.4 | 2.9 | 16.7 | 7.2 | >10000 |
| 367 | 0.3 | 0.4 | 0.1 | 1.2 | 1.6 | 3.5 | 3.9 | 25.6 | 7.6 | >10000 |
| 368 | 0.4 | 0.4 | 0.1 | 0.2 | 0.6 | 0.7 | 0.7 | 1.4 | 0.8 | 197.0 |
| 369 | 0.9 | 0.4 | 0.3 | 0.4 | 1.9 | 2.0 | 2.4 | 6.4 | 3.1 | 1198.0 |
| 370 | 0.3 | 0.3 | 0.1 | 0.8 | 0.9 | 0.9 | 1.4 | 5.1 | 1.9 | >10000 |
| 371 | 0.3 | 0.3 | 0.1 | 0.4 | 1.5 | 2.5 | 3.3 | 53.2 | 9.4 | 3732.0 |
| 372 | 0.2 | 0.3 | 0.1 | 0.3 | 0.8 | 1.6 | 1.0 | 22.9 | 5.5 | 5114.0 |
| 373 | 0.2 | 0.2 | 0.1 | 0.4 | 1.6 | 1.8 | 2.5 | 41.6 | 10.8 | 9540.0 |
| 374 | 0.3 | 0.3 | 0.3 | 0.6 | 1.3 | 2.4 | 4.1 | 75.1 | 10.4 | 9814.0 |
| 375 | 2.5 | 3.2 | 1.3 | 8.0 | 13.1 | 34.8 | 82.0 | 1918.0 | 121.6 | >10000 |
| 376 | 0.3 | 0.5 | 3.4 | 1.1 | 1.4 | 2.5 | 7.8 | 102.0 | 15.1 | >10000 |
| 377 | 3.0 | 4.1 | 1.2 | 10.6 | 20.3 | 34.6 | 52.2 | 1554.0 | 131.7 | >10000 |
| 378 | 0.1 | 0.3 | 0.1 | 0.4 | 0.5 | 1.0 | 1.3 | 34.0 | 3.9 | 2899.0 |
| 379 | 0.6 | 0.7 | 0.4 | 0.8 | 1.9 | 3.9 | 1.9 | 30.1 | 9.7 | >10000 |
| 380 | 2.4 | 1.5 | 2.6 | 5.4 | 32.5 | 58.7 | 32.6 | 1168.0 | 114.1 | >10000 |
| 381 | 2.9 | 3.1 | 3.4 | 7.9 | 33.3 | 75.5 | 37.9 | 1288.0 | 226.0 | >10000 |
| 382 | 0.2 | 0.2 | 0.2 | 0.4 | 2.1 | 2.9 | 5.5 | 32.4 | 10.4 | 5004.0 |
| 383 | 1.0 | 1.2 | 0.6 | 1.2 | 3.7 | 8.2 | 14.5 | 86.8 | 40.8 | >10000 |
| 384 | | 1.3 | | 3.1 | | 10.9 | | 49.6 | | >10000 |
| 385 | | 0.7 | | 2.1 | | 11.2 | | 37.6 | | >10000 |
| 386 | 0.1 | 0.3 | 0.1 | 0.4 | 0.9 | 1.4 | 0.9 | 7.6 | 3.0 | 1794.0 |
| 387 | 0.3 | 0.6 | 0.2 | 0.7 | 1.2 | 4.4 | 2.7 | 36.7 | 9.5 | >10000 |
| 388 | 2.7 | 6.6 | 2.0 | 19.3 | 33.3 | 127.1 | 38.6 | 624.2 | 311.9 | >10000 |
| 389 | 0.3 | 0.5 | 0.1 | 0.7 | 0.4 | 2.1 | 1.6 | 14.5 | 4.6 | 5195.0 |
| 390 | 2.5 | 5.3 | 1.1 | 8.3 | 7.3 | 11.6 | 30.1 | 192.2 | 47.7 | >10000 |

TABLE 16

| | Del19/T790M/ C797S (nM) | | L858R/T790M/ C797S (nM) | | Del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 391 | 0.6 | 1.3 | 0.4 | 2.1 | 3.0 | 5.1 | 19.2 | 63.4 | 25.6 | >10000 |
| 392 | | 22.0 | | 60.1 | | 211.7 | | 4297.0 | | >10000 |
| 393 | 0.5 | 0.6 | 0.4 | 1.2 | 7.3 | 7.9 | 3.4 | 50.0 | 21.3 | >10000 |
| 394 | 0.5 | 0.6 | 0.2 | 1.5 | 7.5 | 12.3 | 4.3 | 52.5 | 15.7 | >10000 |
| 395 | 0.6 | 0.7 | 0.3 | 1.3 | 6.6 | 8.3 | 2.7 | 51.2 | 16.9 | 9219.0 |
| 396 | 1.0 | 0.5 | 0.1 | 0.7 | 0.5 | 1.0 | 0.6 | 12.2 | 6.5 | 3386.0 |
| 397 | 1.5 | 0.9 | 0.5 | 1.3 | 0.7 | 1.5 | 1.5 | 31.3 | 16.9 | >10000 |
| 398 | 26.7 | 14.9 | 24.7 | 29.3 | 16.6 | 44.3 | 17.8 | 971.1 | 294.5 | >10000 |
| 399 | 1.3 | 5.7 | 0.8 | 1.2 | 0.6 | 1.4 | 1.6 | 28.2 | 10.2 | >10000 |
| 400 | 34.0 | 19.3 | 26.1 | 22.5 | 12.8 | 35.6 | 17.9 | 1568.0 | 310.2 | >10000 |
| 401 | 0.7 | 0.4 | 0.4 | 0.5 | 0.3 | 0.6 | 0.8 | 11.9 | 3.9 | 3015.0 |
| 402 | | 2.6 | | 3.9 | 7.9 | 8.4 | 3.9 | 104.4 | 62.7 | >10000 |

TABLE 16-continued

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 403 |  | 16.2 |  | 50.3 |  | 140.0 |  | 1924.0 |  | >10000 |
| 404 |  | 1.7 |  | 2.9 | 5.3 | 3.6 | 2.7 | 55.6 | 45.8 | 9350.0 |
| 405 |  | 46.5 |  | 94.2 |  | 248.6 |  | 3899.0 |  | >10000 |
| 406 |  | 0.9 |  | 1.3 | 3.3 | 4.3 | 2.7 | 58.2 | 35.2 | >10000 |
| 407 |  | 0.3 |  | 0.4 | 0.6 | 0.7 | 0.8 | 13.0 | 4.4 | 1264.0 |
| 408 |  | 0.1 |  | 0.2 |  | 2.1 |  | 26.0 |  | 6567.0 |
| 409 |  | 4.3 |  | 10.5 |  | 81.3 |  | 648.3 |  | >10000 |
| 410 |  | 0.2 |  | 0.6 |  | 3.1 |  | 29.4 |  | 7425.0 |
| 411 |  | 7.3 |  | 35.9 |  | 59.8 |  | 978.6 |  | >10000 |
| 412 |  | 0.3 |  | 2.7 |  | 3.3 |  | 21.5 |  | >10000 |
| 413 |  | 0.1 |  | 1.4 |  | 0.8 |  | 10.3 |  | 2913.0 |
| 414 |  | 0.4 |  | 3.9 |  | 1.8 |  | 24.1 |  | 5187.0 |
| 415 |  | 0.2 |  | 1.7 |  | 1.2 |  | 21.6 |  | 5056.0 |
| 416 | 2.6 | 2.7 | 0.9 | 2.8 | 7.2 | 8.2 | 33.6 | 165.1 | 84.5 | >10000 |
| 417 | 1.5 | 1.6 | 0.8 | 2.6 | 7.0 | 7.9 | 30.7 | 156.9 | 96.1 | >10000 |
| 418 |  | 1.1 |  | 2.3 |  | 10.1 |  | 235.3 |  | >10000 |
| 419 | 1.1 | 1.0 | 0.4 | 1.5 | 3.9 | 4.8 | 7.1 | 97.5 | 31.0 | >10000 |
| 420 | 1.6 | 1.3 | 0.5 | 2.3 | 6.4 | 6.9 | 12.6 | 119.2 | 52.7 | >10000 |

TABLE 17

| EX. NO. | Del19/T790M/C797S (nM) Km ATP | Del19/T790M/C797S (nM) 100 μM ATP | L858R/T790M/C797S (nM) Km ATP | L858R/T790M/C797S (nM) 100 μM ATP | Del19/C797S (nM) Km ATP | Del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 421 | 1.5 | 1.8 | 0.8 | 2.3 | 4.0 | 5.8 | 17.2 | 116.7 | 35.1 | >10000 |
| 422 | 0.9 | 0.4 | 0.4 | 0.5 | 2.6 | 2.6 | 3.2 | 59.4 | 10.5 | 6514.0 |
| 423 |  | 1.2 |  | 3.2 |  | 104.8 |  | 1767.0 |  | >10000 |
| 424 | 0.3 | 0.2 | 0.2 | 0.3 | 2.0 | 2.4 | 1.9 | 47.7 | 8.8 | 5451.0 |
| 425 |  | 2.5 |  | 5.4 |  | 120.2 |  | 1820.0 |  | >10000 |
| 426 | 0.2 | 0.2 | 0.1 | 0.2 | 1.0 | 0.8 | 1.3 | 31.7 | 4.2 | 1618.0 |
| 427 | 0.3 | 0.2 | 0.2 | 0.3 | 2.7 | 2.4 | 3.2 | 80.1 | 12.0 | >10000 |
| 428 | 0.1 | 0.5 | 0.1 | 0.2 | 4.0 | 1.9 | 4.9 | 28.5 | 18.6 | >10000 |
| 429 | 0.2 | 0.5 | 0.2 | 0.3 | 4.9 | 3.4 | 4.8 | 39.7 | 38.9 | 6021.0 |
| 430 | 0.6 | 1.0 | 0.3 | 0.9 | 1.3 | 3.8 | 4.3 | 107.1 | 6.9 | 7476.0 |
| 431 | 1.2 | 2.7 | 1.0 | 4.7 |  | 78.1 |  | 2090.0 |  | >10000 |
| 432 | 0.4 | 0.6 | 0.3 | 0.7 | 3.1 | 5.2 | 5.3 | 141.3 | 11.4 | >10000 |
| 433 | 0.4 | 0.5 | 0.2 | 0.7 | 1.0 | 3.2 | 4.0 | 90.8 | 7.7 | 8717.0 |
| 434 | 0.4 | 0.3 | 0.2 | 0.5 | 2.3 | 5.2 | 2.4 | 125.4 | 21.2 | 8893.0 |
| 435 | 0.2 | 0.2 | 0.1 | 0.3 | 1.3 | 2.9 | 2.0 | 66.6 | 14.2 | 8716.0 |
| 436 | 0.1 | 0.2 | 0.1 | 0.3 | 1.7 | 3.1 | 2.5 | 110.9 | 12.5 | >10000 |
| 437 | 0.1 | 0.1 | 0.1 | 0.1 | 0.6 | 1.3 | 0.8 | 39.3 | 3.7 | >10000 |
| 438 | 0.3 | 0.3 | 0.2 | 0.7 | 1.7 | 3.3 | 1.9 | 85.5 | 5.8 | 6423.0 |
| 439 | 2.1 | 1.7 | 1.3 | 3.7 | 12.5 | 24.5 | 11.1 | 62.7 | 122.3 | >10000 |
| 440 | 0.5 | 0.5 | 0.5 | 1.3 | 7.6 | 9.7 | 10.3 | 61.5 | 48.4 | >10000 |
| 441 | 2.1 | 2.2 | 0.5 | 0.8 |  | 2.3 |  | 47.1 |  | >10000 |
| 442 | 0.7 | 0.9 | 0.1 | 0.3 |  | 1.3 |  | 20.3 |  | 9928.0 |
| 443 | 4.3 | 7.7 | 1.2 | 4.0 |  | 53.5 |  | 4608.0 |  | >10000 |
| 444 | 0.9 | 1.5 | 0.3 | 1.5 |  | 10.2 |  | 549.3 |  | >10000 |
| 445 | 0.5 | 0.9 | 0.1 | 0.4 |  | 2.0 |  | 104.2 |  | >10000 |
| 446 | 1.0 | 1.2 | 0.2 | 0.4 |  | 1.3 |  | 18.9 |  | 2674.0 |
| 447 | 0.3 | 0.4 | 0.2 | 0.5 | 1.5 | 2.1 | 3.5 | 59.8 | 16.9 | >10000 |
| 448 | 1.0 | 1.7 | 1.2 | 6.1 | 27.7 | 44.7 | 5.8 | 503.1 | 299.9 | >10000 |
| 449 | 165.4 |  | 51.7 |  | 268.1 |  | 69.3 |  | 563.6 |  |

What is claimed is:

1. A compound of formula (I) or a pharmaceutically acceptable salt thereof,

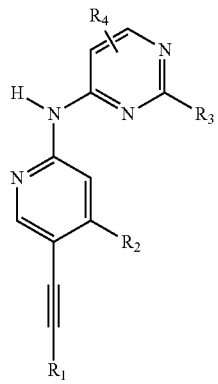

Wherein
R$_1$ is selected from the group consisting of
—H;
—Si(C$_{1-6}$ alkyl)$_3$;
C$_{1-6}$ alkyl optionally or independently substituted by one or more substituents selected from the group consisting of OH, halogen, C$_{1-3}$alkoxy, C$_{3-6}$ cycloalkyl, —NHC$_{1-6}$ alkyl, —NHC$_{1-6}$haloalkyl, —N(C$_{1-6}$ alkyl)$_2$, —N(C$_{1-6}$ haloalkyl)$_2$, —NHC(O)C$_{1-6}$ alkyl, —NHC(O)C$_{1-6}$ haloalkyl, —NHC(O)C$_{3-6}$ cycloalkyl, —NHC(O)-4-7 membered heterocyclic, —C(O)-4-7 membered heterocyclic, and 4-7 membered heterocyclic optionally or independently substituted by one or more substituents selected from the group consisting of C$_{1-6}$ alkyl, halogen, OH, and oxo;
C$_{2-5}$alkenyl;
—C(O)NHC$_{1-6}$ alkyl;
—C(O)N(C$_{1-6}$ alkyl)$_2$;
—C(O)-4-7 membered heterocyclyl;
—NHC$_{1-6}$ alkyl optionally or independently substituted by one or more substituents selected from the group consisting of OH; and halogen;
—N(C$_{1-6}$ alkyl)$_2$ optionally or independently substituted by one or more substituents selected from the group consisting of OH; and halogen; and
-A-(R$_{1A}$)$_m$,
A is selected from the group consisting of C$_{3-6}$ cycloalkyl; C$_{6-10}$ aryl; 4-8 membered heterocyclyl; and 5-10 membered heteroaryl,
R$_{1A}$ is independently selected from the group consisting of
H;
OH;
NH$_2$;
halogen;
C$_{1-6}$alkyl optionally substituted by one or more substituents selected from the group consisting of OH, halogen, C$_{3-6}$ cycloalkyl, —NHC$_{1-6}$ alkyl, —NHC$_{3-6}$ cycloalkyl, —N(C$_{1-6}$ alkyl)$_2$, —C(O)N(C$_{1-6}$ alkyl)$_2$, —NHC(O) C$_{1-6}$ alkyl, 4-7 membered heterocyclyl optionally substituted by one or more substituents selected from the group consisting of halogen, C$_{1-6}$ alkyl, C$_{1-6}$ haloalkyl, C$_{1-6}$ hydroxyalkyl, and —C(O)C$_{1-6}$ alkyl;
C$_{3-6}$ cycloalkyl optionally substituted by one or more substituents selected from the group consisting of OH, halogen and —N(C$_{1-6}$ alkyl)$_2$;
—C(O)C$_{1-6}$ alkyl optionally substituted by one or more substituents selected from the group consisting of OH and halogen;
—C(O)N(C$_{1-6}$ alkyl)$_2$;
—C(O)-4-7 membered heterocyclyl optionally substituted by one or more substituents selected from the group consisting of OH and halogen;
—NHC$_{1-6}$ alkyl optionally substituted by 4-7 membered heterocyclyl;
—N(C$_{1-6}$ alkyl)$_2$;
—S(O)$_2$C$_{1-6}$ alkyl;
—S(O)$_2$C$_{3-6}$ cycloalkyl;
oxo; and
4-11 membered heterocyclyl optionally or independently substituted by one or more substituents selected from the group consisting of halogen, C$_{1-6}$alkyl optionally substituted by —N(C$_{1-6}$ alkyl)$_2$, C$_{3-6}$ cycloalkyl, C$_{1-6}$ haloalkyl, —C(O)C$_{1-6}$ alkyl, and 4-7 membered heterocyclyl,
m is an integer of 0-2,
R$_2$ is selected from the group consisting of —N(C$_{1-6}$ alkyl)$_2$ optionally substituted by one or more OHs; —XC$_{1-6}$ alkyl optionally substituted by OH, halogen, C$_{3-6}$ cycloalkyl, C$_{1-3}$ alkoxy, —NHC$_{1-6}$ alkyl, or —N(C$_{1-6}$ alkyl)$_2$; and —X(CH$_2$)$_n$—B—(R$_{2A}$)$_o$,
X is bond, —NH— or —O—,
n is an integer of 0-1,
o is an integer of 0-3,
B is selected from the group consisting of C$_{3-7}$ cycloalkyl; C$_{6-10}$ aryl; 4-12 membered heterocyclyl; and 5-6 membered heteroaryl,
R$_{2A}$ is each independently selected from the group consisting of H;
OH;
halogen;
C$_{1-6}$ alkyl optionally or independently substituted by one or more substituents selected from the group consisting of OH, halogen, —NHC$_{1-6}$ alkyl, —NHC$_{1-6}$ haloalkyl, —N(C$_{1-6}$ alkyl)$_2$, 4-7 membered heterocyclyl, and C$_{1-3}$ alkoxy;
C$_{3-6}$cycloalkyl optionally or independently substituted by one or more substituents selected from the group consisting of OH, and halogen;
C$_{1-3}$alkoxy optionally or independently substituted by one or more halogens;
—C(O)NHC$_{1-6}$ alkyl;
—C(O)N(C$_{1-6}$ alkyl)$_2$; —C(O)NHC$_{3-6}$ cycloalkyl;
—NHC$_{1-6}$alkyl optionally or independently substituted by one or more substituents selected from the group consisting of OH, halogen, C$_{3-6}$cycloalkyl, C$_{1-3}$alkoxy, —NHC$_{1-6}$ alkyl, —N(C$_{1-6}$ alkyl)$_2$, and 4-7 membered heterocyclyl;
—NHC$_{3-6}$ cycloalkyl optionally or independently substituted by one or more substituents selected from the group consisting of OH and halogen;
—N(C$_{1-6}$ alkyl)$_2$ optionally or independently substituted by one or more substituents selected from the group consisting of OH and halogen;
—NHC(O)C$_{1-6}$ alkyl;
—NHC(O)C$_{3-6}$ cycloalkyl;
—NHS(O)$_2$C$_{1-6}$ alkyl;
—S(O)$_2$C$_{1-6}$ alkyl;
4-7 membered heterocyclyl optionally or independently substituted by one or more substituents selected from the group consisting of halogen and C$_{1-6}$ alkyl;

=O; and
C(O)C$_{1-6}$ alkyl,
R$_3$ is Y-Q-(R$_{3A}$)$_p$,
Y is —NH— or bond,
p is an integer of 0 to 2,
Q is selected from the group consisting of 4-7 membered heterocyclyl; C$_{6-10}$ aryl; and 5-6 membered heteroaryl,
R$_{3A}$ is independently selected from the group consisting of H; halogen; C$_{1-6}$ alkyl optionally substituted by one or more substituents selected from the group consisting of halogen and C$_{3-6}$ cycloalkyl; C$_{3-6}$ cycloalkyl; 4-7 membered heterocyclyl; —S(O)$_2$C$_{1-6}$ alkyl optionally substituted by one to three halogens; —S(O)$_2$C$_{3-6}$ cycloalkyl optionally substituted by one or more halogens; and —S(O)$_2$N(C$_{1-6}$ alkyl), and
R$_4$ is selected from the group consisting of H, halogen and C$_{1-6}$ alkyl.

2. The compound, or a pharmaceutically acceptable salt thereof according to claim 1, wherein R$_1$ is selected from the group consisting of H; Si(C$_{1-3}$ alkyl)$_3$; C$_{1-4}$alkyl optionally or independently substituted by one to three substituents selected from the group consisting of OH, F, Cl, C$_{1-3}$alkoxy, —NHC$_{1-4}$alkyl —NHC$_{1-4}$haloalkyl, —N(C$_{1-4}$alkyl)$_2$, —N(C$_{1-4}$haloalkyl)$_2$,—NHC(O)C$_{1-4}$alkyl, —NHC(O)C$_{3-6}$ cycloalkyl, —NHC(O)-4-6 membered heterocyclyl, —C(O)-4-6 membered heterocyclyl having one to three heteroatoms selected from a group consisting of N, O and S, 4-6 membered heterocyclyl having one to three heteroatoms selected from a group consisting of N, O and S, optionally or independently substituted by one to three substituents selected from the group consisting of C$_{1-4}$alkyl, F, Cl, OH, and oxo; C$_{2-5}$alkenyl; —C(O)NHC$_{1-6}$alkyl; —C(O)N(C$_{1-4}$ alkyl)$_2$; —C(O)-4-6 membered heterocyclyl having one to three heteroatoms selected from a group consisting of N, O and S; —NHC$_{1-4}$alkyl optionally or independently substituted by one to three substituents selected from the group consisting of OH; F; Cl; —N(C$_{1-4}$alkyl)$_2$ optionally or independently substituted by one to three substituents selected from the group consisting of OH, F and Cl; and A-(R$_{1A}$)$_m$.

3. The compound, or a pharmaceutically acceptable salt thereof according to claim 1, wherein R$_1$ is selected from the group consisting of —H; —Si(C$_{1-6}$ alkyl)$_3$; C$_{1-6}$ alkyl optionally or independently substituted by one or more substituents selected from the group consisting of OH, halogen, C$_{1-3}$ alkoxy, —NHC(O)C$_{1-6}$ haloalkyl, —NHC(O)-4-7 membered heterocyclyl, —C(O)-4-7 membered heterocyclyl, and 4-7 membered heterocyclyl optionally or independently substituted by oxo; C$_{2-5}$ alkenyl; and -A-(R$_{1A}$)$_m$.

4. The compound, or a pharmaceutically acceptable salt thereof according to claim 3, wherein R$_1$ is C$_{1-6}$ alkyl substituted by the 4-7 membered heterocyclyl, wherein the 4-7 membered heterocyclyl is selected from the group consisting of morpholinyl, pyrrolidinyl, 1,1-dioxo-1,4-thiazinanyl, and oxetanyl, wherein the 4-7 membered heterocyclyl is optionally substituted by oxo.

5. The compound, or a pharmaceutically acceptable salt thereof according to claim 1, wherein A is selected from the group consisting of C$_{3-6}$cycloalkyl; phenyl; 4-7 membered heterocycloalkyl; 5-6 membered heteroaryl; and 9-10 membered heteroaryl.

6. The compound, or a pharmaceutically acceptable salt thereof according to claim 1, wherein A is selected from the group consisting of C$_{3-6}$cycloalkyl; phenyl; pyrazolyl; pyridinyl; 4,5,6,7-tetrahydropyrazolo[1,5-a]pyrazinyl; triazolyl; thiazolyl; pyrazinyl; tetrahydropyranyl, pyrrolidinyl, piperidinyl, thienyl, pyrimidinyl, tetrahydrofuranyl, imidazolyl, pyrrolyl, pyrrolo[3,2-c]pyridinyl, oxetanyl, 7-oxabicyclo[2.2.1]heptanyl, and 1,1-dioxo-thiolanyl.

7. The compound, or a pharmaceutically acceptable salt thereof according to claim 1, wherein R$_{1A}$ is selected from the group consisting of H; OH; NH$_2$; F; Cl; C$_{1-4}$alkyl optionally substituted by one to three substituents selected from the group consisting of OH, F, Cl, C$_{3-6}$cycloalkyl, —NHC$_{1-4}$alkyl, —NHC$_{3-4}$cycloalkyl, —N(C$_{1-4}$alkyl)$_2$, —C(O)N(C$_{1-4}$alkyl)$_2$, —NHC(O)C$_{1-4}$alkyl, 4-7 membered heterocyclyl having one to three heteroatoms selected from a group consisting of N, O and S, optionally substituted by one to three substituents selected from the group consisting of F, Cl, C$_{1-4}$alkyl, C$_{1-4}$haloalkyl, C$_{1-4}$hydroxyalkyl, and —C(O)C$_{1-4}$alkyl; C$_{3-6}$cycloalkyl optionally substituted by one to three substituents selected from the group consisting of OH, F, Cl and —N(C$_{1-4}$alkyl)$_2$; —C(O)C$_{1-6}$alkyl optionally substituted by one to three substituents selected from the group consisting of OH, F and Cl; —C(O)N(C$_{1-4}$alkyl)$_2$; —C(O)-4-7 membered heterocyclyl having one to three heteroatoms selected from a group consisting of N, O and S, optionally substituted by one to three OHs; —NHC$_{1-6}$alkyl optionally substituted by 4-7 membered heterocyclyl having one to three heteroatoms selected from a group consisting of N, O and S; —N(C$_{1-6}$alkyl)$_2$; —S(O)$_2$Calkyl; —S(O)$_2$C$_{3-6}$ cycloalkyl; and 4-11 membered heterocyclyl optionally or independently substituted by one to three substituents selected from the group consisting of F, Cl, C$_{1-4}$alkyl optionally substituted by —N(C$_{1-4}$alkyl)$_2$, C$_{3-6}$cycloalkyl, C$_{1-4}$haloalkyl, —C(O)C$_{1-4}$alkyl, and 4-7 membered heterocyclyl having one to three heteroatoms selected from a group consisting of N, O and S.

8. The compound, or a pharmaceutically acceptable salt thereof according to claim 1, wherein R$_{1A}$ is selected from the group consisting of C$_{1-6}$alkyl optionally substituted by one or more substituents selected from the group consisting of OH, halogen, C$_{3-6}$cycloalkyl, —NHC$_{1-6}$alkyl, —NHC$_{3-6}$ cycloalkyl, —N(C$_{1-6}$alkyl)$_2$, —C(O)N(C$_{1-6}$alkyl)$_2$, —NHC(O)C$_{1-6}$alkyl, 4-7 membered heterocyclyl optionally substituted by one or more substituents selected from the group consisting of halogen, C$_{1-6}$alkyl, C$_{1-6}$haloalkyl, C$_{1-6}$hydroxyalkyl, and —C(O)C$_{1-6}$alkyl; C$_{3-6}$cycloalkyl optionally substituted by one or more substituents selected from the group consisting of OH, halogen and —N(C$_{1-6}$alkyl)$_2$; and 4-7 membered heterocyclyl optionally or independently substituted by one or more substituents selected from the group consisting of halogen, C$_{1-6}$alkyl optionally substituted by —N(C$_{1-6}$alkyl)$_2$, C$_{3-6}$cycloalkyl, C$_{1-6}$haloalkyl, —C(O)C$_{1-6}$alkyl, and 4-7 membered heterocyclyl.

9. The compound, or a pharmaceutically acceptable salt thereof according to claim 1, wherein R$_{1A}$ is selected from the group consisting of
H;
OH;
NH$_2$;
halogen;
C$_{1-6}$ alkyl optionally substituted by one or more substituents selected from the group consisting of OH, halogen, C$_{3-6}$ cycloalkyl, —N(C$_{1-6}$ alkyl)$_2$, —C(O)N(C$_{1-6}$ alkyl)$_2$, 4-7 membered heterocyclyl optionally substituted by one or more substituents selected from the group consisting of halogen, and C$_{1-6}$alkyl;
C$_{3-6}$ cycloalkyl optionally substituted by one or more halogens;
—C(O)C$_{1-6}$ alkyl optionally substituted by one or more halogens;
—C(O)N(C$_{1-6}$ alkyl)$_2$;

—C(O)-4-7 membered heterocyclyl optionally substituted by one or more OHs;
—NHC$_{1-6}$ alkyl optionally substituted by 4-7 membered heterocyclyl;
—S(O)$_2$C$_{1-6}$ alkyl;
—S(O)$_2$C$_{3-6}$ cycloalkyl; and
4-11 membered heterocyclyl optionally or independently substituted by one or more substituents selected from the group consisting of C$_{1-6}$ alkyl and —C(O)C$_{1-6}$alkyl.

10. The compound, or a pharmaceutically acceptable salt thereof according to claim 9,
wherein R$_{1A}$ is C$_{1-6}$ alkyl substituted by 7 membered heterocyclyl, wherein the 4-7 membered heterocyclyl is selected from the group consisting of tetrahydropyranyl, piperidinyl, azetidinyl, morpholinyl, piperazinyl, dioxanyl, tetrahydrofuranyl, and oxetanyl, wherein the 4-7 membered heterocyclyl is optionally substituted by one or more substituents selected from the group consisting of halogen, and C$_{1-6}$alkyl; or
R$_{1A}$ is 4-11 membered heterocyclyl is selected from the group consisting of tetrahydropyranyl, piperidinyl, azetidinyl, morpholinyl, piperazinyl, dioxanyl, tetrahydrofuranyl, and oxetanyl, wherein the 4-11 membered heterocyclyl is optionally substituted by one or more substituents selected from the group consisting of C$_{1-6}$alkyl and —C(O)C$_{1-6}$alkyl.

11. The compound, or a pharmaceutically acceptable salt thereof according to claim 1, wherein R$_2$ is selected from the group consisting of —N(C$_{1-6}$alkyl)$_2$ optionally or independently substituted by one to three OHs; —XC$_{1-4}$alkyl optionally substituted by OH, F, Cl, C$_{3-6}$cycloalkyl, C$_{1-3}$alkoxy, —NHC$_{1-4}$alkyl, or —N(C$_{1-4}$alkyl)$_2$; and X(CH$_2$)$_n$—B—(R$_{2A}$)$_o$ wherein X is bond, —NH— or —O—; n is an integer of 0-1; o is an integer of 0-3.

12. The compound, or a pharmaceutically acceptable salt thereof according to claim 1, wherein R$_2$ is selected from the group consisting of —N(C$_{1-6}$alkyl)$_2$ optionally substituted by one or more OHs; —XC$_{1-6}$alkyl optionally substituted by OH; and —X(CH$_2$)$_n$—B—(R$_{2A}$)$_o$.

13. The compound, or a pharmaceutically acceptable salt thereof according to claim 1, wherein B is selected from the group consisting of C$_{3-6}$cycloalkyl; phenyl; 4-11 membered heterocycloalkyl having one to three heteroatoms selected from a group consisting of N, O and S; and 5-6 membered heteroaryl having one to three heteroatoms selected from a group consisting of N, O and S.

14. The compound, or a pharmaceutically acceptable salt thereof according to claim 1, wherein B is selected from the group consisting of C$_{3-6}$cycloalkyl; phenyl; piperazinyl, piperidinyl, 4-oxopiperidinyl, azaspiro[3.5]nonanyl, pyrrolidinyl, azetidinyl, azepanyl, 2,8-diazaspiro[4.5]decan-onyl, 2,8-diazaspiro[4.5]decanyl, 2,7-diazaspiro[3.5]nonanyl, pyrzaolyl, 1-oxa-8-azaspiro[4.5]decanyl, 1-oxa-7-azaspiro[3.5]nonanyl, 3,9-diazaspiro[5.5]undecanyl, 3-azabicyclo[3.1.0]hexanyl, 8-azabicyclo[3.2.1]octanyl, and 1-azaspiro[4.5]decanonyl.

15. The compound, or a pharmaceutically acceptable salt thereof according to claim 1, wherein R$_{2A}$ is each independently selected from the group consisting of H; OH; F; Cl; C$_{1-6}$alkyl optionally or independently substituted by one to three substituents selected from the group consisting of OH, F, Cl, —NHC$_{1-4}$alkyl, —NHC$_{1-4}$haloalkyl, —N(C$_{1-4}$alkyl)$_2$, and C$_{1-3}$alkoxy; C$_{3-6}$cycloalkyl optionally substituted by one to three OHs; C$_{1-3}$alkoxy optionally or independently substituted by one to three substituents selected from the group consisting of F and Cl; —C(O)NHC$_{1-4}$alkyl; —C(O)NHC$_{3-6}$cycloalkyl; —NHC$_{1-4}$alkyl optionally or independently substituted by one or more substituents selected from the group consisting of OH, F, Cl, C$_{3-6}$cycloalkyl, C$_{1-3}$alkoxy, —NHC$_{1-4}$alkyl, —N(C$_{1-4}$alkyl)$_2$, and 4-7 membered heterocyclyl having one to three heteroatoms selected from a group consisting of N, O and S; —NHC$_{3-6}$cycloalkyl optionally or independently substituted by one to three substituents selected from the group consisting of OH, F and Cl; —N(C$_{1-4}$alkyl)$_2$ optionally or independently substituted by one to three substituents selected from the group consisting of OH, F and Cl; —NHC(O)C$_{1-4}$alkyl; —NHC(O)C$_{3-6}$cycloalkyl; —NHS(O)$_2$C$_{1-4}$alkyl; —S(O)$_2$C$_{1-4}$alkyl; 4-7 membered heterocyclyl having one to three heteroatoms selected from a group consisting of N, O and S, optionally or independently substituted by one to three substituents selected from the group consisting of F, Cl and C$_{1-6}$alkyl; —C(O)C$_{1-6}$alkyl; and =O.

16. The compound, or a pharmaceutically acceptable salt thereof according to claim 1, wherein R$_{2A}$ is each independently selected from the group consisting of OH; halogen; C$_{1-6}$alkyl optionally or independently substituted by one or more substituents selected from the group consisting of OH, halogen, —NHC$_{1-6}$alkyl, —NHC$_{1-6}$haloalkyl, —N(C$_{1-6}$alkyl)$_2$, and C$_{1-3}$alkoxy; C$_{3-6}$cycloalkyl; —NHC$_{1-6}$alkyl optionally or independently substituted by one or more substituents selected from the group consisting of OH, halogen, C$_{3-6}$cycloalkyl, C$_{1-3}$alkoxy, —NHC$_{1-6}$alkyl, —N(C$_{1-6}$alkyl)$_2$, and 4-7 membered heterocyclyl; —NHC$_{3-6}$ cycloalkyl optionally or independently substituted by one or more substituents selected from the group consisting of OH and halogen; and —N(C$_{1-6}$alkyl)$_2$ optionally or independently substituted by one or more substituents selected from the group consisting of OH and halogen.

17. The compound, or a pharmaceutically acceptable salt thereof according to claim 1, wherein R$_{2A}$ is each independently selected from the group consisting of
H;
OH;
halogen;
C$_{1-6}$alkyl optionally or independently substituted by one or more substituents selected from the group consisting of OH, halogen, —NHC$_{1-6}$alkyl, —NHC$_{1-6}$haloalkyl, and —N(C$_{1-6}$alkyl)$_2$;
C$_{3-6}$cycloalkyl optionally or independently substituted by one or more OHs;
C$_{1-3}$alkoxy optionally or independently substituted by one or more halogens;
—NHC$_{1-6}$alkyl optionally or independently substituted by one or more substituents selected from the group consisting of OH, halogen, C$_{3-6}$cycloalkyl, C$_{1-3}$alkoxy, and —N(C$_{1-6}$alkyl)$_2$;
—NHS(O)$_2$C$_{1-6}$alkyl;
—S(O)$_2$C$_{1-6}$alkyl;
4-7 membered heterocyclyl optionally or independently substituted by one or more substituents selected from the group consisting of halogen and C$_{1-6}$alkyl;
=O; and
C(O)C$_{1-6}$alkyl.

18. The compound, or a pharmaceutically acceptable salt thereof according to claim 17, wherein R$_{2A}$ is 4-7 membered heterocyclyl selected from the group consisting of is piperazinyl and azetidinyl, wherein the 4-7 membered heterocyclyl is optionally substituted by one or more substituents selected from the group consisting of halogen and C$_{1-6}$alkyl.

19. The compound, or a pharmaceutically acceptable salt thereof according to claim 1, wherein Q is selected from the group consisting of pyrazolyl, pyridinyl, phenyl, and piperzinyl.

20. The compound, or a pharmaceutically acceptable salt thereof according to claim 1, wherein $R_{3A}$ is selected from the group consisting of H; halogen; $C_{1-4}$alkyl optionally substituted by one to three substituents selected from the group consisting of F, Cl and $C_{3-6}$cycloalkyl; $C_{3-6}$cycloalkyl; 4-7 membered heterocyclyl having one to three heteroatoms selected from a group consisting of N, O and S; —S(O)$_2$C$_{1-4}$alkyl; —S(O)$_2$C$_{3-6}$cycloalkyl optionally substituted by one to three F and Cl; and —S(O)$_2$N(C$_{1-4}$alkyl).

21. The compound, or a pharmaceutically acceptable salt thereof according to claim 1, wherein $R_3$ is selected from the group consisting of halogen; $C_{1-6}$alkyl optionally substituted by one or more halogens; —S(O)$_2$C$_{1-6}$alkyl; —S(O)$_2$C$_{3-6}$cycloalkyl; and —S(O)$_2$N(C$_{1-6}$alkyl).

22. The compound of claim 1, or a pharmaceutically acceptable salt thereof, wherein $R_4$ is H.

23. The compound of claim 1, which is selected from any one of the compounds as described below, or a pharmaceutically acceptable salt thereof:

(1) 2-(1-(Cyclopropylsulfonyl)-1H-pyrazol-4-yl)-N-(5-((1-methyl-1H-pyrazol-4-yl)ethynyl)-4-(4-methylpiperazin-1-yl)pyridin-2-yl)pyrimidin-4-amine;

(2) N$^4$-Cyclohexyl-N$^2$-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine;

(3) 2-(1-(Cyclopropylsulfonyl)-1H-pyrazol-4-yl)-N-(4-(4-(ethylsulfonyl)piperazin-1-yl)-5-((1-methyl-1H-pyrazol-4-yl)ethynyl)pyridin-2-yl)pyrimidin-4-amine;

(4) (R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)butan-1-ol;

(5) (S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-2-methylbutan-2-ol;

(6) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-ol;

(7) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-one;

(8) 2-(1-(Cyclopropylsulfonyl)-1H-pyrazol-4-yl)-N-(4-(4-fluoropiperidin-1-yl)-5-((1-methyl-1H-pyrazol-4-yl)ethynyl)pyridin-2-yl)pyrimidin-4-amine;

(9) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-3-yl)methanol;

(10) 1-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)ethan-1-ol;

(11) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)propan-2-ol;

(12) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-methylpiperidin-4-yl)methanol;

(13) 7-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2-methyl-7-azaspiro[3.5]nonan-2-ol;

(14) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-2-methylpropan-1-ol;

(15) 2-(1-(Cyclopropylsulfonyl)-1H-pyrazol-4-yl)-N-(4-(4-methoxypiperidin-1-yl)-5-((1-methyl-1H-pyrazol-4-yl)ethynyl)pyridin-2-yl)pyrimidin-4-amine;

(16) 2-(4-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperazin-1-yl)ethan-1-ol;

(17) 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)ethan-1-ol;

(18) N$^2$-(2-(1-(Cyclopropylsulfonyl)-1H-pyrazol-4-yl)pyrimidin-4-yl)-N$^4$-isopropyl-5-((1-methyl-1H-pyrazol-4-yl)ethynyl)pyridine-2,4-diamine;

(19) N$^2$-(2-(1-(Cyclopropylsulfonyl)-1H-pyrazol-4-yl)pyrimidin-4-yl)-N$^4$-isopropyl-5-((1-isopropyl-1H-pyrazol-4-yl)ethynyl)pyridine-2,4-diamine;

(20) N$^2$-(2-(1-(Cyclopropylsulfonyl)-1H-pyrazol-4-yl)pyrimidin-4-yl)-5-((1-(2-fluoroethyl)-1H-pyrazol-4-yl)ethynyl)-N$^4$-isopropylpyridine-2,4-diamine;

(21) N$^2$-(2-(1-(Cyclopropylsulfonyl)-1H-pyrazol-4-yl)pyrimidin-4-yl)-N$^4$-isopropyl-5-(pyridin-3-ylethynyl)pyridine-2,4-diamine;

(22) N$^2$-(2-(1-(Cyclopropylsulfonyl)-1H-pyrazol-4-yl)pyrimidin-4-yl)-N$^4$-isopropyl-5-(4-methoxybut-1-yn-1-yl)pyridine-2,4-diamine;

(23) N$^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-N$^4$-isopropylpyridine-2,4-diamine;

(24) N$^4$-(sec-Butyl)-N$^2$-(2-(1-(cyclopropylsulfonyl)-1H-pyrazol-4-yl)pyrimidin-4-yl)-5-((1-methyl-1H-pyrazol-4-yl)ethynyl)pyridine-2,4-diamine;

(25) N$^4$-(sec-Butyl)-N$^2$-(2-(1-(cyclopropylsulfonyl)-1H-pyrazol-4-yl)pyrimidin-4-yl)-5-((1-isopropyl-1H-pyrazol-4-yl)ethynyl)pyridine-2,4-diamine;

(26) N$^4$-(sec-Butyl)-N$^2$-(2-(1-(cyclopropylsulfonyl)-1H-pyrazol-4-yl)pyrimidin-4-yl)-5-((1-(2-fluoroethyl)-1H-pyrazol-4-yl)ethynyl)pyridine-2,4-diamine;

(27) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-ol;

(28) 1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-ol;

(29) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanol;

(30) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-4-yl)methanol;

(31) (R)-1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-ol;

(32) (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-ol;

(33) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)pyrrolidin-3-yl)methanol;

(34) (1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)pyrrolidin-3-yl)methanol;

(35) 2-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azetidin-3-yl)propan-2-ol;

(36) 2-(1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)azetidin-3-yl)propan-2-ol;

(37) 2-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)(methyl)amino)ethan-1-ol;

(38) 2-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)(methyl)amino)ethan-1-ol;

(39) 3-((2-((2-(1-Cyclopropylsulfonylpyrazol-4-yl)pyrimidin-4-yl)amino)-5-(2-(1-methylpyrazol-4-yl)ethynyl)-4-pyridyl)amino)-2,2-dimethyl-propan-1-ol;

(40) 3-((2-((2-(1-Cyclopropylsulfonylpyrazol-4-yl)pyrimidin-4-yl)amino)-5-(2-(1-(2-fluoroethyl)pyrazol-4-yl)ethynyl)-4-pyridyl)amino)-2,2-dimethyl-propan-1-ol;

(41) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(42) (1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(43) (1S,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(44) (1S,3S)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(45) (1S,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(46) (1S,3R)-3-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexan-1-ol;

(47) (1-(5-((1-Cyclopropyl-1H-pyrazol-4-yl)ethynyl)-2-((2-(1-cyclopropylsulfonyl)-1H-pyrazol-4-yl)pyrimidin-4-yl)amino)pyridin-4-yl)-4-methylpiperidin-4-yl)methanol;

(48) (1-(5-((1-(Cyclopropylmethyl)-1H-pyrazol-4-yl)ethynyl)-2-((2-(1-cyclopropylsulfonyl)-1H-pyrazol-4-yl)pyrimidin-4-yl)amino)pyridin-4-yl)-4-methylpiperidin-4-yl)methanol;

(49) (1-(2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)-4-methylpiperidin-4-yl)methanol;

(50) $N^2$-(2-(1-(Cyclopropylsulfonyl)-1H-pyrazol-4-yl)pyrimidin-4-yl)-$N^4$-(4-((dimethylamino)methyl)benzyl)-5-((1-methyl-1H-pyrazol-4-yl)ethynyl)pyridine-2,4-diamine;

(51) $N^2$-(2-(1-(Cyclopropylsulfonyl)-1H-pyrazol-4-yl)pyrimidin-4-yl)-$N^4$-(4-((dimethylamino)methyl)benzyl)-5-((1-(2-fluoroethyl)-1H-pyrazol-4-yl)ethynyl)pyridine-2,4-diamine;

(52) $N^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-$N^4$-(4-((dimethylamino)methyl)benzyl)pyridine-2,4-diamine;

(53) $N^2$-(2-(1-(Cyclopropylsulfonyl)-1H-pyrazol-4-yl)pyrimidin-4-yl)-$N^4$-(((1r,4r)-4-((dimethylamino)methyl)cyclohexyl)methyl)-5-((1-methyl-1H-pyrazol-4-yl)ethynyl)pyridine-2,4-diamine;

(54) 2-(1-(Cyclopropylsulfonyl)-1H-pyrazol-4-yl)-N-(4-isopropoxy-5-((1-methyl-1H-pyrazol-4-yl)ethynyl)pyridin-2-yl)pyrimidin-4-amine;

(55) 2-(1-(Cyclopropylsulfonyl)-1H-pyrazol-4-yl)-N-(5-((1-(2-fluoroethyl)-1H-pyrazol-4-yl)ethynyl)-4-isopropoxypyridin-2-yl)pyrimidin-4-amine;

(56) N-(4-(sec-Butoxy)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(57) N-(4-(sec-Butoxy)-5-((1-isopropyl-1H-pyrazol-4-yl)ethynyl)pyridin-2-yl)-2-(1-(cyclopropylsulfonyl)-1H-pyrazol-4-yl)pyrimidin-4-amine;

(58) 2-(1-(Cyclopropylsulfonyl)-1H-pyrazol-4-yl)-N-(4-(((1r,4r)-4-((dimethylamino)methyl)cyclohexyl)methoxy)-5-((1-methyl-1H-pyrazol-4-yl)ethynyl)pyridin-2-yl)pyrimidin-4-amine;

(59) 2-(1-(Cyclopropylsulfonyl)-1H-pyrazol-4-yl)-N-(4-(((1r,4r)-4-((dimethylamino)methyl)cyclohexyl)methoxy)-5-((1-isopropyl-1H-pyrazol-4-yl)ethynyl)pyridin-2-yl)pyrimidin-4-amine;

(60) N-(5-((1-Cyclopropyl-1H-pyrazol-4-yl)ethynyl)-4-(((1r,4r)-4-((dimethylamino)methyl)cyclohexyl)methoxy)pyridin-2-yl)-2-(1-(cyclopropylsulfonyl)-1H-pyrazol-4-yl)pyrimidin-4-amine;

(61) 2-(1-(Cyclopropylsulfonyl)-1H-pyrazol-4-yl)-N-(4-(((1r,4r)-4-((dimethylamino)methyl)cyclohexyl)methoxy)-5-((1-(2-fluoroethyl)-1H-pyrazol-4-yl)ethynyl)pyridin-2-yl)pyrimidin-4-amine;

(62) 2-(1-(Cyclopropylsulfonyl)-1H-pyrazol-4-yl)-N-(4-(((1r,4r)-4-((dimethylamino)methyl)cyclohexyl)methoxy)-5-(pyridin-3-ylethynyl)pyridin-2-yl)pyrimidin-4-amine;

(63) N-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)methanesulfonamide;

(64) 2-(1-(Cyclopropylsulfonyl)-1H-pyrazol-4-yl)-N-(4-(4-(isopropylamino)piperidin-1-yl)-5-((1-methyl-1H-pyrazol-4-yl)ethynyl)pyridin-2-yl)pyrimidin-4-amine;

(65) 2-(1-(Cyclopropylsulfonyl)-1H-pyrazol-4-yl)-N-(5-((1-methyl-1H-pyrazol-4-yl)ethynyl)-4-(4-(trifluoromethyl)piperidin-1-yl)pyridin-2-yl)pyrimidin-4-amine;

(66) 2-(1-(Cyclopropylsulfonyl)-1H-pyrazol-4-yl)-N-(4-(4-fluoro-4-(trifluoromethyl)piperidin-1-yl)-5-((1-methyl-1H-pyrazol-4-yl)ethynyl)pyridin-2-yl)pyrimidin-4-amine;

(67) 2-(1-(Cyclopropylsulfonyl)-1H-pyrazol-4-yl)-N-(5-((1-methyl-1H-pyrazol-4-yl)ethynyl)-4-(4-(trifluoromethoxy)piperidin-1-yl)pyridin-2-yl)pyrimidin-4-amine;

(68) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-difluoropiperidin-4-ol;

(69) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-3,3-dimethylpiperidin-4-ol;

(70) 2-(1-(Cyclopropylsulfonyl)-1H-pyrazol-4-yl)-N-(4-(3-fluoropiperidin-1-yl)-5-((1-methyl-1H-pyrazol-4-yl)ethynyl)pyridin-2-yl)pyrimidin-4-amine;

(71) 2-(1-(Cyclopropylsulfonyl)-1H-pyrazol-4-yl)-N-(5-((1-methyl-1H-pyrazol-4-yl)ethynyl)-4-(3-(trifluoromethyl)piperidin-1-yl)pyridin-2-yl)pyrimidin-4-amine;

(72) 2-(1-(Cyclopropylsulfonyl)-1H-pyrazol-4-yl)-N-(4-(3-(fluoromethyl)piperidin-1-yl)-5-((1-methyl-1H-pyrazol-4-yl)ethynyl)pyridin-2-yl)pyrimidin-4-amine;

(73) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-fluoropiperidin-4-yl)methanol;

(74) $N^2$-(2-(1-(Cyclopropylsulfonyl)-1H-pyrazol-4-yl)pyrimidin-4-yl)-$N^4$-(3-fluorocyclohexyl)-5-((1-methyl-1H-pyrazol-4-yl)ethynyl)pyridine-2,4-diamine;

(75) (1R,3S)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(76) (1R,3R)-3-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)cyclohexan-1-ol;

(77) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-ol;

(78) (1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)azepan-4-yl)methanol;

(79) 8-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-2,8-diazaspiro[4.5]decan-1-one;

(80) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-((1-methyl-1H-pyrazol-4-yl)ethynyl)pyridine-2,4-diamine;

(81) (1s,4s)-4-((2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)amino)-1-methylcyclohexan-1-ol;

(82) 1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-ol;

(83) (1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)methanol;

(84) 2-(1-(2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)piperidin-4-yl)ethan-1-ol;

(85) (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexan-1-ol;

(86) 1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-ol;

(87) 2-(1-(5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)ethan-1-ol;

(88) (1s,4s)-4-((5-((5-Cyclopropyl-1-methyl-1H-pyrazol-4-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(89) 1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-ol;

(90) (1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)methanol;

(91) 2-(1-(2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)piperidin-4-yl)ethan-1-ol;

(92) (1s,4s)-4-((2-((2-(1-(Cyclopropylsulfonyl)-1H-pyrazol-4-yl)pyrimidin-4-yl)amino)-5-((1-methyl-3-(trifluoromethyl)-1H-pyrazol-4-yl)ethynyl)pyridin-4-yl)amino)cyclohexan-1-ol;

(93) 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-one;

(94) (1s,4s)-4-((2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)amino)cyclohexan-1-ol;

(95) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-methylpiperidin-4-yl)methanol;

(96) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)-4-fluoropiperidin-4-yl)methanol;

(97) 2-(1-(Cyclopropylsulfonyl)-1H-pyrazol-4-yl)-N-(4-(4-fluoropiperidin-1-yl)-5-((1-(tetrahydro-2H-pyran-4-yl)-1H-pyrazol-4-yl)ethynyl)pyridin-2-yl)pyrimidin-4-amine;

(98) 2-(1-(Cyclopropylsulfonyl)-1H-pyrazol-4-yl)-N-(4-(4-methoxypiperidin-1-yl)-5-((1-(tetrahydro-2H-pyran-4-yl)-1H-pyrazol-4-yl)ethynyl)pyridin-2-yl)pyrimidin-4-amine;

(99) 1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-ol;

(100) (1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-3-yl)methanol;

(101) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(102) (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol;

(103) (1 S,3S)-3-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexan-1-ol;

(104) 7-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-2-methyl-7-azaspiro[3.5]nonan-2-ol;

(105) (1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)-1-methylcyclohexan-1-ol;

(106) (1s,4s)-4-((2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)amino)cyclohexan-1-ol;

(107) (1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)-4-methylpiperidin-4-yl)methanol;

(108) 1-(5-((1-(1-Acetylpiperidin-4-yl)-1H-pyrazol-4-yl)ethynyl)-2-((2-(1-(cyclopropylsulfonyl)-1H-pyrazol-4-yl)pyrimidin-4-yl)amino)pyridin-4-yl)piperidin-4-one;

(109) 1-(4-(4-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)-1H-pyrazol-1-yl)piperidin-1-yl)ethan-1-one;

(110) 1-(4-(4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-1H-pyrazol-1-yl)piperidin-1-yl)ethan-1-one;

(1H) 1-(4-(4-((6-((2-(1-(Cyclopropylsulfonyl)-1H-pyrazol-4-yl)pyrimidin-4-yl)amino)-4-(4-fluoro-4-(hydroxymethyl)piperidin-1-yl)pyridin-3-yl)ethynyl)-1H-pyrazol-1-yl)piperidin-1-yl)ethan-1-one;

(112) 1-(4-(4-((6-((2-(1-(Cyclopropylsulfonyl)-1H-pyrazol-4-yl)pyrimidin-4-yl)amino)-4-(4-fluoropiperidin-1-yl)pyridin-3-yl)ethynyl)-1H-pyrazol-1-yl)piperidin-1-yl)ethan-1-one;

(113) 1-(4-(4-((6-((2-(1-(Cyclopropylsulfonyl)-1H-pyrazol-4-yl)pyrimidin-4-yl)amino)-4-(4-methoxypiperidin-1-yl)pyridin-3-yl)ethynyl)-1H-pyrazol-1-yl)piperidin-1-yl)ethan-1-one;

(114) 1-(4-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)-1H-pyrazol-1-yl)piperidin-1-yl)ethan-1-one;

(115) 1-(4-(4-((6-((2-(1-(Cyclopropylsulfonyl)-1H-pyrazol-4-yl)pyrimidin-4-yl)amino)-4-(3-(hydroxymethyl)piperidin-1-yl)pyridin-3-yl)ethynyl)-1H-pyrazol-1-yl)piperidin-1-yl)ethan-1-one;

(116) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-methylpiperidin-4-yl)methanol;

(117) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)-4-fluoropiperidin-4-yl)methanol;

(118) (1-(2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)piperidin-3-yl)methanol;

(119) (1s,4s)-4-((2-((2-(1-(Cyclopropylsulfonyl)-1H-pyrazol-4-yl)pyrimidin-4-yl)amino)-5-((1-(2-(dimethylamino)ethyl)-1H-pyrazol-4-yl)ethynyl)pyridin-4-yl)amino)cyclohexan-1-ol;

(120) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-methylpiperidin-4-yl)methanol;

(121) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-4-fluoropiperidin-4-yl)methanol;

(122) (1-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)piperidin-3-yl)methanol;

(123) (1s,4s)-4-((2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)amino)cyclohexan-1-ol;

(124) N-(4-(4-((Cyclopropylmethyl)amino)piperidin-1-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(125) 2-(1-(Cyclopropylsulfonyl)-1H-pyrazol-4-yl)-N-(4-(4-(isopentylamino)piperidin-1-yl)-5-((1-methyl-1H-pyrazol-4-yl)ethynyl)pyridin-2-yl)pyrimidin-4-amine;

(126) 2-(1-(Cyclopropylsulfonyl)-1H-pyrazol-4-yl)-N-(4-(4-((2,2-difluoroethyl)amino)piperidin-1-yl)-5-((1-methyl-1H-pyrazol-4-yl)ethynyl)pyridin-2-yl)pyrimidin-4-amine;

(127) 2-(1-(Cyclopropylsulfonyl)-1H-pyrazol-4-yl)-N-(5-((1-methyl-1H-pyrazol-4-yl)ethynyl)-4-(4-((3,3,3-trifluoropropyl)amino)piperidin-1-yl)pyridin-2-yl)pyrimidin-4-amine;

(128) 2-(1-(Cyclopropylsulfonyl)-1H-pyrazol-4-yl)-N-(4-(4-(3,3-difluoroazetidin-1-yl)piperidin-1-yl)-5-((1-methyl-1H-pyrazol-4-yl)ethynyl)pyridin-2-yl)pyrimidin-4-amine;

(129) 2-(1-(Cyclopropylsulfonyl)-1H-pyrazol-4-yl)-N-(4-(4-((2-fluoroethyl)amino)piperidin-1-yl)-5-((1-methyl-1H-pyrazol-4-yl)ethynyl)pyridin-2-yl)pyrimidin-4-amine;

(130) 2-(1-(Cyclopropylsulfonyl)-1H-pyrazol-4-yl)-N-(5-((1-methyl-1H-pyrazol-4-yl)ethynyl)-4-(4-(methylamino)piperidin-1-yl)pyridin-2-yl)pyrimidin-4-amine;

(131) 2-((1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)amino)ethan-1-ol;

(132) 2-(1-(Cyclopropylsulfonyl)-1H-pyrazol-4-yl)-N-(4-(4-((2-methoxyethyl)amino)piperidin-1-yl)-5-((1-methyl-1H-pyrazol-4-yl)ethynyl)pyridin-2-yl)pyrimidin-4-amine;

(133) $N^1$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-$N^2,N^2$-dimethylethane-1,2-diamine;

(134) $N^1$-(1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)piperidin-4-yl)-$N^2,N^2$,2-trimethylpropane-1,2-diamine;

(135) 2-(1-(Cyclopropylsulfonyl)-1H-pyrazol-4-yl)-N-(5-((1-methyl-1H-pyrazol-4-yl)ethynyl)-4-(4-((2,2,2-trifluoroethyl)amino)piperidin-1-yl)pyridin-2-yl)pyrimidin-4-amine;

(136) 2-(1-(Cyclopropylsulfonyl)-1H-pyrazol-4-yl)-N-(4-(4-((2-fluoroethyl)amino)piperidin-1-yl)-5-((1-(tetrahydro-2H-pyran-4-yl)-1H-pyrazol-4-yl)ethynyl)pyridin-2-yl)pyrimidin-4-amine;

(137) 2-((1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)amino)ethan-1-ol;

(138) $N^1$-(1-(2-((2-(1-(Cyclopropylsulfonyl)-1H-pyrazol-4-yl)pyrimidin-4-yl)amino)-5-((1-(tetrahydro-2H-pyran-4-yl)-1H-pyrazol-4-yl)ethynyl)pyridin-4-yl)piperidin-4-yl)-$N^2,N^2$-dimethylethane-1,2-diamine;

(139) 1-(4-(4-((6-((2-(1-(Cyclopropylsulfonyl)-1H-pyrazol-4-yl)pyrimidin-4-yl)amino)-4-(4-((2-(dimethylamino)ethyl)amino)piperidin-1-yl)pyridin-3-yl)ethynyl)-1H-pyrazol-1-yl)piperidin-1-yl)ethan-1-one;

(140) 2-(1-(Cyclopropylsulfonyl)-1H-pyrazol-4-yl)-N-(5-((1-methyl-1H-pyrazol-3-yl)ethynyl)-4-(4-(methylamino)piperidin-1-yl)pyridin-2-yl)pyrimidin-4-amine;

(141) 2-(1-(Cyclopropylsulfonyl)-1H-pyrazol-4-yl)-N-(4-(4-((2-fluoroethyl)amino)piperidin-1-yl)-5-((1-methyl-1H-pyrazol-3-yl)ethynyl)pyridin-2-yl)pyrimidin-4-amine;

(142) $N^1$-(1-(2-((2-(1-(Cyclopropylsulfonyl)-1H-pyrazol-4-yl)pyrimidin-4-yl)amino)-5-((1-methyl-1H-pyrazol-3-yl)ethynyl)pyridin-4-yl)piperidin-4-yl)-$N^2,N^2$-dimethylethane-1,2-diamine;

(143) $N^1$-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)-$N^2,N^2$-dimethylethane-1,2-diamine;

(144) 2-(1-(Cyclopropylsulfonyl)-1H-pyrazol-4-yl)-N-(5-((1-(2-(dimethylamino)ethyl)-1H-pyrazol-4-yl)ethynyl)-4-(4-((2-fluoroethyl)amino)piperidin-1-yl)pyridin-2-yl)pyrimidin-4-amine;

(145) 2-(1-(Cyclopropylsulfonyl)-1H-pyrazol-4-yl)-N-(5-((1-(3-(dimethylamino)propyl)-1H-pyrazol-4-yl)ethynyl)-4-(4-((2-fluoroethyl)amino)piperidin-1-yl)pyridin-2-yl)pyrimidin-4-amine;

(146) 2-(1-(Cyclopropylsulfonyl)-1H-pyrazol-4-yl)-N-(5-((1-methyl-1H-pyrazol-4-yl)ethynyl)-4-(4-methyl-4-((methylamino)methyl)piperidin-1-yl)pyridin-2-yl)pyrimidin-4-amine;

(147) (1-(2-((2-(1-(Cyclopropylsulfonyl)-1H-pyrazol-4-yl)pyrimidin-4-yl)amino)-5-((1-(1-methylpiperidin-4-yl)-1H-pyrazol-4-yl)ethynyl)pyridin-4-yl)-4-methylpiperidin-4-yl)methanol;

(148) (1-(2-((2-(1-(Cyclopropylsulfonyl)-1H-pyrazol-4-yl)pyrimidin-4-yl)amino)-5-((1-(1-methylazetidin-3-yl)-1H-pyrazol-4-yl)ethynyl)pyridin-4-yl)-4-methylpiperidin-4-yl)methanol;

(149) (1-(2-((2-(1-(Cyclopropylsulfonyl)-1H-pyrazol-4-yl)pyrimidin-4-yl)amino)-5-((4,5,6,7-tetrahydropyrazolo[1,5-a]pyrazin-3-yl)ethynyl)pyridin-4-yl)-4-methylpiperidin-4-yl)methanol;

(150) (1-(2-((2-(1-(Cyclopropylsulfonyl)-1H-pyrazol-4-yl)pyrimidin-4-yl)amino)-5-((5-methyl-4,5,6,7-tetrahydropyrazolo[1,5-a]pyrazin-3-yl)ethynyl)pyridin-4-yl)-4-methylpiperidin-4-yl)methanol;

(151) (1-(2-((2-(1-(Cyclopropylsulfonyl)-1H-pyrazol-4-yl)pyrimidin-4-yl)amino)-5-((5-(2,2-difluoroethyl)-4,5,6,7-tetrahydropyrazolo[1,5-a]pyrazin-3-yl)ethynyl)pyridin-4-yl)-4-methylpiperidin-4-yl)methanol;

(152) 7-(2-((2-(1-(Cyclopropylsulfonyl)-1H-pyrazol-4-yl)pyrimidin-4-yl)amino)-5-((1-(3-(dimethylamino)propyl)-1H-pyrazol-4-yl)ethynyl)pyridin-4-yl)-2-methyl-7-azaspiro[3.5]nonan-2-ol;

(153) 2-(1-(Cyclopropylsulfonyl)-1H-pyrazol-4-yl)-N-(5-((1-methyl-1H-pyrazol-4-yl)ethynyl)-4-(4-(2-(methylamino)ethyl)piperidin-1-yl)pyridin-2-yl)pyrimidin-4-amine;

(154) 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-2-yl)pyridin-2-yl)pyrimidin-4-amine;

(155) 2-(1-(Cyclopropylsulfonyl)-1H-pyrazol-4-yl)-N-(5-((1-methyl-1H-pyrazol-4-yl)ethynyl)-4-(2,7-diazaspiro[3.5]nonan-2-yl)pyridin-2-yl)pyrimidin-4-amine;

(156) 2-(1-(Cyclopropylsulfonyl)-1H-pyrazol-4-yl)-N-(5-((1-methyl-1H-pyrazol-4-yl)ethynyl)-4-(2,8-diazaspiro[4.5]decan-8-yl)pyridin-2-yl)pyrimidin-4-amine;

(157) (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(158) (1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)-1-methylcyclohexan-1-ol;

(159) (1R,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(160) (1S,3R)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(161) (1S,3S)-3-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexan-1-ol;

(162) 2-((1s,4s)-4-((2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)amino)cyclohexyl)propan-2-ol;

(163) (1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexan-1-ol;

(164) (1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-yl)methanol;

(165) (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)cyclohexan-1-ol;

(166) (1s,4s)-4-((2-((2-(1-(Cyclopropylsulfonyl)-1H-pyrazol-4-yl)pyrimidin-4-yl)amino)-5-(3-morpholinoprop-1-yn-1-yl)pyridin-4-yl)amino)-1-methylcyclohexan-1-ol;

(167) (1s,4s)-4-((2-((2-(1-(Cyclopropylsulfonyl)-1H-pyrazol-4-yl)pyrimidin-4-yl)amino)-5-((1-methyl-1,2,4-triazol-3-yl)ethynyl)pyridin-4-yl)amino)cyclohexan-1-ol;

(168) (1S,3R)-3-((2-((2-(1-(Cyclopropylsulfonyl)-1H-pyrazol-4-yl)pyrimidin-4-yl)amino)-5-((5-ethylthiazol-2-yl)ethynyl)pyridin-4-yl)amino)cyclohexan-1-ol;

(169) (1S,3R)-3-((5-((3-Aminophenyl)ethynyl)-2-((2-(1-(cyclopropylsulfonyl)-1H-pyrazol-4-yl)pyrimidin-4-yl)amino)pyridin-4-yl)amino)cyclohexan-1-ol;

(170) (1S,3R)-3-((2-((2-(1-(Cyclopropylsulfonyl)-1H-pyrazol-4-yl)pyrimidin-4-yl)amino)-5-((5-methylpyrazin-2-yl)ethynyl)pyridin-4-yl)amino)cyclohexan-1-ol;

(171) (1s,4s)-4-((2-((2-(1-(Cyclopropylsulfonyl)-1H-pyrazol-4-yl)pyrimidin-4-yl)amino)-5-(3-(pyrrolidin-1-yl)prop-1-yn-1-yl)pyridin-4-yl)amino)cyclohexan-1-ol;

(172) (1s,4s)-4-((2-((2-(1-(Cyclopropylsulfonyl)-1H-pyrazol-4-yl)pyrimidin-4-yl)amino)-5-((4-((2-morpholinoethyl)amino)phenyl)ethynyl)pyridin-4-yl)amino)cyclohexan-1-ol;

(173) (1s,4s)-4-((2-((2-(1-(Cyclopropylsulfonyl)-1H-pyrazol-4-yl)pyrimidin-4-yl)amino)-5-((3-((2-morpholinoethyl)amino)phenyl)ethynyl)pyridin-4-yl)amino)cyclohexan-1-ol;

(174) 1-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)cyclohexan-1-ol;

(175) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclohexan-1-ol;

(176) (1s,4s)-4-((2-((2-(1-(Cyclopropylsulfonyl)-1H-pyrazol-4-yl)pyrimidin-4-yl)amino)-5-((1-hydroxycyclopentyl)ethynyl)pyridin-4-yl)amino)cyclohexan-1-ol;

(177) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclopentan-1-ol;

(178) (1s,4s)-4-((2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)amino)cyclohexan-1-ol;

(179) (1-(2-((2-(1-(Cyclopropylsulfonyl)-1H-pyrazol-4-yl)pyrimidin-4-yl)amino)-5-((tetrahydro-2H-pyran-4-yl)ethynyl)pyridin-4-yl)-4-methylpiperidin-4-yl)methanol;

(180) (1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methylpiperidin-4-yl)methanol;

(181) (1s,4s)-4-((2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)amino)cyclohexan-1-ol;

(182) (1-(2-((2-(1-(Cyclopropylsulfonyl)-1H-pyrazol-4-yl)pyrimidin-4-yl)amino)-5-((1-methylpiperidin-4-yl)ethynyl)pyridin-4-yl)-4-methylpiperidin-4-yl)methanol;

(183) (1-(2-((2-(1-(Cyclopropylsulfonyl)-1H-pyrazol-4-yl)pyrimidin-4-yl)amino)-5-((4-methyltetrahydro-2H-pyran-4-yl)ethynyl)pyridin-4-yl)-4-methylpiperidin-4-yl)methanol;

(184) (1s,4s)-4-((2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)amino)cyclohexan-1-ol;

(185) (1-(2-((2-(1-(Cyclopropylsulfonyl)-1H-pyrazol-4-yl)pyrimidin-4-yl)amino)-5-((5-(morpholinomethyl)pyridin-2-yl)ethynyl)pyridin-4-yl)-4-methylpiperidin-4-yl)methanol;

(186) (1s,4s)-4-((2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)amino)cyclohexan-1-ol;

(187) (1-(2-((2-(1-(Cyclopropylsulfonyl)-1H-pyrazol-4-yl)pyrimidin-4-yl)amino)-5-((6-(morpholinomethyl)pyridin-3-yl)ethynyl)pyridin-4-yl)-4-methylpiperidin-4-yl)methanol;

(188) (1s,4s)-4-((2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)amino)cyclohexan-1-ol;

(189) (1-(2-((2-(1-(Cyclopropylsulfonyl)-1H-pyrazol-4-yl)pyrimidin-4-yl)amino)-5-((2-(morpholinomethyl)thiazol-4-yl)ethynyl)pyridin-4-yl)-4-methylpiperidin-4-yl)methanol;

(190) (1s,4s)-4-((2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)amino)cyclohexan-1-ol;

(191) (1-(2-((2-(1-(Cyclopropylsulfonyl)-1H-pyrazol-4-yl)pyrimidin-4-yl)amino)-5-((5-(morpholinomethyl)thiophen-2-yl)ethynyl)pyridin-4-yl)-4-methylpiperidin-4-yl)methanol;

(192) (1-(2-((2-(1-(Cyclopropylsulfonyl)-1H-pyrazol-4-yl)pyrimidin-4-yl)amino)-5-((2-(morpholinomethyl)thiazol-5-yl)ethynyl)pyridin-4-yl)-4-methylpiperidin-4-yl)methanol;

(193) (1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-yl)methanol;

(194) (1s,4s)-4-((2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)amino)cyclohexan-1-ol;

(195) 4-((6-((2-(1-(cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-4-ol;

(196) 4-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)tetrahydro-2H-pyran-4-ol;

(197) (1-(2-((2-(1-(Cyclopropylsulfonyl)-1H-pyrazol-4-yl)pyrimidin-4-yl)amino)-5-((tetrahydrofuran-3-yl)ethynyl)pyridin-4-yl)-4-methylpiperidin-4-yl)methanol;

(198) (1s,4s)-4-((2-((2-(1-(Cyclopropylsulfonyl)-1H-pyrazol-4-yl)pyrimidin-4-yl)amino)-5-((tetrahydrofuran-3-yl)ethynyl)pyridin-4-yl)amino)cyclohexan-1-ol;

(199) $N^2$-(2-(1-(Cyclopropylsulfonyl)-1H-pyrazol-4-yl)pyrimidin-4-yl)-$N^4$-isopropyl-5-((2-methylthiazol-4-yl)ethynyl)pyridine-2,4-diamine;

(200) $N^2$-(2-(1-(cyclopropylsulfonyl)-1H-pyrazol-4-yl)pyrimidin-4-yl)-5-((2-(fluoromethyl)thiazol-4-yl)ethynyl)-$N^4$-isopropylpyridine-2,4-diamine;

(201) 4-(3-(6-((2-(1-(Cyclopropylsulfonyl)-1H-pyrazol-4-yl)pyrimidin-4-yl)amino)-4-(isopropylamino)pyridin-3-yl)prop-2-yn-1-yl)thiomorpholine 1,1-dioxide;

(202) $N^2$-(2-(1-(Cyclopropylsulfonyl)-1H-pyrazol-4-yl)pyrimidin-4-yl)-$N^4$-isopropyl-5-(3-morpholinoprop-1-yn-1-yl)pyridine-2,4-diamine;

(203) $N^2$-(2-(1-(Cyclopropylsulfonyl)-1H-pyrazol-4-yl)pyrimidin-4-yl)-$N^4$-isopropyl-5-(3-(pyrrolidin-1-yl)prop-1-yn-1-yl)pyridine-2,4-diamine;

(204) 4-(6-((2-(1-(Cyclopropylsulfonyl)-1H-pyrazol-4-yl)pyrimidin-4-yl)amino)-4-(isopropylamino)pyridin-3-yl)-2-methylbut-3-yn-2-ol;

(205) $N^2$-(2-(1-(Cyclopropylsulfonyl)-1H-pyrazol-4-yl)pyrimidin-4-yl)-5-((2-cyclopropylthiazol-4-yl)ethynyl)-$N^4$-isopropylpyridine-2,4-diamine;

(206) $N^2$-(2-(1-(Cyclopropylsulfonyl)-1H-pyrazol-4-yl)pyrimidin-4-yl)-$N^4$-isopropyl-5-((tetrahydro-2H-pyran-4-yl)ethynyl)pyridine-2,4-diamine;

(207) N-(5-(6-((2-(1-(Cyclopropylsulfonyl)-1H-pyrazol-4-yl)pyrimidin-4-yl)amino)-4-(isopropylamino)pyridin-3-yl)pent-4-yn-1-yl)morpholine-4-carboxamide;

(208) 6-(6-((2-(1-(Cyclopropylsulfonyl)-1H-pyrazol-4-yl)pyrimidin-4-yl)amino)-4-(isopropylamino)pyridin-3-yl)-1-morpholinohex-5-yn-1-one;

(209) N-(6-(6-((2-(1-(Cyclopropylsulfonyl)-1H-pyrazol-4-yl)pyrimidin-4-yl)amino)-4-(isopropylamino)pyridin-3-yl)hex-5-yn-1-yl)morpholine-4-carboxamide;

(210) 7-(6-((2-(1-(Cyclopropylsulfonyl)-1H-pyrazol-4-yl)pyrimidin-4-yl)amino)-4-(isopropylamino)pyridin-3-yl)-1-morpholinohept-6-yn-1-one;

(2H) 1-(2-((2-(1-(Cyclopropylsulfonyl)-1H-pyrazol-4-yl)pyrimidin-4-yl)amino)-5-((2-methylthiazol-4-yl)ethynyl)pyridin-4-yl)piperidin-4-ol;

(212) 1-(2-((2-(1-(Cyclopropylsulfonyl)-1H-pyrazol-4-yl)pyrimidin-4-yl)amino)-5-((2-(fluoromethyl)thiazol-4-yl)ethynyl)pyridin-4-yl)piperidin-4-ol;

(213) 1-(2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)piperidin-4-ol;

(214) 1-(2-((2-(1-(Cyclopropylsulfonyl)-1H-pyrazol-4-yl)pyrimidin-4-yl)amino)-5-((1-methyl-1H-1,2,4-triazol-3-yl)ethynyl)pyridin-4-yl)piperidin-4-ol;

(215) 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-4-ol;

(216) (1s,4s)-4-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclohexan-1-ol;

(217) (1s,4s)-4-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol;

(218) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)cyclohexan-1-ol;

(219) (1s,4s)-4-((2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)amino)cyclohexan-1-ol;

(220) (1s,4s)-4-((2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)amino)-1-methylcyclohexan-1-ol;

(221) 2-(4-((6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)ethynyl)-1H-pyrazol-1-yl)-N, N-dimethylacetamide;

(222) (1S,3S)-3-((2-((2-(1-(Cyclopropylsulfonyl)-1H-pyrazol-4-yl)pyrimidin-4-yl)amino)-5-((2-methylthiazol-4-yl)ethynyl)pyridin-4-yl)amino)cyclopentan-1-ol;

(223) (1S,3R)-3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)cyclopentan-1-ol;

(224) 3-((2-((2-(1-(Cyclopropylsulfonyl)-1H-pyrazol-4-yl)pyrimidin-4-yl)amino)-5-((1-methyl-1H-imidazol-4-yl)ethynyl)pyridin-4-yl)amino)-2,2-dimethylpropan-1-ol;

(225) (1S,3S)-3-((2-((2-(1-(Cyclopropylsulfonyl)-1H-pyrazol-4-yl)pyrimidin-4-yl)amino)-5-(thiophen-3-ylethynyl)pyridin-4-yl)amino)cyclohexan-1-ol;

(226) 2-(1-(Cyclopropylsulfonyl)-1H-pyrazol-4-yl)-N-(4-(4-(4-methylpiperazin-1-yl)piperidin-1-yl)-5-(thiophen-3-ylethynyl)pyridin-2-yl)pyrimidin-4-amine;

(227) 1-(2-((2-(1-(Cyclopropylsulfonyl)-1H-pyrazol-4-yl)pyrimidin-4-yl)amino)-5-((6-morpholinopyridin-3-yl)ethynyl)pyridin-4-yl)piperidin-3-ol;

(228) (S)-1-(2-((2-(1-(Cyclopropylsulfonyl)-1H-pyrazol-4-yl)pyrimidin-4-yl)amino)-5-(thiophen-3-ylethynyl)pyridin-4-yl)piperidin-3-ol;

(229) 1-(2-((2-(1-(Cyclopropylsulfonyl)-1H-pyrazol-4-yl)pyrimidin-4-yl)amino)-5-(thiophen-3-ylethynyl)pyridin-4-yl)-3,3-dimethylpiperidin-4-ol;

(230) (1s,4s)-4-((2-((2-(1-(Cyclopropylsulfonyl)-1H-pyrazol-4-yl)pyrimidin-4-yl)amino)-5-(3-methyl-3-morpholinobut-1-yn-1-yl)pyridin-4-yl)amino)cyclohexan-1-ol;

(231) (1-(2-((2-(1-(Cyclopropylsulfonyl)-1H-pyrazol-4-yl)pyrimidin-4-yl)amino)-5-((1-((tetrahydro-2H-pyran-4-yl)methyl)-1H-pyrazol-4-yl)ethynyl)pyridin-4-yl)-4-methylpiperidin-4-yl)methanol;

(232) (1-(2-((2-(1-(Cyclopropylsulfonyl)-1H-pyrazol-4-yl)pyrimidin-4-yl)amino)-5-((1-(2-morpholinoethyl)-1H-pyrazol-4-yl)ethynyl)pyridin-4-yl)-4-methylpiperidin-4-yl)methanol;

(233) 2-(1-(Cyclopropylsulfonyl)-1H-pyrazol-4-yl)-N-(4-(1-methyl-1H-pyrazol-4-yl)-5-((1-methyl-1H-pyrazol-4-yl)ethynyl)pyridin-2-yl)pyrimidin-4-amine;

(234) 2-(1-(Cyclopropylsulfonyl)-1H-pyrazol-4-yl)-N-(5-((1-(2-fluoroethyl)-1H-pyrazol-4-yl)ethynyl)-4-(1-methyl-1H-pyrazol-4-yl)pyridin-2-yl)pyrimidin-4-amine;

(235) N-(4-(1-Cyclopropyl-1H-pyrazol-4-yl)-5-((1-methyl-1H-pyrazol-4-yl)ethynyl)pyridin-2-yl)-2-(1-(cyclopropylsulfonyl)-1H-pyrazol-4-yl)pyrimidin-4-amine;

(236) N-(4-(1-cyclopropyl-1H-pyrazol-4-yl)-5-((1-isopropyl-1H-pyrazol-4-yl)ethynyl)pyridin-2-yl)-2-(1-(cyclopropylsulfonyl)-1H-pyrazol-4-yl)pyrimidin-4-amine;

(237) N-(4-(1-Cyclopropyl-1H-pyrazol-4-yl)-5-((1-(2-fluoroethyl)-1H-pyrazol-4-yl)ethynyl)pyridin-2-yl)-2-(1-(cyclopropylsulfonyl)-1H-pyrazol-4-yl)pyrimidin-4-amine;

(238) 2-(1-(Cyclopropylsulfonyl)-1H-pyrazol-4-yl)-N-(4-(((1 r,4r)-4-((dimethylamino)methyl)cyclohexyl)methoxy)-5-((2-methylthiazol-4-yl)ethynyl)pyridin-2-yl)pyrimidin-4-amine;

(239) 4-(3-(6-((2-(1-(Cyclopropylsulfonyl)-1H-pyrazol-4-yl)pyrimidin-4-yl)amino)-4-(((1 r,4r)-4-((dimethylamino)methyl)cyclohexyl)methoxy)pyridin-3-yl)prop-2-yn-1-yl)thiomorpholine 1,1-dioxide;

(240) 2-(1-(Cyclopropylsulfonyl)-1H-pyrazol-4-yl)-N-(4-(((1 r,4r)-4-((dimethylamino)methyl)cyclohexyl)methoxy)-5-(3-(pyrrolidin-1-yl)prop-1-yn-1-yl)pyridin-2-yl)pyrimidin-4-amine;

(241) (1-(2-((2-(1-(Cyclopropylsulfonyl)-1H-pyrazol-4-yl)pyrimidin-4-yl)amino)-5-((1-((tetrahydro-2H-pyran-3-yl)methyl)-1H-pyrazol-4-yl)ethynyl)pyridin-4-yl)-4-methylpiperidin-4-yl)methanol;

(242) (1-(5-((1-((1,4-Dioxan-2-yl)methyl)-1H-pyrazol-4-yl)ethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(243) (1-(2-((2-(1-(Cyclopropylsulfonyl)-1H-pyrazol-4-yl)pyrimidin-4-yl)amino)-5-((1-((tetrahydrofuran-3-yl)methyl)-1H-pyrazol-4-yl)ethynyl)pyridin-4-yl)-4-methylpiperidin-4-yl)methanol;

(244) (1-(2-((2-(1-(Cyclopropylsulfonyl)-1H-pyrazol-4-yl)pyrimidin-4-yl)amino)-5-((1-(tetrahydrofuran-3-yl)-1H-pyrazol-4-yl)ethynyl)pyridin-4-yl)-4-methylpiperidin-4-yl)methanol;

(245) (1-(2-((2-(1-(Cyclopropylsulfonyl)-1H-pyrazol-4-yl)pyrimidin-4-yl)amino)-5-((1-(oxetan-3-yl)-1H-pyrazol-4-yl)ethynyl)pyridin-4-yl)-4-methylpiperidin-4-yl)methanol;

(246) (1-(2-((2-(1-(Cyclopropylsulfonyl)-1H-pyrazol-4-yl)pyrimidin-4-yl)amino)-5-((trimethylsilyl)ethynyl)pyridin-4-yl)-4-methylpiperidin-4-yl)methanol;

(247) (1-(2-((2-(1-(Cyclopropylsulfonyl)-1H-pyrazol-4-yl)pyrimidin-4-yl)amino)-5-ethynylpyridin-4-yl)-4-methylpiperidin-4-yl)methanol;

(248) (1-(2-((2-(1-(Cyclopropylsulfonyl)-1H-pyrazol-4-yl)pyrimidin-4-yl)amino)-5-((5-((3,3-difluoroazetidin-1-yl)methyl)-1-(2,2-difluoroethyl)-1H-pyrrol-3-yl)ethynyl)pyridin-4-yl)-4-methylpiperidin-4-yl)methanol;

(249) (1-(2-((2-(1-(Cyclopropylsulfonyl)-1H-pyrazol-4-yl)pyrimidin-4-yl)amino)-5-((1-(2,2-difluoroethyl)-1H-pyrrolo[3,2-c]pyridin-3-yl)ethynyl)pyridin-4-yl)-4-methylpiperidin-4-yl)methanol;

(250) (1-(5-(Cyclopropylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(251) (1-(5-(Cyclopentylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(252) (1-(5-(Cyclohexylethynyl)-2-((2-(1-(cyclopropylsulfonyl)-1H-pyrazol-4-yl)pyrimidin-4-yl)amino)pyridin-4-yl)-4-methylpiperidin-4-yl)methanol;

(253) (1-(2-((2-(1-(Cyclopropylsulfonyl)-1H-pyrazol-4-yl)pyrimidin-4-yl)amino)-5-((4-(morpholinomethyl)phenyl)ethynyl)pyridin-4-yl)-4-methylpiperidin-4-yl)methanol;

(254) (1-(2-((2-(1-(Cyclopropylsulfonyl)-1H-pyrazol-4-yl)pyrimidin-4-yl)amino)-5-((4-((dimethylamino)methyl)phenyl)ethynyl)pyridin-4-yl)-4-methylpiperidin-4-yl)methanol;

(255) (1-(2-((2-(1-(Cyclopropylsulfonyl)-1H-pyrazol-4-yl)pyrimidin-4-yl)amino)-5-((3-((dimethylamino)methyl)phenyl)ethynyl)pyridin-4-yl)-4-methylpiperidin-4-yl)methanol;

(256) (1-(2-((2-(1-(Cyclopropylsulfonyl)-1H-pyrazol-4-yl)pyrimidin-4-yl)amino)-5-(phenylethynyl)pyridin-4-yl)-4-methylpiperidin-4-yl)methanol;

(257) (1-(2-((2-(1-(Cyclopropylsulfonyl)-1H-pyrazol-4-yl)pyrimidin-4-yl)amino)-5-((2-fluorophenyl)ethynyl)pyridin-4-yl)-4-methylpiperidin-4-yl)methanol;

(258) (1-(2-((2-(1-(Cyclopropylsulfonyl)-1H-pyrazol-4-yl)pyrimidin-4-yl)amino)-5-(pyridin-4-ylethynyl)pyridin-4-yl)-4-methylpiperidin-4-yl)methanol;

(259) (1-(2-((2-(1-(Cyclopropylsulfonyl)-1H-pyrazol-4-yl)pyrimidin-4-yl)amino)-5-(pyridin-2-ylethynyl)pyridin-4-yl)-4-methylpiperidin-4-yl)methanol;

(260) (1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-yl)methanol;

(261) (3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(262) 4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylbenzamide;

(263) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(morpholino)methanone;

(264) 6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)-N,N-dimethylpicolinamide;

(265) (6-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyridin-2-yl)(morpholino)methanone;

(266) 2-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutyl)propan-2-ol;

(267) (1-(2-((2-(1-(2,2-Difluoroethyl)-1H-pyrazol-4-yl)pyrimidin-4-yl)amino)-5-((1-(trifluoromethyl)-1H-pyrazol-4-yl)ethynyl)pyridin-4-yl)-4-methylpiperidin-4-yl)methanol;

(268) (4-Methyl-1-(2-((2-(1-(methylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)methanol;

(269) (1-(2-((2-(6-Fluoropyridin-3-yl)pyrimidin-4-yl)amino)-5-((1-(trifluoromethyl)-1H-pyrazol-4-yl)ethynyl)pyridin-4-yl)-4-methylpiperidin-4-yl)methanol;

(270) (4-Methyl-1-(5-((1-methyl-1H-pyrazol-4-yl)ethynyl)-2-((2-((2-(methylsulfonyl)phenyl)amino)pyrimidin-4-yl)amino)pyridin-4-yl)piperidin-4-yl)methanol;

(271) (1-(5-((1-(Difluoromethyl)-1H-pyrazol-4-yl)ethynyl)-2-((2-((2-(methylsulfonyl)phenyl)amino)pyrimidin-4-yl)amino)pyridin-4-yl)-4-methylpiperidin-4-yl)methanol;

(272) 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N,3-trimethyl-1H-pyrazole-1-sulfonamide;

(273) 4-(4-((4-(4-(Hydroxymethyl)-4-methylpiperidin-1-yl)-5-((1-(trifluoromethyl)-1H-pyrazol-4-yl)ethynyl)pyridin-2-yl)amino)pyrimidin-2-yl)-N,N-dimethyl-1H-pyrazole-1-sulfonamide;

(274) 4-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)but-3-yn-1-ol;

(275) (1-(2-((2-(1-(Cyclopropylsulfonyl)-1H-pyrazol-4-yl)pyrimidin-4-yl)amino)-5-(4,4,4-trifluorobut-1-yn-1-yl)pyridin-4-yl)-4-methylpiperidin-4-yl)methanol;

(276) (1-(2-((2-(1-(Cyclopropylsulfonyl)-1H-pyrazol-4-yl)pyrimidin-4-yl)amino)-5-(4-fluorobut-1-yn-1-yl)pyridin-4-yl)-4-methylpiperidin-4-yl)methanol;

(277) (1-(5-(But-3-en-1-yn-1-yl)-2-((2-(1-(cyclopropylsulfonyl)-1H-pyrazol-4-yl)pyrimidin-4-yl)amino)pyridin-4-yl)-4-methylpiperidin-4-yl)methanol;

(278) (1-(2-((2-(1-(Cyclopropylsulfonyl)-1H-pyrazol-4-yl)pyrimidin-4-yl)amino)-5-((6-((dimethylamino)methyl)pyridin-3-yl)ethynyl)pyridin-4-yl)-4-methylpiperidin-4-yl)methanol;

(2791 (1-(2-((2-(1-(Cyclopropylsulfonyl)-1H-pyrazol-4-yl)pyrimidin-4-yl)amino)-5-((6-((4-methylpiperazin-1-yl)methyl)pyridin-3-yl)ethynyl)pyridin-4-yl)-4-methylpiperidin-4-yl)methanol;

(280) 1-(2-((2-(1-(Cyclopropylsulfonyl)-1H-pyrazol-4-yl)pyrimidin-4-yl)amino)-5-(pyridin-3-ylethynyl)pyridin-4-yl)-4-methylpiperidin-4-ol;

(281) 2-(1-(Cyclopropylsulfonyl)-1H-pyrazol-4-yl)-N-(4-(4-methoxy-4-methylpiperidin-1-yl)-5-(pyridin-3-ylethynyl)pyridin-2-yl)pyrimidin-4-amine;

(282) 2-(1-(Cyclopropylsulfonyl)-1H-pyrazol-4-yl)-N-(5-(pyridin-3-ylethynyl)-4-(1-oxa-8-azaspiro[4.5]decan-8-yl)pyridin-2-yl)pyrimidin-4-amine;

(283) 2-(1-(Cyclopropylsulfonyl)-1H-pyrazol-4-yl)-N-(5-(pyridin-3-ylethynyl)-4-(1-oxa-7-azaspiro[3.5]nonan-7-yl)pyridin-2-yl)pyrimidin-4-amine;

(284) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)-2-methylpent-4-yn-2-ol;

(285) (1-(2-((2-(1-(Cyclopropylsulfonyl)-1H-pyrazol-4-yl)pyrimidin-4-yl)amino)-5-(4-morpholinobut-1-yn-1-yl)pyridin-4-yl)-4-methylpiperidin-4-yl)methanol;

(286) 3-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)oxetan-3-ol;

(287) 5-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)pent-4-yn-2-ol;

(288) N-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)-2,2,2-trifluoroacetamide;

(289) 4-(3-(6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)prop-2-yn-1-yl)thiomorpholine 1,1-dioxide;

(290) (1-(2-((2-(1-(Cyclopropylsulfonyl)-1H-pyrazol-4-yl)pyrimidin-4-yl)amino)-5-((3-(trifluoromethyl)-1H-pyrazol-5-yl)ethynyl)pyridin-4-yl)-4-methylpiperidin-4-yl)methanol;

(291) (1-(2-((2-(1-(Cyclopropylsulfonyl)-1H-pyrazol-4-yl)pyrimidin-4-yl)amino)-5-((4-(trifluoromethyl)thiazol-2-yl)ethynyl)pyridin-4-yl)-4-methylpiperidin-4-yl)methanol;

(292) (1-(2-((2-(1-(Cyclopropylsulfonyl)-1H-pyrazol-4-yl)pyrimidin-4-yl)amino)-5-((2-(trifluoromethyl)thiazol-5-yl)ethynyl)pyridin-4-yl)-4-methylpiperidin-4-yl)methanol;

(293) 2-(1-(Cyclopropylsulfonyl)-1H-pyrazol-4-yl)-N-(4-(4-((dimethylamino)methyl)-4-fluoropiperidin-1-yl)-5-((1-methyl-1H-pyrazol-4-yl)ethynyl)pyridin-2-yl)pyrimidin-4-amine;

(294) 2-(1-(Cyclopropylsulfonyl)-1H-pyrazol-4-yl)-N-(4-(4-(2-(dimethylamino)ethyl)piperidin-1-yl)-5-((1-methyl-1H-pyrazol-4-yl)ethynyl)pyridin-2-yl)pyrimidin-4-amine;

(295) 2-(1-(Cyclopropylsulfonyl)-1H-pyrazol-4-yl)-N-(4-(4-((dimethylamino)methyl)piperidin-1-yl)-5-((1-methyl-1H-pyrazol-4-yl)ethynyl)pyridin-2-yl)pyrimidin-4-amine;

(296) 2-(1-(Cyclopropylsulfonyl)-1H-pyrazol-4-yl)-N-(4-(4-((dimethylamino)methyl)-4-methylpiperidin-1-yl)-5-((1-methyl-1H-pyrazol-4-yl)ethynyl)pyridin-2-yl)pyrimidin-4-amine;

(297) 2-(1-(Cyclopropylsulfonyl)-1H-pyrazol-4-yl)-N-(5-((1-methyl-1H-pyrazol-4-yl)ethynyl)-4-(2-methyl-2,8-diazaspiro[4.5]decan-8-yl)pyridin-2-yl)pyrimidin-4-amine;

(298) N-(5-((1-Cyclopropyl-1H-pyrazol-4-yl)ethynyl)-4-(4-((dimethylamino)methyl)piperidin-1-yl)pyridin-2-yl)-2-(1-(cyclopropylsulfonyl)-1H-pyrazol-4-yl)pyrimidin-4-amine;

(299) N-(5-((1-Cyclopropyl-1H-pyrazol-4-yl)ethynyl)-4-(4-((dimethylamino)methyl)-4-methylpiperidin-1-yl)pyridin-2-yl)-2-(1-cyclopropylsulfonyl)-1H-pyrazol-4-yl)pyrimidin-4-amine;

(300) N-(5-((1-Cyclopropyl-1H-pyrazol-4-yl)ethynyl)-4-(4-((dimethylamino)methyl)-4-fluoropiperidin-1-yl)pyridin-2-yl)-2-(1-(cyclopropylsulfonyl)-1H-pyrazol-4-yl)pyrimidin-4-amine;

(301) 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)piperidin-1-yl)pyridin-2-yl)pyrimidin-4-amine;

(302) 2-(1-(Cyclopropylsulfonyl)-1H-pyrazol-4-yl)-N-(5-((1-(2,2-difluoroethyl)-1H-pyrazol-4-yl)ethynyl)-4-(4-((dimethylamino)methyl)-4-methylpiperidin-1-yl)pyridin-2-yl)pyrimidin-4-amine;

(303) 2-(1-(Cyclopropylsulfonyl)-1H-pyrazol-4-yl)-N-(5-((1-(2,2-difluoroethyl)-1H-pyrazol-4-yl)ethynyl)-4-(4-(2-(dimethylamino)ethyl)piperidin-1-yl)pyridin-2-yl)pyrimidin-4-amine;

(304) (1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)-1-(hydroxymethyl)cyclohexan-1-ol;

(305) (1-(2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)-4-methylpiperidin-4-yl)methanol;

(306) (1R,3S)-3-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclopentan-1-ol;

(307) (1r,4r)-4-(((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)methyl)cyclohexan-1-ol;

(308) ((1s,4s)-4-((2-((2-(1-(Cyclopropylsulfonyl)-1H-pyrazol-4-yl)pyrimidin-4-yl)amino)-5-((1-(difluoromethyl)-1H-pyrazol-4-yl)ethynyl)pyridin-4-yl)amino)cyclohexyl)methanol;

(309) 5-((1-(Cyclopropylmethyl)-1H-pyrazol-4-yl)ethynyl)-$N^2$-(2-(1-(cyclopropylsulfonyl)-1H-pyrazol-4-yl)pyrimidin-4-yl)-$N^4$-((1s,4s)-4-((dimethylamino)methyl)cyclohexyl)pyridine-2,4-diamine;

(310) $N^2$-(2-(1-(Cyclopropylsulfonyl)-1H-pyrazol-4-yl)pyrimidin-4-yl)-5-((1-(difluoromethyl)-1H-pyrazol-4-yl)ethynyl)-$N^4$-((1s,4s)-4-((dimethylamino)methyl)cyclohexyl)pyridine-2,4-diamine;

(3H) $N^2$-(2-(1-(Cyclopropylsulfonyl)-1H-pyrazol-4-yl)pyrimidin-4-yl)-5-((1-(2,2-difluoroethyl)-1H-pyrazol-4-yl)ethynyl)-$N^4$-((1s,4s)-4-((dimethylamino)methyl)cyclohexyl)pyridine-2,4-diamine;

(312) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-((1-methyl-1H-pyrazol-4-yl)ethynyl)pyridine-2,4-diamine;

(313) 5-((1-Cyclopropyl-1H-pyrazol-4-yl)ethynyl)-$N^2$-(2-(1-cyclopropylsulfonyl)-1H-pyrazol-4-yl)pyrimidin-4-yl)-$N^4$-((1s,4s)-4-((dimethylamino)methyl)cyclohexyl)pyridine-2,4-diamine;

(314) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-((1-(trifluoromethyl)-1H-pyrazol-4-yl)ethynyl)pyridine-2,4-diamine;

(315) 1-(2-((2-(1-(Cyclopropylsulfonyl)-1H-pyrazol-4-yl)pyrimidin-4-yl)amino)-5-((1-methyl-1H-pyrazol-4-yl)ethynyl)pyridin-4-yl)-4-((dimethylamino)methyl)piperidin-4-ol;

(316) 1-(5-((1-Cyclopropyl-1H-pyrazol-4-yl)ethynyl)-2-((2-(1-(cyclopropylsulfonyl)-1H-pyrazol-4-yl)pyrimidin-4-yl)amino)pyridin-4-yl)-4-((dimethylamino)methyl)piperidin-4-ol;

(317) 1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-((dimethylamino)methyl)piperidin-4-ol;

(318) 2-(1-(Cyclopropylsulfonyl)-1H-pyrazol-4-yl)-N-(5-((1-methyl-1H-pyrazol-4-yl)ethynyl)-4-(9-methyl-3,9-diazaspiro[5.5]undecan-3-yl)pyridin-2-yl)pyrimidin-4-amine;

(319) N-(5-((1-Cyclopropyl-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine;

(320) N-(5-((1-(Cyclopropylmethyl)-1H-pyrazol-4-yl)ethynyl)-4-(9-methyl-3,9-diazaspiro[5.5]undecan-3-yl)pyridin-2-yl)-2-(1-(cyclopropylsulfonyl)-1H-pyrazol-4-yl)pyrimidin-4-amine;

(321) 2-(1-(Cyclopropylsulfonyl)-1H-pyrazol-4-yl)-N-(5-((1-(difluoromethyl)-1H-pyrazol-4-yl)ethynyl)-4-(9-methyl-3,9-diazaspiro[5.5]undecan-3-yl)pyridin-2-yl)pyrimidin-4-amine;

(322) 2-(1-(Cyclopropylsulfonyl)-1H-pyrazol-4-yl)-N-(5-((1-(2,2-difluoroethyl)-1H-pyrazol-4-yl)ethynyl)-4-(9-methyl-3,9-diazaspiro[5.5]undecan-3-yl)pyridin-2-yl)pyrimidin-4-amine;

(323) (1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)-1-methylcyclohexan-1-ol;

(324) ((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)methanol;

(325) 2-((1s,4s)-4-((2-((2-(1-(Cyclopropylsulfonyl)-1H-pyrazol-4-yl)pyrimidin-4-yl)amino)-5-((1-(2,2-difluoroethyl)-1H-pyrazol-4-yl)ethynyl)pyridin-4-yl)amino)cyclohexyl)propan-2-ol;

(326) (1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)-1-methylcyclohexan-1-ol;

(327) ((1s,4s)-4-((2-((2-(1-(Cyclopropylsulfonyl)-1H-pyrazol-4-yl)pyrimidin-4-yl)amino)-5-((1-(2,2-difluorocyclopropyl)-1H-pyrazol-4-yl)ethynyl)pyridin-4-yl)amino)cyclohexyl)methanol;

(328) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-ol;

(329) 2-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)propan-2-ol;

(330) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)cyclopropan-1-ol;

(331) ((1R,5S,6r)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-6-yl)methanol;

(332) ((1R,3s,5S)-8-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-8-azabicyclo[3.2.1]octan-3-yl)methanol;

(333) ((1 S,5S)-3-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-azabicyclo[3.1.0]hexan-1-yl)methanol;

(334) 1-(1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-4-yl)ethan-1-one;

(335) 2-(1-(Cyclopropylsulfonyl)-1H-pyrazol-4-yl)-N-(4-(4-(2-(dimethylamino)ethyl)piperidin-1-yl)-5-((1-(trifluoromethyl)-1H-pyrazol-4-yl)ethynyl)pyridin-2-yl)pyrimidin-4-amine;

(336) ((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)methanol;

(337) 2-((1s,4s)-4-((2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)amino)cyclohexyl)propan-2-ol;

(338) (1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-4-fluoropiperidin-4-yl)methanol;

(339) (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol;

(340) ((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)methanol;

(341) (1 S,3S)-3-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexan-1-ol;

(342) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-fluoropiperidin-4-yl)methanol;

(343) 1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)piperidin-3-ol;

(344) (1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)-1-methylcyclohexan-1-ol;

(345) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-((1-(2,2,2-trifluoroethyl)-1H-pyrazol-4-yl)ethynyl)pyridine-2,4-diamine;

(346) 2-((1s,4s)-4-((2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)amino)cyclohexyl)propan-2-ol;

(347) 7-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-2-methyl-7-azaspiro[3.5]nonan-2-ol;

(348) (1-(2-((2-(1-(Cyclopropylsulfonyl)-1H-pyrazol-4-yl)pyrimidin-4-yl)amino)-5-((1-(2,2,2-trifluoroethyl)-1H-pyrazol-4-yl)ethynyl)pyridin-4-yl)-4-methylpiperidin-4-yl)methanol;

(349) 2-(1-(Cyclopropylsulfonyl)-1H-pyrazol-4-yl)-N-(4-(4-(2-(dimethylamino)ethyl)piperidin-1-yl)-5-((1-

(2,2,2-trifluoroethyl)-1H-pyrazol-4-yl)ethynyl)pyridin-2-yl)pyrimidin-4-amine;
(350) (1s,4s)-4-((2-((2-(1-(Cyclopropylsulfonyl)-1H-pyrazol-4-yl)pyrimidin-4-yl)amino)-5-((3-methyloxetan-3-yl)ethynyl)pyridin-4-yl)amino)cyclohexan-1-ol;
(351) 1-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)cyclobutan-1-ol;
(352) (1-(2-((2-(1-(Cyclopropylsulfonyl)-1H-pyrazol-4-yl)pyrimidin-4-yl)amino)-5-(oxetan-3-ylethynyl)pyridin-4-yl)-4-methylpiperidin-4-yl)methanol;
(353) (1s,4s)-4-((2-((2-(1-(Cyclopropylsulfonyl)-1H-pyrazol-4-yl)pyrimidin-4-yl)amino)-5-(oxetan-3-ylethynyl)pyridin-4-yl)amino)cyclohexan-1-ol;
(354) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)oxetan-3-ol;
(355) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrofuran-3-ol;
(356) 3-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)tetrahydrofuran-3-ol;
(357) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydro-2H-pyran-3-ol;
(358) (1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-yl)methanol;
(359) (1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexan-1-ol;
(360) ((1s,4s)-4-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)cyclohexyl)methanol;
(361) (1 r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)cyclohexan-1-ol;
(362) (5s,8s)-8-((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)-1-azaspiro[4.5]decan-2-one;
(363) (1 r,4r)-4-(((2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)amino)methyl)-1-methylcyclohexan-1-ol;
(364) 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methylpiperidin-4-ol;
(365) 1-(2-((2-(1-(Cyclopropylsulfonyl)-1H-pyrazol-4-yl)pyrimidin-4-yl)amino)-5-((5-(morpholinomethyl)pyrimidin-2-yl)ethynyl)pyridin-4-yl)-4-methoxypiperidin-4-ol;
(366) 2-(1-(Cyclopropylsulfonyl)-1H-pyrazol-4-yl)-N-(5-((5-(morpholinomethyl)pyrimidin-2-yl)ethynyl)-4-(1-oxa-8-azaspiro[4.5]decan-8-yl)pyridin-2-yl)pyrimidin-4-amine;
(367) 2-(1-(Cyclopropylsulfonyl)-1H-pyrazol-4-yl)-N-(5-((5-(morpholinomethyl)pyrimidin-2-yl)ethynyl)-4-(1-oxa-7-azaspiro[3.5]nonan-7-yl)pyridin-2-yl)pyrimidin-4-amine;
(368) 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methylpiperidin-4-ol;
(369) 1-(2-((2-(1-(Cyclopropylsulfonyl)-1H-pyrazol-4-yl)pyrimidin-4-yl)amino)-5-((4-((4-methylpiperazin-1-yl)methyl)phenyl)ethynyl)pyridin-4-yl)-4-methoxypiperidin-4-ol;
(370) 2-(1-(Cyclopropylsulfonyl)-1H-pyrazol-4-yl)-N-(5-((4-((4-methylpiperazin-1-yl)methyl)phenyl)ethynyl)-4-(1-oxa-7-azaspiro[3.5]nonan-7-yl)pyridin-2-yl)pyrimidin-4-amine;
(371) 1-(2-((2-(1-(Cyclopropylsulfonyl)-1H-pyrazol-4-yl)pyrimidin-4-yl)amino)-5-((1-methylpyrrolidin-3-yl)ethynyl)pyridin-4-yl)-4-methoxypiperidin-4-ol;
(372) 2-(1-(Cyclopropylsulfonyl)-1H-pyrazol-4-yl)-N-(5-((1-methylpyrrolidin-3-yl)ethynyl)-4-(1-oxa-8-azaspiro[4.5]decan-8-yl)pyridin-2-yl)pyrimidin-4-amine;
(373) 2-(1-(Cyclopropylsulfonyl)-1H-pyrazol-4-yl)-N-(5-((1-methylpyrrolidin-3-yl)ethynyl)-4-(1-oxa-7-azaspiro[3.5]nonan-7-yl)pyridin-2-yl)pyrimidin-4-amine;
(374) ((1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexyl)methanol;
(375) (1 r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)cyclohexan-1-ol;
(376) (1s,4s)-4-((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)cyclohexan-1-ol;
(377) (1 r,4r)-4-(((2-((2-(1-(Cyclopropylsulfonyl)-1H-pyrazol-4-yl)pyrimidin-4-yl)amino)-5-((tetrahydrofuran-2-yl)ethynyl)pyridin-4-yl)amino)methyl)-1-methylcyclohexan-1-ol;
(378) (1-(2-((2-(1-(Cyclopropylsulfonyl)-1H-pyrazol-4-yl)pyrimidin-4-yl)amino)-5-((tetrahydrofuran-2-yl)ethynyl)pyridin-4-yl)-4-methylpiperidin-4-yl)methanol;
(379) ((1s,4s)-4-((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)cyclohexyl)methanol;
(380) (1 r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)-1-methylcyclohexan-1-ol;
(381) ((1 r,4r)-4-(((2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)amino)methyl)cyclohexyl)methanol;
(382) 2-(1-(Cyclopropylsulfonyl)-1H-pyrazol-4-yl)-N-(4-(4-fluoro-4-((methylamino)methyl)piperidin-1-yl)-5-((1-methyl-1H-pyrazol-4-yl)ethynyl)pyridin-2-yl)pyrimidin-4-amine;

(383) 2-(1-(Cyclopropylsulfonyl)-1H-pyrazol-4-yl)-N-(4-(4-fluoro-4-(((2-fluoroethyl)amino)methyl)piperidin-1-yl)-5-((1-methyl-1H-pyrazol-4-yl)ethynyl)pyridin-2-yl)pyrimidin-4-amine;

(384) (S)-2-(1-(Cyclopropylsulfonyl)-1H-pyrazol-4-yl)-N-(4-(3-((dimethylamino)methyl)piperidin-1-yl)-5-((1-methyl-1H-pyrazol-4-yl)ethynyl)pyridin-2-yl)pyrimidin-4-amine;

(385) (S)-2-(1-(Cyclopropylsulfonyl)-1H-pyrazol-4-yl)-N-(4-(3-((dimethylamino)methyl)piperidin-1-yl)-5-((1-(2-fluoroethyl)-1H-pyrazol-4-yl)ethynyl)pyridin-2-yl)pyrimidin-4-amine;

(386) 2-(1-(Cyclopropylsulfonyl)-1H-pyrazol-4-yl)-N-(4-(3-(2-(dimethylamino)ethyl)piperidin-1-yl)-5-((1-(2-fluoroethyl)-1H-pyrazol-4-yl)ethynyl)pyridin-2-yl)pyrimidin-4-amine;

(387) ((1s,4s)-4-((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)cyclohexyl)methanol;

(388) ((1r,4r)-4-(((2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)amino)methyl)cyclohexyl)methanol;

(389) 1-(2-((2-(1-(Cyclopropylsulfonyl)-1H-pyrazol-4-yl)pyrimidin-4-yl)amino)-5-((1-(methylsulfonyl)piperidin-4-yl)ethynyl)pyridin-4-yl)-4-methylpiperidin-4-yl)methanol;

(390) ((1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexyl)methanol;

(391) (1s,4s)-4-((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)cyclohexan-1-ol;

(392) ((1r,4r)-4-(((2-((2-(1-(Cyclopropylsulfonyl)-1H-pyrazol-4-yl)pyrimidin-4-yl)amino)-5-((1-(cyclopropylsulfonyl)piperidin-4-yl)ethynyl)pyridin-4-yl)amino)methyl)cyclohexyl)methanol;

(393) ((1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexyl)methanol;

(394) (1s,4s)-4-((2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)amino)cyclohexan-1-ol;

(395) (1-(2-((2-(1-(Cyclopropylsulfonyl)-1H-pyrazol-4-yl)pyrimidin-4-yl)amino)-5-((1-(cyclopropylsulfonyl)pyrrolidin-3-yl)ethynyl)pyridin-4-yl)-4-methylpiperidin-4-yl)methanol;

(396) 2-(1-(Cyclopropylsulfonyl)-1H-pyrazol-4-yl)-N-(4-(3-(2-(dimethylamino)ethyl)piperidin-1-yl)-5-((1-methyl-1H-pyrazol-4-yl)ethynyl)pyridin-2-yl)pyrimidin-4-amine;

(397) ((1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexyl)methanol;

(398) (1 r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexan-1-ol;

(399) (1s,4s)-4-((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)cyclohexan-1-ol;

(400) ((1r,4r)-4-(((2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)amino)methyl)cyclohexyl)methanol;

(401) (1-(2-((2-(1-(Cyclopropylsulfonyl)-1H-pyrazol-4-yl)pyrimidin-4-yl)amino)-5-((1-(methylsulfonyl)pyrrolidin-3-yl)ethynyl)pyridin-4-yl)-4-methylpiperidin-4-yl)methanol;

(402) ((1s,4s)-4-((2-((2-(1-(Cyclopropylsulfonyl)-1H-pyrazol-4-yl)pyrimidin-4-yl)amino)-5-((1-methylcyclopropyl)ethynyl)pyridin-4-yl)amino)cyclohexyl)methanol;

(403) (1 r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexan-1-ol;

(404) 1-(2-((2-(1-(Cyclopropylsulfonyl)-1H-pyrazol-4-yl)pyrimidin-4-yl)amino)-5-((1-methylcyclopropyl)ethynyl)pyridin-4-yl)-4-methylpiperidin-4-ol;

(405) ((1r,4r)-4-(((2-((2-(1-(Cyclopropylsulfonyl)-1H-pyrazol-4-yl)pyrimidin-4-yl)amino)-5-((1-methylcyclopropyl)ethynyl)pyridin-4-yl)amino)methyl)cyclohexyl)methanol;

(406) 2-(1-(Cyclopropylsulfonyl)-1H-pyrazol-4-yl)-N-(4-(4-((dimethylamino)methyl)-4-methylpiperidin-1-yl)-5-((1-methylcyclopropyl)ethynyl)pyridin-2-yl)pyrimidin-4-amine;

(407) 2-(1-(Cyclopropylsulfonyl)-1H-pyrazol-4-yl)-N-(4-(4-(2-(dimethylamino)ethyl)piperidin-1-yl)-5-((1-methylcyclopropyl)ethynyl)pyridin-2-yl)pyrimidin-4-amine;

(408) 1-(3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)pyrrolidin-1-yl)-2,2,2-trifluoroethan-1-one;

(409) 1-(3-((6-((2-(1-(Cyclopropylsulfonyl)-1H-pyrazol-4-yl)pyrimidin-4-yl)amino)-4-((((1 r,4r)-4-hydroxycyclohexyl)methyl)amino)pyridin-3-yl)ethynyl)pyrrolidin-1-yl)-2,2,2-trifluoroethan-1-one;

(410) 1-(3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)pyrrolidin-1-yl)-2,2,2-trifluoroethan-1-one;

(4H) 1-(3-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)pyrrolidin-1-yl)-2,2,2-trifluoroethan-1-one;

(412) 1-(3-((6-((2-(1-(Cyclopropylsulfonyl)-1H-pyrazol-4-yl)pyrimidin-4-yl)amino)-4-(4-((dimethylamino)methyl)-4-methylpiperidin-1-yl)pyridin-3-yl)ethynyl)pyrrolidin-1-yl)-2,2,2-trifluoroethan-1-one;

(413) 1-(3-((6-((2-(1-(Cyclopropylsulfonyl)-1H-pyrazol-4-yl)pyrimidin-4-yl)amino)-4-(4-(2-(dimethylamino)ethyl)piperidin-1-yl)pyridin-3-yl)ethynyl)pyrrolidin-1-yl)-2,2,2-trifluoroethan-1-one;

(414) 1-(3-((6-((2-(1-(Cyclopropylsulfonyl)-1H-pyrazol-4-yl)pyrimidin-4-yl)amino)-4-(((1s,4s)-4-hydroxycyclohexyl)amino)pyridin-3-yl)ethynyl)pyrrolidin-1-yl)-2,2,2-trifluoroethan-1-one;

(415) 1-(3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)pyrrolidin-1-yl)-2,2,2-trifluoroethan-1-one;

(416) ((1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexyl)methanol;

(417) 1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-ol;

(418) 2-(1-(Cyclopropylsulfonyl)-1H-pyrazol-4-yl)-N-(4-(4-((dimethylamino)methyl)-4-methylpiperidin-1-yl)-5-(((2R)-2-(trifluoromethyl)tetrahydrofuran-3-yl)ethynyl)pyridin-2-yl)pyrimidin-4-amine;

(419) 2-(1-(Cyclopropylsulfonyl)-1H-pyrazol-4-yl)-N-(4-(4-(2-(dimethylamino)ethyl)piperidin-1-yl)-5-(((2R)-2-(trifluoromethyl)tetrahydrofuran-3-yl)ethynyl)pyridin-2-yl)pyrimidin-4-amine;

(420) (1s,4s)-4-((2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)amino)cyclohexan-1-ol;

(421) (1-(2-((2-(1-(Cyclopropylsulfonyl)-1H-pyrazol-4-yl)pyrimidin-4-yl)amino)-5-(((2R)-2-(trifluoromethyl)tetrahydrofuran-3-yl)ethynyl)pyridin-4-yl)-4-methylpiperidin-4-yl)methanol;

(422) ((1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexyl)methanol;

(423) (1 r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexan-1-ol;

(424) 1-(5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)-4-methylpiperidin-4-ol;

(425) ((1 r,4r)-4-(((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)methyl)cyclohexyl)methanol;

(426) N-(5-((7-Oxabicyclo[2.2.1]heptan-2-yl)ethynyl)-4-(4-(2-(dimethylamino)ethyl)piperidin-1-yl)pyridin-2-yl)-2-(1-(cyclopropylsulfonyl)-1H-pyrazol-4-yl)pyrimidin-4-amine;

(427) (1s,4s)-4-((5-((7-Oxabicyclo[2.2.1]heptan-2-yl)ethynyl)-2-((2-(1-(cyclopropylsulfonyl)-1H-pyrazol-4-yl)pyrimidin-4-yl)amino)pyridin-4-yl)amino)cyclohexan-1-ol;

(428) 3-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)tetrahydrothiophene 1,1-dioxide;

(429) 3-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)tetrahydrothiophene 1,1-dioxide;

(430) ((1s,4s)-4-((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexyl)methanol;

(431) (1 r,4r)-4-(((2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)amino)methyl)cyclohexan-1-ol;

(432) 1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-ol;

(433) (1s,4s)-4-((2-((2-(1-(cyclopropylsulfonyl)-1H-pyrazol-4-yl)pyrimidin-4-yl)amino)-5-((2-methyltetrahydrofuran-3-yl)ethynyl)pyridin-4-yl)amino)cyclohexan-1-ol;

(434) ((1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexyl)methanol;

(435) 1-(2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)-4-methylpiperidin-4-ol;

(436) (1s,4s)-4-((2-((2-(1-(Cyclopropylsulfonyl)-1H-pyrazol-4-yl)pyrimidin-4-yl)amino)-5-((3-fluorotetrahydrofuran-3-yl)ethynyl)pyridin-4-yl)amino)cyclohexan-1-ol;

(437) 3-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)tetrahydrothiophene 1,1-dioxide;

(438) (1-(2-((2-(1-(Cyclopropylsulfonyl)-1H-pyrazol-4-yl)pyrimidin-4-yl)amino)-5-((2-methyltetrahydrofuran-3-yl)ethynyl)pyridin-4-yl)-4-methylpiperidin-4-yl)methanol;

(439) (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)piperidin-3-ol;

(440) (R)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)piperidin-3-ol;

(441) (4-((6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)ethynyl)phenyl)(4-hydroxypiperidin-1-yl)methanone;

(442) (4-((6-((2-(1-(Cyclopropylsulfonyl)-1H-pyrazol-4-yl)pyrimidin-4-yl)amino)-4-(4-hydroxy-4-methylpiperidin-1-yl)pyridin-3-yl)ethynyl)phenyl)(4-hydroxypiperidin-1-yl)methanone;

(443) (4-((6-((2-(1-(Cyclopropylsulfonyl)-1H-pyrazol-4-yl)pyrimidin-4-yl)amino)-4-((((1 r,4r)-4-(hydroxymethyl)cyclohexyl)methyl)amino)pyridin-3-yl)ethynyl)phenyl)(4-hydroxypiperidin-1-yl)methanone;

(444) (R)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone;

(445) (S)-(4-((6-((2-(1-(Cyclopropylsulfonyl)-1H-pyrazol-4-yl)pyrimidin-4-yl)amino)-4-(3-hydroxypiperidin-1-yl)pyridin-3-yl)ethynyl)phenyl)(4-hydroxypiperidin-1-yl)methanone;

(446) (4-((6-((2-(1-(Cyclopropylsulfonyl)-1H-pyrazol-4-yl)pyrimidin-4-yl)amino)-4-(4-(hydroxymethyl)-4-methylpiperidin-1-yl)pyridin-3-yl)ethynyl)phenyl)(4-hydroxypiperidin-1-yl)methanone;

(447) (S)-1-(2-((2-(1-(Cyclopropylsulfonyl)-1H-pyrazol-4-yl)pyrimidin-4-yl)amino)-5-((1-(2-fluoroethyl)-1H-pyrazol-4-yl)ethynyl)pyridin-4-yl)-3-methylpiperidin-3-ol;

(448) (S)-1-(2-((2-(1-(Cyclopropylsulfonyl)-1H-pyrazol-4-yl)pyrimidin-4-yl)amino)-5-((1-(trifluoromethyl)-1H-pyrazol-4-yl)ethynyl)pyridin-4-yl)-3-methylpiperidin-3-ol; and (449) (1-(2-((2-(4-(Cyclopropylsulfonyl)piperazin-1-yl)pyrimidin-4-yl)amino)-5-((1-(trifluoromethyl)-1H-pyrazol-4-yl)ethynyl)pyridin-4-yl)-4-methylpiperidin-4-yl)methanol.

24. A method of treating a protein kinase-mediated disease in a patient having said protein kinase-mediated disease, comprising administering to said patient a therapeutically effective amount of a compound of claim 1, or a pharmaceutically acceptable salt thereof.

25. The method of claim 24, wherein the protein kinase-mediated disease is cancer or immune disease.

26. The method of claim 25, wherein the cancer is bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, thyroid cancer, prostate cancer, skin cancer or hematological tumors.

27. The method of claim 25, wherein the cancer is lung cancer.

28. The method of claim 25, wherein the cancer is non-small cell lung cancer.

29. A method of selectively inhibiting at least one mutant of EGFR, in biological sample or in a patient, comprising contacting the biological sample with or administering to a patient a compound of claim 1, or a pharmaceutically acceptable salt thereof.

30. The method according to claim 29, wherein the at least one mutant is at least one single mutant selected from the group consisting of EGFR Del19 (Del E746-A750) and EGFR L858R.

31. The method according to claim 29, wherein the at least one mutant is at least one double mutant selected from the group consisting of EGFR Del19/T790M, EGFR Del19/C797S, EGFR Del19/C797X wherein X is G or N, EGFR Del19/L792X wherein X is F, H, P, R, V, or Y, EGFR Del19/L718X wherein X is Q or V, EGFR L858R/T790M, EGFR L858R/C797S, EGFR L858R/C797X wherein X is G or N, EGFR L858R/L792X wherein X is F, H, P, R, V, or Y and EGFR L858R/L718X wherein X is Q or V.

32. The method according to claim 29, wherein the at least one mutant is at least one double mutant selected from the group consisting of EGFR Del19/C797S and EGFR L858R/C797S.

33. The method according to claim 29, wherein the at least one mutant is at least one triple mutant selected from the group consisting of EGFR Del19/T790M/C797S, EGFR Del19/T790M/C797X wherein X is G or N, EGFR Del19/T790M/L792X wherein X is F, H, P, R, V, or Y, EGFR Del19/T790M/L718X wherein X is Q or V, EGFR L858R/T790M/C797S, EGFR L858R/T790M/C797X wherein X is G or N, EGFR L858R/T790M/L792X wherein X is F, H, P, R, V, or Y, and EGFR L858R/T790M/L718X wherein X is Q or V.

34. The method according to claim 29, wherein the at least one mutant is at least one triple mutant selected from the group consisting of EGFR Del19/T790M/C797S and EGFR L858R/T790M/C797S.

35. A pharmaceutical composition for treating a protein kinase-mediated disease, comprising a compound of claim 1, or a pharmaceutically acceptable salt thereof as an active ingredients.

36. The composition of claim 35, the protein kinase-mediated disease is cancer or immune disease.

37. The composition of claim 36, wherein the cancer is bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, thyroid cancer, prostate cancer, skin cancer or hematological tumors.

38. A pharmaceutical composition for inhibiting at least one mutant of EGFR selectively as compared to wild type EGFR, comprising a compound of claim 1, or a pharmaceutically acceptable salt thereof as an active ingredients.

39. The compound of claim 1, or a pharmaceutically acceptable salt thereof, which is selected from the group consisting of:
- (293) 2-(1-(Cyclopropylsulfonyl)-1H-pyrazol-4-yl)-N-(4-(4-((dimethylamino)methyl)-4-fluoropiperidin-1-yl)-5-((1-methyl-1H-pyrazol-4-yl)ethynyl)pyridin-2-yl)pyrimidin-4-amine formate;
- (294) 2-(1-(Cyclopropylsulfonyl)-1H-pyrazol-4-yl)-N-(4-(4-(2-(dimethylamino)ethyl)piperidin-1-yl)-5-((1-methyl-1H-pyrazol-4-yl)ethynyl)pyridin-2-yl)pyrimidin-4-amine formate; and
- (297) 2-(1-(Cyclopropylsulfonyl)-1H-pyrazol-4-yl)-N-(5-((1-methyl-1H-pyrazol-4-yl)ethynyl)-4-(2-methyl-2,8-diazaspiro[4.5]decan-8-yl)pyridin-2-yl)pyrimidin-4-amine formate.

* * * * *

UNITED STATES PATENT AND TRADEMARK OFFICE
CERTIFICATE OF CORRECTION

PATENT NO. : 11,981,658 B2  Page 1 of 2
APPLICATION NO. : 17/822450
DATED : May 14, 2024
INVENTOR(S) : Lee et al.

It is certified that error appears in the above-identified patent and that said Letters Patent is hereby corrected as shown below:

In the Specification

Column 6, Line 32: please delete "-S(O)$_2$N(C$_{1-6}$alkyl)," and insert -- -S(O)$_2$N(C$_{1-6}$alkyl)$_2$, --

Column 11, Line 10: please delete "-S(O)$_2$N(C$_{1-6}$alkyl)," and insert -- -S(O)$_2$N(C$_{1-6}$alkyl)$_2$, --

Column 12, Line 14: please delete "-S(O)$_2$Calkyl;" and insert -- -S(O)$_2$C$_{1-6}$alkyl; --

Column 14, Line 39: please delete "-S(O)$_2$N(C$_{1-4}$alkyl)." and insert -- -S(O)$_2$N(C$_{1-4}$alkyl)$_2$. --

Column 14, Line 43: please delete "-S(O)$_2$N(C$_{1-6}$alkyl)." and insert -- -S(O)$_2$N(C$_{1-6}$alkyl)$_2$. --

In the Claims

Column 343, Claim 1, Line 15: please delete "-S(O)$_2$N(C$_{1-6}$ alkyl)" and insert -- -S(O)$_2$N(C$_{1-6}$ alkyl)$_2$ --

Column 344, Claim 7, Line 25: please delete "-S(O)$_2$Calkyl" and insert -- S(O)$_2$C$_{1-6}$alkyl --

Column 345, Claim 10, Line 13: please delete "7 membered" and insert -- 4-7 membered --

Column 347, Claim 20, Line 13: please delete "-S(O)$_2$N(C$_{1-4}$ alkyl)" and insert -- -S(O)$_2$N(C$_{1-4}$ alkyl)$_2$ --

Column 347, Claim 21, Line 15: Please delete "R$_3$" and insert -- R$_{3A}$ --

Column 347, Claim 21, Line 21: please delete "-S(O)$_2$N(C$_{1-6}$ alkyl)" and insert -- -S(O)$_2$N(C$_{1-6}$ alkyl)$_2$ --

Signed and Sealed this
Twenty-first Day of January, 2025

Coke Morgan Stewart
*Acting Director of the United States Patent and Trademark Office*

CERTIFICATE OF CORRECTION (continued)
U.S. Pat. No. 11,981,658 B2

Column 353, Claim 23, Line 24: please delete "(1H)" and insert -- (111) --

Column 359, Claim 23, Line 7: please delete "(2H)" and insert -- (211) --

Column 364, Claim 23, Line 47: please delete "(3H)" and insert -- (311) --

Column 370, Claim 23, Line 48: please delete "(4H)" and insert -- (411) --